US007928244B2

(12) United States Patent
Castro et al.

(10) Patent No.: US 7,928,244 B2
(45) Date of Patent: Apr. 19, 2011

(54) COMPOUNDS AND METHODS FOR INHIBITING THE INTERACTION OF BCL PROTEINS WITH BINDING PARTNERS

(75) Inventors: Alfredo C. Castro, Winchester, MA (US); Kristopher M. Depew, Acton, MA (US); Michael J. Grogan, Winchester, MA (US); Charles W. Johannes, Newbury, MA (US); Edward B. Holson, Newton Highlands, MA (US); Brian T. Hopkins, Newton, MA (US); Gregg F. Keaney, Belmont, MA (US); Nii O. Koney, Brighton, MA (US); Tao Liu, Ashland, MA (US); David A. Mann, Swampscott, MA (US); Marta Nevalainen, Quincy, MA (US); Stephane Peluso, Somerville, MA (US); Lawrence B. Perez, Hopkinton, MA (US); Daniel A. Snyder, Somerville, MA (US); Thomas T. Tibbitts, Westford, MA (US)

(73) Assignee: Infinity Discovery, Inc., Cambridge, MA (US)

( * ) Notice: Subject to any disclaimer, the term of this patent is extended or adjusted under 35 U.S.C. 154(b) by 909 days.

(21) Appl. No.: 11/842,581

(22) Filed: Aug. 21, 2007

(65) Prior Publication Data

US 2008/0114167 A1 May 15, 2008

Related U.S. Application Data

(60) Provisional application No. 60/838,987, filed on Aug. 21, 2006.

(51) Int. Cl.
*C07D 261/02* (2006.01)
*A61K 31/42* (2006.01)
(52) U.S. Cl. ...................... 548/240; 514/378
(58) Field of Classification Search .................. 548/240; 514/378
See application file for complete search history.

(56) References Cited

U.S. PATENT DOCUMENTS

| | | | |
|---|---|---|---|
| 5,294,617 | A | 3/1994 | Venkatesan et al. |
| 5,514,505 | A | 5/1996 | Limburg et al. |
| 6,221,865 | B1 | 4/2001 | Sebti et al. |
| 6,747,050 | B1 | 6/2004 | Kim et al. |

FOREIGN PATENT DOCUMENTS

| | | |
|---|---|---|
| DE | 3643012 | 6/1988 |
| EP | 0769296 A1 | 4/1997 |
| EP | 0970950 | 1/2000 |
| JP | 11343285 A | 12/1999 |
| WO | WO-95/24398 A1 | 9/1995 |
| WO | WO-9806694 | 2/1998 |
| WO | WO-9816830 | 4/1998 |
| WO | WO-0116115 | 3/2001 |
| WO | WO-02/097053 | 12/2002 |
| WO | WO-03105788 | 2/2003 |
| WO | WO 2006/009869 | * 1/2006 |
| WO | WO-2006/009869 | 1/2006 |

OTHER PUBLICATIONS

Akmanova, N. A. et al., "Dipolar Addition to Carbamoyl Nitrones", *Zhurnal Organicheskoi Khimii*, 15(10):2061-2065 (Oct. 1979) (English translation).
Baell, J. et al., "Prospects for targeting the Bcl-2 family of proteins to develope novel cytotoxic drugs", *Biochem. Pharmacol.*, 64:851-863 (2002).
Banerji, A. et a., "1,3-Dipolar cycloadditions: Part VII—Cycloaddition of C,N-diarylnitrones to ethyl crotonate", Ind. Journ. of Chem., 43B:1925-1933 (Sep. 2004).
Ding, X. et al., "Catalytic Asymmetric 1,3-Dipolar Cycloaddition of a Nitrone Bearing a Bulky Amide Moiety to γ-Substituted Allylic Alcohols", *Chemistry Letters*, 2002:302-303 (2002).
Dugovic, B., et al., "Reversal of Regioselectivity of Nitrone Cycloadditions by Lewis Acids", Helvetica Chimica Acta, 88:1432-1443 (2005).
Foley, M., "Infinity Pharmaceuticals—Infiniplex Libraries: Developing a Platform for Chemical Genetic Studies", PowerPoint Presentation Oct. 2, 2006.
Foley, M., "Infinity Pharmaceuticals—Chemical Genomics-Linking the Genome to Therapies", PowerPoint Presentation Jun. 11, 2002.
Foley, M., "Infinity Pharmaceuticals—ACS Short Course on Drug Discovery in the 21st Century—Arrayed Split-Pool Libraries: Developing a Platform for Chemical Genetic Studies", PowerPoint Presentation Jul. 10, 2002.
"Infinity Pharmaceuticals—ACS Prospectives Conference Series", PowerPoint Presentation Sep. 22, 2003.
"Infinity Pharmaceuticals—Cambridge Health Institute's Conference on Diversity-Oriented Synthesis (DOS) and Natural Product Chemistry", PowerPoint Presentation Oct. 9, 2003.
Inouye, Y., et al., "Regioselective Effects of the Allylic Heteroatoms in 1,3-Dipolar Cycloaddition of Nitrones to Several Allyl Derivatives", Heterocycles, 25:109-111 (1987).
Jen, W. S., et al., "New Strategies for Organic Catalysis: The First Enantioselective Organocatalytic 1,3-Dipolar Cycloaddition", J. Am. Chem. Soc., 122:9874-9875 (2000).
Kanemasa, S. et al., "Metal Ion-Mediated Diastereoface-Selective Nitrone Cycloadditions. Reaction Mechanism for the Reversal of Regioselectivity Observed in the Magnesium and Zinc Ion-Mediated Nitrone Cycloadditions of Allylic Alcohols", Tetrahedron Letters, 36(28):5019-5022 (1995). Kanemasa, S. et al., "Metallic Base-Induced and Lewis Acid-Catalyzed Nitrone Cycloadditions to Allyl Alcohol Dipolarophiles. Highly Effective Regio- and Stereocontrol", Tetrahedron Letters, 34(1):87-90 (1993).
Kano, T. et al., "Asymmetric 1,3-Dipolar Cycloaddition Reaction of Nitrones and Acrolein with a Bis-Titanium Catalyst as Chiral Lewis Acid", J. Am. Chem. Soc., 127:11926-11927 (2005).
Merino, P. et al., "1,3-Dipolar Cycloadditions of N-Benzyl Furfuryl Nitrones with Electron-rich Alkenes", Molecules, 5:132-152 (2000).
Merino, P. et al., "A DFT Study on the 1,3-Dipolar Cycloaddition Reactions of C-(methylcarbonyl)-N-methyl nitrone with methyl acrylate and vinyl acetate", Tetrahedron, 59:3581-3592 (2003).

(Continued)

*Primary Examiner* — Robert Havlin
(74) *Attorney, Agent, or Firm* — Foley Hoag LLP

(57) ABSTRACT

The invention relates to isoxazolidine containing compounds that bind to bcl proteins and inhibit Bcl function. The compounds may be used for treating and modulating disorders associated with hyperproliferation, such as cancer.

37 Claims, 6 Drawing Sheets

OTHER PUBLICATIONS

Niu, D. et al., "Non-Cycloaddition Approach to Regioselective Synthesis of Isoxazolidines", Synlett, 979-980 (Sep. 1998).

Puglisi, A. et al., "Enantioselective 1,3-Dipolar Cycloadditions of Unsaturated Aldehydes Promoted by a Poly(ethylene glycol)-Supported Organic Catalyst", Eur. J. Org. Chem., 567-573 (2004).

Ratts, K. W. et al., "Chemistry of Resonance-Stabilized Sulfonium Ylids", *Journal of Organic Chemistry*, 31(6):1689-1693 (1966).

Revuelta, J. et al., "Samarium(II) iodide reduction of isoxazolidines", Tetrahedron Letters, 45:8375-8377 (2004).

Saito, T. et al., "Evaluation of chiral bidentate ligand-metal complexes in asymmetric 1,3 dipolar cycloaddition reaction of nitrones with 3-alkenoyl-2-oxazolidinones", Tetrahedron Letters, 45:9581-9584 (2004).

Sibi, M. P. et al., "Exo Selective Enantioselective Nitrone Cycloadditions", J. Am. Chem. Soc., 126:718-719 (2004).

Tan, D. S. et al., "Stereoselective Synthesis of over Two Million Compounds Having Structural Features Both Reminiscent of Natural Products and Compatible with Miniaturized Cell-Based Assays", *J. Am. Chem. Soc.*, 12:08565-8566 (1998).

Byrn, S. et al., "Pharmaceutical Solids: A Strategic Approach to Regulatory Considerations," *Pharmaceutical Research*, 12(7):945-954 (Plenum Publishing, USA) (1995).

Kubinyi, E. H. (ED QSAR in Drug Design: Ligand-Protein Interactions and Molecular Similarity, vol. 2-3, Springer, 1998, 800 pages).

Blanáriková-Hlobilová, I. et al., "Stereoselectivity of 1,3-dipolar cycloadditions of L-valine-derived nitrones with methyl acrylate", Tetrahedron 59, 3333-3339 (2003).

International Search Report for PCT/US2007/018471 dated Feb. 25, 2008.

International Search Report for PCT/US2007/023941 dated Feb. 28, 2008.

\* cited by examiner

R=

R=

R = H, CH₃, or (CH₂)₂OH

R=

COMPOUNDS AND METHODS FOR INHIBITING THE INTERACTION OF BCL PROTEINS WITH BINDING PARTNERS

RELATED APPLICATIONS

This application claims the benefit of priority to U.S. Provisional Patent Application Ser. No. 60/838,987, filed Aug. 21, 2006.

BACKGROUND OF THE INVENTION

Apoptosis, or programmed cell death, is important for normal embryological/anatomical development, host defense and suppression of oncogenesis. Faulty regulation of apoptosis has been implicated in cancer and in many other human diseases which result from an imbalance between the process of cell division and cell death. A central check point of apoptosis is the regulation of cytochrome c release from mitochondria. Cytochrome c release is regulated, in part, by Bcl-2 family members. The Bcl-2 family of proteins includes both anti-apoptotic molecules, such as Bcl-2 and Bcl-XL, and pro-apoptotic molecules, such as Bax, Bak, Bid and Bad. Bcl-2 contributes to cancer cell progression by preventing normal cell turnover caused by physiological cell-death mechanisms. Overexpression of Bcl-2 has been observed in 70% of breast cancer and many other forms of cancer.

Various small molecules have been shown to inhibit the function of Bcl-2. Nevertheless, the need exists for additional small organic molecules that bind to Bcl-2 and block its anti-apoptotic function in cancer and promote cell death in tumors.

SUMMARY OF THE INVENTION

The present invention generally relates to isoxazolidine compounds useful for treating cancer. The isoxazolidine compounds of the invention bind to one or more Bcl proteins and block Bcl anti-apoptotic function in cancer cells and tumor tissue that express the Bcl protein.

The present invention relates to isoxazolidine compounds (e.g., compounds of formulas 1, 2, and 3), pharmaceutical compositions, and methods of using them. In one embodiment, the present invention relates to a compound of formula 1:

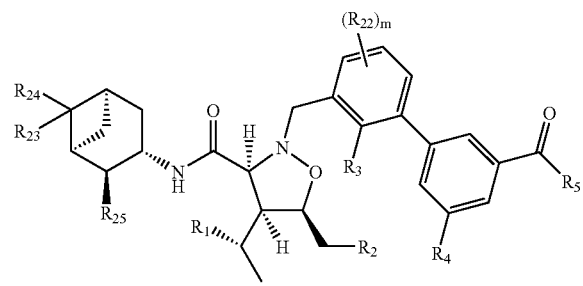

or a pharmaceutically acceptable salt thereof;
wherein independently for each occurrence
m is 0, 1, 2, or 3;
n, o, and p are independently for each occurrence 1, 2, 3, 4, or 5;

$R_1$ is —OH, —OC(O)$R_6$, —OC(O)N($R_6$)($R_7$), or —N($R_6$)($R_7$);

$R_2$ is —OH, —N($R_8$)($R_9$), —N(R)C(O)N($R_8$)($R_9$), or —N(R)C(O)$R_{10}$; or has the formula 1b;

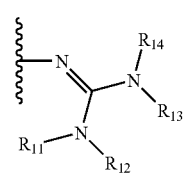

$R_3$ is alkyl, halide, alkoxy, (cycloalkyl)alkoxy, aralkyloxy, or —O(CH$_2$)$_2$—N($R_{15}$)($R_{16}$);

$R_4$ is alkyl, alkoxy, hydroxyalkyl, alkoxyalkyl, halide, nitro, amino, acyl, amido, acylamino, aminoalkyl, acylaminoalkyl, acylaminoalkylamino, sulfonylaminoalkylamino, carboxylate, or —N=C(N(R)$_2$)$_2$;

$R_5$ is —OH or —N($R_{17}$)($R_{18}$);

$R_6$ and $R_7$ are independently for each occurrence H, alkyl, aralkyl, heteroaralkyl, or —[C($R_{15}$)($R_{16}$)]$_n$—$R_{19}$;

$R_8$ and $R_9$ are independently for each occurrence H, alkyl, aralkyl, or heteroaralkyl;

$R_{10}$ is alkyl, haloalkyl, or —[C($R_{15}$)($R_{16}$)]$_o$—COOR;

R, $R_{11}$, $R_{12}$, $R_{13}$, $R_{14}$, $R_{15}$, and $R_{16}$ are independently for each occurrence H or alkyl;

$R_{17}$ and $R_{18}$ are independently for each occurrence H, alkyl, aralkyl, heteroaralkyl, alkoxy, or —[C($R_{19}$)($R_{20}$)]$_p$—$R_{21}$;

$R_{19}$ and $R_{20}$ are independently for each occurrence H, hydroxy, alkyl, alkoxy, amino, aminoalkyl, acylamino, sulfonylamino, aryl, aralkyl, cycloalkyl, heterocyclyl, heterocyclylalkyl, heteroaryl, or heteroaralkyl;

$R_{21}$ is independently for each occurrence H, alkyl, aryl, heteroaryl, heterocyclyl, heterocyclylalkyl, alkoxy, alkylsulfonyl, arylsulfonyl, alkylsulfonamido, arylsulfonamido, amino, amido, or carboxyl;

$R_{22}$ independently for each occurrence is halide or alkyl;

$R_{23}$ is selected from the group consisting of alkyl, hydroxyalkyl, alkoxyalkyl, acyloxyalkyl, and haloalkyl;

$R_{24}$ is selected from the group consisting of alkyl, hydroxyalkyl, alkoxyalkyl, acyloxyalkyl, and haloalkyl; and $R_{25}$ is selected from the group consisting of alkyl, hydroxyalkyl, alkoxyalkyl, acyloxyalkyl, and haloalkyl.

In certain embodiments, the present invention relates to the aforementioned compound and any of the attendant definitions, wherein $R_1$ is selected from the group consisting of —OH, —OC(O)Me, —OC(O)(CH$_2$)$_2$Ph, —OC(O)CH$_2$CHMe$_2$, —OC(O)NHMe, —OC(O)NMe$_2$, —OC(O)NHCH$_2$(4-(OH)-Ph), —OC(O)NHPh, —OC(O)NHCH$_2$Ph, —OC(O)NH(CH$_2$)$_4$Ph, —OC(O)NH(CH$_2$)$_2$Ph, —OC(O)NH(CH$_2$)$_2$Me, —OC(O)NH(CH$_2$)$_2$NMe$_2$, —OC(O)NH(CH$_2$)$_2$NHC(O)Me, —OC(O)NH(CH$_2$)$_2$CHMe$_2$, —NHMe, —NH(CH$_2$)$_2$Ph, —NHC(O)Me, and —NH(CH$_2$)$_2$NMe$_2$.

In certain embodiments, the present invention relates to the aforementioned compound and any of the attendant definitions, wherein $R_1$ is —OH.

In certain embodiments, the present invention relates to the aforementioned compound and any of the attendant definitions, wherein $R_2$ is —OH, —OC(O)Me, —OCH$_2$CO$_2$H, —OCH$_2$CO$_2$Et, —N$_3$, —N=C(NMe$_2$)$_2$, —NH$_2$, —NMe$_2$, —NHC(O)Me, —NHC(O)CF$_3$, —NHC(O)Ph, —NHC(O)NHPh, —NHC(O)CH$_2$CH$_2$CO$_2$H, —NHC(O)CH$_2$CH$_2$CO$_2$Me, —NHCH$_2$Ph, —NHCH$_2$(4-pyridyl), —NHCH$_2$(2-pyridyl), —NHCH$_2$(4-(CO$_2$H)Ph), —NHCH$_2$(3-(CO$_2$H)Ph), —NHEt, —NHCHMe$_2$, —NHCH$_2$CHMe$_2$, —N(CH$_2$CHMe$_2$)$_2$, —NHCH$_2$(cyclopropyl), or —NHC(O)CH$_2$CH$_2$NMe$_2$.

In certain embodiments, the present invention relates to the aforementioned compound and any of the attendant definitions, wherein R$_2$ is —OH or —NH$_2$.

In certain embodiments, the present invention relates to the aforementioned compound and any of the attendant definitions, wherein R$_2$ is —NH$_2$.

In certain embodiments, the present invention relates to the aforementioned compound and any of the attendant definitions, wherein R$_2$ is —OH.

In certain embodiments, the present invention relates to the aforementioned compound and any of the attendant definitions, wherein R$_3$ is —OMe, —OEt, —OCH$_2$(cyclopropyl), F, —O(CH$_2$)$_2$NMe$_2$, —O(CH$_2$)$_2$(4-morpholino), —OCH$_2$(4-(MeO)Ph), or —OCH$_2$(2-pyridyl).

In certain embodiments, the present invention relates to the aforementioned compound and any of the attendant definitions, wherein R$_3$ is —OMe.

In certain embodiments, the present invention relates to the aforementioned compound and any of the attendant definitions, wherein R$_4$ is —NMe$_2$, —NEt$_2$, —NHEt, —NHCH$_2$CHMe$_2$, —N(Me)CH$_2$CHMe$_2$, —N(Me)CH$_2$CH$_2$NHC(O)Me, —N(Me)CH$_2$CH$_2$NHS(O)$_2$Me, —N(Me)CH$_2$CH$_2$NHS(O)$_2$CF$_3$, —NHCH$_2$CH$_2$NMe$_2$, —NHCH$_2$CH$_2$NMeCH$_2$CH$_2$Cl, —NHCH$_2$CH$_2$OH, —N(Me)CH$_2$CH$_2$OH, —N(CH$_2$CH$_2$OH)$_2$, —N(Me)CH$_2$CO$_2$H, —N(Me)CH$_2$C(O)NH$_2$, —N(Me)CH$_2$C(O)NHMe, —N(Me)CH$_2$C(O)NMe$_2$, —NHC(O)Me, —NHC(O)CHMe$_2$, 1-pyrrolidinyl, 1-piperidinyl, 4-morpholino, (R)-2-(hydroxymethyl)-1-pyrrolidinyl, (S)-2-(hydroxymethyl)-1-pyrrolidinyl, (R)-2-(C(O)NMe$_2$)-1-pyrrolidinyl, (S)-2-(C(O)NMe$_2$)-1-pyrrolidinyl, —NH$_2$, —NO$_2$, Br, Cl, F, —C(O)Me, —C(O)NMe$_2$, —C(O)NH$_2$, —CO$_2$H, —CHO, —CH$_2$OH, —CH(Me)OH, —CH$_2$NH$_2$, —CH$_2$NHMe, —CH$_2$NMe$_2$, —CH$_2$NHC(O)Me, —CF$_3$, or tert-butyl.

In certain embodiments, the present invention relates to the aforementioned compound and any of the attendant definitions, wherein R$_4$ is amino.

In certain embodiments, the present invention relates to the aforementioned compound and any of the attendant definitions, wherein R$_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In certain embodiments, the present invention relates to the aforementioned compound and any of the attendant definitions, wherein R$_4$ is —NMe$_2$.

In certain embodiments, the present invention relates to the aforementioned compound and any of the attendant definitions, wherein R$_{22}$ is selected from the group consisting of F, Cl, and tert-butyl; and m is 0 or 1.

In certain embodiments, the present invention relates to the aforementioned compound and any of the attendant definitions, wherein R$_{22}$ is F; and m is 0 or 1.

In certain embodiments, the present invention relates to the aforementioned compound and any of the attendant definitions, wherein R$_{22}$ is selected from the group consisting of F, Cl, and tert-butyl; and m is 1.

In certain embodiments, the present invention relates to the aforementioned compound and any of the attendant definitions, wherein R$_{22}$ is F; and m is 1.

In certain embodiments, the present invention relates to the aforementioned compound and any of the attendant definitions, wherein R$_{23}$ is selected from the group consisting of methyl, hydroxymethyl, alkoxymethyl, acyloxymethyl, and halomethyl.

In certain embodiments, the present invention relates to the aforementioned compound and any of the attendant definitions, wherein R$_{24}$ is selected from the group consisting of methyl, hydroxymethyl, alkoxymethyl, acyloxymethyl, and halomethyl.

In certain embodiments, the present invention relates to the aforementioned compound and any of the attendant definitions, wherein R$_{23}$ is methyl.

In certain embodiments, the present invention relates to the aforementioned compound and any of the attendant definitions, wherein R$_{24}$ is methyl.

In certain embodiments, the present invention relates to the aforementioned compound and any of the attendant definitions, wherein R$_{23}$ is methyl; and R$_{24}$ is methyl.

In certain embodiments, the present invention relates to the aforementioned compound and any of the attendant definitions, wherein R$_{25}$ is selected from the group consisting of methyl, hydroxymethyl, alkoxymethyl, acyloxymethyl, and halomethyl.

In certain embodiments, the present invention relates to the aforementioned compound and any of the attendant definitions, wherein R$_{25}$ is methyl.

In certain embodiments, the present invention relates to the aforementioned compound and any of the attendant definitions, wherein R$_{23}$ is methyl; R$_{24}$ is methyl; and R$_{25}$ is methyl.

In certain embodiments, the present invention relates to the aforementioned compound and any of the attendant definitions, wherein R$_1$ is —OH; and R$_2$ is —OH or —NH$_2$.

In certain embodiments, the present invention relates to the aforementioned compound and any of the attendant definitions, wherein R$_1$ is —OH; R$_2$ is —OH or —NH$_2$; and R$_3$ is —OMe.

In certain embodiments, the present invention relates to the aforementioned compound and any of the attendant definitions, wherein R$_1$ is —OH; R$_2$ is —OH or —NH$_2$; R$_3$ is —OMe; and R$_4$ is amino.

In certain embodiments, the present invention relates to the aforementioned compound and any of the attendant definitions, wherein R$_1$ is —OH; R$_2$ is —OH or —NH$_2$; R$_3$ is —OMe; and R$_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In certain embodiments, the present invention relates to the aforementioned compound and any of the attendant definitions, wherein R$_1$ is —OH; R$_2$ is —OH or —NH$_2$; R$_3$ is —OMe; and R$_4$ is —NMe$_2$.

In certain embodiments, the present invention relates to the aforementioned compound and any of the attendant definitions, wherein R$_1$ is —OH; R$_2$ is —OH or —NH$_2$; R$_{23}$ is methyl; R$_{24}$ is methyl; and R$_{25}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_{23}$ is methyl; R$_{24}$ is methyl; and R$_{25}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_4$ is amino; R$_{23}$ is methyl; R$_{24}$ is methyl; and R$_{25}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_4$ is —NMe$_2$, —N(Me)CH$_2$CH$_2$OH, —N(Me)

CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl; R$_{23}$ is methyl; R$_{24}$ is methyl; and R$_{25}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_4$ is —NMe$_2$; R$_{23}$ is methyl; R$_{24}$ is methyl; and R$_{25}$ is methyl.

In another embodiment, the present invention relates to a compound of formula 2:

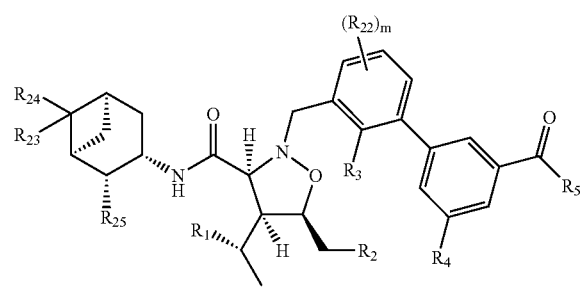

2 or a pharmaceutically acceptable salt thereof;
wherein independently for each occurrence
m is 0, 1, 2, or 3;
n, o, and p are independently for each occurrence 1, 2, 3, 4, or 5;
R$_1$ is —OH, —OC(O)R$_6$, —OC(O)N(R$_6$)(R$_7$), or —N(R$_6$)(R$_7$);
R$_2$ is —OH, —N(R$_8$)(R$_9$), —N(R)C(O)N(R$_8$)(R$_9$), or —N(R)C(O)R$_{10}$; or has the formula 1b;

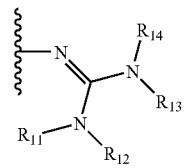

R$_3$ is alkyl, halide, alkoxy, (cycloalkyl)alkoxy, aralkyloxy, or —O(CH$_2$)$_2$—N(R$_{15}$)(R$_{16}$);
R$_4$ is alkyl, alkoxy, hydroxyalkyl, alkoxyalkyl, halide, nitro, amino, acyl, amido, acylamino, aminoalkyl, acylaminoalkyl, acylaminoalkylamino, sulfonylaminoalkylamino, carboxylate, or —N=C(N(R)$_2$)$_2$;
R$_5$ is —OH or —N(R$_{17}$)(R$_{18}$);
R$_6$ and R$_7$ are independently for each occurrence H, alkyl, aralkyl, heteroaralkyl, or —[C(R$_{15}$)(R$_{16}$)]$_n$—R$_{19}$;
R$_8$ and R$_9$ are independently for each occurrence H, alkyl, aralkyl, or heteroaralkyl;
R$_{10}$ is alkyl, haloalkyl, or —[C(R$_{15}$)(R$_{16}$)]$_o$—COOR;
R, R$_{11}$, R$_{12}$, R$_{13}$, R$_{14}$, R$_{15}$, and R$_{16}$ are independently for each occurrence H or alkyl;
R$_{17}$ and R$_{18}$ are independently for each occurrence H, alkyl, aralkyl, heteroaralkyl, alkoxy, or —[C(R$_{19}$)(R$_{20}$)]$_p$—R$_{21}$;
R$_{19}$ and R$_{20}$ are independently for each occurrence H, hydroxy, alkyl, alkoxy, amino, aminoalkyl, acylamino, sulfonylamino, aryl, aralkyl, cycloalkyl, heterocyclyl, heterocyclylalkyl, heteroaryl, or heteroaralkyl;
R$_{21}$ is independently for each occurrence H, alkyl, aryl, heteroaryl, heterocyclyl, heterocyclylalkyl, alkoxy, alkylsulfonyl, arylsulfonyl, alkylsulfonamido, arylsulfonamido, amino, amido, or carboxyl;
R$_{22}$ independently for each occurrence is halide or alkyl;
R$_{23}$ is selected from the group consisting of alkyl, hydroxyalkyl, alkoxyalkyl, acyloxyalkyl, and haloalkyl;
R$_{24}$ is selected from the group consisting of alkyl, hydroxyalkyl, alkoxyalkyl, acyloxyalkyl, and haloalkyl; and
R$_{25}$ is selected from the group consisting of alkyl, hydroxyalkyl, alkoxyalkyl, acyloxyalkyl, and haloalkyl.

In certain embodiments, the present invention relates to the aforementioned compound and any of the attendant definitions, wherein R$_1$ is selected from the group consisting of —OH, —OC(O)Me, —OC(O)(CH$_2$)$_2$Ph, —OC(O)CH$_2$CHMe$_2$, —OC(O)NHMe, —OC(O)NMe$_2$, —OC(O)NHCH$_2$(4-(OH)-Ph), —OC(O)NHPh, —OC(O)NHCH$_2$Ph, —OC(O)NH(CH$_2$)$_4$Ph, —OC(O)NH(CH$_2$)$_2$Ph, —OC(O)NH(CH$_2$)$_2$Me, —OC(O)NH(CH$_2$)$_2$NMe$_2$, —OC(O)NH(CH$_2$)$_2$NHC(O)Me, —OC(O)NH(CH$_2$)$_2$CHMe$_2$, —NHMe, —NH(CH$_2$)$_2$Ph, —NHC(O)Me, and —NH(CH$_2$)$_2$NMe$_2$.

In certain embodiments, the present invention relates to the aforementioned compound and any of the attendant definitions, wherein R$_1$ is —OH.

In certain embodiments, the present invention relates to the aforementioned compound and any of the attendant definitions, wherein R$_2$ is —OH, —OC(O)Me, —OCH$_2$CO$_2$H, —OCH$_2$CO$_2$Et, —N$_3$, —N=C(NMe$_2$)$_2$, —NH$_2$, —NMe$_2$, —NHC(O)Me, —NHC(O)CF$_3$, —NHC(O)Ph, —NHC(O)NHPh, —NHC(O)CH$_2$CH$_2$CO$_2$H, —NHC(O)CH$_2$CH$_2$CO$_2$Me, —NHCH$_2$Ph, —NHCH$_2$(4-pyridyl), —NHCH$_2$(2-pyridyl), —NHCH$_2$(4-(CO$_2$H)Ph), —NHCH$_2$(3-(CO$_2$H)Ph), —NHEt, —NHCHMe$_2$, —NHCH$_2$CHMe$_2$, —N(CH$_2$CHMe$_2$)$_2$, —NHCH$_2$(cyclopropyl), or —NHC(O)CH$_2$CH$_2$NMe$_2$.

In certain embodiments, the present invention relates to the aforementioned compound and any of the attendant definitions, wherein R$_2$ is —OH or —NH$_2$.

In certain embodiments, the present invention relates to the aforementioned compound and any of the attendant definitions, wherein R$_2$ is —NH$_2$.

In certain embodiments, the present invention relates to the aforementioned compound and any of the attendant definitions, wherein R$_2$ is —OH.

In certain embodiments, the present invention relates to the aforementioned compound and any of the attendant definitions, wherein R$_3$ is —OMe, —OEt, —OCH$_2$(cyclopropyl), F, —O(CH$_2$)$_2$NMe$_2$, —O(CH$_2$)$_2$(4-morpholino), —OCH$_2$(4-(MeO)Ph), or —OCH$_2$(2-pyridyl).

In certain embodiments, the present invention relates to the aforementioned compound and any of the attendant definitions, wherein R$_3$ is —OMe.

In certain embodiments, the present invention relates to the aforementioned compound and any of the attendant definitions, wherein R$_4$ is —NMe$_2$, —NEt$_2$, —NHEt, —NHCH$_2$CHMe$_2$, —N(Me)CH$_2$CHMe$_2$, —N(Me)CH$_2$CH$_2$NHC(O)Me, —N(Me)CH$_2$CH$_2$NHS(O)$_2$Me, —N(Me)CH$_2$CH$_2$NHS(O)$_2$CF$_3$, —NHCH$_2$CH$_2$NMe$_2$, —NHCH$_2$CH$_2$NMeCH$_2$CH$_2$Cl, —NHCH$_2$CH$_2$OH, —N(Me)CH$_2$CH$_2$OH, —N(CH$_2$CH$_2$OH)$_2$, —N(Me)CH$_2$CO$_2$H, —N(Me)CH$_2$C(O)NH$_2$, —N(Me)CH$_2$C(O)NHMe, —N(Me)CH$_2$C(O)NMe$_2$, —NHC(O)Me, —NHC(O)CHMe$_2$, 1-pyrrolidinyl, 1-piperidinyl, 4-morpholino, (R)-2-(hydroxymethyl)-1-pyrrolidinyl, (S)-2-(hydroxymethyl)-1-pyrrolidinyl, (R)-2-(C(O)NMe$_2$)-1-pyrrolidinyl, (S)-2-(C(O)NMe$_2$)-1-pyrrolidinyl, —NH$_2$, —NO$_2$, Br, Cl, F, —C(O)Me, —C(O)NMe$_2$, —C(O)NH$_2$, —CO$_2$H, —CHO, —CH$_2$OH, —CH(Me)OH, —CH$_2$NH$_2$, —CH$_2$NHMe, —CH$_2$NMe$_2$, —CH$_2$NHC(O)Me, —CF$_3$, or tert-butyl.

In certain embodiments, the present invention relates to the aforementioned compound and any of the attendant definitions, wherein $R_4$ is amino.

In certain embodiments, the present invention relates to the aforementioned compound and any of the attendant definitions, wherein $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In certain embodiments, the present invention relates to the aforementioned compound and any of the attendant definitions, wherein $R_4$ is —NMe$_2$.

In certain embodiments, the present invention relates to the aforementioned compound and any of the attendant definitions, wherein $R_{22}$ is selected from the group consisting of F, Cl, and tert-butyl; and m is 0 or 1.

In certain embodiments, the present invention relates to the aforementioned compound and any of the attendant definitions, wherein $R_{22}$ is F; and m is 0 or 1.

In certain embodiments, the present invention relates to the aforementioned compound and any of the attendant definitions, wherein $R_{22}$ is selected from the group consisting of F, Cl, and tert-butyl; and m is 1.

In certain embodiments, the present invention relates to the aforementioned compound and any of the attendant definitions, wherein $R_{22}$ is F; and m is 1.

In certain embodiments, the present invention relates to the aforementioned compound and any of the attendant definitions, wherein $R_{23}$ is selected from the group consisting of methyl, hydroxymethyl, alkoxymethyl, acyloxymethyl, and halomethyl.

In certain embodiments, the present invention relates to the aforementioned compound and any of the attendant definitions, wherein $R_{24}$ is selected from the group consisting of methyl, hydroxymethyl, alkoxymethyl, acyloxymethyl, and halomethyl.

In certain embodiments, the present invention relates to the aforementioned compound and any of the attendant definitions, wherein $R_{23}$ is methyl.

In certain embodiments, the present invention relates to the aforementioned compound and any of the attendant definitions, wherein $R_{24}$ is methyl.

In certain embodiments, the present invention relates to the aforementioned compound and any of the attendant definitions, wherein $R_{23}$ is methyl; and $R_{24}$ is methyl.

In certain embodiments, the present invention relates to the aforementioned compound and any of the attendant definitions, wherein $R_{25}$ is selected from the group consisting of methyl, hydroxymethyl, alkoxymethyl, acyloxymethyl, and halomethyl.

In certain embodiments, the present invention relates to the aforementioned compound and any of the attendant definitions, wherein $R_{25}$ is methyl.

In certain embodiments, the present invention relates to the aforementioned compound and any of the attendant definitions, wherein $R_{23}$ is methyl; $R_{24}$ is methyl; and $R_{25}$ is methyl.

In certain embodiments, the present invention relates to the aforementioned compound and any of the attendant definitions, wherein $R_1$ is —OH; and $R_2$ is —OH or —NH$_2$.

In certain embodiments, the present invention relates to the aforementioned compound and any of the attendant definitions, wherein $R_1$ is —OH; $R_2$ is —OH or —NH$_2$; and $R_3$ is —OMe.

In certain embodiments, the present invention relates to the aforementioned compound and any of the attendant definitions, wherein $R_1$ is —OH; $R_2$ is —OH or —NH$_2$; $R_3$ is —OMe; and $R_4$ is amino.

In certain embodiments, the present invention relates to the aforementioned compound and any of the attendant definitions, wherein $R_1$ is —OH; $R_2$ is —OH or —NH$_2$; $R_3$ is —OMe; and $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In certain embodiments, the present invention relates to the aforementioned compound and any of the attendant definitions, wherein $R_1$ is —OH; $R_2$ is —OH or —NH$_2$; $R_3$ is —OMe; and $R_4$ is —NMe$_2$.

In certain embodiments, the present invention relates to the aforementioned compound and any of the attendant definitions, wherein $R_1$ is —OH; $R_2$ is —OH or —NH$_2$; $R_{23}$ is methyl; $R_{24}$ is methyl; and $R_{25}$ is methyl.

In certain embodiments, the present invention relates to the aforementioned compound and any of the attendant definitions, wherein $R_1$ is —OH; $R_2$ is —OH or —NH$_2$; $R_3$ is —OMe; $R_{23}$ is methyl; $R_{24}$ is methyl; and $R_{25}$ is methyl.

In certain embodiments, the present invention relates to the aforementioned compound and any of the attendant definitions, wherein $R_1$ is —OH; $R_2$ is —OH or —NH$_2$; $R_3$ is —OMe; $R_4$ is amino; $R_{23}$ is methyl; $R_{24}$ is methyl; and $R_{25}$ is methyl.

In certain embodiments, the present invention relates to the aforementioned compound and any of the attendant definitions, wherein $R_1$ is —OH; $R_2$ is —OH or —NH$_2$; $R_3$ is —OMe; $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl; $R_{23}$ is methyl; $R_{24}$ is methyl; and $R_{25}$ is methyl.

In certain embodiments, the present invention relates to the aforementioned compound and any of the attendant definitions, wherein $R_1$ is —OH; $R_2$ is —OH or —NH$_2$; $R_3$ is —OMe; $R_4$ is —NMe$_2$; $R_{23}$ is methyl; $R_{24}$ is methyl; and $R_{25}$ is methyl.

In an additional embodiment, the present invention relates to a compound of formula 3:

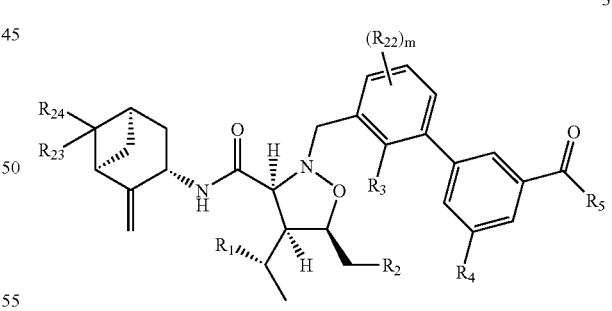

3 or a pharmaceutically acceptable salt thereof;

wherein independently for each occurrence m is 0, 1, 2, or 3;

n, o, and p are independently for each occurrence 1, 2, 3, 4, or 5;

$R_1$ is —OH, —OC(O)R$_6$, —OC(O)N(R$_6$)(R$_7$), or —N(R$_6$)(R$_7$);

$R_2$ is —OH, —N(R$_5$)(R$_5$), —N(R)C(O)N(R$_9$)(R$_9$), or —N(R)C(O)R$_{10}$; or has the formula 1b;

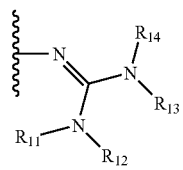

$R_3$ is alkyl, halide, alkoxy, (cycloalkyl)alkoxy, aralkyloxy, or —O(CH$_2$)$_2$—N(R$_{15}$)(R$_{16}$);

$R_4$ is alkyl, alkoxy, hydroxyalkyl, alkoxyalkyl, halide, nitro, amino, acyl, amido, acylamino, aminoalkyl, acylaminoalkyl, acylaminoalkylamino, sulfonylaminoalkylamino, carboxylate, or —N=C(N(R)$_2$)$_2$;

$R_5$ is —OH or —N(R$_{17}$)(R$_{18}$);

$R_6$ and $R_7$ are independently for each occurrence H, alkyl, aralkyl, heteroaralkyl, or —[C(R$_{15}$)(R$_{16}$)]$_n$—R$_{19}$;

$R_8$ and $R_9$ are independently for each occurrence H, alkyl, aralkyl, or heteroaralkyl;

$R_{10}$ is alkyl, haloalkyl, or —[C(R$_{15}$)(R$_{16}$)]$_o$—COOR;

R, $R_{11}$, $R_{12}$, $R_{13}$, $R_{14}$, $R_{15}$, and $R_{16}$ are independently for each occurrence H or alkyl;

$R_{17}$ and $R_{18}$ are independently for each occurrence H, alkyl, aralkyl, heteroaralkyl, alkoxy, or —[C(R$_{19}$)(R$_{20}$)]$_p$—R$_{21}$;

$R_{19}$ and $R_{20}$ are independently for each occurrence H, hydroxy, alkyl, alkoxy, amino, aminoalkyl, acylamino, sulfonylamino, aryl, aralkyl, cycloalkyl, heterocyclyl, heterocyclylalkyl, heteroaryl, or heteroaralkyl;

$R_{21}$ is independently for each occurrence H, alkyl, aryl, heteroaryl, heterocyclyl, heterocyclylalkyl, alkoxy, alkylsulfonyl, arylsulfonyl, alkylsulfonamido, arylsulfonamido, amino, amido, or carboxyl;

$R_{22}$ independently for each occurrence is halide or alkyl;

$R_{23}$ is selected from the group consisting of alkyl, hydroxyalkyl, alkoxyalkyl, acyloxyalkyl, and haloalkyl; and $R_{24}$ is selected from the group consisting of alkyl, hydroxyalkyl, alkoxyalkyl, acyloxyalkyl, and haloalkyl.

In certain embodiments, the present invention relates to the aforementioned compound and any of the attendant definitions, wherein $R_1$ is selected from the group consisting of —OH, —OC(O)Me, —OC(O)(CH$_2$)$_2$Ph, —OC(O)CH$_2$CHMe$_2$, —OC(O)NHMe, —OC(O)NMe$_2$, —OC(O)NHCH$_2$(4-(OH)-Ph), —OC(O)NHPh, —OC(O)NHCH$_2$Ph, —OC(O)NH(CH$_2$)$_4$Ph, —OC(O)NH(CH$_2$)$_2$Ph, —OC(O)NH(CH$_2$)$_2$Me, —OC(O)NH(CH$_2$)$_2$NMe$_2$, —OC(O)NH(CH$_2$)$_2$NHC(O)Me, —OC(O)NH(CH$_2$)$_2$CHMe$_2$, —NHMe, —NH(CH$_2$)$_2$Ph, —NHC(O)Me, and —NH(CH$_2$)$_2$NMe$_2$.

In certain embodiments, the present invention relates to the aforementioned compound and any of the attendant definitions, wherein $R_1$ is —OH.

In certain embodiments, the present invention relates to the aforementioned compound and any of the attendant definitions, wherein $R_2$ is —OH, —OC(O)Me, —OCH$_2$CO$_2$H, —OCH$_2$CO$_2$Et, —N$_3$, —N=C(NMe$_2$)$_2$, —NH$_2$, —NMe$_2$, —NHC(O)Me, —NHC(O)CF$_3$, —NHC(O)Ph, —NHC(O)NHPh, —NHC(O)CH$_2$CH$_2$CO$_2$H, —NHC(O)CH$_2$CH$_2$CO$_2$Me, —NHCH$_2$Ph, —NHCH$_2$(4-pyridyl), —NHCH$_2$(2-pyridyl), —NHCH$_2$(4-(CO$_2$H)Ph), —NHCH$_2$(3-(CO$_2$H)Ph), —NHEt, —NHCHMe$_2$, —NHCH$_2$CHMe$_2$, —N(CH$_2$CHMe$_2$)$_2$, —NHCH$_2$(cyclopropyl), or —NHC(O)CH$_2$CH$_2$NMe$_2$.

In certain embodiments, the present invention relates to the aforementioned compound and any of the attendant definitions, wherein $R_2$ is —OH or —NH$_2$.

In certain embodiments, the present invention relates to the aforementioned compound and any of the attendant definitions, wherein $R_2$ is —NH$_2$.

In certain embodiments, the present invention relates to the aforementioned compound and any of the attendant definitions, wherein $R_2$ is —OH.

In certain embodiments, the present invention relates to the aforementioned compound and any of the attendant definitions, wherein $R_3$ is —OMe, —OEt, —OCH$_2$(cyclopropyl), F, —O(CH$_2$)$_2$NMe$_2$, —O(CH$_2$)$_2$(4-morpholino), —OCH$_2$(4-(MeO)Ph), or —OCH$_2$(2-pyridyl).

In certain embodiments, the present invention relates to the aforementioned compound and any of the attendant definitions, wherein $R_3$ is —OMe.

In certain embodiments, the present invention relates to the aforementioned compound and any of the attendant definitions, wherein $R_4$ is —NMe$_2$, —NEt$_2$, —NHEt, —NHCH$_2$CHMe$_2$, —N(Me)CH$_2$CHMe$_2$, —N(Me)CH$_2$CH$_2$NHC(O)Me, —N(Me)CH$_2$CH$_2$NHS(O)$_2$Me, —N(Me)CH$_2$CH$_2$NHS(O)$_2$CF$_3$, —NHCH$_2$CH$_2$NMe$_2$, —NHCH$_2$CH$_2$NMeCH$_2$CH$_2$Cl, —NHCH$_2$CH$_2$OH, —N(Me)CH$_2$CH$_2$OH, —N(CH$_2$CH$_2$OH)$_2$, —N(Me)CH$_2$CO$_2$H, —N(Me)CH$_2$C(O)NH$_2$, —N(Me)CH$_2$C(O)NHMe, —N(Me)CH$_2$C(O)NMe$_2$, —NHC(O)Me, —NHC(O)CHMe$_2$, 1-pyrrolidinyl, 1-piperidinyl, 4-morpholino, (R)-2-(hydroxymethyl)-1-pyrrolidinyl, (S)-2-(hydroxymethyl)-1-pyrrolidinyl, (R)-2-(C(O)NMe$_2$)-1-pyrrolidinyl, (S)-2-(C(O)NMe$_2$)-1-pyrrolidinyl, —NH$_2$, —NO$_2$, Br, Cl, F, —C(O)Me, —C(O)NMe$_2$, —C(O)NH$_2$, —CO$_2$H, —CHO, —CH$_2$OH, —CH(Me)OH, —CH$_2$NH$_2$, —CH$_2$NHMe, —CH$_2$NMe$_2$, —CH$_2$NHC(O)Me, —CF$_3$, or tert-butyl.

In certain embodiments, the present invention relates to the aforementioned compound and any of the attendant definitions, wherein $R_4$ is amino.

In certain embodiments, the present invention relates to the aforementioned compound and any of the attendant definitions, wherein $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In certain embodiments, the present invention relates to the aforementioned compound and any of the attendant definitions, wherein $R_4$ is —NMe$_2$.

In certain embodiments, the present invention relates to the aforementioned compound and any of the attendant definitions, wherein $R_{22}$ is selected from the group consisting of F, Cl, and tert-butyl; and m is 0 or 1.

In certain embodiments, the present invention relates to the aforementioned compound and any of the attendant definitions, wherein $R_{22}$ is F; and m is 0 or 1.

In certain embodiments, the present invention relates to the aforementioned compound and any of the attendant definitions, wherein $R_{22}$ is selected from the group consisting of F, Cl, and tert-butyl; and m is 1.

In certain embodiments, the present invention relates to the aforementioned compound and any of the attendant definitions, wherein $R_{22}$ is F; and m is 1.

In certain embodiments, the present invention relates to the aforementioned compound and any of the attendant definitions, wherein $R_{23}$ is selected from the group consisting of methyl, hydroxymethyl, alkoxymethyl, acyloxymethyl, and halomethyl.

In certain embodiments, the present invention relates to the aforementioned compound and any of the attendant definitions, wherein $R_{24}$ is selected from the group consisting of methyl, hydroxymethyl, alkoxymethyl, acyloxymethyl, and halomethyl.

In certain embodiments, the present invention relates to the aforementioned compound and any of the attendant definitions, wherein R$_{23}$ is methyl.

In certain embodiments, the present invention relates to the aforementioned compound and any of the attendant definitions, wherein R$_{24}$ is methyl.

In certain embodiments, the present invention relates to the aforementioned compound and any of the attendant definitions, wherein R$_{23}$ is methyl; and R$_{24}$ is methyl.

In certain embodiments, the present invention relates to the aforementioned compound and any of the attendant definitions, wherein R$_1$ is —OH; and R$_2$ is —OH or —NH$_2$.

In certain embodiments, the present invention relates to the aforementioned compound and any of the attendant definitions, wherein R$_1$ is —OH; R$_2$ is —OH or —NH$_2$; and R$_3$ is —OMe.

In certain embodiments, the present invention relates to the aforementioned compound and any of the attendant definitions, wherein R$_1$ is —OH; R$_2$ is —OH or —NH$_2$; R$_3$ is —OMe; and R$_4$ is amino.

In certain embodiments, the present invention relates to the aforementioned compound and any of the attendant definitions, wherein R$_1$ is —OH; R$_2$ is —OH or —NH$_2$; R$_3$ is —OMe; and R$_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

In certain embodiments, the present invention relates to the aforementioned compound and any of the attendant definitions, wherein R$_1$ is —OH; R$_2$ is —OH or —NH$_2$; R$_3$ is —OMe; and R$_4$ is —NMe$_2$.

In certain embodiments, the present invention relates to the aforementioned compound and any of the attendant definitions, wherein R$_1$ is —OH; R$_2$ is —OH or —NH$_2$; R$_{23}$ is methyl; and R$_{24}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_{23}$ is methyl; and R$_{24}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_4$ is amino; R$_{23}$ is methyl; and R$_{24}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl; R$_{23}$ is methyl; and R$_{24}$ is methyl.

In certain embodiments, the present invention relates to the aforementioned compound and any of the attendant definitions, wherein R$_1$ is —OH; R$_2$ is —OH or —NH$_2$; R$_3$ is —OMe; R$_4$ is —NMe$_2$; R$_{23}$ is methyl; and R$_{24}$ is methyl.

In another embodiment, the present invention relates to a compound selected from the group consisting of:

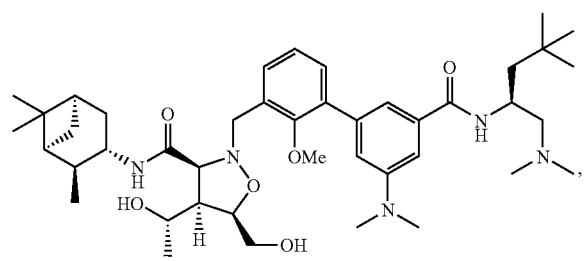

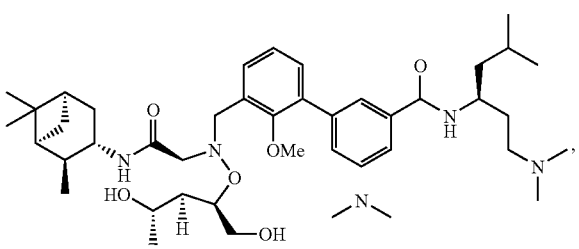

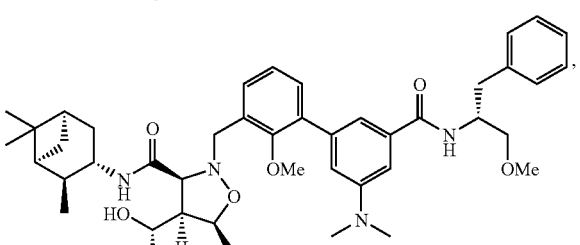

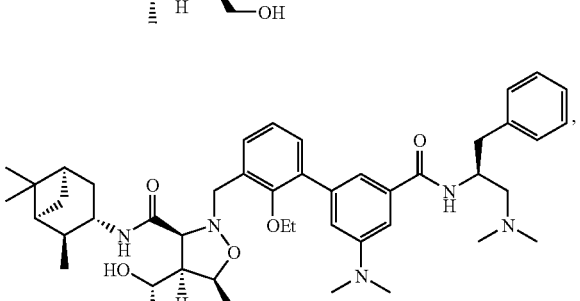

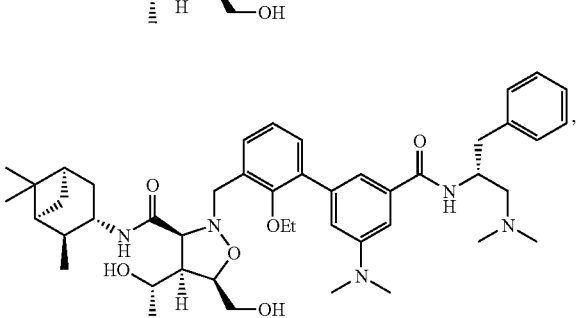

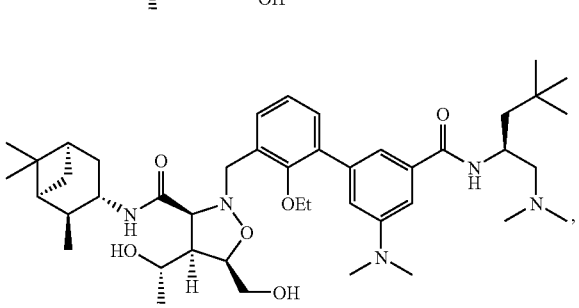

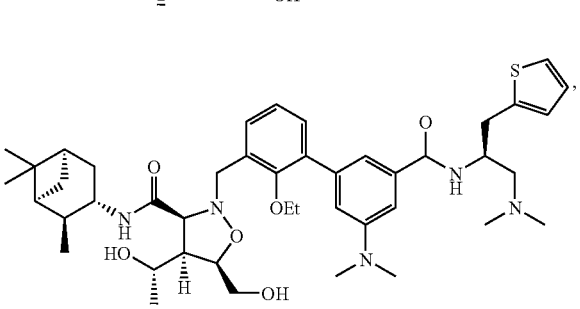

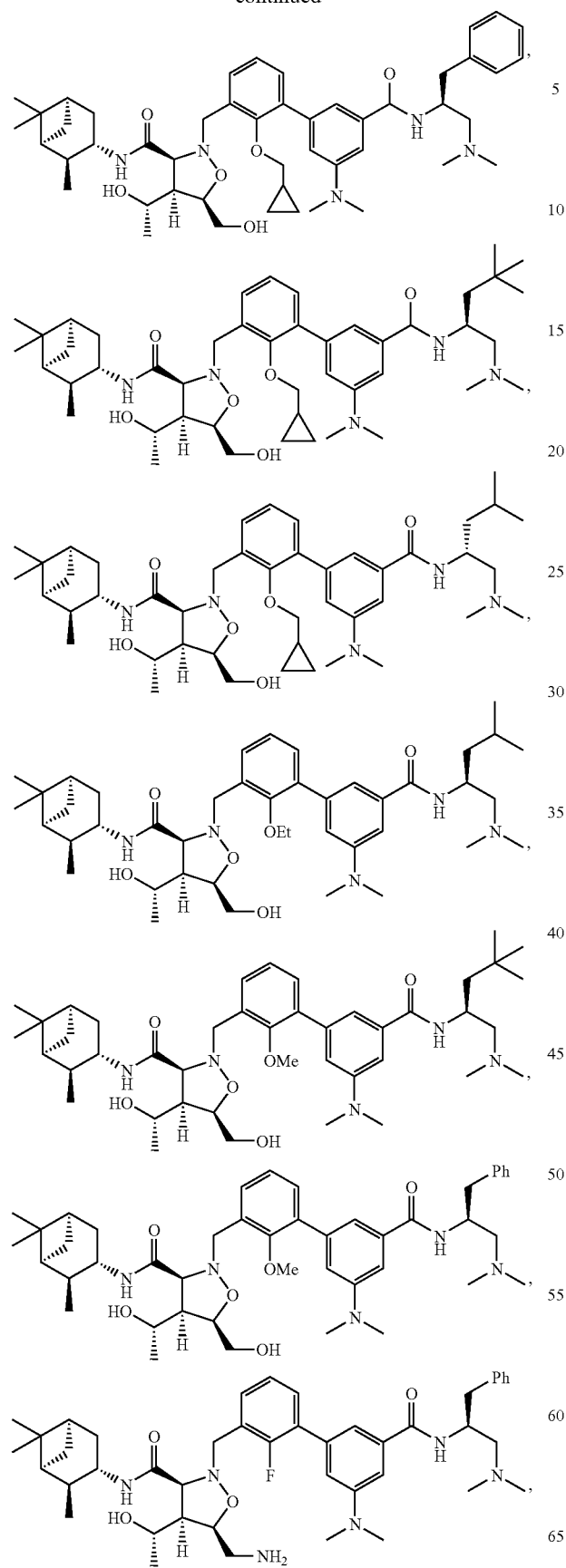
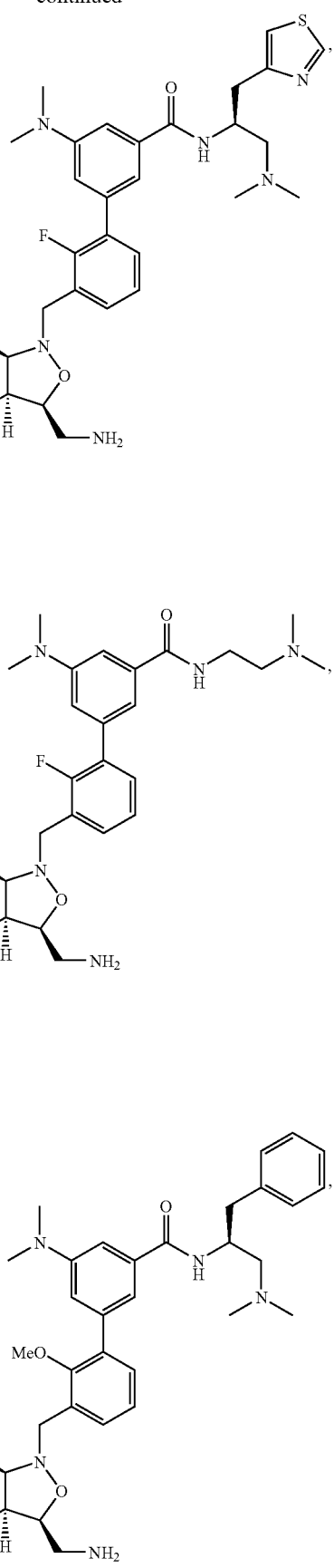

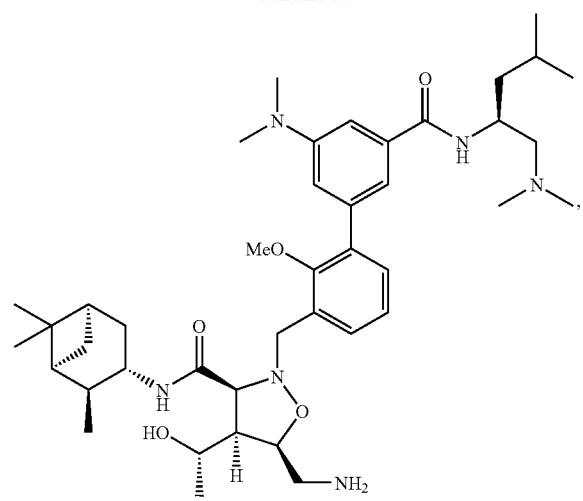
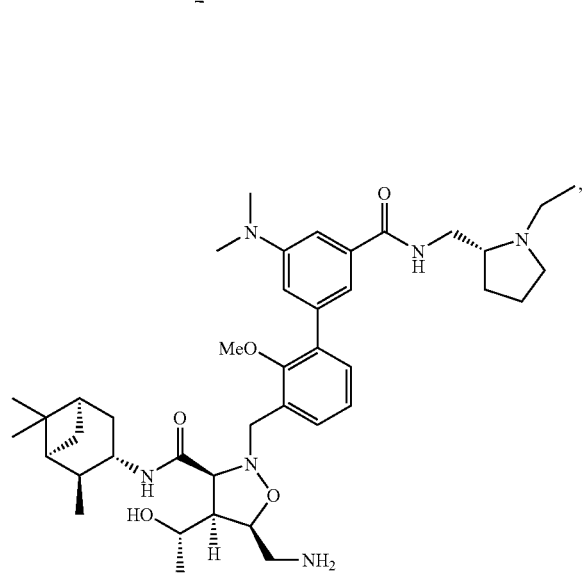

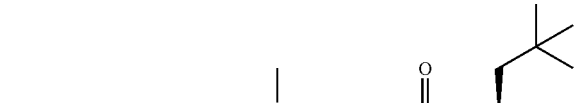
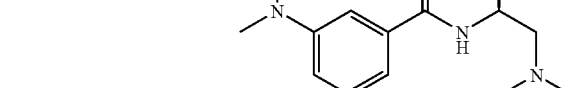
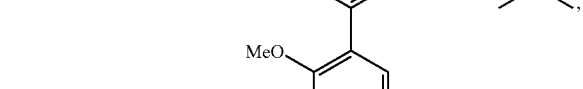
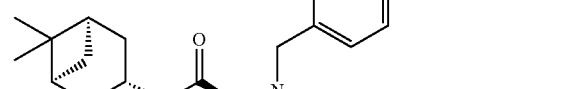
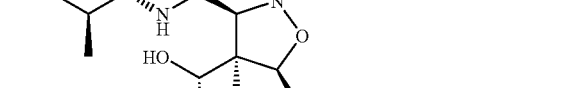
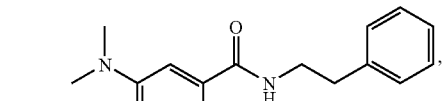
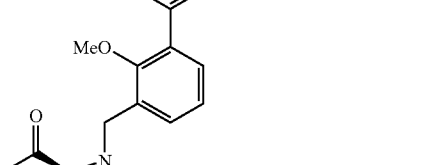
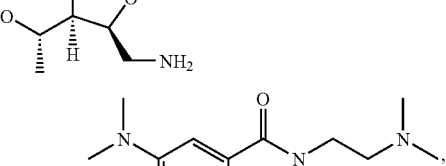
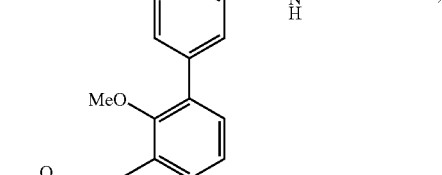
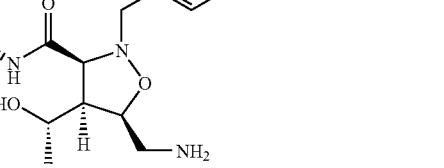
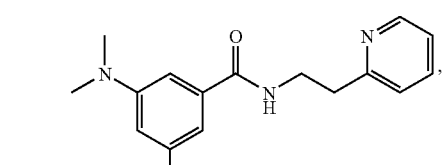
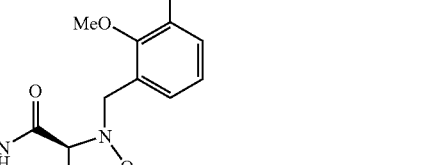
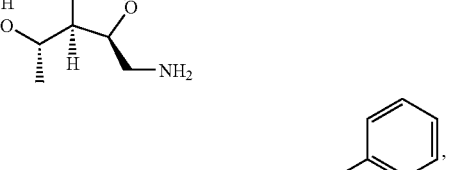
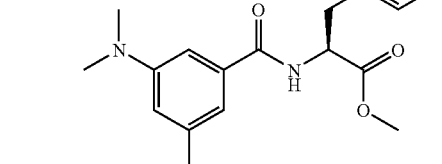
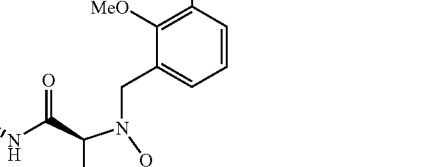
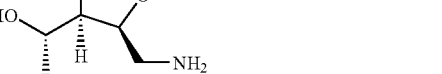

17
-continued
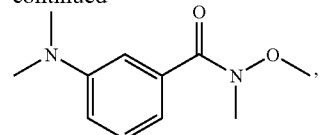
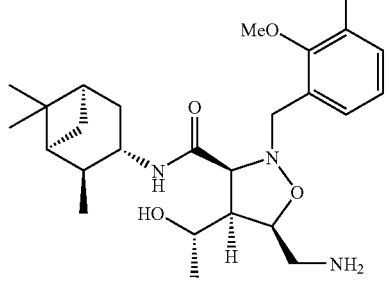
18
-continued
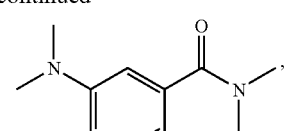
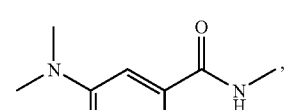
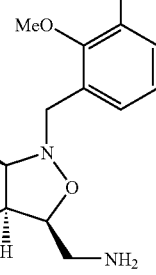
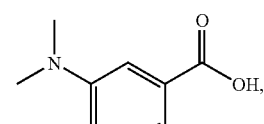
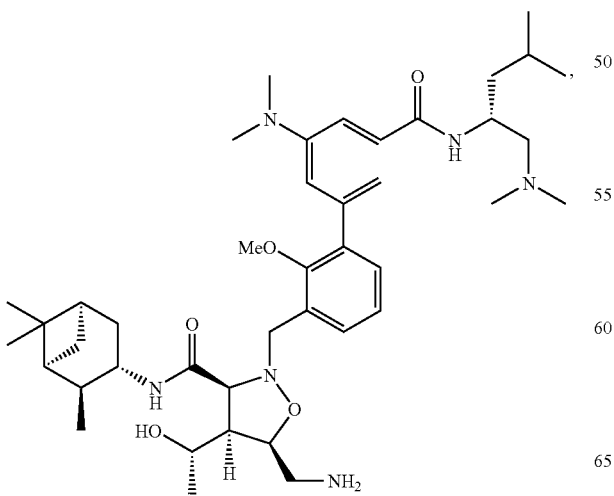
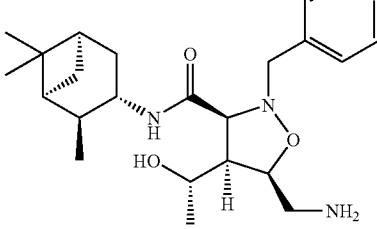

19
-continued
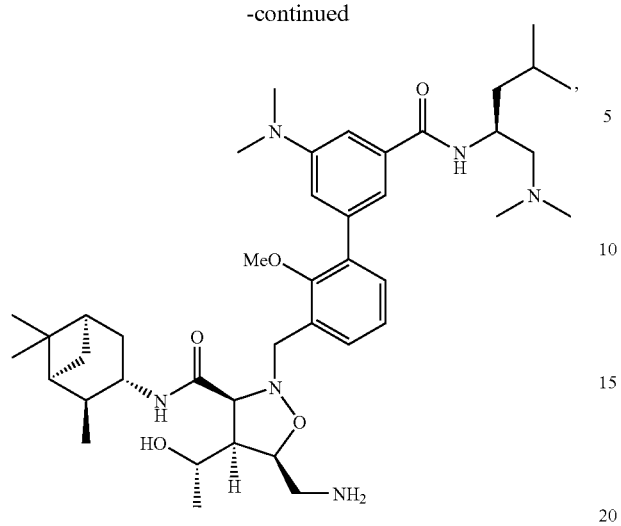
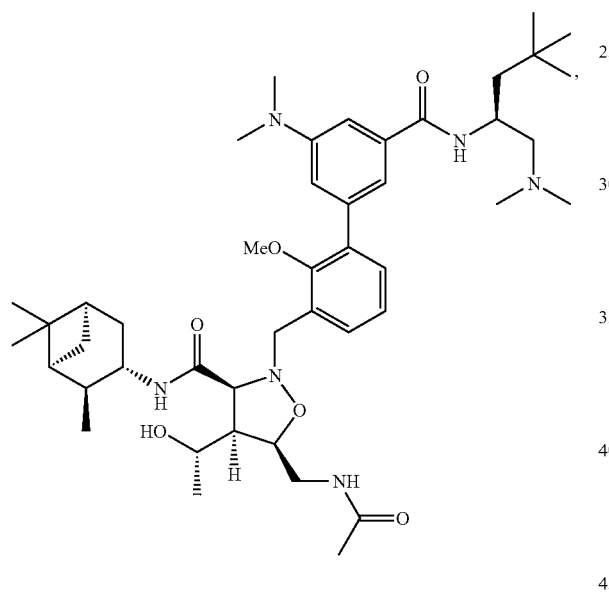
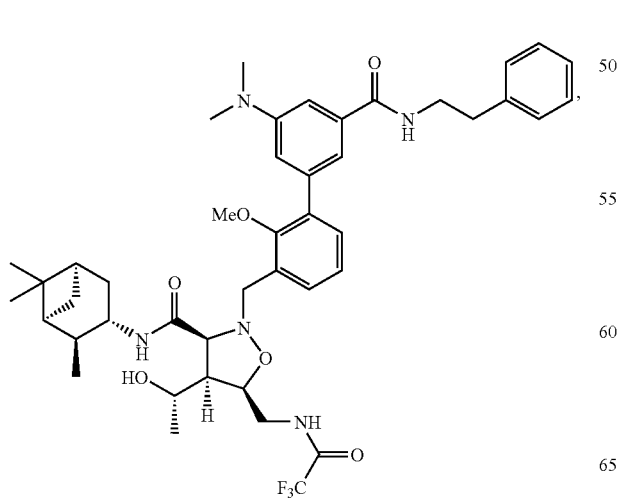
20
-continued
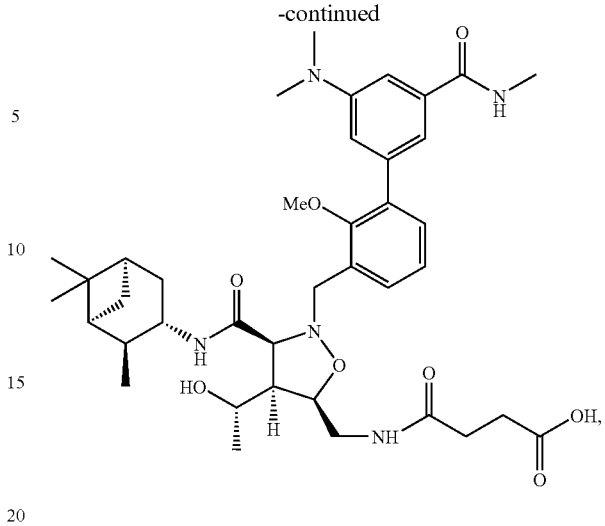
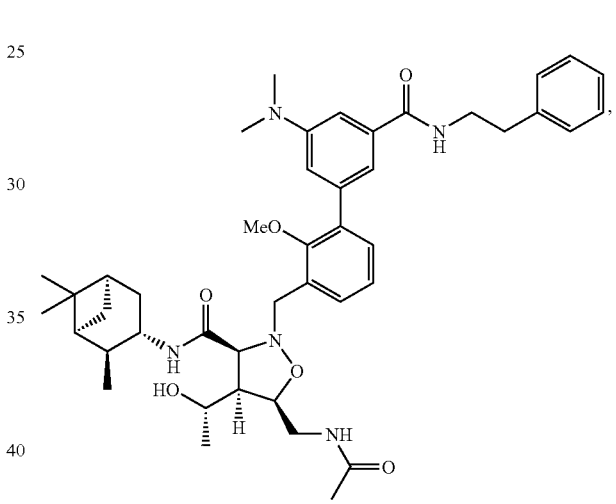
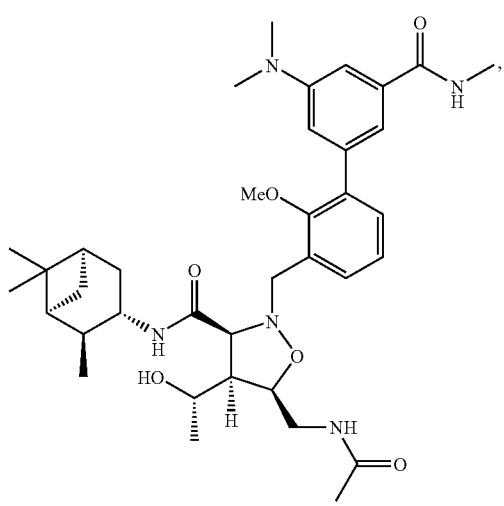

21
-continued
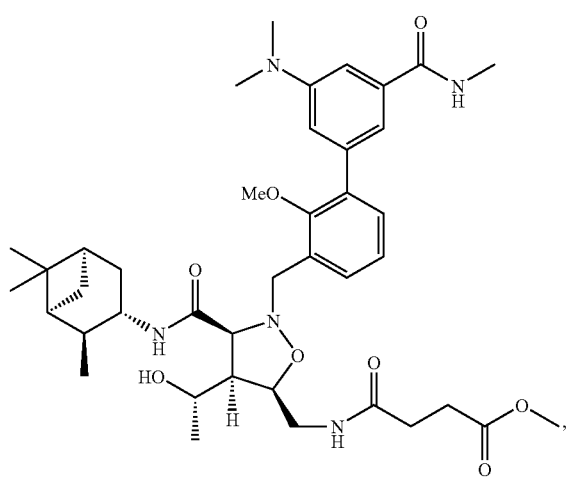
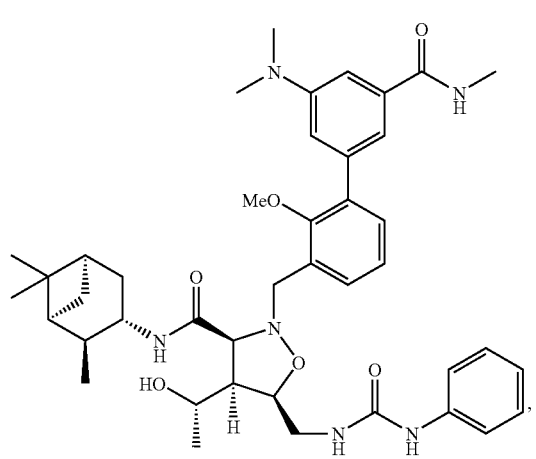
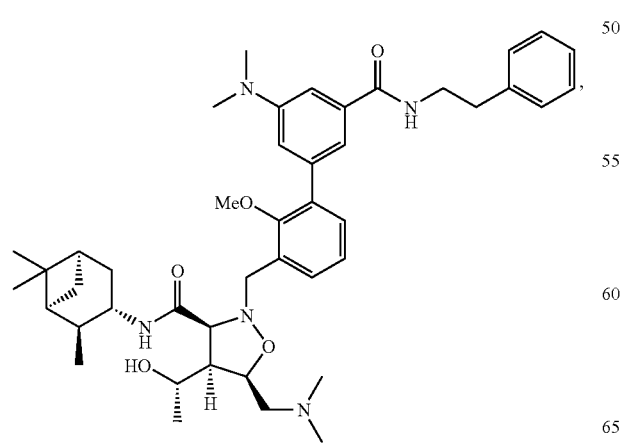
22
-continued
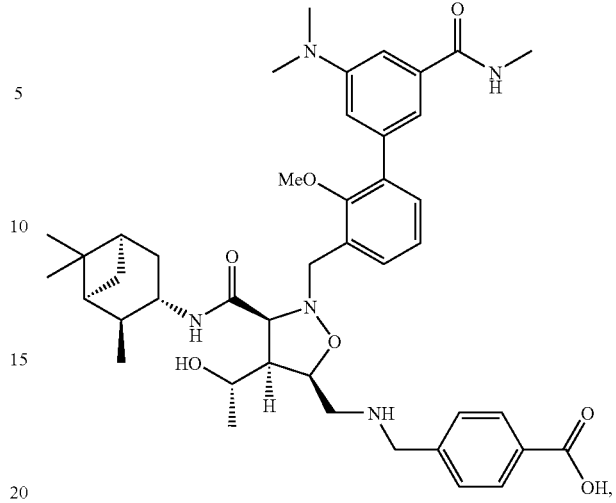
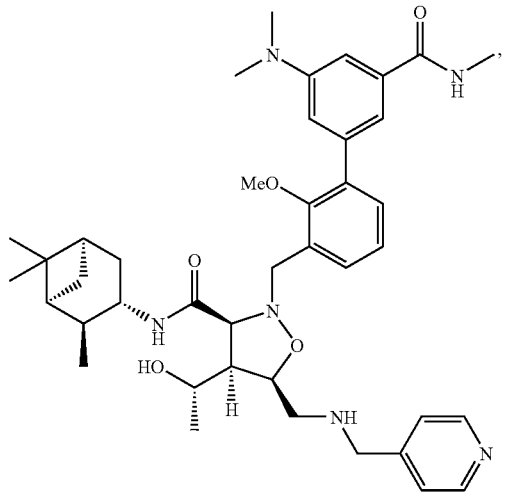
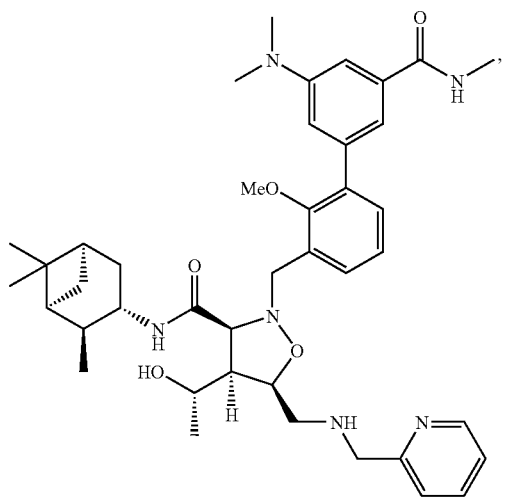

23
-continued
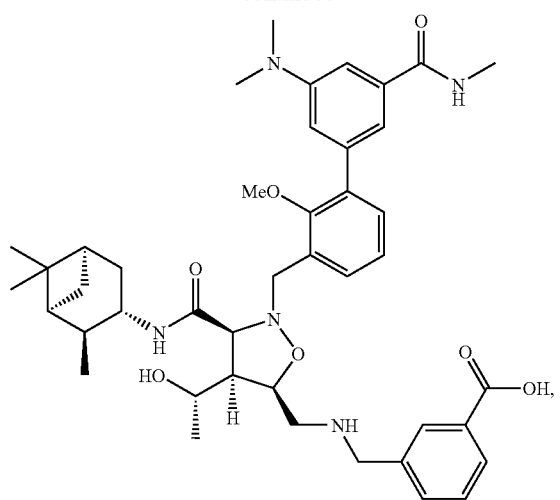
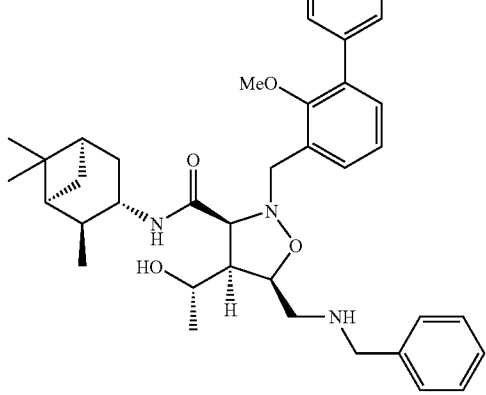
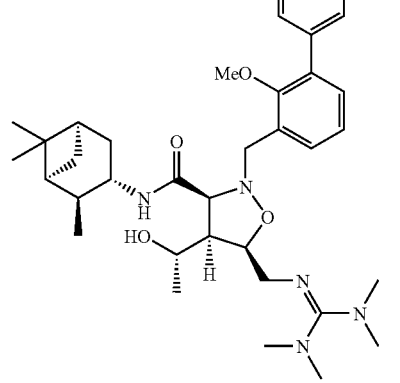
24
-continued
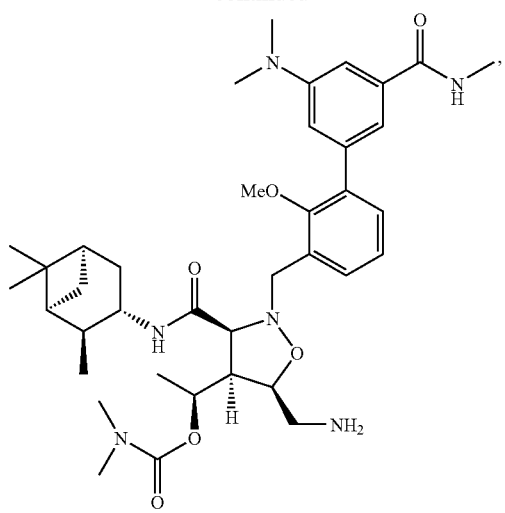
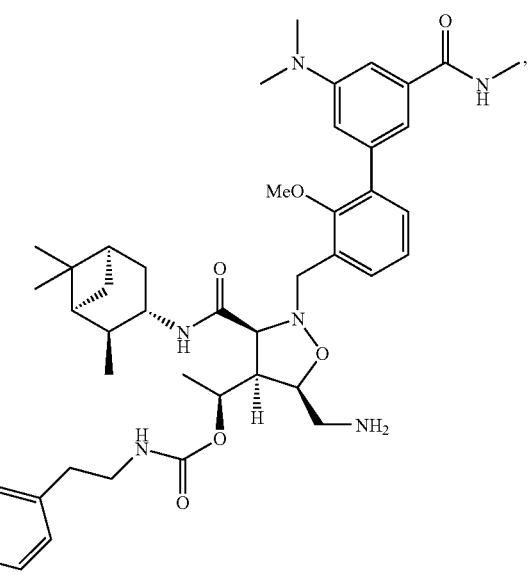
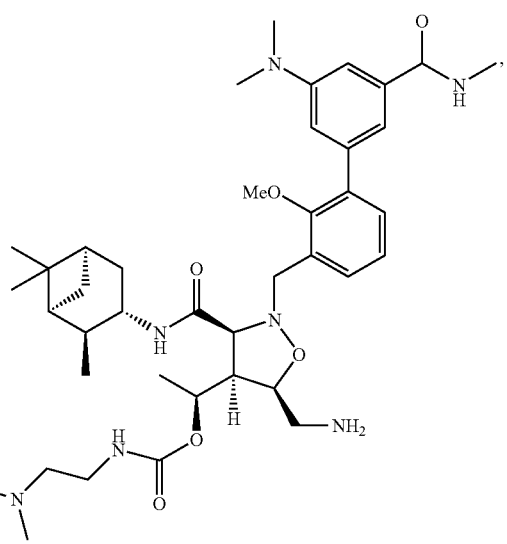

25
-continued
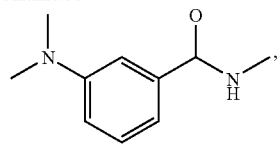
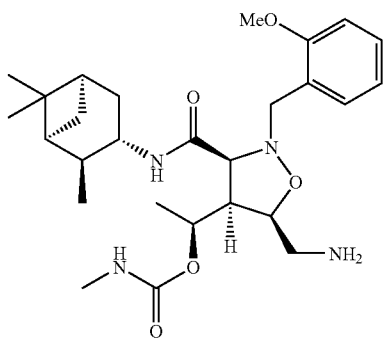
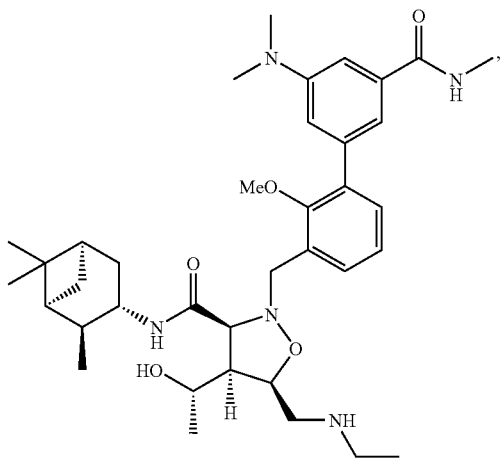
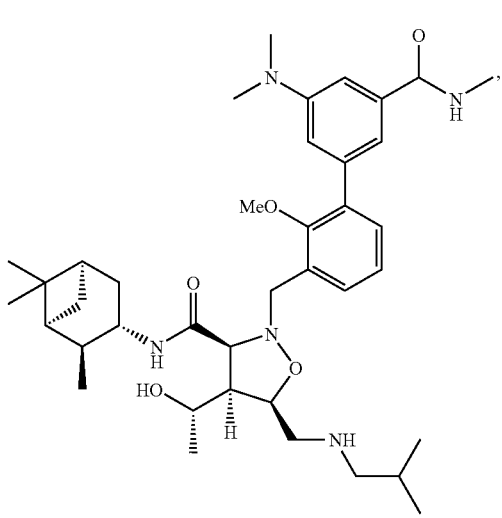
26
-continued
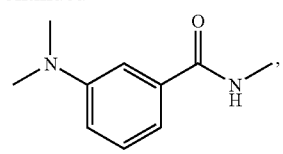
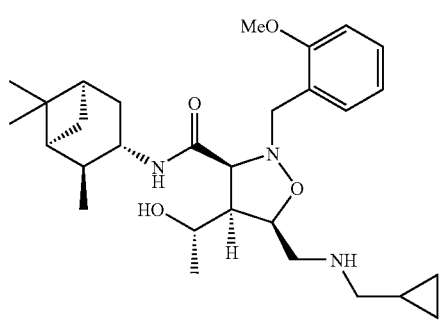
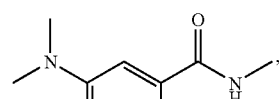
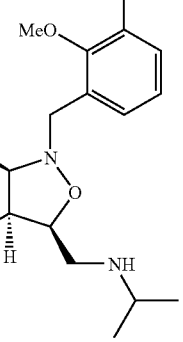
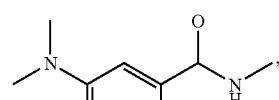
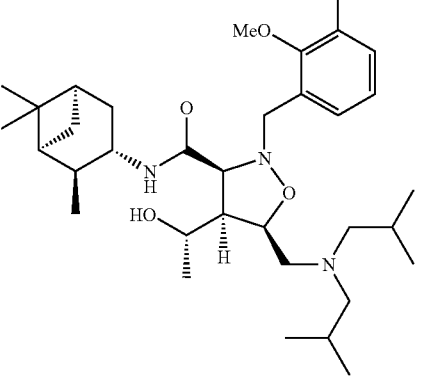

27
-continued
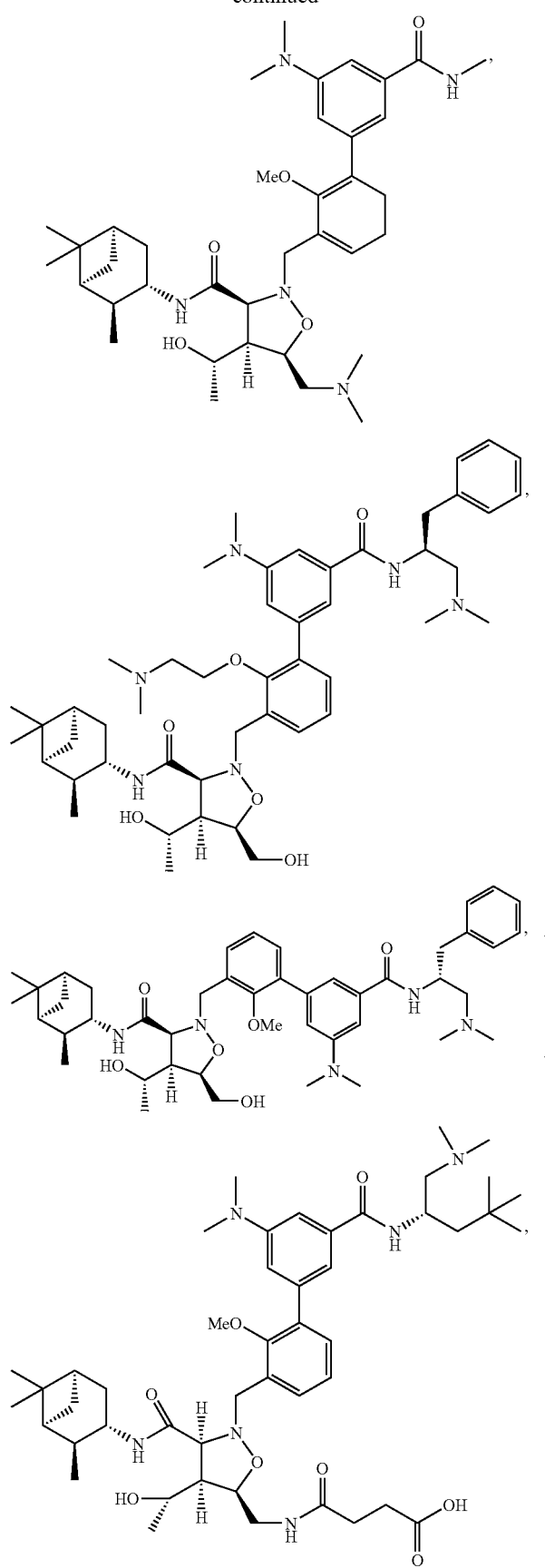
28
-continued
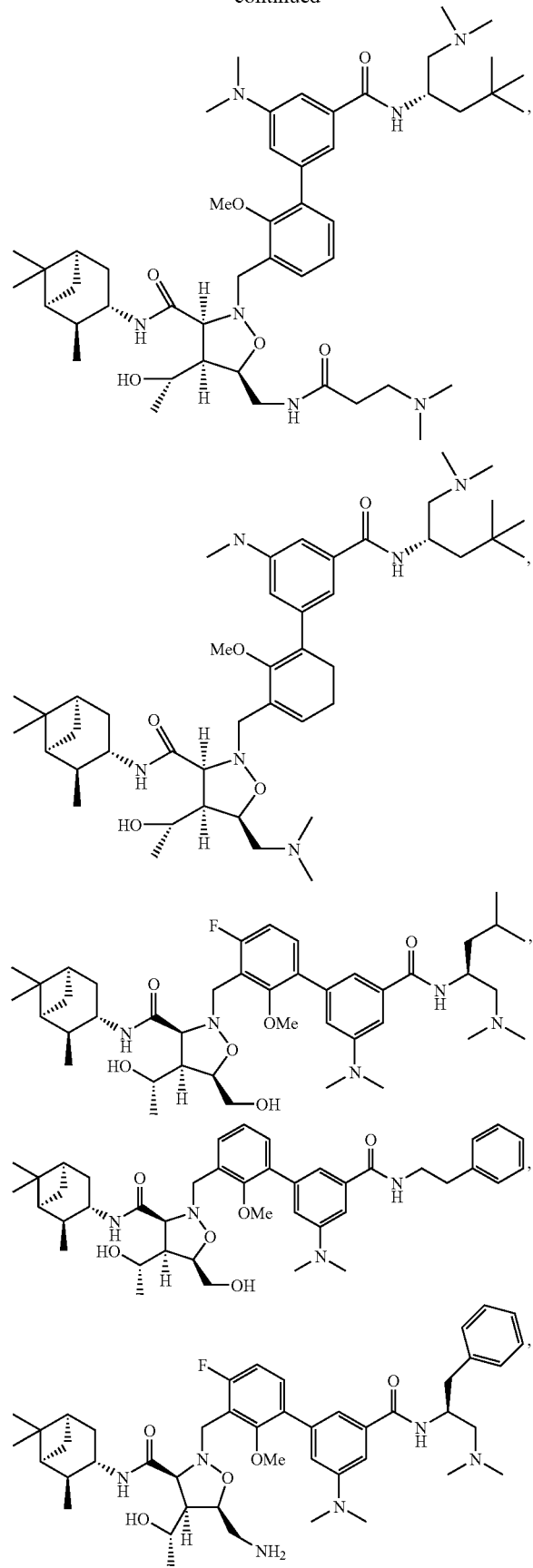

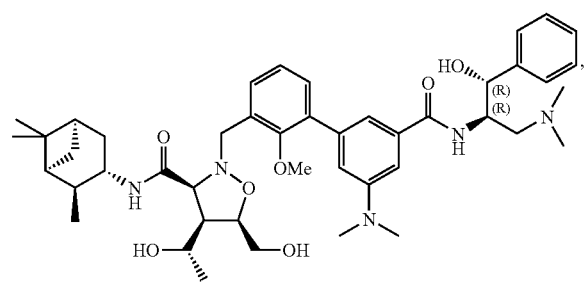
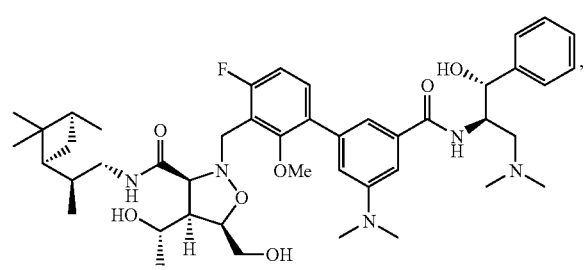
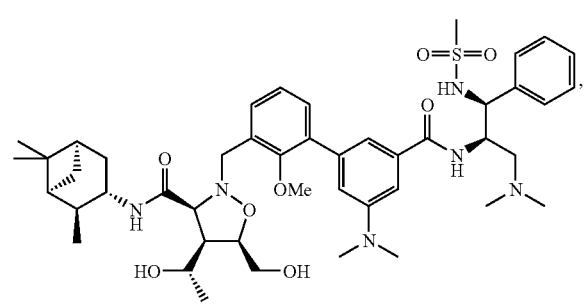
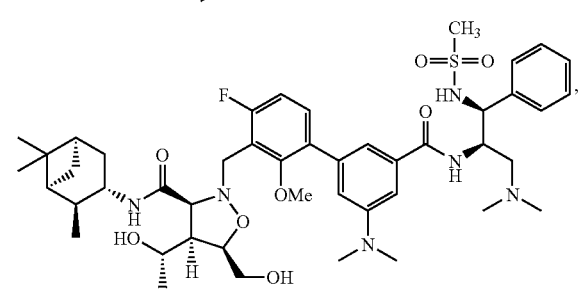
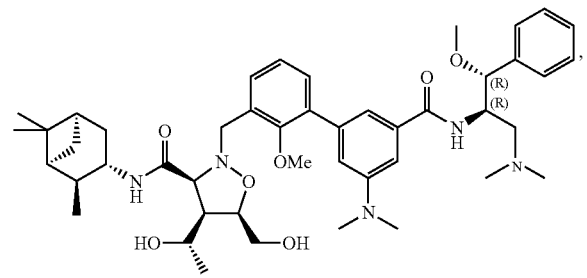
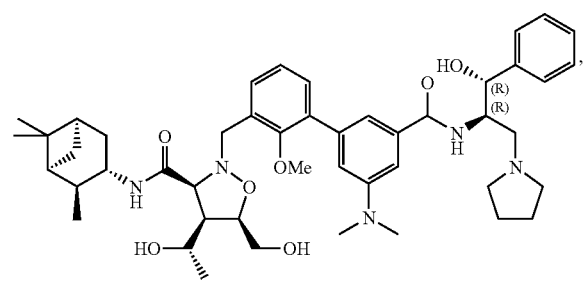
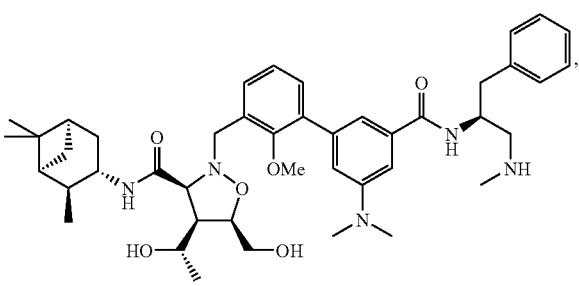
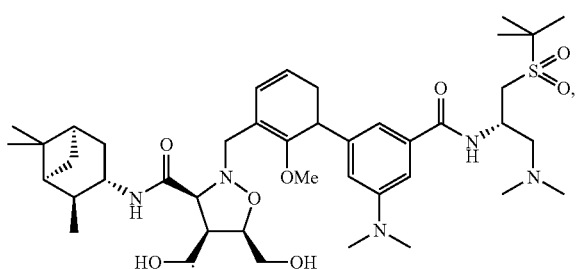
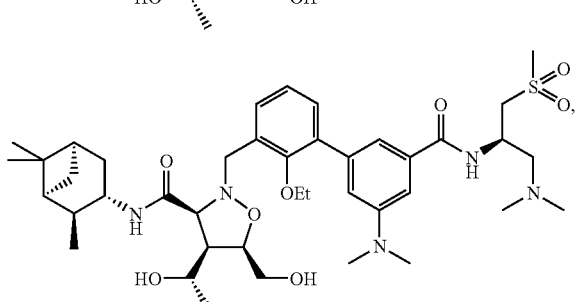
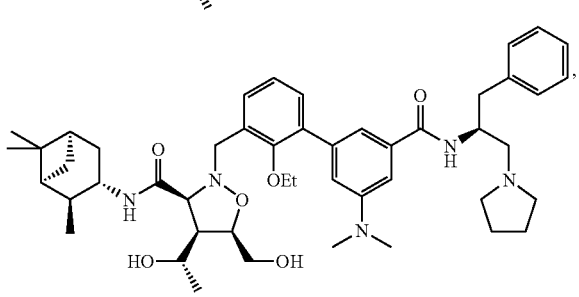
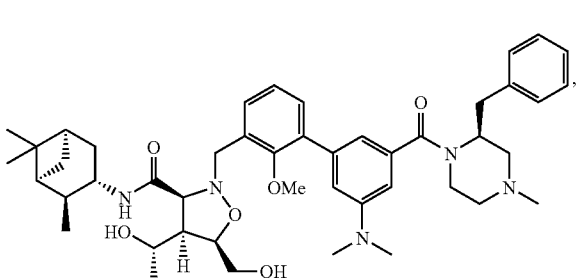

31
-continued
32
-continued
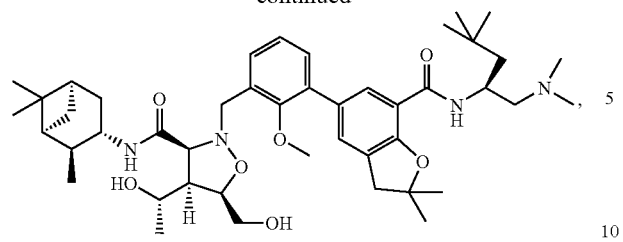
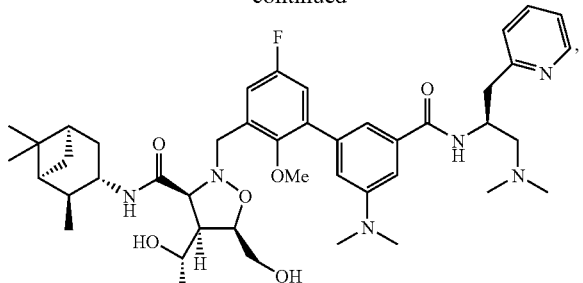
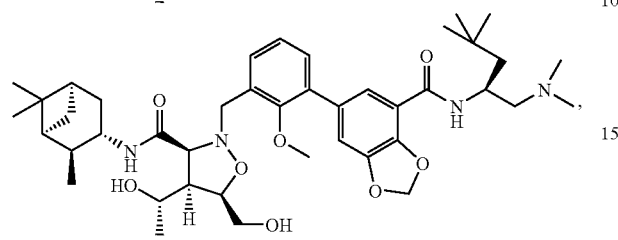
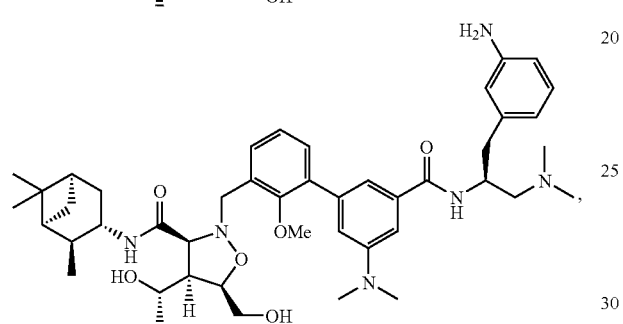
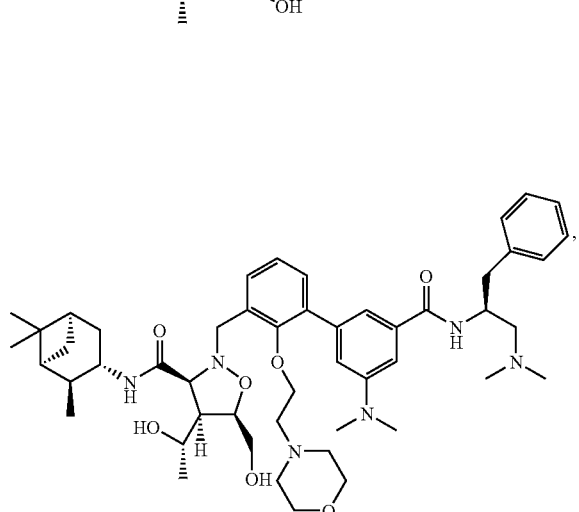
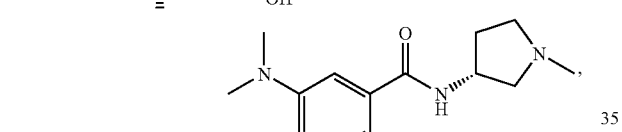
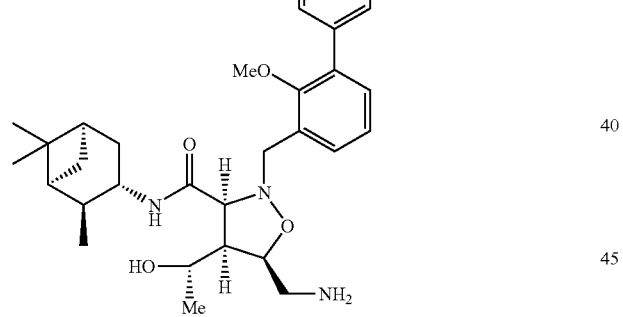
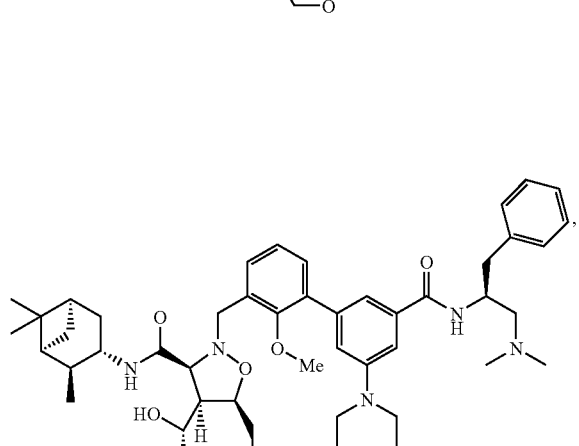
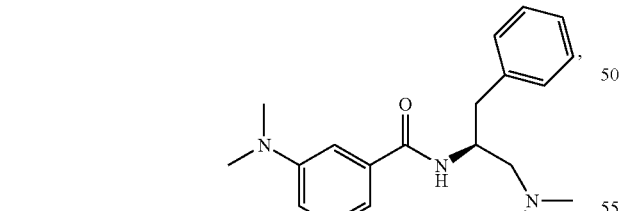
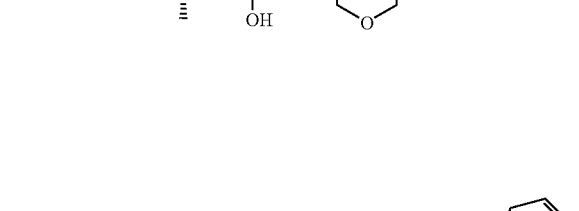
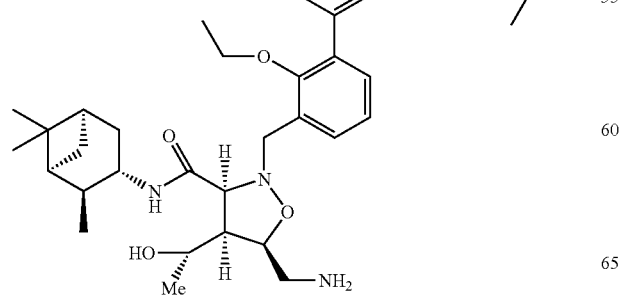
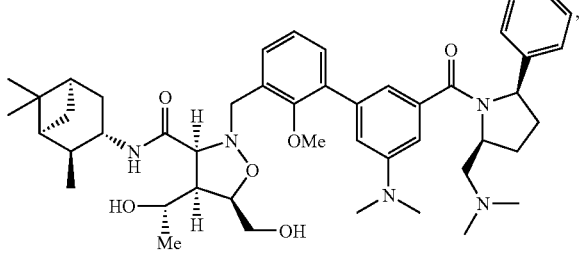

33
-continued
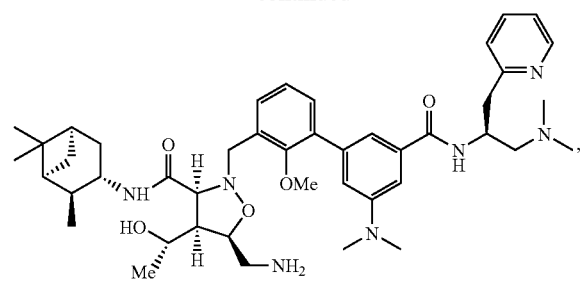
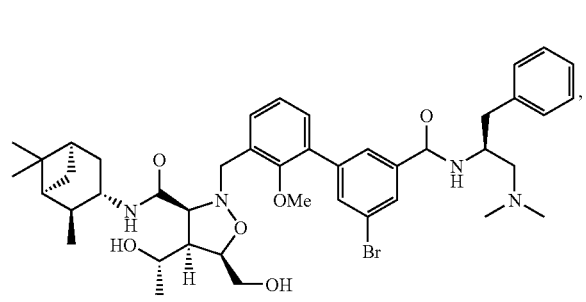
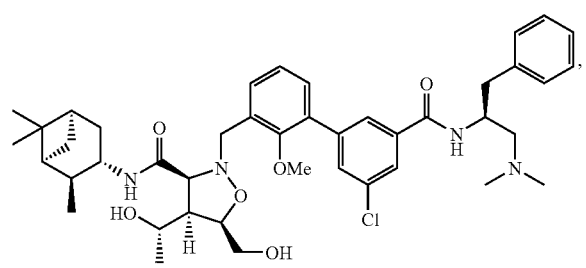
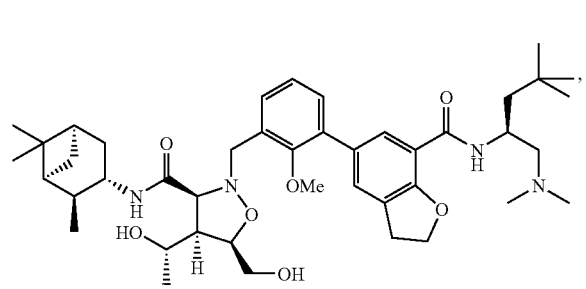
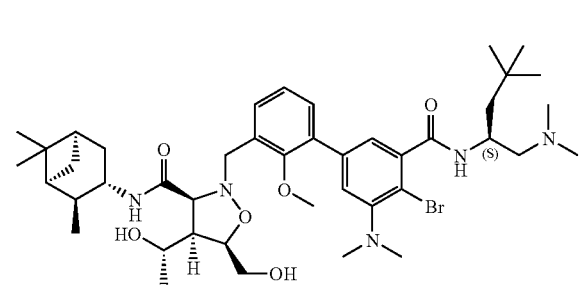
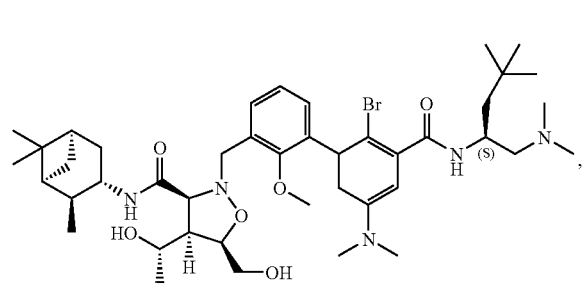
34
-continued
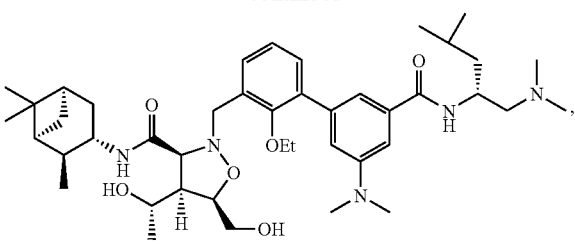
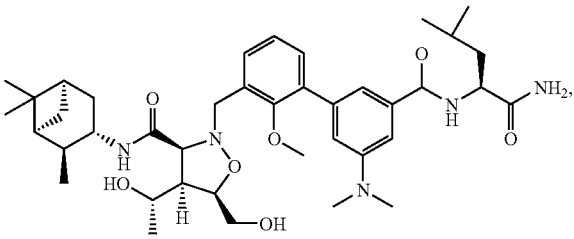
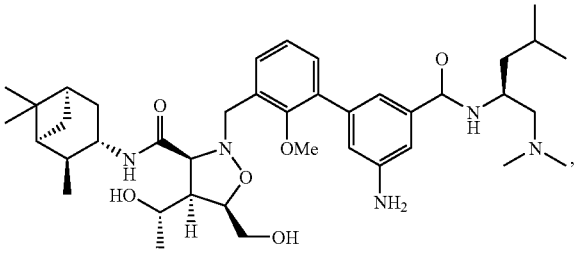
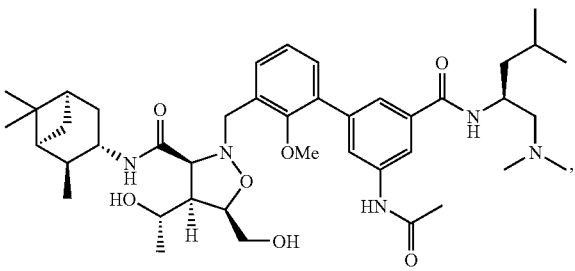
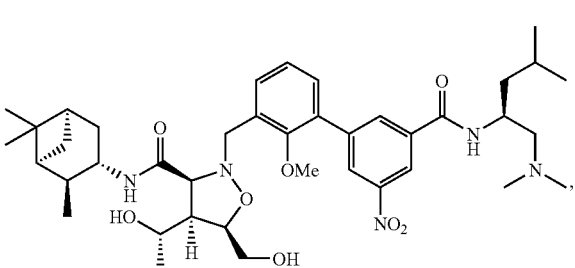
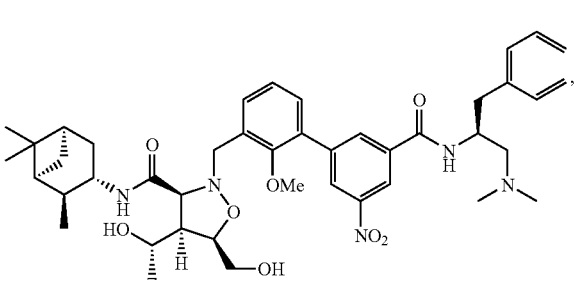

35
-continued
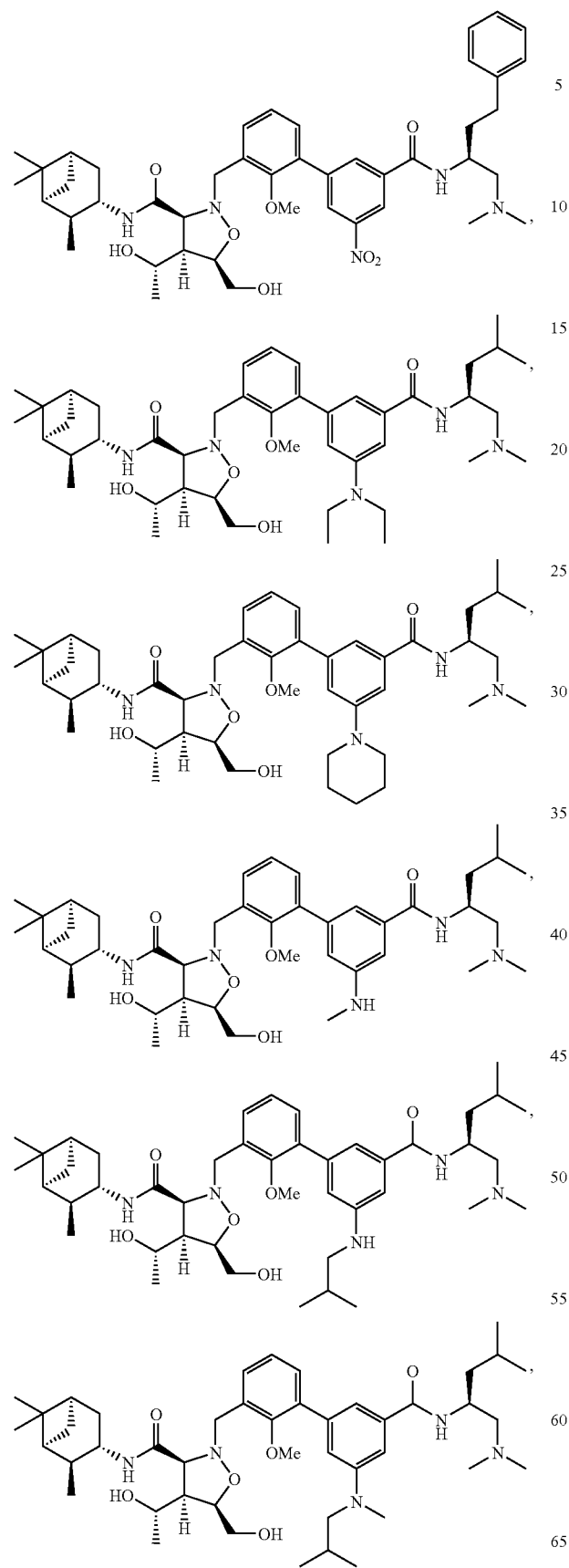
36
-continued
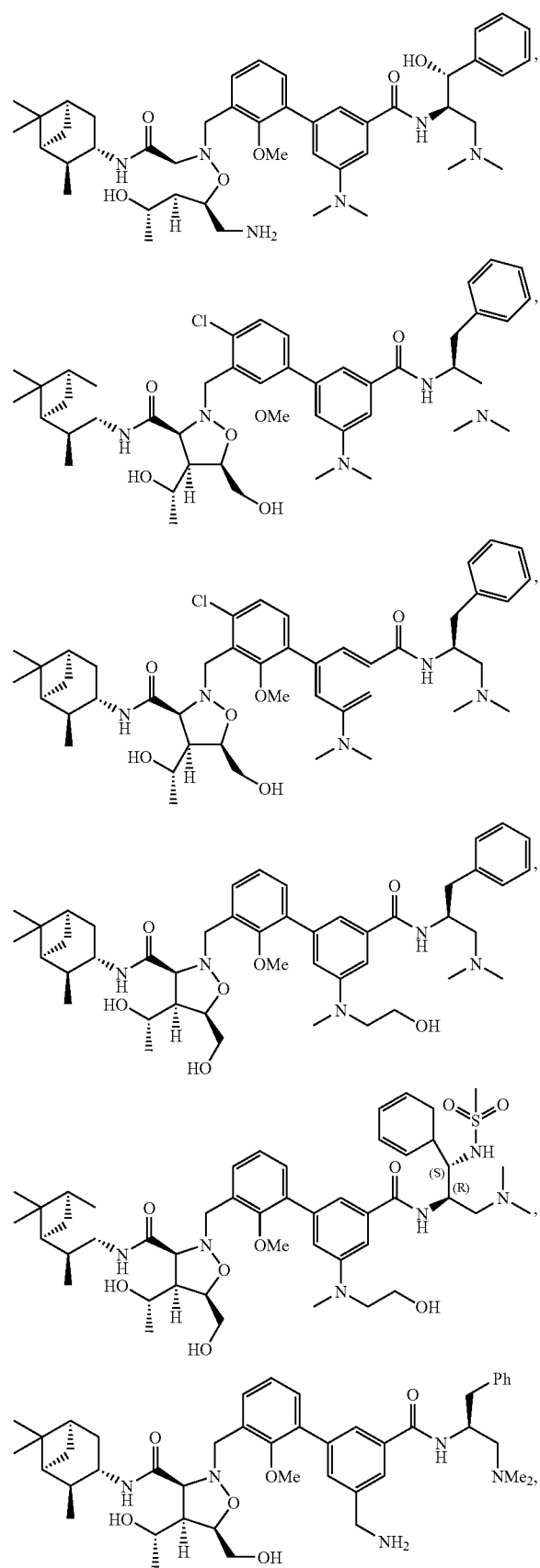

37
-continued
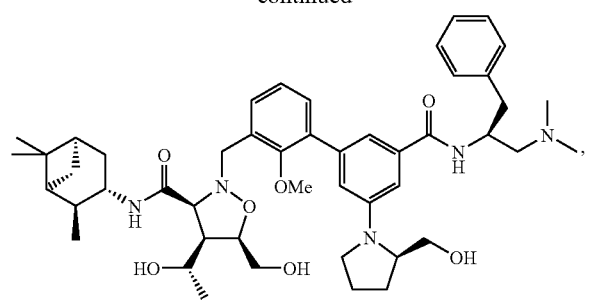
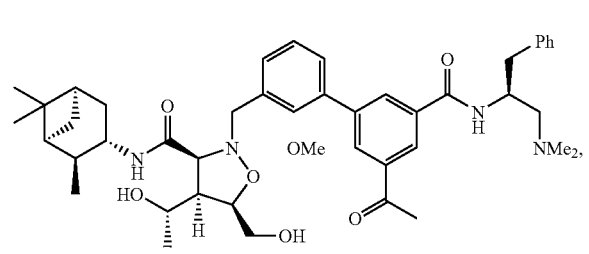
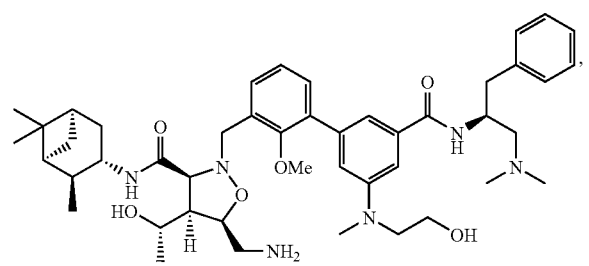
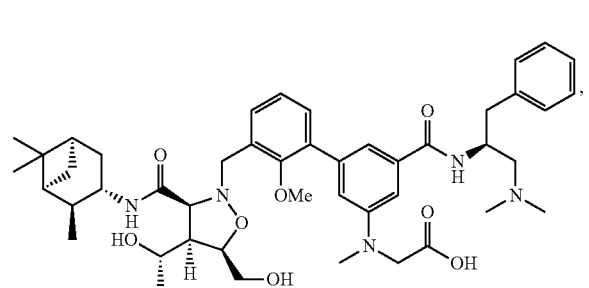
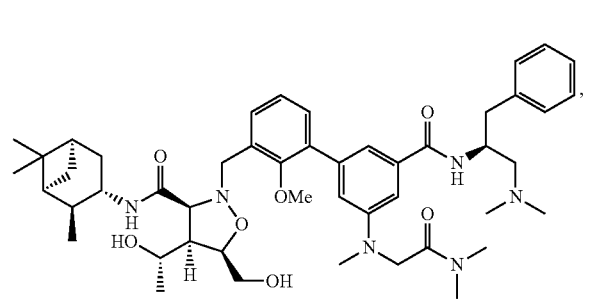
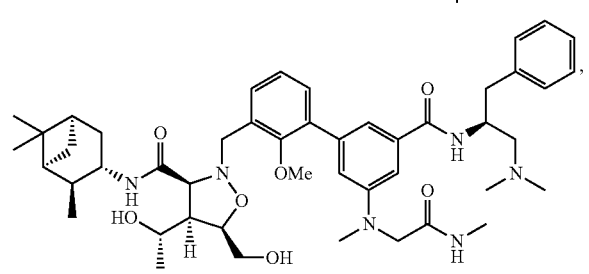
38
-continued
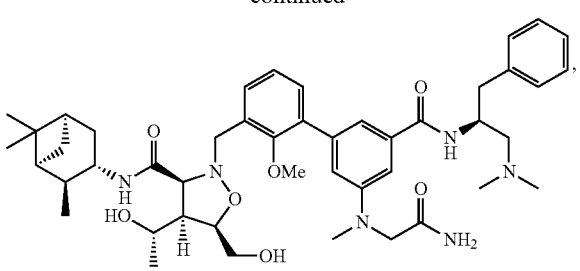
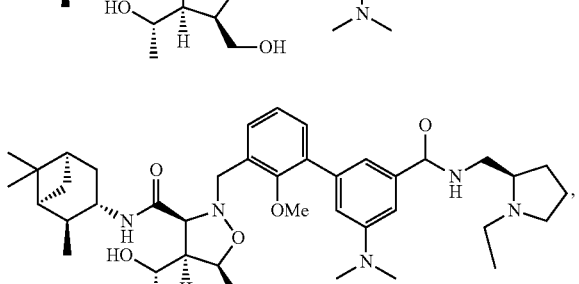
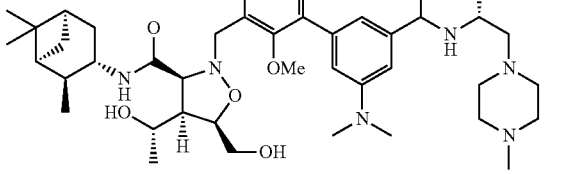
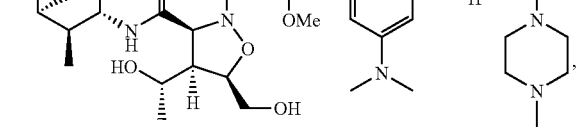
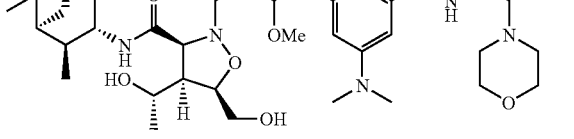

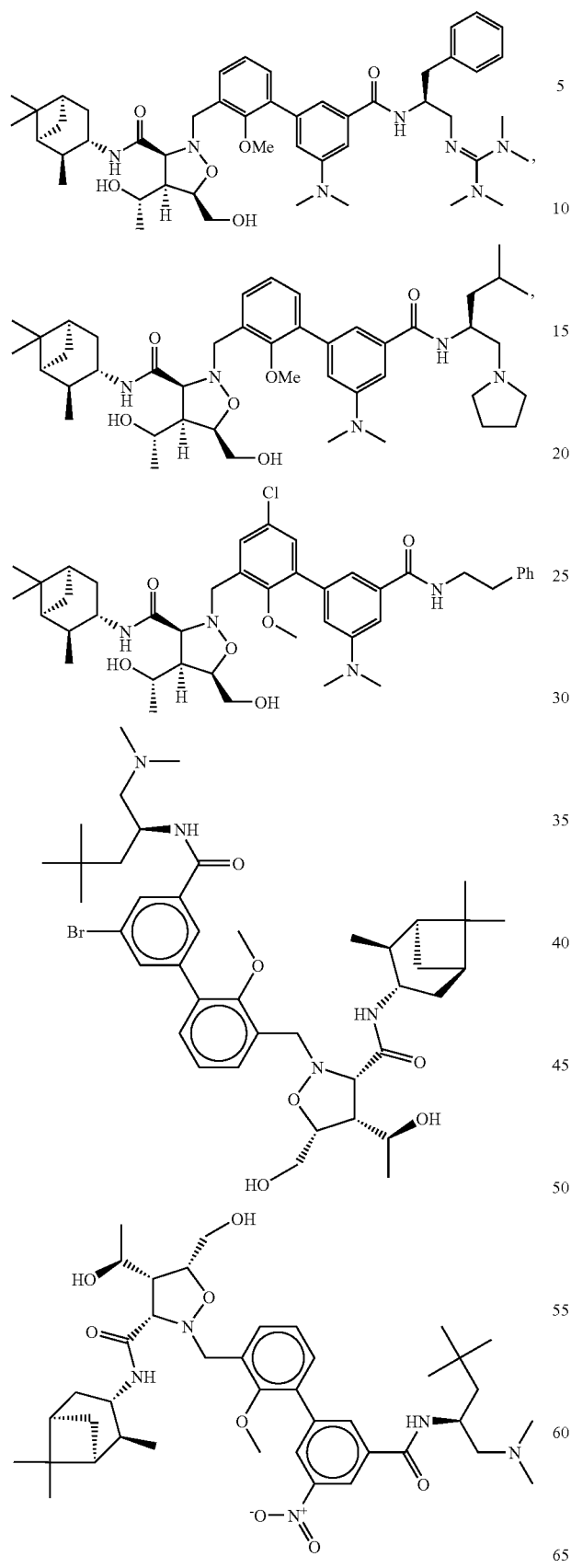
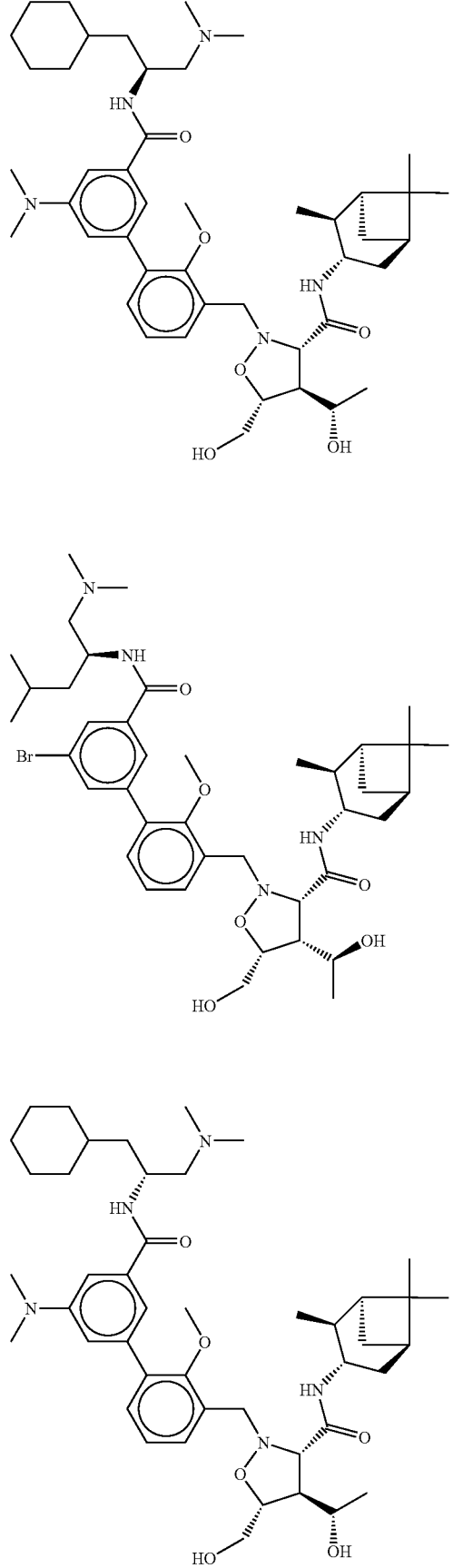

41
-continued
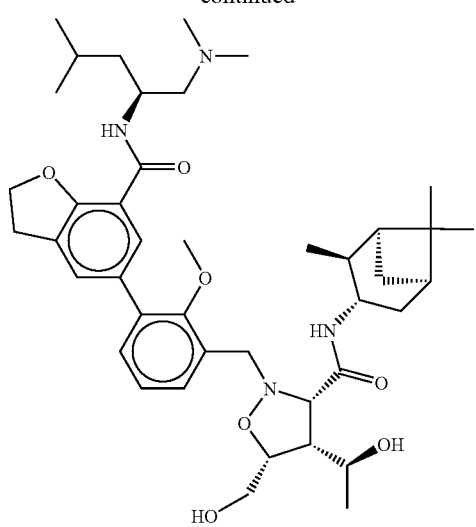
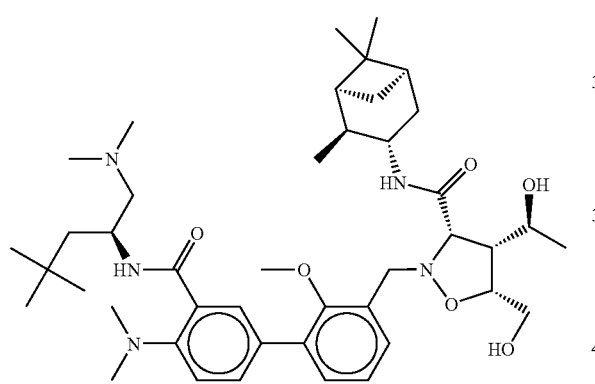
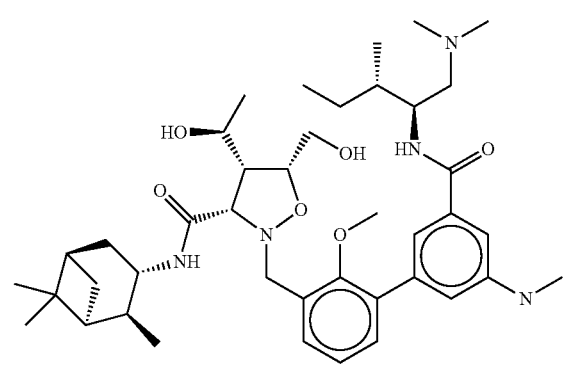
42
-continued
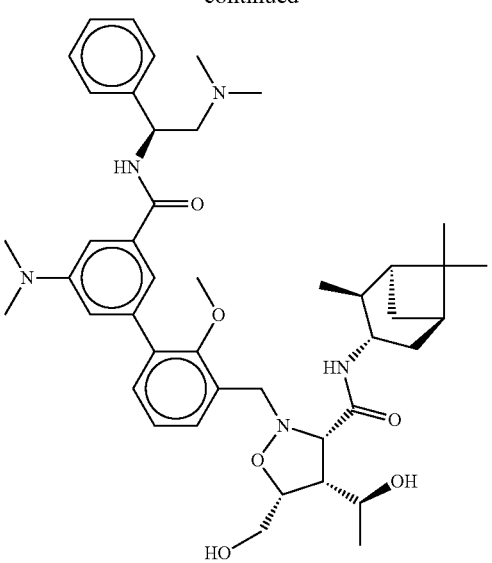
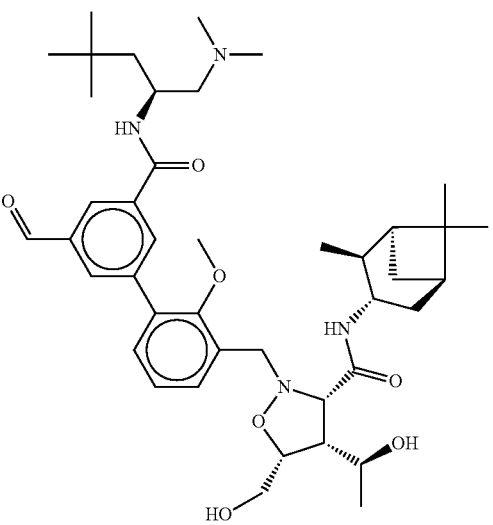
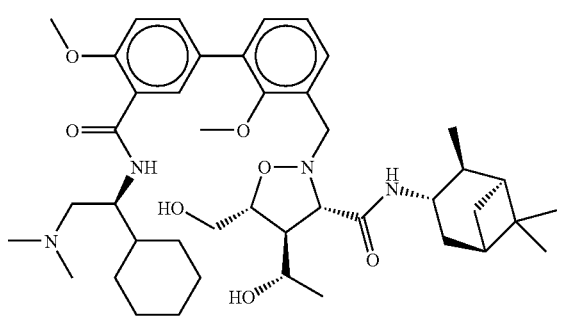

43
-continued
44
-continued
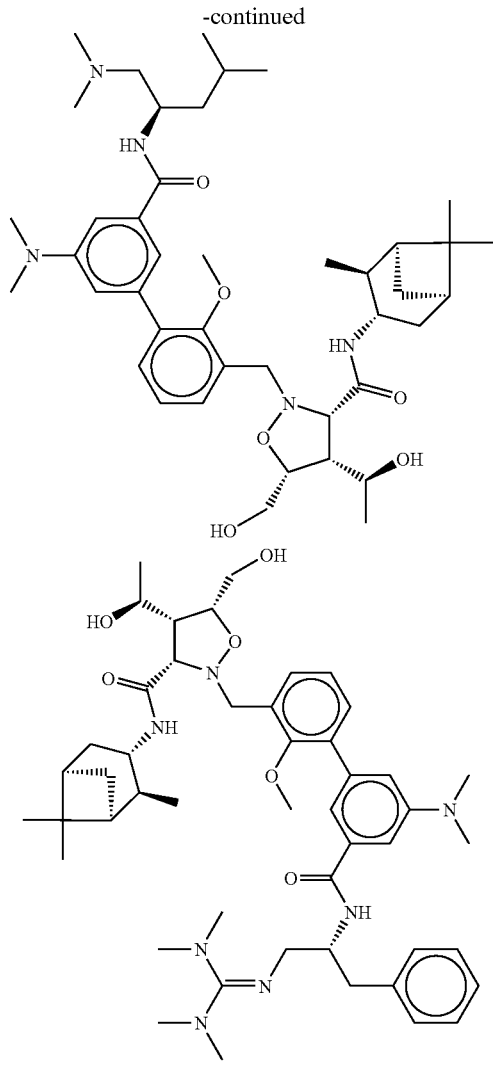
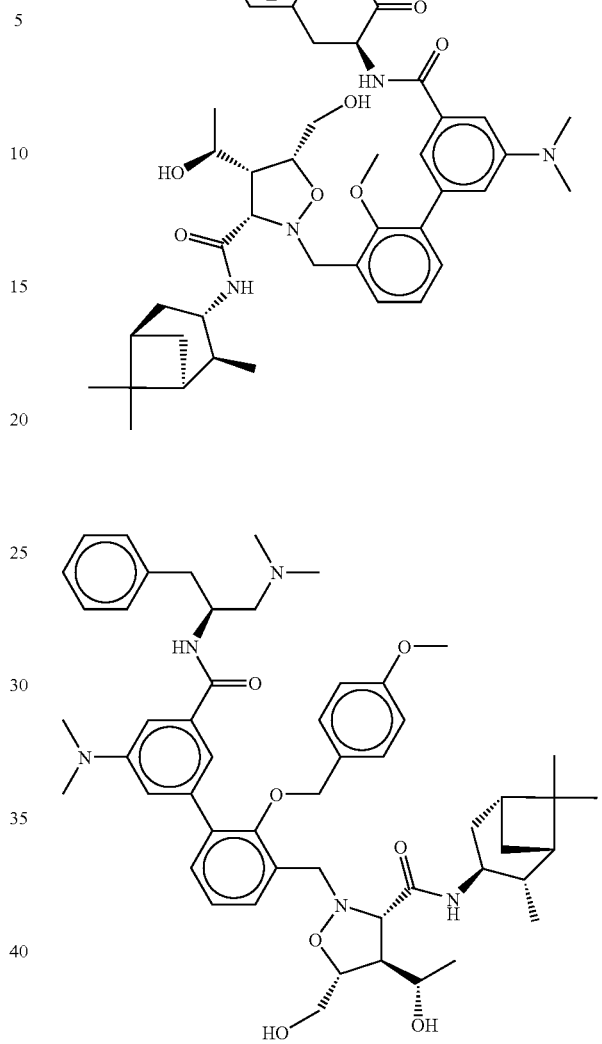
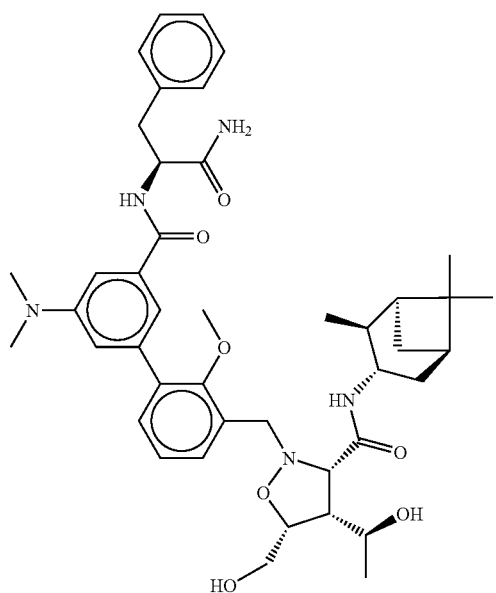
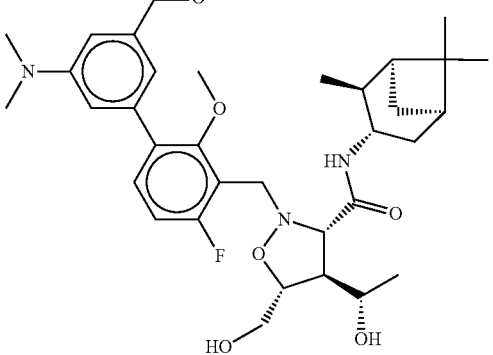

45 46
-continued -continued
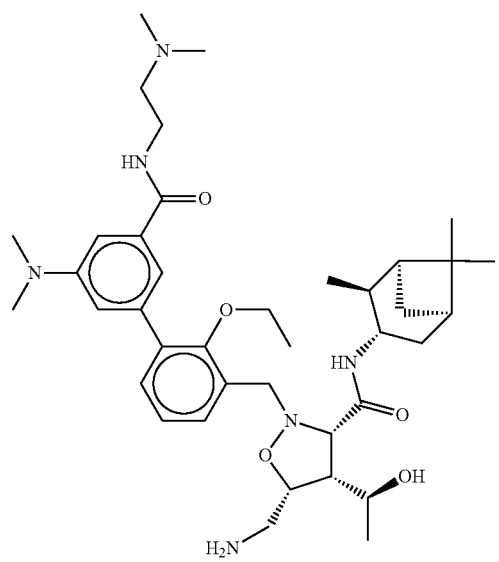
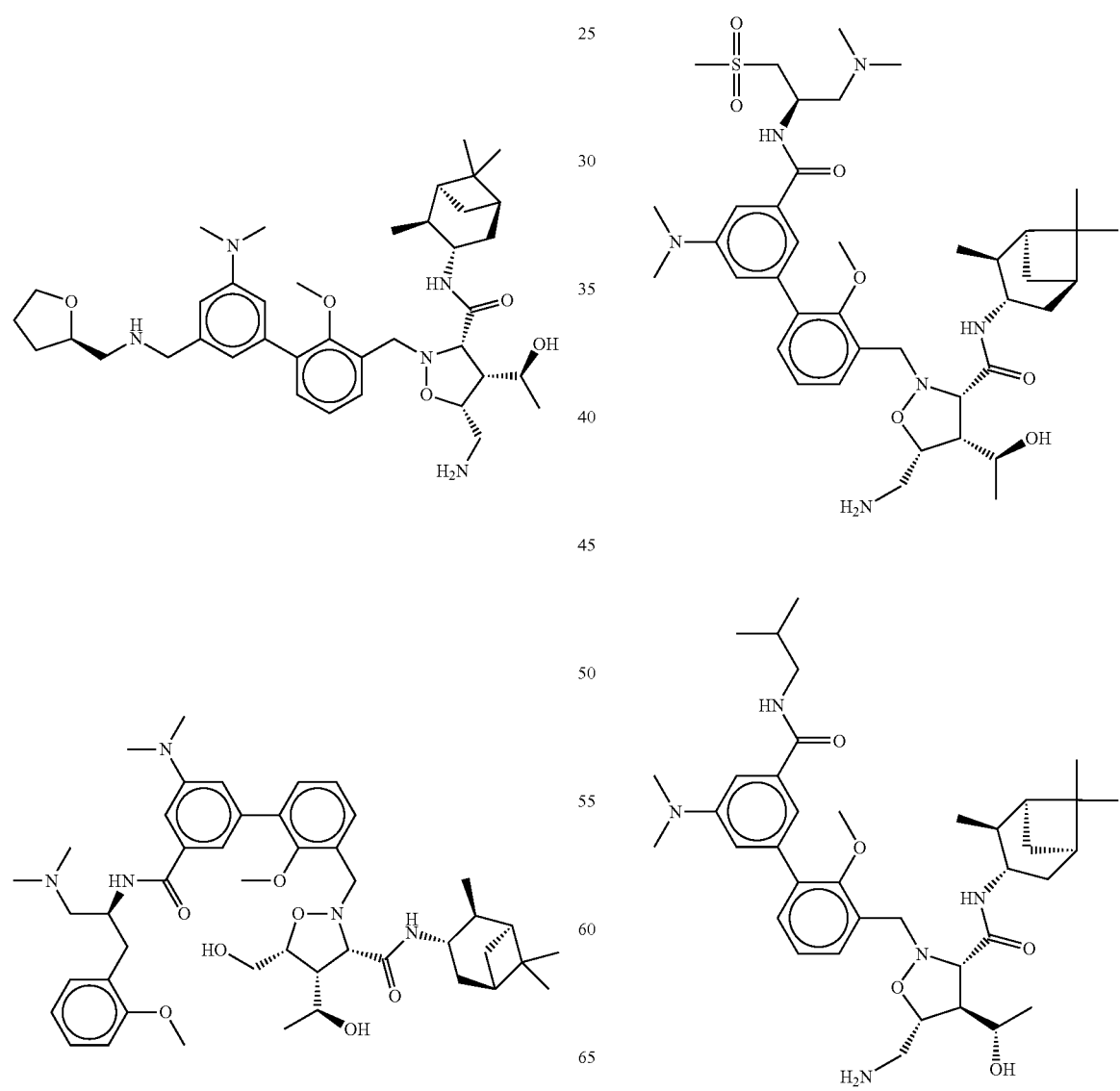

47
-continued
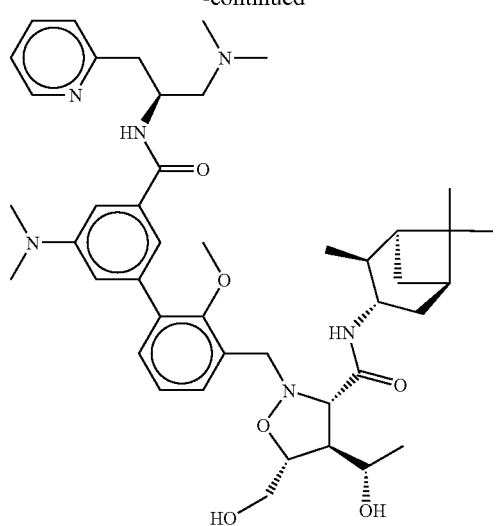
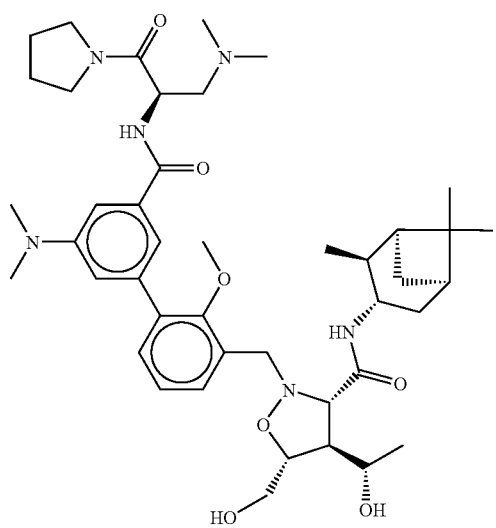
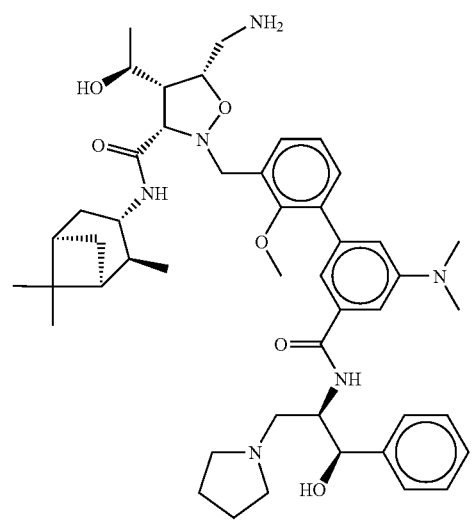
48
-continued
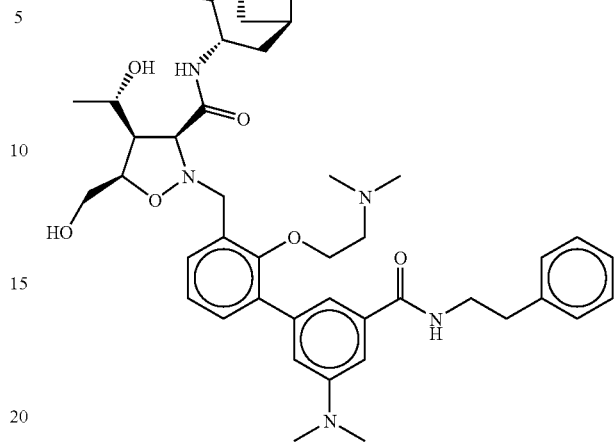
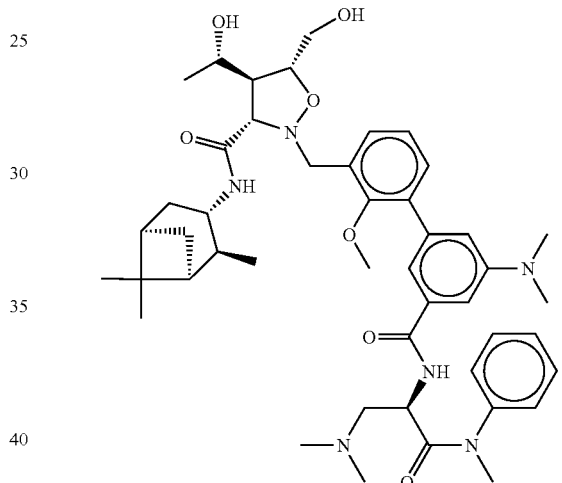
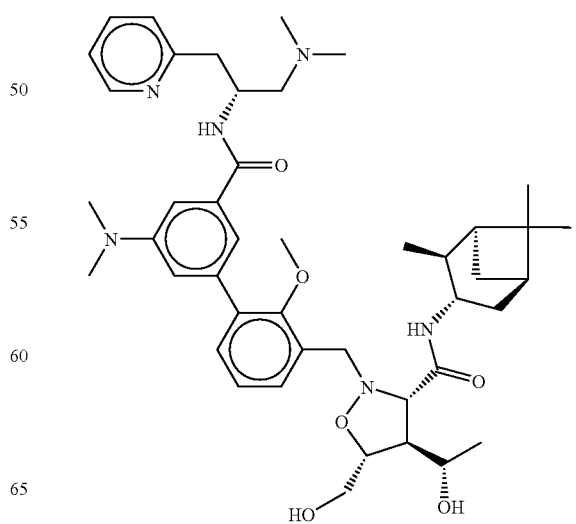

49
-continued
50
-continued
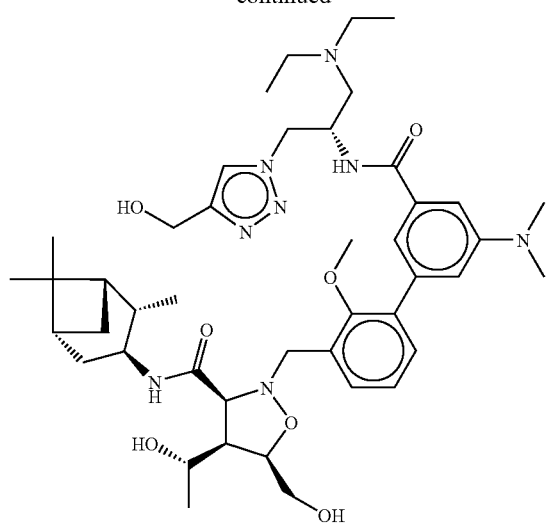
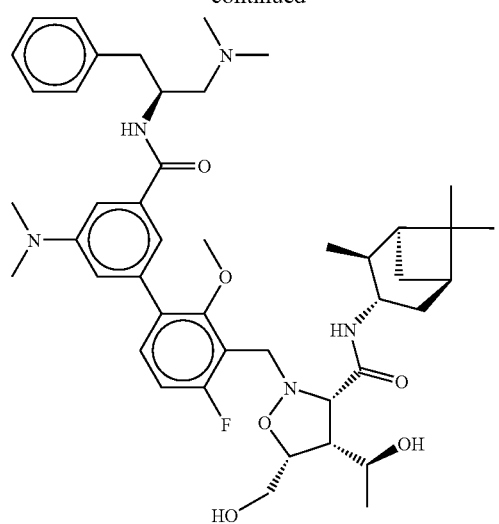
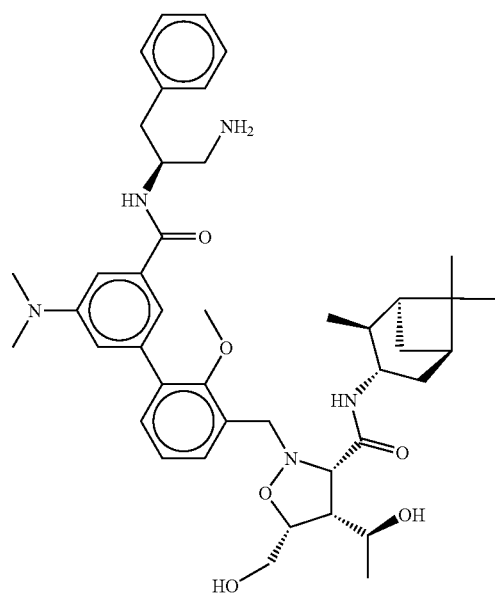
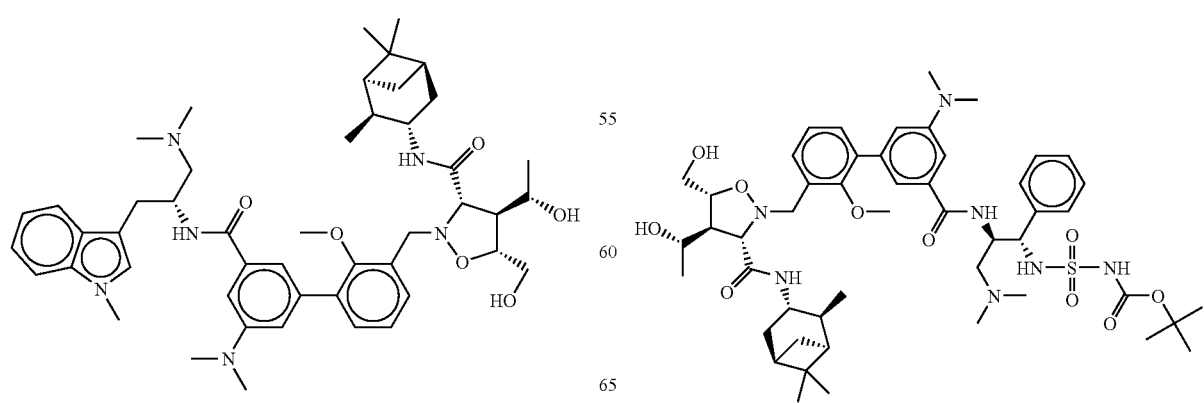

51
-continued
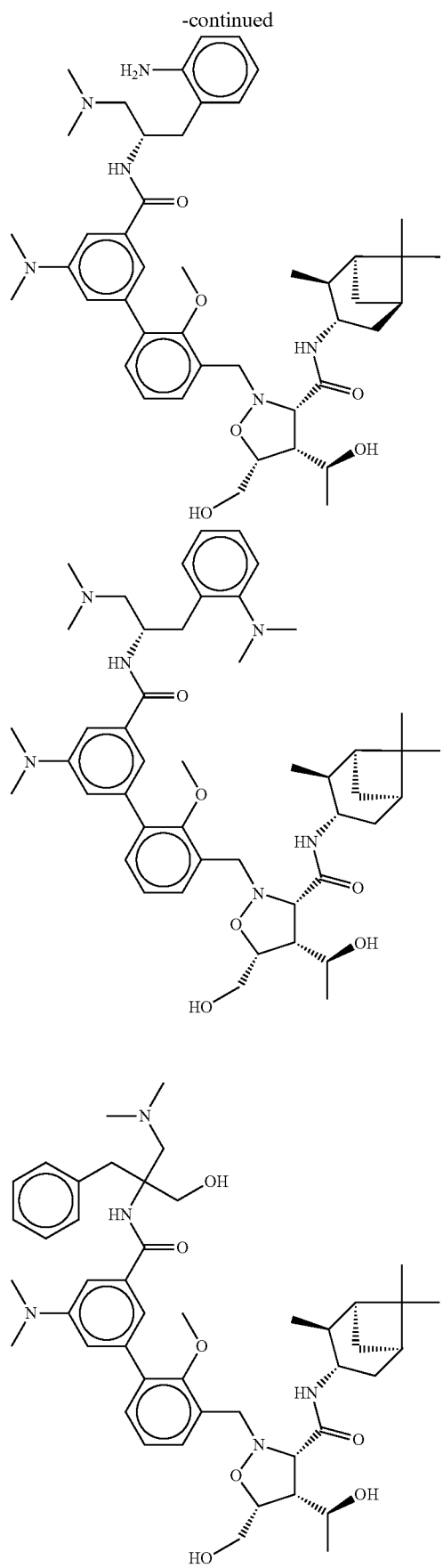
52
-continued
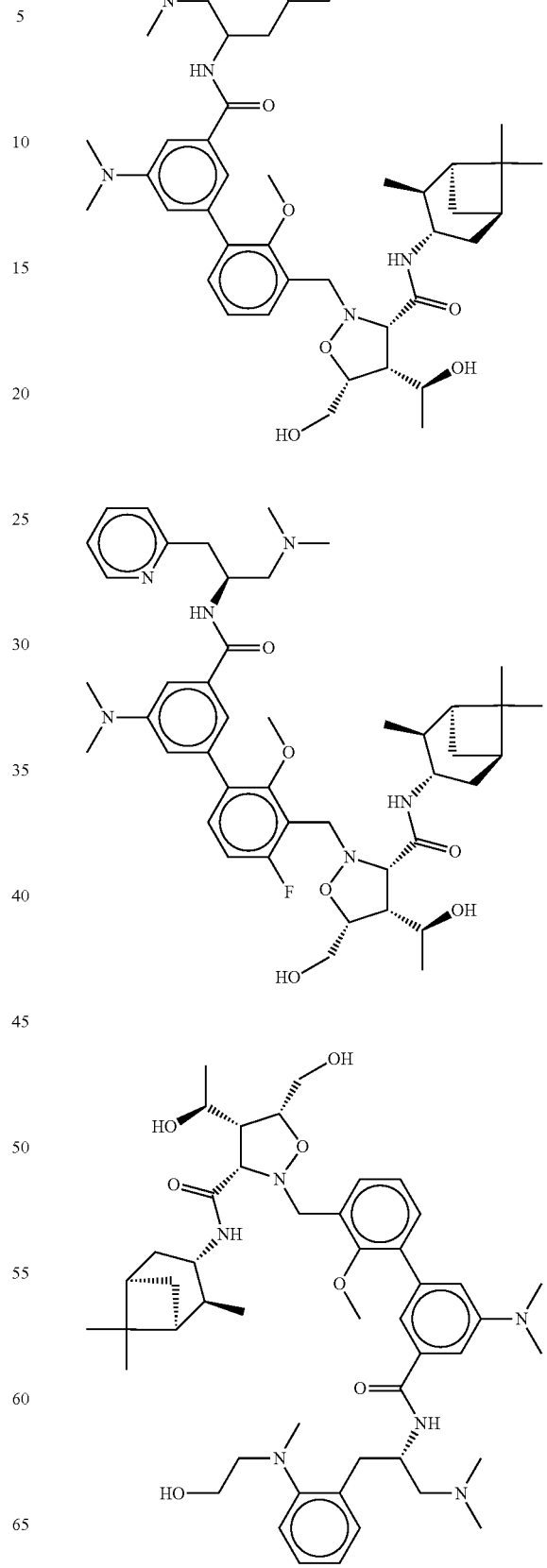

53
-continued
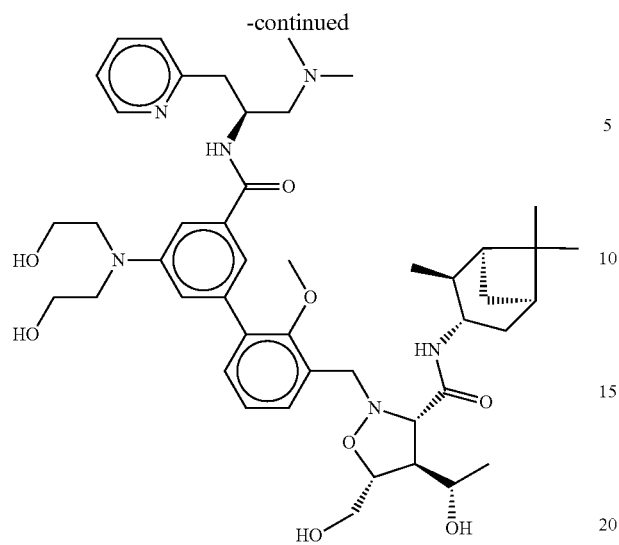
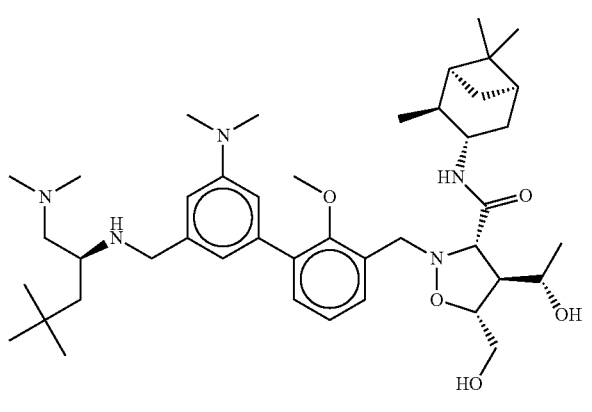
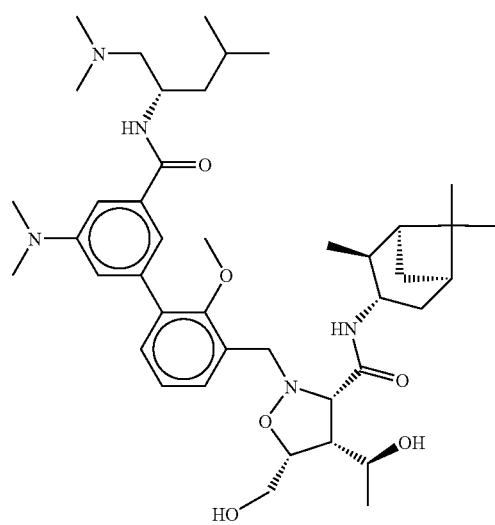
54
-continued
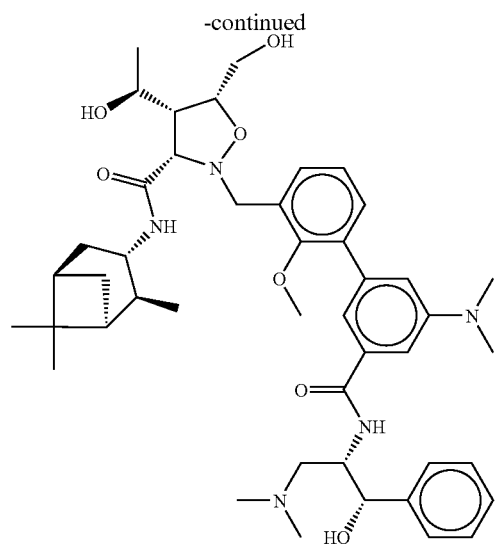
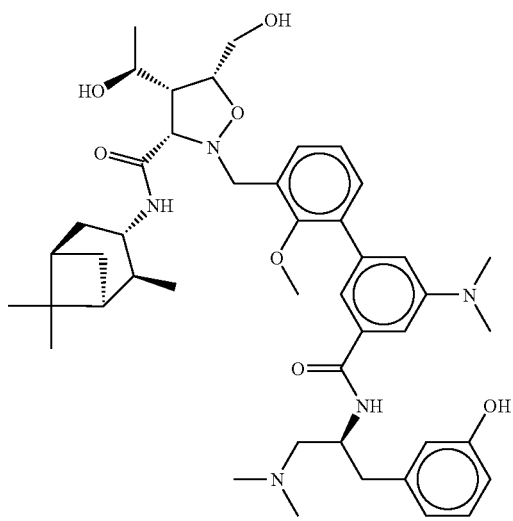
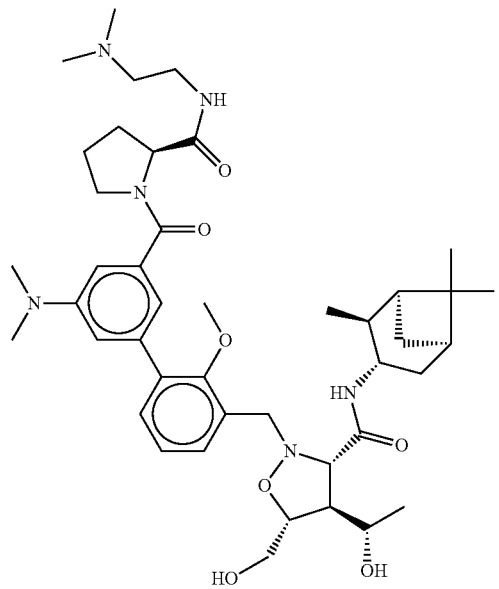

55
-continued
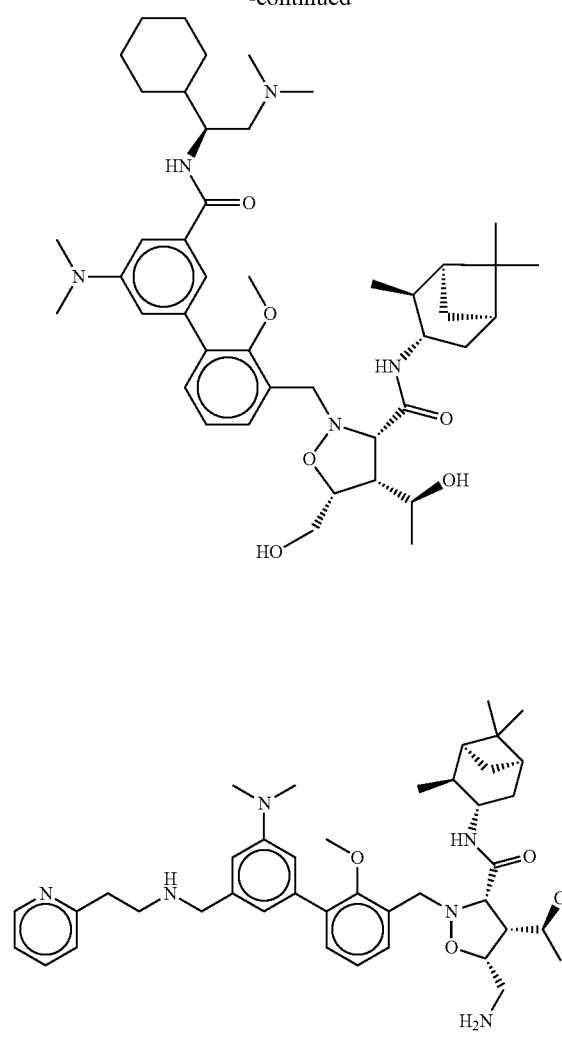
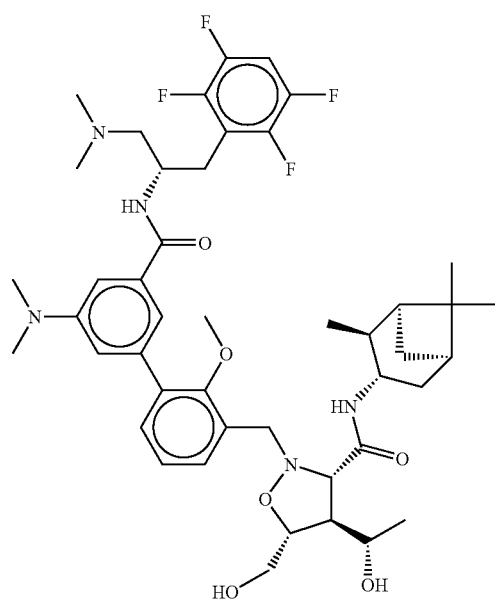
56
-continued
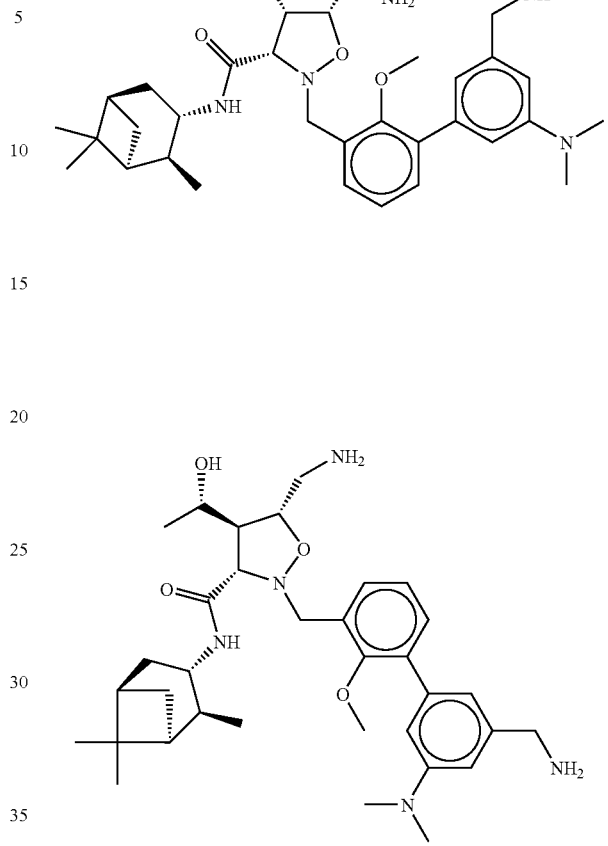
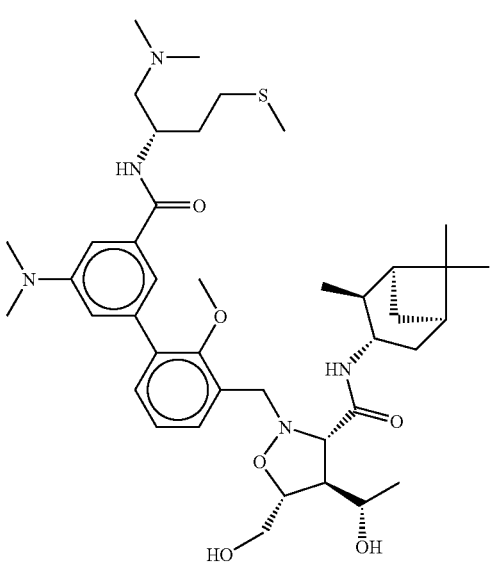

57
-continued
58
-continued
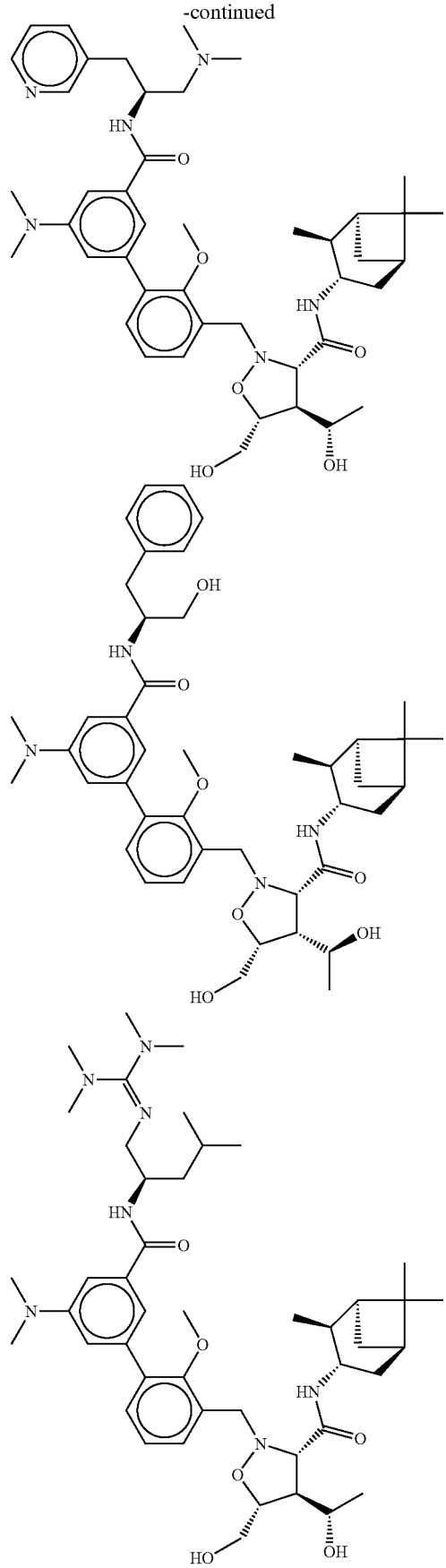
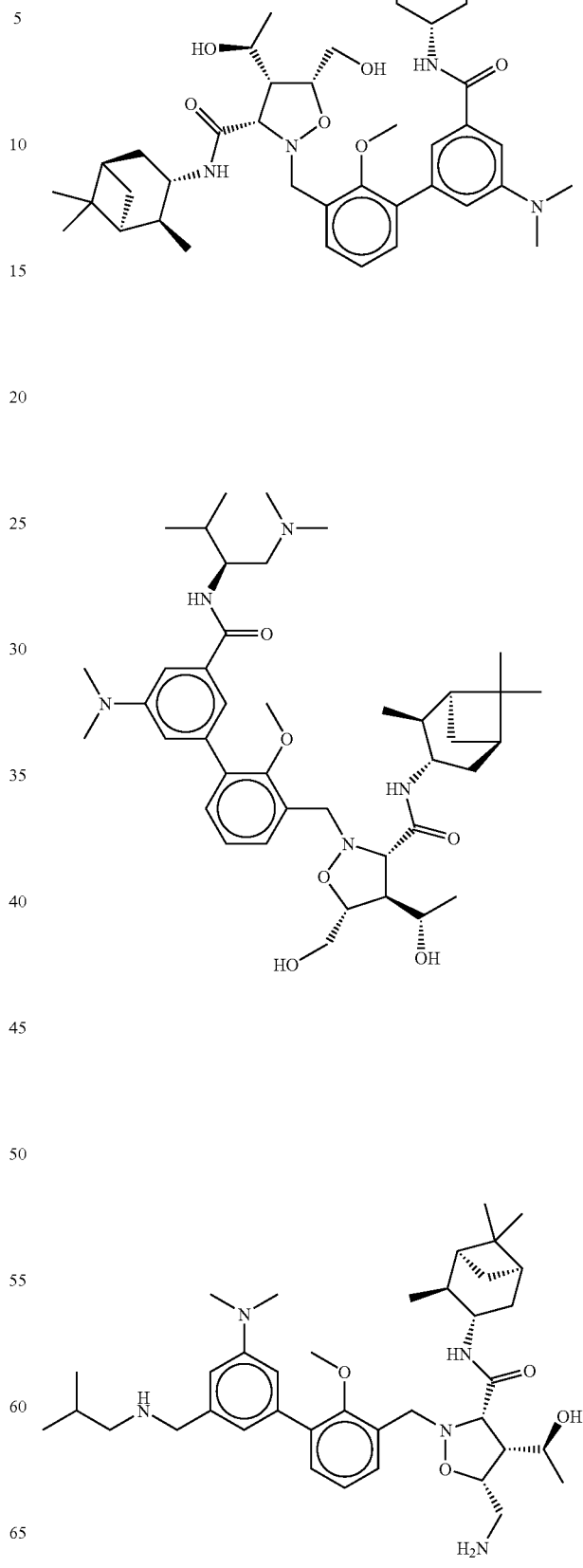

59
-continued
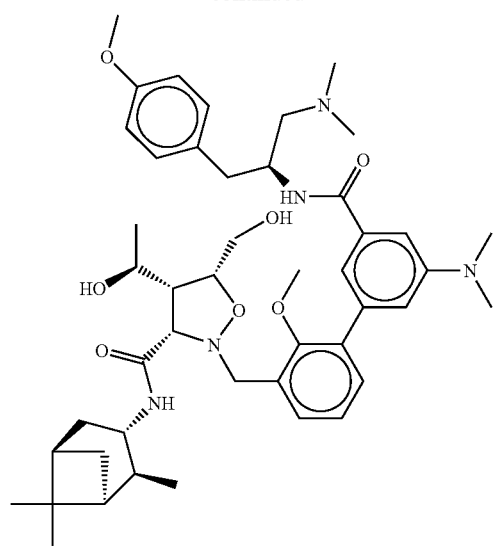
60
-continued
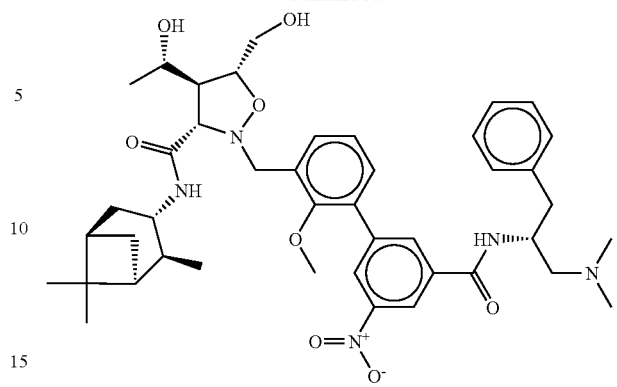
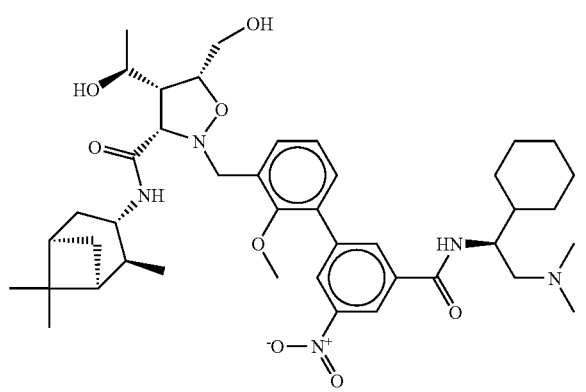
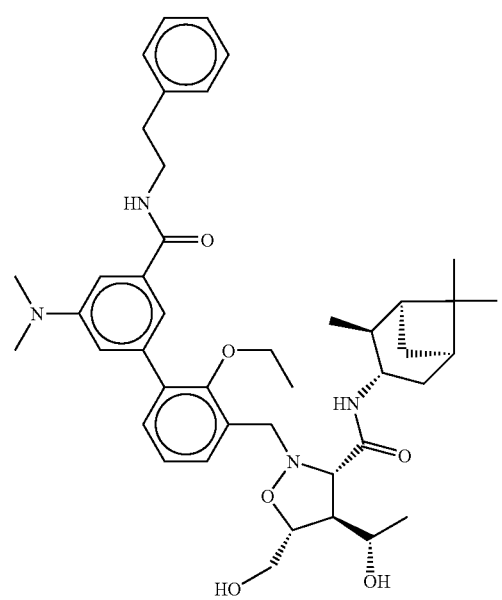
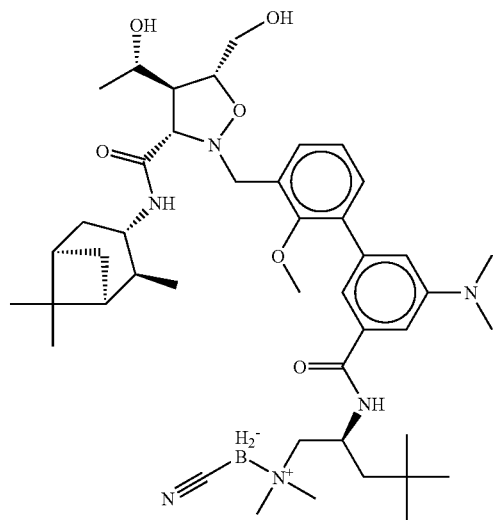
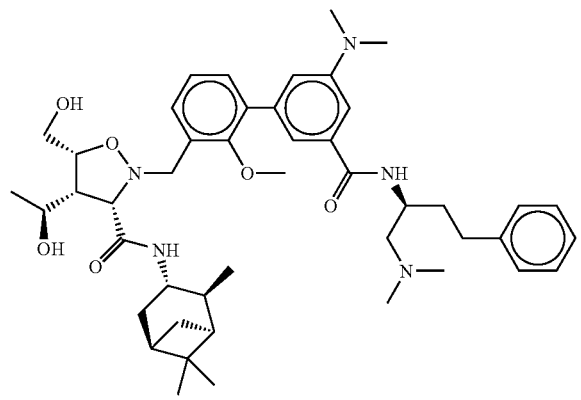

61
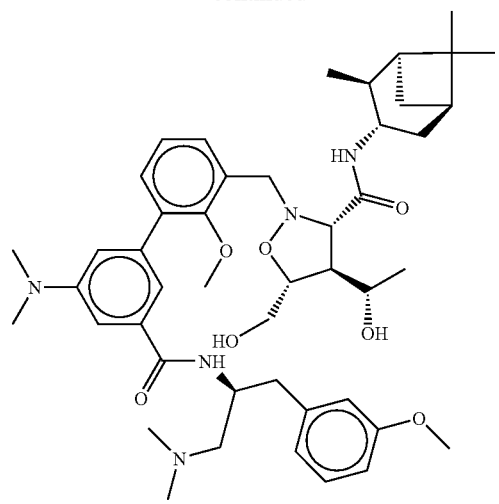
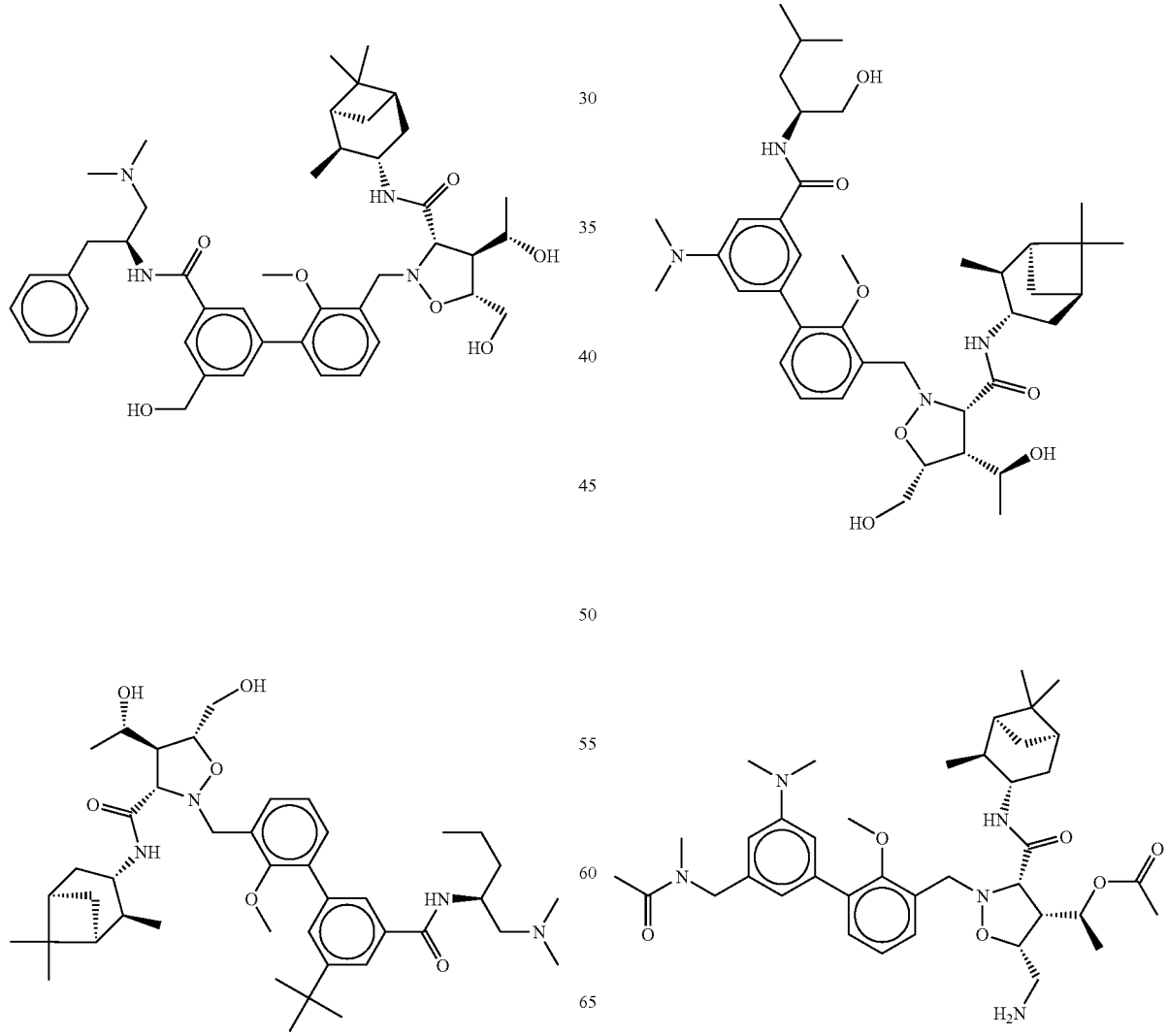
62
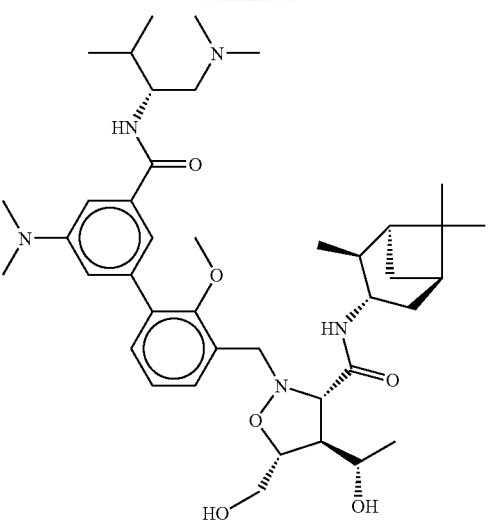

63
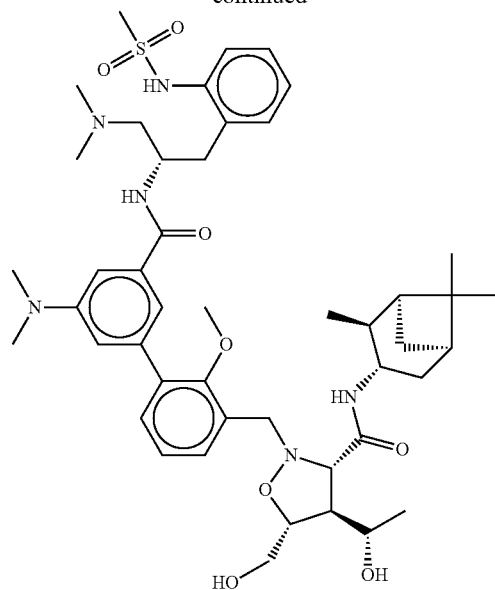
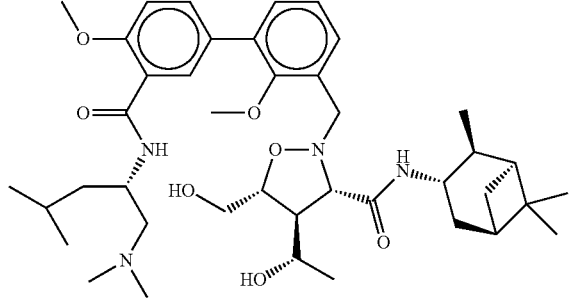
64
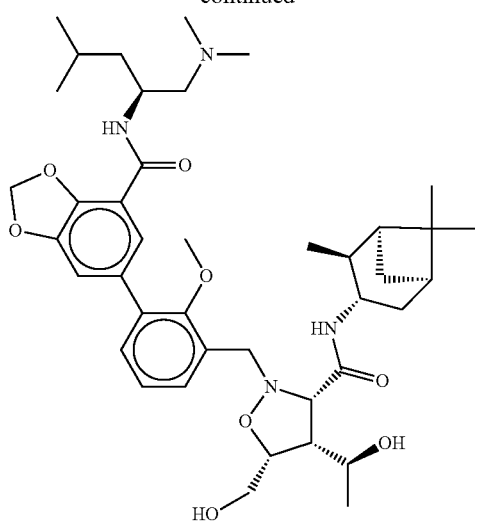
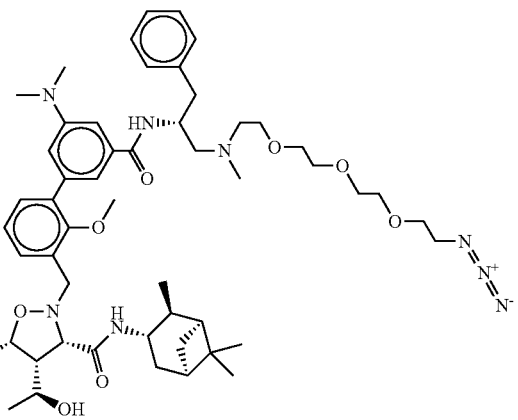
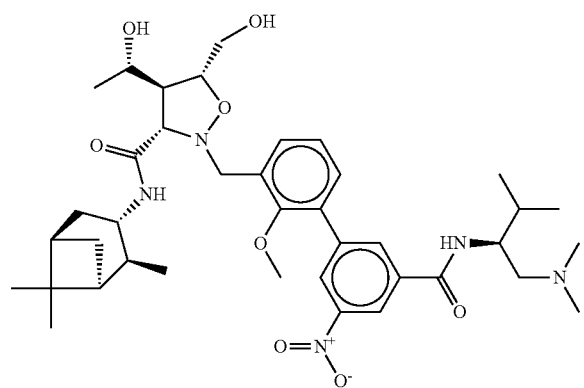
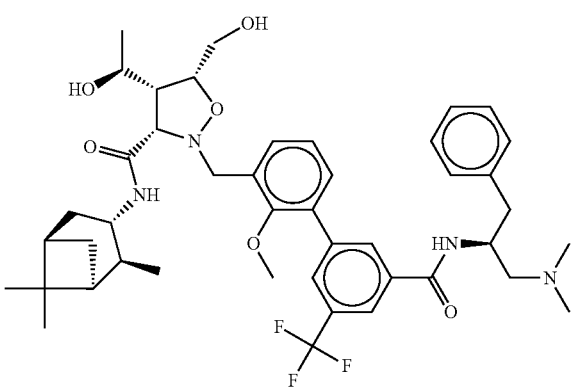

65                                              66
-continued                                  -continued
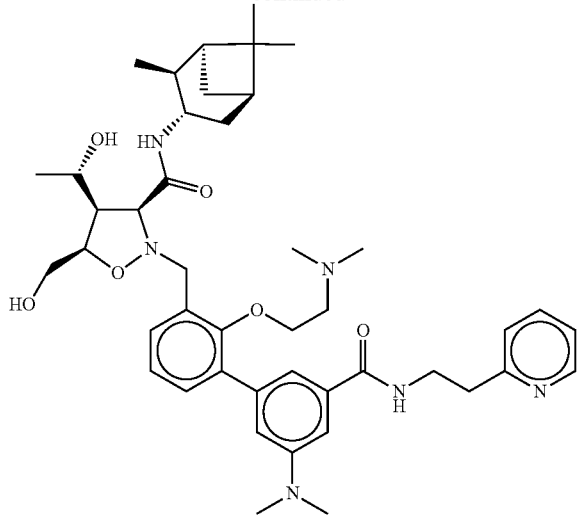
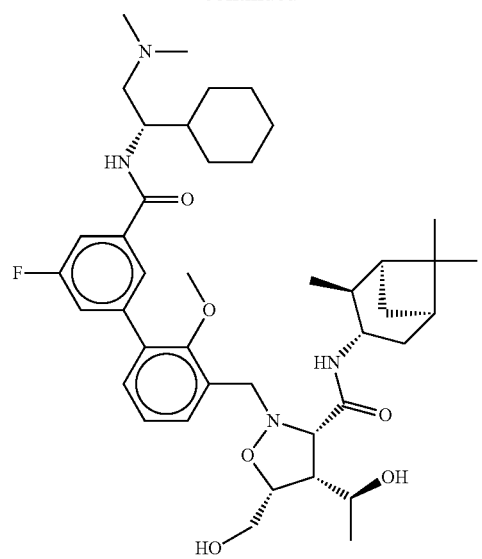
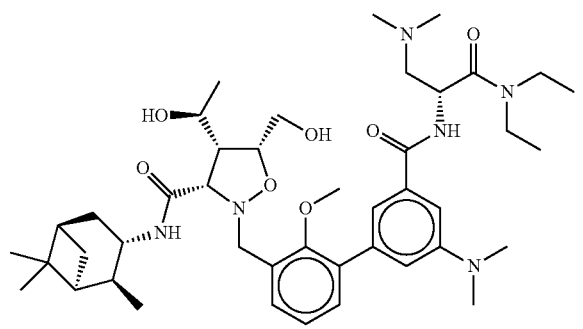
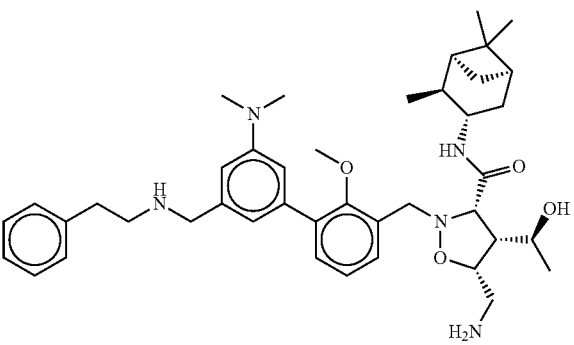
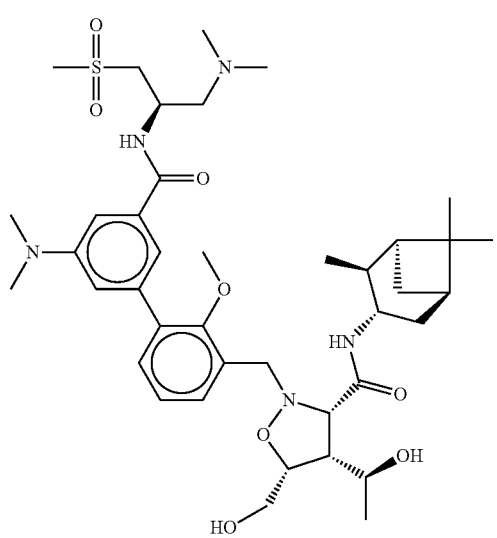
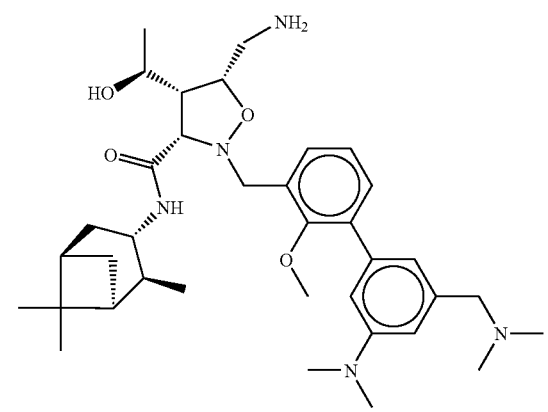

67
-continued
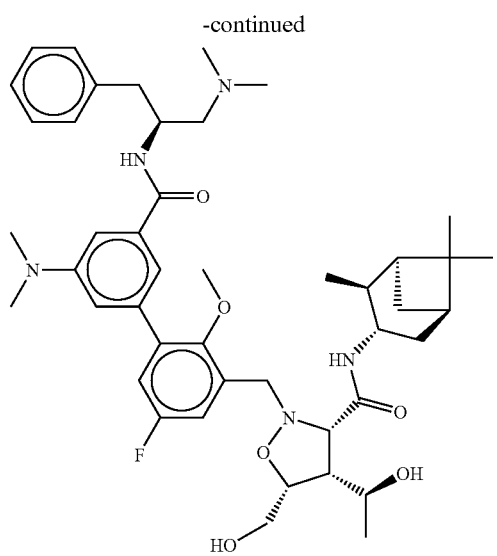
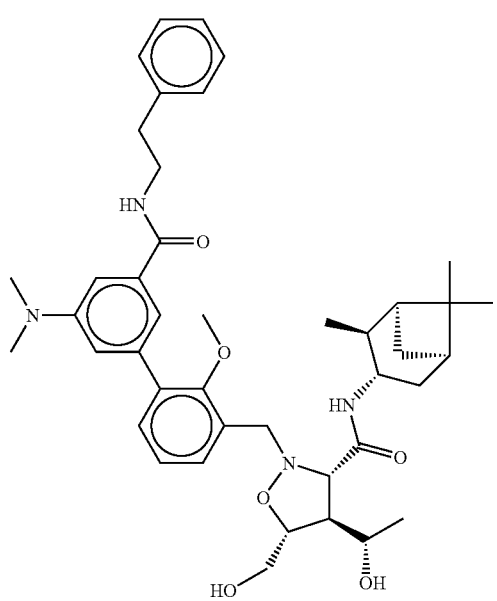
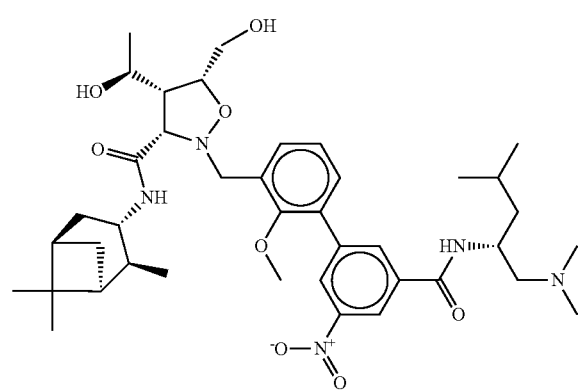
68
-continued
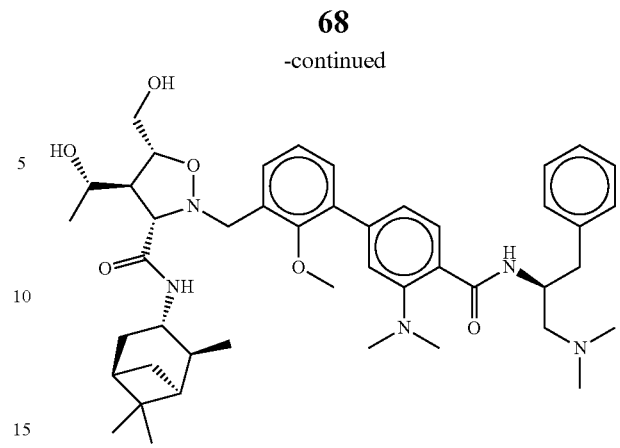
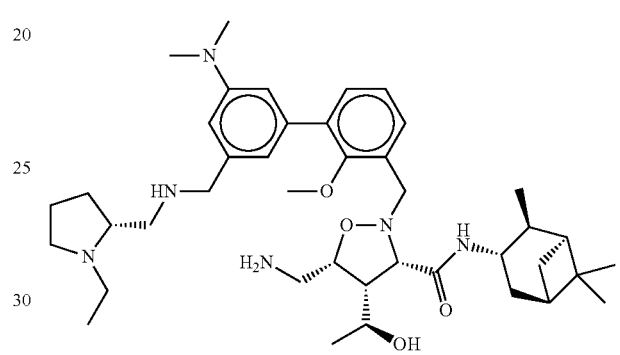
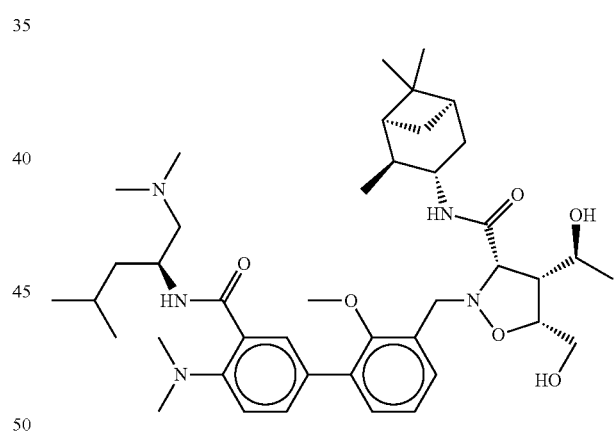
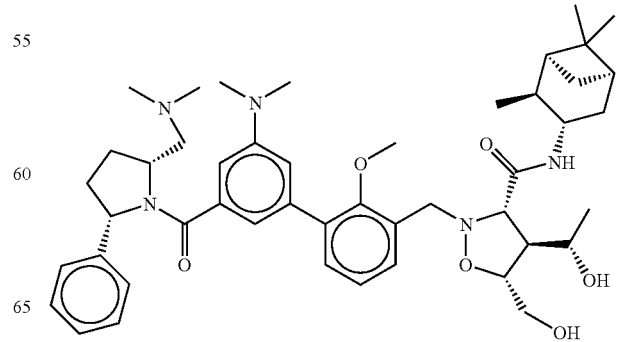

69
-continued
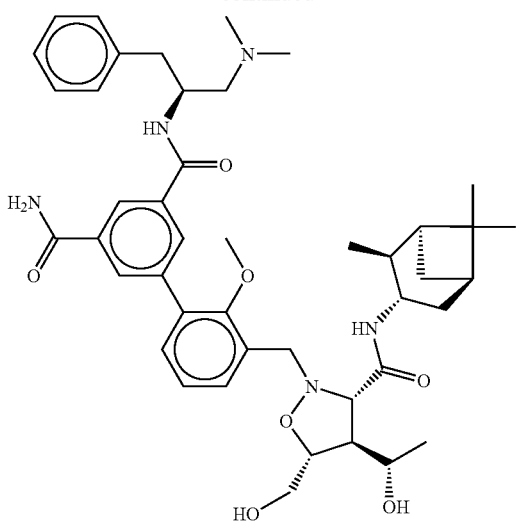
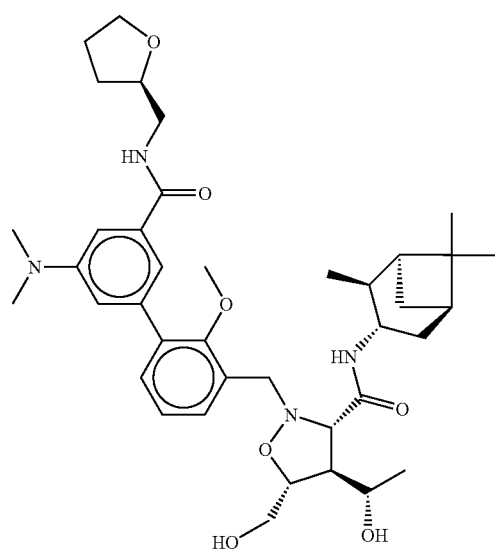
70
-continued
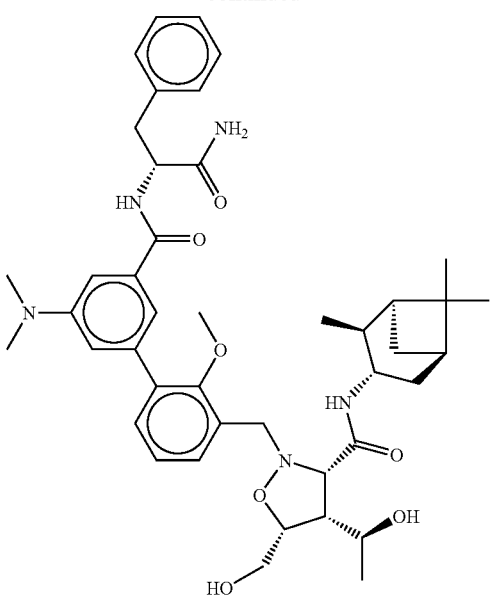
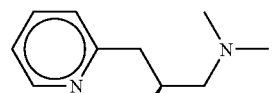
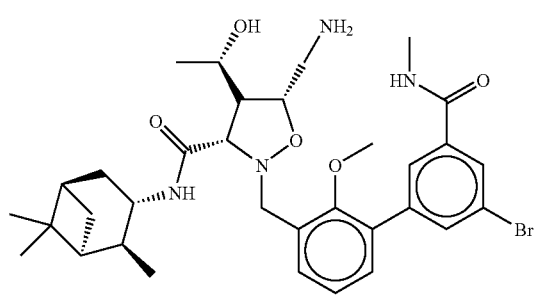
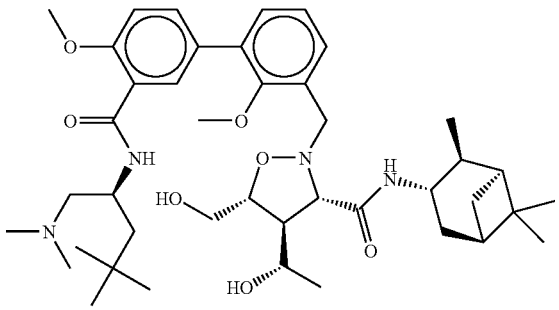

71
-continued
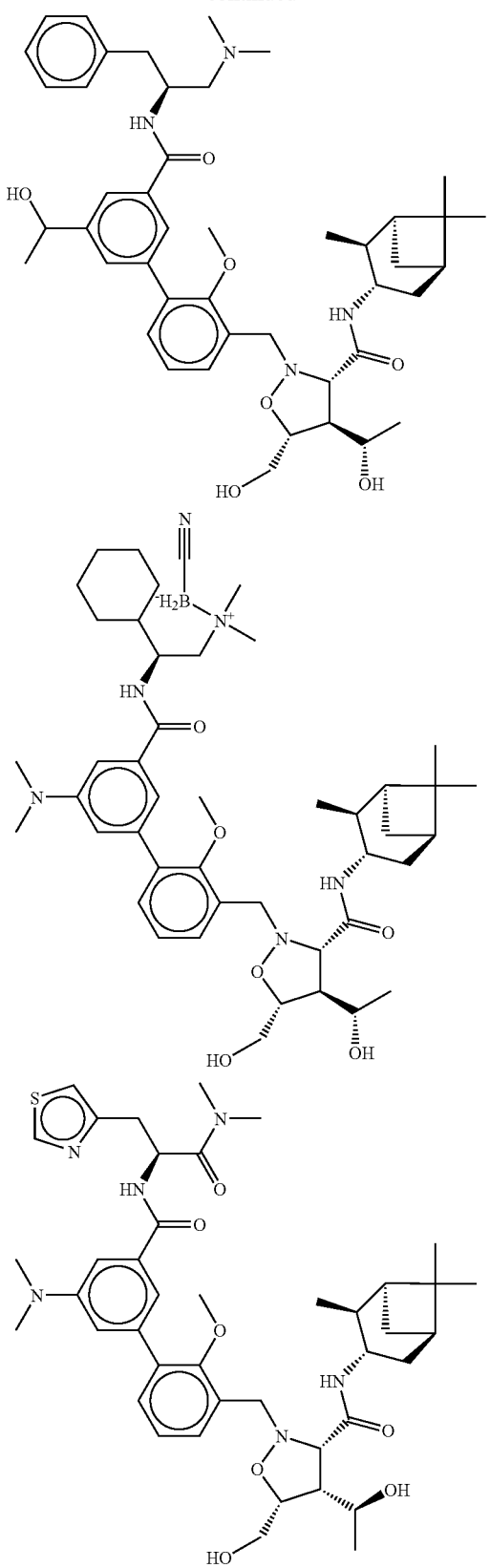
72
-continued
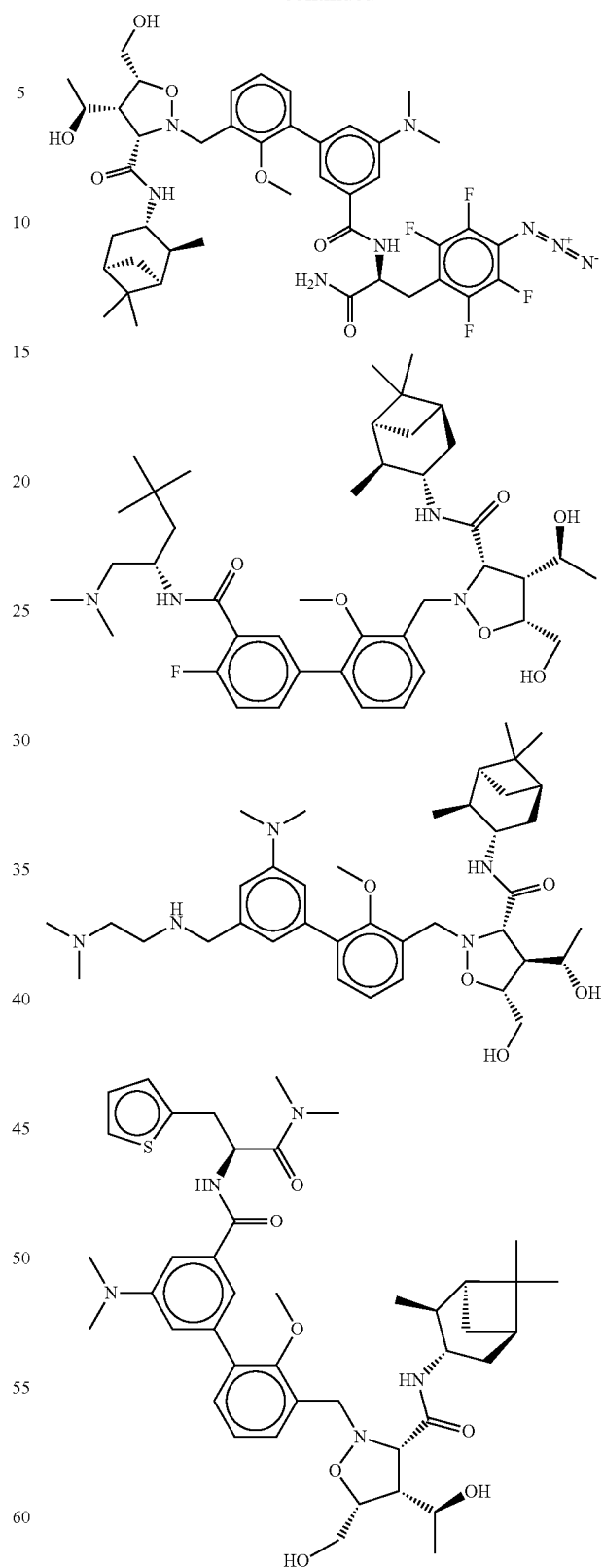

73
-continued
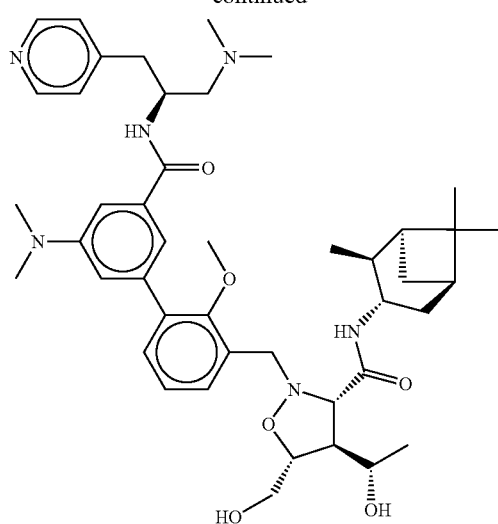
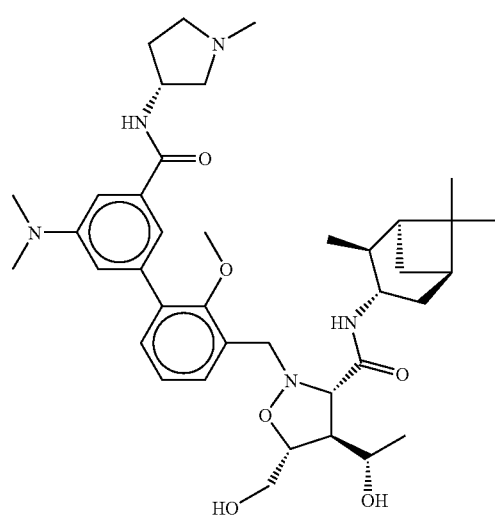
74
-continued
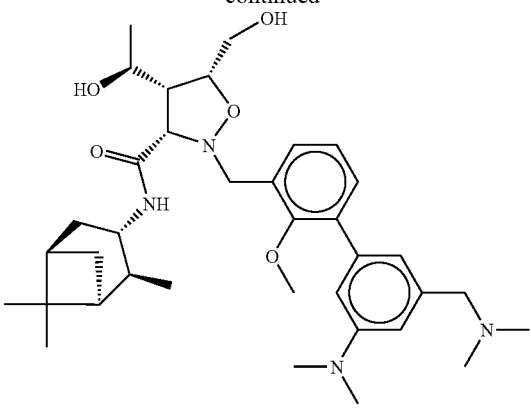
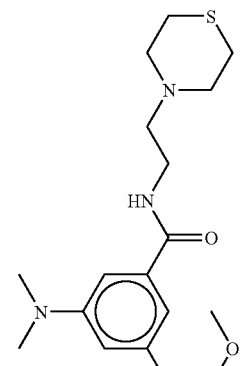
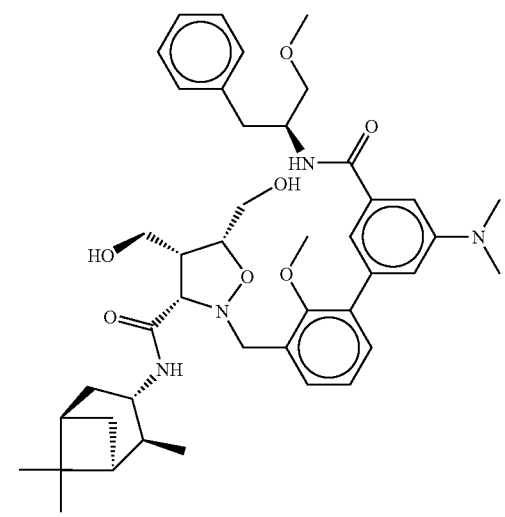

| 75 -continued | 76 -continued |
|---|---|
| 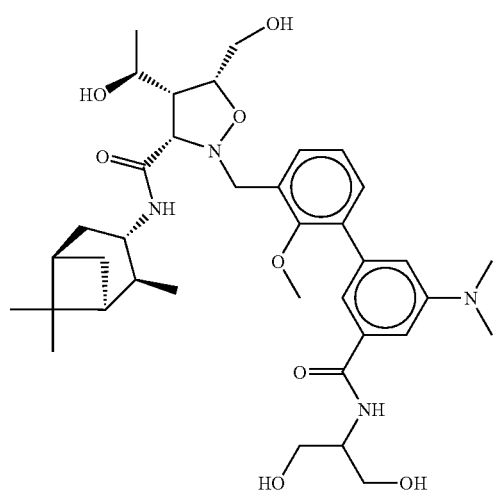 | 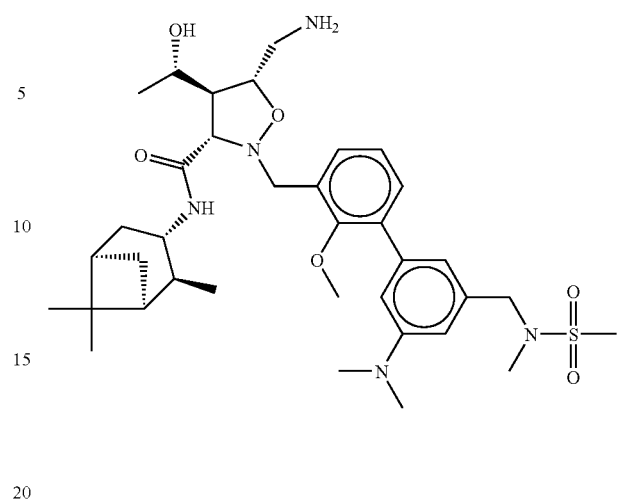 |
| 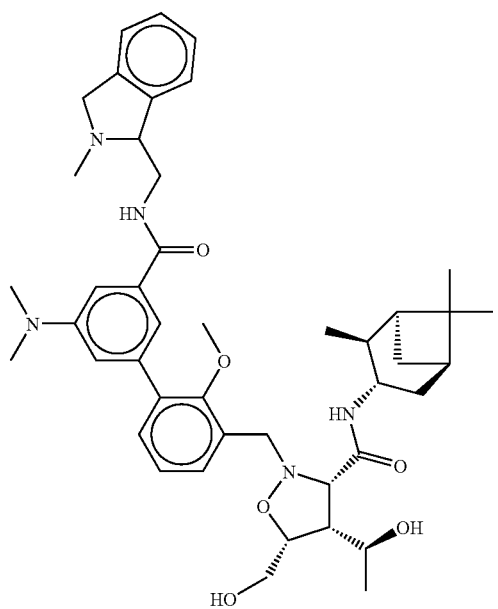 | 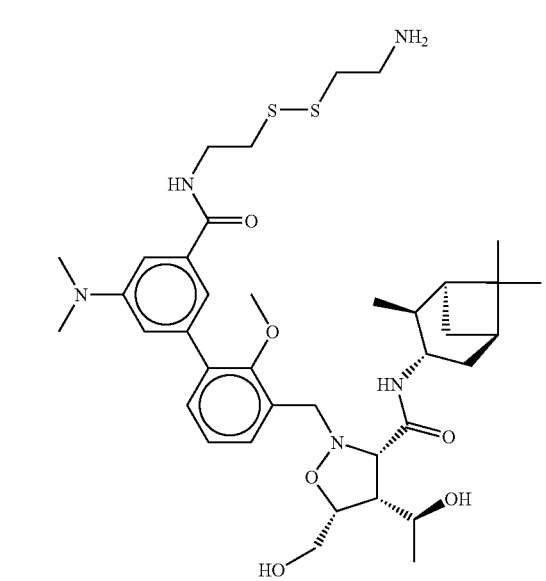 |
| 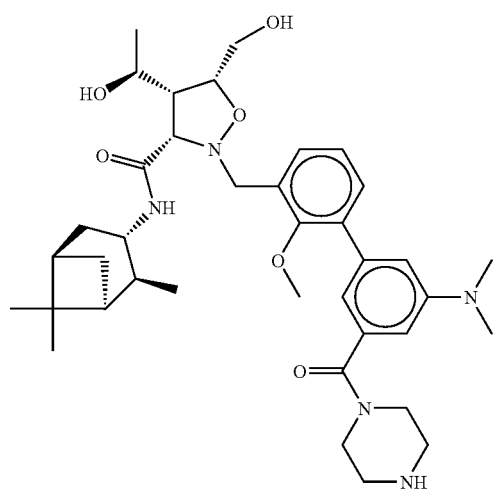 | 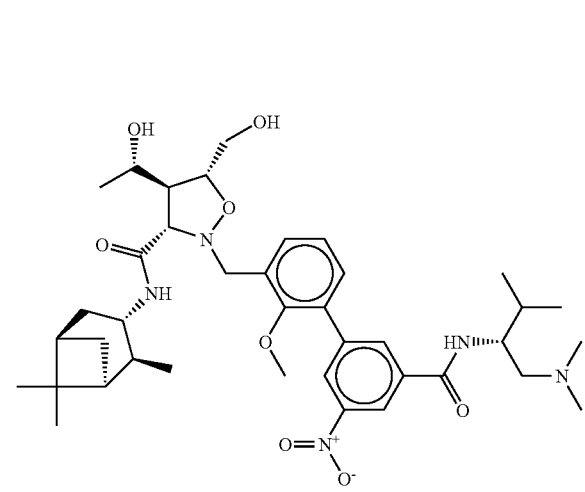 |

77
-continued
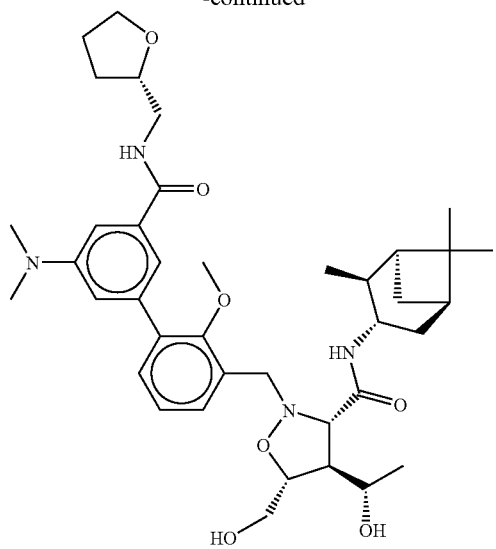
78
-continued
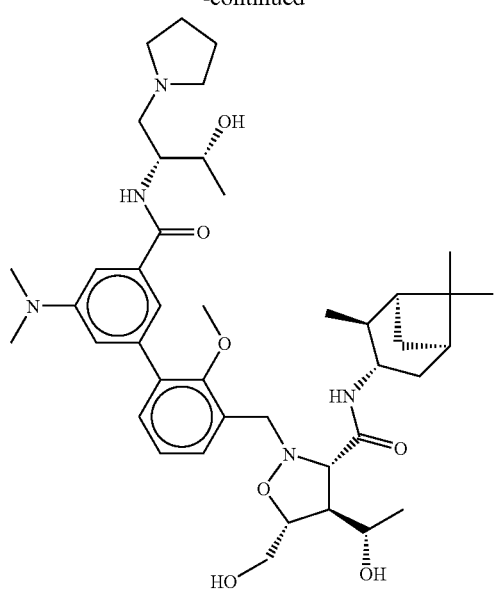
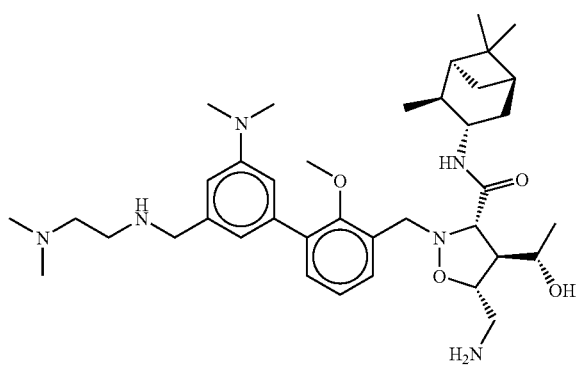
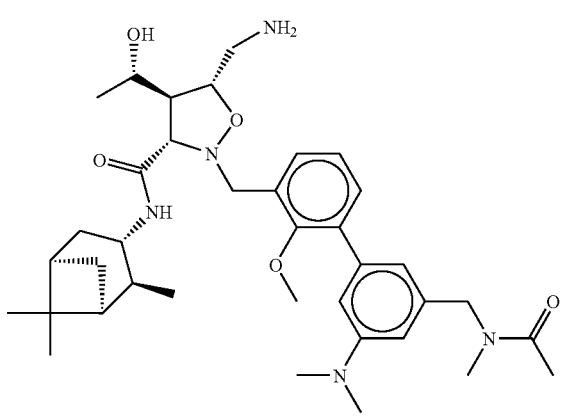
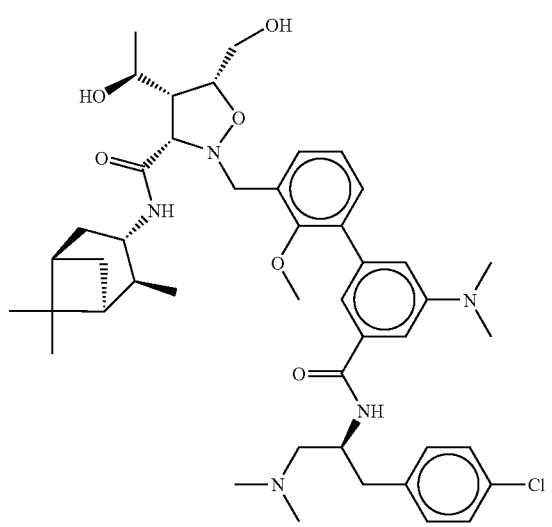
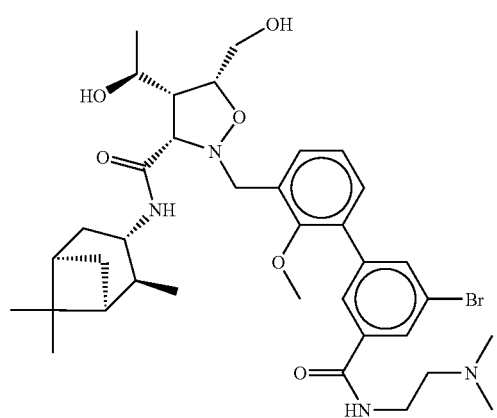

79
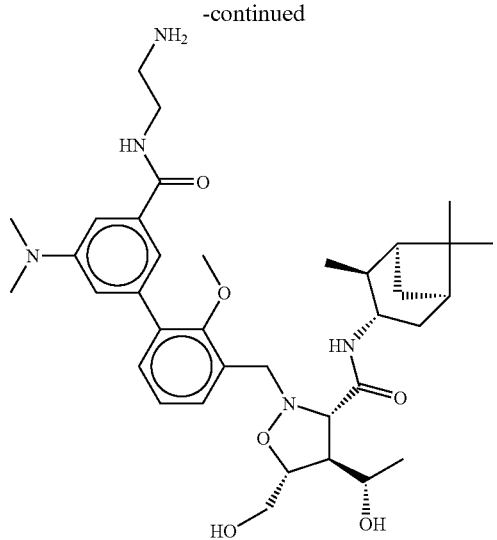
80
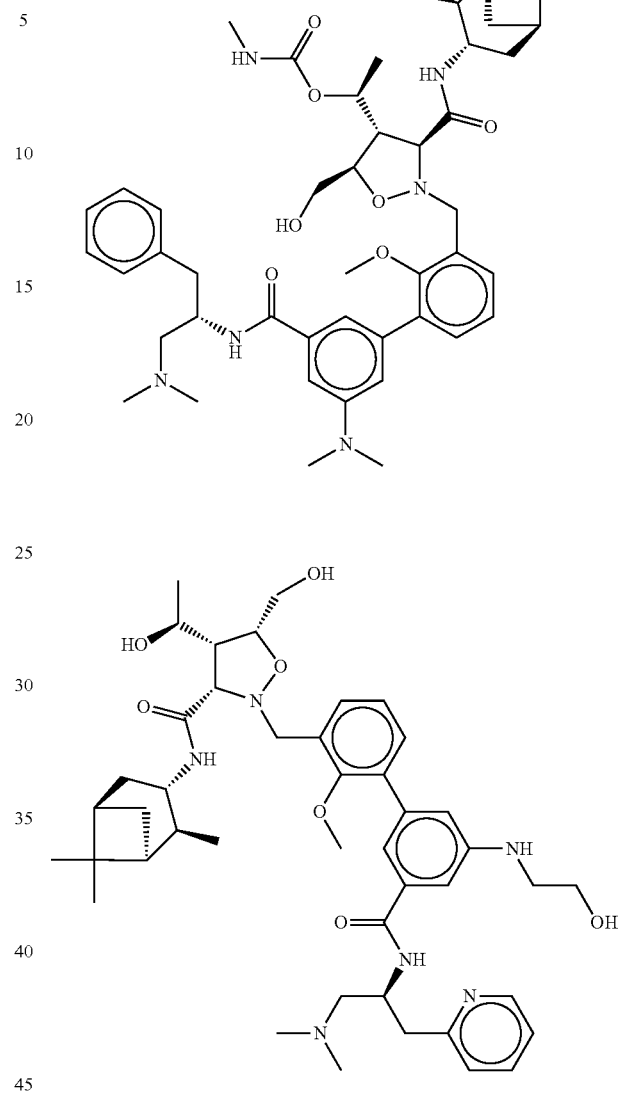
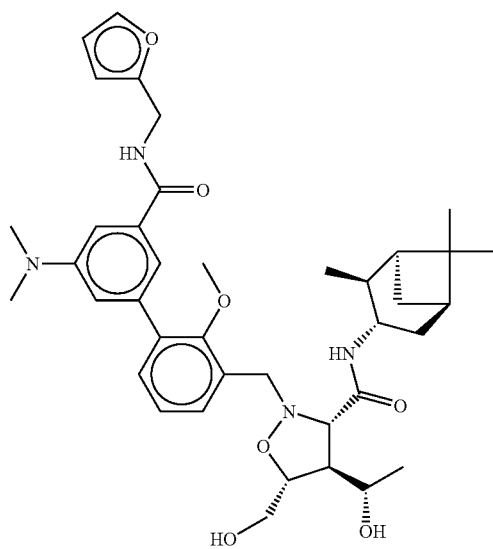
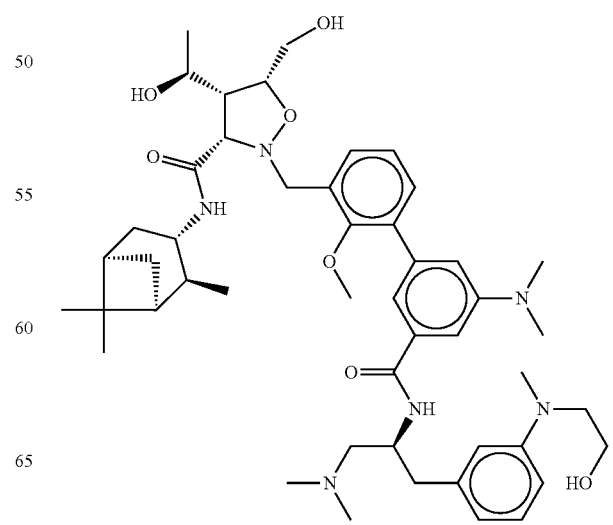

81
-continued
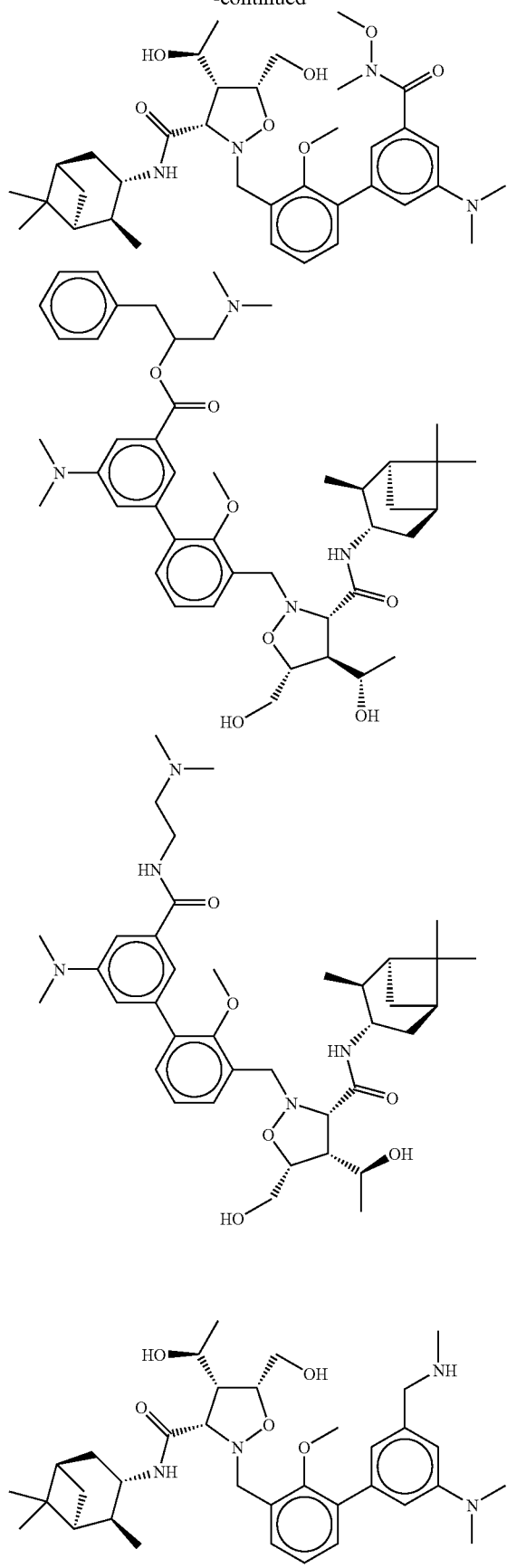
82
-continued
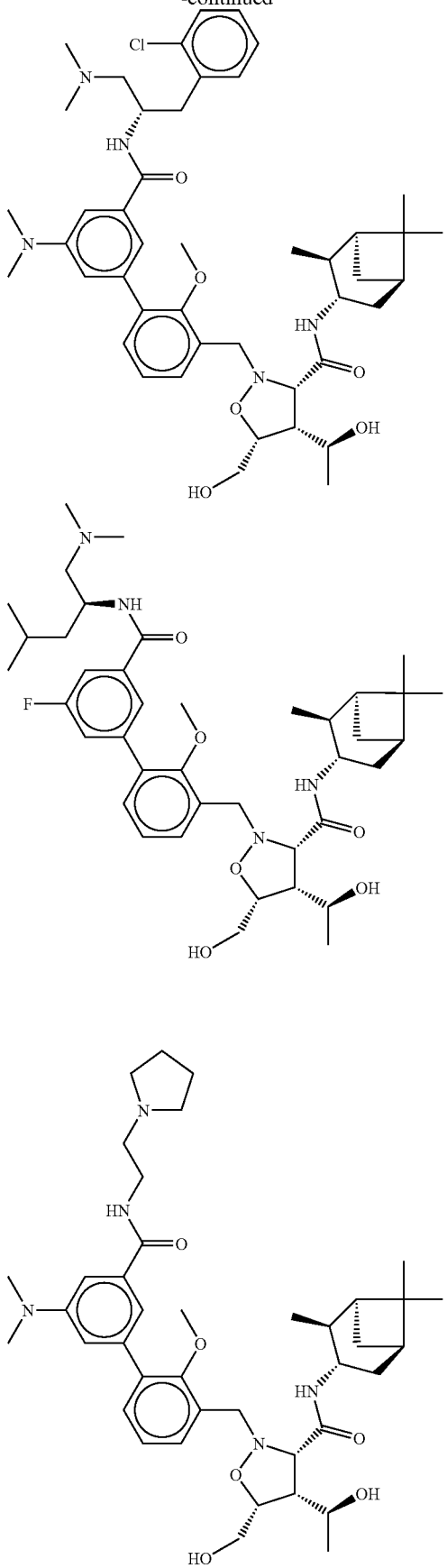

83
-continued
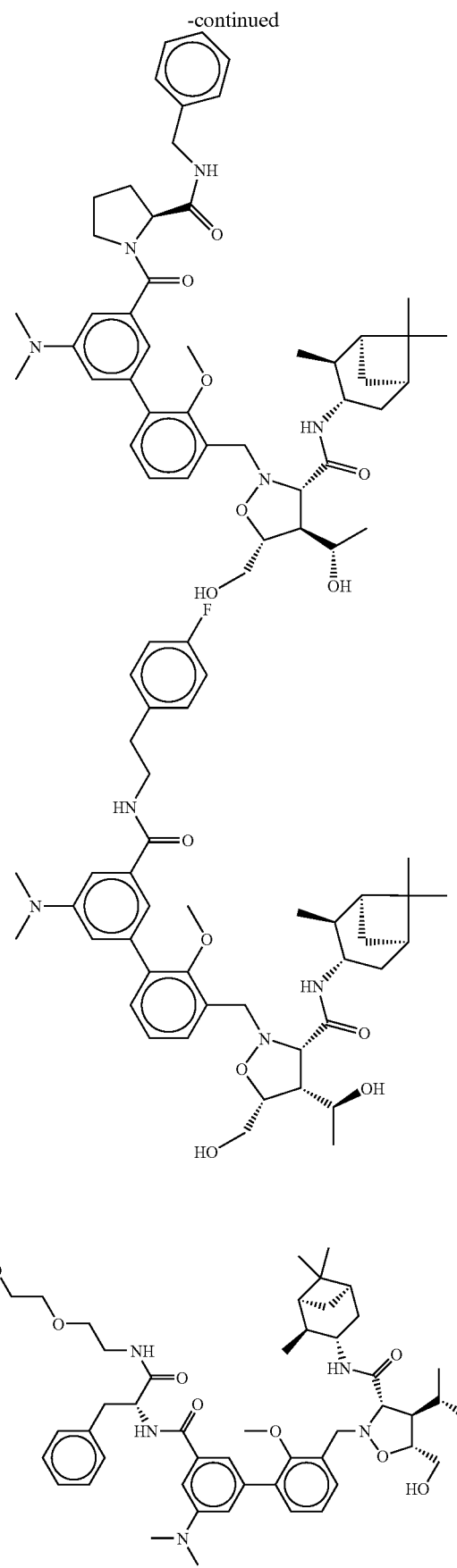
84
-continued
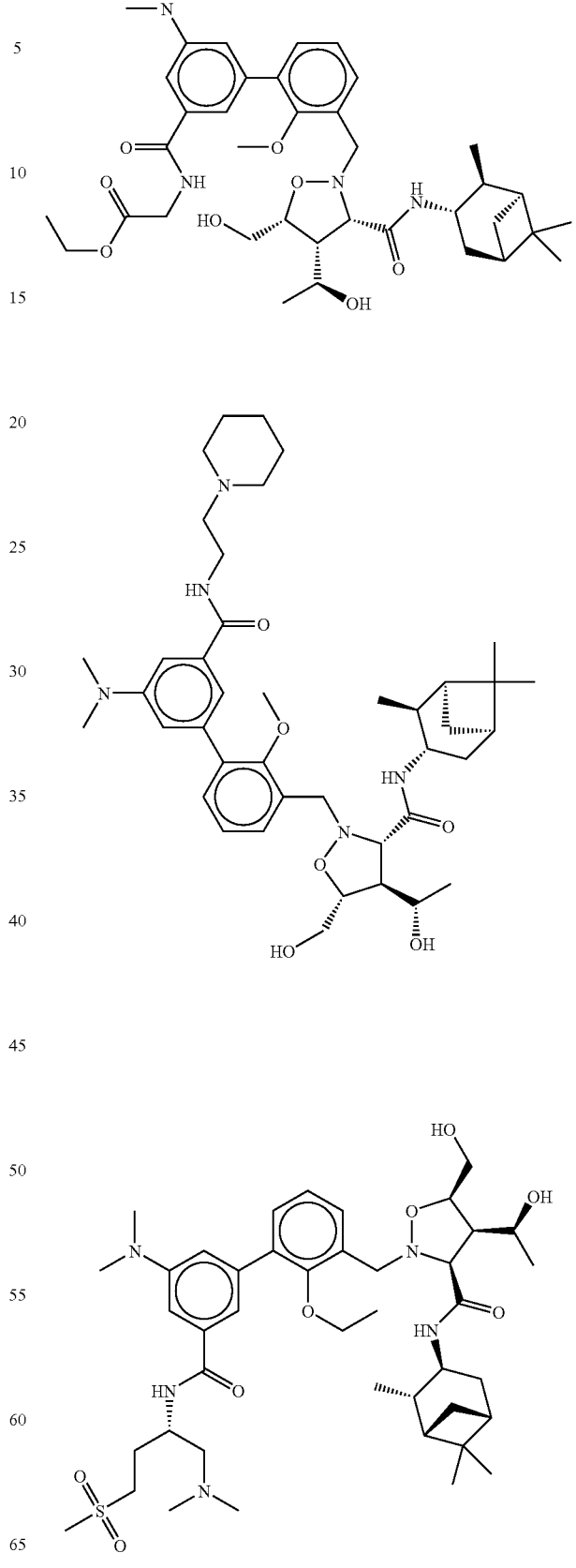

85
-continued
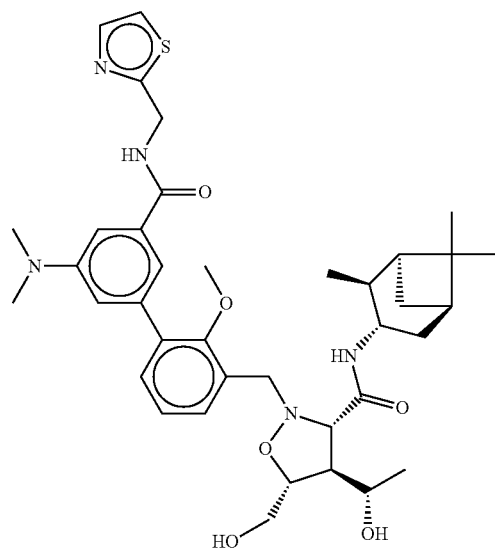
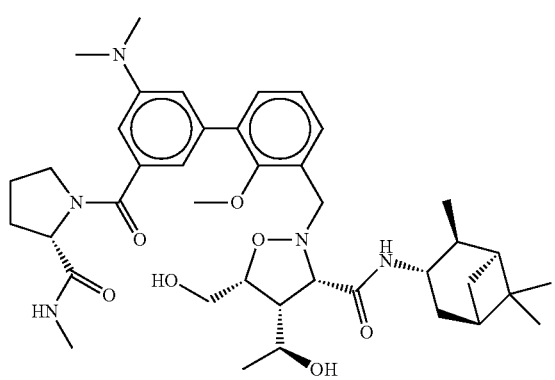
86
-continued
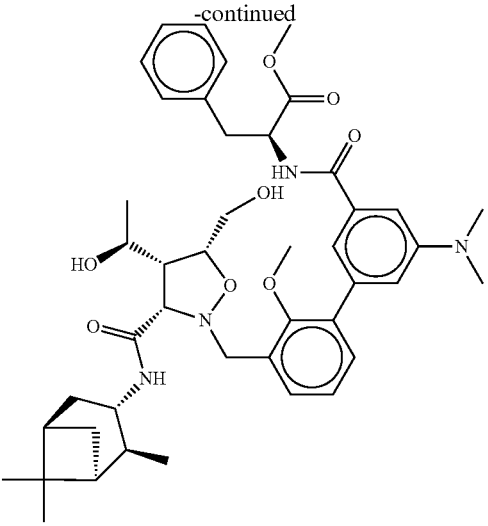
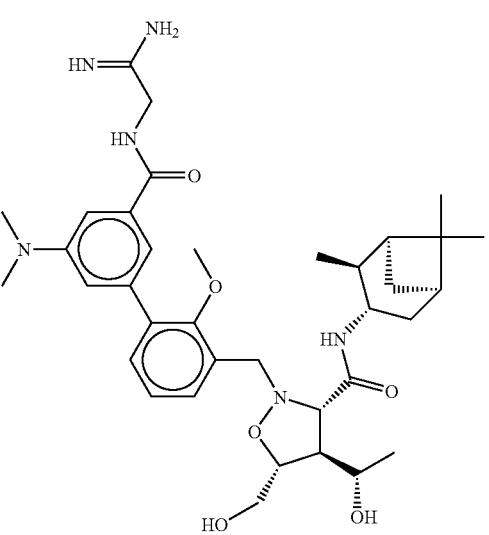
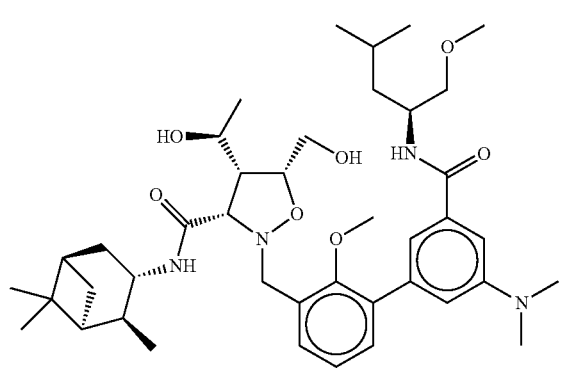
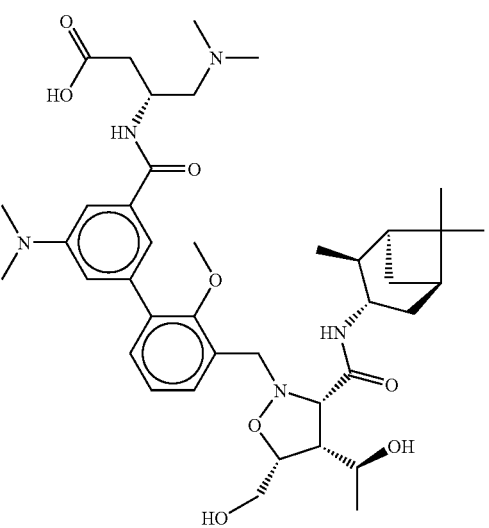

87
-continued
88
-continued
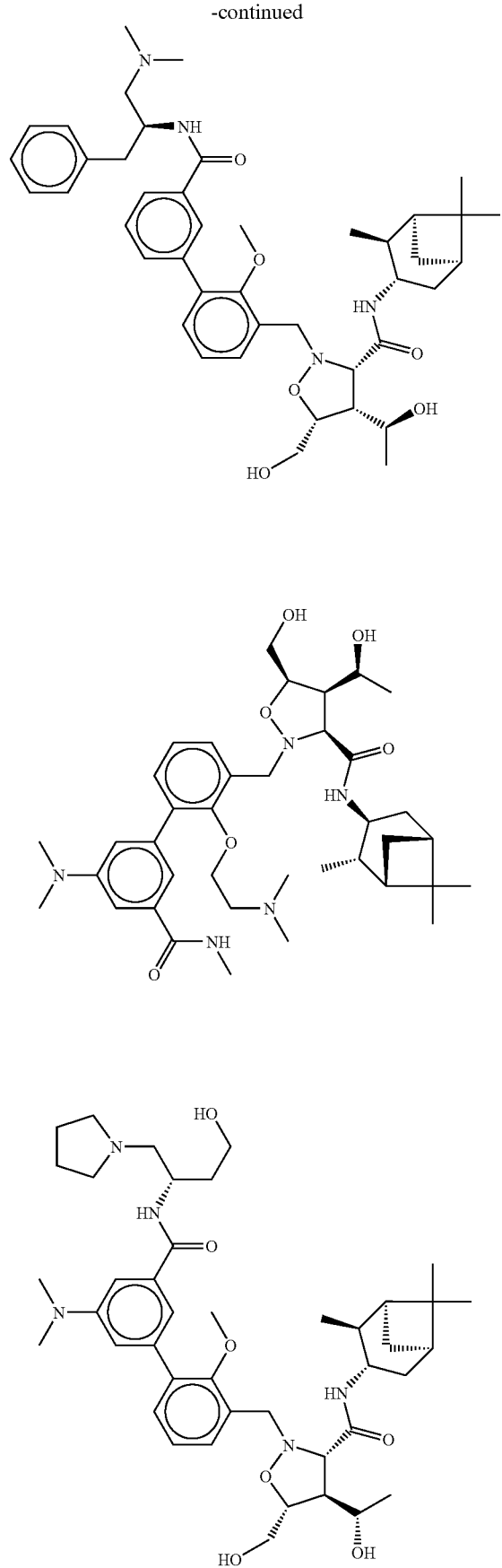
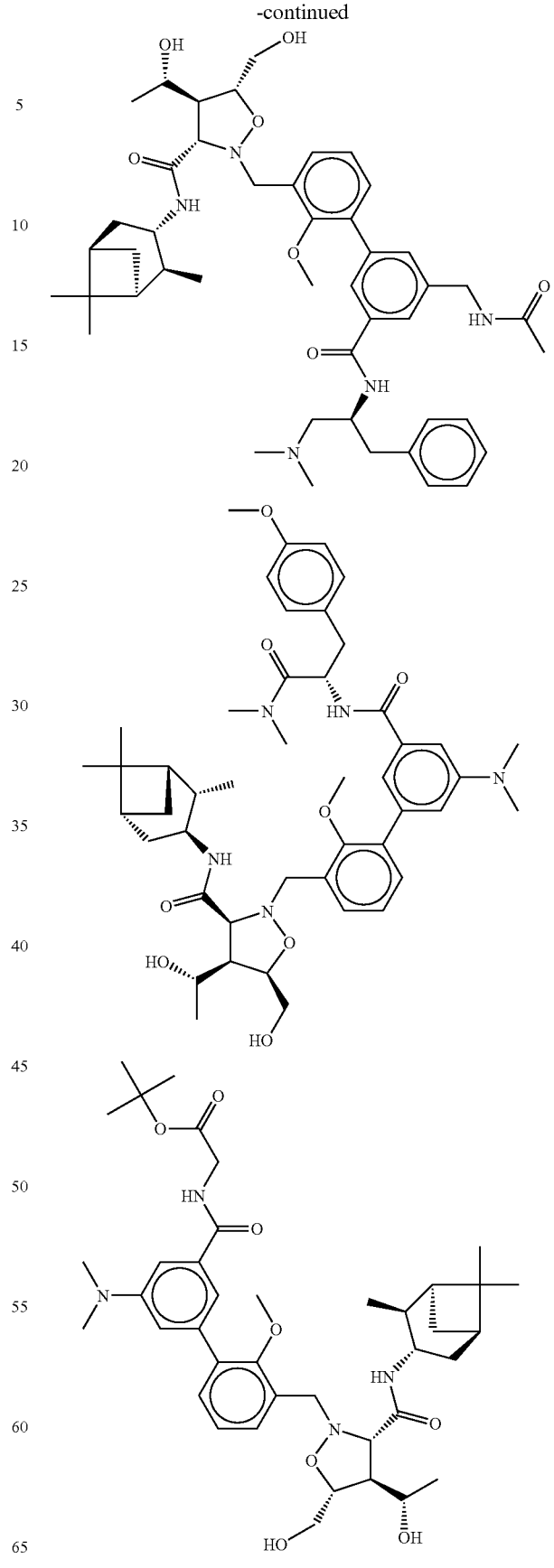

89
-continued
90
-continued
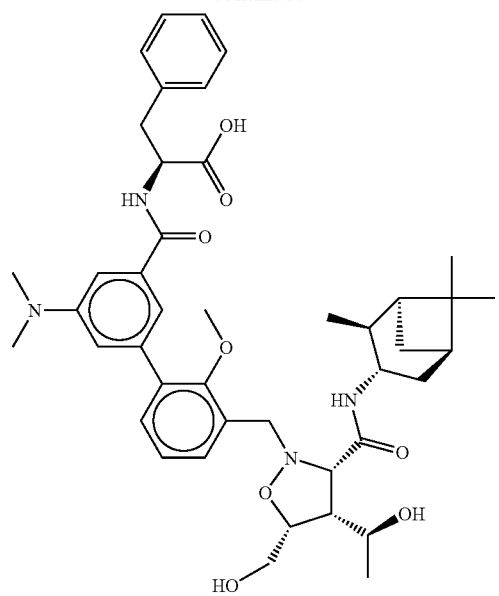
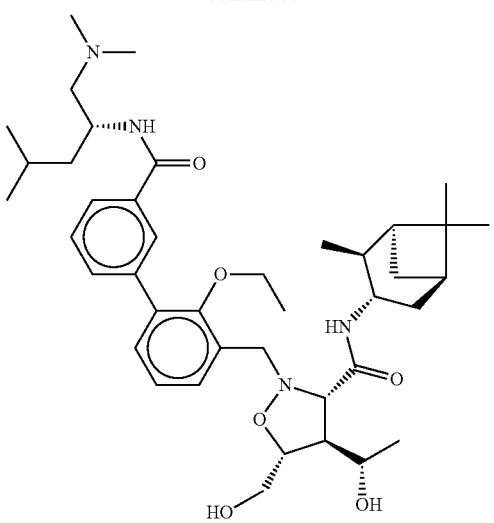
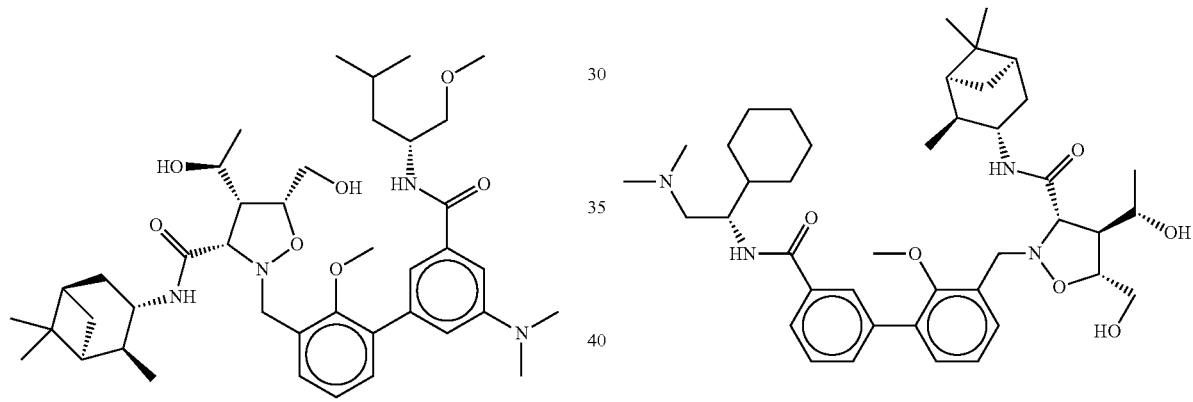
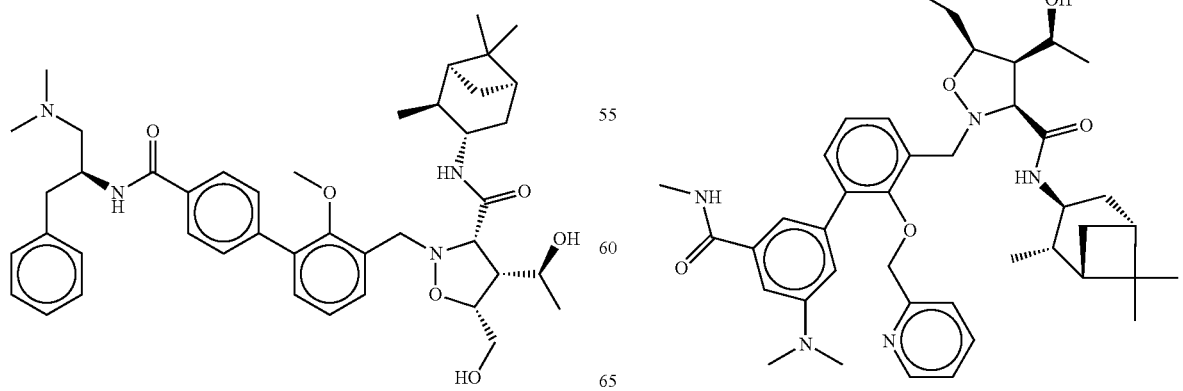

91
-continued
92
-continued
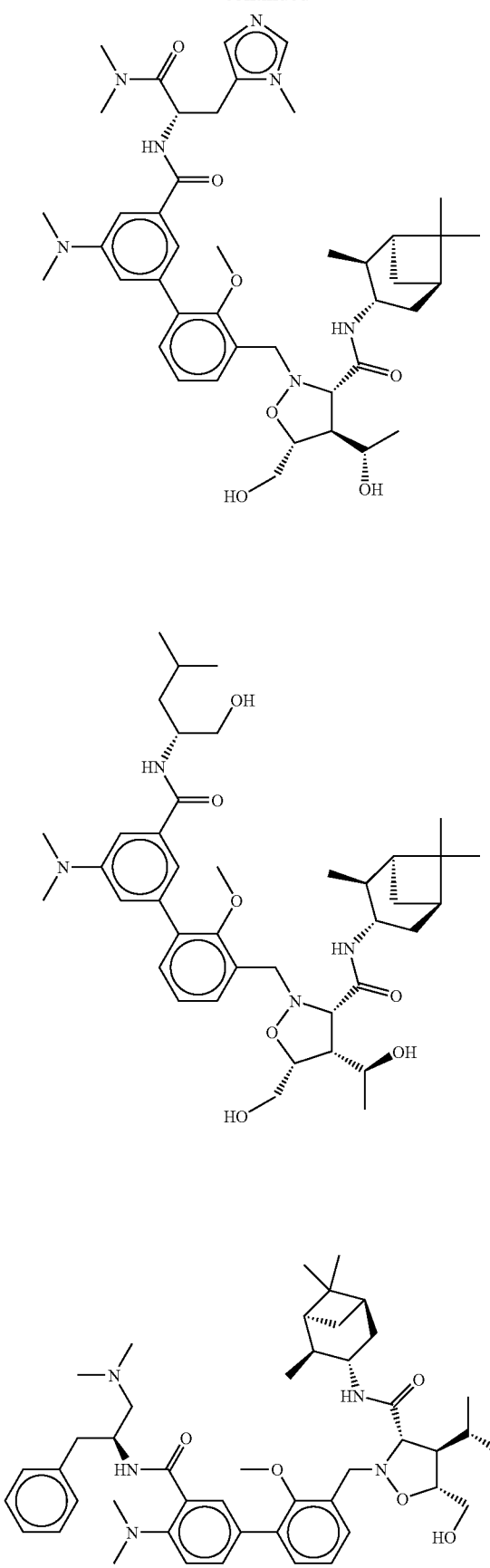
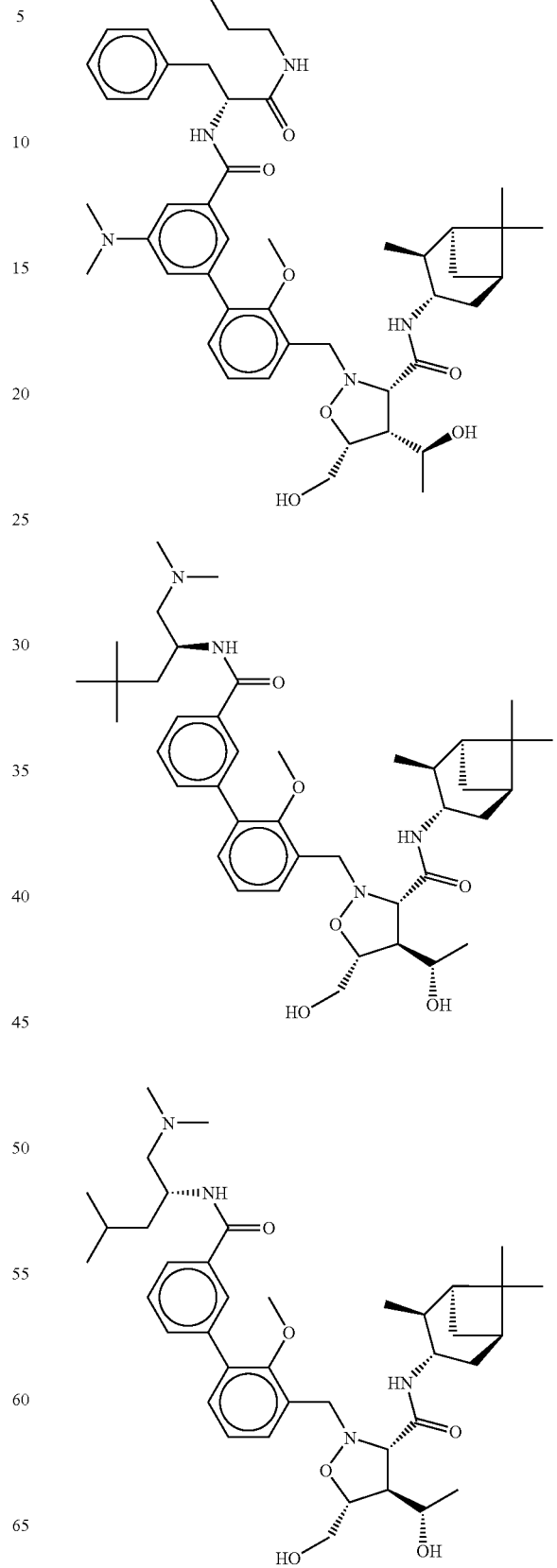

93
-continued
94
-continued
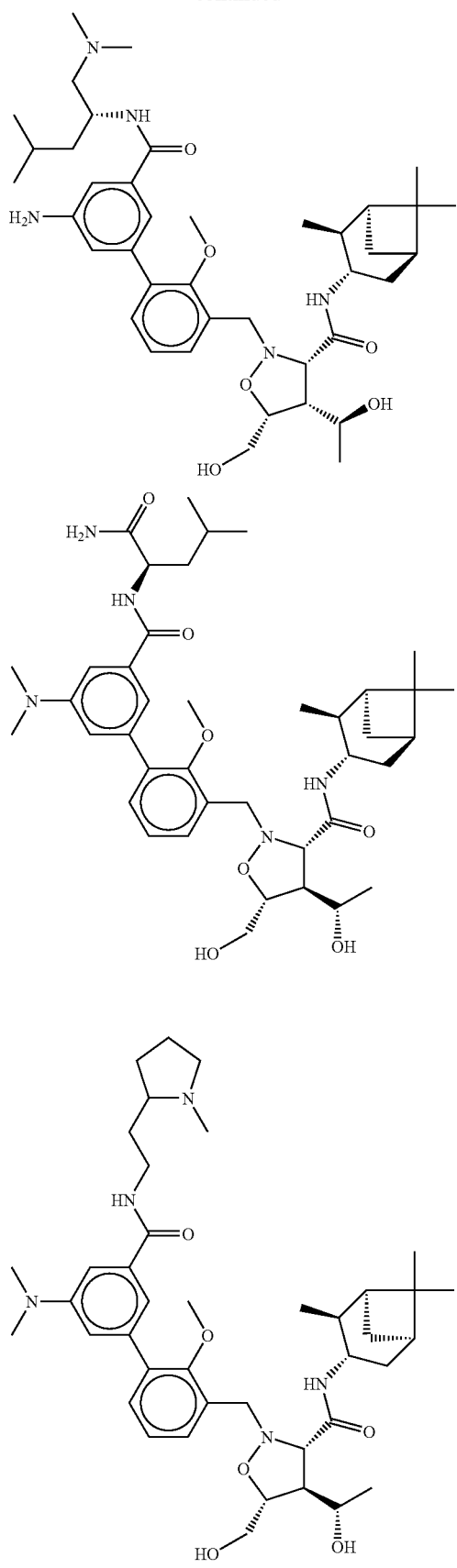
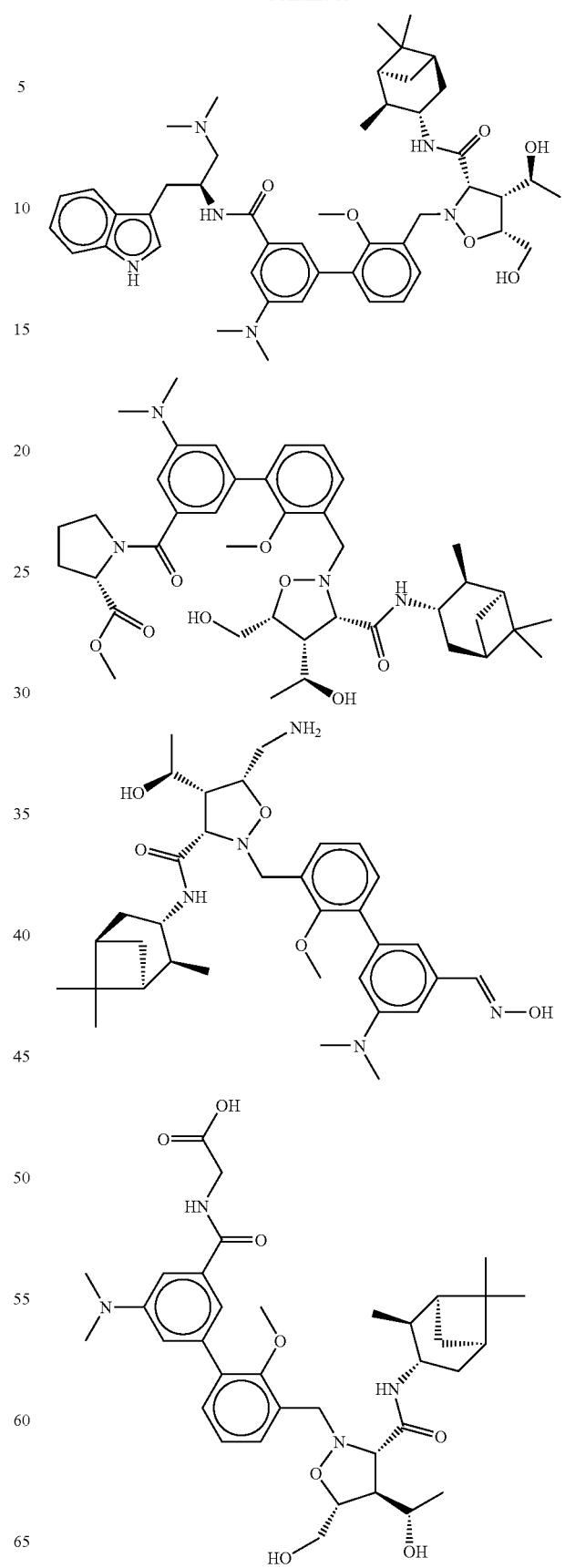

95
-continued
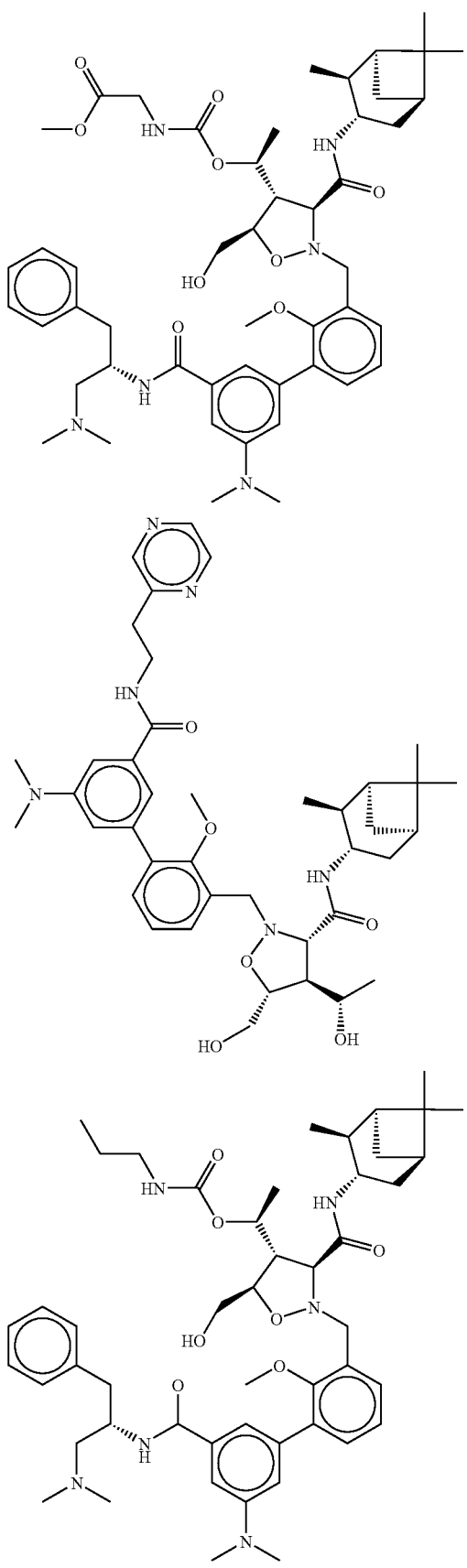
96
-continued
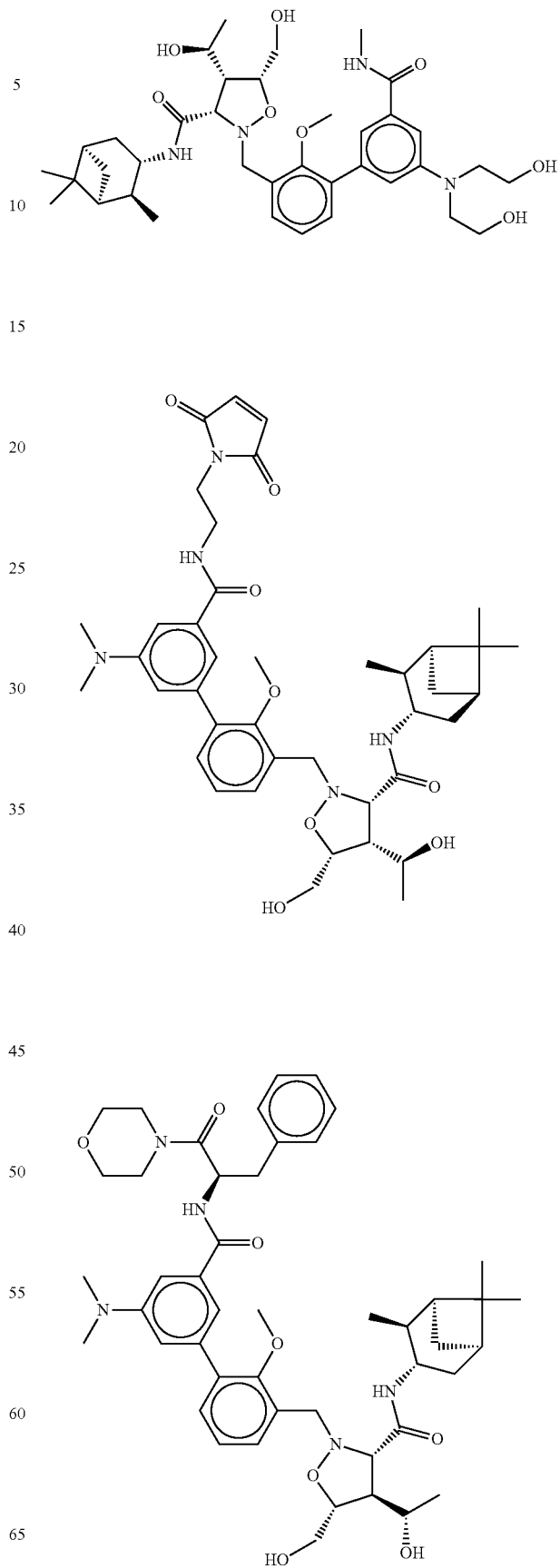

97
-continued
98
-continued
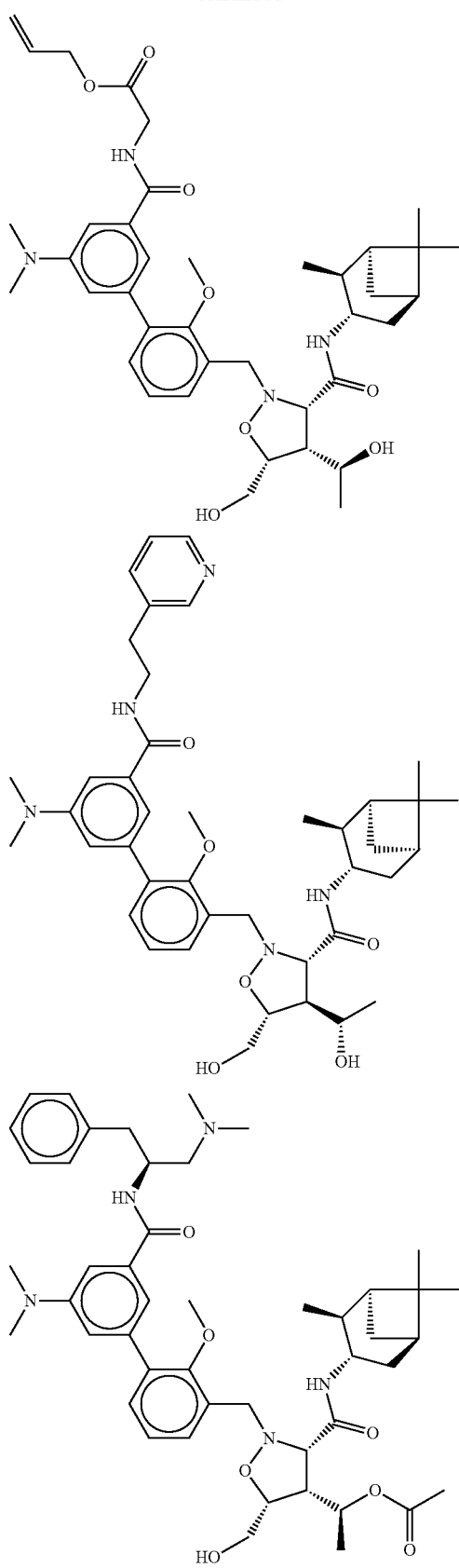
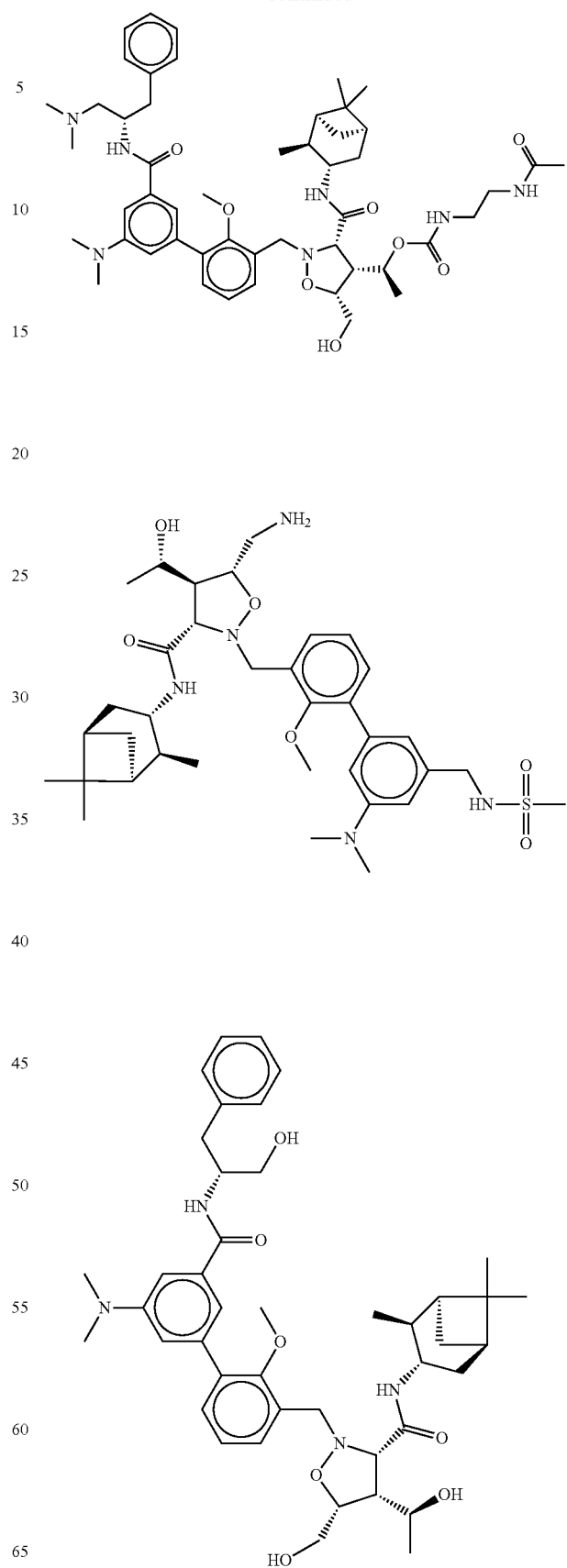

99
-continued
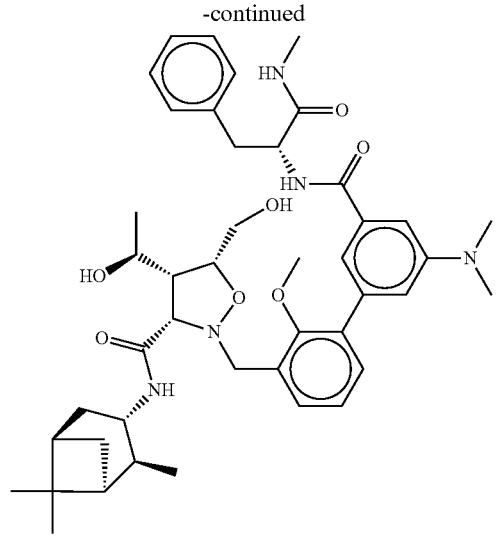
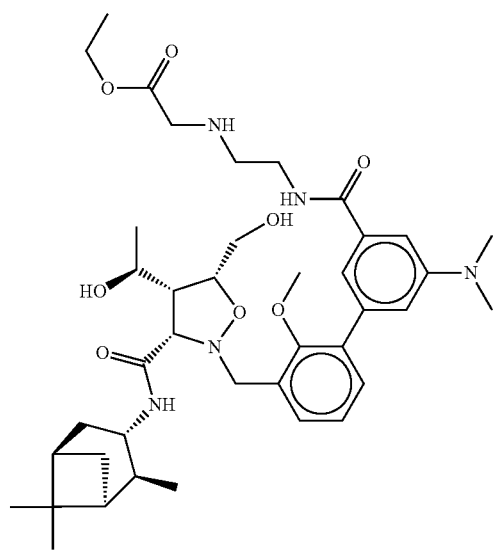
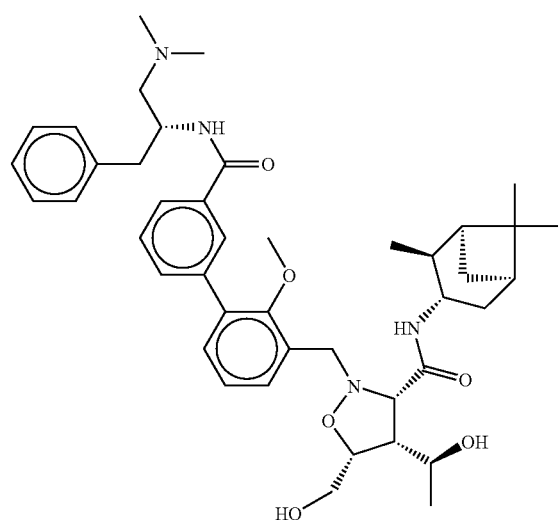
100
-continued
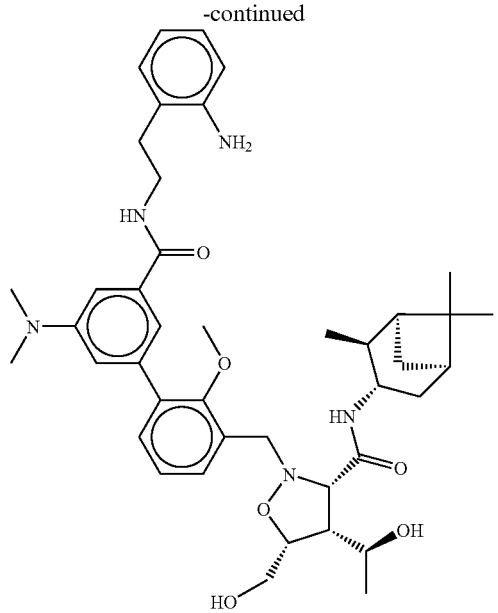
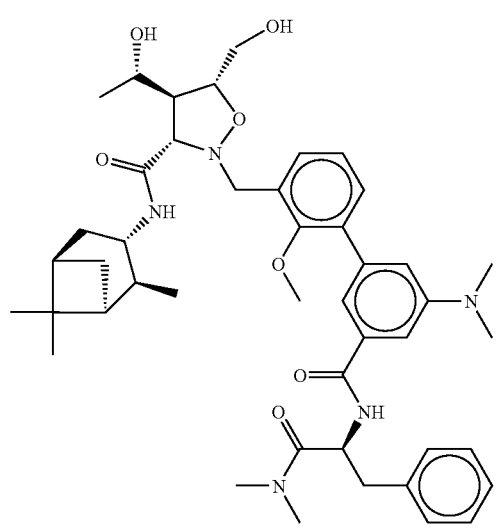
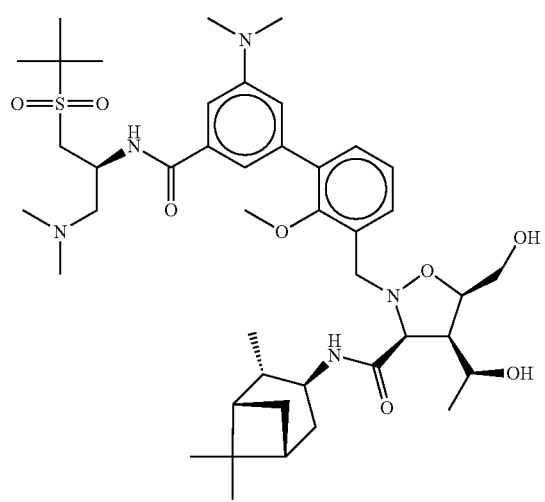

101
-continued
102
-continued
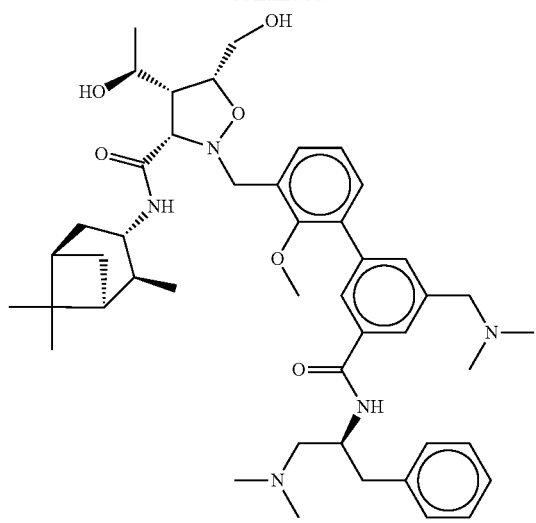
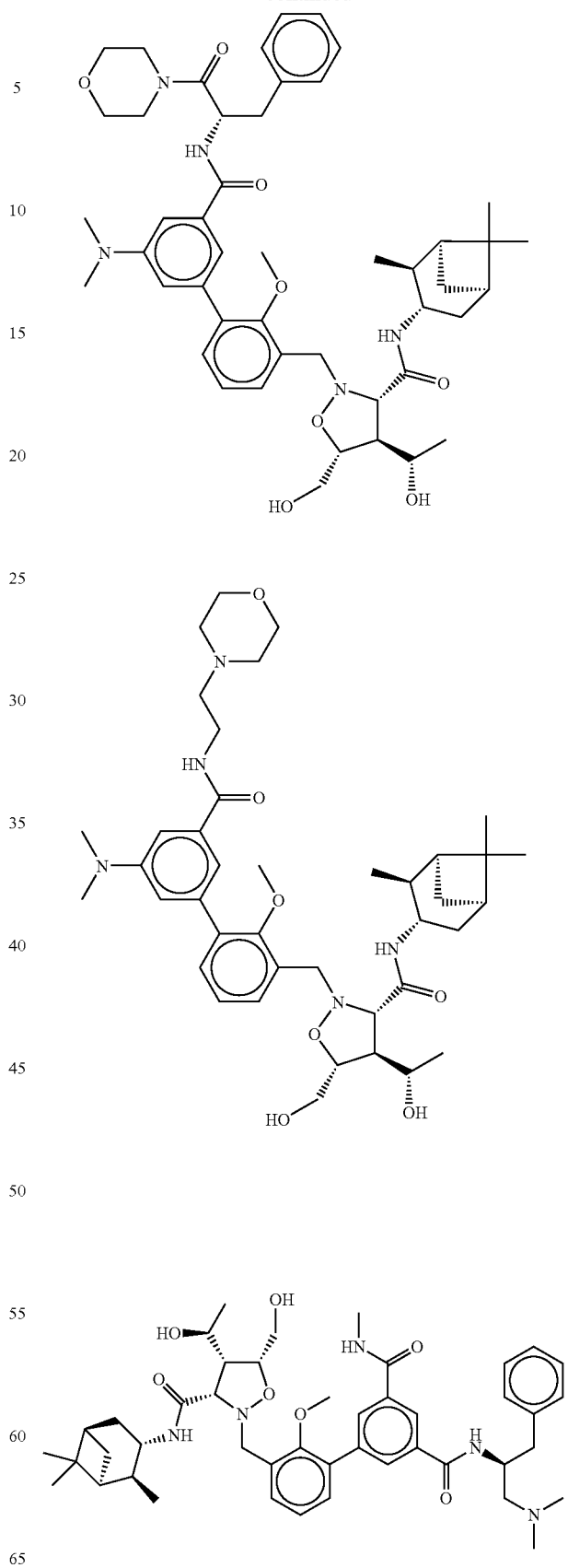

103
-continued
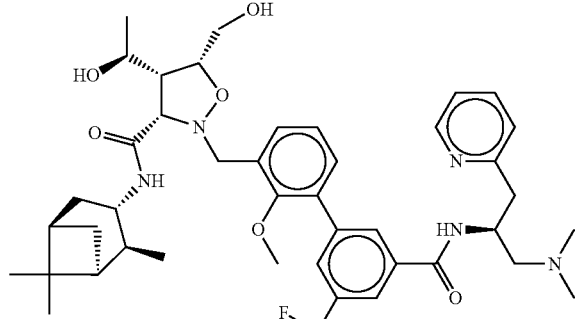
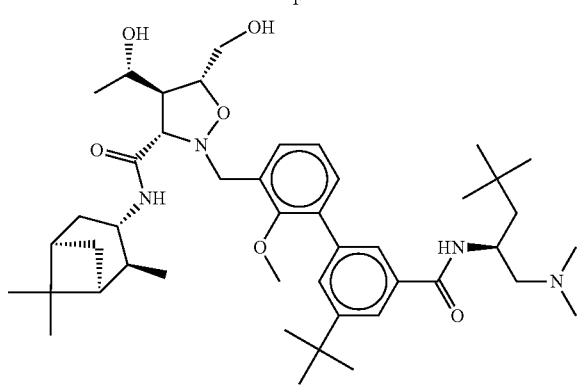
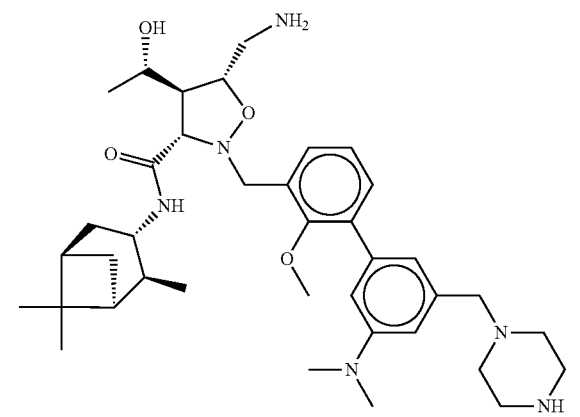
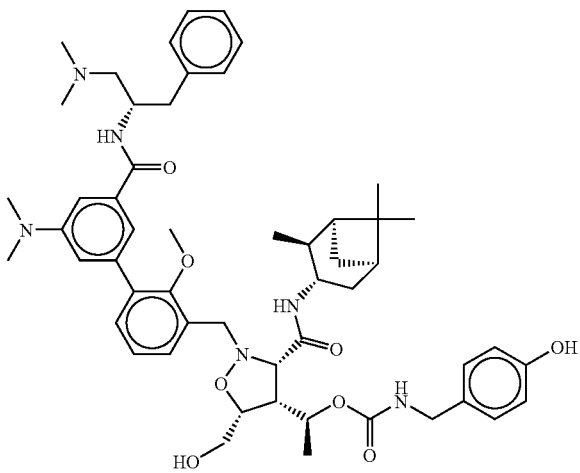
104
-continued
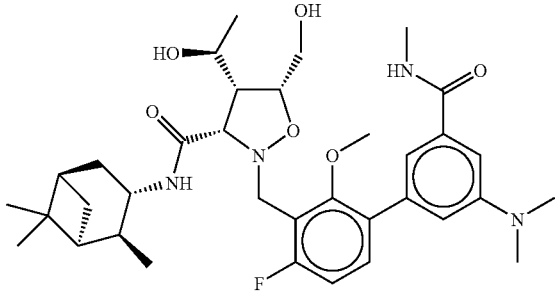
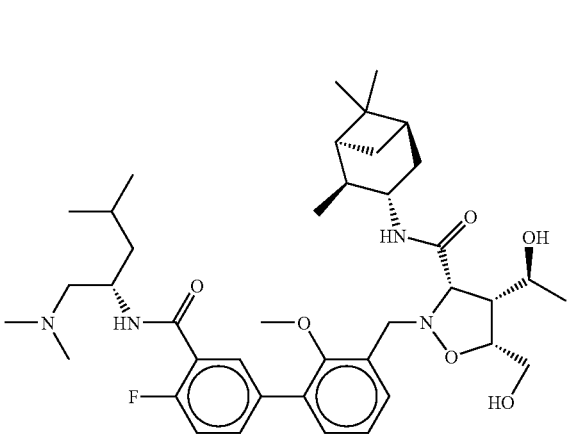
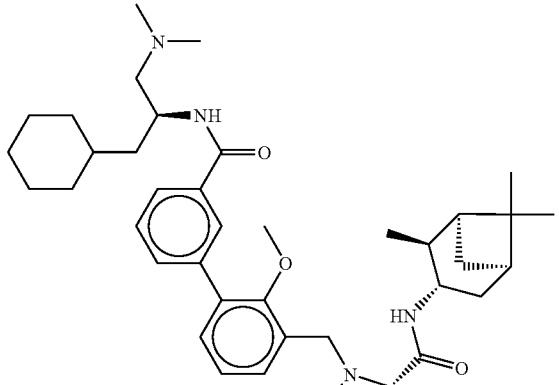

105
-continued
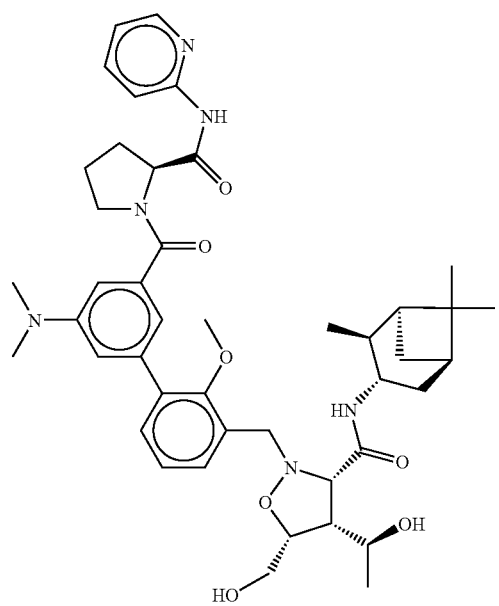
106
-continued
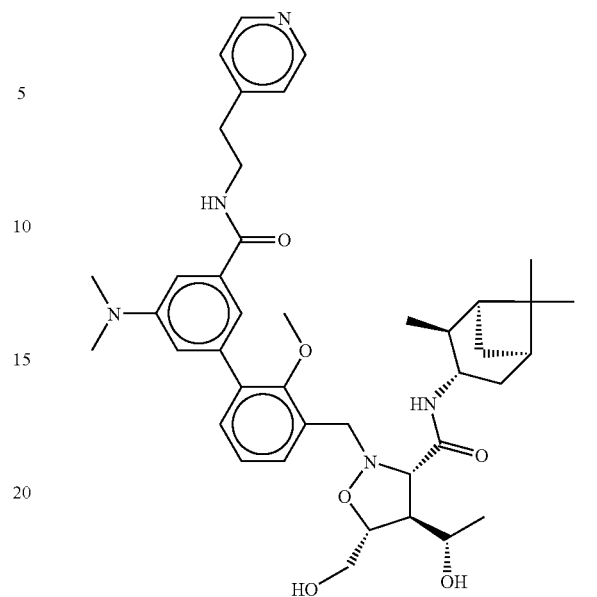
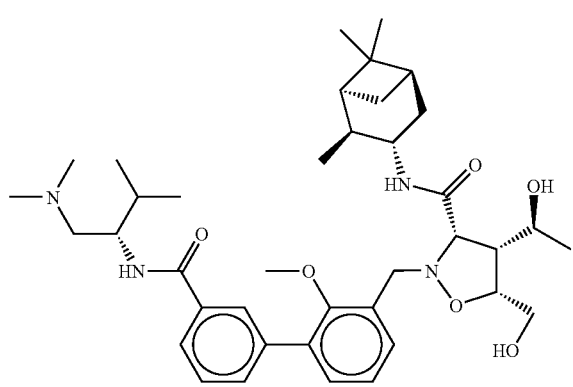
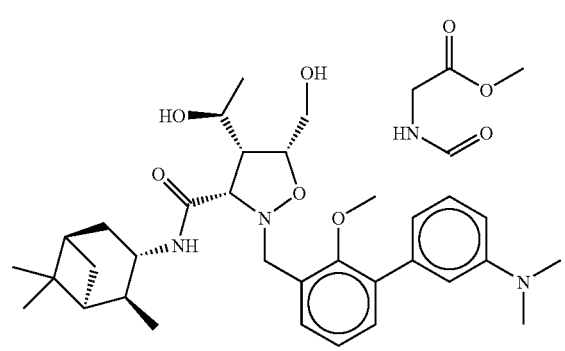
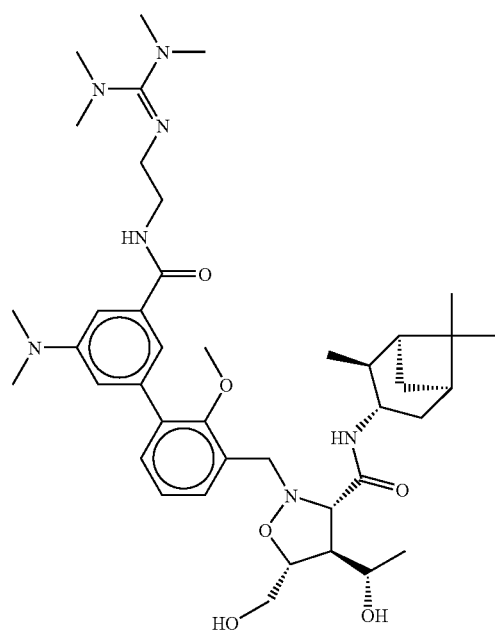
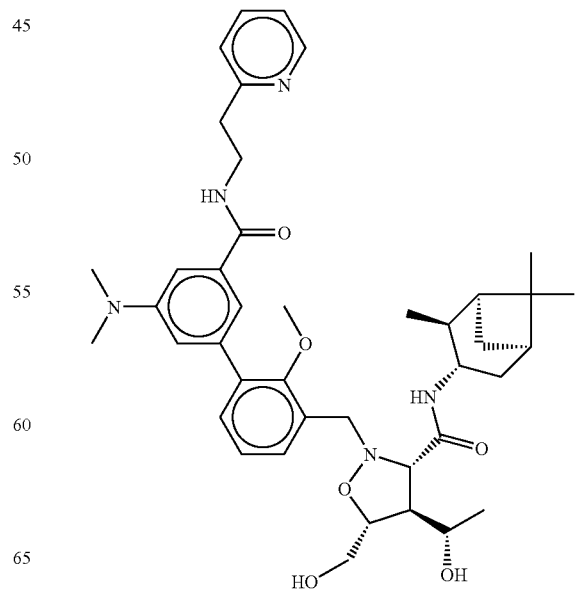

107
-continued
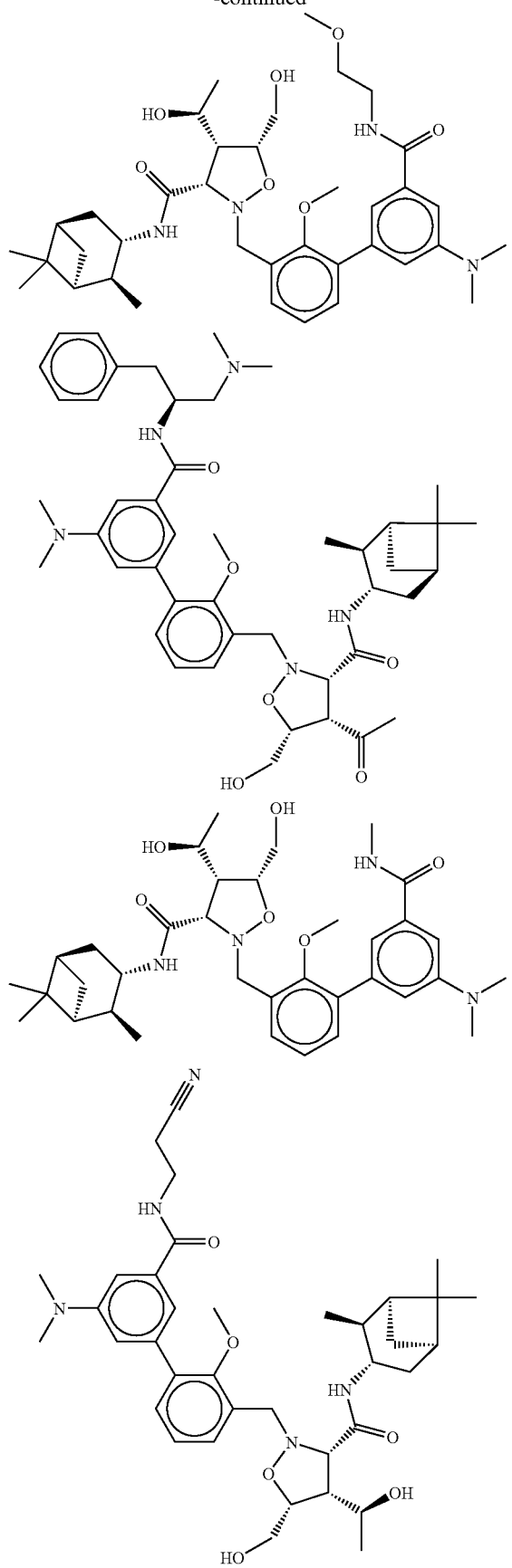
108
-continued
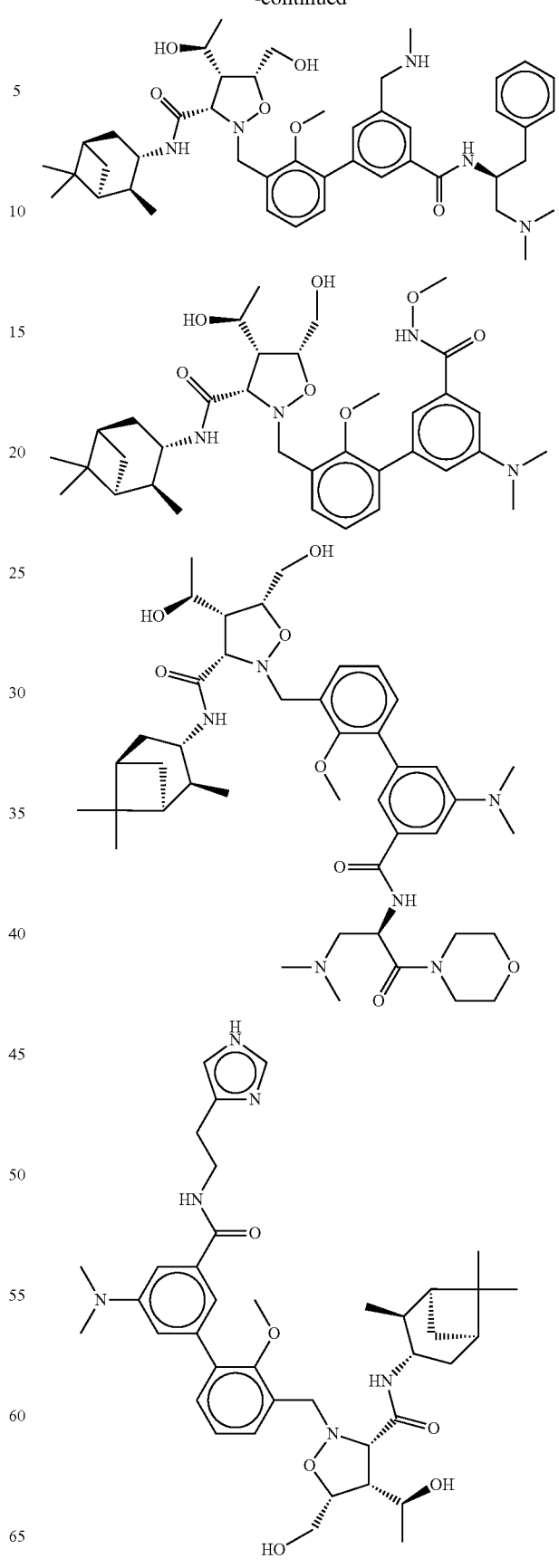

109
-continued
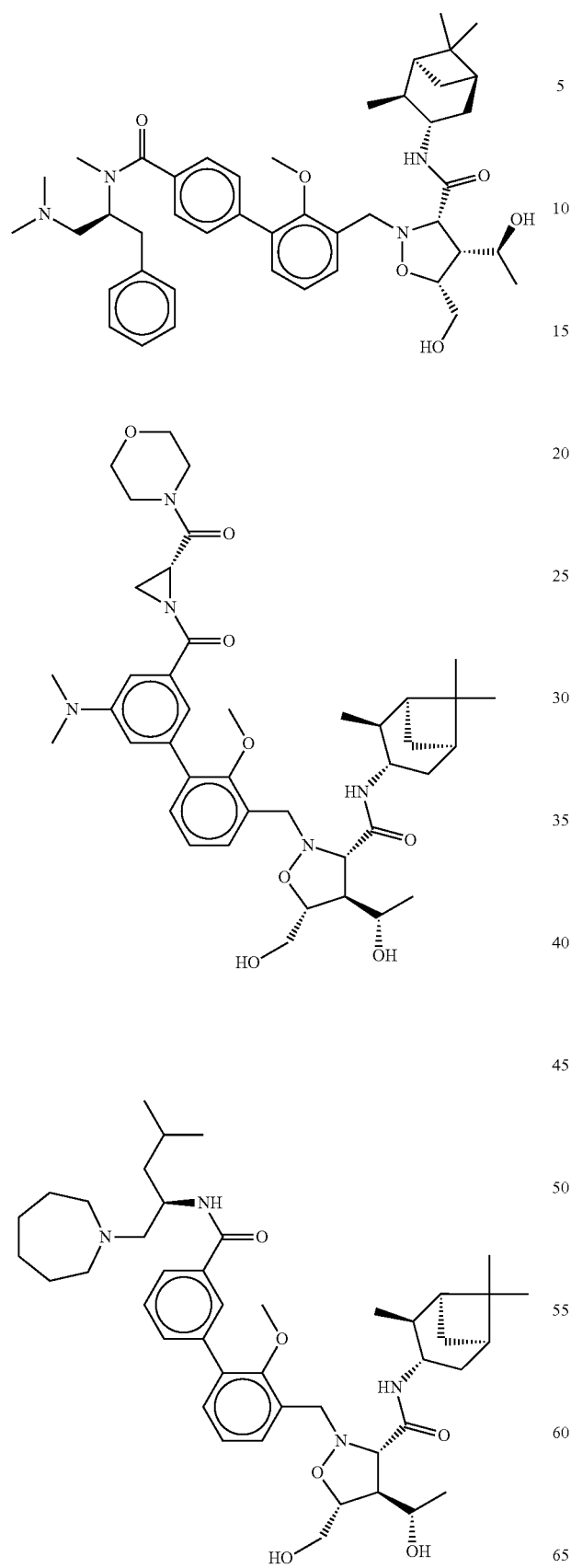
110
-continued
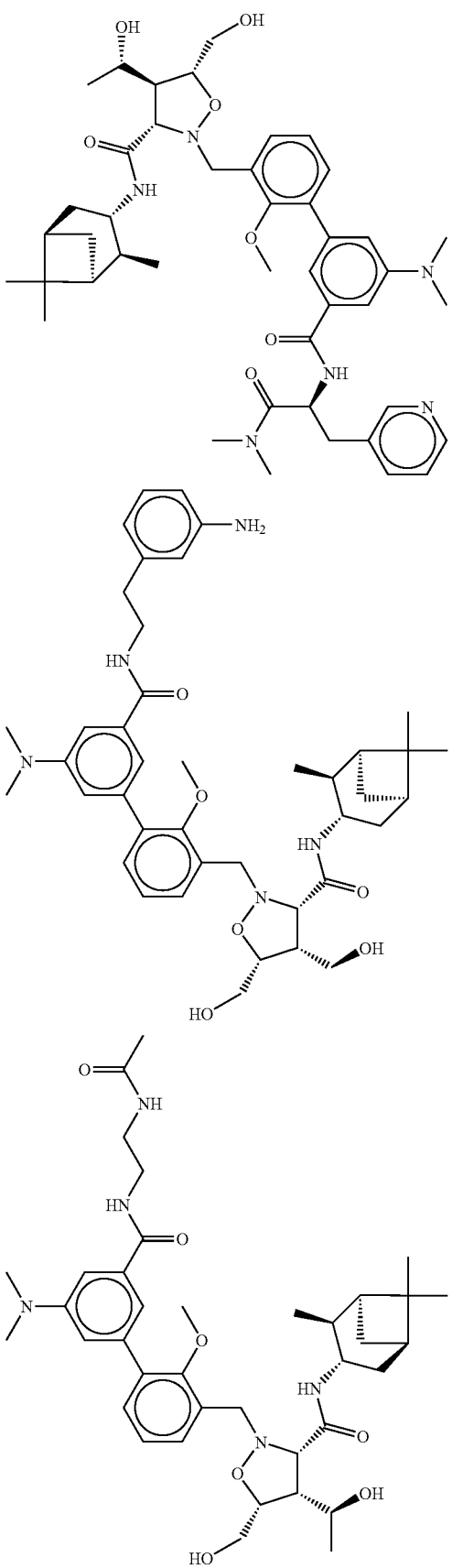

111
-continued
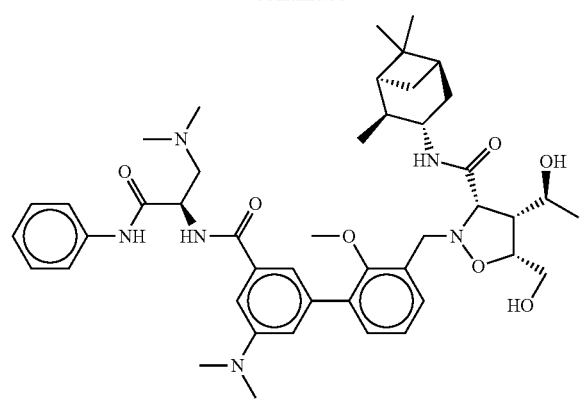
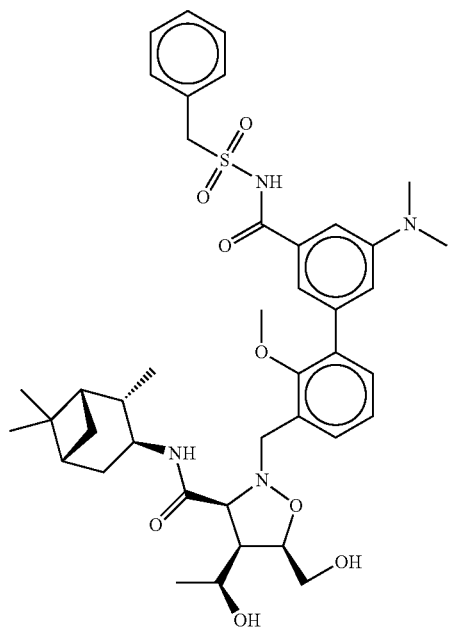
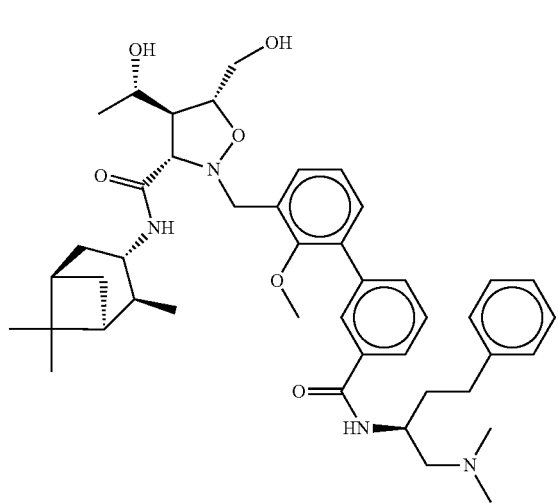
112
-continued
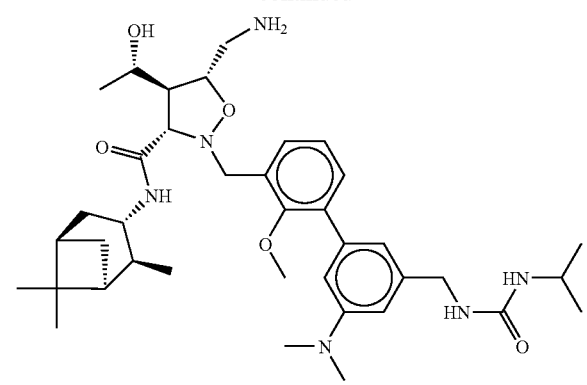
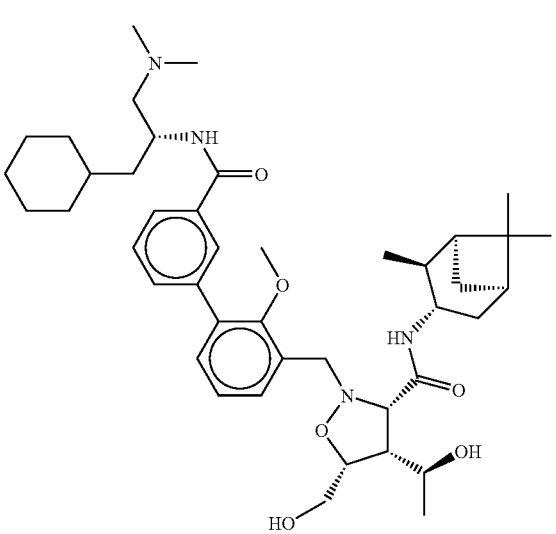
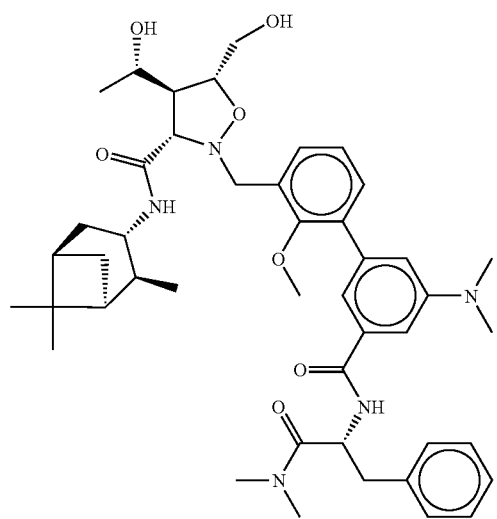

113
-continued
114
-continued
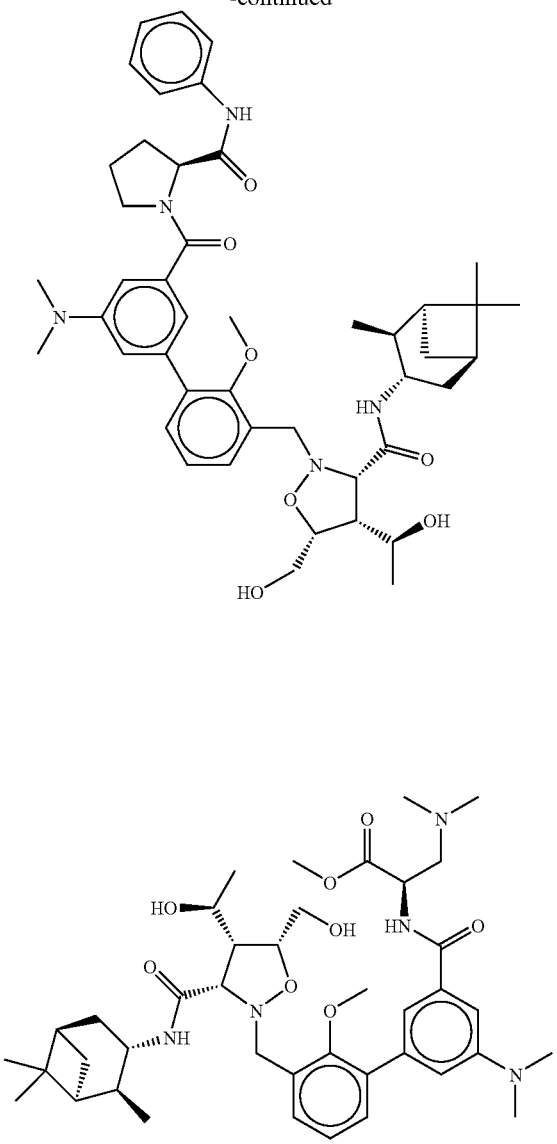
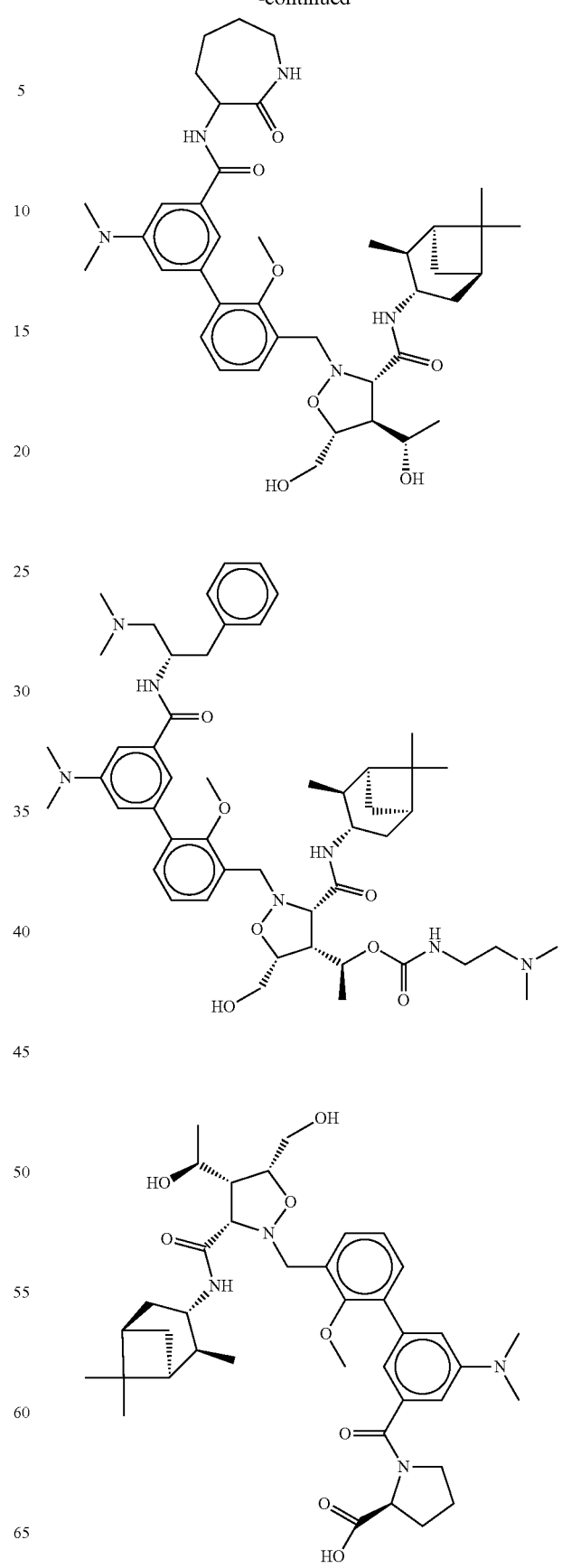

115
-continued
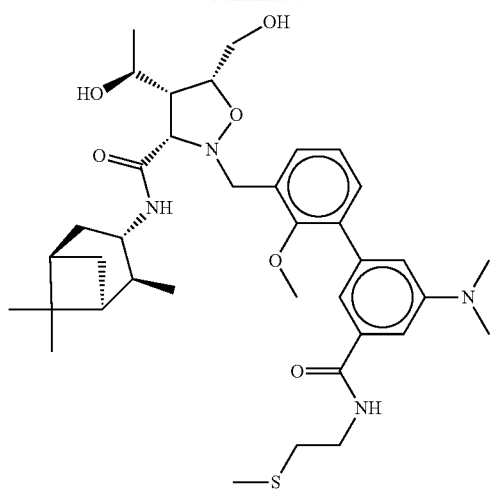
116
-continued
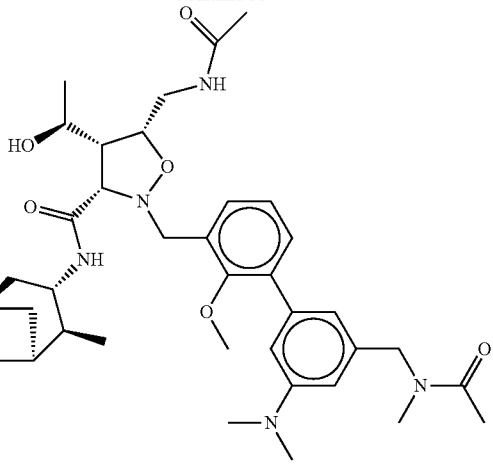
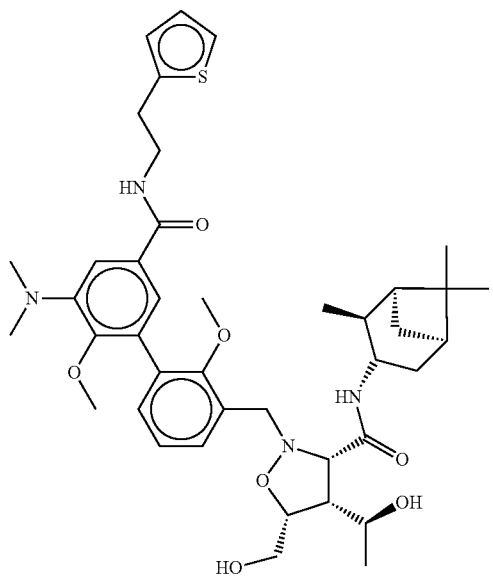
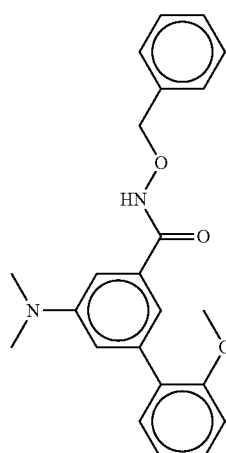
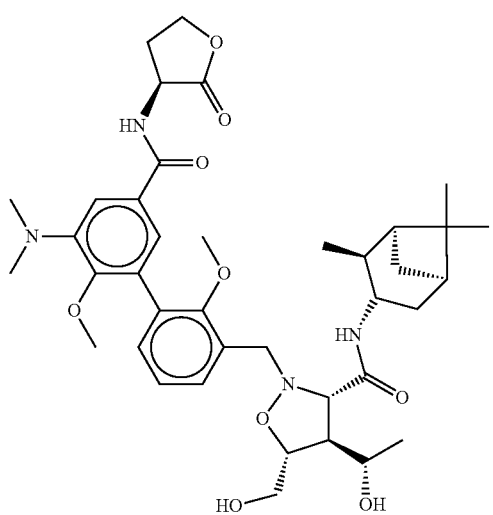
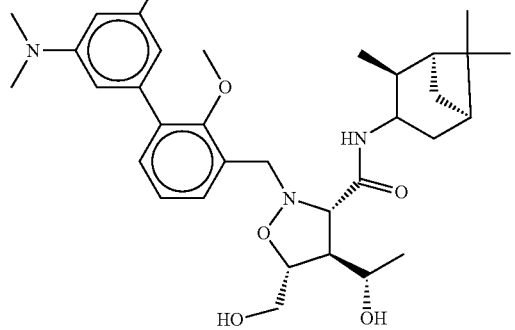

117
118
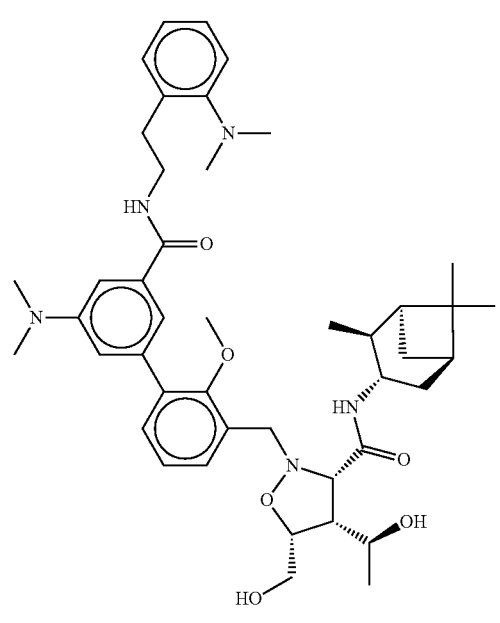
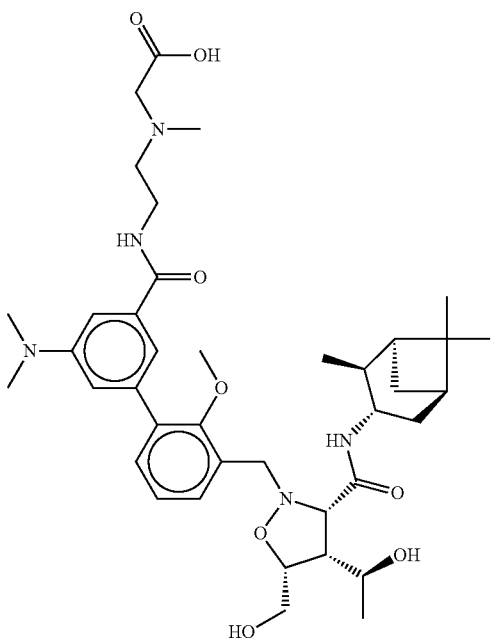
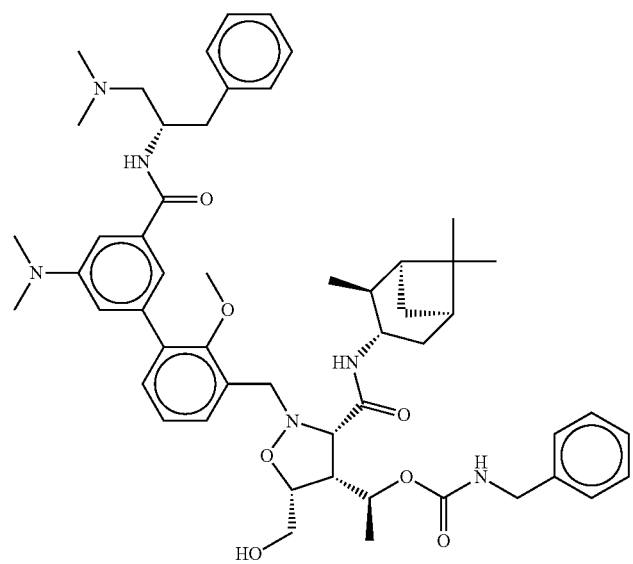
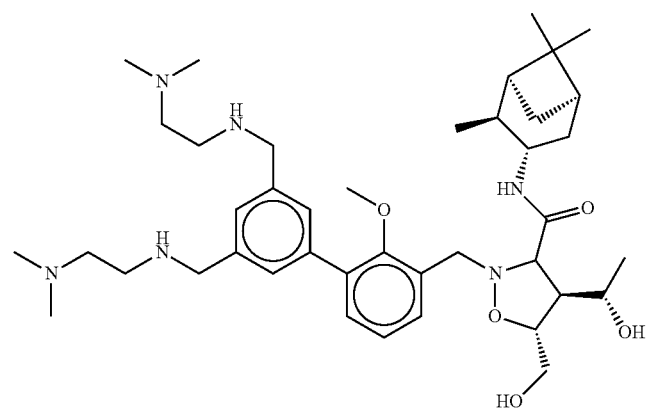

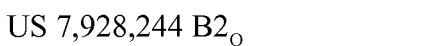
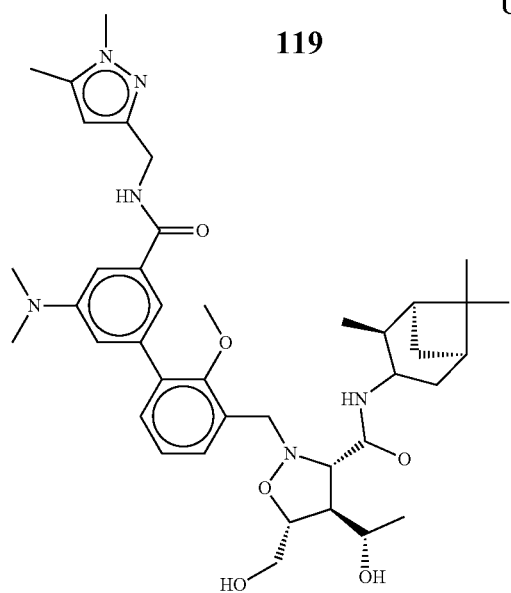
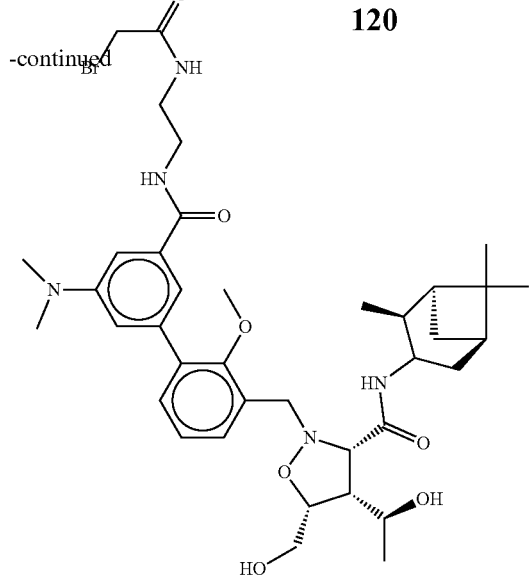
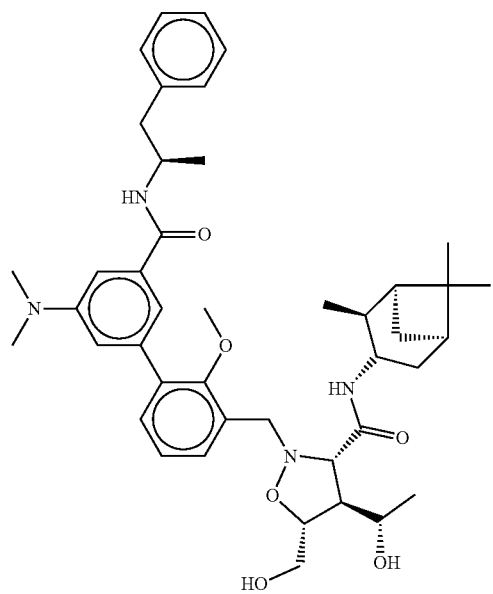
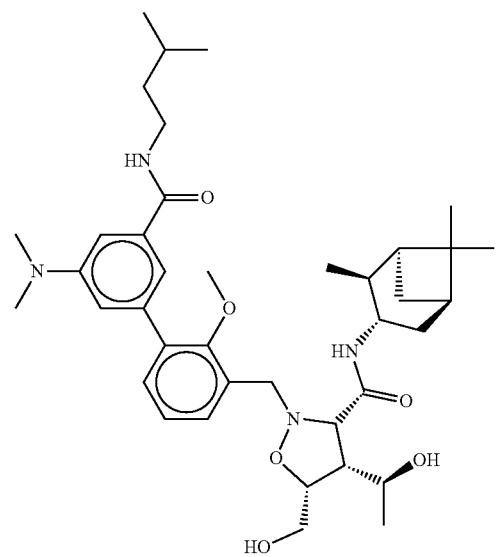
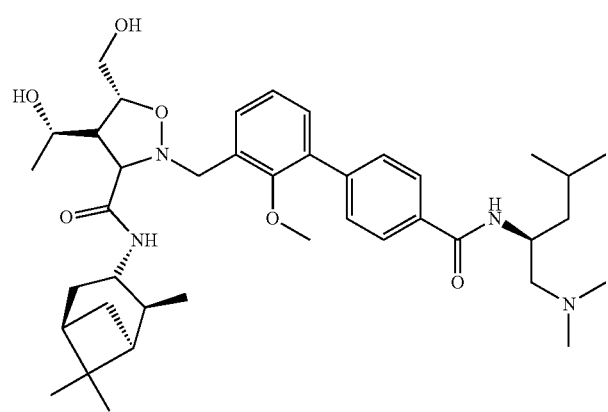

-continued
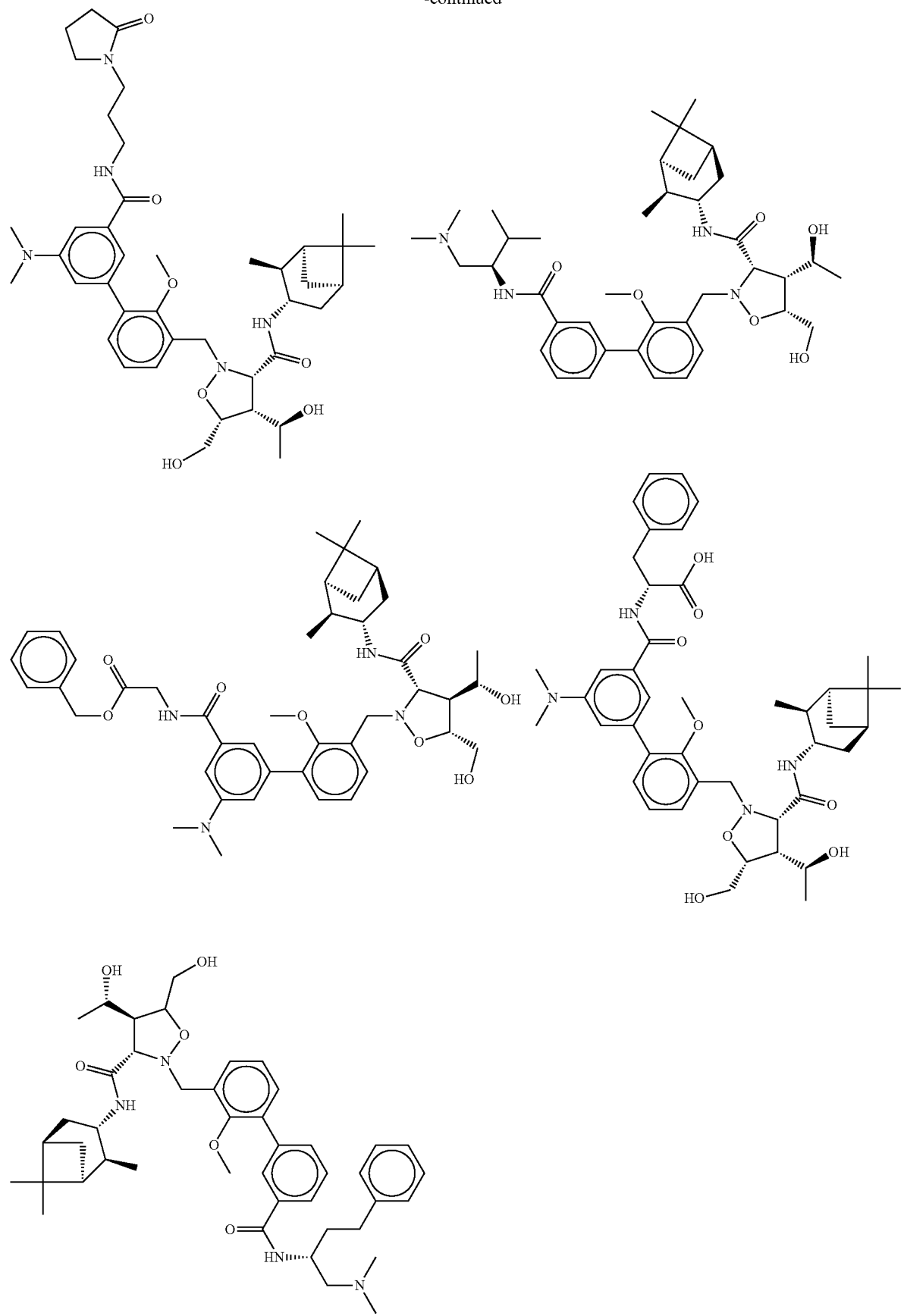

-continued
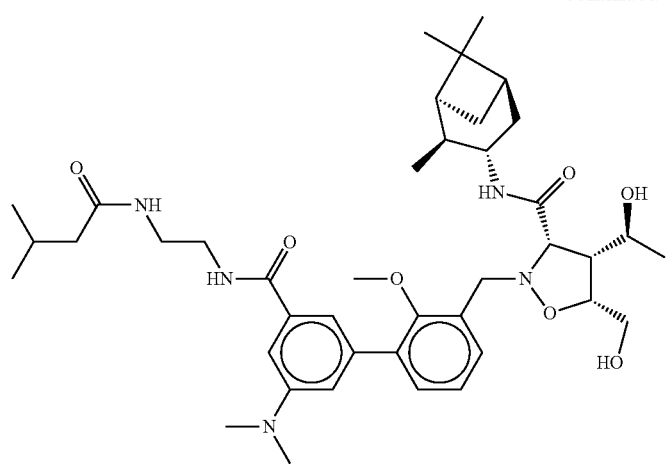
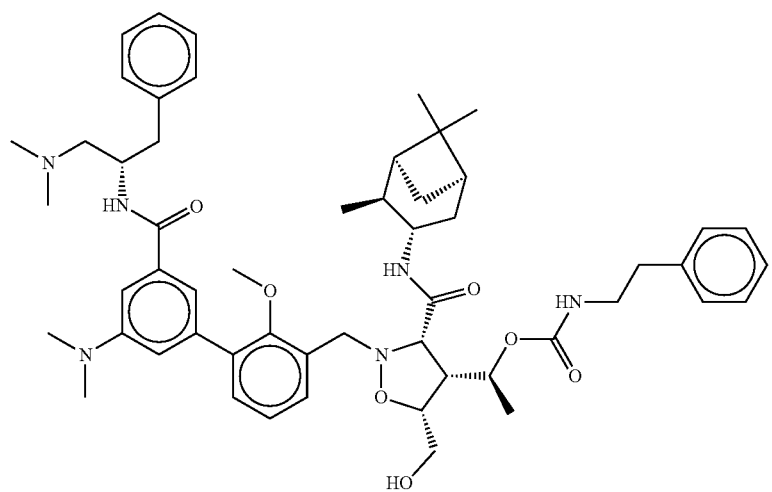
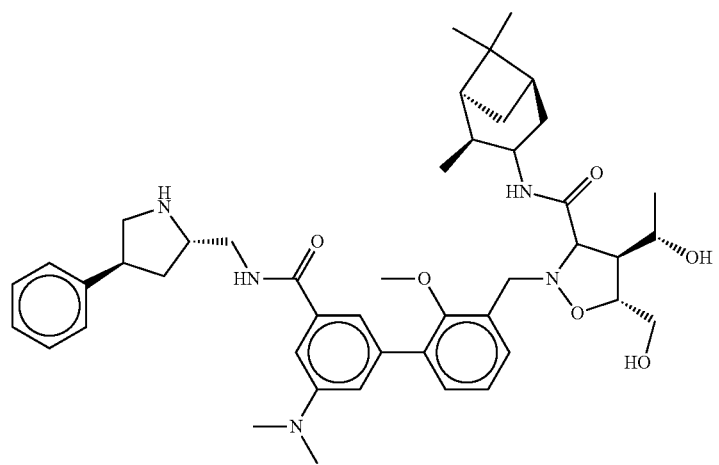

-continued
125
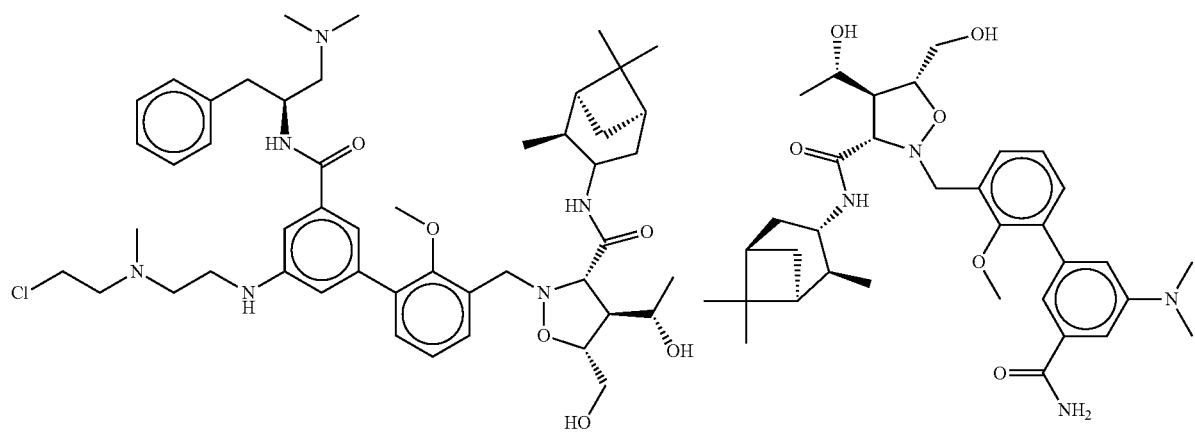
126
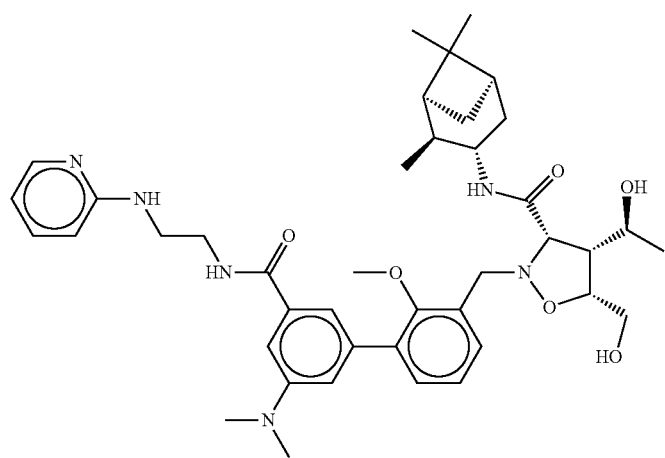

127    128
-continued
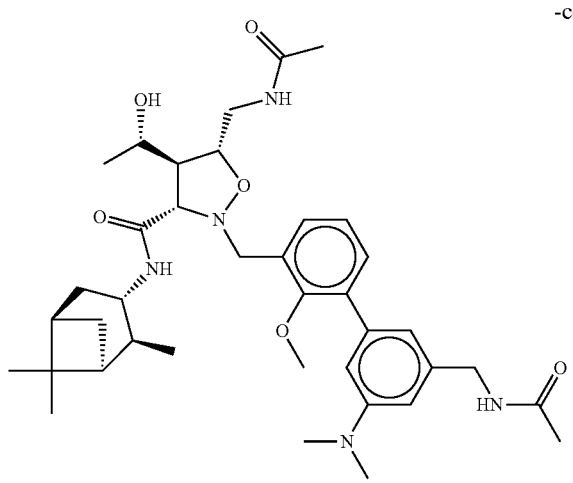
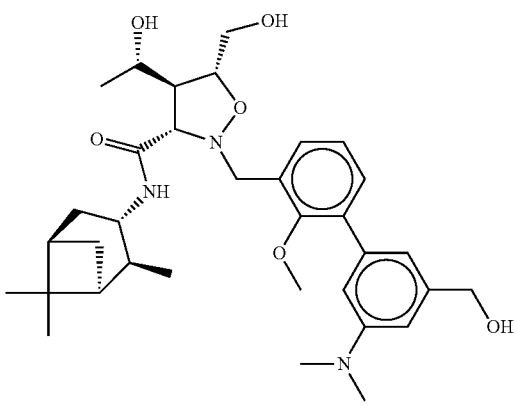
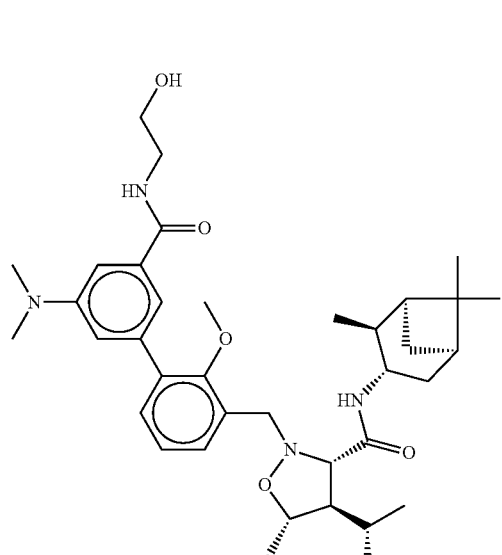
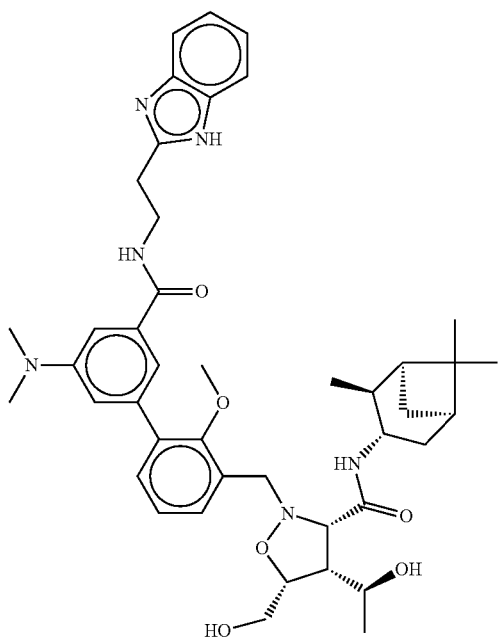
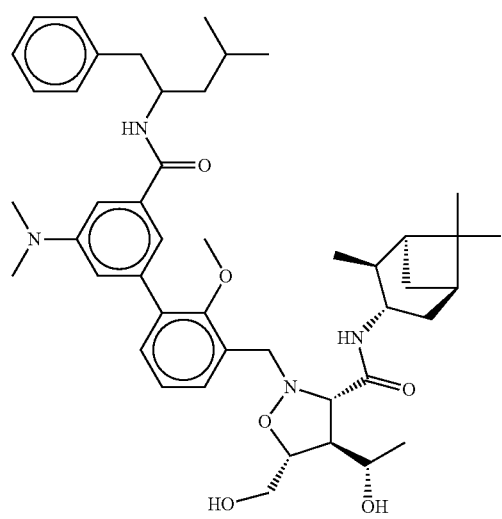
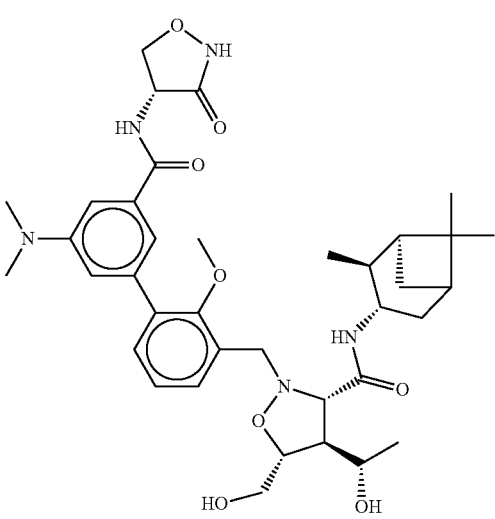

129 130
-continued
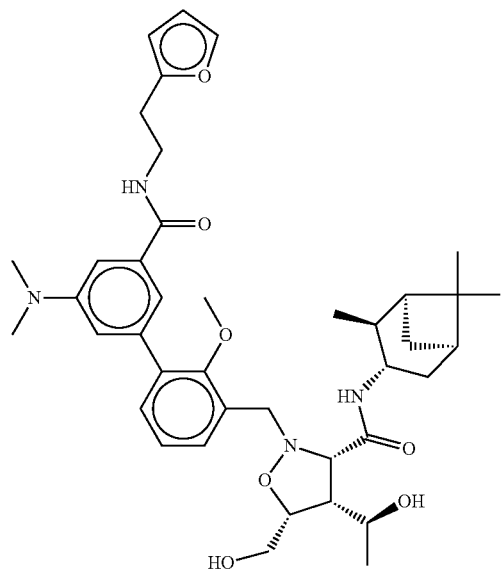
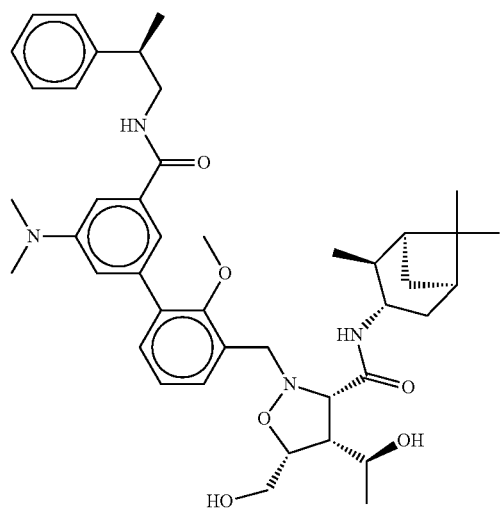
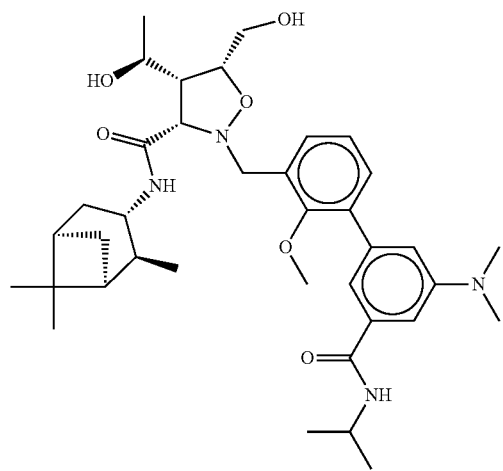
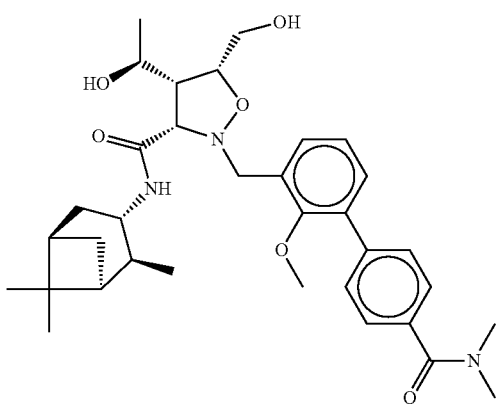
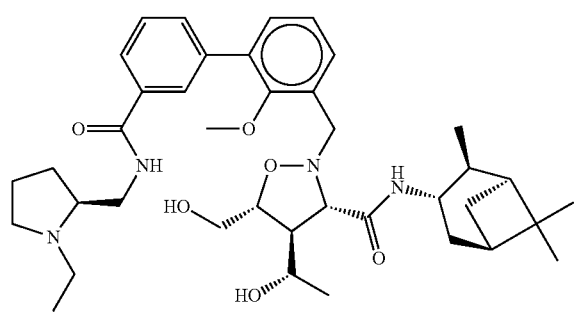
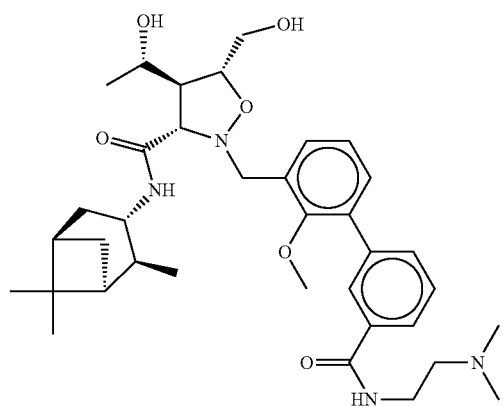

-continued
| 131 | 132 |
|---|---|
| 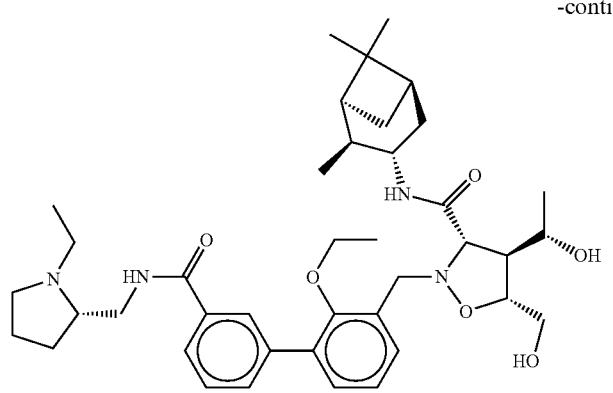 | |
| 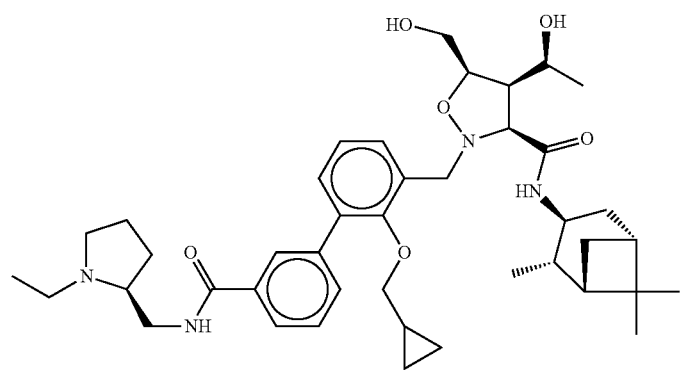 | |
| 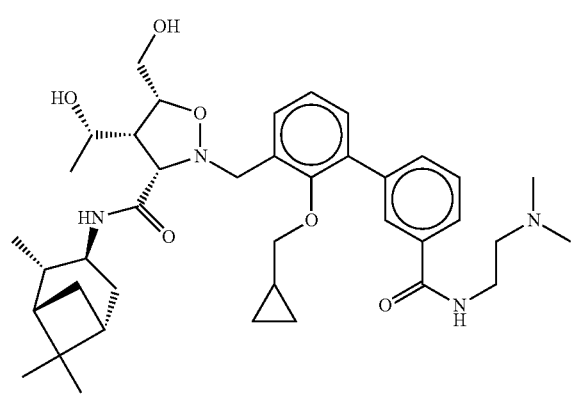 | 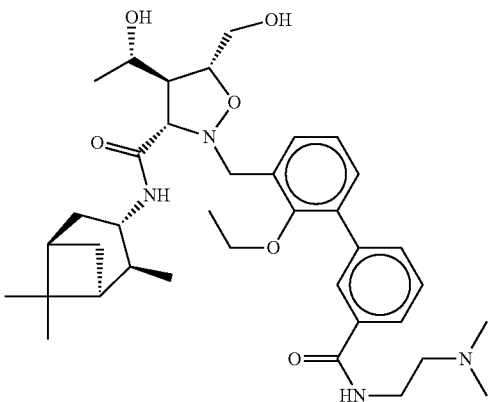 |
| 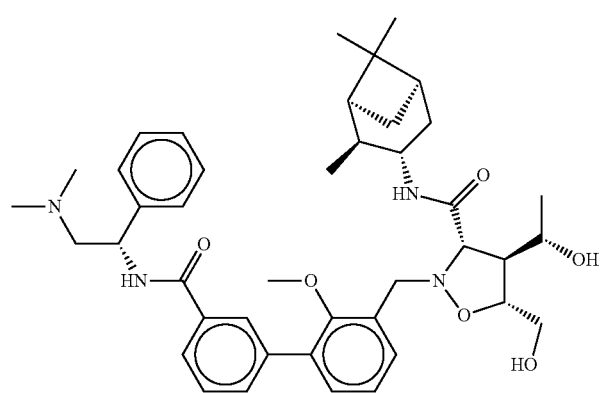 | 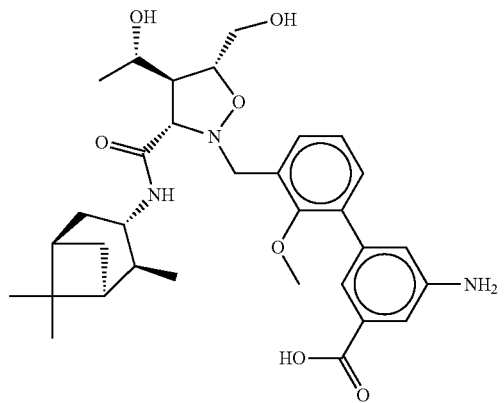 |

-continued
133
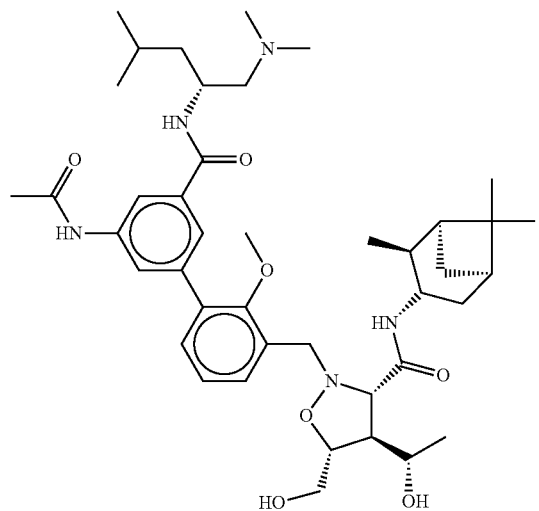
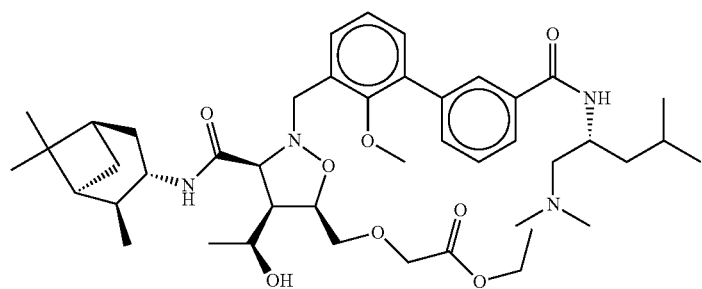
134
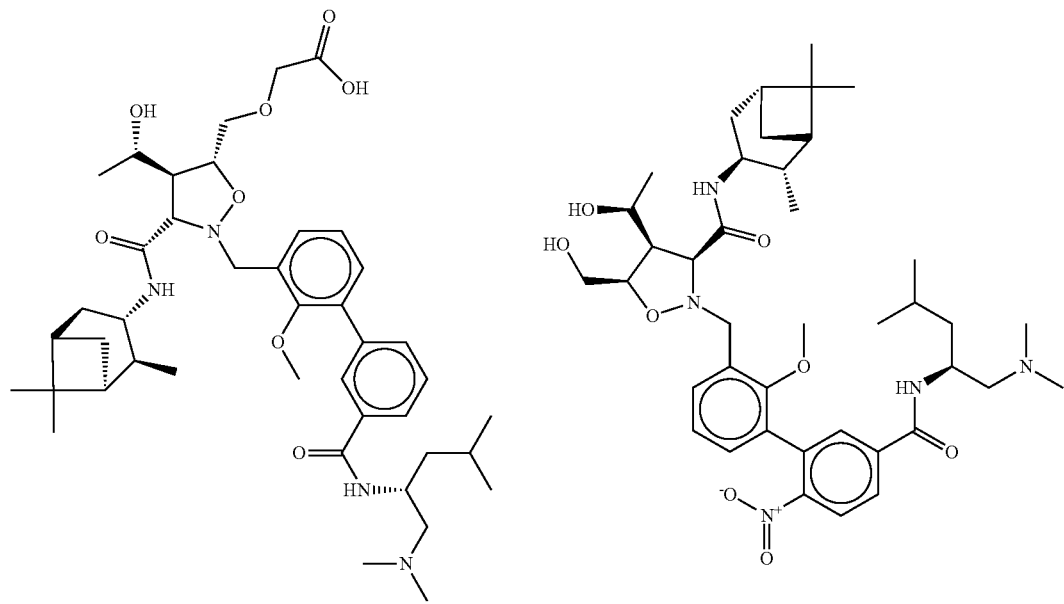

135
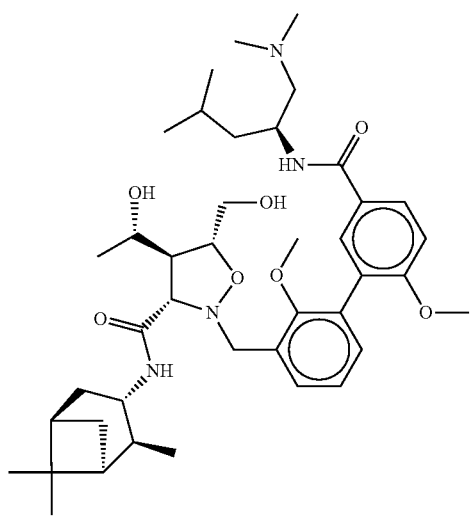
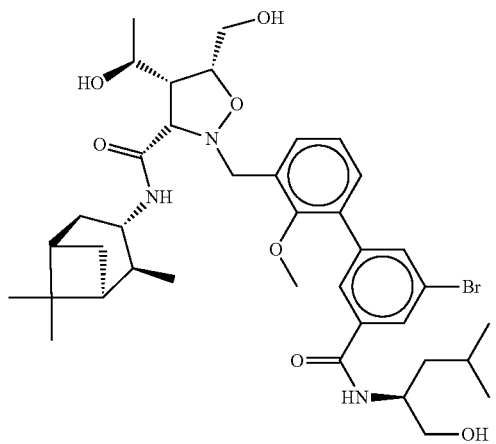
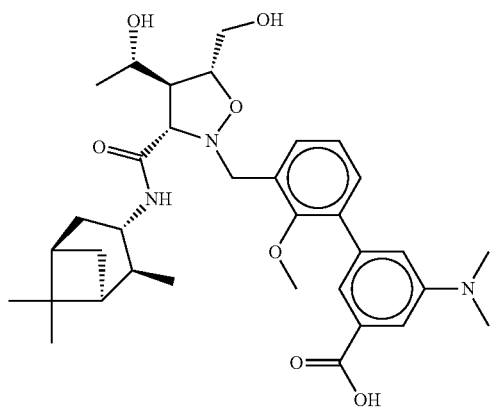
136
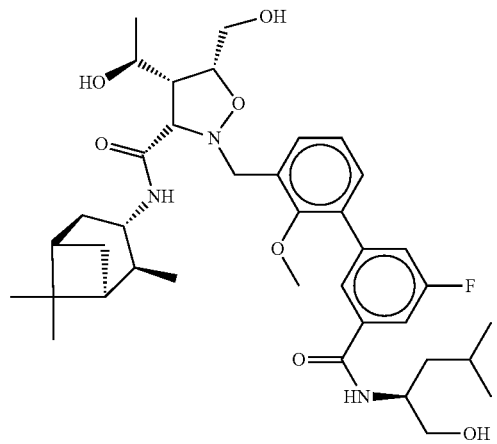
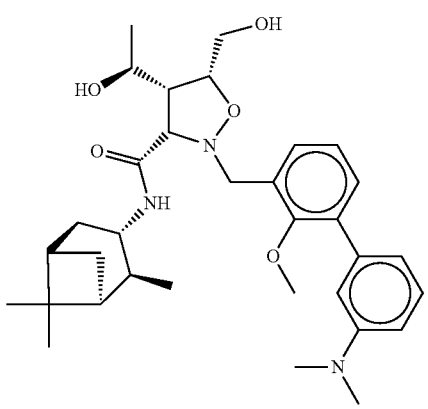
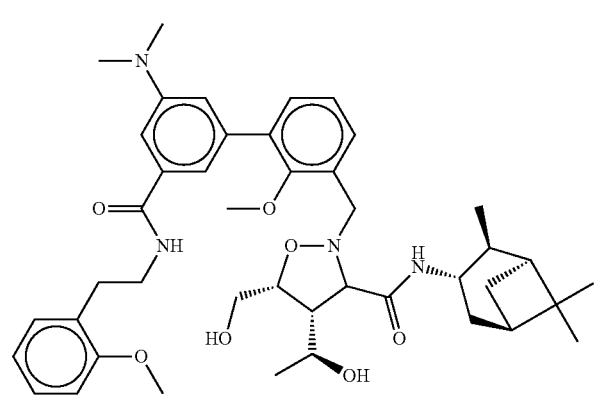

-continued
137
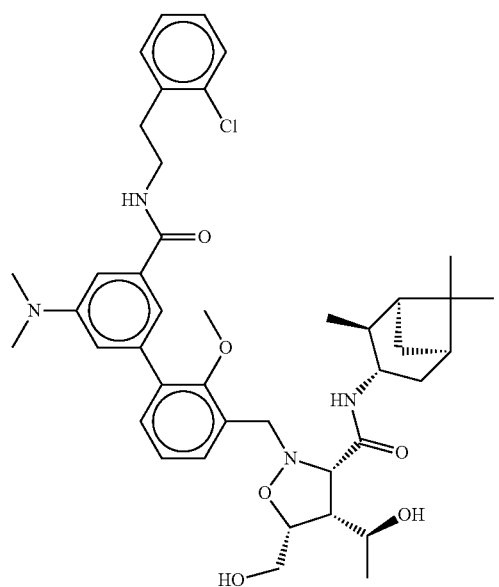
138
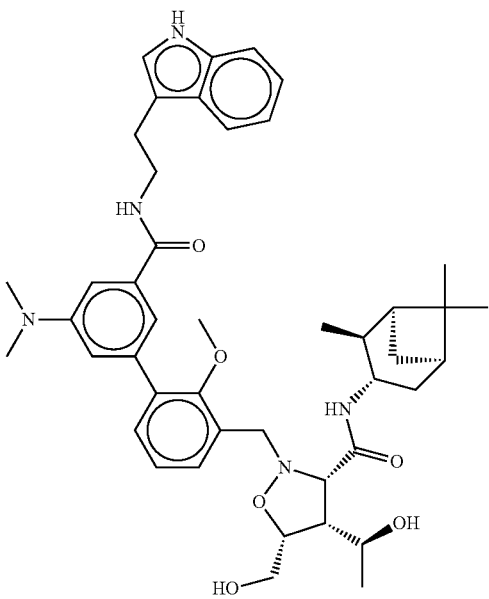
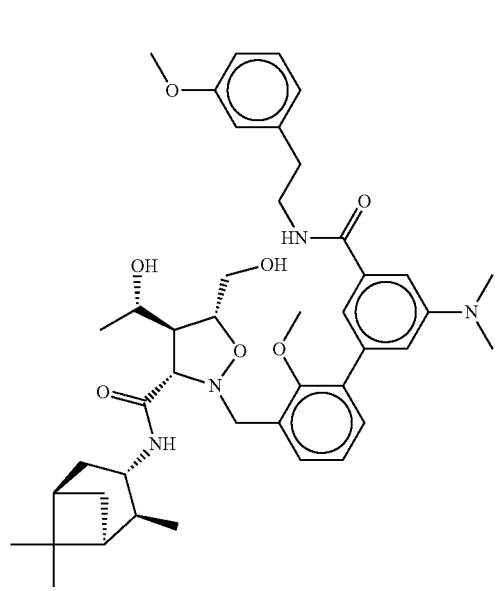
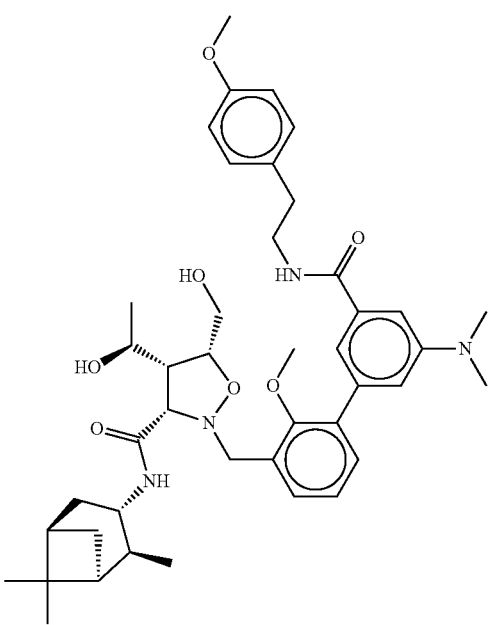

-continued
| 139 | 140 |
|---|---|
| 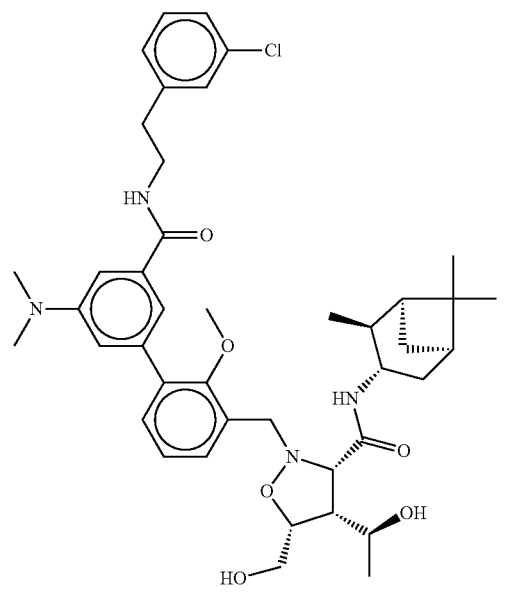 | 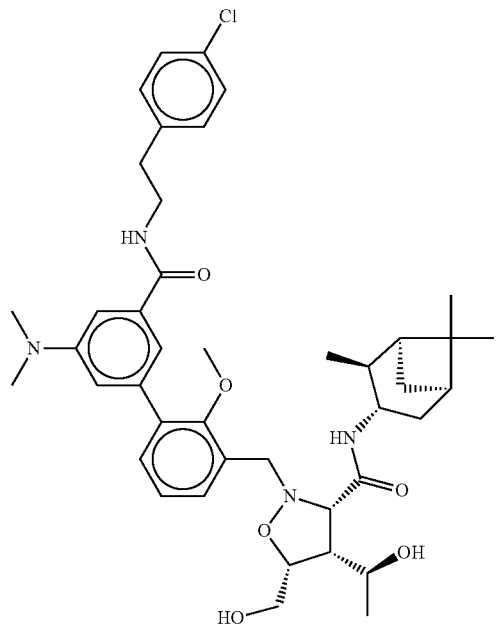 |
| 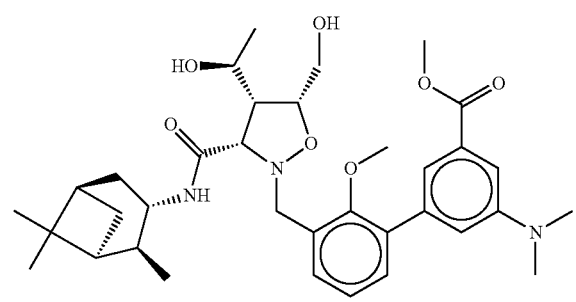 | 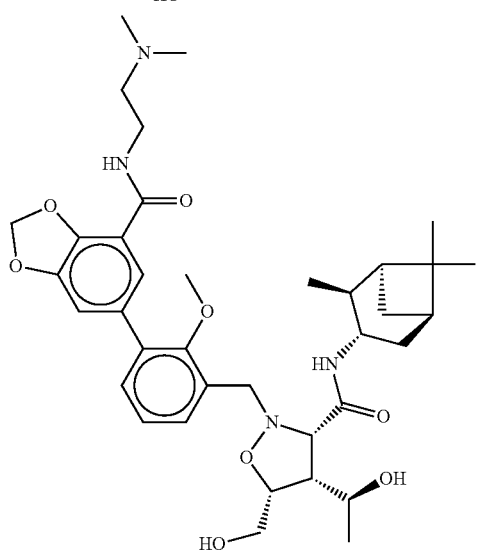 |
| 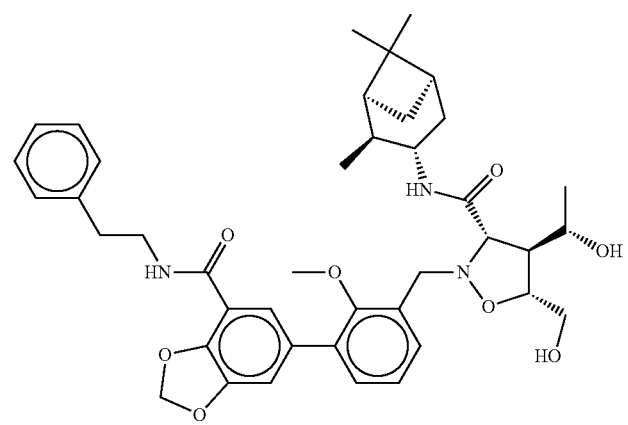 | 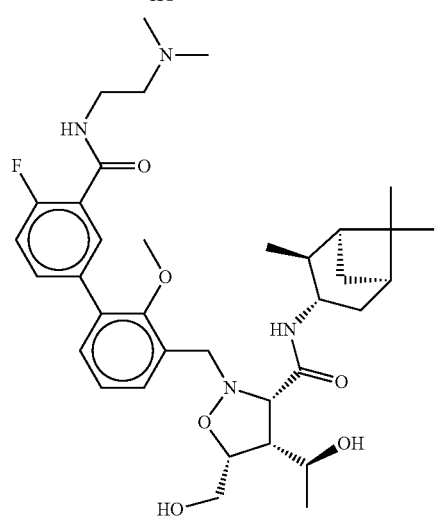 |

141
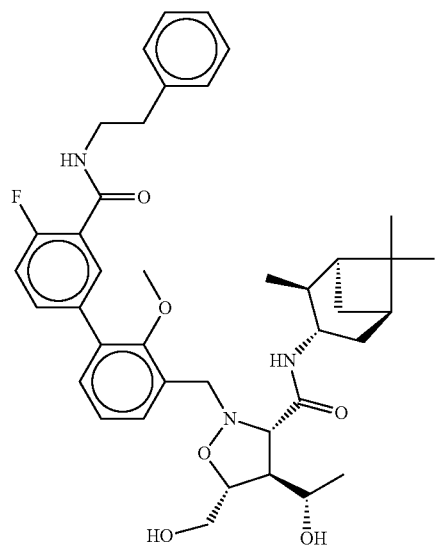
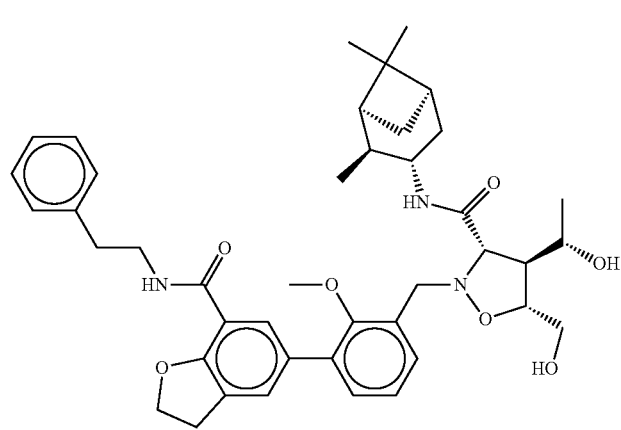
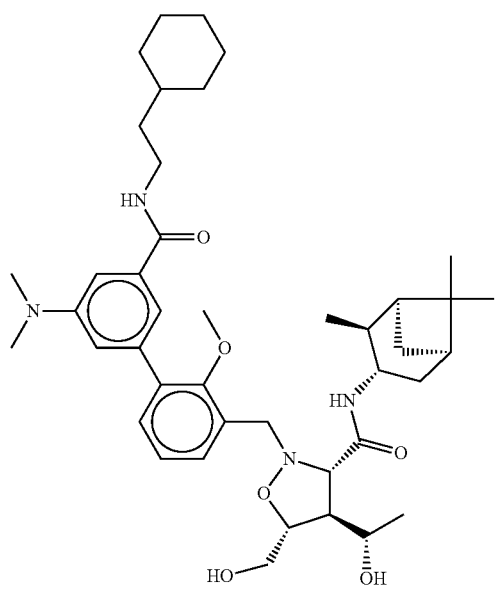
142
-continued
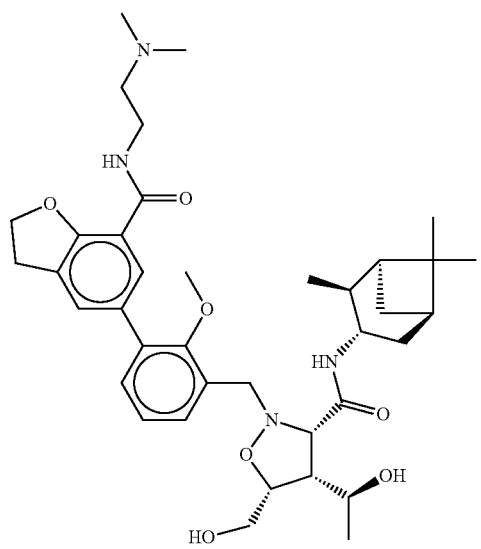
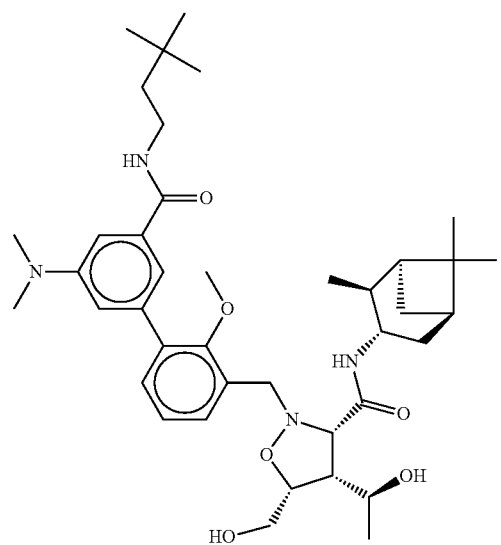
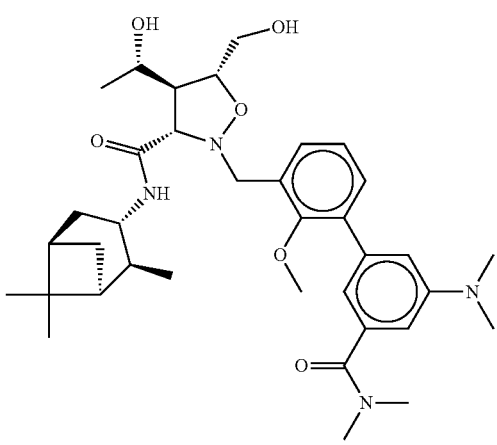

143 144
-continued
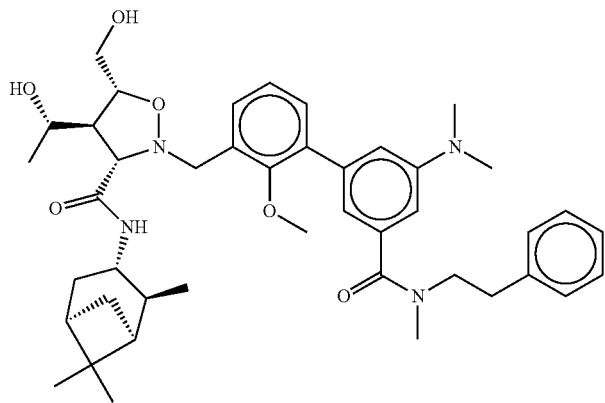
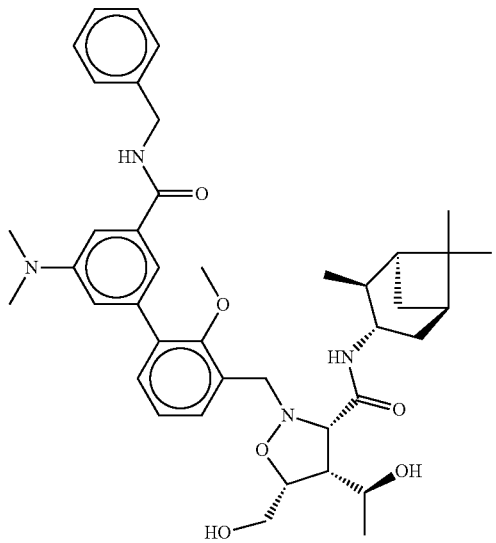
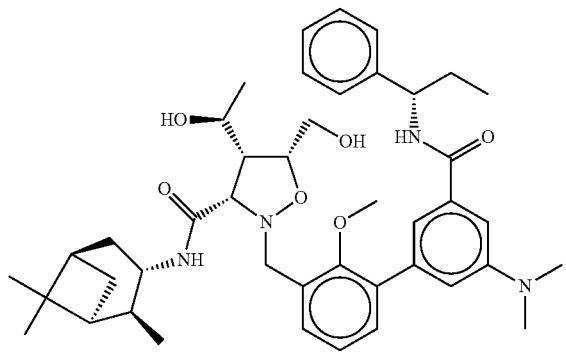
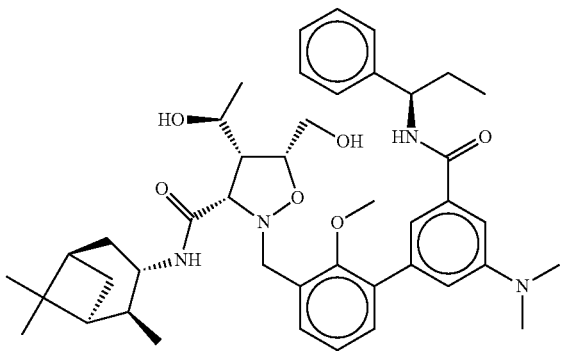
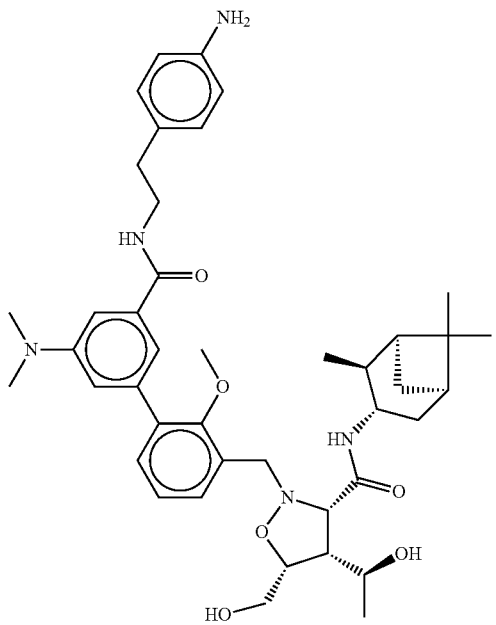
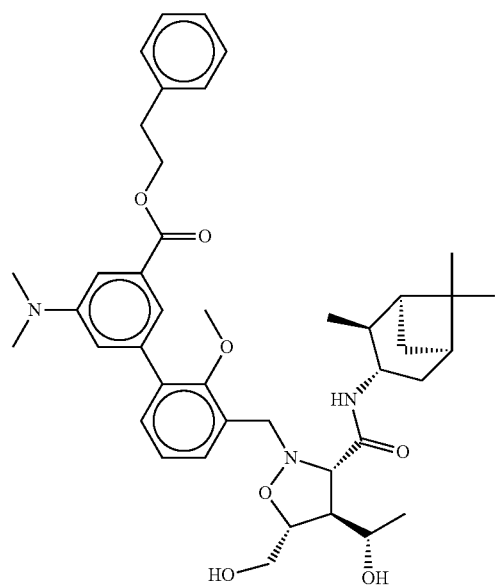

145 146
-continued
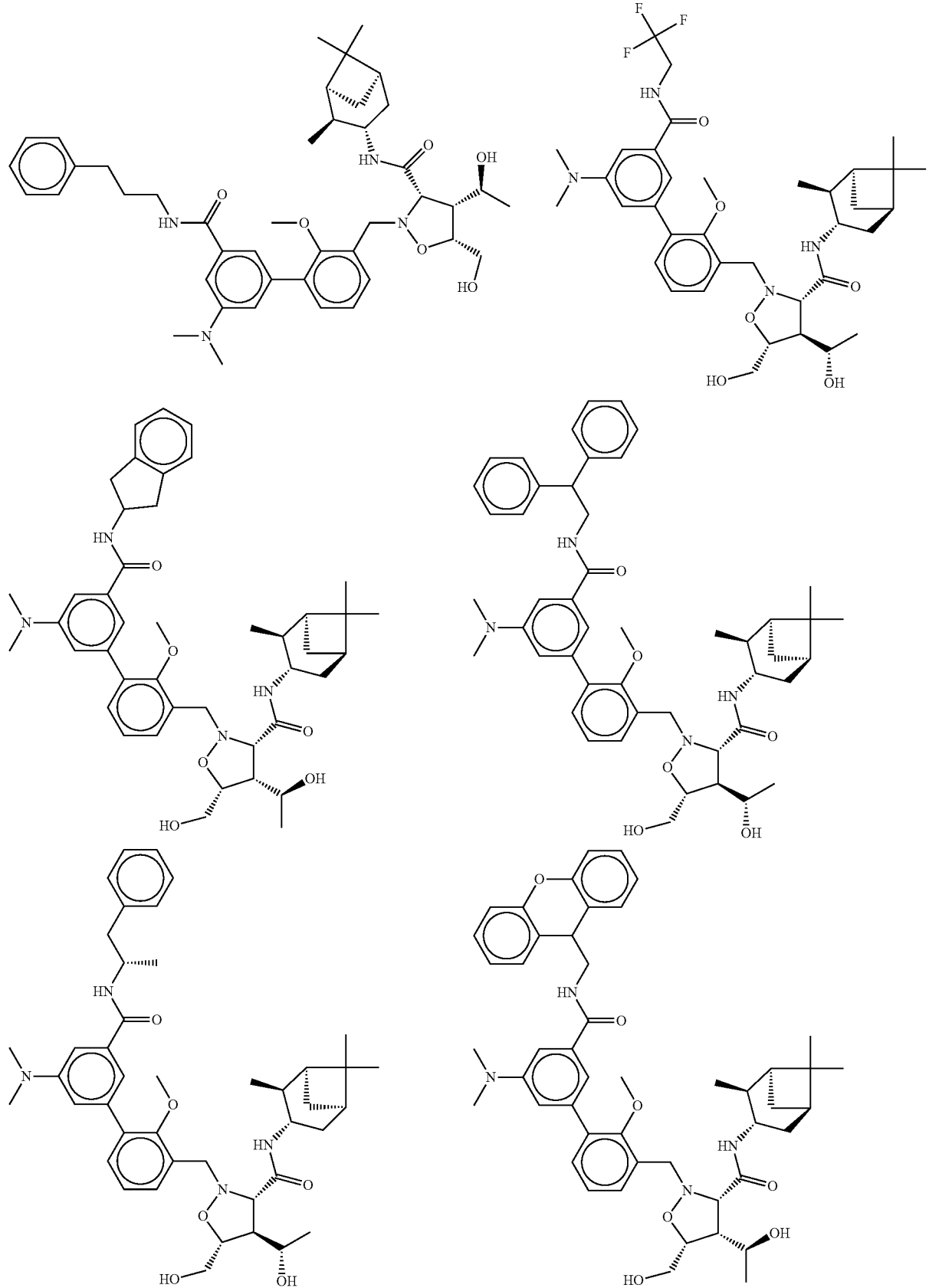

-continued
147
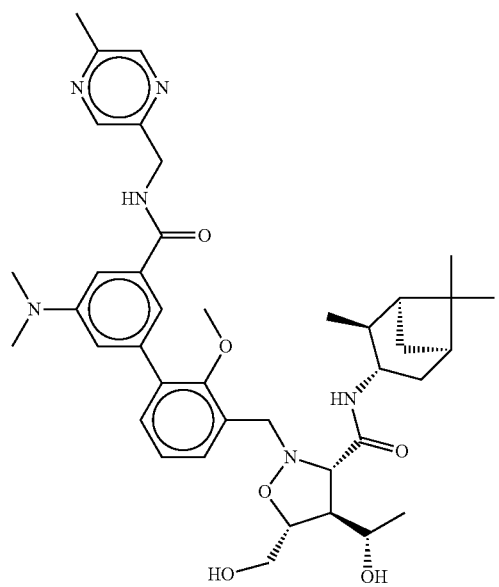
148
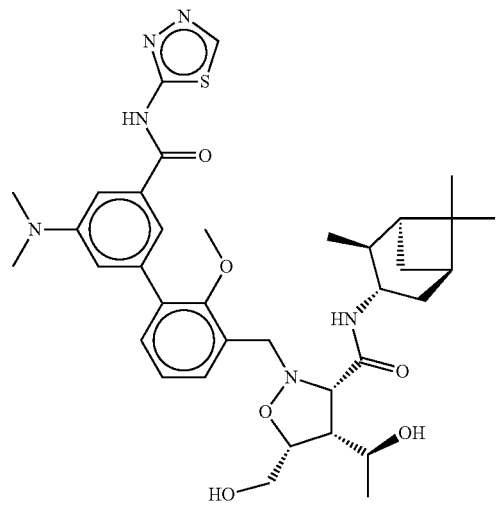
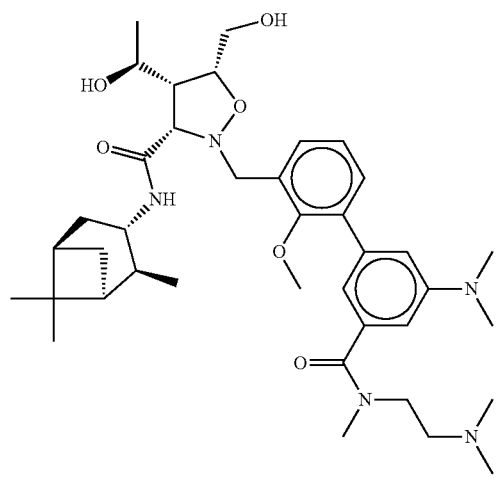
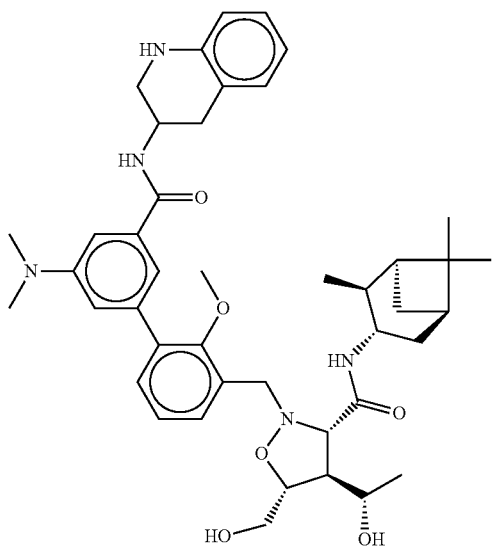

149
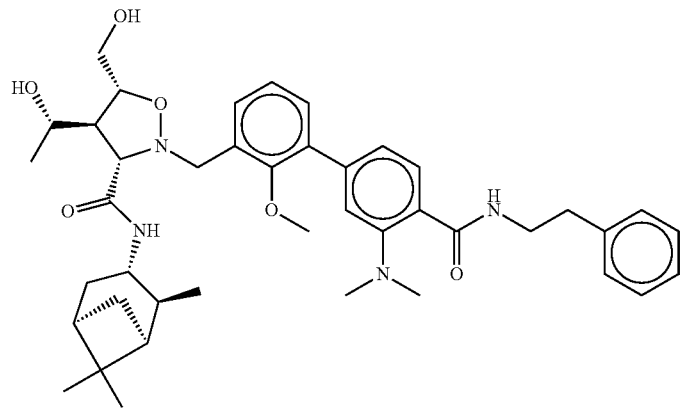
-continued
150
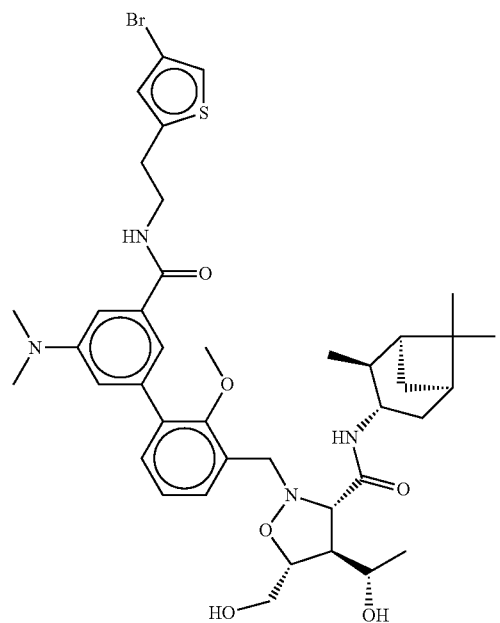
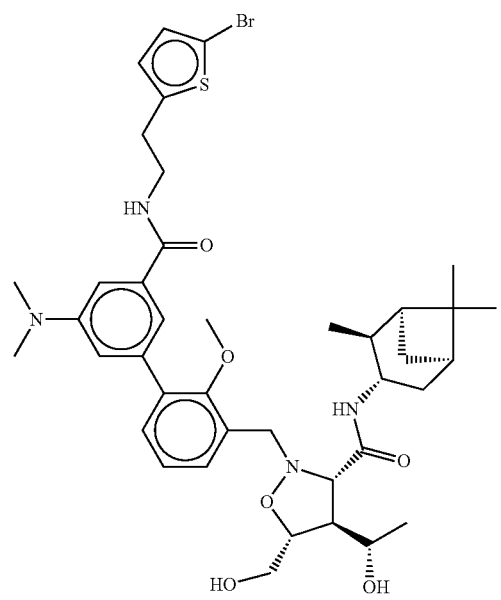
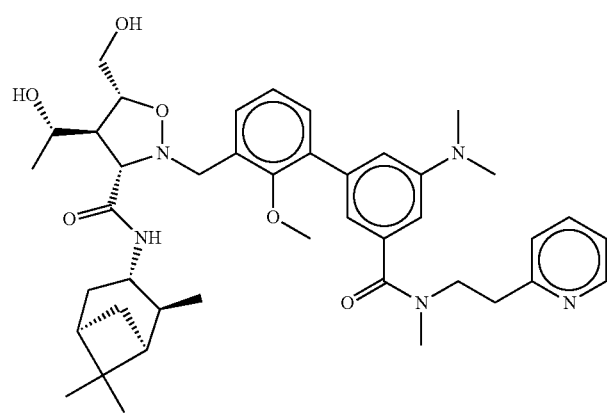

151
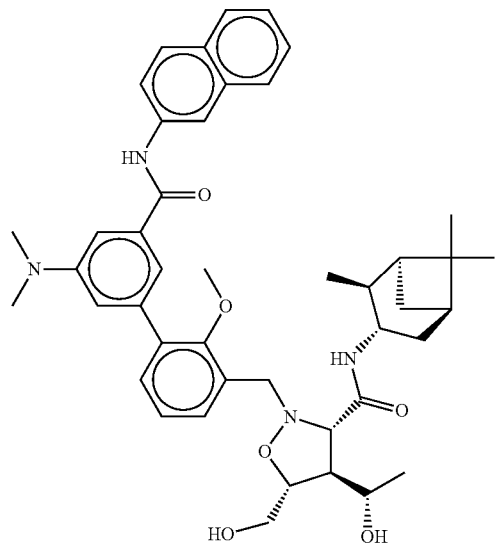
152
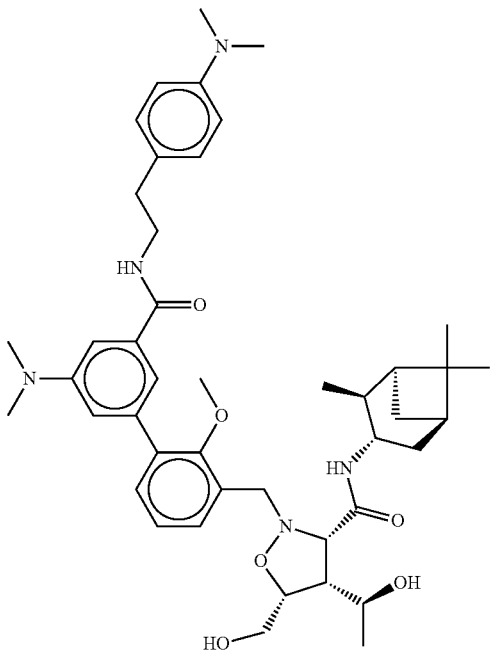
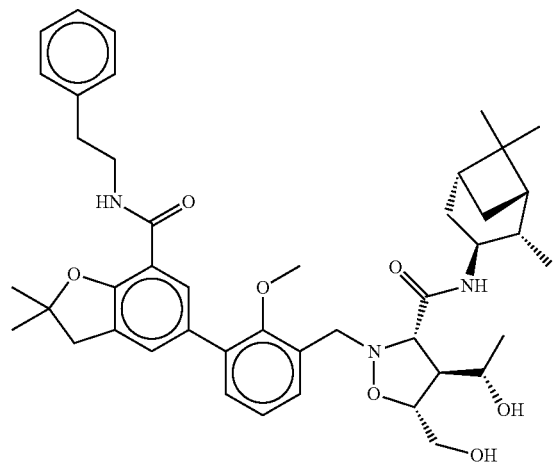
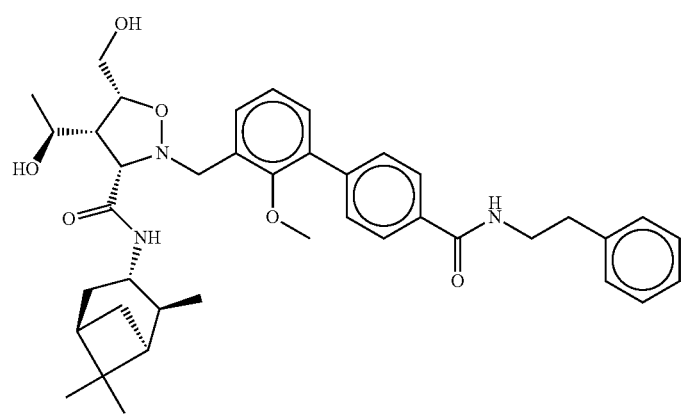

153
154
-continued
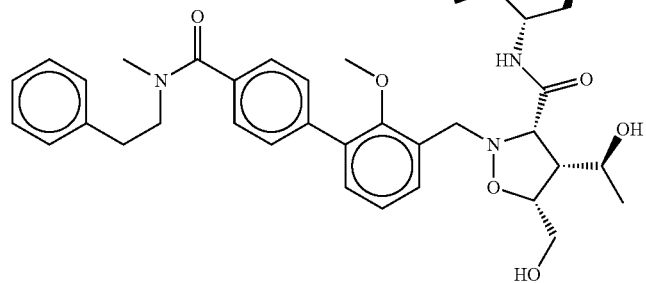
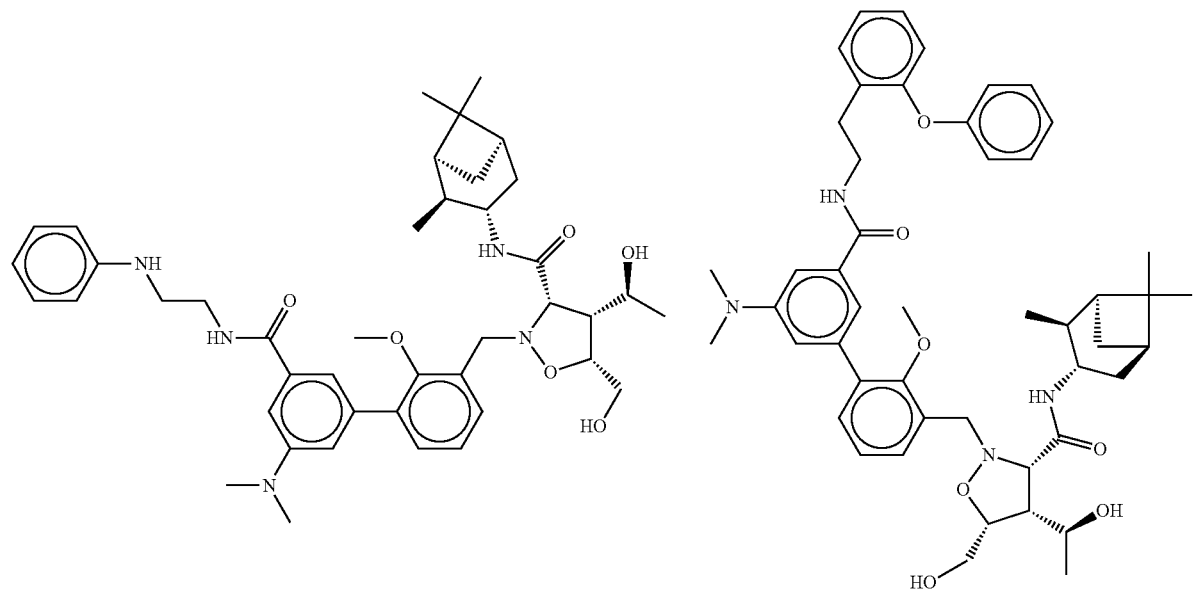
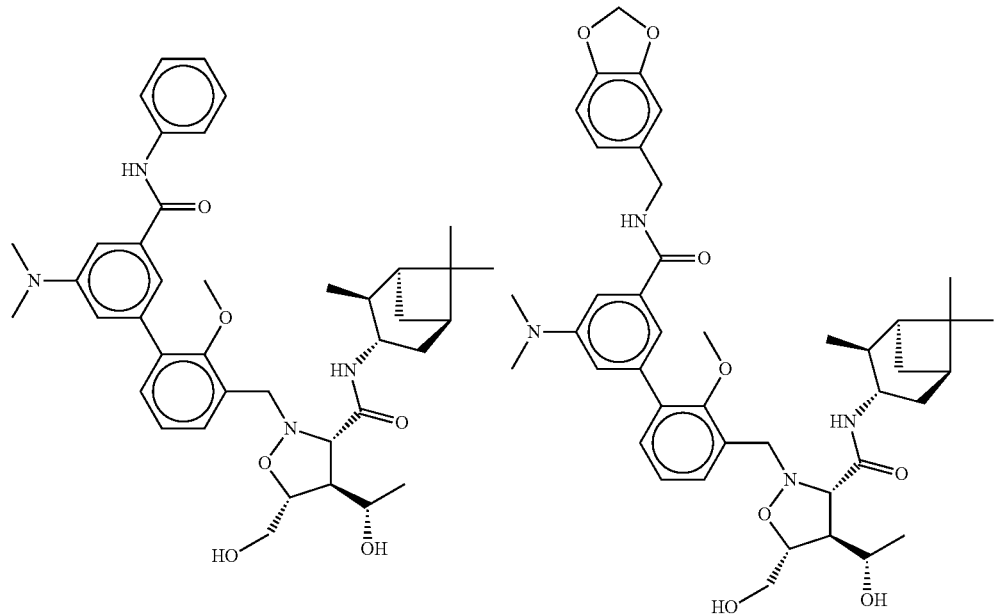

155 156
-continued
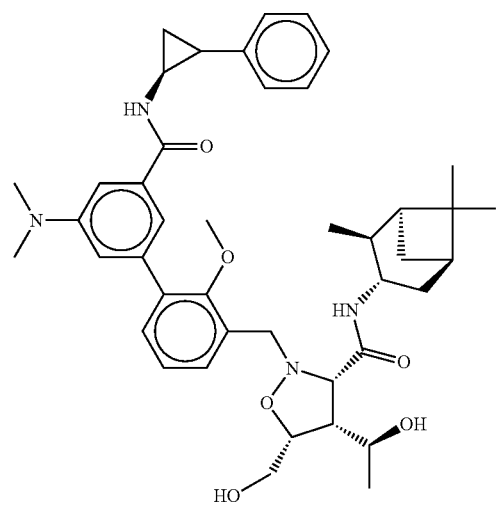
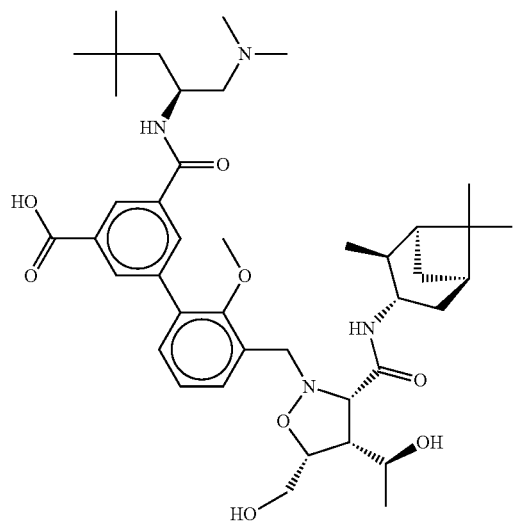
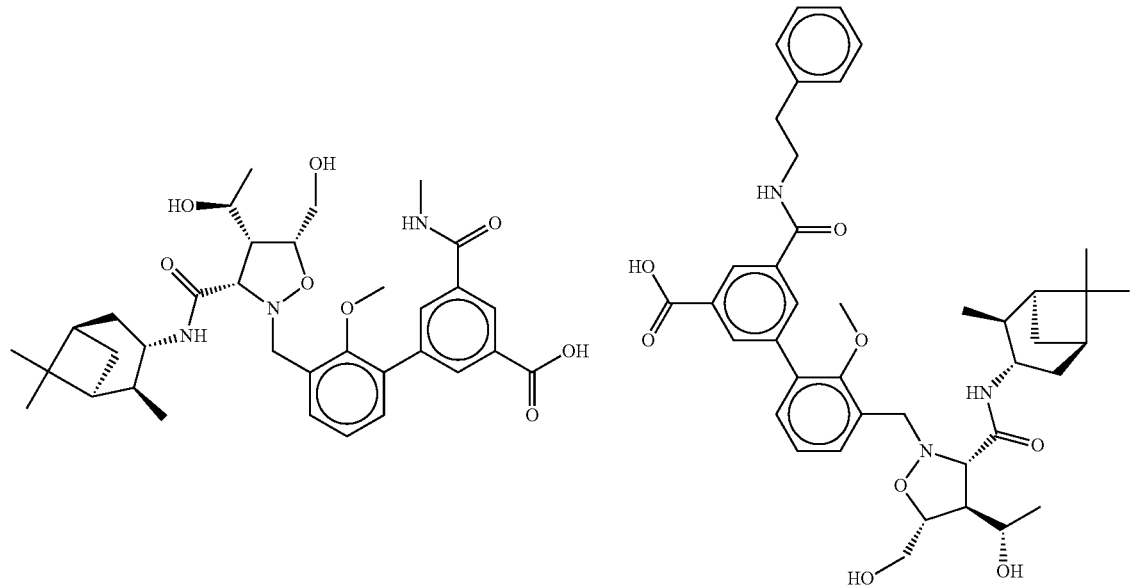
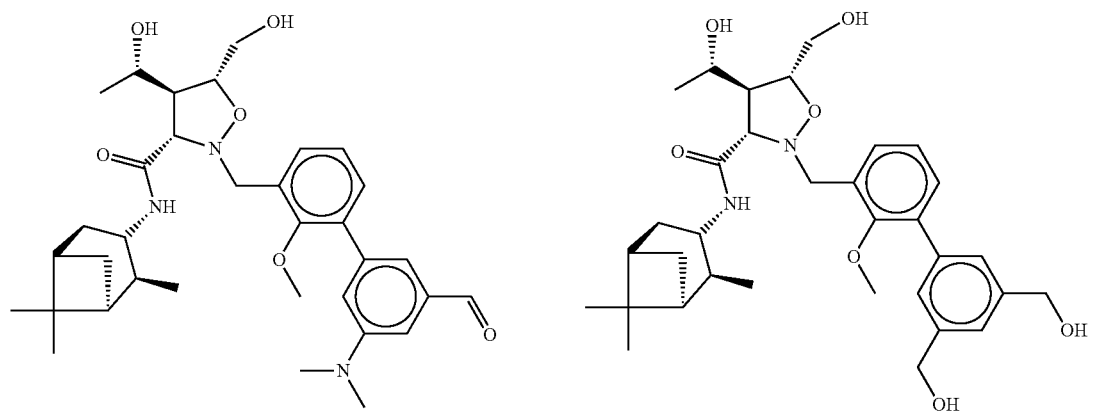

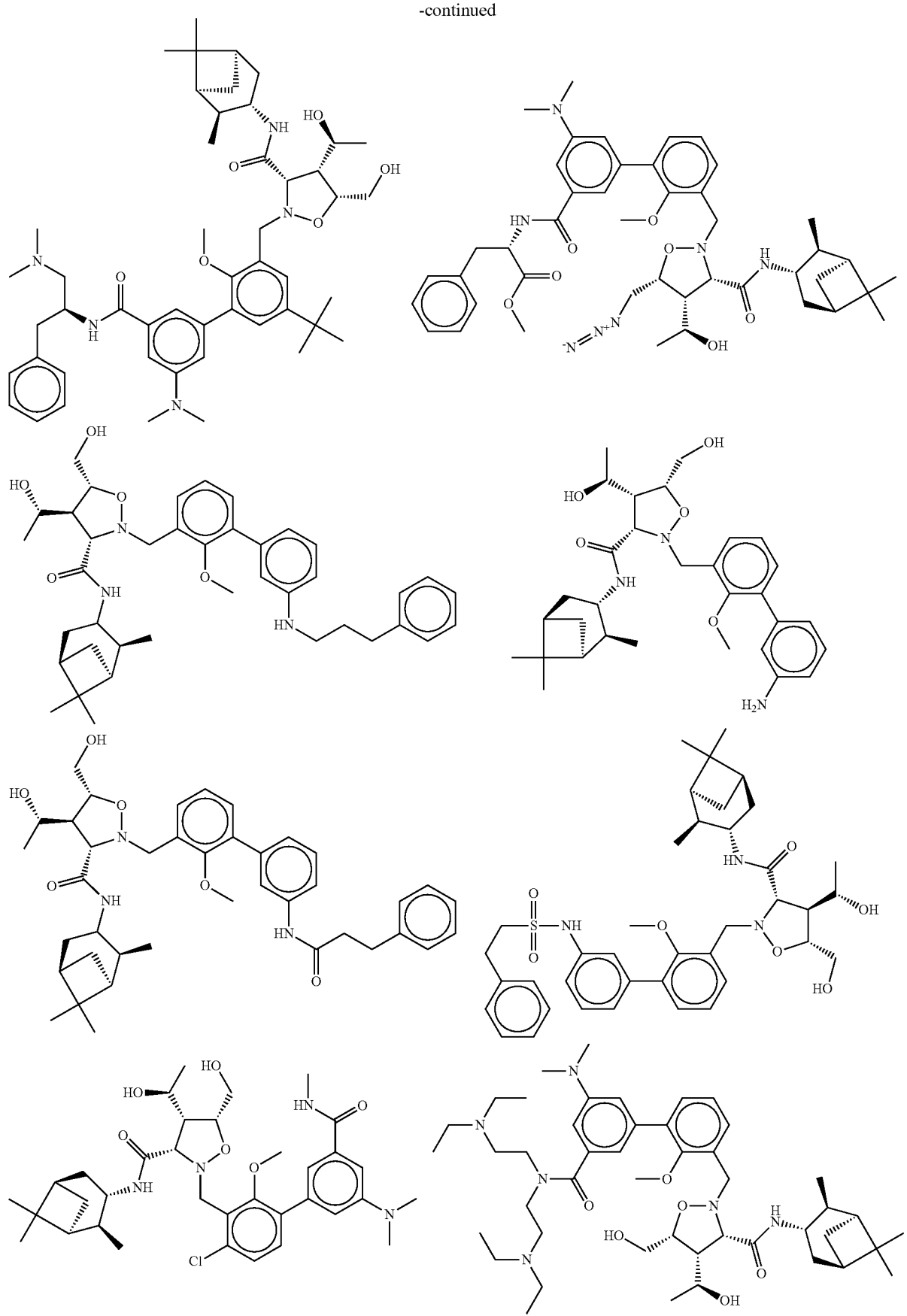

-continued
159
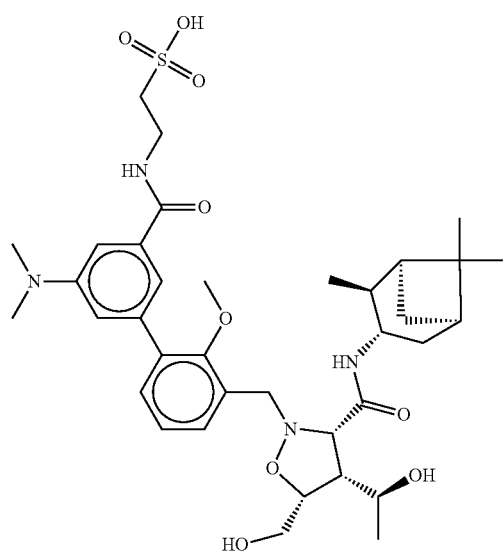
160
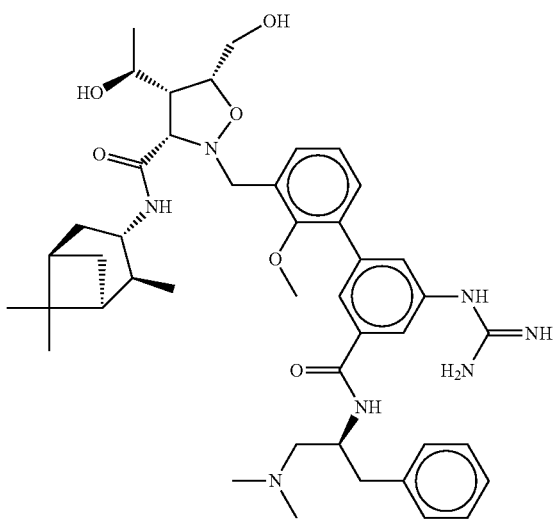
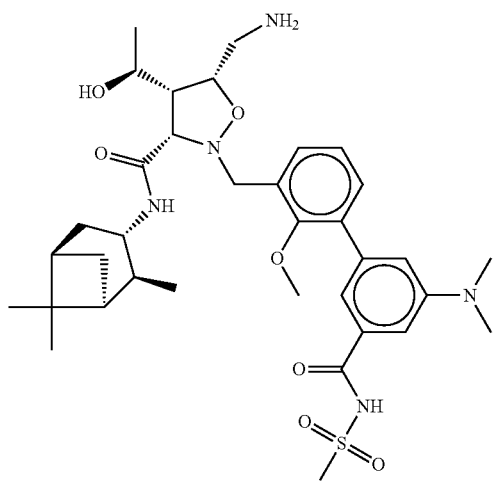
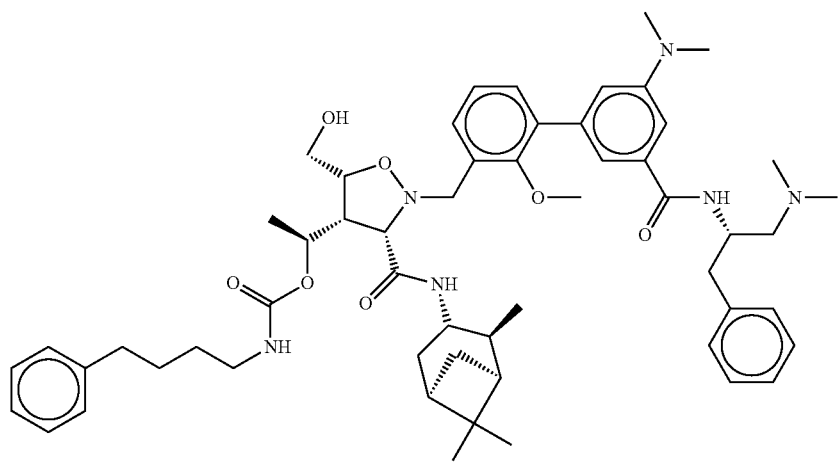

161 162
-continued
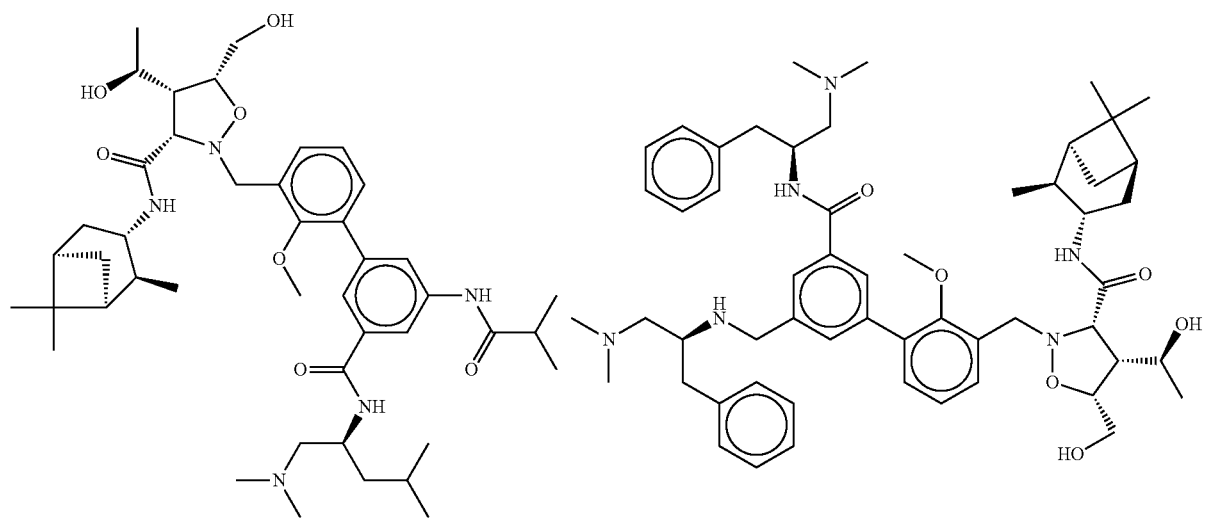
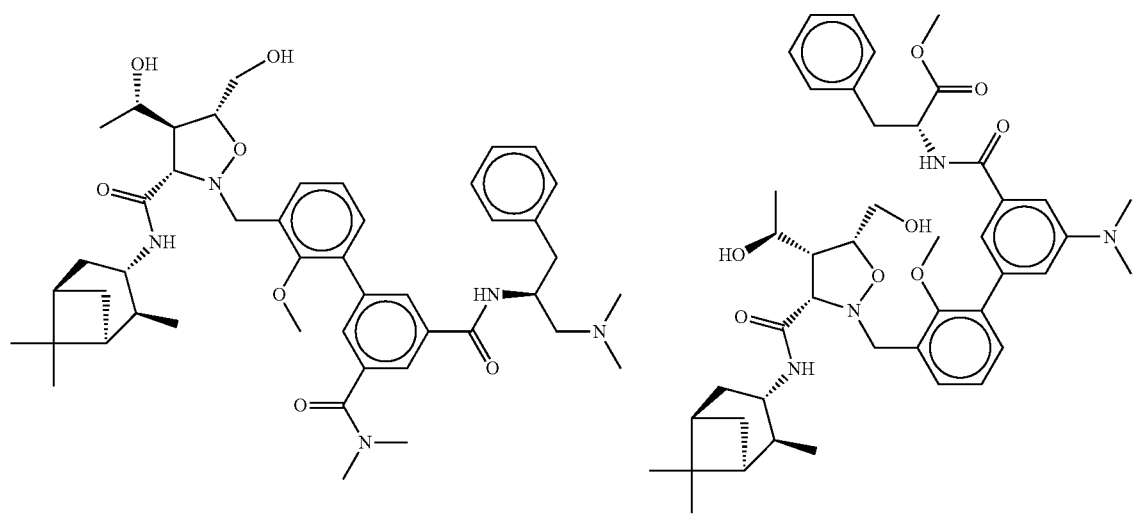
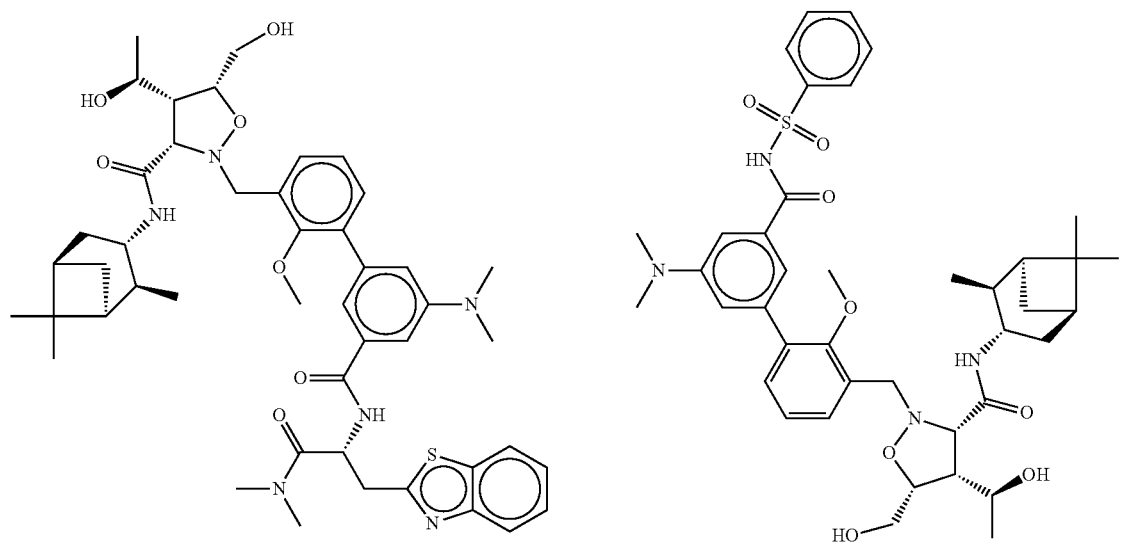

163
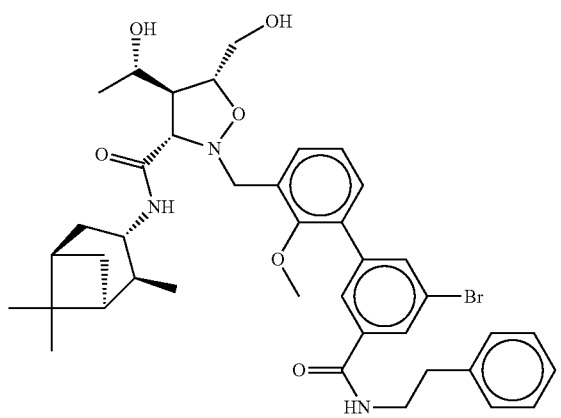
164
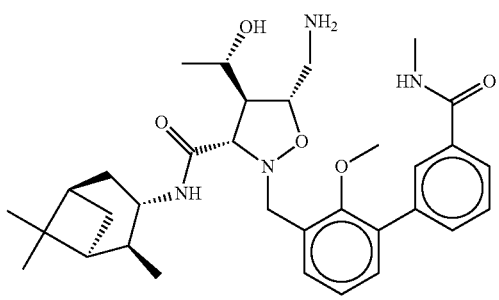
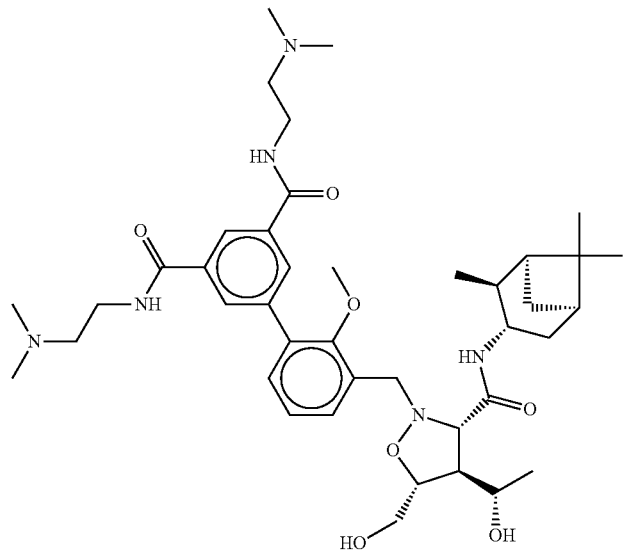
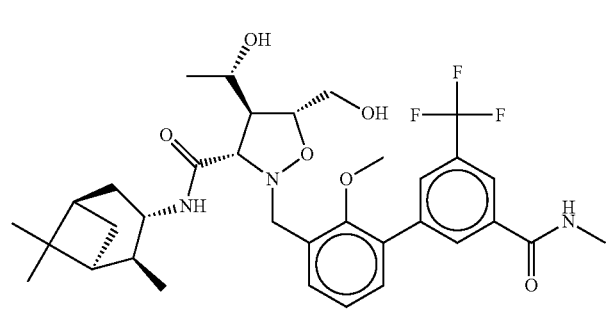
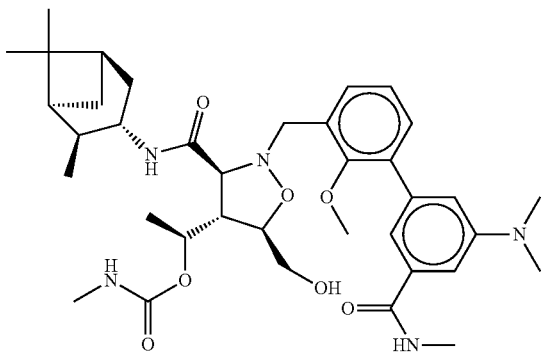

165
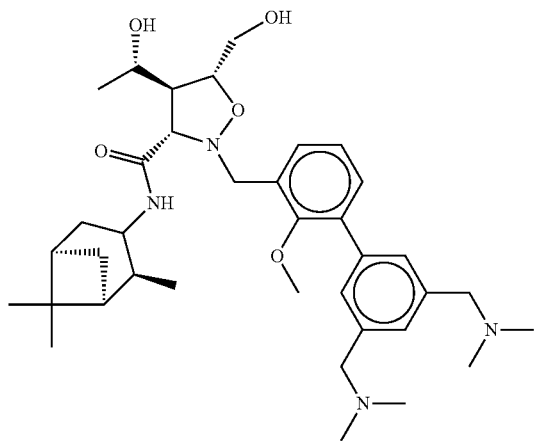
166
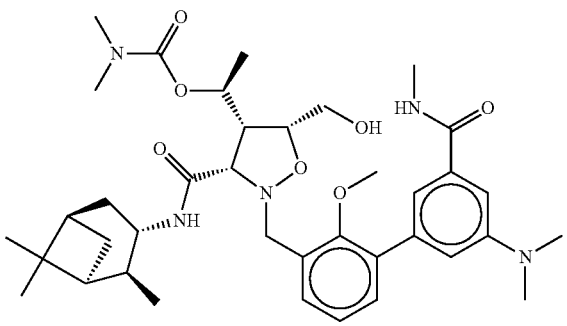
-continued
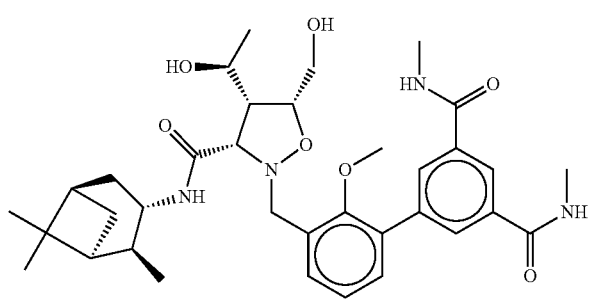
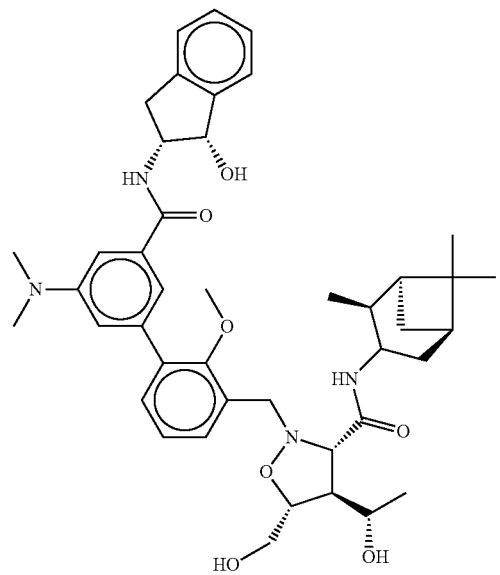
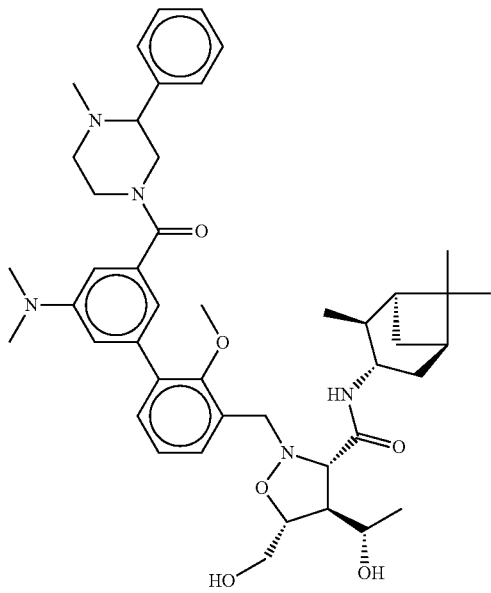
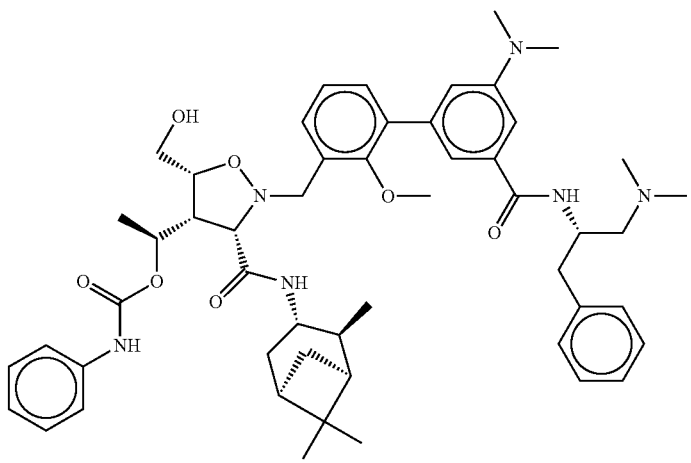

167 168
-continued
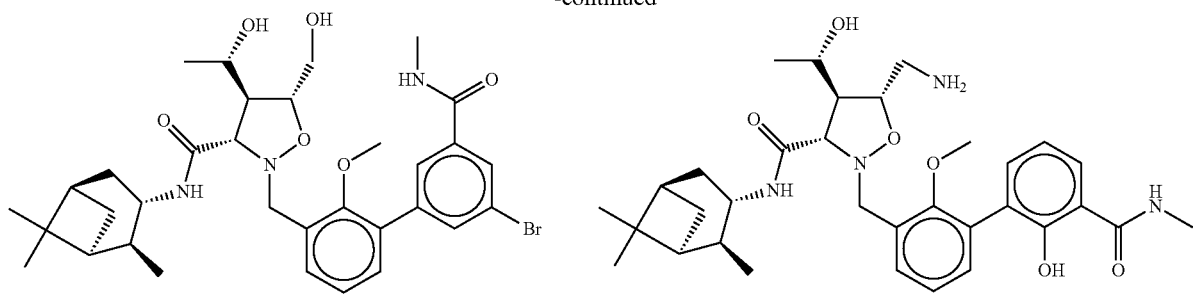
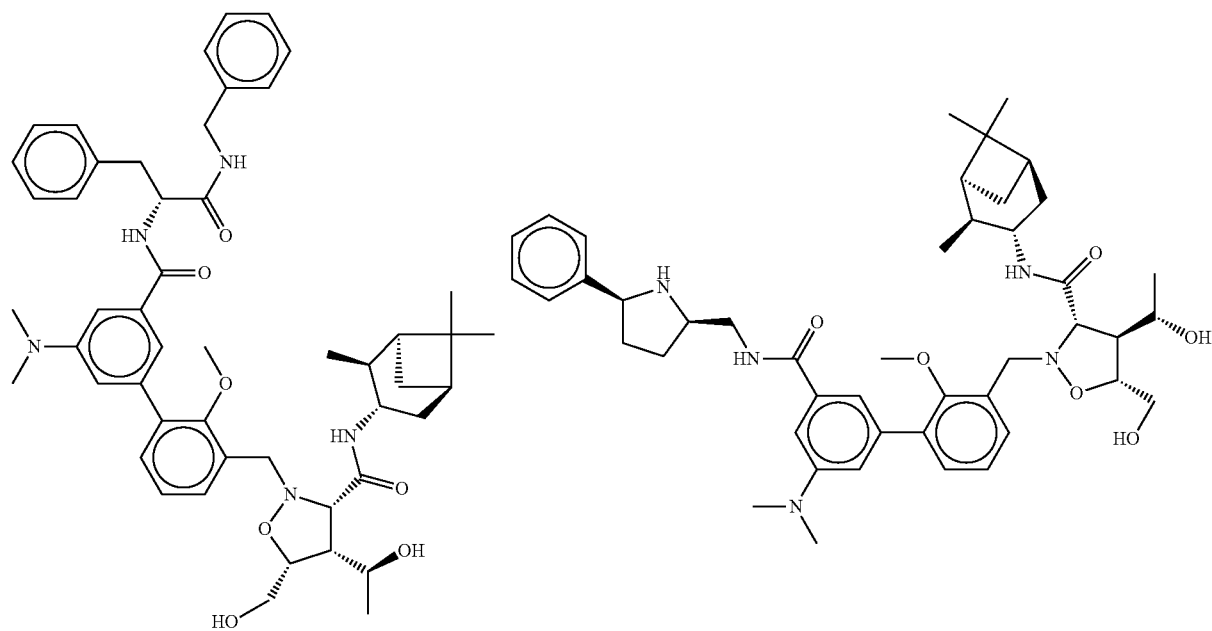
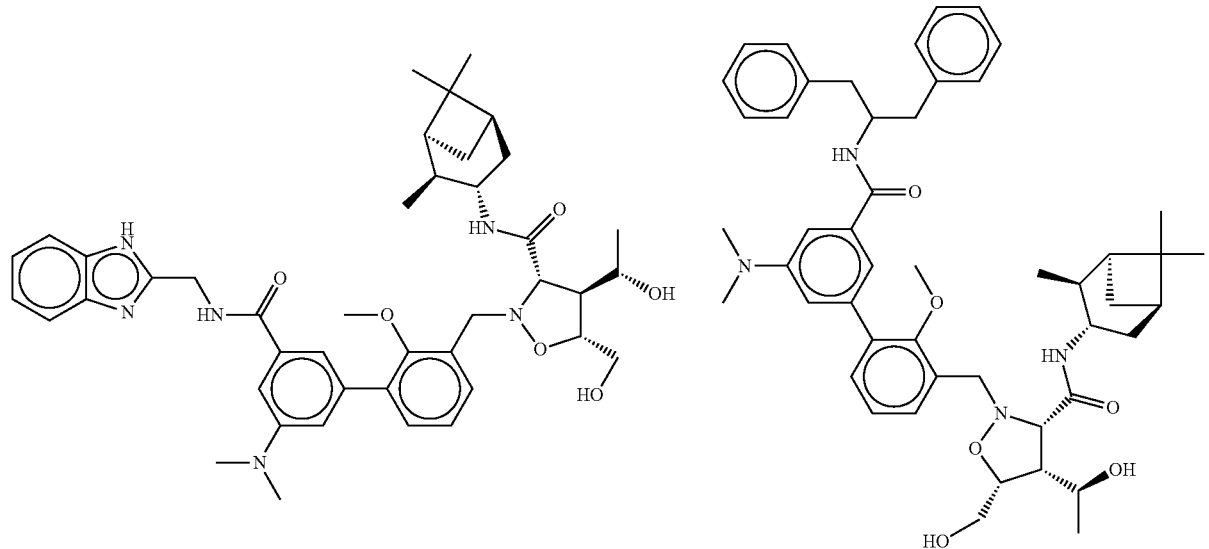

169
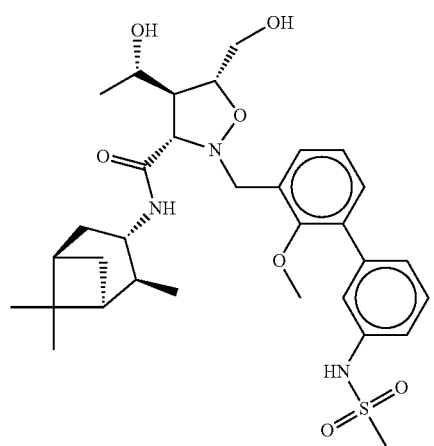
170
-continued
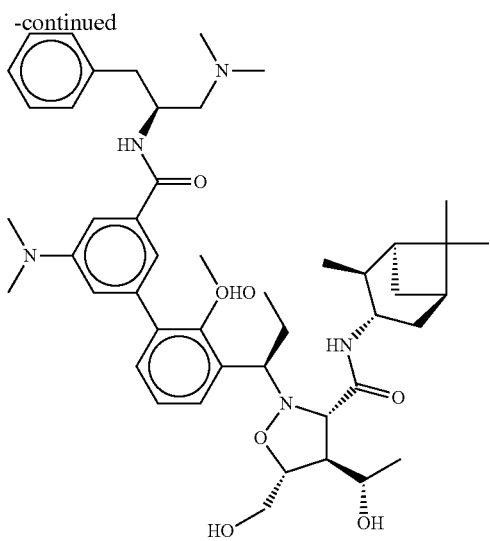
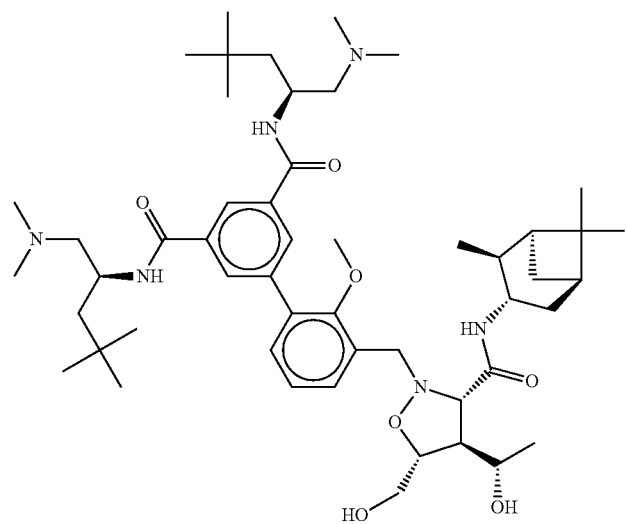
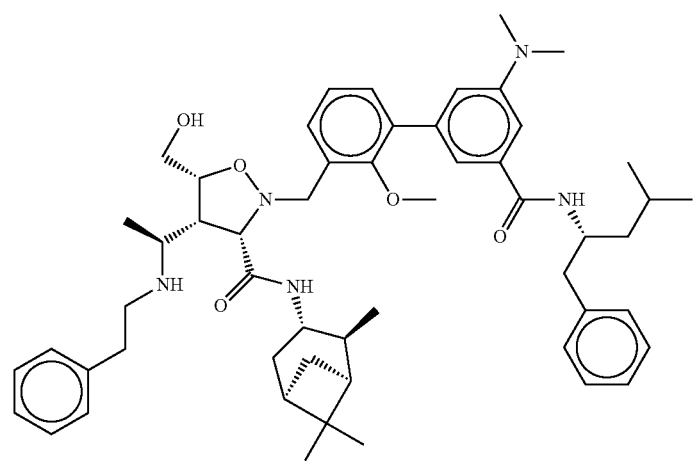

171 172
-continued
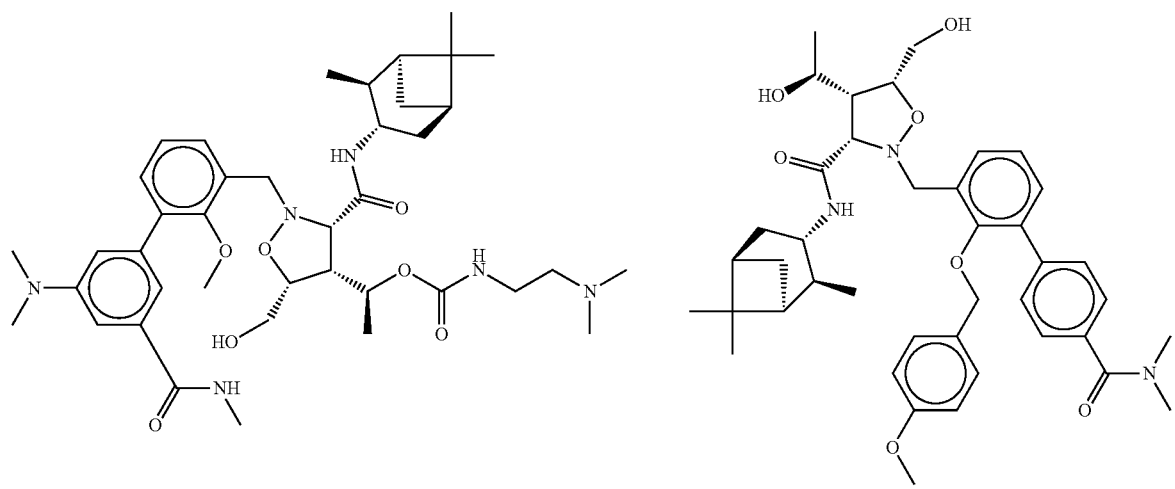
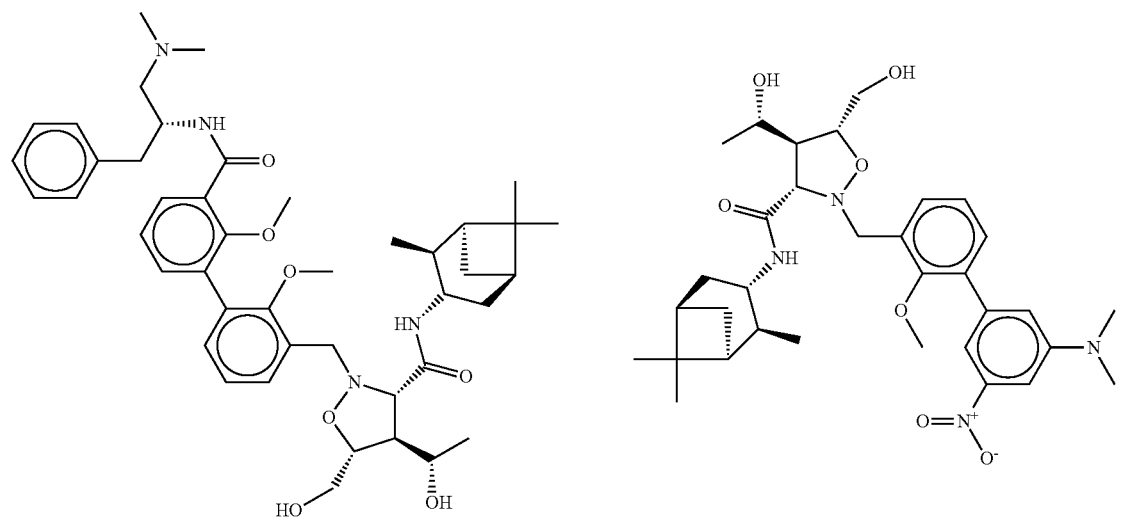
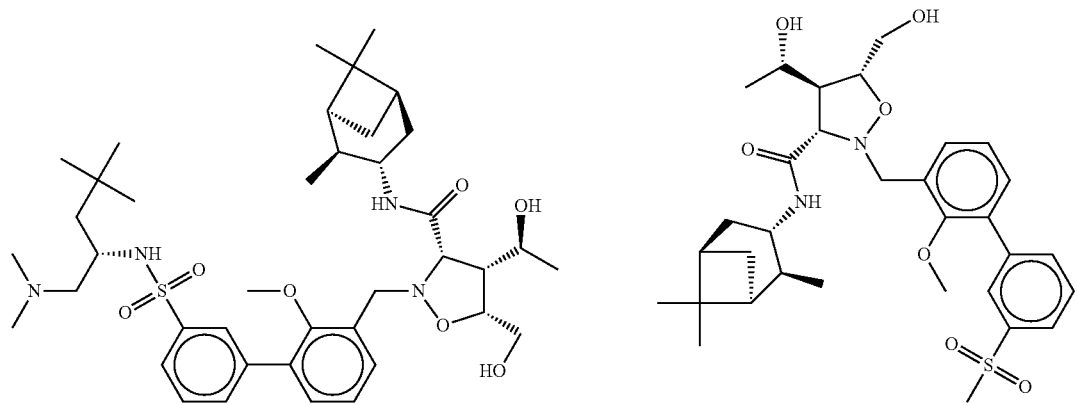

173
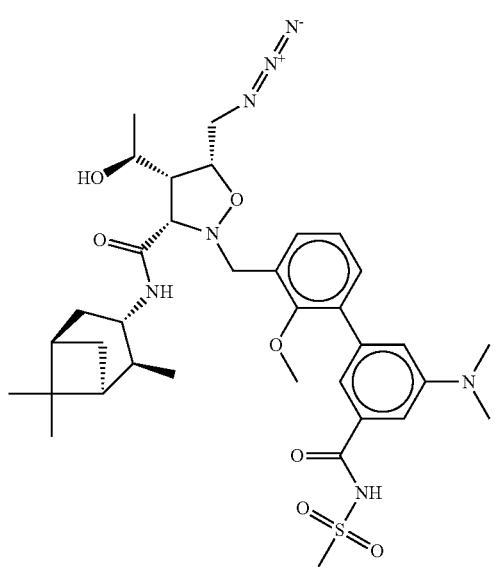
174
-continued
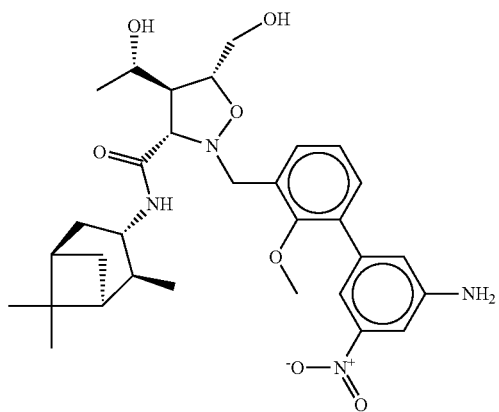
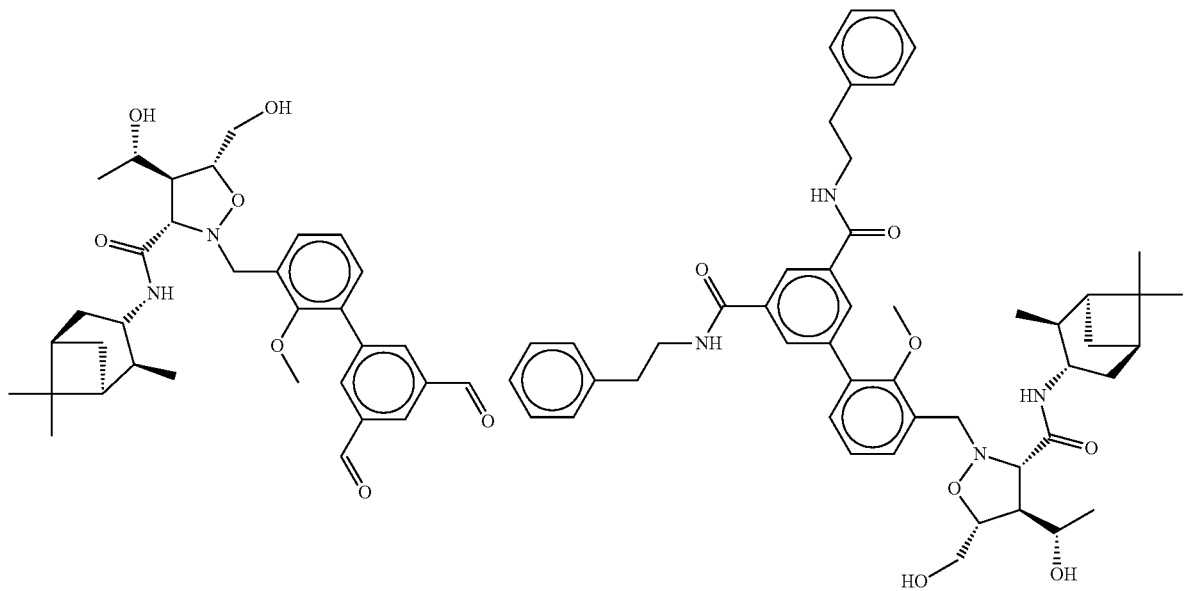
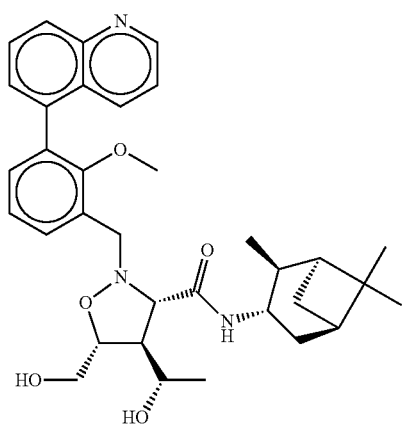
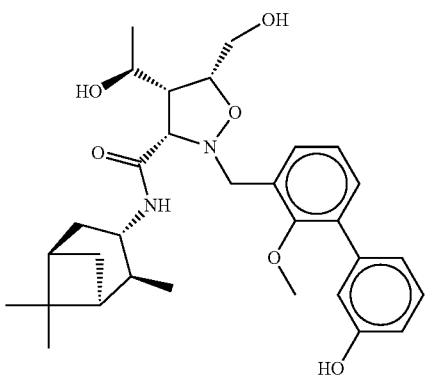

175
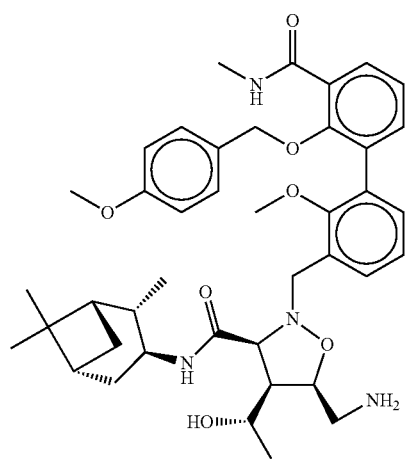
176
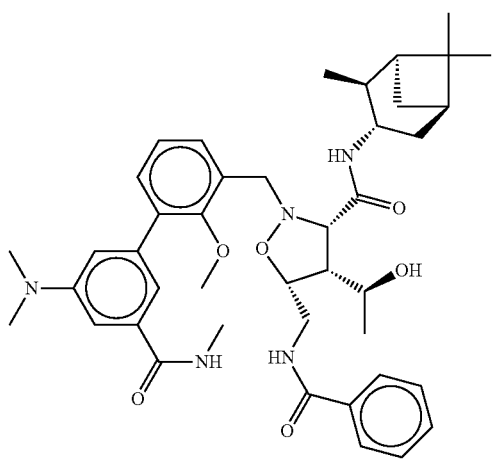
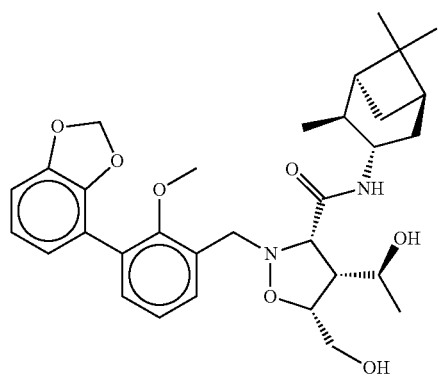
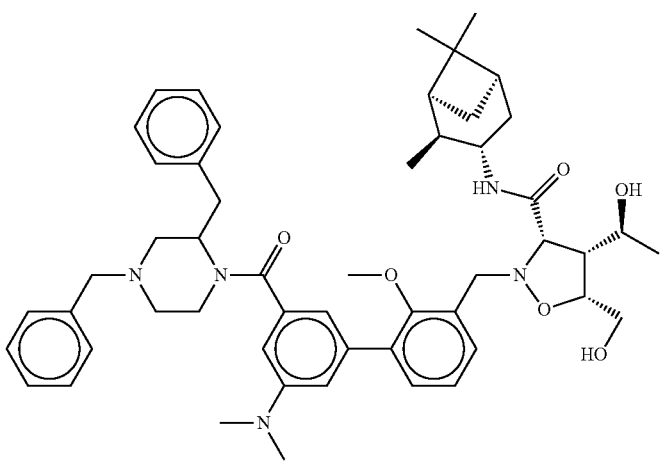
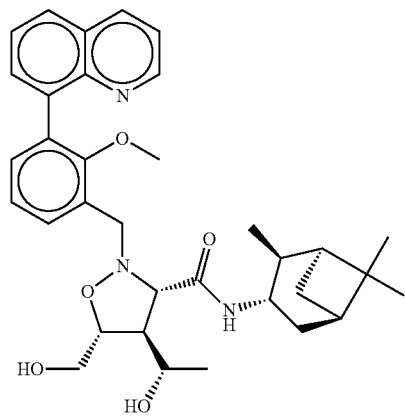
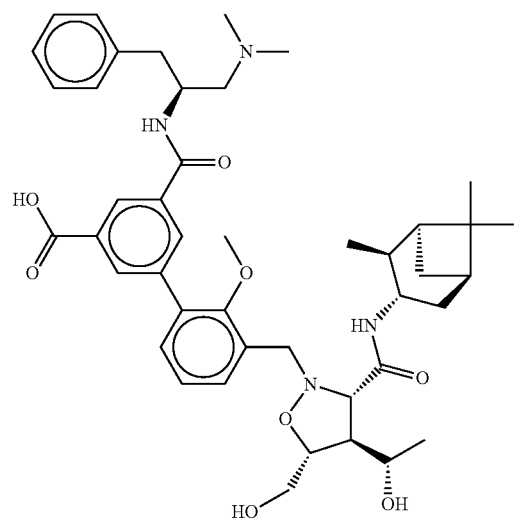

-continued
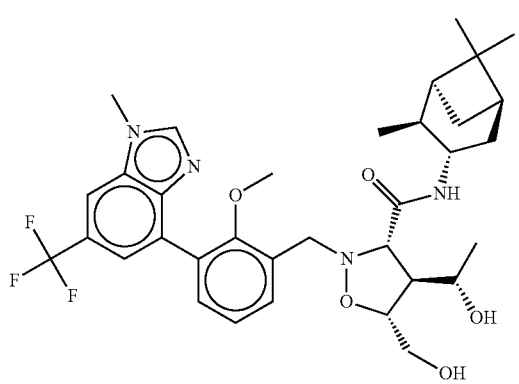
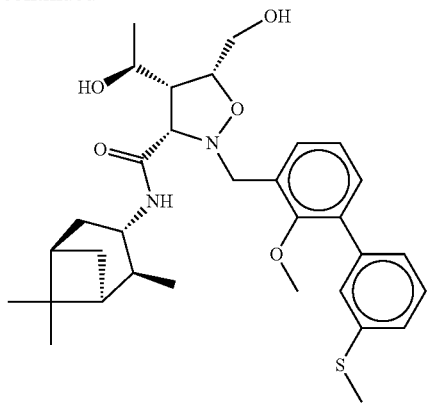
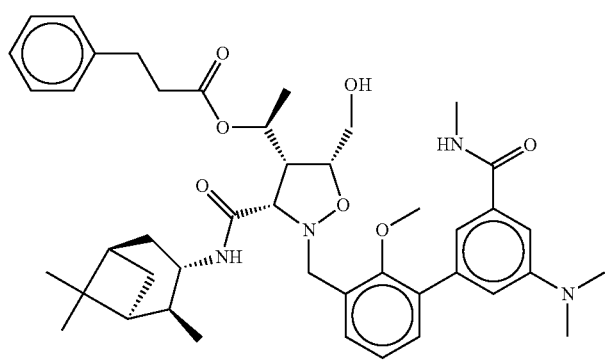
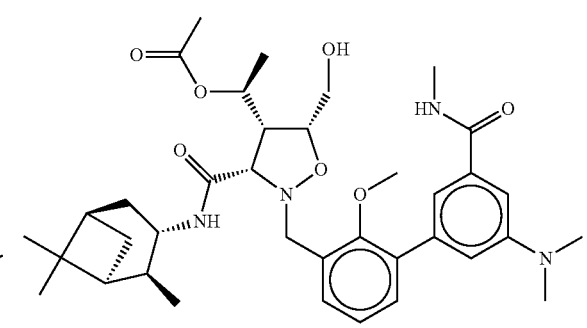
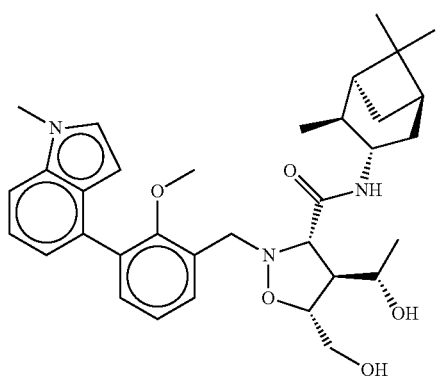
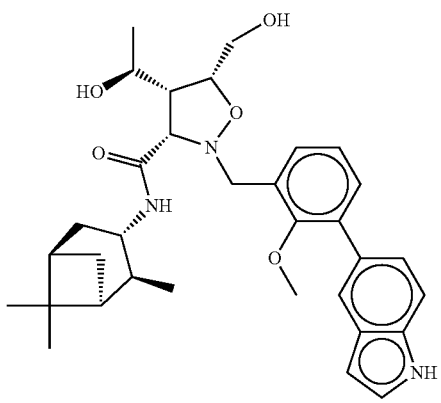
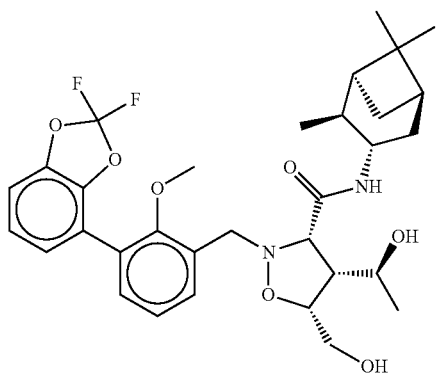
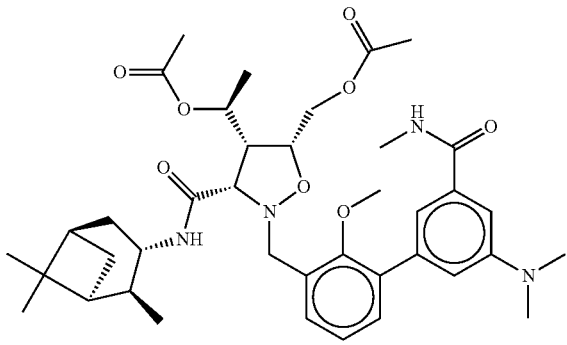

-continued
| 179 | 180 |
|---|---|
| 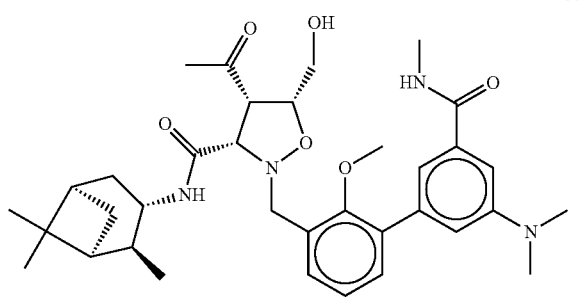 | 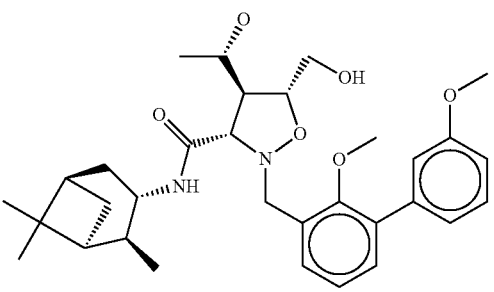 |
| 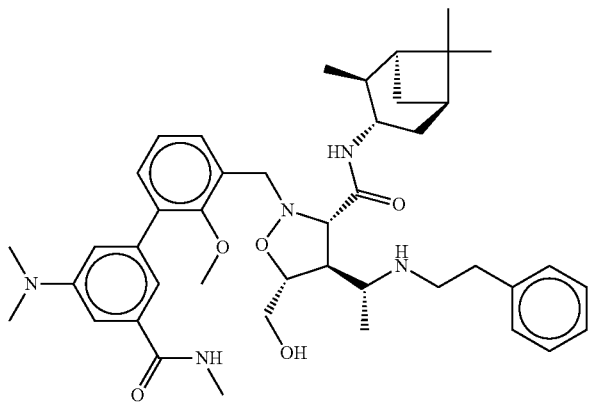 | 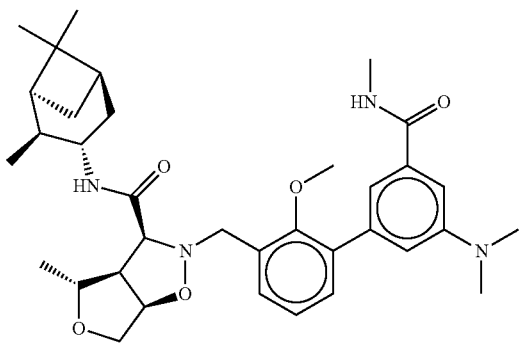 |
| 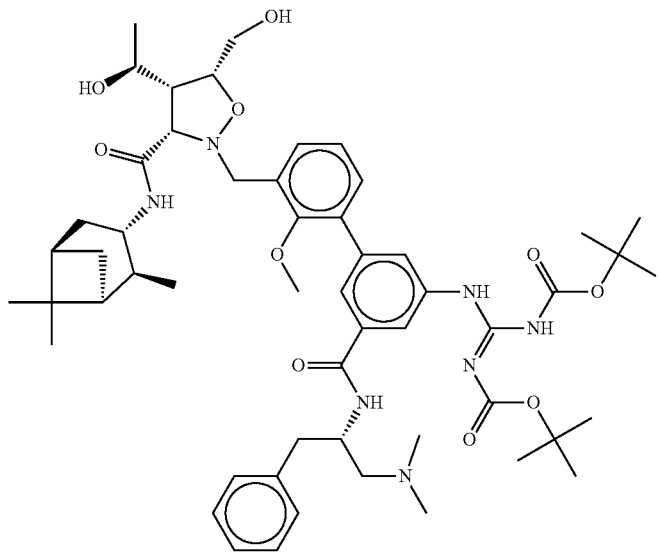 | |
| 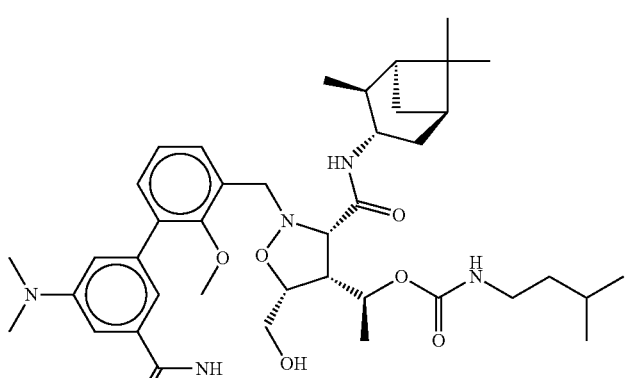 | 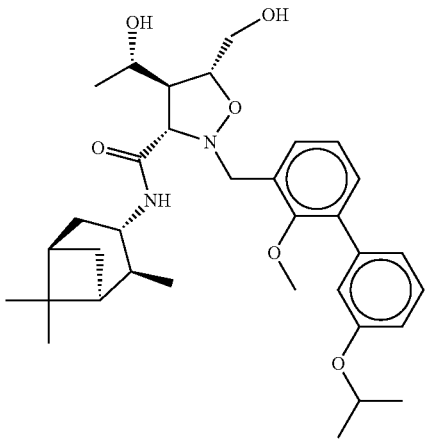 |

-continued
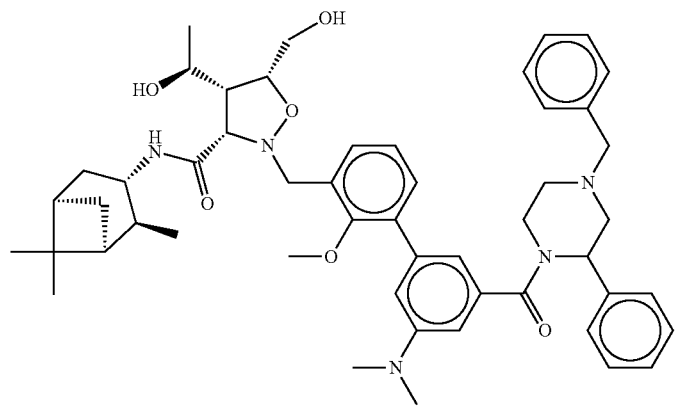
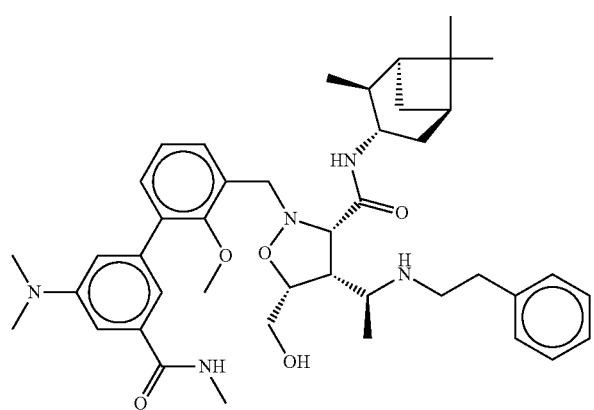
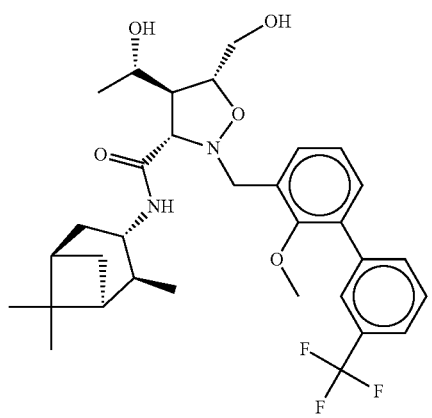
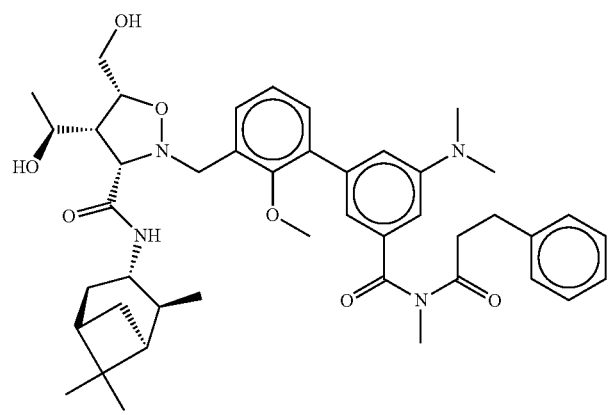
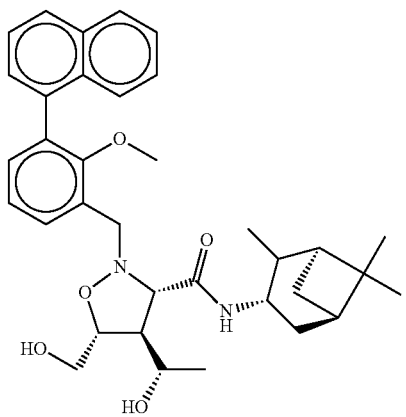
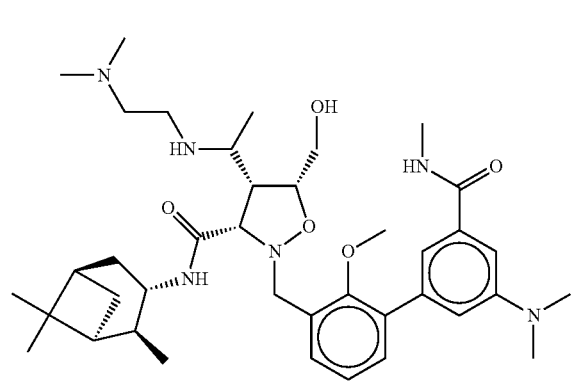
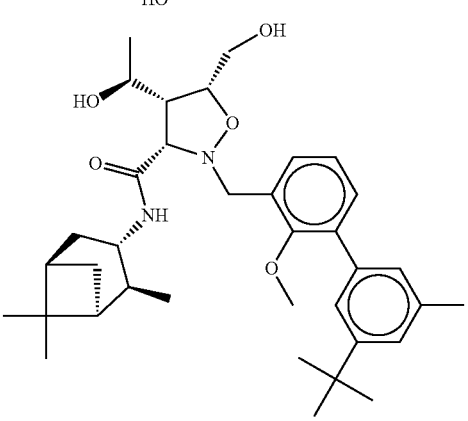

183
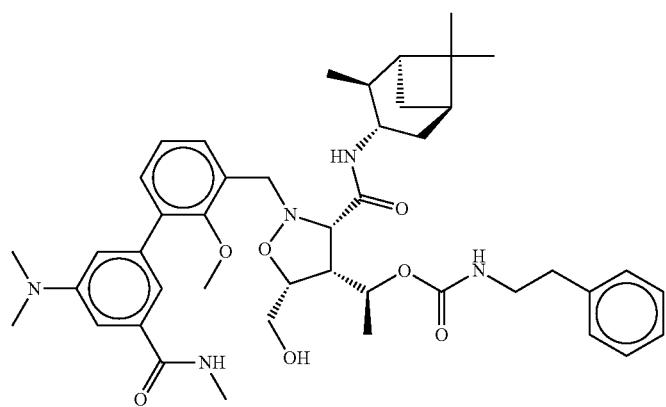
184
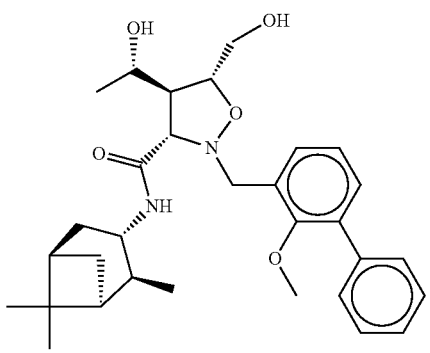
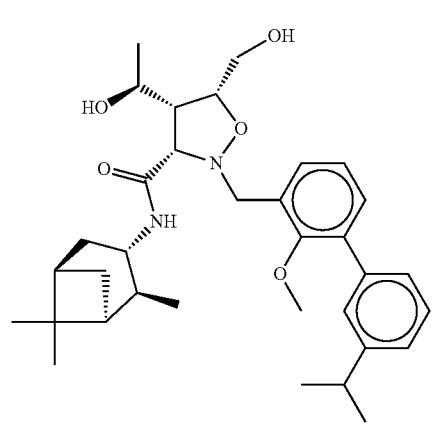
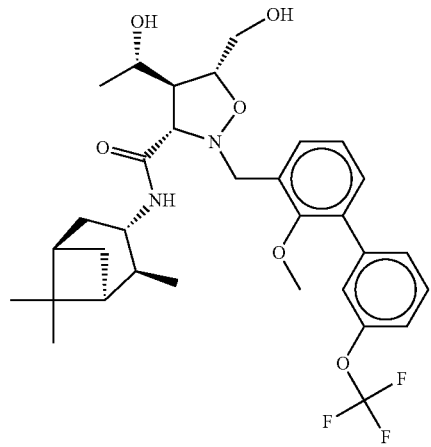
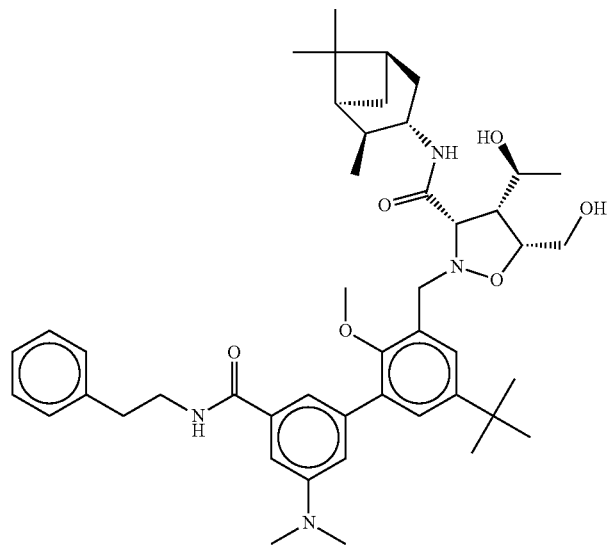
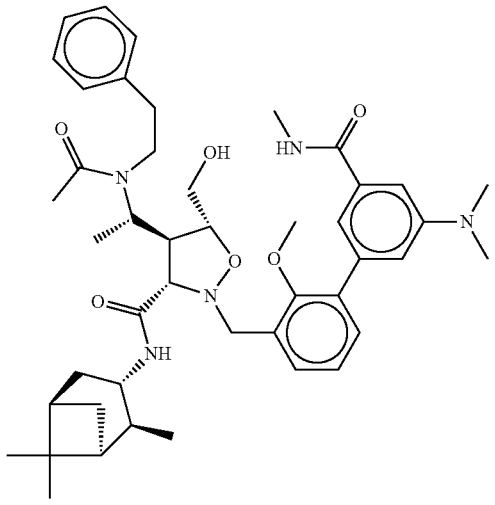

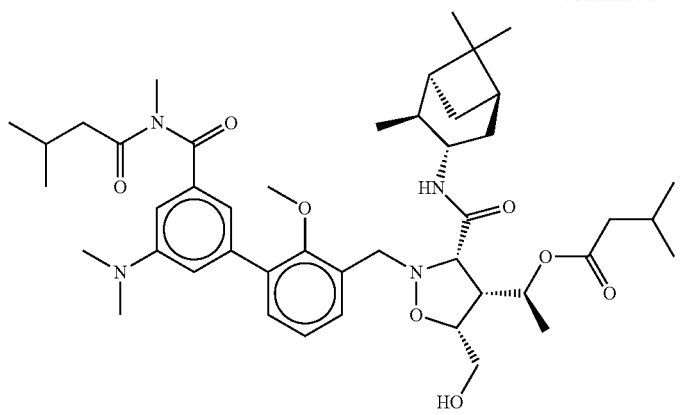
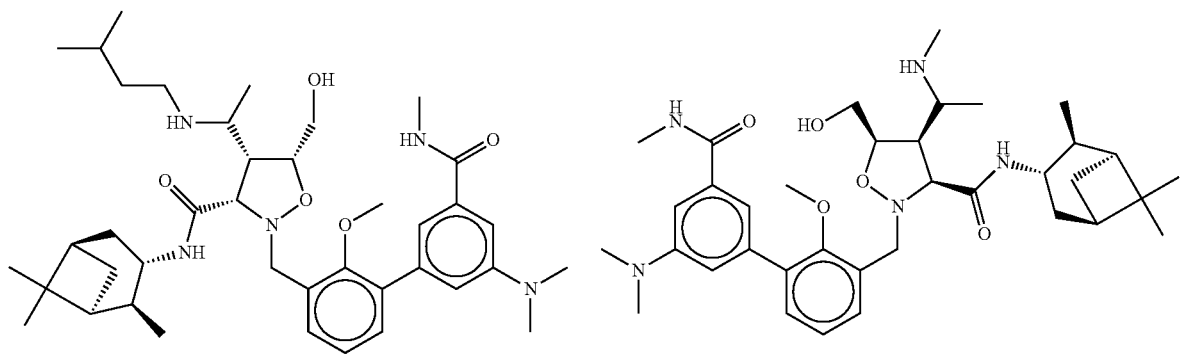
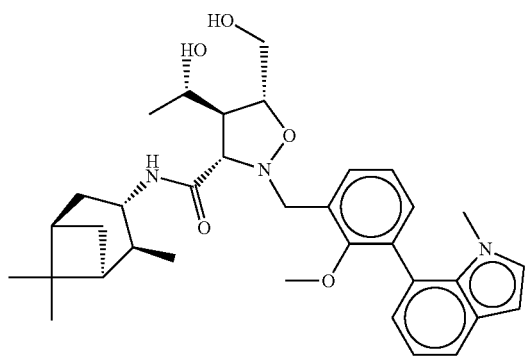
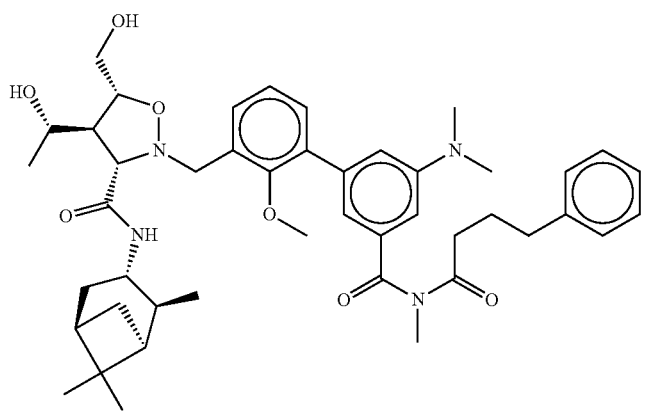

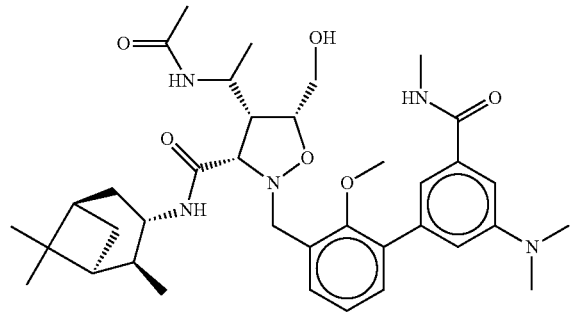
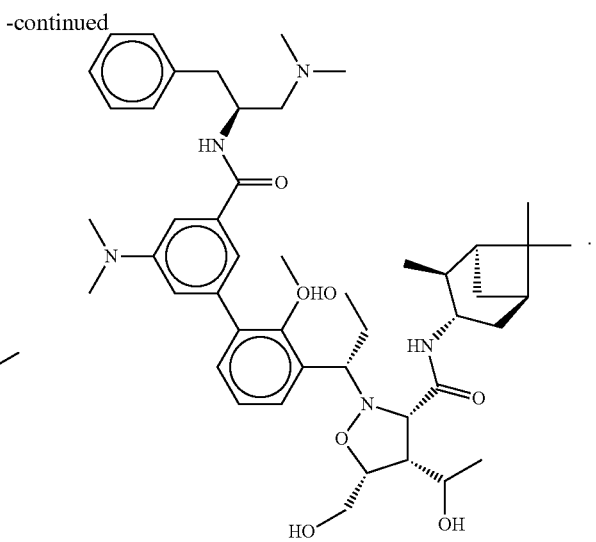
-continued
In another embodiment, the present invention relates to a compound selected from the group consisting of:
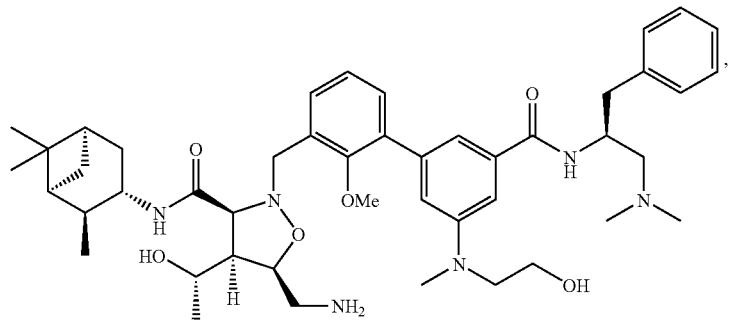
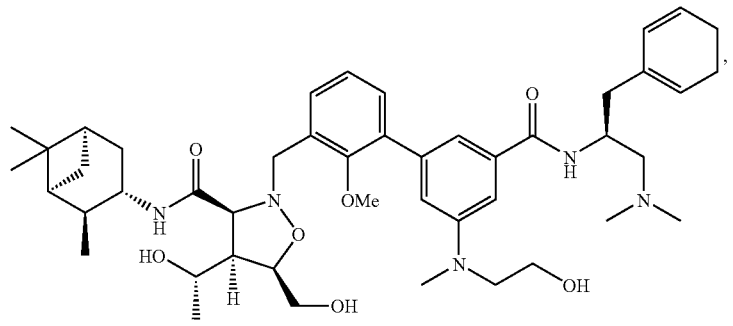
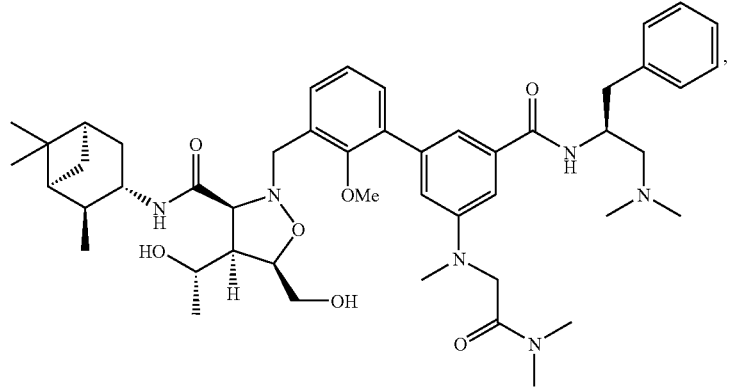

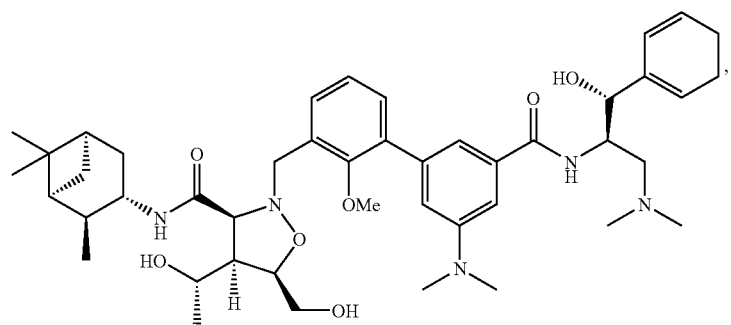
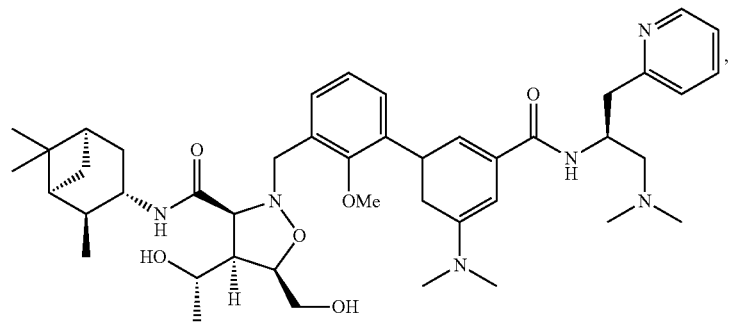
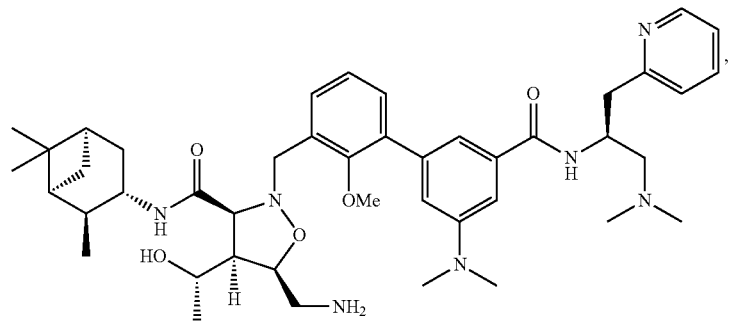
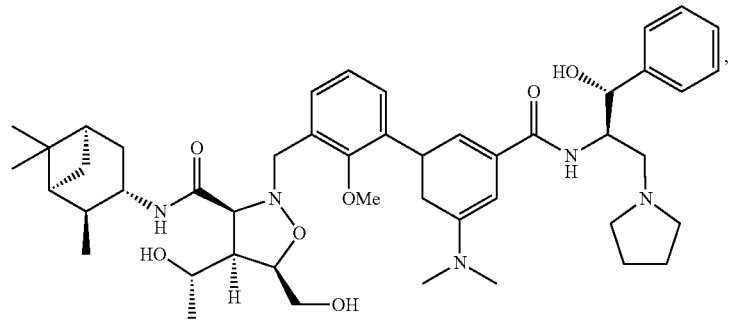
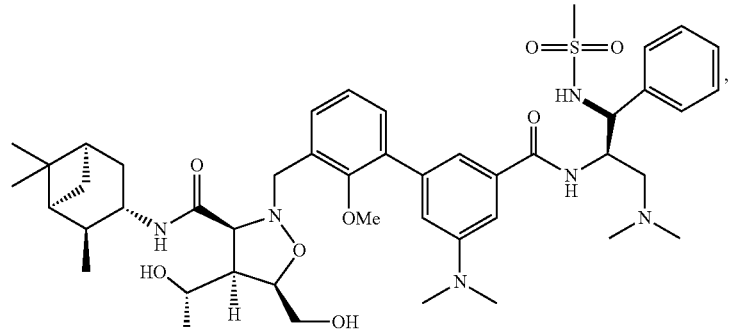

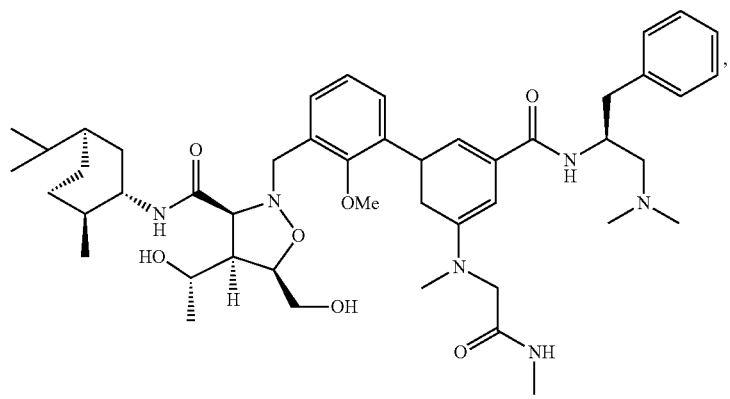
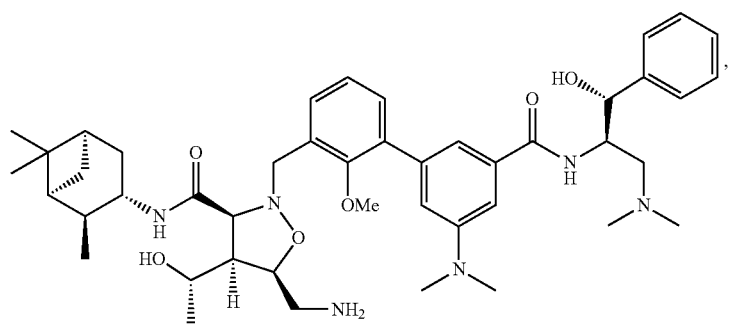
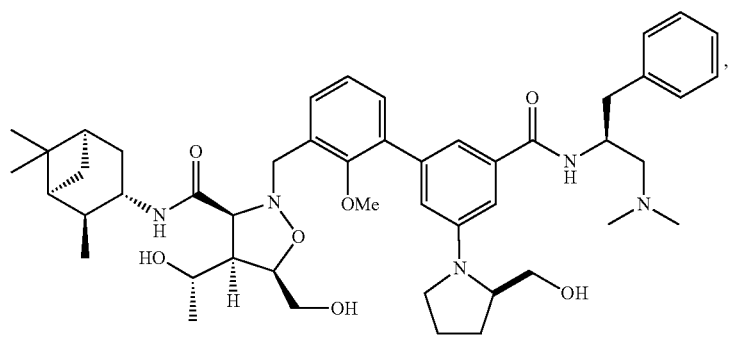
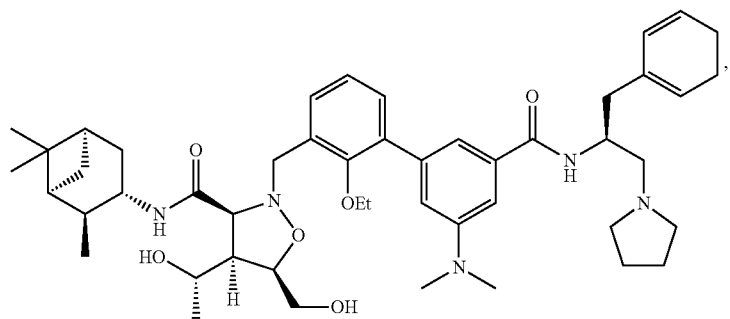
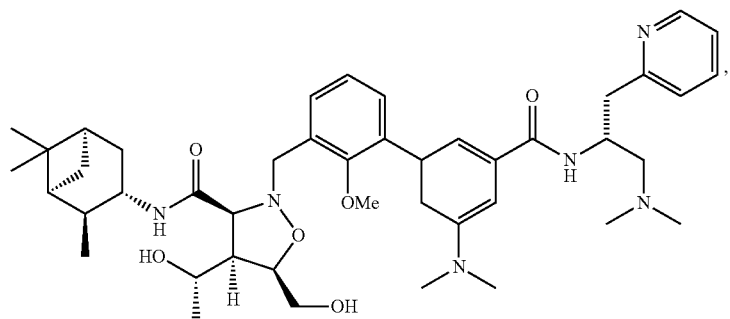

-continued
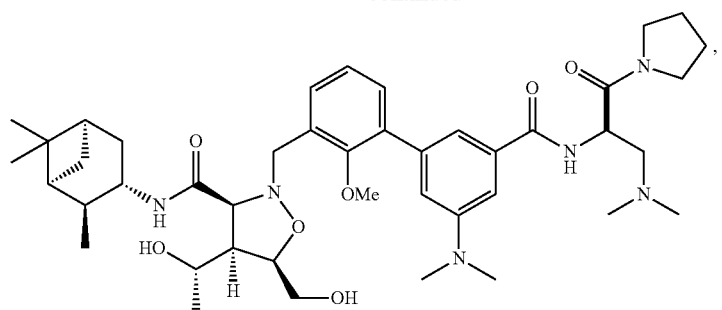
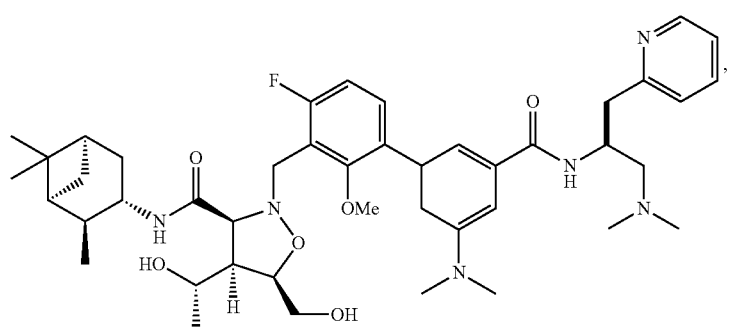
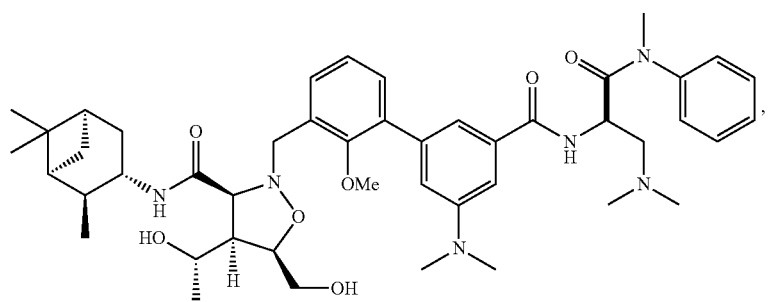
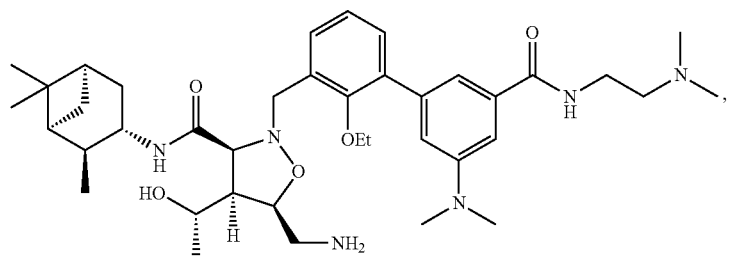
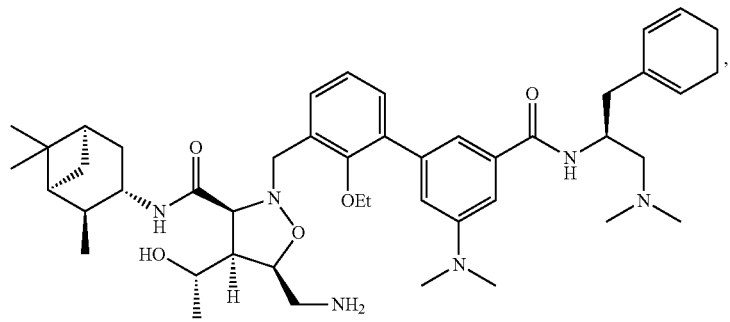

-continued
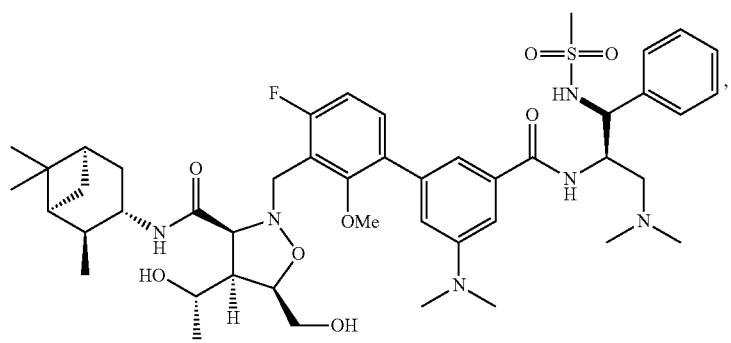
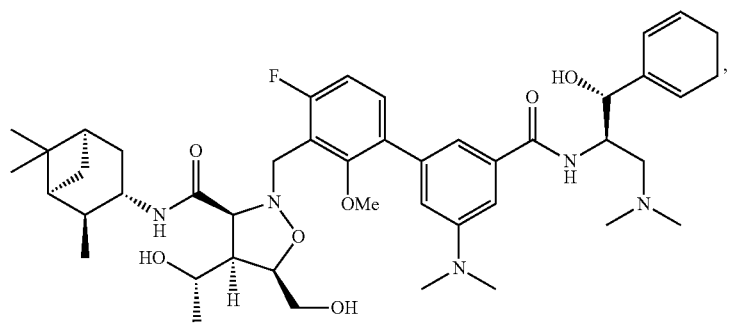
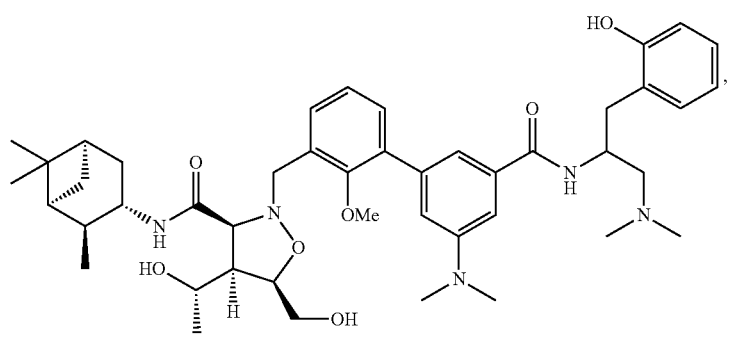
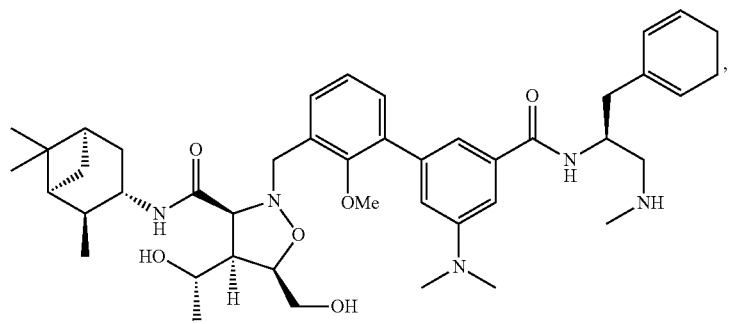
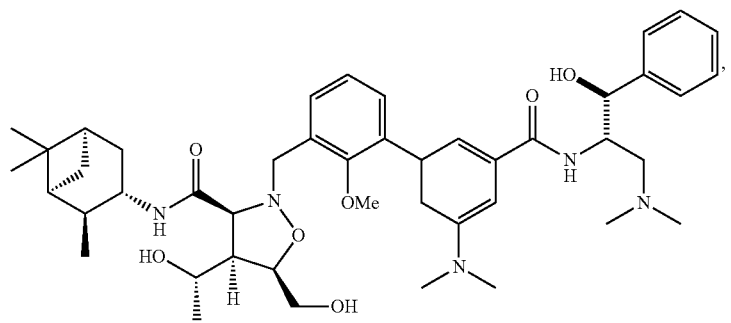

-continued
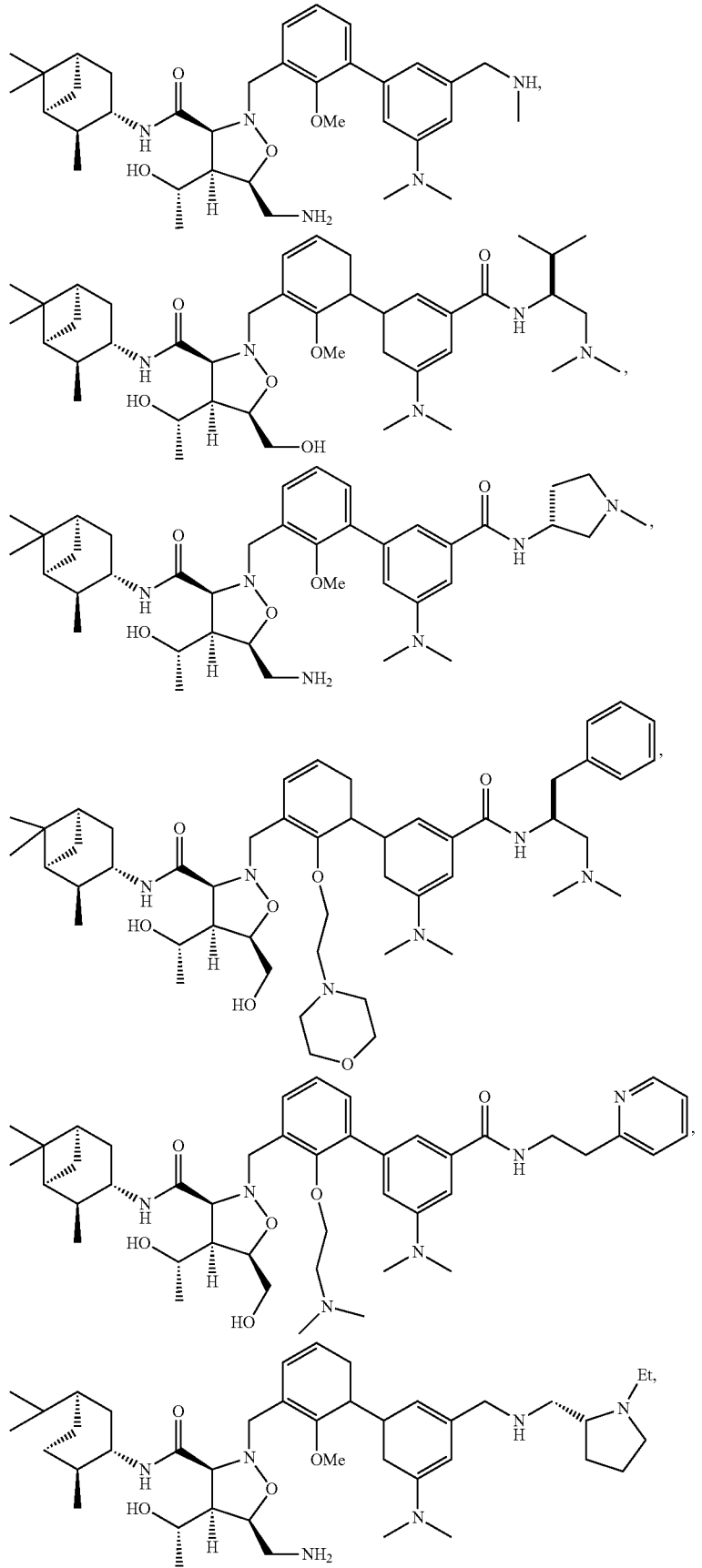

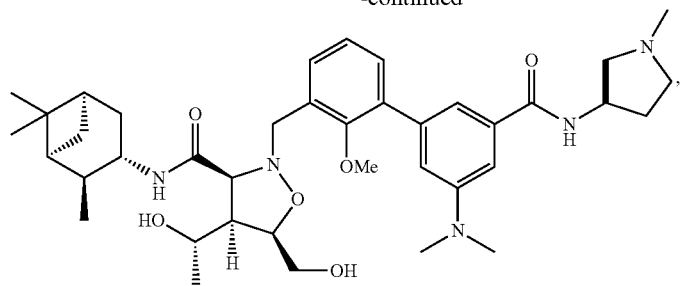
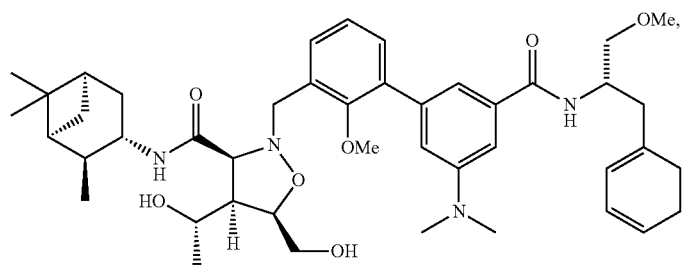
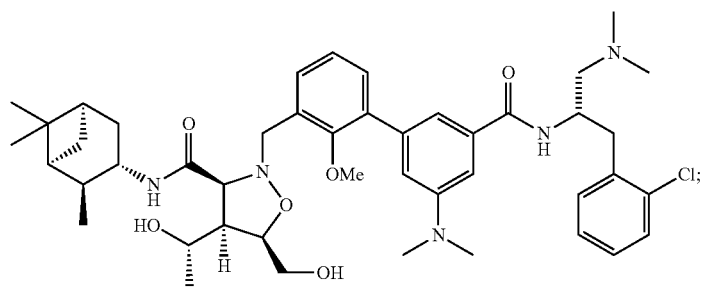
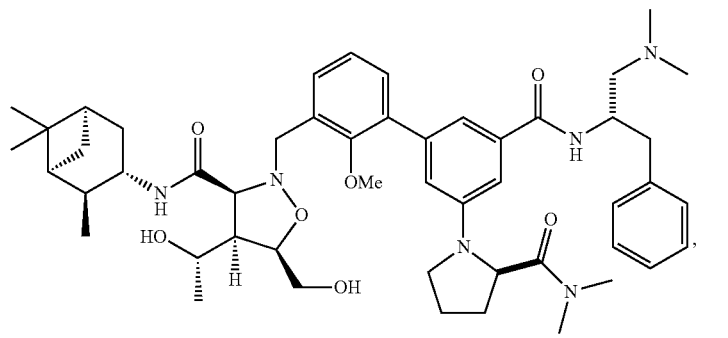
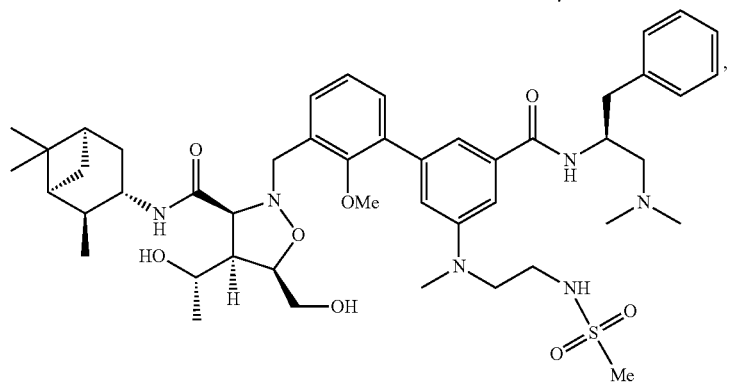

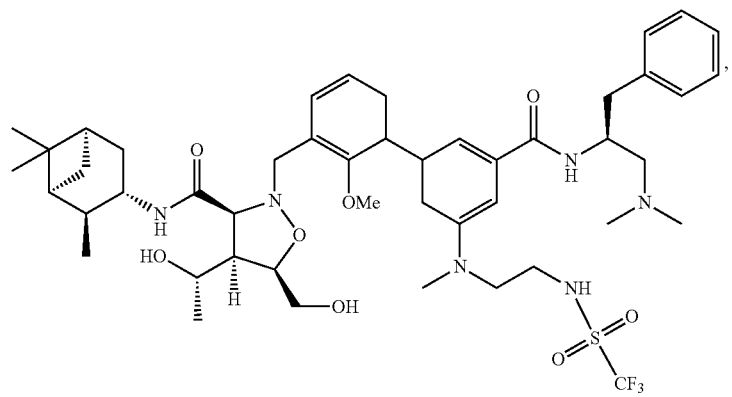
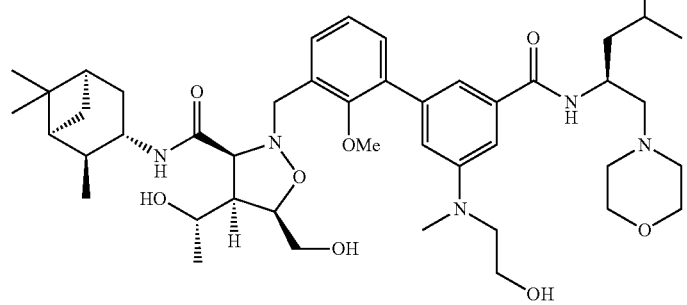
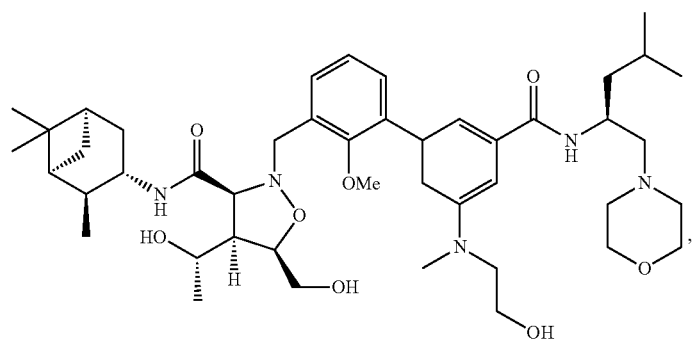
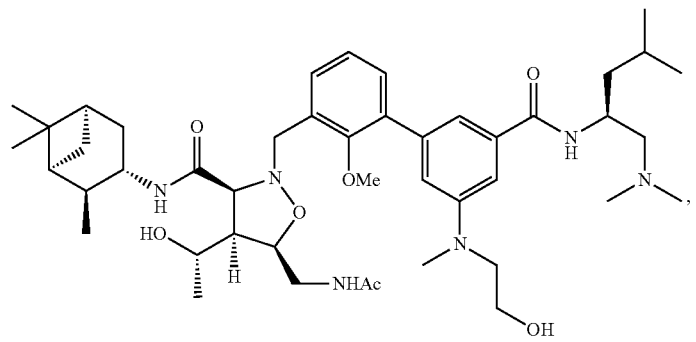
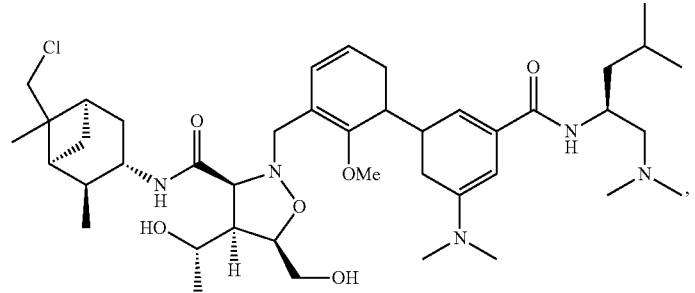

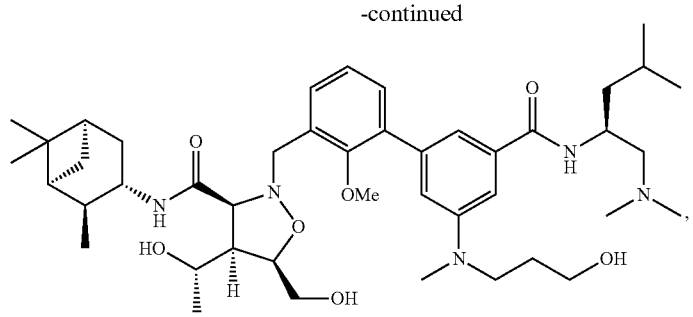

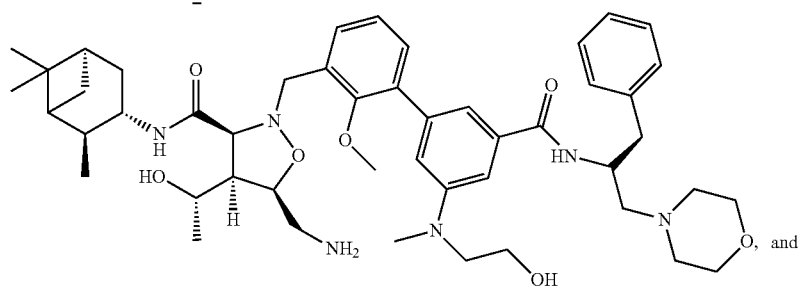

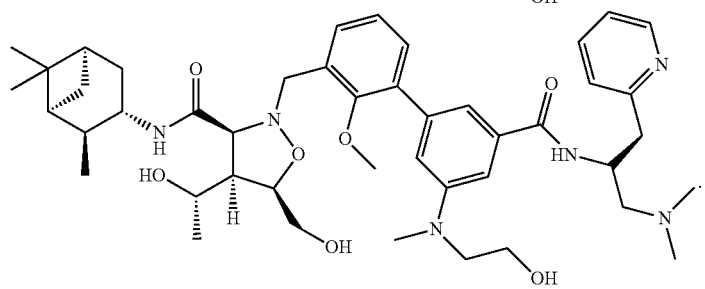

Another aspect of the invention relates to a pharmaceutical composition, comprising at least one of the compounds of the present invention; and at least one pharmaceutically acceptable excipient.

The present invention also relates to a method of treating a bcl-mediated disorder, comprising the step of:

administering to a patient in need thereof a therapeutically effective amount of at least one of the compounds of the present invention.

In certain embodiments, the bcl-mediated disorder is cancer or neoplastic disease. For example, the bcl-mediated disorder may be acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

In addition, the cancer may be follicular lymphoma, diffuse large B-cell lymphoma, mantle cell lymphoma, chronic lymphocytic leukemia prostrate cancer, breast cancer, neuroblastoma, colorectal, endometrial, ovarian, lung cancer, hepatocellular carcinoma, multiple myeloma, head and neck or testicular cancer.

In some embodiments the cancer over-expresses a Bcl protein. In addition, the cancer can also be dependent upon a Bcl protein for growth and survival. In some embodiments the Bcl protein specified may be Bcl-2 and/or Bcl-xL. In some embodiments the cancer exhibits a t(14; 18) chromosomal translocation.

The present invention also relates to a method of treating a bcl-mediated disorder, comprising the step of:

co-administering to a patient in need thereof a therapeutically effective amount of at least one chemotherapeutic agent; and a therapeutically effective amount of at least one of the compounds of the present invention.

The compound or compounds may be administered parenterally, intramuscularly, intravenously, subcutaneously, orally, topically or intranasally. In some embodiments the compound or compounds are administered systemically.

The patient specified above may be a mammal, primate, or human.

DETAILED DESCRIPTION OF THE INVENTION

Definitions

Figure 1:
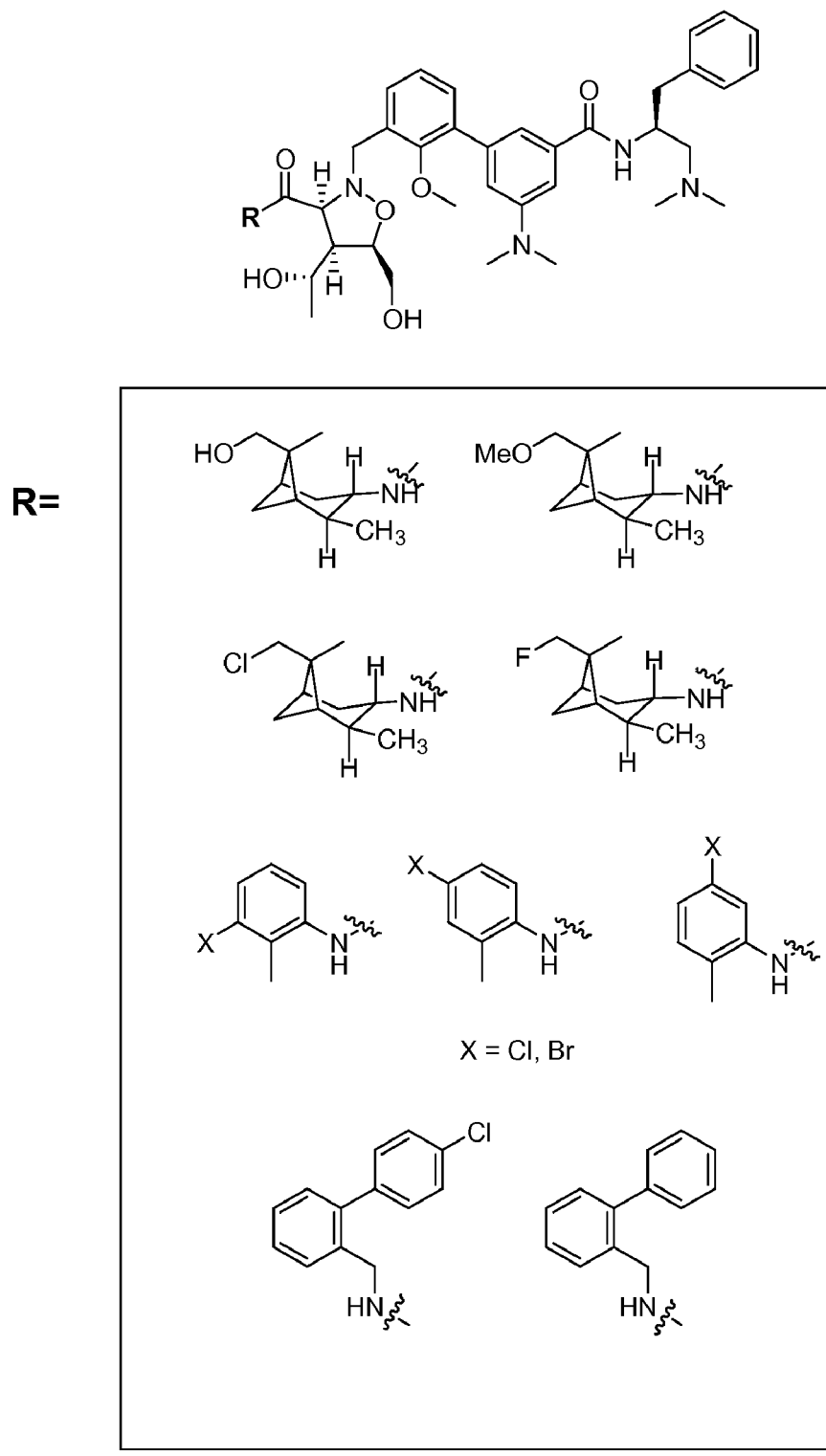
FIG. 1 depicts certain compounds of the invention, some of which are prophetic embodiments.
Figure 2:
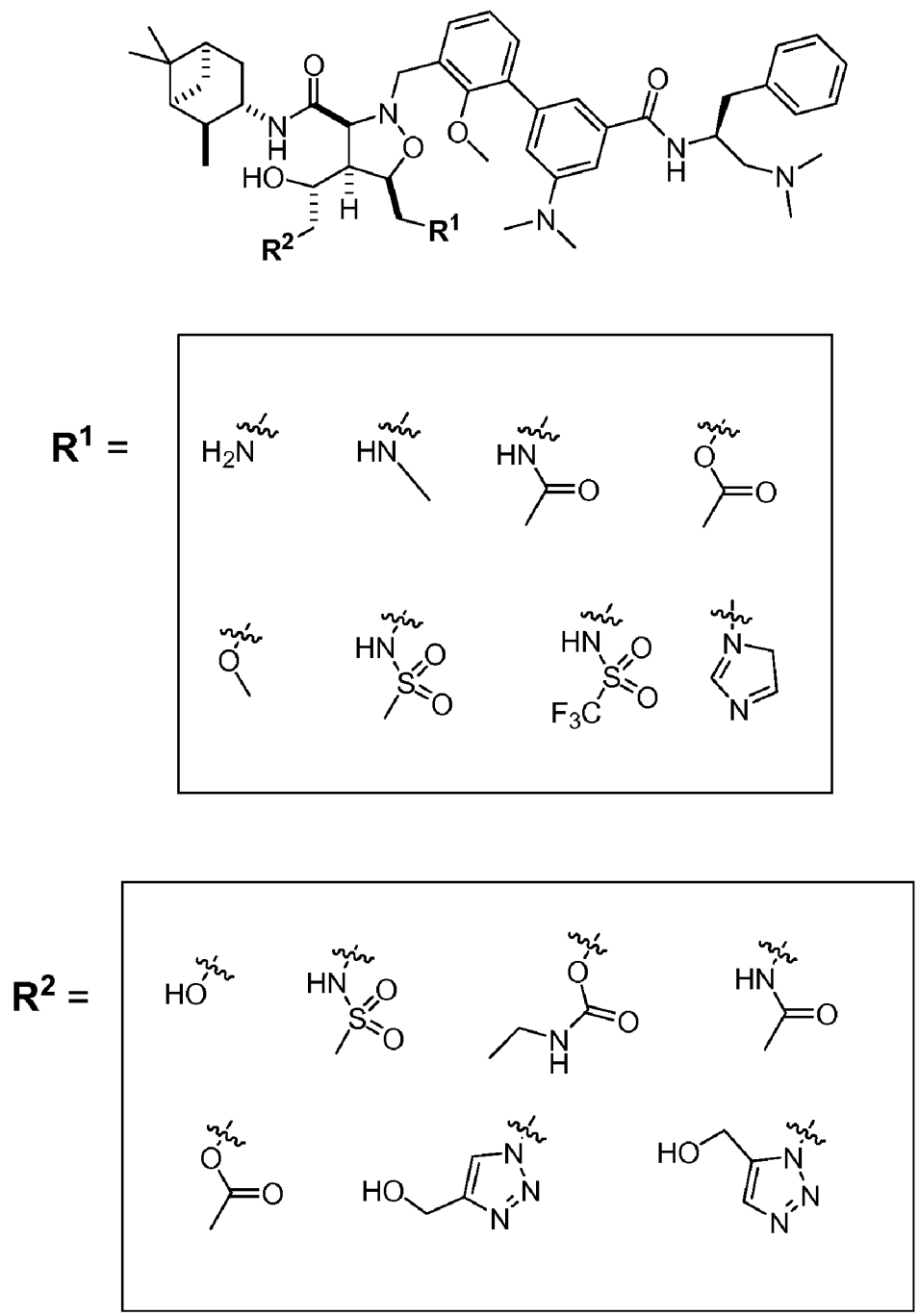
FIG. 2 depicts certain compounds of the invention, some of which are prophetic embodiments.
Figure 3:
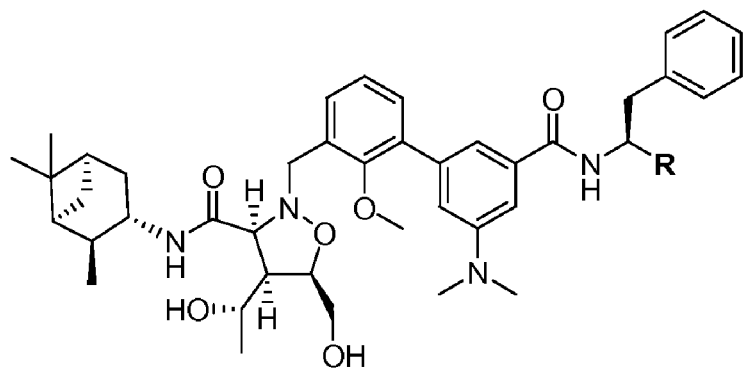
FIG. 3 depicts certain compounds of the invention, some of which are prophetic embodiments.
Figure 3:
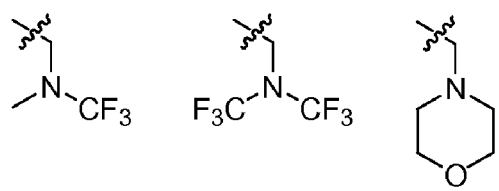
Figure 3:
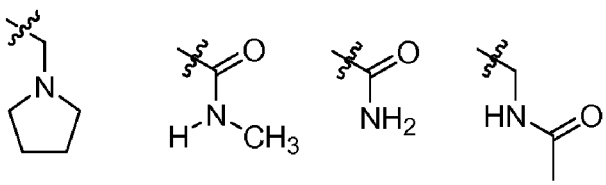
Figure 3:
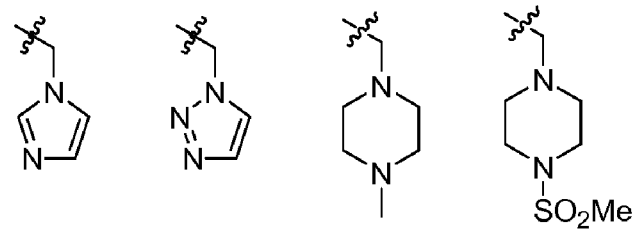
Figure 3:
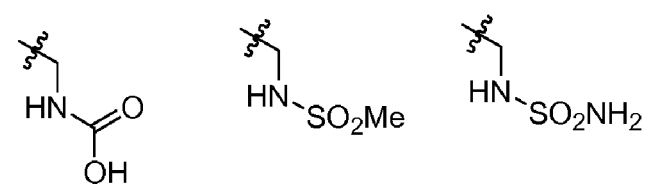
Figure 4:
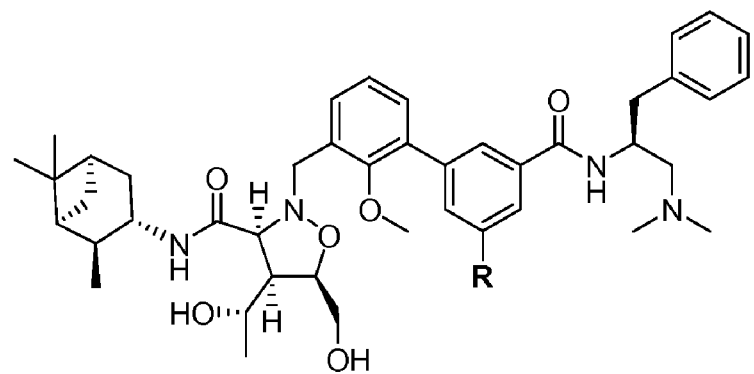
FIG. 4 depicts certain compounds of the invention, some of which are prophetic embodiments.
Figure 4:
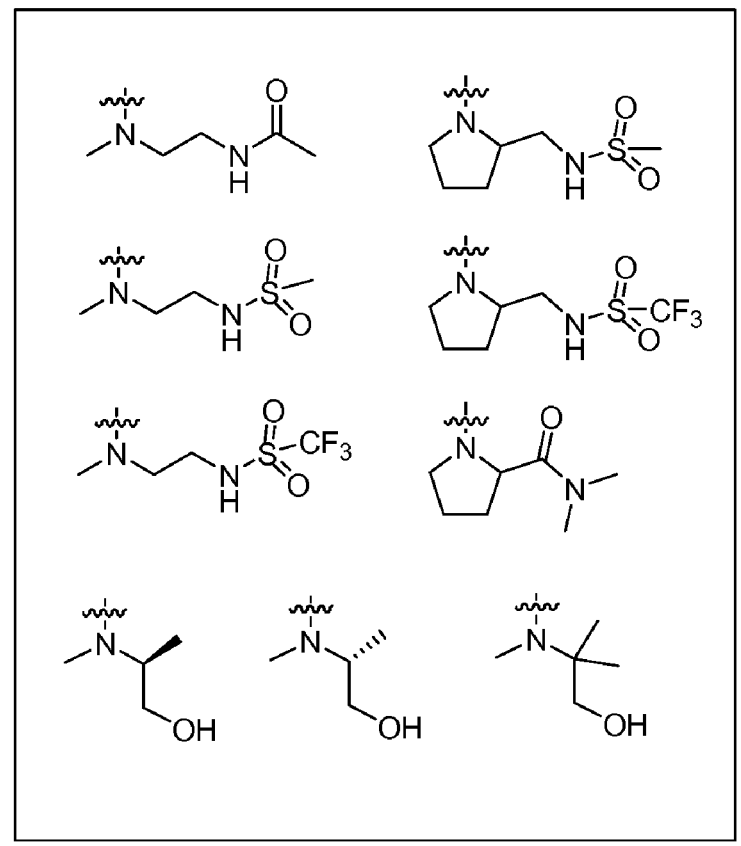
Figure 5:
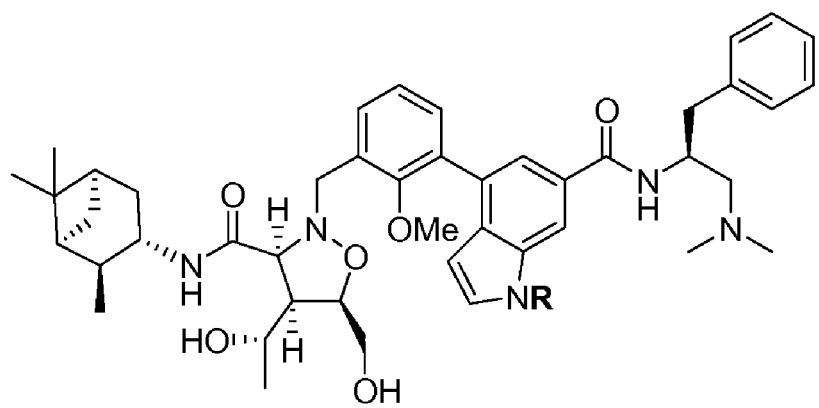
FIG. 5 depicts certain compounds of the invention, some of which are prophetic embodiments.
Figure 6:
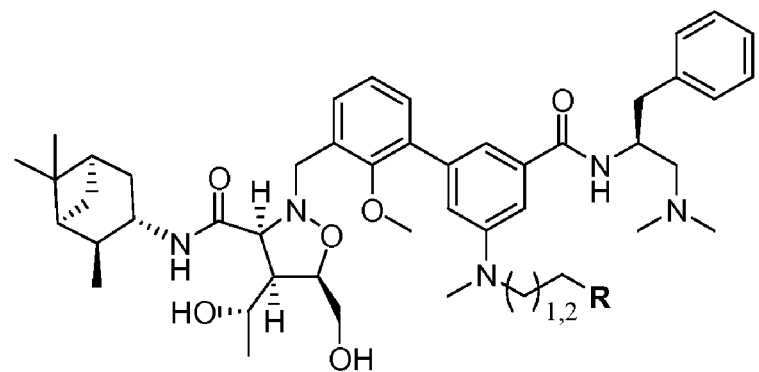
FIG. 6 depicts certain compounds of the invention, some of which are prophetic embodiments.
Figure 6:
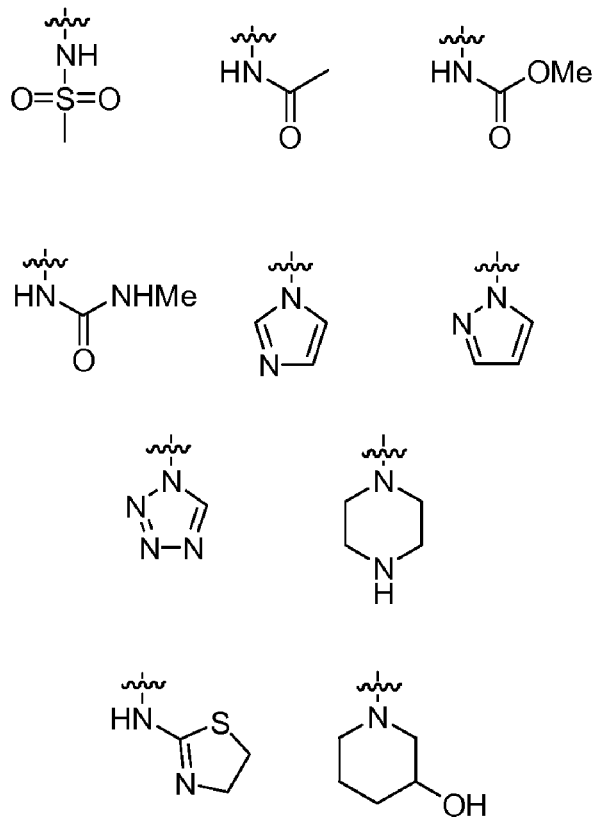

For convenience, certain terms employed in the specification, examples, and appended claims are collected here.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "haloalkyl", as used herein, refers to an alkyl group where anywhere from 1 to all hydrogens have been replaced with a halide. A "perhaloalkyl" is where all of the hydrogens have been replaced with a halide.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that may be represented by the general formulas:

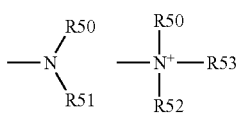

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

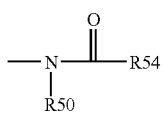

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

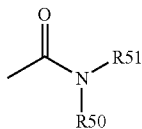

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

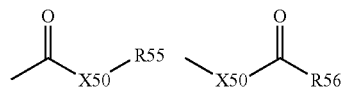

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that may be represented by the general formula:

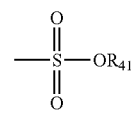

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "carbamoyl" refers to —O(C=O)NRR', where R and R' are independently H, aliphatic groups, aryl groups or heteroaryl groups.

The term "alkylamino" refers to —NHR, where R is an alkyl group.

The term "dialkylamino" refers to —NRR', where both R and R' are alkyl groups.

The term "hydroxyalkyl" refers to —R—OH, where R is an aliphatic group.

The term "aminoalkyl" refers to —R—NH$_2$, where R is an aliphatic group.

The term "alkylaminoalkyl" refers to —R—NH—R', where both R and R' are aliphatic groups.

The term "dialkylaminoalkyl" refers to —R—N(R')—R", where R, R', and R" are aliphatic groups.

The term "arylaminoalkyl" refers to —R—NH—R', where R is an aliphatic and R' is an aryl group.

The term "oxo" refers to a carbonyl oxygen (=O).

The term "thioxo" refers to a carbonyl sulfur (=S).

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that may be represented by the general formula:

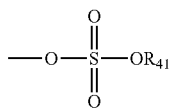

in which $R_{41}$ is as defined above.

The term "sulfonylamino" is art recognized and includes a moiety that may be represented by the general formula:

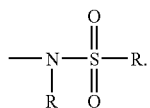

The term "sulfamoyl" is art-recognized and includes a moiety that may be represented by the general formula:

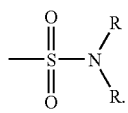

The term "sulfonyl", as used herein, refers to a moiety that may be represented by the general formula:

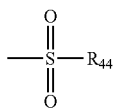

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that may be represented by the general formula:

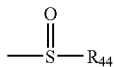

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The term "subject" as used herein, refers to an animal, typically a mammal or a human, that has been the object of treatment, observation, and/or experiment. When the term is used in conjunction with administration of a compound or drug, then the subject has been the object of treatment, observation, and/or administration of the compound or drug.

The term "therapeutically effective amount" as used herein, means that amount of active compound or pharmaceutical agent that elicits the biological or medicinal response in a cell culture, tissue system, animal, or human that is being sought by a researcher, veterinarian, clinician, or physician, which includes alleviation of the symptoms of the disease, condition, or disorder being treated. In the present invention, such an amount will be sufficient to bind to Bcl-2 in a cell and inhibit at least part of the anti-apoptotic activity of the protein. Such an amount may be sufficient to provide therapeutic effectiveness in a patient or may serve to sensitize the cell to treatment with another anticancer agent.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the site of the Bcl mediated disorder, such that it enters the patient's system and, thus, is subject to metabolism and other like processes, for example, subcutaneous administration.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrases "Bcl-mediated disorder" and "disorder mediated by cells expressing Bcl proteins" refer to pathological and disease conditions in which a Bcl protein plays a role. Such roles may be directly related to the pathological condition or may be indirectly related to the condition. The feature common to this class of conditions is that they may be ameliorated by inhibiting the activity of, function of, or association with Bcl proteins.

As used herein, the terms "Bcl" and "Bcl protein" are intended to encompass one or more of the Bcl-2 subfamily of anti-apoptotic proteins Bcl-2, Bcl-w, Mcl-1, Bcl-XL, A1, Bfl1, Bcl-B, BOO/DIVA, and their homologues.

Synthesis of Heterocyclic Compounds

The isoxazolidine compounds of the invention may be prepared using a [3+2]cycloaddition reaction between a nitrone and an alkene. The nitrone substrate and alkene may contain functional groups suitable for chemical derivatization following synthesis of the isoxazolidine core. In certain instances, a Lewis acid is added to the reaction. In a preferred embodiment, the Lewis acid is Ti(Oi-Pr)$_4$. In certain instances, the reaction mixture is subjected to microwave radiation. In general, the subject reactions are carried out in a liquid reaction medium, but may be carried out on a solid support. The reactions may be conducted in an aprotic solvent, preferably one in which the reaction ingredients are substantially soluble. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, chlorobenzene, carbon tetrachloride, and the like; aliphatic or aromatic hydrocarbon solvents, such as benzene, xylene, toluene, hexane, pentane and the like; esters and ketones, such as ethyl acetate, acetone, and 2-butanone; polar aprotic solvents, such as acetonitrile, dimethylsulfoxide, dimethylformamide, pyridine, and the like; or combinations of two or more solvents. The reactions may be conducted at a variety of temperatures. In certain instances, the cycloaddition reaction is conducted using a substrate attached to a solid support. Following synthesis of the isoxazolidine core, the isoxazolidine compound may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts may be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Biological Activity Analysis

The following in vitro binding and cellular assays may be used to determine the activity and specificity of compounds of the present invention to bind to Bcl-2 and inhibit Bcl-2 function in a cell.

Bcl-2 Binding Assay

Bcl-2 and Bcl-xL binding may be determined using a variety of known methods. One such assay is a sensitive and quantitative in vitro binding assay using fluorescence polarization (FP) described by Wang, J.-L.; Zhang, Z-J.; Choksi, S.; Sjam. S.; Lu, Z.; Croce, C. M.; Alnemri, E. S.; Komgold, R.; Huang, Z. Cell permeable Bcl-2 binding peptides: a chemical approach to apoptosis induction in tumor cells. Cancer Res. 2000, 60, 1498-1502).

Cell Based Assays

The ability of isoxazolidine compounds of the present invention to inhibit cell-viability in cancer cells with Bcl-2 protein over-expression was demonstrated. When RL-cells are exposed to isoxazolidine compounds of the present invention, the inhibitors show a dose-dependent cell-killing in Alamar blue cytoxicity assays. When Panc1 cells are exposed to the isoxazolidine compounds of the present invention in combination with camptothecin, the inhibitors show a synergistic dose-dependent cell killing in propidium iodide exclusion cell survival assays.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which may be combined with a carrier material to produce a single dosage form will vary depending upon the host being treated, the particular mode of administration. The amount of active ingredient which may be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release may be controlled. Examples of other biodegradable polymers include poly(orthoesters) and poly(anhydrides). Depot injectable formulations are also prepared by entrapping the drug in liposomes or microemulsions which are compatible with body tissue.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the compound in the proper medium. Absorption enhancers can also be used to increase the flux of the compound across the skin. The rate of such flux may be controlled by either providing a rate controlling membrane or dispersing the compound in a polymer matrix or gel.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Ophthalmic formulations, eye ointments, powders, solutions and the like, are also contemplated as being within the scope of this invention.

When the compounds of the present invention are administered as pharmaceuticals, to humans and animals, they may be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Methods of Therapy and Treatment

The present invention further provides methods for treating and reducing the severity of cancer as well as other Bcl-mediated disorders or conditions.

Bcl-2 inhibitors have been shown to be active against a number of cancer cell lines as single agent, including, but not limited to, breast cancer (US 2003/0119894, published PCT applications WO 02/097053 and WO 02/13833), lymphomas (*Nature* (2005) 435, 677-681), small cell lung cancer (*Nature* (2005) 435, 677-681), head and neck cancer (published PCT application WO 02/097053), and leukemias (published PCT application WO 02/13833).

Bcl-2 inhibitors have been shown to be active against a number of cancer cell lines in combination with other anticancer agents and radiation, including, but not limited to, breast cancer (With docetaxel, published PCT application WO 02/097053), prostate cancer (With docetaxel, published PCT application WO 02/097053), head and neck cancer (With docetaxel, published PCT application WO 02/097053), and non small-cell lung cancer (With paclitaxel, *Nature* (2005) 435, 677-681). In addition to the aforementioned combination chemotherapeutics, small molecule inhibitors of Bcl-2 proteins display synergy with other anticancer agents, including, but not limited to etoposide, doxorubicin, cisplatin, paclitaxel, and radiation (*Nature* (2005) 435, 677-681).

Cancers or neoplastic diseases and related disorders that may be treated by administration of compounds and compositions of the present invention, include, but are not limited to those listed in Table 1 (for a review of such disorders, see Fishman et al., 1985, Medicine, 2d Ed., J. B. Lippincott Co., Philadelphia):

TABLE 1

CANCERS AND NEOPLASTIC DISORDERS

Leukemia
    acute leukemia
    acute lymphocytic leukemia
    acute myelocytic leukemia
        myeloblastic
        promyelocytic
        myelomonocytic
        monocytic
        erythroleukemia
    chronic leukemia
    chronic myelocytic (granulocytic) leukemia
    chronic lymphocytic leukemia
Polycythemia vera
Lymphoma
    Hodgkin's disease
    non-Hodgkin's disease
Multiple myeloma
Waldenstrom's macroglobulinemia
Heavy chain disease
Solid tumors
    sarcomas and carcinomas
        fibrosarcoma
        myxosarcoma
        liposarcoma
        chondrosarcoma
        osteogenic sarcoma
        chordoma
        angiosarcoma
        lymphangiosarcoma
        lymphangioendotheliosarcoma
        synovioma
        mesothelioma
        Ewing's tumor TABLE 1-continued

| CANCERS AND NEOPLASTIC DISORDERS |
| --- |
| leiomyosarcoma |
| rhabdomyosarcoma |
| colon carcinoma |
| pancreatic cancer |
| breast cancer |
| ovarian cancer |
| prostate cancer |
| squamous cell carcinoma |
| basal cell carcinoma |
| adenocarcinoma |
| sweat gland carcinoma |
| sebaceous gland carcinoma |
| papillary carcinoma |
| papillary adenocarcinomas |
| cystadenocarcinoma |
| medullary carcinoma |
| bronchogenic carcinoma |
| renal cell carcinoma |
| hepatoma |
| bile duct carcinoma |
| choriocarcinoma |
| seminoma |
| embryonal carcinoma |
| Wilms' tumor |
| cervical cancer |
| uterine cancer |
| testicular tumor |
| lung carcinoma |
| small cell lung carcinoma |
| bladder carcinoma |
| epithelial carcinoma |
| glioma |
| astrocytoma |
| medulloblastoma |
| craniopharyngioma |
| ependymoma |
| pinealoma |
| hemangioblastoma |
| acoustic neuroma |
| oligodendroglioma |
| meningioma |
| melanoma |
| neuroblastoma |
| retinoblastoma |

In certain embodiments, the compounds of the present invention are used to treat cancers including, but not limited to lymphomas (preferably follicular lymphoma, diffuse large B-cell lymphoma, mantle cell lymphoma, or chronic lymphocytic leukemia), prostate cancer (more preferably hormone insensitive), breast cancer (preferably estrogen receptor positive), neuroblastoma, colorectal, endometrial, ovarian, lung (preferably small cell), hepatocellular carcinoma, multiple myeloma, head and neck or testicular cancer (preferably germ cell).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In one embodiment, dosing is one administration per day.

The compound of the invention may be administered as such or in admixtures with pharmaceutically acceptable carriers and can also be administered in conjunction with anti-microbial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Treatment of Cancer in Combination with Chemotherapy or Radiotherapy

In certain embodiments, one or more compounds of the present invention are used to treat or prevent cancer or neoplastic disease in combination with one or more anti-cancer, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, one or more compound of the present invention is used to treat or prevent cancer or neoplastic disease in combination with one or more chemotherapeutic or other anti-cancer agents including, but not limited to those presented in Table 2.

TABLE 2

| CHEMOTHERAPEUTICS AND OTHER ANTI-CANCER AGENTS | |
| --- | --- |
| Radiation: | γ-radiation |
| | Alkylating agents |
| Nitrogen mustards: | cyclophosphamide |
| | Ifosfamide |
| | trofosfamide |
| | Chlorambucil |
| | Estramustine |
| | melphalan |
| Nitrosoureas: | carmustine (BCNU) |
| | Lomustine (CCNU) |
| Alkylsulphonates | busulfan |
| | Treosulfan |
| Triazenes: | Dacarbazine |

TABLE 2-continued

CHEMOTHERAPEUTICS AND OTHER ANTI-CANCER AGENTS

| | |
|---|---|
| Platinum containing compounds: | Cisplatin |
| | carboplatin |
| | oxaplatin |

Plant Alkaloids

| | |
|---|---|
| Vinca alkaloids: | vincristine |
| | Vinblastine |
| | Vindesine |
| | Vinorelbine |
| Taxoids: | paclitaxel |
| | Docetaxol |

DNA Topoisomerase Inhibitors

| | |
|---|---|
| Epipodophyllins: | etoposide |
| | Teniposide |
| | Topotecan |
| | 9-aminocamptothecin |
| | campto irinotecan |
| | crisnatol | mytomycins

| | |
|---|---|
| mytomycin C | Mytomycin C |

Anti-metabolites

Anti-folates:

| | |
|---|---|
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonuclotide reductase Inhibitors: | hydroxyurea |
| | deferoxamine |

Pyrimidine analogs:

| | |
|---|---|
| Uracil analogs | 5-Fluorouracil |
| | Floxuridine |
| | Doxifluridine |
| | Ratitrexed |
| | capecitabine |
| Cytosine analogs | cytarabine (ara C) |
| | Cytosine arabinoside |
| | fludarabine |
| Purine analogs: | mercaptopurine |
| | Thioguanine |

Hormonal therapies:

Receptor antagonists:

| | |
|---|---|
| Anti-estrogens | Tamoxifen |
| | Raloxifene |
| | megestrol |
| LHRH agonists: | goscrelin |
| | Leuprolide acetate |
| Anti-androgens: | flutamide |
| | bicalutamide |

Retinoids/Deltoids

| | |
|---|---|
| Vitamin D3 analogs: | EB 1089 |
| | CB 1093 |
| | KH 1060 |
| Photodyamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon α |
| | Interferon γ |
| | Tumor necrosis factor |

Others:

Prednisilone
Imatinib
Thalidomide
Lenalidomide
Bortezomib
Gemcitabine
Erlotinib

TABLE 2-continued

CHEMOTHERAPEUTICS AND OTHER ANTI-CANCER AGENTS

| | |
|---|---|
| | Gefitinib |
| | Sorafenib |
| | Sutinib |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ATPase inhibitors: | thapsigargin |
| Antibodies | Avastin |
| | Erbitux |
| | Rituxan |

The chemotherapeutic agent and/or radiation therapy may be administered according to therapeutic protocols well known in the art. It will be apparent to those skilled in the art that the administration of the chemotherapeutic agent and/or radiation therapy may be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) may be varied in view of the observed effects of the administered therapeutic agents (i.e., antineoplastic agent or radiation) on the patient, and in view of the observed responses of the disease to the administered therapeutic agents.

Also, in general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration may be made according to established protocols known in the art, and then, based upon the observed effects, the dosage, modes of administration and times of administration may be modified by the skilled clinician.

The particular choice of chemotherapeutic agent or radiation will depend upon the diagnosis of the attending physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/ or radiation to be administered in conjunction (i.e., within a single treatment protocol) with a compound of the present invention.

If a compound of the present invention, and the chemotherapeutic agent and/or radiation are not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

EXEMPLIFICATION

The invention now being generally described, it will be more readily understood by reference to the following examples, which are included merely for purposes of illustration of certain aspects and embodiments of the present invention, and are not intended to limit the invention.

Example 1

Part A

To a solution of phenol 2 (750 mg, 3 mmol, 1 eq) in DMF (5 mL) at 0° C. was added NaH (130 mg, 3.6 mmol, 1.2 eq) followed by MeI (280 μL, 4.5 mmol, 1.5 eq). The reaction mixture was stirred at rt for 24 h and then quenched with water. The mixture was diluted with EtOAc and washed twice with water then brine. The solution was dried over MgSO₄, filtered and concentrated to afford 790 mg of crude product 3. Yield 100%.

Part B

Aldehyde 3 (790 mg, 3.0 mmol, 1 eq) and hydroxylamine hydrochloride (250 mg, 3.6 mmol, 1.2 eq) were dissolved in THF/MeOH (3:2, 10 mL). Water (2 mL) was added and the pH was adjusted to 9 with 6 N KOH. The reaction mixture was stirred at rt overnight. After 16 h, NaBH₃CN (380 mg, 6.07 mmol, 2 eq) was added followed by a crystal of methyl orange. The pH was adjusted to 2 and the resulting ruby red color was maintained for the duration of the reaction by the frequent addition of 1 N HCl. After stirring for 2 h, another portion of NaBH₃CN (380 mg, 6.10 mmol, 2 eq) was added. After stirring for a total of 16 h, the pH of the reaction mixture was brought to 7 and DCM was added. The mixture was washed twice with water, brine and then dried over MgSO₄. The crude product was purified by silica gel chromatography (50-100% EtOAc/hexane) to afford 706 mg of hydroxylamine 4. Yield 83%.

Part C

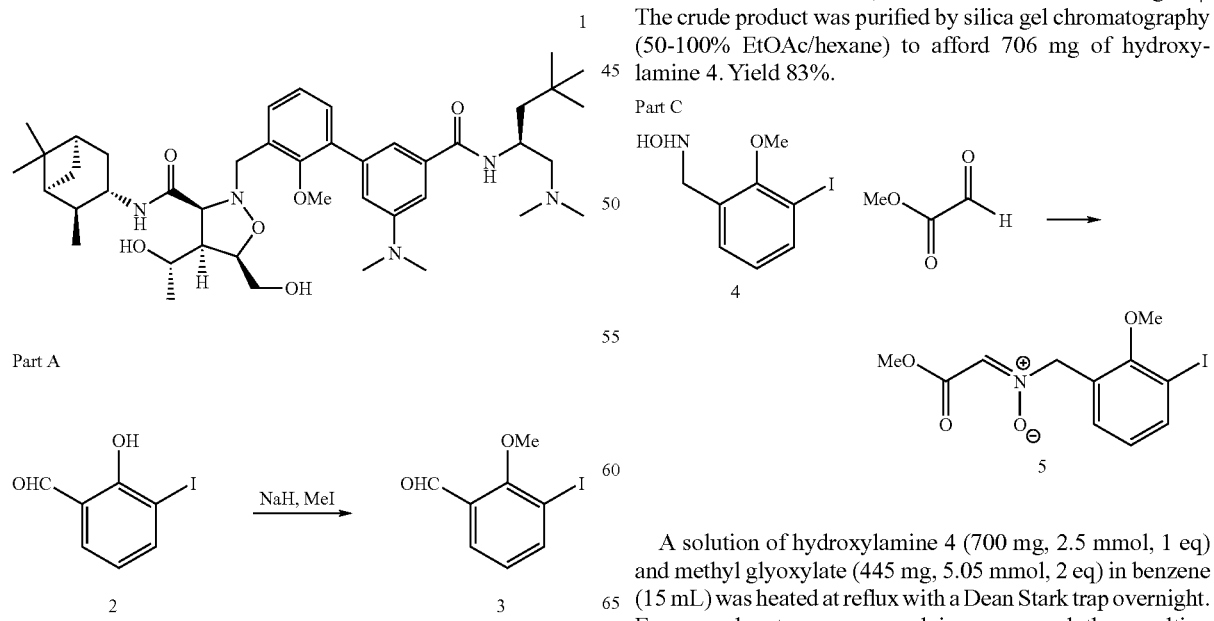

A solution of hydroxylamine 4 (700 mg, 2.5 mmol, 1 eq) and methyl glyoxylate (445 mg, 5.05 mmol, 2 eq) in benzene (15 mL) was heated at reflux with a Dean Stark trap overnight. Excess solvent was removed in vacuo and the resulting nitrone 5 was taken on crude in the next step.

Part D

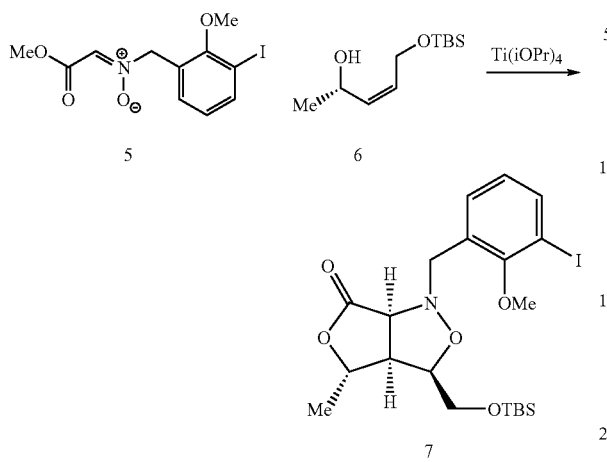

Nitrone 5 (880 mg, 2.5 mmol, 1 eq), allylic alcohol 6 (820 mg, 3.80 mmol, 1.5 eq) and Ti(iOPr)$_4$ (1.1 mL, 3.8 mmol, 1.5 eq) were dissolved in toluene (5 mL) and heated in the microwave at 120° C. for 10 min The reaction mixture was diluted with EtOAc (15 mL) and 3-(dimethylamino)-1,2-propanediol (500 μL) was added. After stirring for 2 h, EtOAc was added and the mixture was washed twice with water and then brine, dried over MgSO$_4$, filtered over Celite and concentrated in vacuo to afford an oil. The crude residue was purified by silica gel chromatography (20% hexanes/EtOAc) to afford 575 mg of lactone 7. Yield 43%.

Part E

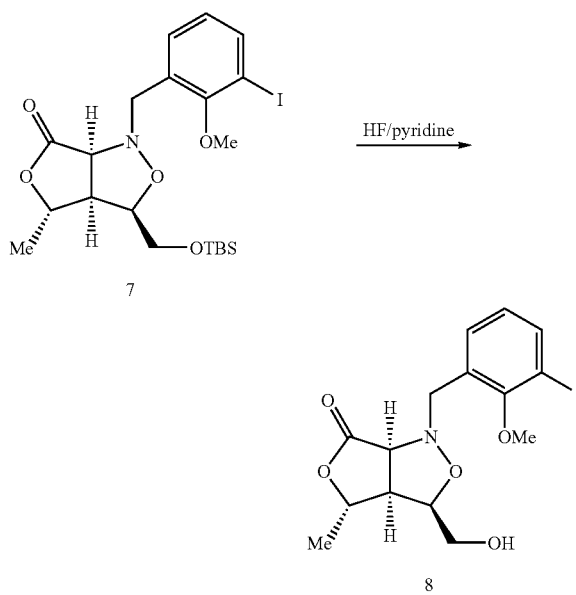

To a solution of lactone 7 (225 mg, 42 μmol) in THF (6 mL) was added pyridine (2 mL) and HF/pyridine (2 mL). The mixture was stirred at rt for 4 h then TMSOMe (8 mL) was added. Solvent was removed in vacuo and the crude product was purified by silica gel chromatography (EtOAc) to afford 128 mg of 8 as a white foam. Yield 72%.

Part F

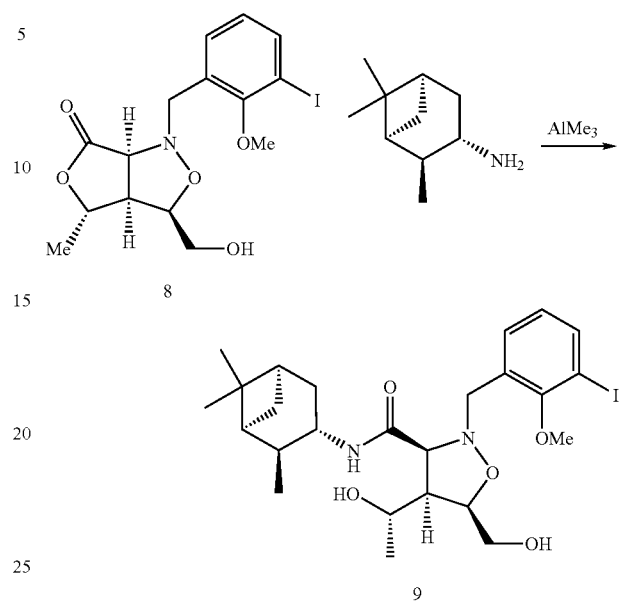

To a flame-dried 10-mL round bottom flask containing (+)-isopinocampheylamine (110 μL, 0.61 mmol, 2 eq) and DCM (2 mL) was added trimethylaluminum (300 μL, 2 M in hexane, 0.61 mmol, 2 eq). After stirring for 15 min, a solution of lactone 8 (128 mg, 0.31 mmol, 1 eq) in DCM (4 mL) was added and the mixture was stirred at rt overnight. The reaction was quenched by the addition of a saturated aqueous Rochelle salt solution (5 mL) and the mixture was rapidly stirred for 2 h. DCM was added and the mixture washed three times with water and then brine. The solution was dried over MgSO$_4$, filtered and concentrated in vacuo to afford a oil. The crude material was purified by silica gel chromatography (EtOAc) to afforded 160 mg of 9. Yield 91%.

Part G

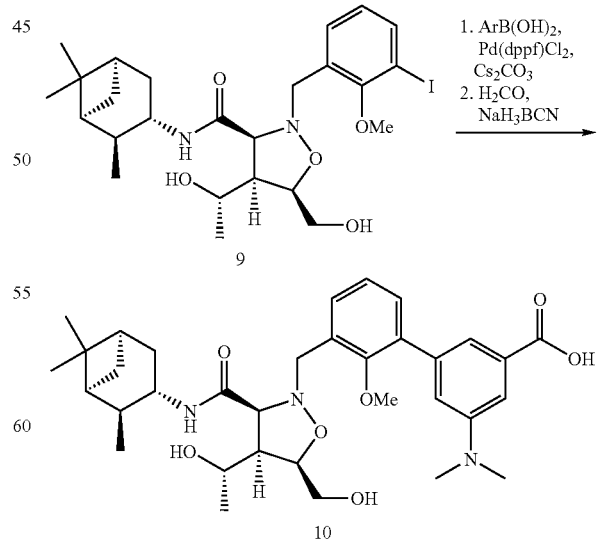

A flask containing aryl iodide 9 (2.0 g, 3.5 mmol, 1 eq), 3-amino-5-carboxyphenylboronic acid (1.2 g, 7.0 mmol, 2 eq), cesium carbonate (3.5 g, 10 mmol, 3 eq), potassium acetate (300 mg, 3.5 mmol, 1 eq) and Pd(dppf)Cl$_2$ (300 mg, 0.35 mmol, 0.1 eq) was purged with argon and DMSO (35 mL) added. The mixture was heated at 60° C. for 18 h, then additional Pd(dppf)Cl$_2$ (300 mg, 0.35 mmol, 0.1 eq) was added and heating continued for an additional 18 h. The reaction mixture was added to water (300 mL), acidified with 6 N HCl until the aqueous layer attained a pH of 4, and extracted with DCM (3×100 mL). The combined organic layers were dried over Na$_2$SO$_4$, filtered and concentrated in vacuo to afford a brown oil.

This crude oil was dissolved in MeOH (50 mL) and treated with AcOH (1 mL), 37% formalin (2 mL, 27 mmol, 8 eq) and NaBH$_3$CN (600 mg, 10 mmol, 2.7 eq). After stirring at rt for 2 h, the reaction mixture was partitioned between water (300 mL) and DCM (100 mL) and acidified with 6 N HCl until the aqueous layer attained a pH of 4. The layers were separated and the aqueous extracted with DCM (3×80 mL). The combined organic layers were dried over Na$_2$SO$_4$, filtered, treated with Et$_3$N (2 mL), and concentrated in vacuo to afford a brown oil. The oil was purified by silica gel chromatography (5-7.5% MeOH/DCM) to give 1.34 g of 10 as a brown solid. Yield 63%.

Part H

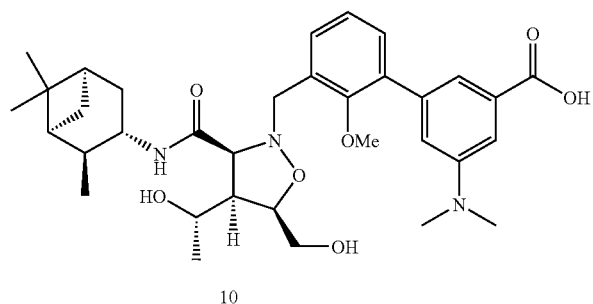

10

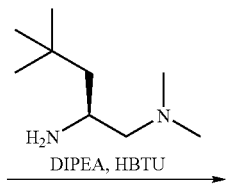

DIPEA, HBTU
→

A solution of 10 (300 mg, 0.5 mmol, 1 eq) in DCM (10 mL) was treated with DIPEA (150 uL, 0.86 mmol, 1.8 eq), (S)—N$^1$,N$^1$,4,4-tetramethylpentane-1,2-diamine (120 mg, 0.74 mmol, 1.5 eq), and HBTU (230 mg, 0.62 mmol, 1.3 eq). After stirring overnight at rt, the mixture was added to water (90 mL), and extracted with DCM (3×50 mL). The organic phases were dried over Na$_2$SO$_4$, filtered and concentrated in vacuo to give a brown solid. This material was purified by silica gel chromatography (5-10% MeOH/DCM) to give 161 mg 1 as a tan solid. Yield 44%. MS (ESI(+)) m/z 750.91 (M+H)$^+$.

Example 2

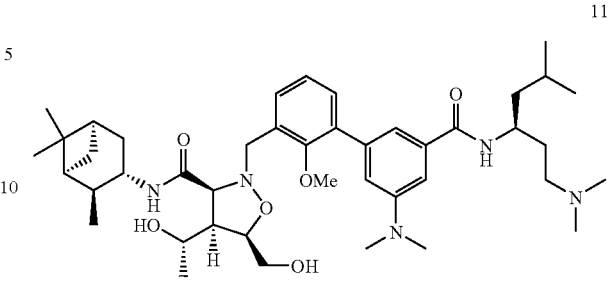

11

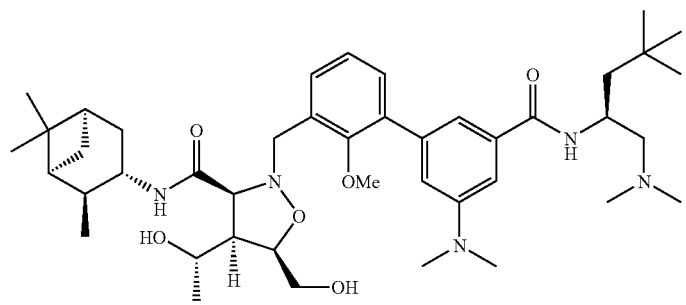

1

Compound II was synthesized according to the procedure described in Example 1 using (S)—N$^1$,N$^1$1,5-trimethylhexane-1,3-diamine in place of (S)—N1,N1,4,4-tetramethylpentane-1,2-diamine. 49% yield. MS (ESI(+)) m/z 376.23 (M+2H)$^{2+}$.

Example 3

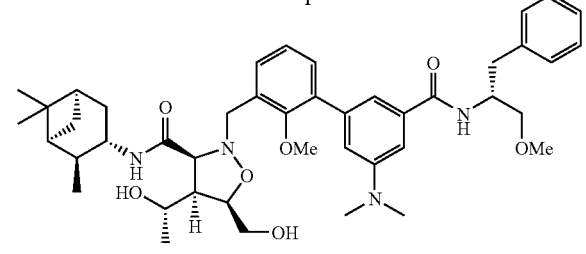

12

Part A

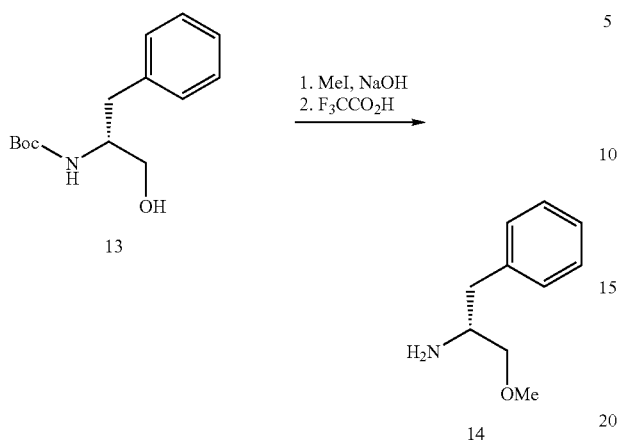

To a flask containing Boc-D-phenylalaminol 13 (100 mg, 0.4 mmol, 1 eq), and triethylbenzylammonium chloride (10 mg, 0.04 mmol, 0.1 eq) was added THF (4 mL), 50% NaOH (3 mL), and MeI (26 uL, 0.4 mmol, 1 eq). After stirring at rt for 72 h, the reaction mixture was diluted with water (30 mL) and extracted with DCM (3×20 mL). The organic layers were dried over $Na_2SO_4$, concentrated, and purified by silica gel flash chromatography (15% EtOAc/hexanes), providing a clear oil (ca. 50 mg, 50%).

This resulting oil was dissolved in trifluoroacetic acid (5 mL) and stirred for 2 h. The acid was removed in vacuo and the residue co-evaporated with toluene to give the trifluoroacetate salt of 27 as a clear oil which was used without further purification.

Part B

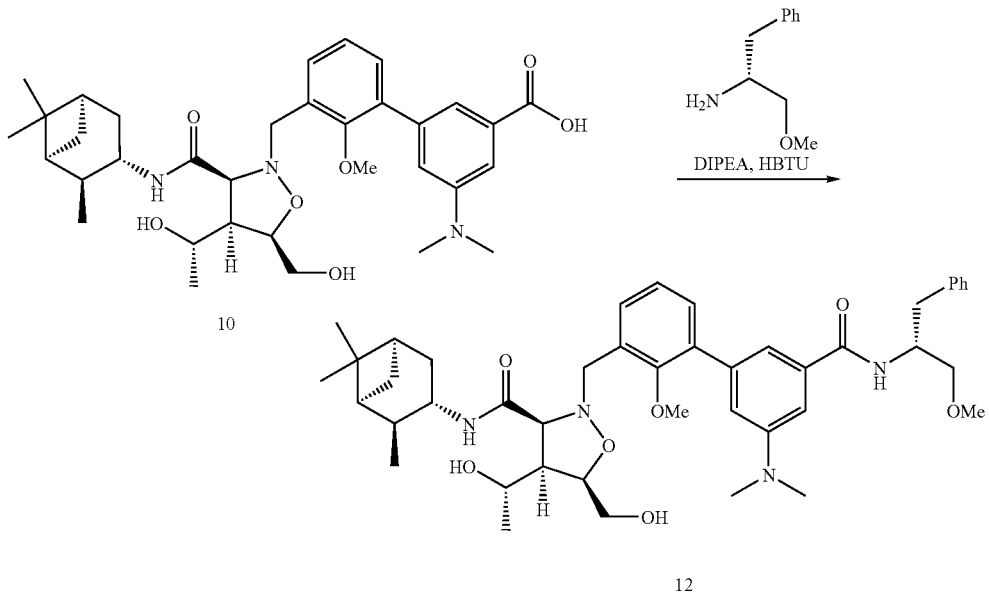

Compound 12 was synthesized according to the procedure described in Example 1, using amine 14 in place of (S)—$N^1$, $N^1$,4,4-tetramethylpentane-1,2-diamine. 56% yield. MS (ESI (+)) m/z 757.93 (M+H)$^+$.

Example 4

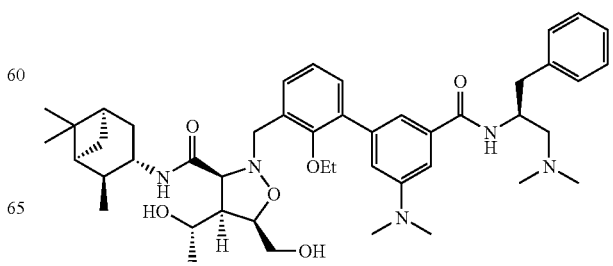

Part A

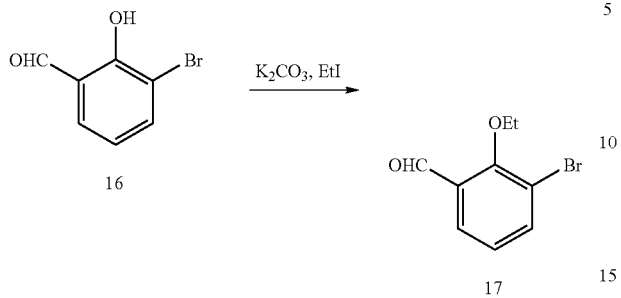

To a solution of phenol 16 (2.0 g, 10 mmol, 1 eq) in DMF (5 mL) was added $K_2CO_3$ (2.1 g, 15 mmol, 1.5 eq) followed by EtI (880 μL, 11 mmol, 1.1 eq). The reaction mixture was stirred at 60° C. for 24 h and then cooled to rt and quenched with water. The mixture was diluted with EtOAc and washed twice with water and then brine. The solution was dried over $MgSO_4$, filtered and concentrated in vacuo. The crude material was purified by silica gel chromatography (10% hexanes/EtOAc) to afford 1.63 g of the desired product 17. Yield 72%.

Part B

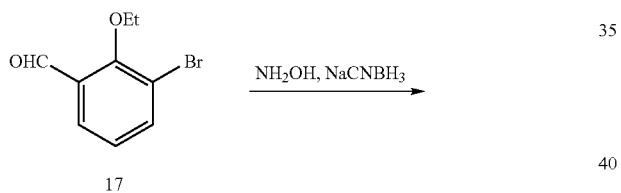

Aldehyde 17 (1.6 g, 7.0 mmol, 1 eq) and hydroxylamine hydrochloride (590 mg, 8.5 mmol, 1.2 eq) were dissolved in THF/MeOH (3:2, 10 mL). Water (2 mL) was added and the pH was adjusted to 9 with 6 N KOH. The reaction mixture was stirred at rt for 4 h then $NaBH_3CN$ (890 mg, 14 mmol, 2 eq) was added followed by a crystal of methyl orange. The pH was adjusted to 2 and the resulting ruby red color was maintained for the duration of the reaction by the frequent addition of 1 N HCl. After stirring for 2 h another portion of $NaBH_3CN$ (890 mg, 14 mmol, 2 eq) was added. After stirring for a total of 16 h, the pH of the reaction mixture was brought to 7 and DCM was added. The mixture was washed twice with water, brine and dried over $MgSO_4$. The crude product was used directly in the next reaction without further purification.

Part C

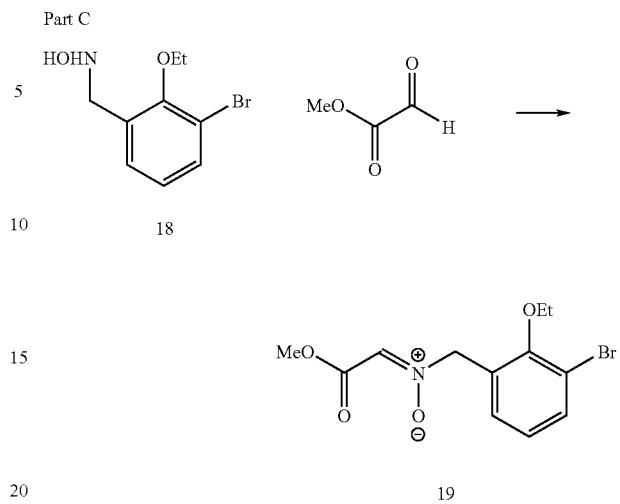

A solution of hydroxylamine 18 (1.5 g, 6.1 mmol, 1 eq) and methyl glyoxylate (1.07 g, 12.2 mmol, 2 eq) in benzene (30 mL) was heated at reflux with a Dean Stark trap overnight. Excess solvent was removed in vacuo and the resulting nitrone 19 was taken on crude in the next step.

Part D

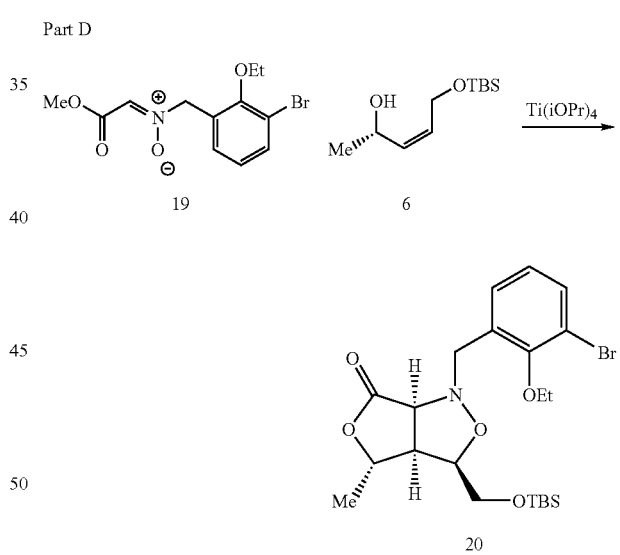

Nitrone 19 (2.0 g, 6.3 mmol, 1 eq), allylic alcohol 6 (2.0 g, 9.5 mmol, 1.5 eq) and $Ti(iOPr)_4$ (2.8 mL, 9.5 mmol, 1.5 eq) were dissolved in toluene (25 mL) and heated in a microwave at 120° C. for 10 min. The reaction mixture was diluted with EtOAc (50 mL) and 3-(dimethylamino)-1,2-propanediol (1 mL) was added. After stirring for 1 h, EtOAc was added and the mixture was washed twice with water, brine, dried over $MgSO_4$, filtered and concentrated in vacuo. The crude residue was purified by silica gel chromatography (15% hexanes/EtOAc) to afford 944 mg of lactone 20. Yield 30%.

Part E

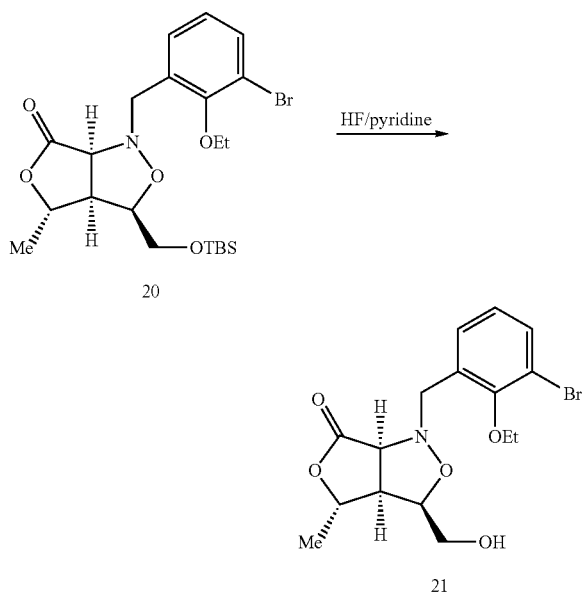

To a solution of 20 (950 mg, 1.9 mmol, 1 eq) in THF (21 mL) was added HF/pyridine (4 mL). The mixture was stirred at rt for 3 h then TMSOMe (25 mL) was added. Solvent was removed in vacuo and the crude product was purified by silica gel chromatography (20-100% EtOAc/hexanes) to afford 256 mg of 21. Yield 35%

Part F

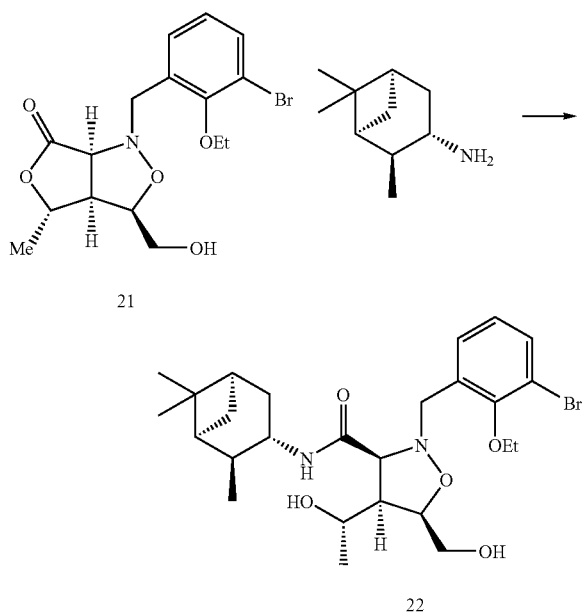

To a flame-dried round bottom flask was added (+)-isopinocampheylamine (235 uL, 1.33 mmol, 2 eq) and DCM (2.0 mL). Trimethylaluminum (660 uL, 2.0 M in hexanes, 1.33 mmol, 2 eq) was added and the reaction mixture was stirred at rt for 15 min. Lactone 21 (256 mg, 0.663 mmol, 1 eq) in DCM (8 mL) was added and the solution was stirred at rt. After stirring for 16 h, a saturated solution of Rochelle's salt (5 mL) was added, followed by DCM (5 mL). The mixture was stirred rapidly at rt for 2 h. DCM was added the mixture washed with water, dried over $MgSO_4$, filtered and concentrated in vacuo to afford an oil. The residue was purified by silica gel chromatography (50-100% EtOAc/hexanes) to afford 200 mg of amide 22 in 56% yield.

Part G

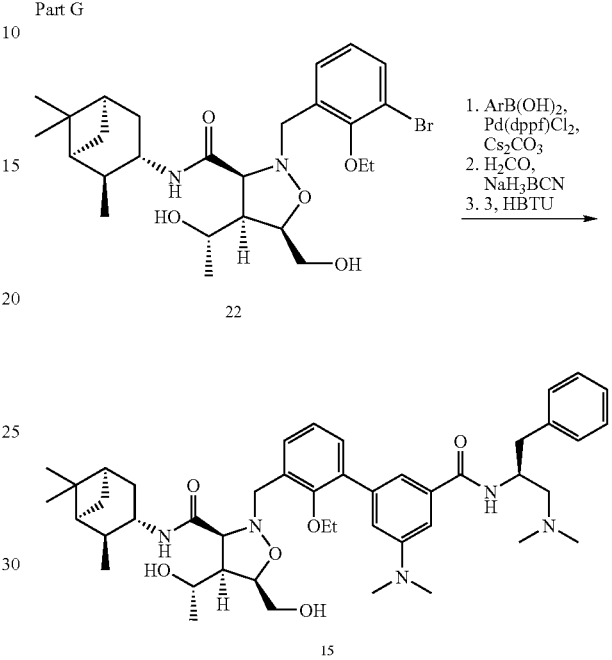

A flask containing aryl bromide 22 (90 mg, 0.17 mmol, 1 eq), 3-amino-5-carboxyphenylboronic acid (60 mg, 0.33 mmol, 2 eq), cesium carbonate (160 mg, 0.50 mmol, 3 eq), potassium acetate (15 mg, 0.17 mmol, 1 eq) and $Pd(dppf)Cl_2$ (15 mg, 0.017 mmol, 0.1 eq) was purged with argon and DMSO (8 mL) added. The mixture was heated at 60° C. for 3 h, then additional $Pd(dppf)Cl_2$ (15 mg, 0.17 mmol, 1 eq) was added and heating continued for 1.5 h. The reaction mixture was partitioned between water (50 mL) and DCM (50 mL) and acidified to pH 4 with 6 M HCl. The layers were separated and the aqueous extracted with DCM (3×25 mL). The combined organic layers were dried over $Na_2SO_4$, filtered and concentrated in vacuo to a brown oil.

The crude oil was dissolved in MeOH (6 mL) and treated with AcOH (30 uL), 37% formalin (50 uL, 0.67 mmol, 4 eq) and $NaBH_3CN$ (30 mg, 0.50 mmol, 3 eq). After stirring at rt overnight, the reaction mixture was partitioned between water (40 mL) and DCM (40 mL) and acidified to pH 4 with 6 M HCl. The layers were separated and the aqueous extracted with DCM (3×20 mL). The combined organic layers were dried on $Na_2SO_4$, filtered and concentrated in vacuo to afford a brown oil.

To an aliquot containing 9% of this crude oil (15 mg, 0.024 mmol, 1 eq) in DMF (1 mL) was added (S)—$N^1,N^1$-dimethyl-3-phenylpropane-1,2-diamine (15 uL, 0.07 mmol, 3 eq) and HBTU (30 mg, 0.07 mmol, 3 eq). The mixture was diluted with MeOH (1 mL) and purified by reverse-phase HPLC (MeCN/water with 40 mM $NH_4HCO_3$) to give 3 mg of compound 15 as a white solid. Yield 16%. MS (ESI(+)) m/z 393.25 $(M+2H)^{2+}$.

Example 5

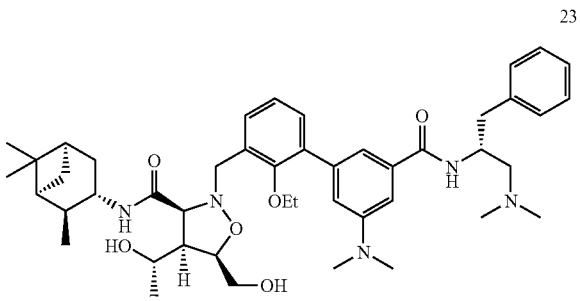

Compound 23 was synthesized according to the procedure described in Example 4, using amine (R)—N$^1$,N$^1$-dimethyl-3-phenylpropane-1,2-diamine in place of (S)—N$^1$,N$^1$-dimethyl-3-phenylpropane-1,2-diamine. 21% yield. MS (ESI(+)) m/z 784.88 (M+H)$^+$.

Example 6

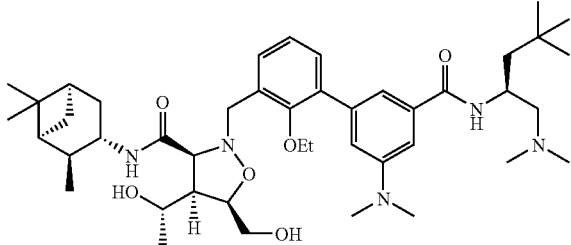

Compound 24 was synthesized according to the procedure described in Example 4, using amine (S)—N$^1$,N$^1$,4,4-tetramethylpentane-1,2-diamine in place of (S)—N$^1$,N$^1$-dimethyl-3-phenylpropane-1,2-diamine. 19% yield. MS (ESI(+)) m/z 764.95 (M+H)$^+$.

Example 7

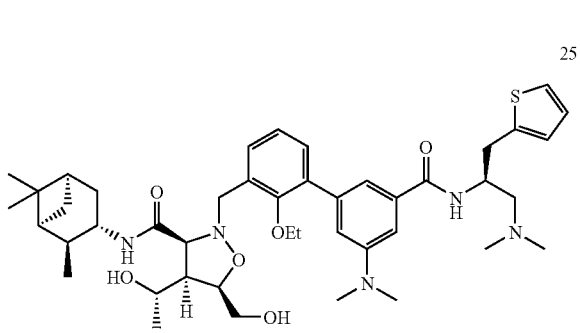

Compound 25 was synthesized according to the procedure described in Example 4, using amine (S)—N$^1$,N$^1$-dimethyl-3-(thiophen-2-yl)propane-1,2-diamine in place of (S)—N$^1$,N$^1$-dimethyl-3-phenylpropane-1,2-diamine. 16% yield. MS (ESI(+)) m/z 396.18 (M+2H)$^{2+}$.

Example 8

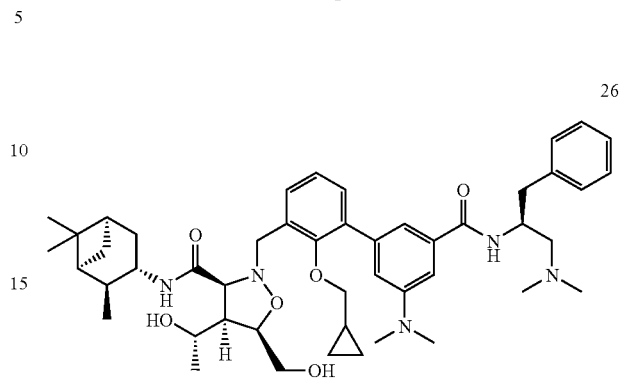

Part A

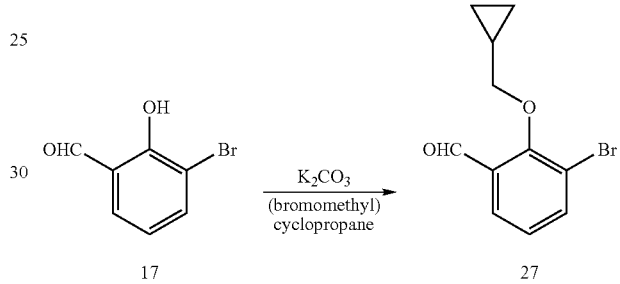

To a solution of phenol 17 (2.2 g, 12 mmol, 1 eq) in DMF (5 mL) was added K$_2$CO$_3$ (2.3 g, 16 mmol, 1.5 eq) followed by (bromomethyl)cyclopropane (1.18 mL, 12.2 mmol, 1.1 eq). The reaction mixture was stirred at 60° C. for 24 h and then cooled to rt and quenched with water. The mixture was diluted with EtOAc and washed twice with water then brine. The solution was dried over MgSO$_4$, filtered and concentrated in vacuo. The crude material was purified by silica gel chromatography (9:1 hexanes/EtOAc) to afford 2.07 g of the desired product 27 as a colorless oil. Yield 73%.

Part B

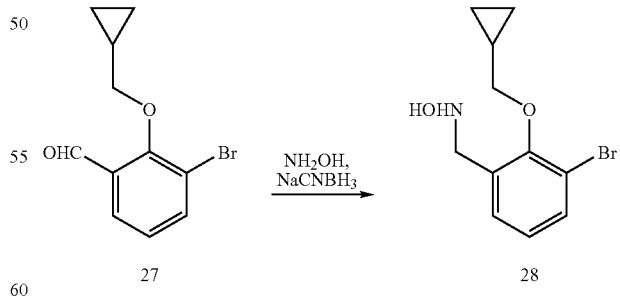

Aldehyde 27 (2.07 g, 8.11 mmol, 1 eq) and hydroxylamine hydrochloride (766 mg, 9.74 mmol, 1.1 eq) were dissolved in THF/MeOH (3:2, 10 mL). Water (2 mL) was added and the pH was adjusted to 9 with 6 N KOH. The reaction mixture was stirred at rt for 4 h then NaBH$_3$CN (1.02 g, 16.2 mmol, 2 eq) was added followed by a crystal of methyl orange. The pH was adjusted to 2 and the resulting ruby red color was maintained for the duration of the reaction by the frequent addition of 1 N HCl. After stirring for 2 h another portion of NaBH₃CN (1.02 g, 16.2 mmol, 2 eq) was added. After stirring for a total of 16 h, the pH of the reaction mixture was brought to 7 and DCM was added. The mixture was washed twice with water, brine and then dried over MgSO₄, filtered and concentrated in vacuo. The crude product was used directly in the next reaction without further purification.

Part C

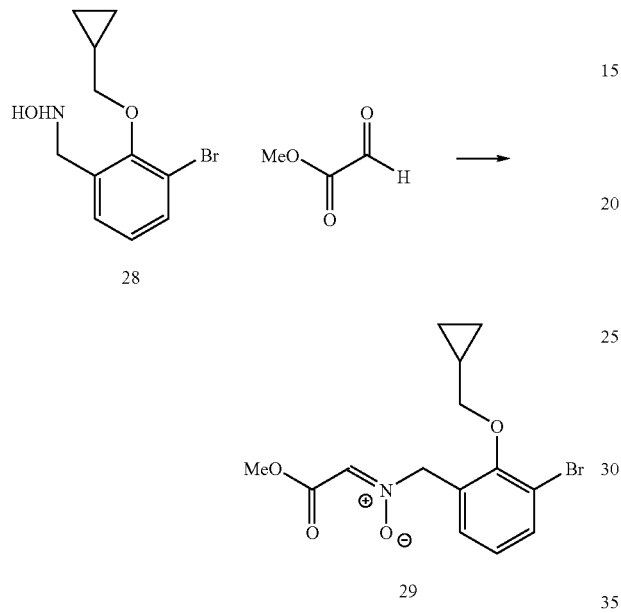

A solution of hydroxylamine 28 (2.15 g, 7.90 mmol, 1 eq) and methyl glyoxylate (1.39 g, 15.8 mmol, 2 eq) in benzene (30 mL) was heated at reflux with a Dean Stark trap overnight. Excess solvent was removed under reduced pressure and the resulting nitrone 29 was taken on crude in the next step.

Part D

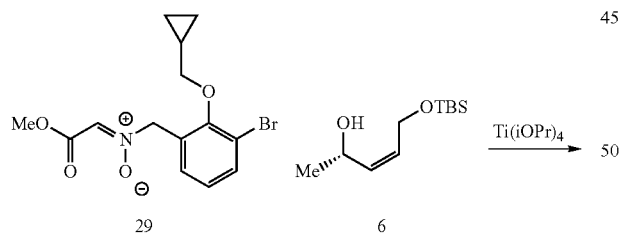

Nitrone 29 (2.7 g, 7.9 mmol, 1 eq), allylic alcohol 6 (2.6 g, 12 mmol, 1.5 eq) and Ti(iOPr)₄ (3.5 mL, 12 mmol, 1.5 eq) were dissolved in toluene (25 mL) and heated in the microwave at 140° C. for 20 min The reaction mixture was diluted with EtOAc (50 mL) and 3-(dimethylamino)-1,2-propanediol (1 mL) was added. After stirring for 1 h, EtOAc was added and the mixture was washed twice with water and then brine, dried over MgSO₄, filtered over Celite and concentrated. The crude residue was purified by silica gel chromatography (15% hexanes/EtOAc) to afford 1.35 g of lactone 30. Yield 33%.

Part E

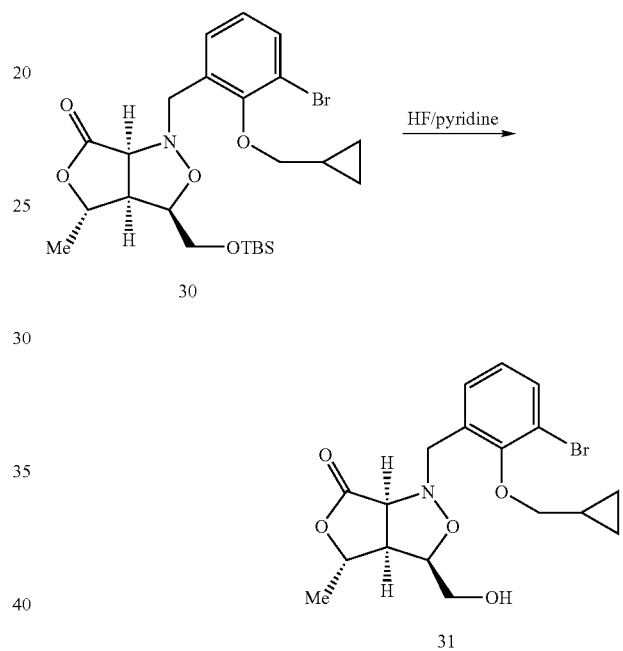

To a solution of 30 (1.35 g, 2.56 mmol, 1 eq) in THF (21 mL) was added HF/pyridine (4 mL). The mixture was stirred at rt for 3 h then TMSOMe (25 mL) was added. Solvent was removed in vacuo and the crude product was purified by flash chromatography (20-100% EtOAc/hexanes) to afford 404 mg of 31. Yield 38%.

Part F

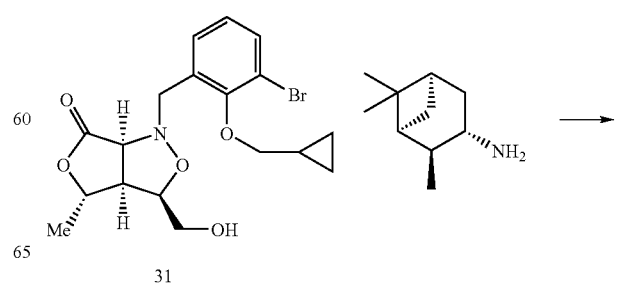

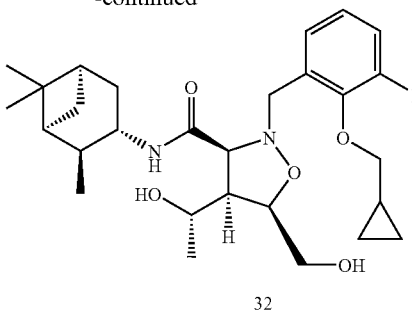

32

To a flame-dried round bottom flask was added (+)-isopinocampheylamine (325 uL, 1.83 mmol, 2 eq) and DCM (2.0 mL). Trimethylaluminum (917 uL, 2.0 M in hexanes, 1.82 mmol, 2 eq) was added and the reaction mixture was stirred at rt for 15 min. The lactone 22 (378 mg, 0.92 mmol, 1 eq) in DCM (8 mL) was added and stirring was continued 16 h. A saturated Rochelle's salt solution (5 mL) was added followed by DCM (5 mL) and the mixture was rapidly stirred at rt for 2 h. DCM was added and the mixture was washed with water, dried over MgSO$_4$, filtered and concentrated in vacuo. The crude material was purified by silica gel chromatography (50-100% EtOAc/hexanes) to afford 415 mg of amide 32. Yield 80%.

Part G

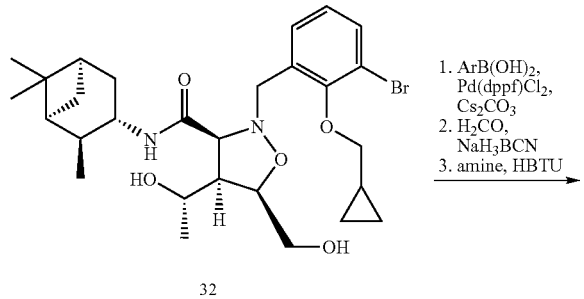

32

1. ArB(OH)$_2$, Pd(dppf)Cl$_2$, Cs$_2$CO$_3$
2. H$_2$CO, NaH$_3$BCN
3. amine, HBTU

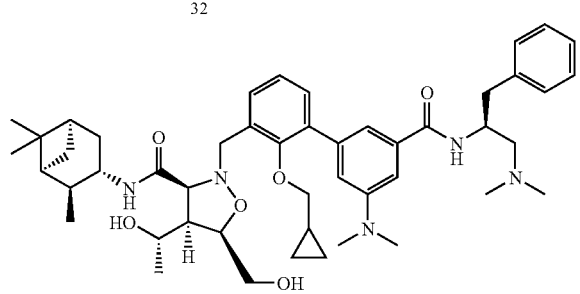

26

A flask containing aryl bromide 32 (90 mg, 0.16 mmol, 1 eq), 3-amino-5-carboxyphenylboronic acid (60 mg, 0.33 mmol, 2 eq), cesium carbonate (160 mg, 0.5 mmol, 3 eq), potassium acetate (15 mg, 0.17 mmol, 1 eq) and Pd(dppf)Cl$_2$ (15 mg, 0.017 mmol, 0.1 eq) was purged with argon and DMSO (5 mL) added. The mixture was heated at 60° C. for 3 h, then additional Pd(dppf)Cl$_2$ (15 mg, 0.17 mmol, 1 eq) was added and heating continued for 1.5 h. The reaction mixture was partitioned between water (50 mL) and DCM (50 mL) and acidified to a pH 4 with 6 N HCl. The layers were separated and the aqueous phase was extracted with DCM (3×25 mL). The combined organic layers were dried over Na$_2$SO$_4$, filtered and concentrated in vacuo to afford a brown oil.

This crude oil was dissolved in MeOH (6 mL) and treated with AcOH (30 uL), 37% formalin (50 uL, 0.67 mmol, 4 eq) and NaBH$_3$CN (32 mg, 0.50 mmol, 3 eq). After stirring at rt for 2 h, the reaction mixture was partitioned between water (40 mL) and DCM (40 mL) and acidified with 6 N HCl until the aqueous layer attained a pH of 4. The layers were separated and the aqueous extracted with DCM (3×20 mL). The combined organic layers were dried over Na$_2$SO$_4$ and concentrated in vacuo to afford a brown oil.

To an aliquot containing 12% of this crude oil (20 mg, 0.031 mmol, 1 eq) in DMF (1 mL) was added (S)—N$^1$,N$^1$-dimethyl-3-phenylpropane-1,2-diamine (20 uL, 0.09 mmol, 3 eq) and HBTU (30 mg, 0.07 mmol, 3 eq). After stirring for 12 h, the mixture was diluted with MeOH (1 mL) and purified by reverse-phase HPLC (MeCN/water with 40 mM NH$_5$CO$_2$) to give 3 mg of compound 26 as a white solid. Yield 12%. MS (ESI(+)) m/z 406.26 (M+2H)$^{2+}$.

Example 9

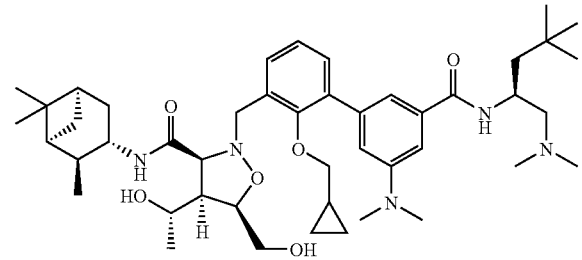

33

Compound 33 was synthesized according to the procedure described in Example 8, using amine (S)—N$^1$,N$^1$,4,4-tetramethylpentane-1,2-diamine in place of (S)—N$^1$,N$^1$-dimethyl-3-phenylpropane-1,2-diamine. Yield 12%. MS (ESI(+)) m/z 396.25 (M+2H)$^{2+}$.

Example 10

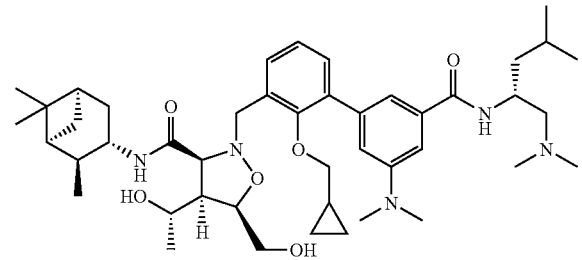

34

Compound 34 was synthesized according to the procedure described in Example 8, using amine (R)—N$^1$,N$^1$,4-trimethylpentane-1,2-diamine in place of (S)—N$^1$,N$^1$-dimethyl-3-phenylpropane-1,2-diamine. Yield 13%. MS (ESI(+)) m/z 389.19 (M+2H)$^{2+}$.

Example 11

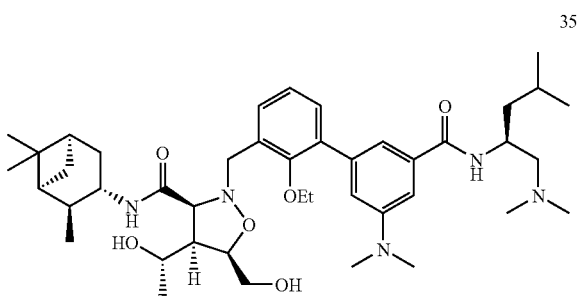

35

Compound 35 was synthesized according to the procedure described in Example 4, using amine (S)—N$^1$,N$^1$,4-trimethylpentane-1,2-diamine in place of (S)—N$^1$,N$^1$-dimethyl-3-phenylpropane-1,2-diamine. Yield 17%. MS (ESI(+)) m/z 374.24 (M+2H)$^{2+}$.

Example 12

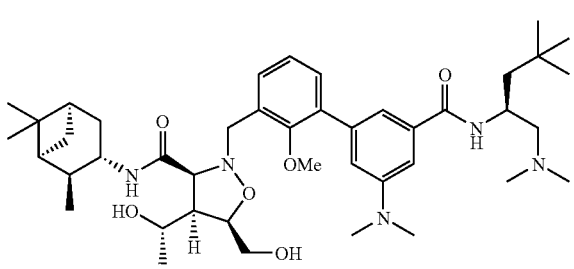

36

Prepared in an analogous fashion as described in Example 1 using (R)—N$^1$,N$^1$,4,4-tetramethylpentane-1,2-diamine in place of (S)—N$^1$,N$^1$,4,4-tetramethylpentane-1,2-diamine. Yield 4%. MS (ESI(+)) m/z 750.5. (M+H)$^+$.

Example 13

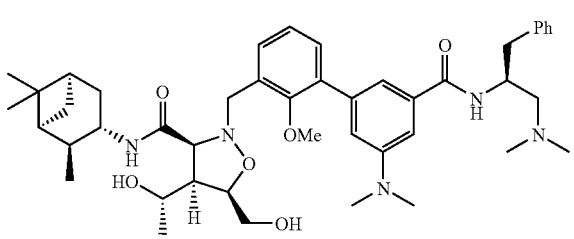

37

Prepared in an analogous fashion as described in Example 1 using (S)—N$^1$,N$^1$-dimethyl-3-phenylpropane-1,2-diamine in place of (S)—N$^1$,N$^1$,4,4-tetramethylpentane-1,2-diamine. Yield 65%. MS (ESI(+)) m/z 770.7. (M+H)$^+$.

Example 14

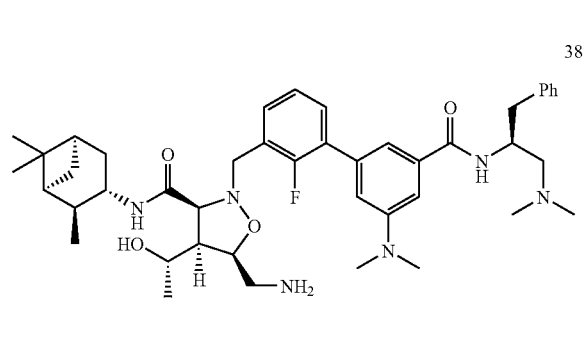

38

Part A

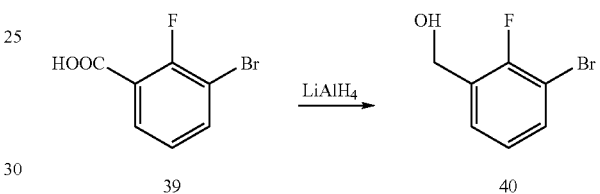

3-Bromo-2-fluoro-benzoic acid 39 (15 g, 69 mmol, 1 eq) was dissolved in THF (400 mL) followed by the addition of LiAlH$_4$ (2.9 g, 76 mmol, 1.1 eq) over the course of 5 min. The reaction mixture was stirred vigorously for 12 h, quenched with a saturated Rochelle's salt solution, and stirred for an additional 2 h. The mixture was then partitioned in DCM/saturated NaHCO$_3$ solution and extracted with DCM (2×200 mL). The combined organics were dried over MgSO$_4$, filtered and concentrated in vacuo to afford 11.2 g of alcohol 40.

Part B

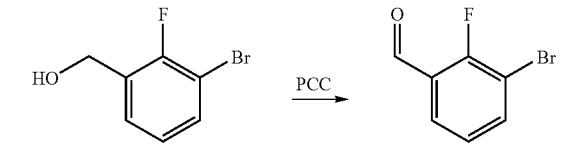

Pyridinium chlorochromate (22.3 g, 103 mmol, 1.91 eq) was dissolved in DCM (140 mL) and 4 Å Molecular Sieves (22.3 g) were added to the solution. The reaction mixture was stirred for 30 minutes. A solution of benzyl alcohol 40 (11 g, 54 mmol, 1 eq) in DCM (140 mL) was added dropwise over the course of 5 min. The orange reaction mixture immediately turned dark brown upon addition of alcohol. After stirring for 30 min, the reaction mixture was diluted with 70% Hexane/EtOAc solution (250 mL) and filtered through a plug of silica gel (150 g). The silica gel was washed with Hexane/EtOAc (500 mL), and concentrated in vacuo to afford 9.8 g of aldehyde 41 as a white solid. Yield 70% over 2 steps.

Part C

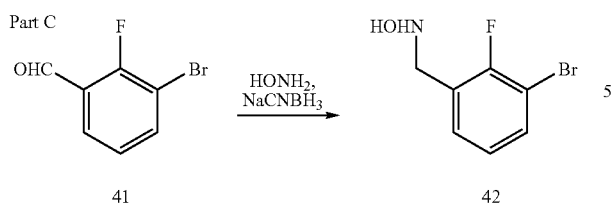

Aldehyde 41 (9.8 g, 48.3 mmol, 1 eq) and hydroxylamine hydrochloride (3.97 g, 57.9 mmol, 1.2 eq) were dissolved in THF/MeOH (3:2, 40 mL) at rt. Water (25 mL) was added and the pH was adjusted to 9 with 6 N KOH. After stirring for 16 h, NaBH$_3$CN (3.03 g, 48.3 mmol, 1 eq) was added followed by a crystal of methyl orange. The pH was adjusted to 2 and the resulting ruby red color of the reaction mixture was maintained for the duration of the reaction by the frequent addition of 1 N HCl. After stirring for 2 h, another portion of NaBH$_3$CN (3.03 g, 48.2 mmol, 1 eq) was added. After stirring for a total of 16 h, the reaction mixture was adjusted to pH 7 with 6 N KOH. The mixture was extracted with DCM (2×100 mL) and the combined organics were washed with water (50 mL), brine (20 mL), dried over MgSO$_4$, filtered and concentrated in vacuo to afford 8.1 g of hydroxylamine 42. The crude material was used without further purification. Crude yield 76%.

Part D

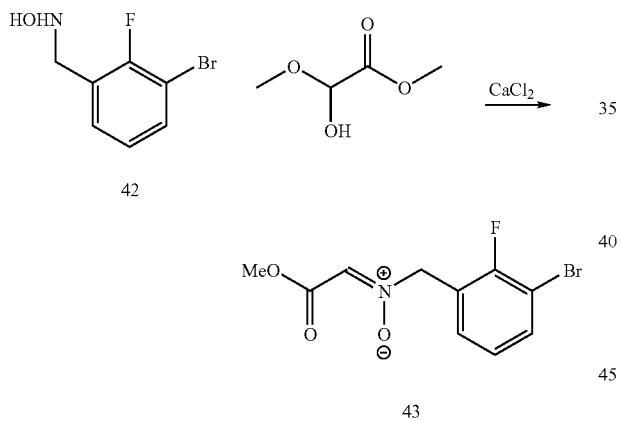

To a solution of hydroxylamine 42 (8.1 g, 36.8 mmol, 1 eq) in ether (200 mL) at rt was added methyl glyoxylate methyl acetal (5.3 g, 44.2 mmol, 1.2 eq), followed by the addition of calcium chloride (4.9 g, 44.2 mmol, 1.2 eq). After stirring for 3 h, the reaction mixture was filtered through celite, washed with DCM (2×200 mL), and concentrated in vacuo to a white solid to afford 10.5 g of 43. The crude material was used without further purification. Yield 98%.

Part E

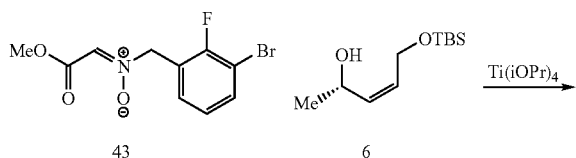

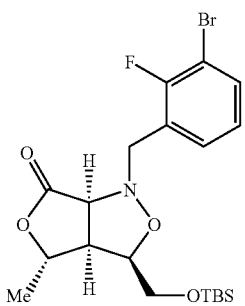

Nitrone 43 (10.5 g, 36 mmol, 1 eq), allylic alcohol 6 (9.8 g, 45 mmol, 1.2 eq) and Ti(iOPr)$_4$ (13 g, 45 mmol, 1.2 eq) were dissolved in THF (50 mL) and heated in a microwave at 140° C. for 30 min. The reaction mixture was allowed to cool to rt and then diluted with EtOAc (150 mL), water (150 mL) and 3-(dimethylamino)-1,2-propanediol (5 mL). After stirring for 2 h, the reaction mixture was extracted with EtOAc (2×100 mL). The combined organics were washed with water (3×50 mL) brine (50 mL), dried over MgSO$_4$, filtered through Celite and concentrated in vacuo. The crude residue was purified by silica gel chromatography (5-25% EtOAc/hexane) to afford 11.45 g of lactone 44. Yield 67%.

Part F

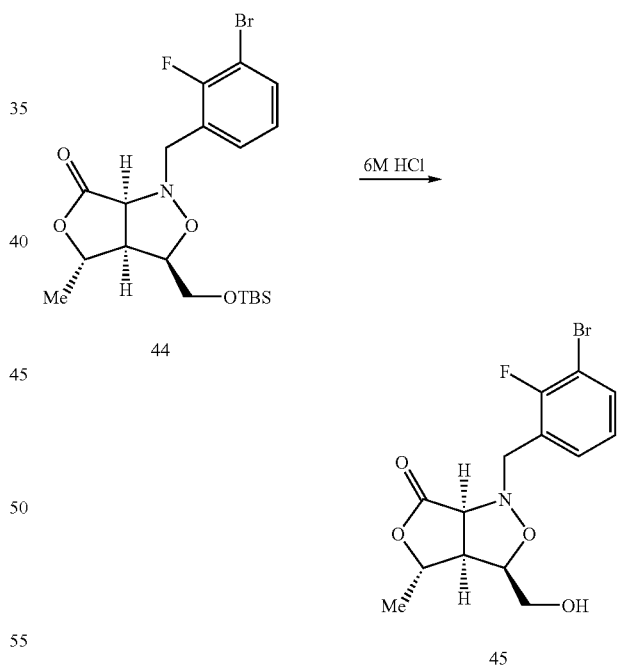

To a 0° C. solution of TBS-protected lactone 44 (11.2 g, 24 mmol, 1 eq) in THF (60 mL) was added 6 N HCl (6 mL). The reaction mixture was stirred for 2 h and then quenched by the addition of a saturated sodium bicarbonate solution (30 mL). The reaction mixture was extracted with EtOAc (2×100 mL) and the combined organics were dried over MgSO$_4$, filtered and concentrated in vacuo. The crude residue was purified by silica gel chromatography (30-70% EtOAc/hexane) to afford 7.7 g of alcohol 45. Yield 91%.

Part G

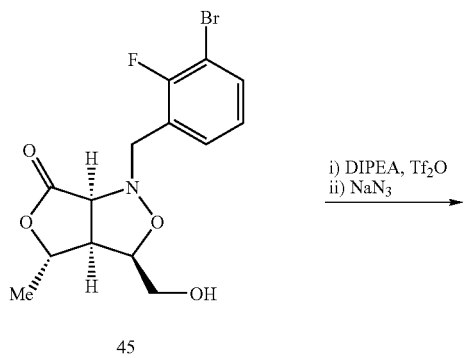

To a solution of alcohol 45 (810 mg, 1.99 mmol, 1 eq) in DCM (20 mL) at 0° C. was added trifluoromethanesulfonic anhydride (0.4 mL, 2.4 mmol, 2.4 eq) dropwise over the course of 5 min. After stirring for 30 minutes, the reaction mixture was diluted with DMF (5 mL) followed by the addition of sodium azide (388 mg, 5.97 mmol, 3 eq) in a single portion. The reaction mixture was stirred for 12 h and then quenched by the addition of water, extracted with EtOAc (2×100 mL) and the combined organics were dried over MgSO$_4$, filtered and concentrated in vacuo to afford an oil. The crude oil was purified by silica gel chromatography (30-80% EtOAc/hexane) to afford 758 mg of 46. Yield 88%.

Part H

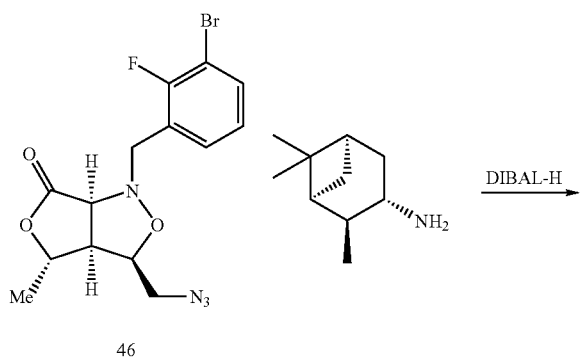

-continued

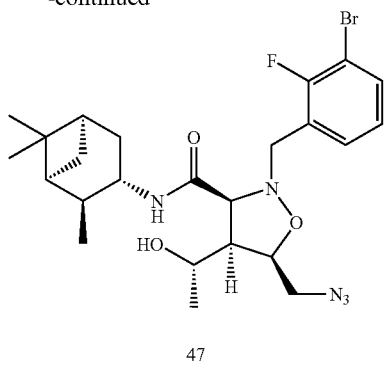

To a 0° C. solution of (+)-isopinocampheylamine (1.98 mL, 11.8 mmol, 6 eq) in THF (20 mL) was added DIBAL (9.8 mL, 1 M in toluene, 9.8 mmol, 5 eq) and the reaction mixture was stirred for 2 h. A solution of lactone 46 (758 mg, dissolved in 5 mL THF, 1.97 mmol, 1 eq) was then added dropwise over the course of 5 min. After stirring for 2 h, the reaction was diluted with a saturated aqueous solution of Rochelle's salt and EtOAc and then stirred vigorously for 5 h. The mixture was extracted with EtOAc (3×100 mL) and the combined organics were dried over MgSO$_4$, filtered and concentrated in vacuo to afford an oil. The crude oil was purified by silica gel chromatography (30-70% EtOAc/Hexane) to afford 500 mg of amide 47. Yield 47%.

Part I

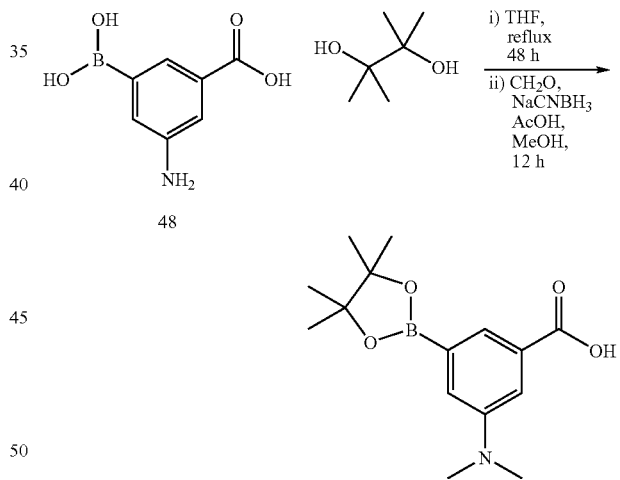

(3-Amino-5-carboxylphenyl)boronic acid 48 (15 g, 83 mmol, 1 eq) and pinacol (29 g, 249 mmol, 3 eq) were combined with THF (72 mL) and heated to reflux. After heating at reflux for 48 h, the reaction mixture was cooled to rt and then concentrated to an orange oil. The orange oil was dissolved in MeOH (250 mL) and the solution was cooled to 0° C. using an ice bath. Formaldehyde (67 g of a 37% solution in water, 829 mmol, 10 eq) was added followed by AcOH (30 g, 497 mmol, 6 eq) and the portion-wise addition of NaBH$_3$CN (7.8 g, 124 mmol, 3 eq). The ice bath was removed and the reaction was allowed to warm slowly to rt. After stirring for 12 h, the reaction mixture was filtered through celite, washed with EtOAc (2×100 mL) and the combined filtrates were concentrated to an orange oil. The oil was dissolved in EtOAc (200 mL), diluted with water and the pH was adjusted to pH 10 using 6 N NaOH and then extracted with EtOAc (2×200 mL). The aqueous phase was adjusted to pH 4 using 6 N HCl and extracted with DCM (2×200 mL). The combined DCM extracts were then dried over MgSO₄, filtered and concentrated to provide 11 g of 49 as an off-white solid. This material was used without further purification.

Part J

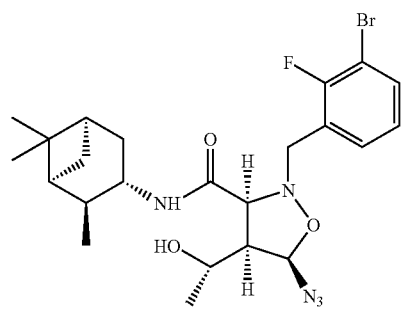

47

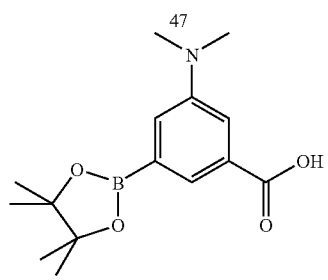

49

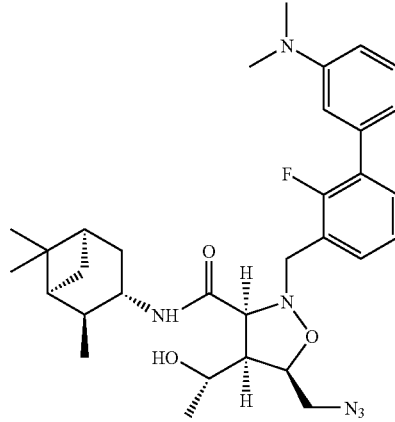

50 concentrated in vacuo to afford an oil. The crude oil was purified by silica gel chromatography (10-35% acetone/hexane) to afford 110 mg of biphenyl acid 50. Yield 28%.

Part K

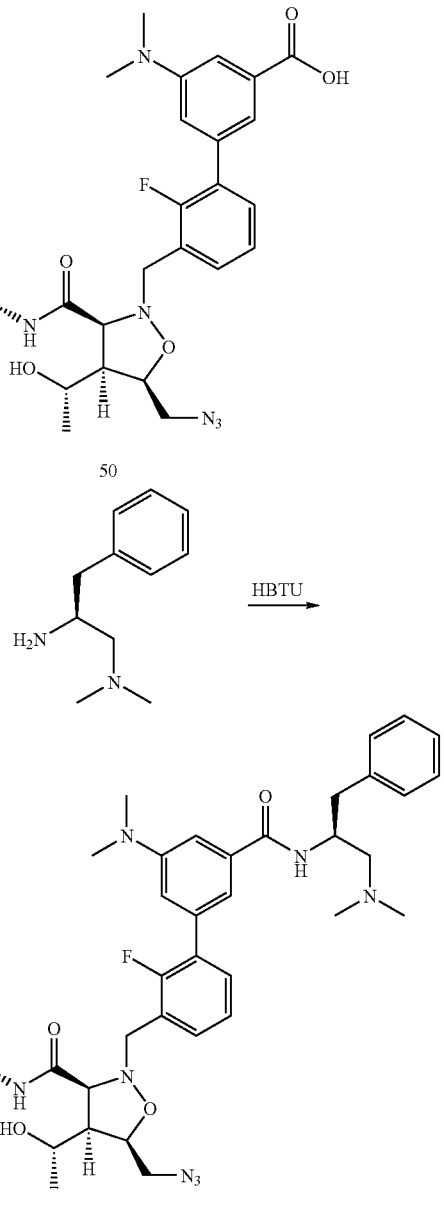

Isoxazolidine 47 (335 mg, 0.622 mmol, 1 eq), pinacolboronate 49 (362 mg, 1.24 mmol, 2 eq), Pd(dppf)Cl₂ (102 mg, 0.124 mmol, 0.1 eq), potassium acetate (79 mg, 0.81 mmol, 1.3 eq), and cesium carbonate (608 mg, 1.87 mmol, 3 eq) were dissolved in anhydrous DMSO (5 mL) and flushed with argon under positive pressure. The reaction mixture was stirred at 60° C. for 2 h, then allowed to cool to rt. The reaction mixture was diluted with EtOAc (20 mL) and water (10 mL) and the aqueous phase was adjusted to pH 4 with 6 M HCl. The reaction mixture was extracted with EtOAc (3×100 mL) and the combined organics were dried over MgSO₄, filtered and Biphenyl acid 50 (40 mg, 0.064 mmol, 1 eq) and HBTU (49 mg, 0.13 mmol, 2 eq) were dissolved in DMF (1 mL) followed by the addition of amine (S)—$N^1,N^1$-dimethyl-3-phenylpropane-1,2-diamine (23 mg, 0.13 mmol, 2 eq). The reaction mixture was stirred for 2 h, diluted with EtOAc and quenched with a saturated aqueous NaHCO₃ solution. The reaction mixture was extracted with EtOAc (3×100 mL) and the combined organics were dried over MgSO₄, filtered and concentrated in vacuo to afford an oil. The crude oil was purified by silica gel chromatography (2-5% MeOH/DCM) to afford 23 mg of biphenyl amide 51. Yield 45%.

Part L

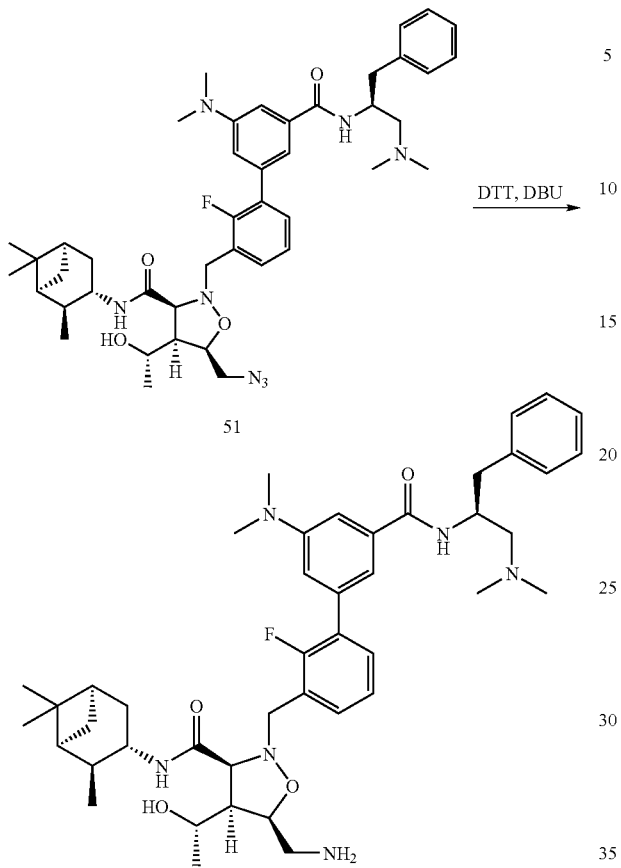

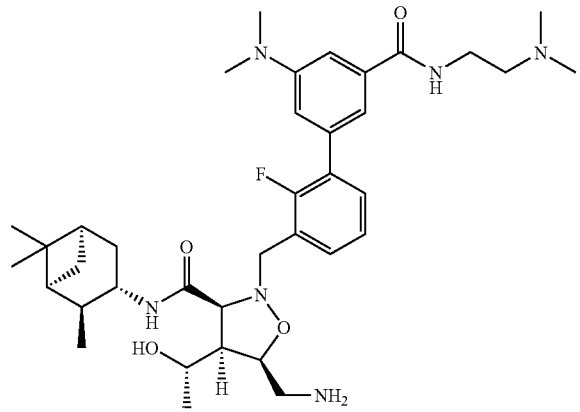

Azide 51 (18 mg, 0.023 mmol, 1 eq) and dithiothreitol (11 mg, 0.07 mmol, 3 eq) were dissolved in DMF (1 mL) followed by the addition of DBU (12 uL, 0.07 mmol, 3 eq). The reaction mixture was stirred for 1 h, then purified directly by reverse-phase HPLC (MeCN/water with 40 mM NH$_4$HCO$_3$), to yield 7 mg of compound 38. MS ((ESI(+)) m/z 757.4 (M+H)$^+$.

Example 15

Prepared in an analogous fashion as described in Example 13 using 2-amino-N,N-dimethyl-3-(thiazol-4-yl)propanamide in place of (S)—N$^1$,N$^1$-dimethyl-3-phenylpropane-1,2-diamine. Yield 29%. MS (ESI(+)) m/z 778.4. (M+H)$^+$.

Example 16

Prepared in an analogous fashion as described in Example 13 using N$^1$,N$^1$-dimethylethane-1,2-diamine in place of (S)—N$^1$,N$^1$-dimethyl-3-phenylpropane-1,2-diamine. Yield 49%. MS (ESI(+)) m/z 667.4. (M+H)$^+$.

Example 17

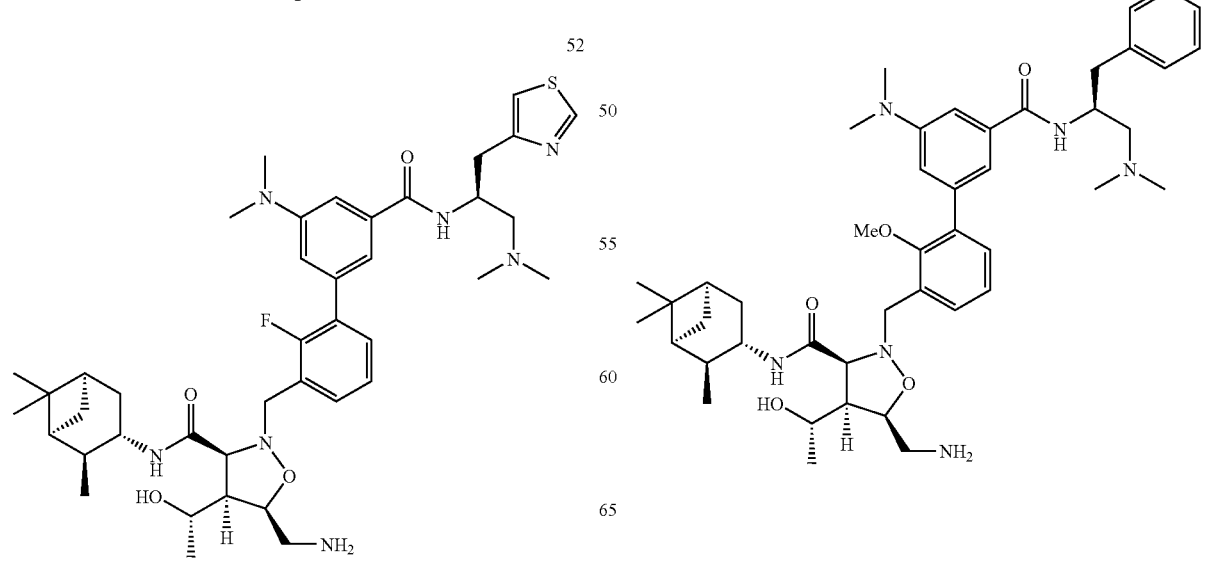

Part A

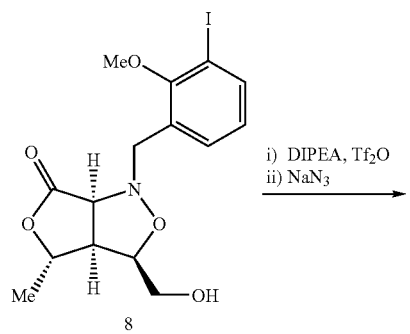

Part B

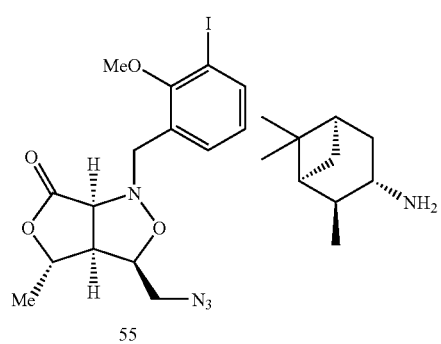

To a solution of lactone 8 (1.8 g, 4.3 mmol, 1 eq) in DCM (42 mL) at 0° C. was added triflic anhydride (0.87 mL, 5.15 mmol, 1.2 eq) dropwise over the course of 5 min. After 30 min, the reaction mixture was diluted with DMF (10 mL) followed by the addition of sodium azide (0.84 g, 12.9 mmol, 3 eq) in a single portion. The reaction mixture was removed from the ice bath and allowed to warm to rt. After stirring for 12 h, the reaction was quenched by the addition of water, extracted with EtOAc (2×100 mL), dried over MgSO₄, filtered and concentrated in vacuo to afford an oil. The crude oil was purified by silica gel chromatography (30-80% EtOAc/hexane) to afford 1.7 g of azide 55. Yield 89%.

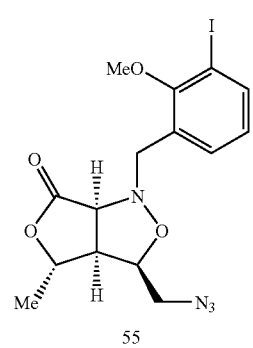

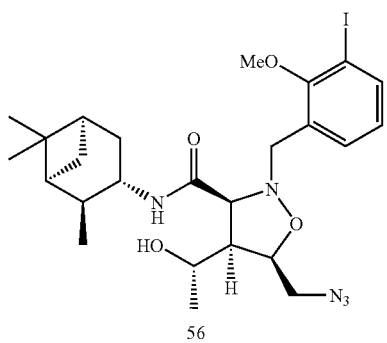

To a 0° C. solution of (+)-isopinocampheylamine (5.75 mL, 34.3 mmol, 6 eq) in THF (60 mL) was added DIBAL (14.3 mL, 2 M in toluene, 28.6 mmol, 5 eq). After stirring for 2 h, the reaction mixture was added to a solution of lactone 55 (2.54 g, 5.72 mmol, 1 eq) dissolved in THF (10 mL). The combined reaction mixture was stirred for 2 h, then diluted with a saturated solution of Rochelle's salt and EtOAc. After stirring for 5 h the reaction mixture was extracted with EtOAc (3×100 mL), dried over MgSO₄, filtered and concentrated in vacuo to afford an oil. The crude oil was purified by silica gel chromatography (30-70% EtOAc/hexane) to afford 2.79 g of azide 56. Yield 82%.

Part C

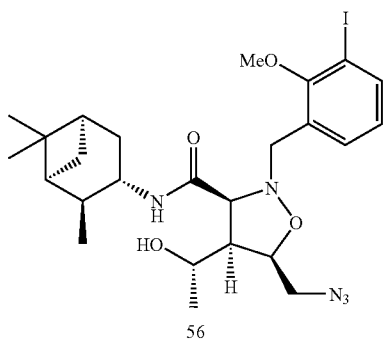

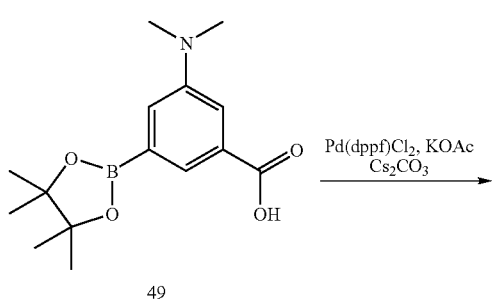

-continued

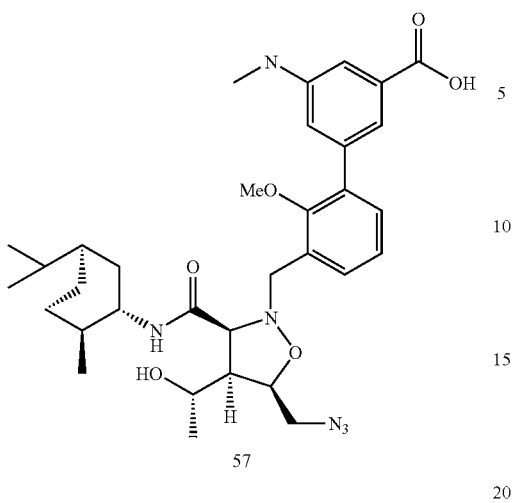

57

Isoxazolidine 56 (300 mg, 0.50 mmol, 1 eq), pinacol boronate 49 (368 mg, 1.26 mmol, 2.5 eq), Pd(dppf)Cl$_2$ (82 mg, 0.10 mmol, 0.2 eq), potassium acetate (65 mg, 0.657 mmol, 1.3 eq), and cesium carbonate (494 mg, 1.52 mmol, 3 eq) were dissolved in anhydrous DMSO (5 mL) and the reaction vessel was flushed under positive argon pressure for 15 min. The reaction mixture was stirred at 60° C. for 2 h, then allowed to cool to rt. The reaction mixture was diluted with EtOAc (20 mL) and water (10 mL) and the aqueous phase was adjusted to pH 4 with 6 N HCl. The reaction mixture was extracted with EtOAc (3×100 mL) and the combined organics were dried over MgSO$_4$, filtered and concentrated in vacuo to afford an oil. The crude oil was purified by gradient silica gel chromatography (10-35% acetone/hexanes) to afford 170 mg of biphenyl acid 57. Yield 53%.

Part D

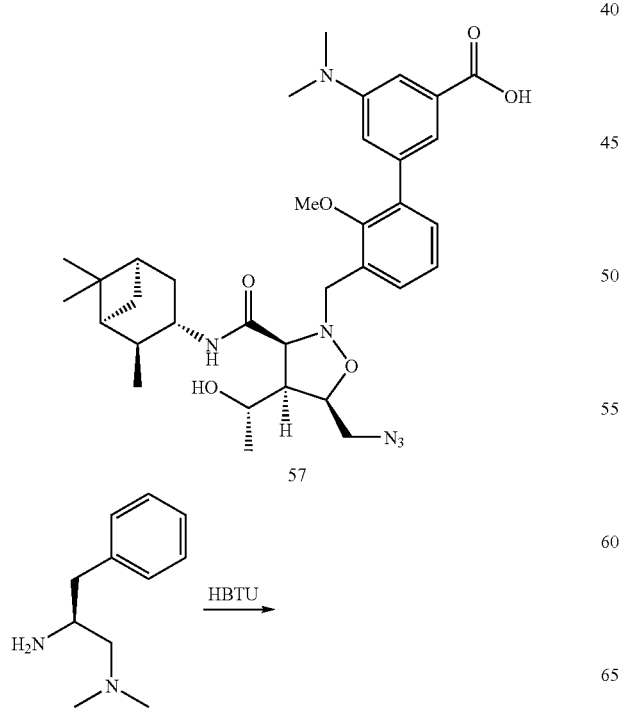

-continued

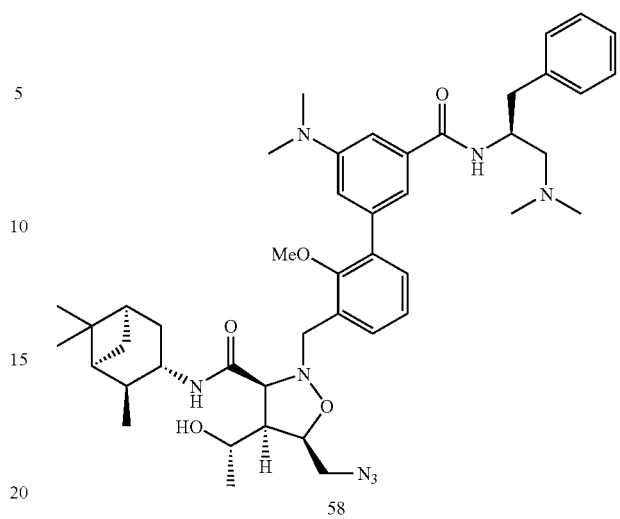

58

Biphenyl acid 57 (320 mg, 0.50 mmol, 1 eq) and HBTU (287 mg, 0.756 mmol, 1.5 eq) were dissolved in DMF (5 mL) followed by addition of (S)—N$^1$,N$^1$-dimethyl-3-phenylpropane-1,2-diamine (180 mg, 1.0 mmol, 2 eq). After stirring for 2 h, the reaction mixture was diluted with EtOAc (100 mL) and a saturated sodium bicarbonate solution. The mixture was extracted with EtOAc (3×100 mL), dried over MgSO$_4$, filtered and concentrated to an oil. The crude oil was purified by silica gel chromatography (2-5% MeOH/DCM) to afford 197 mg of azide 58. Yield 49%.

Part E

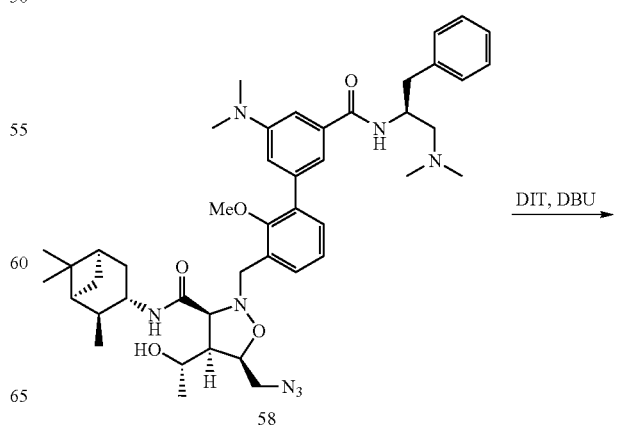

-continued

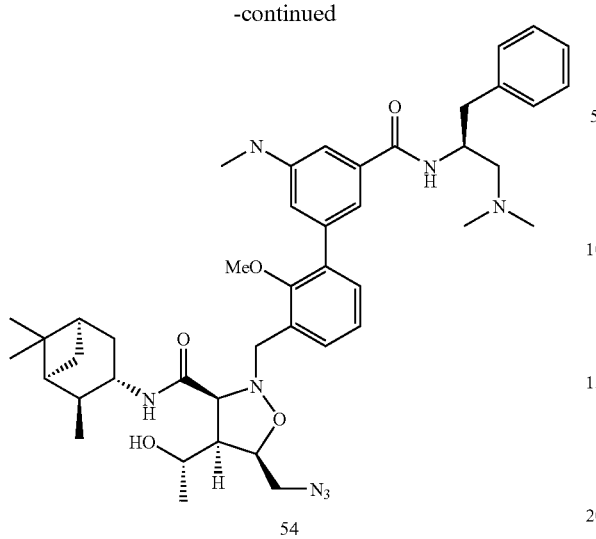

54

Azide 58 (15 mg, 0.018 mmol, 1 eg) and dithiothreitol (8.7 mg, 0054 mmol, 3 eq) were dissolved in DMF (1 mL) followed by addition of DBU (8.5 uL, 0.054 mmol, 3 eq). After stirring for 1 h, the reaction mixture was purified directly by reverse-phase HPLC (CH$_3$CN/water with 40 mM NH$_4$HCO$_3$), to yield 7 mg of amine 54. Yield 47%. MS ((ESI(+)) m/z 769.9 (M+H)$^+$.

Example 18

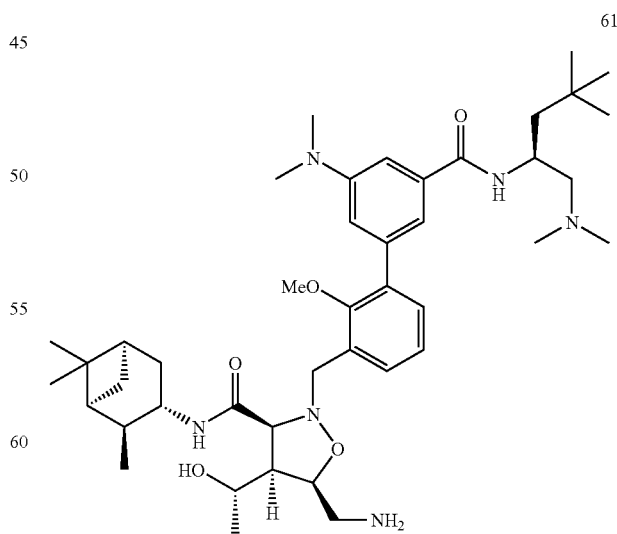

59

Prepared in an analogous fashion as described in Example 17 using (S)—N$^1$,N$^1$-trimethylpentane-1,2-diamine in place of (S)—N$^1$,N$^1$-dimethyl-3-phenylpropane-1,2-diamine 43% Yield. MS (ESI(+)) m/z 73561 (M+H)$^+$.

Example 19

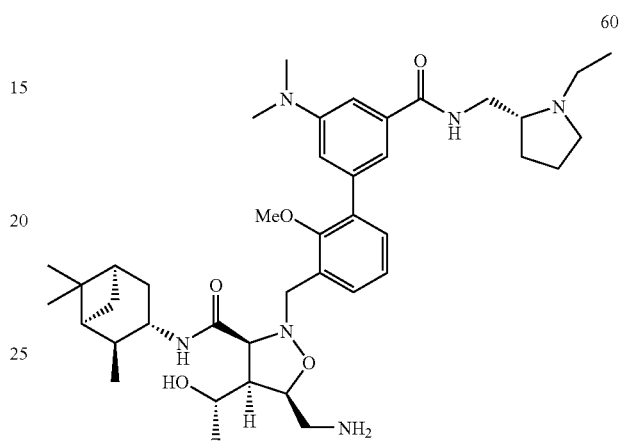

60

Prepared in an analogous fashion as described in Example 17 using (R)-(1-ethylpyrrolidin-2-yl)methylamine in place of (S)—N$^1$,N$^1$-dimethyl-3-phenylpropane-1,2-diamine. Yield 43%. MS (ESI(+)) m/z 733.1 (M+H)$^+$.

Example 20

61

Prepared in an analogous fashion as described in Example 17 using (S)—N$^1$,N$^1$-4,4-tetramethylpentane-1,2-diamine in place of (S)—N¹,N¹-dimethyl-3-phenylpropane-1,2-diamine. Yield 27%. MS (ESI(+)) m/z 749.1 (M+H)⁺.

Example 21

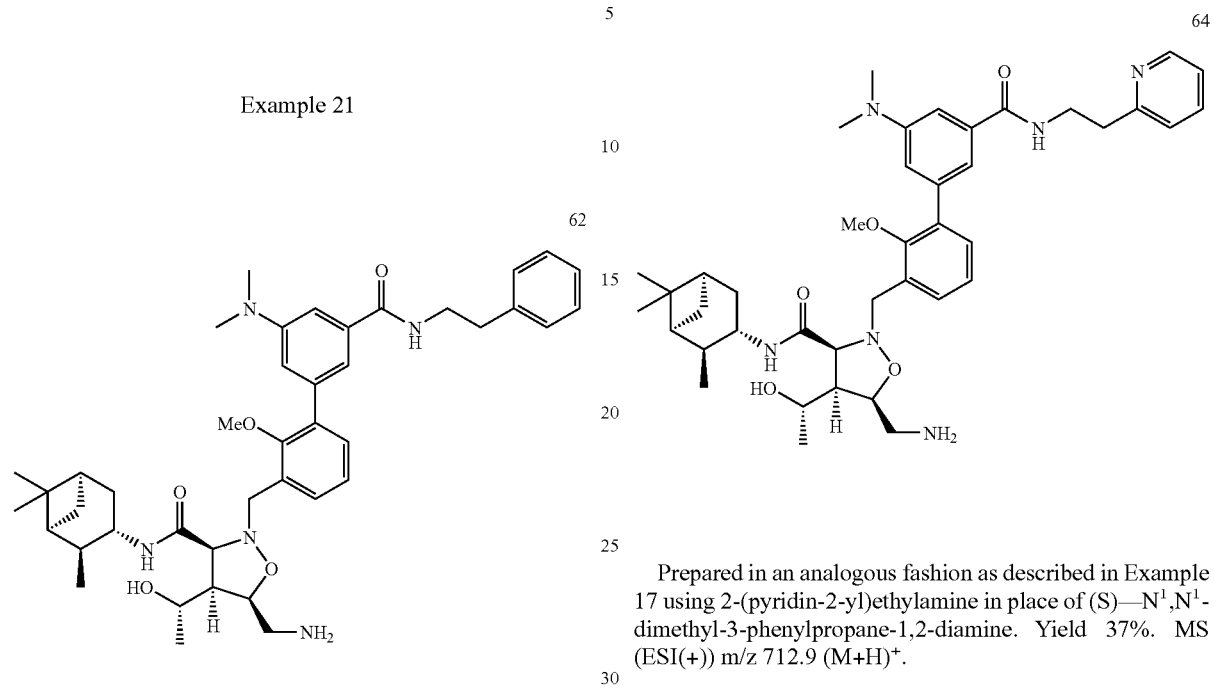

Prepared in an analogous fashion as described in Example 17 using 2-phenylethylamine in place of (S)—N¹,N¹-dimethyl-3-phenylpropane-1,2-diamine. Yield 43%. MS (ESI(+)) m/z 711.9 (M+H)⁺.

Example 22

Example 23

Prepared in an analogous fashion as described in Example 17 using 2-(pyridin-2-yl)ethylamine in place of (S)—N¹,N¹-dimethyl-3-phenylpropane-1,2-diamine. Yield 37%. MS (ESI(+)) m/z 712.9 (M+H)⁺.

Example 24

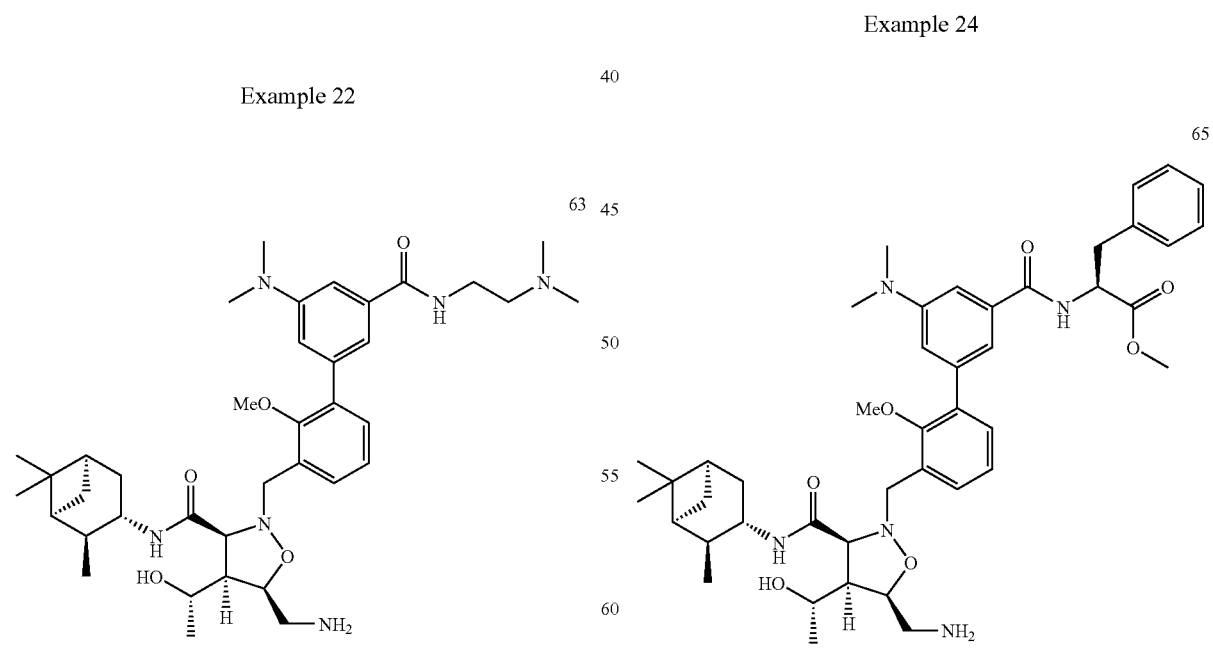

Prepared in an analogous fashion as described in Example 17 using N¹,N¹-dimethylethane-1,2-diamine in place of (S)—N¹,N¹-dimethyl-3-phenylpropane-1,2-diamine. Yield 62%. MS (ESI(+)) m/z 679.1 (M+H)⁺.

Prepared in an analogous fashion as described in Example 17 using (S)-methyl 2-amino-3-phenylpropanoate in place of (S)—N¹,N¹-dimethyl-3-phenylpropane-1,2-diamine. Yield 37%. MS (ESI(+)) m/z 770.1 (M+H)⁺.

Example 25

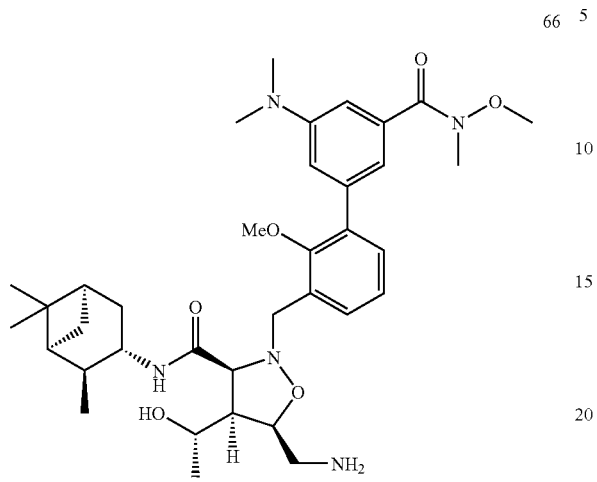

Prepared in an analogous fashion as described in Example 17 using N-methoxymethylamine in place of (S)—N$^1$,N$^1$-dimethyl-3-phenylpropane-1,2-diamine. Yield 87%. MS (ESI(+)) m/z 652.2 (M+H)$^+$.

Example 26

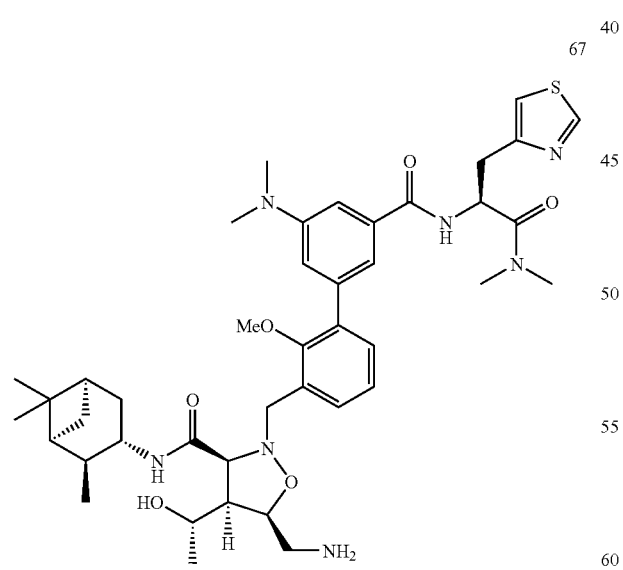

Prepared in an analogous fashion as described in Example 17 using (S)-2-amino-N,N-dimethyl-3-(thiazol-4-yl)propylamide in place of (S)—N$^1$,N$^1$-dimethyl-3-phenylpropane-1,2-diamine. Yield 11%. MS (ESI(+)) m/z 790.0 (M+H)$^+$.

Example 27

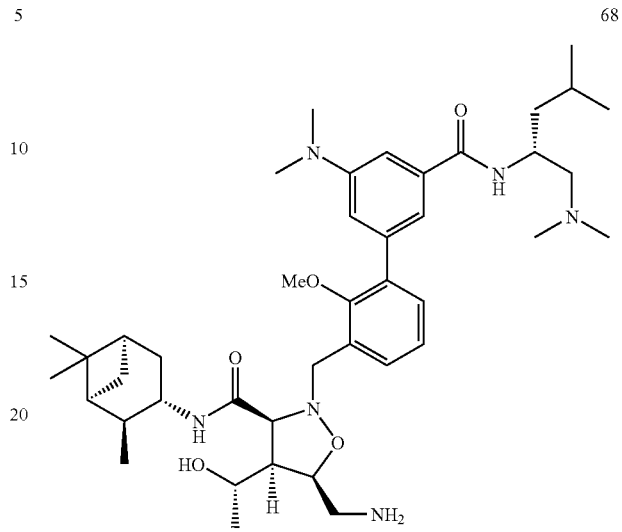

Prepared in an analogous fashion as described in Example 17 using (R)—N$^1$,N$^1$,4-trimethylpentane-1,2-diamine in place of (S)—N$^1$,N$^1$-dimethyl-3-phenylpropane-1,2-diamine. Yield 54%. MS (ESI(+)) m/z 735.1 (M+H)$^+$.

Example 28

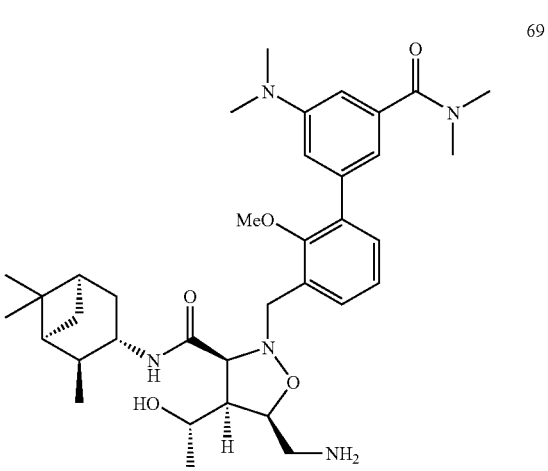

Prepared in an analogous fashion as described in Example 17 using dimethylamine in place of (S)—N$^1$,N$^1$-dimethyl-3-phenylpropane-1,2-diamine. Yield 15%. MS (ESI(+)) m/z 635.8 (M+H)$^+$.

Example 29

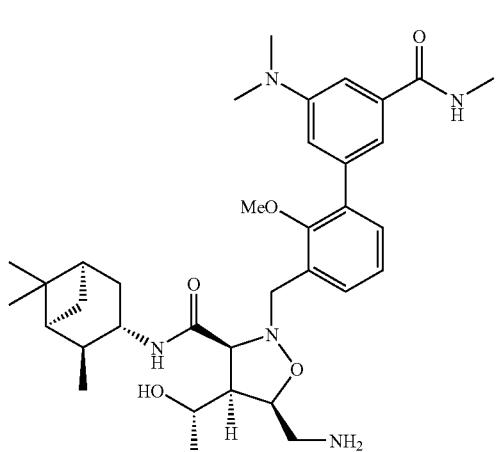

Prepared in an analogous fashion as described in Example 17 using methylamine in place of (S)—$N^1,N^1$-dimethyl-3-phenylpropane-1,2-diamine. Yield 42%. MS (ESI(+)) m/z 622.0 (M+H)$^+$.

Example 30

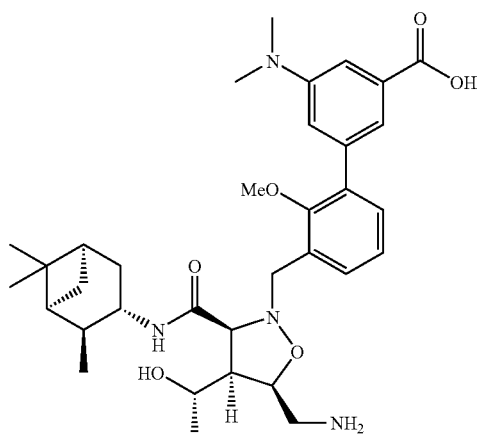

Prepared in an analogous fashion as described in Example 17 using compound 57 in place of compound 58. Yield 33%. MS (ESI(+)) m/z 609.1 (M+H)$^+$.

Example 31

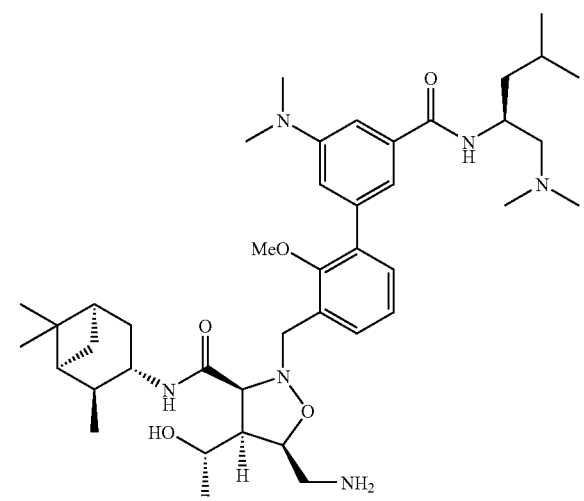

Prepared in an analogous fashion as described in Example 17 using (S)—$N^1,N^1$,4,4-trimethylpentane-1,2-diamine in place of (S)—$N^1,N^1$-dimethyl-3-phenylpropane-1,2-diamine. Yield 54%. MS (ESI(+)) m/z 735.1 (M+H)$^+$.

Example 32

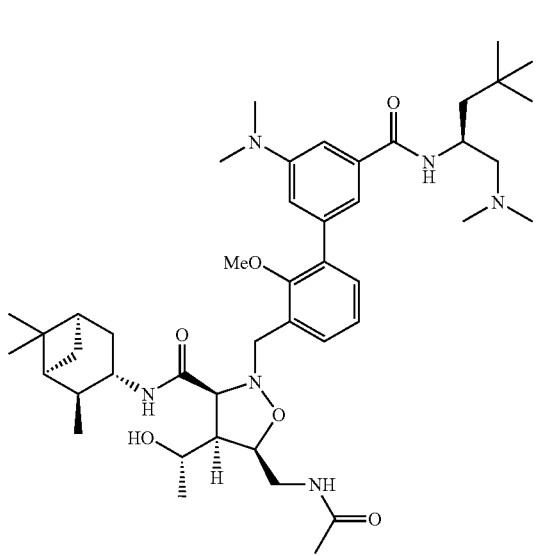

-continued

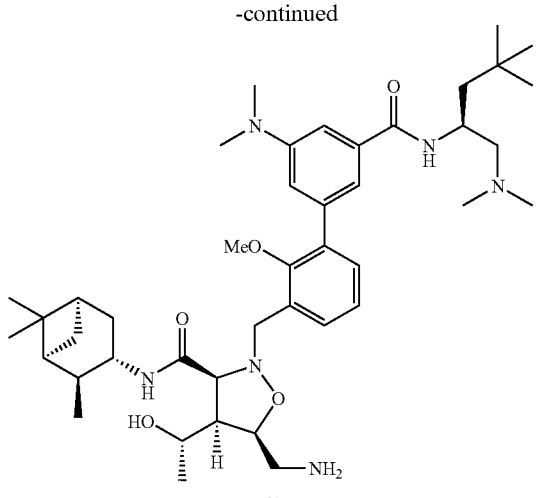

61

+

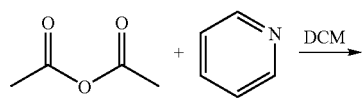 DCM

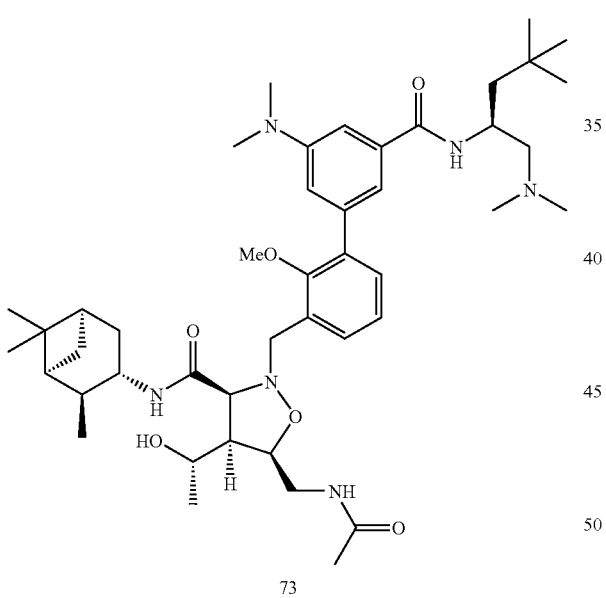

73

Compound 61 (4 mg, 0.006 mmol, 1 eq) was dissolved in DCM (1 mL), followed by the addition of pyridine (1.3 uL, 0.016 mmol, 1.5 eq) and acetic anhydride (1.5 uL, 0.016 mmol, 1.5 eq). After 1 h, the reaction mixture was quenched with water, extracted with DCM, dried over MgSO$_4$, filtered and concentrated in vacuo to afford an oil. The crude material was dissolved in MeOH (1 mL) and purified on reverse-phase HPLC (CH$_3$CN/water 40 mM NH$_4$HCO$_3$) to yield 2 mg of acetamide 73. Yield 47%. MS ((ESI(+)) m/z 791.5 (M+H)$^+$.

Example 33

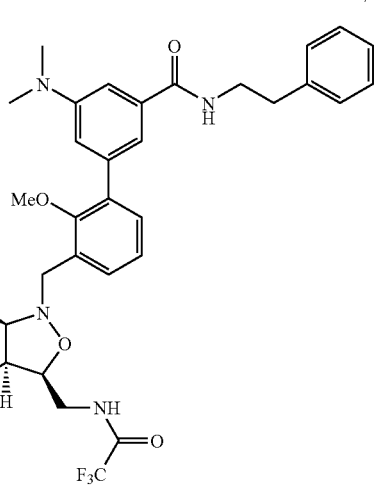

74

Prepared in an analogous fashion as described in Example 32 using compound 62 in place of compound 61 and trifluoroacetic anhydride in place of acetic anhydride. Yield 40%. MS (ESI(+)) m/z 808.4 (M+H)$^+$.

Example 34

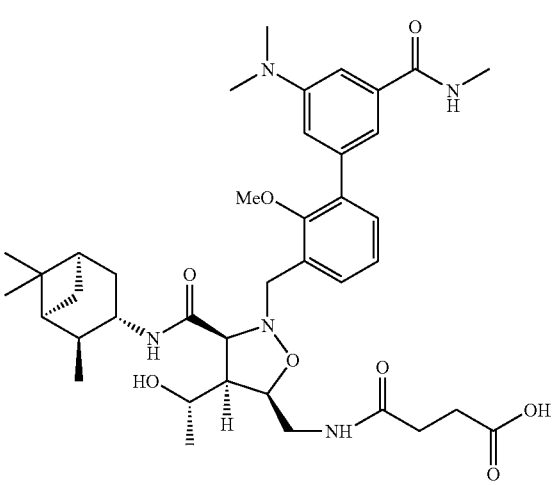

75

Prepared in an analogous fashion as described in Example 31 using compound 70 in place of compound 61 and succinic anhydride in place of acetic anhydride. Yield 28%. MS (ESI(+)) m/z 722.1 (M+H)$^+$.

Example 35
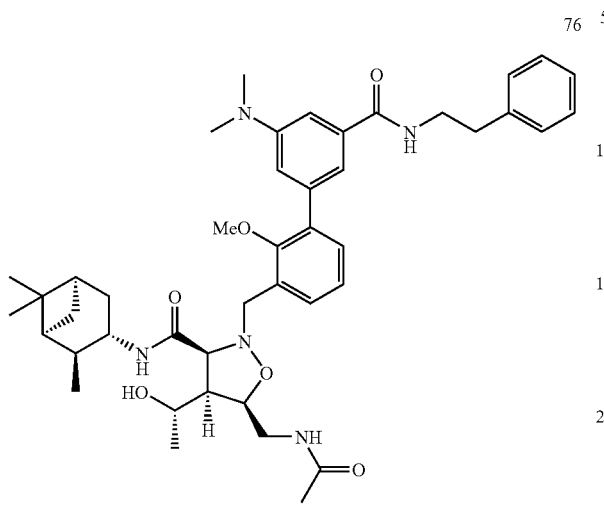
76
Prepared in an analogous fashion as described in Example 31 using compound 62 in place of compound 61. Yield 28%. MS (ESI(+)) m/z 754.4 (M+H)+.
Example 36
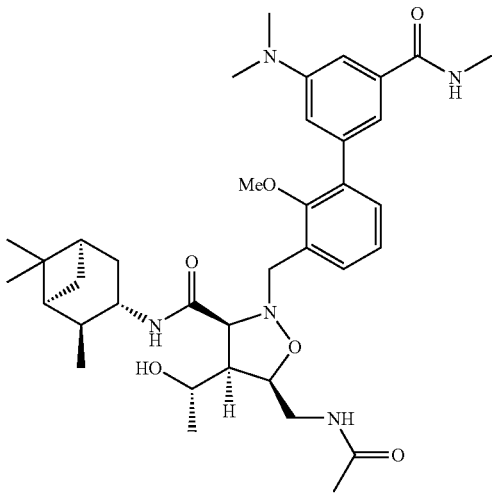
77
Prepared in an analogous fashion as described in Example 31 using compound 70 in place of compound 61. Yield 47%. MS (ESI(+)) m/z 664.4 (M+H)+.
Example 37
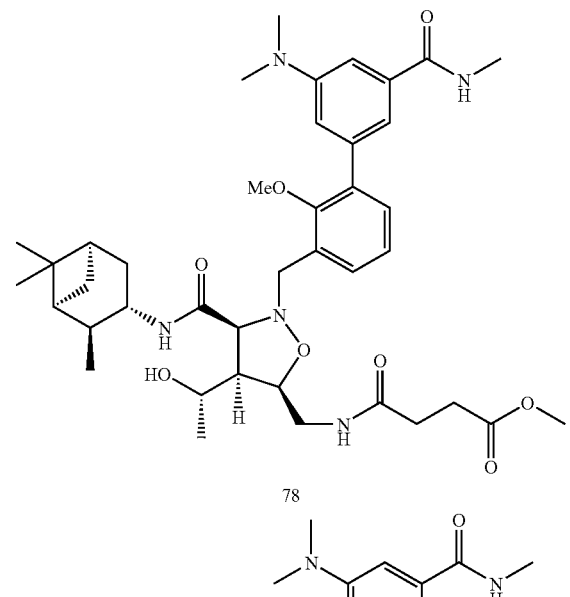
78
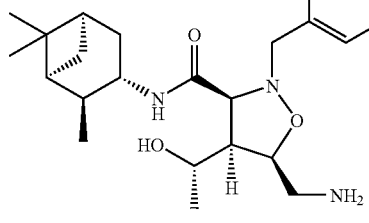
70
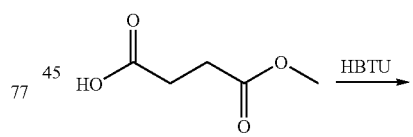
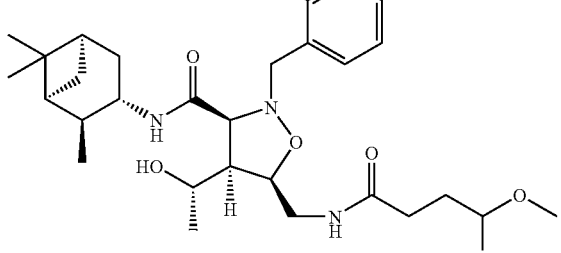
78

To a solution of mono-methylsuccinate (2.5 mg, 19 μmol, 3 eq) in DMF (0.5 mL) was added HBTU (7.3 mg, 19 μmol, 3 eq). After stirring for 15 minutes, compound 70 (4 mg, 64 μmol, 1 eq) was added as a THF solution (0.5 mL). The crude reaction mixture was purified directly by reverse-phase HPLC (MeCN/water with 40 mmol NH₄HCO₃) to yield 2 mg of amide 78. Yield 42%. MS ((ESI(+)) m/z 736.1 (M+H)⁺.

Example 38

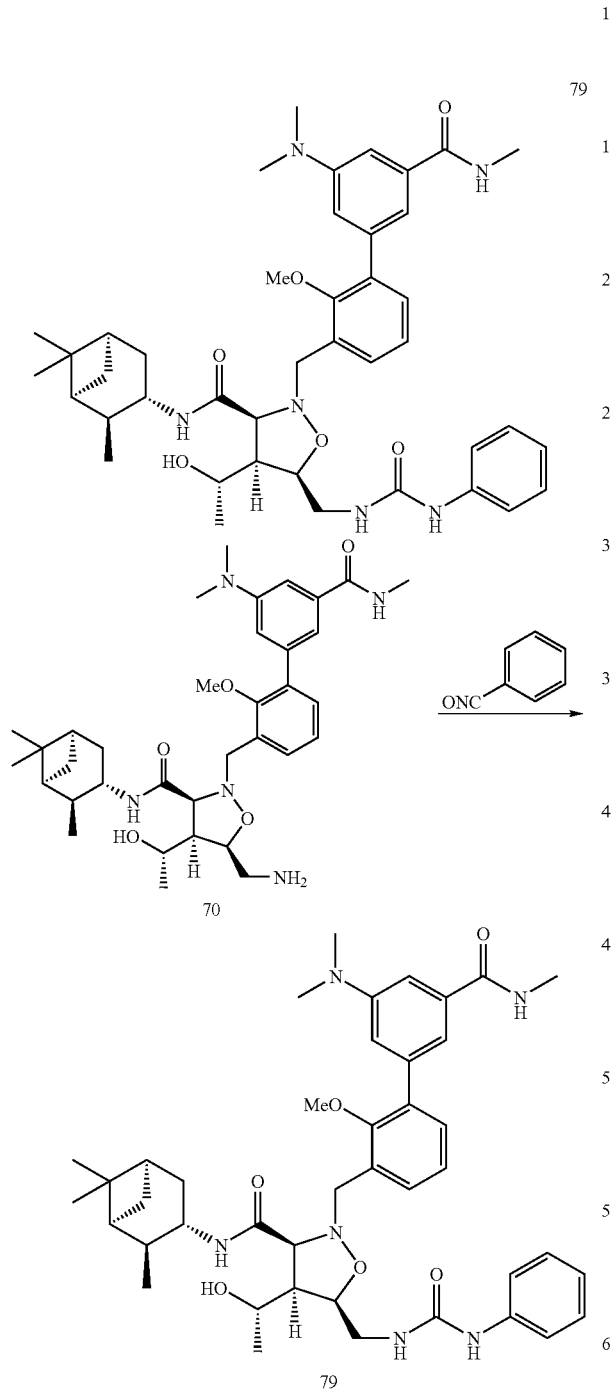

Compound 70 (4 mg, 6 μmol, 1 eq) was dissolved in DCM (1 mL) followed by the addition of phenyl isocyanate (1 uL, 8 μmol, 10.25 eq). After stirring for 30 min. the reaction mixture was purified directly by reverse-phase HPLC (MeCN/water with 40 mmol NH₄HCO₃) to yield 2 mg of urea 76. Yield 42%. MS ((ESI(+)) m/z 741.2 (M+H)⁺.

Example 39

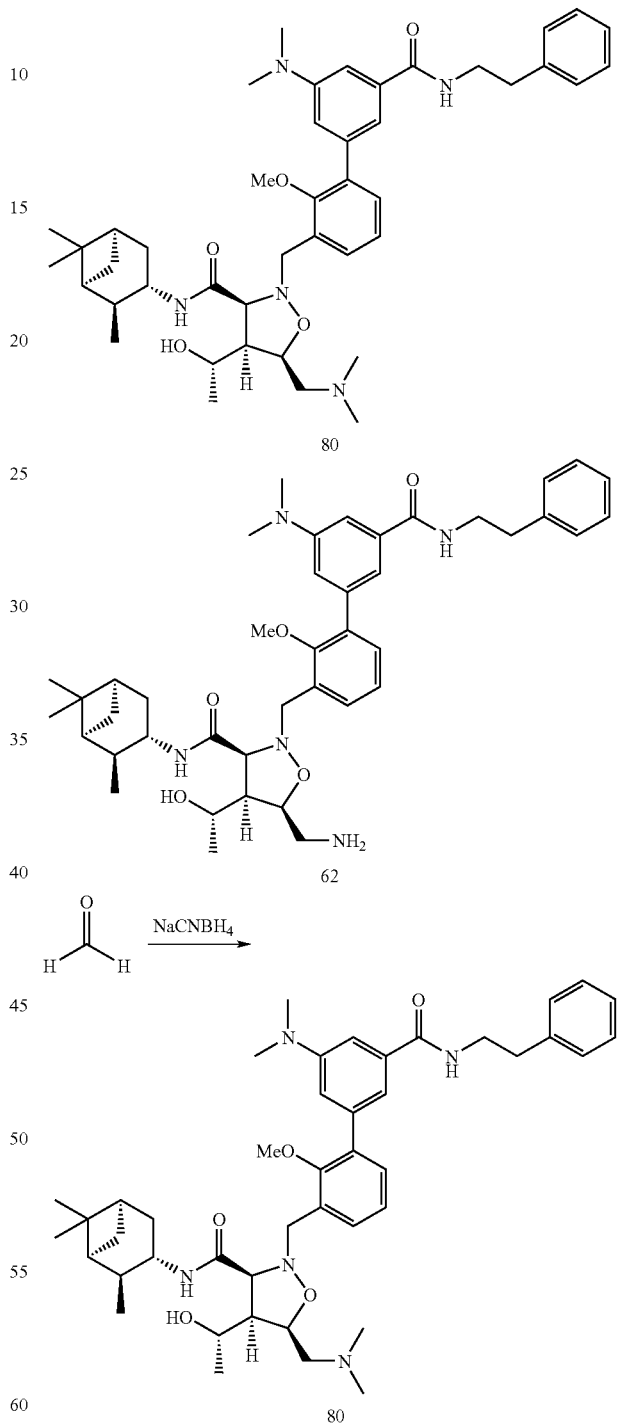

Compound 62 (10 mg, 0.014 mmol, 1 eq) was dissolved in MeOH (1 mL) followed by the addition of formaldehyde (2 mg, 0.07 mmol, 5 eq). After stirring for 30 min, NaBH₃CN (2.6 mg, 0.04 mmol, 3 eq) was then added in a single portion. The reaction mixture was purified by reverse-phase HPLC (MeCN/water with 40 mmol NH₄HCO₃) to yield 5 mg of dimethylamine 77. Yield 50%. MS ((ESI(+)) m/z 740.5 (M+H)⁺.

Example 40

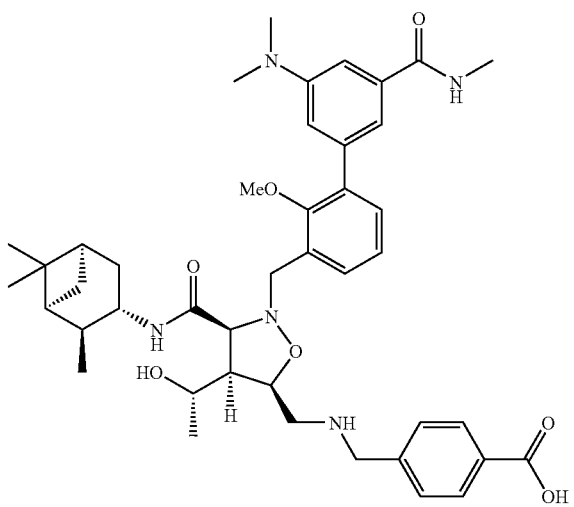

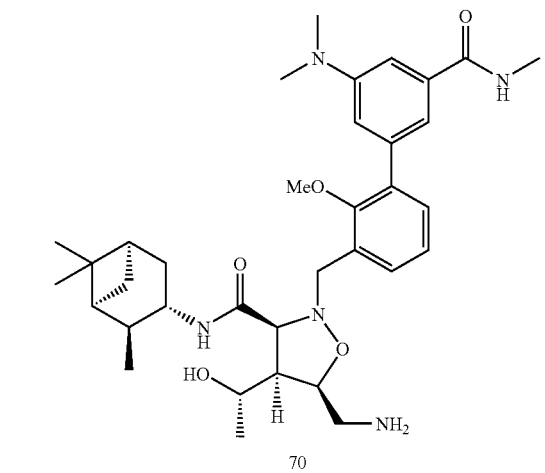

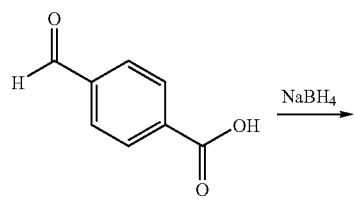

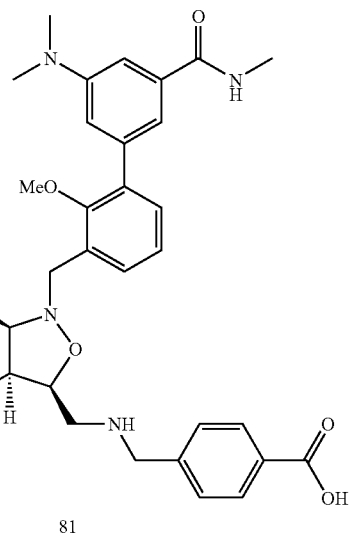

Compound 70 (4 mg, 6 μmol, 1 eq) was dissolved in MeOH (1 mL) followed by the addition of aryl aldehyde (3 mg, 0.02 mmol, 3 eq). After stirring for 3 h, NaBH₃CN (1 mg, 0.02 mmol, 3 eq) was added. The reaction mixture was stirred for an additional 30 min, then purified directly by reverse-phase HPLC (MeCN/water with 40 mmol NH₄HCO₃) to yield 2.5 mg of benzylamine 81. Yield 51%. MS ((ESI(+)) m/z 756.2 (M+H)⁺.

Example 41

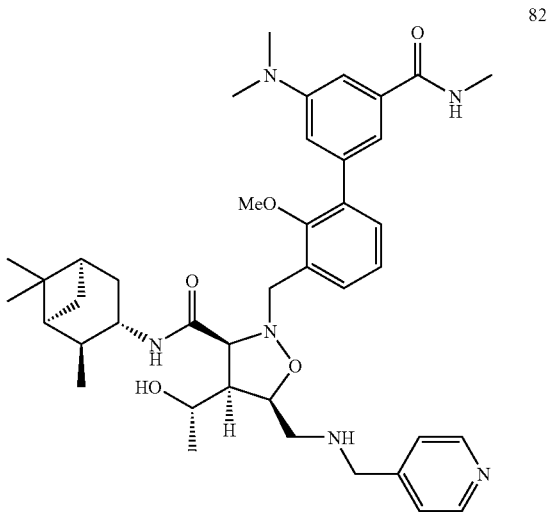

Prepared in an analogous fashion as described in Example 40 using isonicotinaldehyde in place of 4-formylbenzoic acid. Yield 37%. MS (ESI(+)) m/z 713.2 (M+H)+.

Prepared in an analogous fashion as described in Example 40 using 3-formylbenzoic acid in place of 4-formylbenzoic acid. Yield 37%. MS (ESI(+)) m/z 756.2 (M+H)+.

Example 42

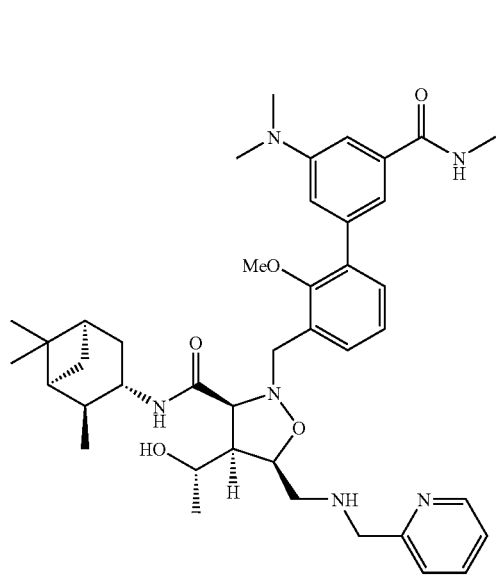

Prepared in an analogous fashion as described in Example 40 using picolinaldehyde in place of 4-formylbenzoic acid. Yield 44%. MS (ESI(+)) m/z 713.2 (M+H)+.

Example 43

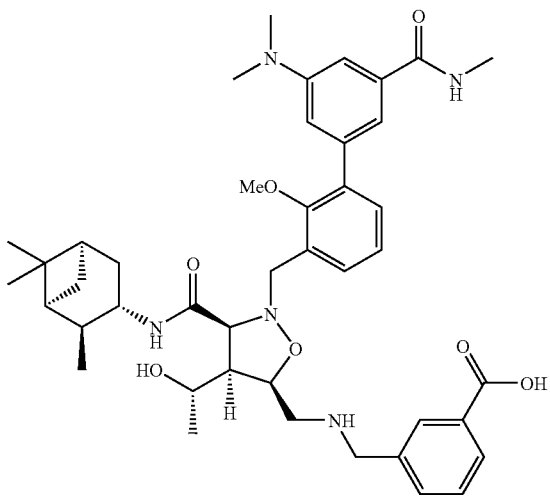

Example 44

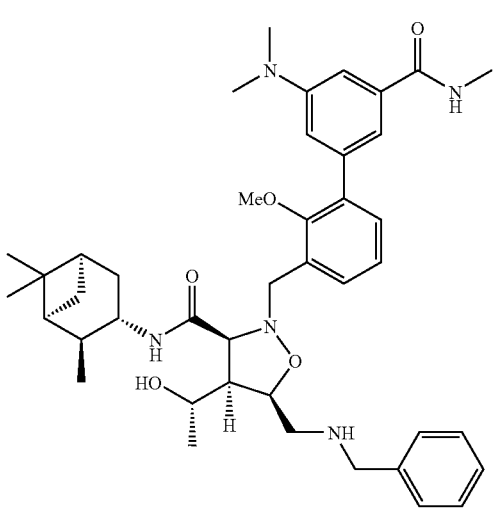

Prepared in an analogous fashion as described in Example 40 using benzaldehyde in place of 4-formylbenzoic acid. Yield 33%. MS (ESI(+)) m/z 712.2 (M+H)+.

Example 45

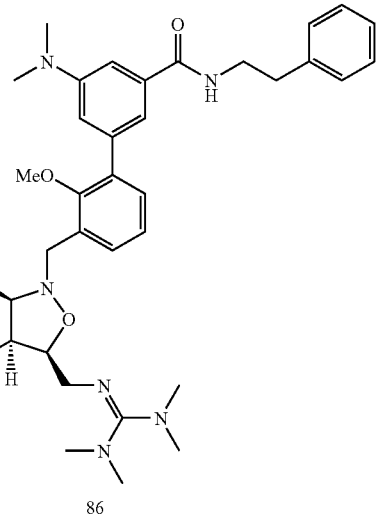

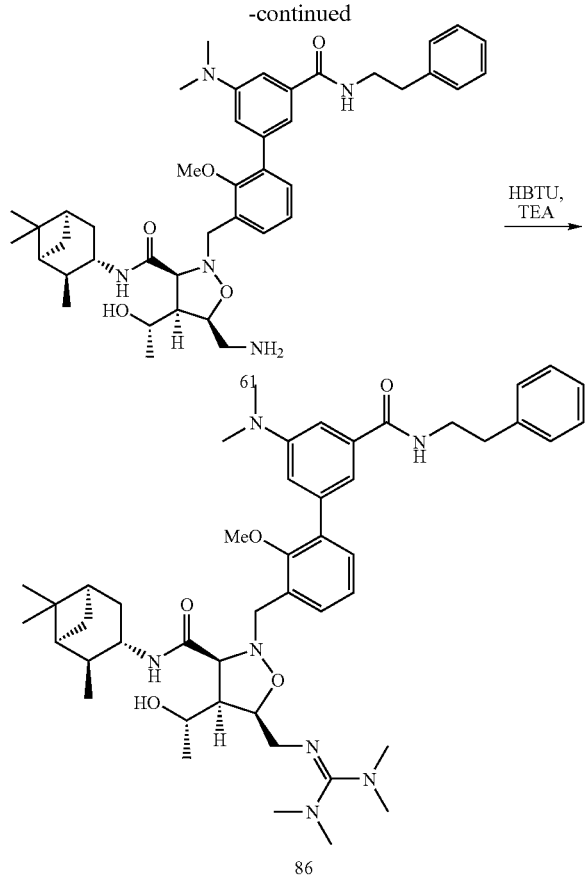

86

To a solution of compound 61 (8 mg, 0.01 mmol, 1 eq) in DCM/DMF (4:1, 1 mL), was added Et$_3$N (5 uL, 0.03 mmol, 3 eq) and HBTU (10 mg, 0.03 mmol, 3 eq). After stirring for 3 h, the reaction mixture was purified directly by reverse-phase HPLC (MeCN/water with 40 mM NH$_4$HCO$_3$) to yield 4 mg of 86. Yield 44%. MS ((ESI(+)) m/z 810.4 (M+H)$^+$.

Example 46

87

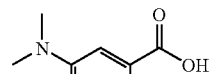

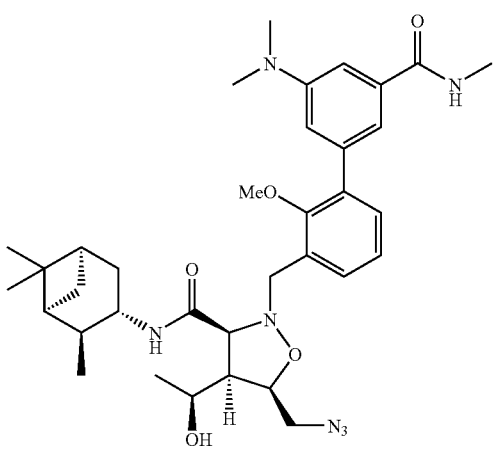

57

88

Prepared in an analogous fashion as described in Example 17 step D using methyl amine in place (S)—N$^1$,N$^1$-dimethyl-3-phenylpropane-1,2-diamine. Yield 26%.

Part B

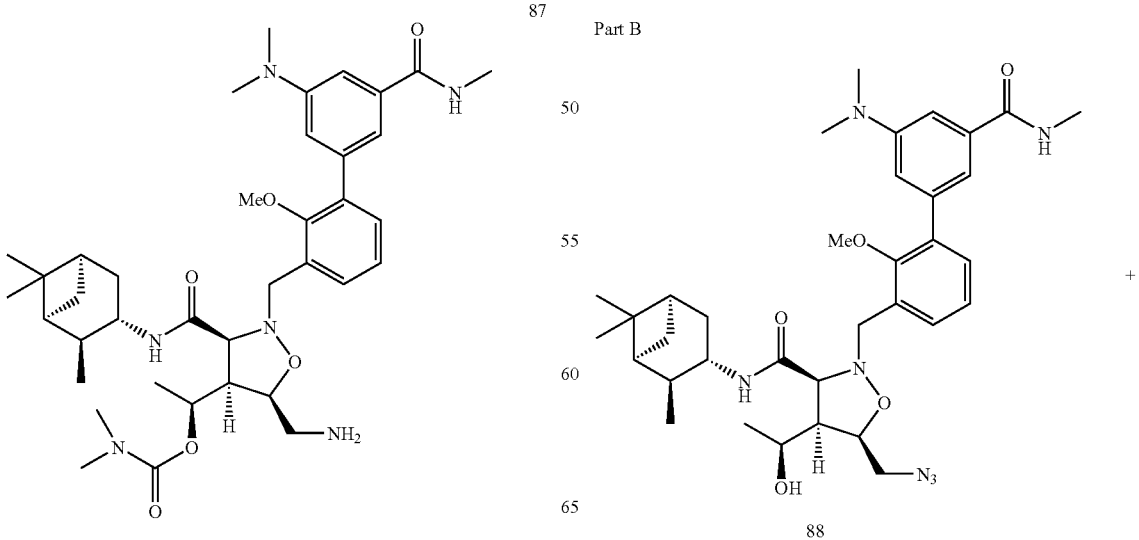

88

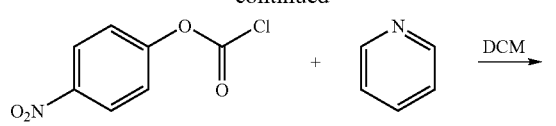

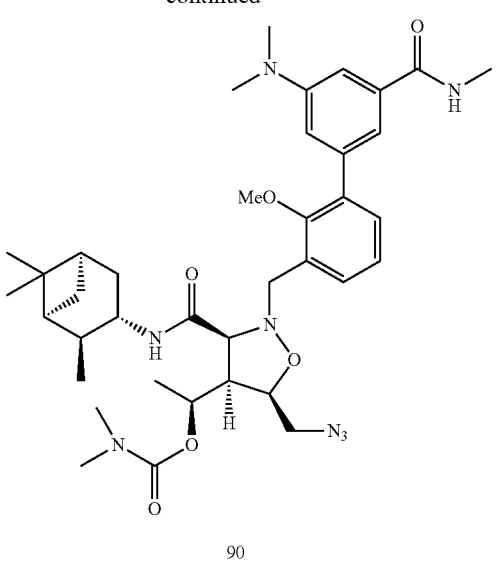

90

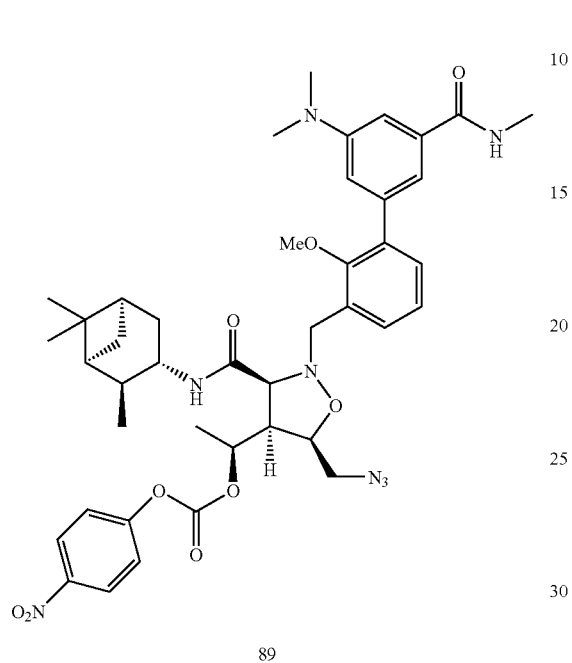

89

Azido alcohol 88 (150 mg, 0.232 mmol, 1 eq) was dissolved in DCM (2.5 mL), followed by the addition of pyridine (55 mL, 0.695 mmol, 3 eq) and para-nitro chloroformate (140 mg, 0.695 mmol, 3 eq). After stirring for 5 h, the reaction mixture was diluted with DCM (20 mL), water (20 mL) and the mixture was extracted with DCM (2×20 mL), dried over MgSO₄, filtered and concentrated in vacuo to afford an oils The crude material was purified by silica gel chromatography (50-90% EtOAc/hexane) to yield 142 mg of p-nitrocarbonate 89. Yield 75%.

To a solution of azido carbonate 89 (15 mg, 0.018 mmol, 1 eq) in THF (0.5 mL) was added dimethylamine (18 uL, 2 M in THF, 0.036 mmol, 2 eq). The reaction mixture immediately turned bright yellow. After stirring for 6 h, the reaction mixture was diluted with EtOAc (10 mL) and washed with water (5 mL). The aqueous layer was extracted with EtOAc (2×15 mL) and the combined organics were dried over MgSO₄, filtered and concentrated in vacuo to afford a yellow oil. The crude oil was used directly in next step.

Part C

Part D

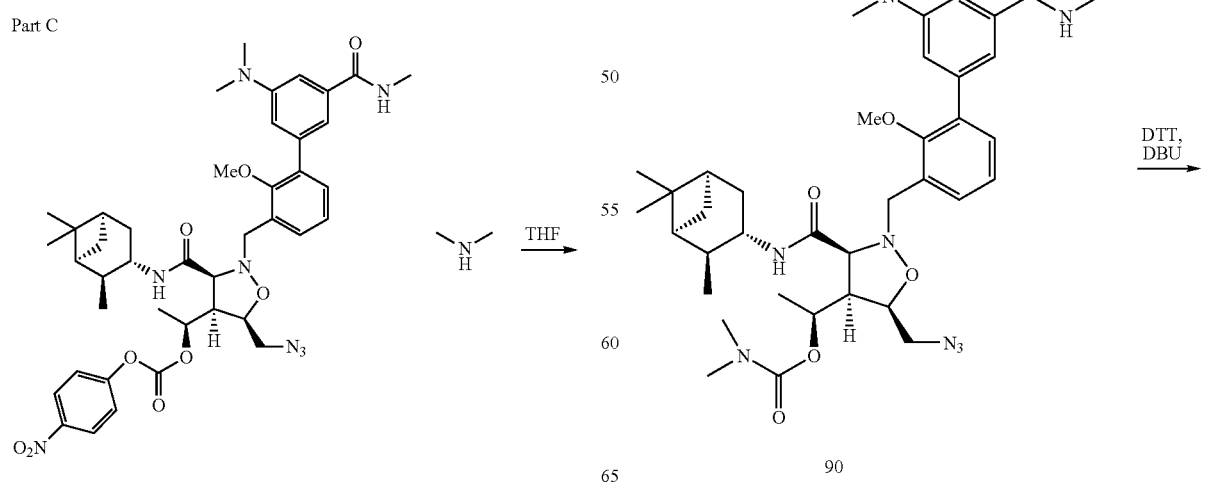

89            90

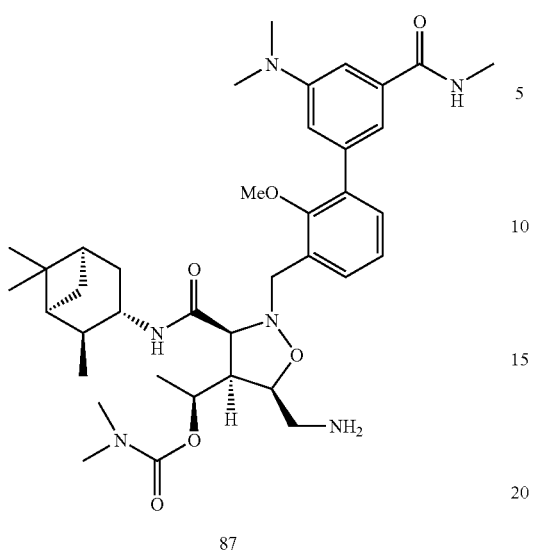

87

To a solution of carbamate 90 (13 mg, 0.018 mmol, 1 eq) in THF (0.5 mL) was added dithiothreitol (8 mg, 0.054 mmol, 3 eq) in DMF (0.5 mL) followed by the addition of DBU (8 mg, 0.054 mmol, 3 eq). After stirring for 1 h, the reaction mixture was purified directly by reverse-phase HPLC (MeCN/water with 40 mmol NH$_4$HCO$_3$) to yield 5 mg of compound 87. Yield 40%. MS ((ESI(+)) m/z 693.4 (M+H)$^+$.

Example 47

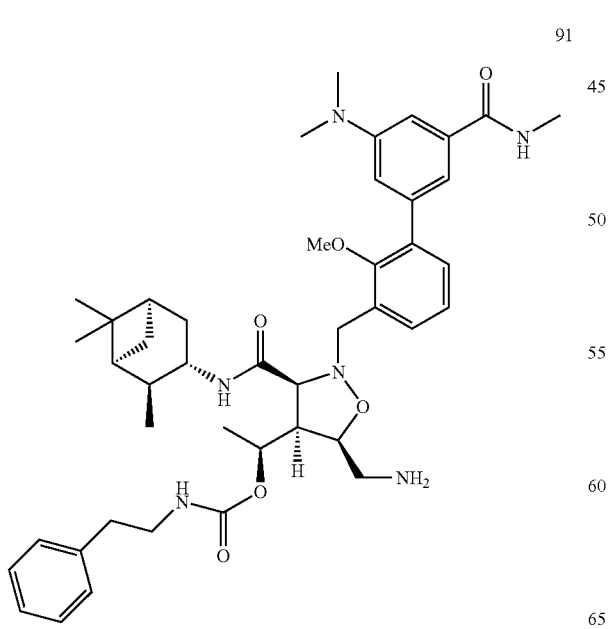

91

Prepared in an analogous fashion as described in Example 46 using 2-phenylethylamine in place of dimethylamine. Yield 42%. MS (ESI(+)) m/z 769.5 (M+H)$^+$.

Example 48

92

Prepared in an analogous fashion as described in Example 46 using N$^1$,N$^1$-dimethylethane-1,2-diamine in place of dimethylamine. Yield 30%. MS (ESI(+)) m/z 736.4 (M+H)$^+$.

Example 49

93

Prepared in an analogous fashion as described in Example 46 using methylamine in place of dimethylamine. Yield 42%. MS (ESI(+)) m/z 679.4 (M+H)⁺.

Example 50

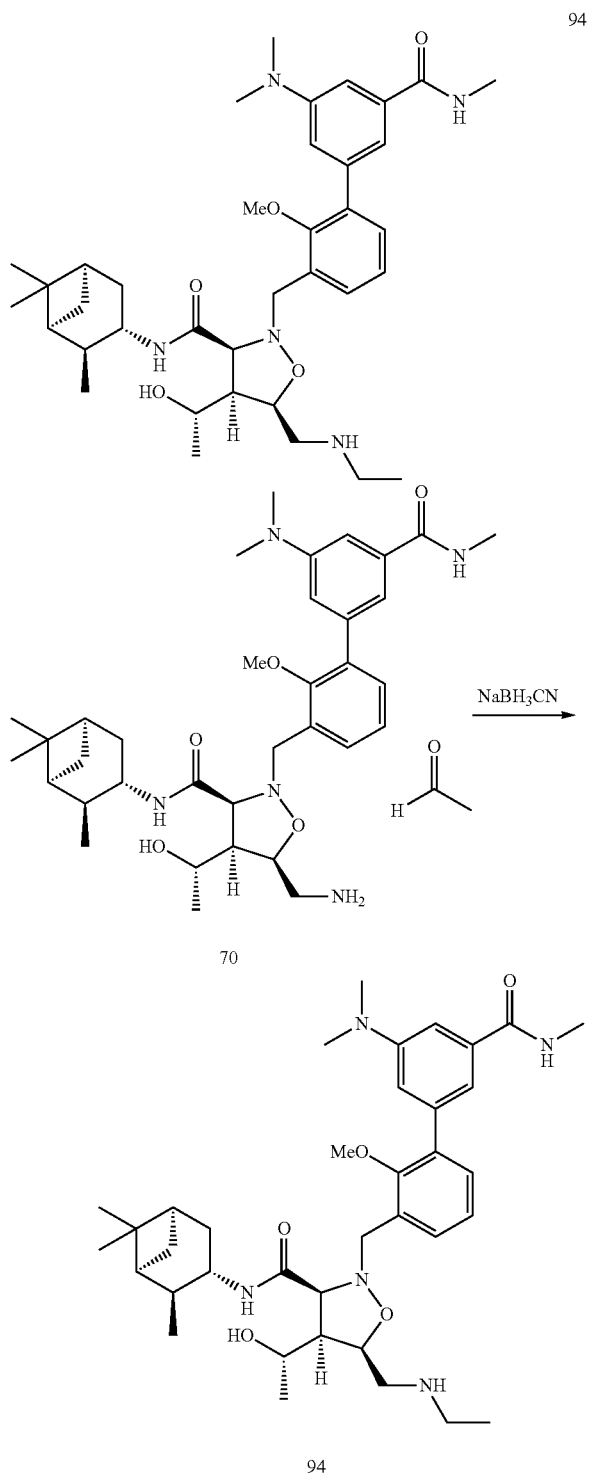

To a solution of amine 70 (10 mg, 0.02 mmol, 1 eq) in EtOH (1 mL) was added acetaldehyde (0.5 mg, 0.01 mmol, 0.5 eq) followed by NaBH₃CN (2 mg, 0.03 mmol, 1.5 eq) and finally AcOH (1 mg, 0.02 mmol, 1 eq). After stirring for 12 h, an additional portion of acetaldehyde (1 mg, 0.02 mmol, 1 eq) and NaBH₃CN (2 mg, 0.03 mmol, 1.5 eq) was added and the reaction was stirred at rt for 4 h. The crude material was purified directly by reverse-phase HPLC (MeCN/water with 40 mM of NH₄HCO₃) to yield 2 mg of 91. Yield 19%. MS (ESI(+)) m/z 650.81. (M+H)⁺.

Example 51

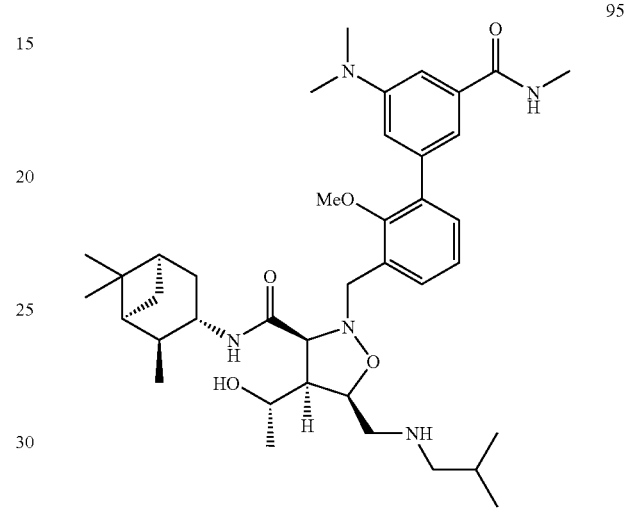

Amine 95 was prepared in an analogous fashion as described in Example 50 using isobutyraldehyde in place of acetaldehyde to yield 3 mg of 95. Yield 28%. MS (ESI(+)) m/z 678.84. (M+H)⁺.

Example 52

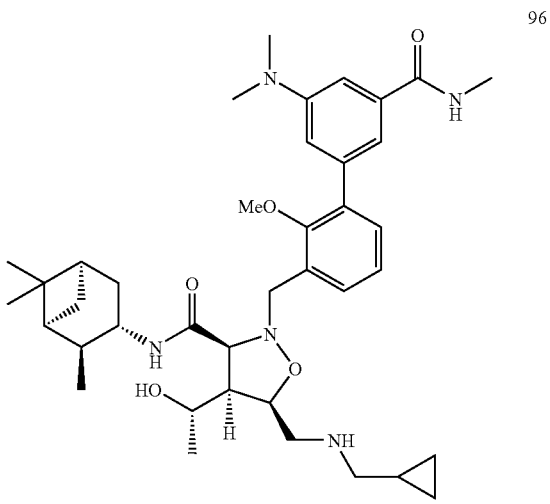

Amine 96 was prepared in an analogous fashion as described in Example 50 using cyclopropylaldehyde in place of acetaldehyde to yield 3 mg of 95. Yield 28%. MS (ESI(+)) m/z 676.9. (M+H)⁺.

Example 53

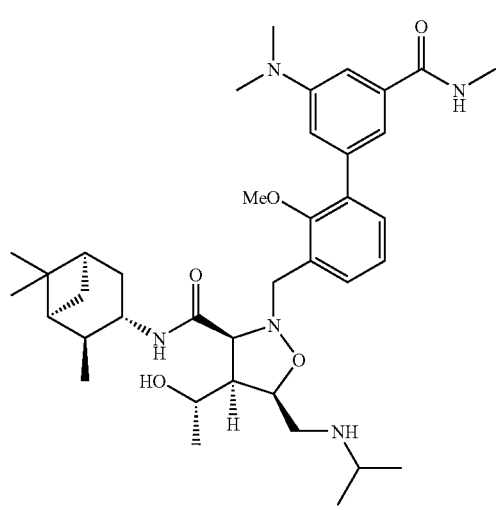

97

Amine 97 was prepared in an analogous fashion as described in Example 50 using acetone in place of acetaldehyde to yield 3 mg of 97. Yield 28%. MS (ESI(+)) m/z 664.8. (M+H)+.

Example 54

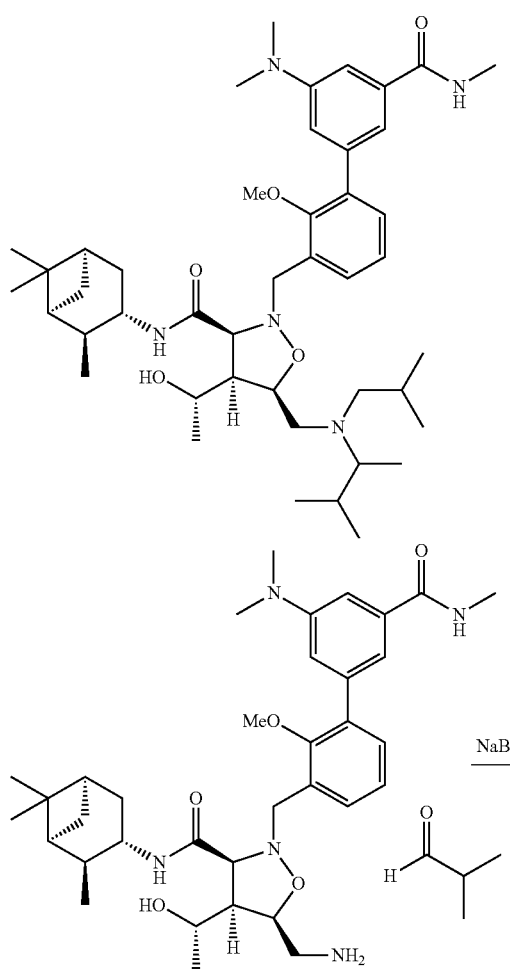

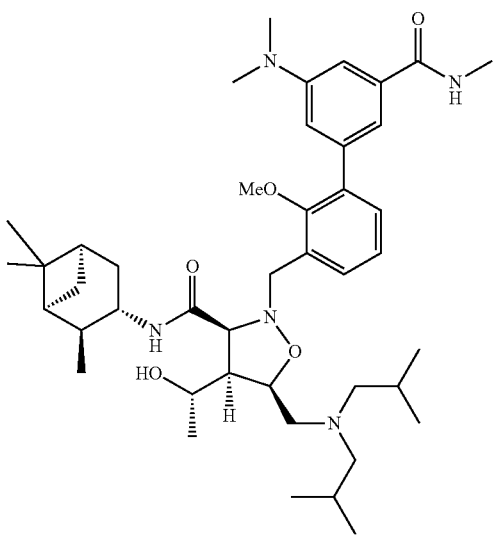

98

To a solution of amine 70 (10 mg, 0.02 mmol, 1 eq) in EtOH (1 mL) was added excess isobutyraldehyde (6 mg, 0.08 mmol, 4 eq) followed by NaBH$_3$CN (2 mg, 0.03 mmol, 1.5 eq) and finally AcOH (1 mg, 0.02 mmol, 1 eq). After stirring for 2 h, the reaction mixture was purified by reverse-phase HPLC (MeCN/water with 40 mM of NH$_4$HCO$_3$) to yield 2 mg of 98. Yield 18%. MS (ESI(+)) m/z 734.9. (M+H)+.

Example 55

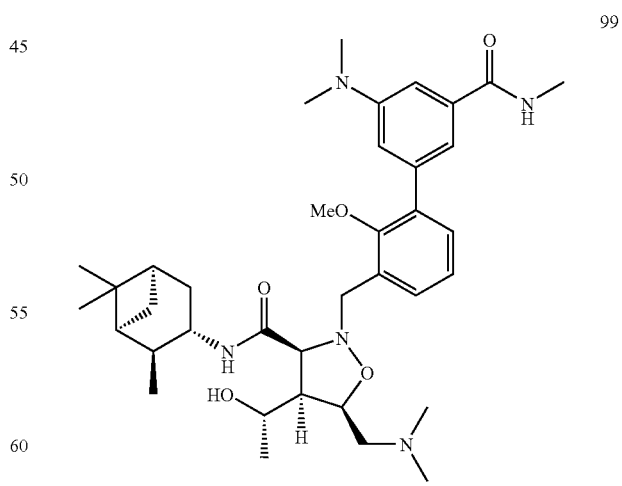

99

Amine 99 was prepared in an analogous fashion as described in Example 53 using formaldehyde in place of isobutyraldehyde to yield 2 mg of 99. Yield 38%. MS (ESI(+)) m/z 650.81. (M+H)+.

Example 56

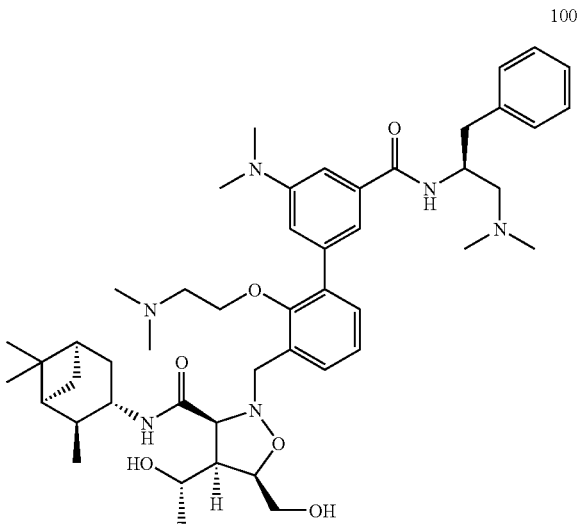

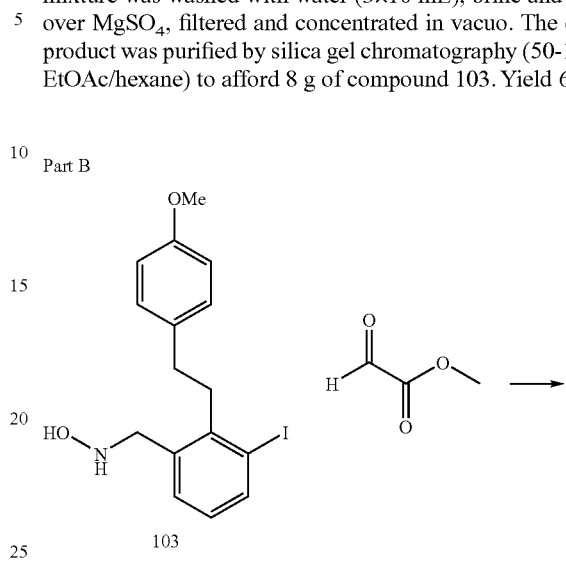

Aldehyde 102 (12 g, 33 mmol, 1 eq) and hydroxylamine hydrochloride (2.7 g, 39 mmol, 1.18 eq) were dissolved in THF/MeOH (3:1, 60 mL). Water (2 mL) was added and the pH was adjusted to 9 with 6 N KOH. The reaction mixture was stirred at rt overnight and then NaBH₃CN (3.1 g, 49 mmol) was added followed by a crystal of methyl orange. The pH was adjusted to 3 and the resulting ruby red color was maintained for the duration of the reaction by the frequent addition of 1 N HCl. After stirring for 2 h another portion of NaBH₃CN (1 g, 13 mmol, 0.4 eq) was added. The solution was stirred for 16 h and then neutralized to pH 7 and diluted with DCM. The mixture was washed with water (3×10 mL), brine and dried over MgSO₄, filtered and concentrated in vacuo. The crude product was purified by silica gel chromatography (50-100% EtOAc/hexane) to afford 8 g of compound 103. Yield 64%.

Part B

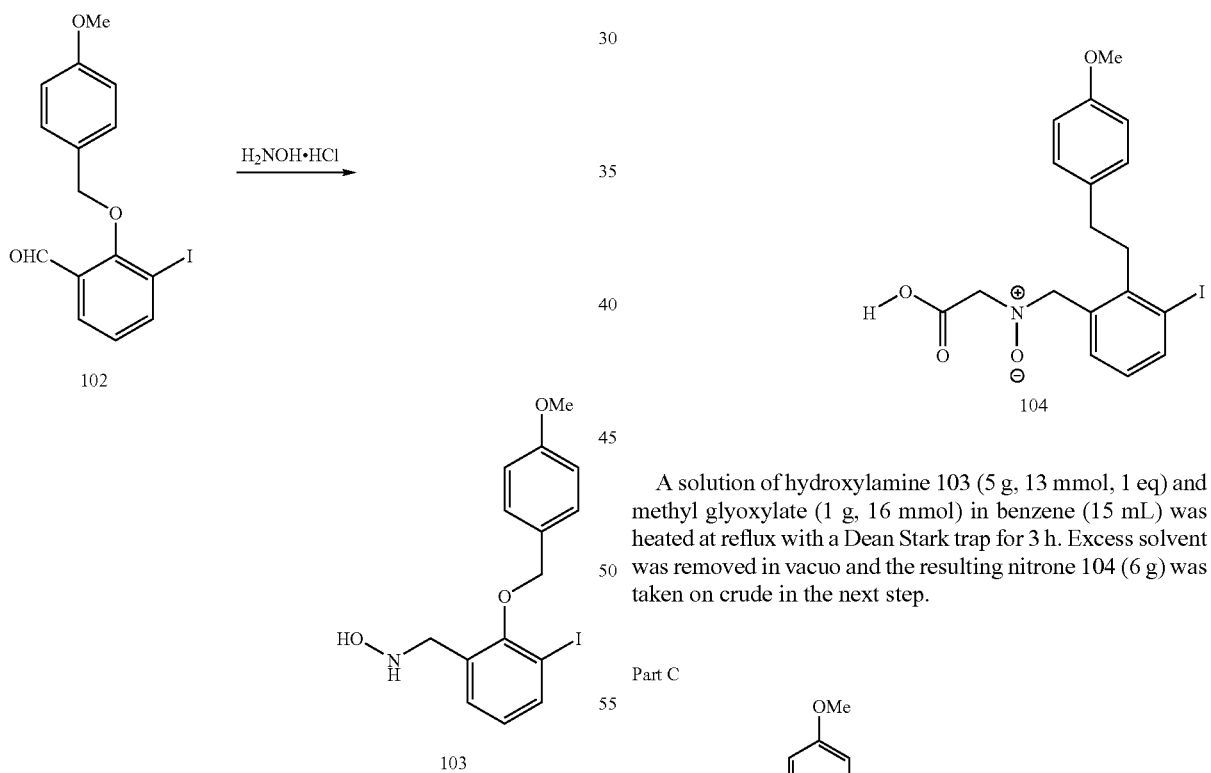

A solution of hydroxylamine 103 (5 g, 13 mmol, 1 eq) and methyl glyoxylate (1 g, 16 mmol) in benzene (15 mL) was heated at reflux with a Dean Stark trap for 3 h. Excess solvent was removed in vacuo and the resulting nitrone 104 (6 g) was taken on crude in the next step.

Part C

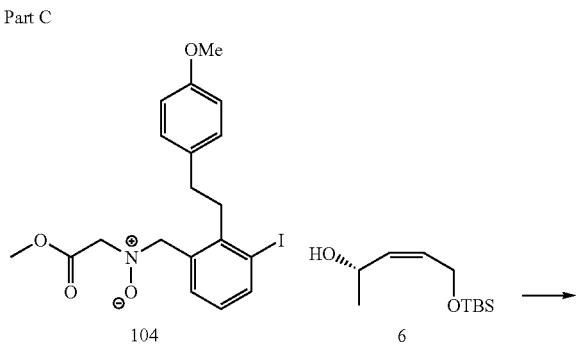

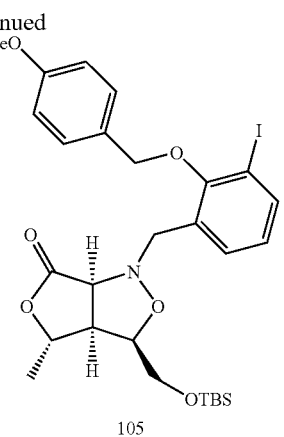

105

Nitrone 104 (5 g, 11 mmol, 1 eq), allylic alcohol (2 g, 11 mmol, 1 eq) and Ti(iOPr)₄ (4 g, 4 mL, 13 mmol, 1.18 eq) were dissolved in toluene (40 mL) and heated in a microwave at 120° C. for 10 min. The reaction mixture was diluted with EtOAc (10 mL) and 3-(dimethylamino)-1,2-propanediol (4 mL) was added. After stirring for 2 h, EtOAc (10 mL) was added and the mixture was washed with water (3×10 mL) then brine (10 mL), dried over MgSO₄, filtered over Celite® and concentrated in vacuo. The crude residue was purified by silica gel chromatography (10-30% Hexane-EtOAc) to afford 2.5 g of compound 105. Yield 35%.

Part D

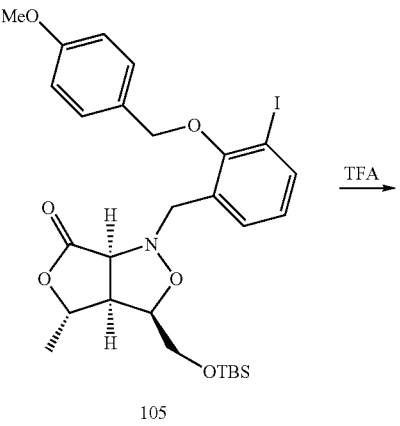

105

To a solution of PMB ether 105 (2 g, 3 mmol, 1 eq) in DCM (150 mL) was added TFA (3 g, 31 mmol, 10.33 eq) dropwise at 0° C. The solution was stirred for 1.5 h and quenched with saturated NaHCO₃ (60 mL). The organic phase was separated, washed with brine, dried over Na₂SO₄, filtered and concentrated in vacuo to afford an oil. The resulting oil was purified by silica chromatography (10-30% hexane-EtOAc) to afford 1.2 g of compound 106 Yield 74%.

Part E

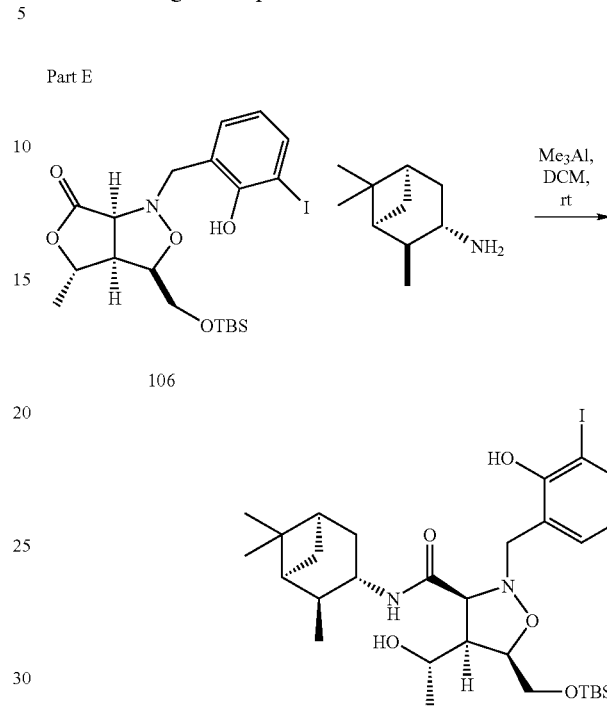

106

To a solution of (+)-isopinocampheylamine (0.6 g, 0.7 mL, 4 mmol, 2 eq) in DCM (10 mL) at rt was added trimethylaluminum (0.4 g, 3 mL, 2 M solution in toluene, 6 mmol, 3 eq) dropwise over 2.5 min. The solution was stirred at rt for 10 min prior to the dropwise addition of a solution of lactone 106 (1 g, 2 mmol, 1 eq) in DCM (15 mL). The reaction was stirred for 24 h, diluted with DCM (125 mL) and a saturated solution of Rochelle's salt (125 mL). The mixture was vigorously stirred for 2 h until two phases formed. The layers were separated and the organic phase was washed with water, brine, dried over MgSO₄, filtered and concentrated in vacuo to afford a solid. The solid was purified by silica gel chromatography (25% hexane/EtOAc) to afford 0.5 g of compound 107. Yield 39%.

Part F

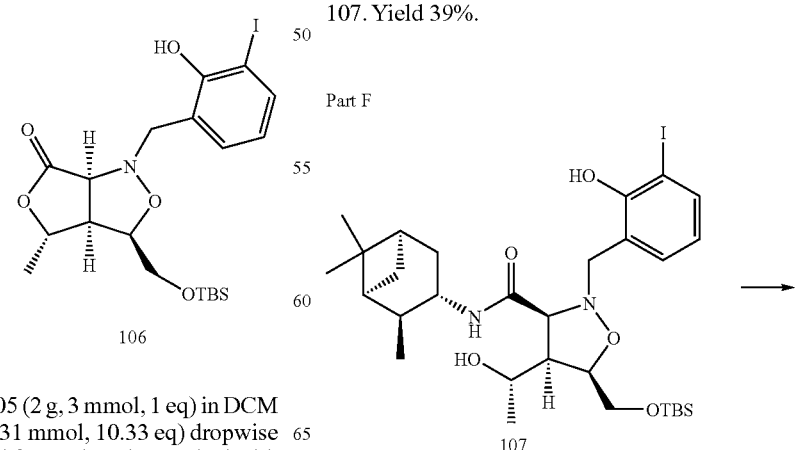

107

-continued

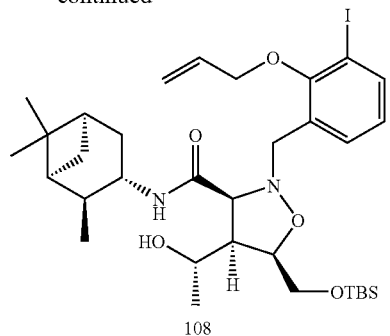
108

Phenol 107 (187 mg, 0.27 mmol, 1 eq) was dissolved in DMF (3.5 mL) and treated with K$_2$CO$_3$ (111 mg, 0.8 mmol, 3 eq), and allylbromide (49 mg, 0.4 mmol, 10.48 eq). The solution was stirred for 2.5 h, diluted with water and extracted with ether (3×4 mL). The organic phase was separated, dried over Na$_2$SO$_4$, filtered and concentrated in vacuo to afford a solid. The resulting solid was dissolved in THF/Et$_3$N (1:1, 6 mL) and treated with a solution of HF/pyridine (1 mL) at 0° C. The solution was stirred for 1 h at rt and quenched with TMSOMe (25 mL) and concentrated in vacuo to afford a solid which was purified by silica gel chromatography (20% DCM/hexane) to afford 0.21 g of compound 108 as a white solid. Yield 67%.

Part G

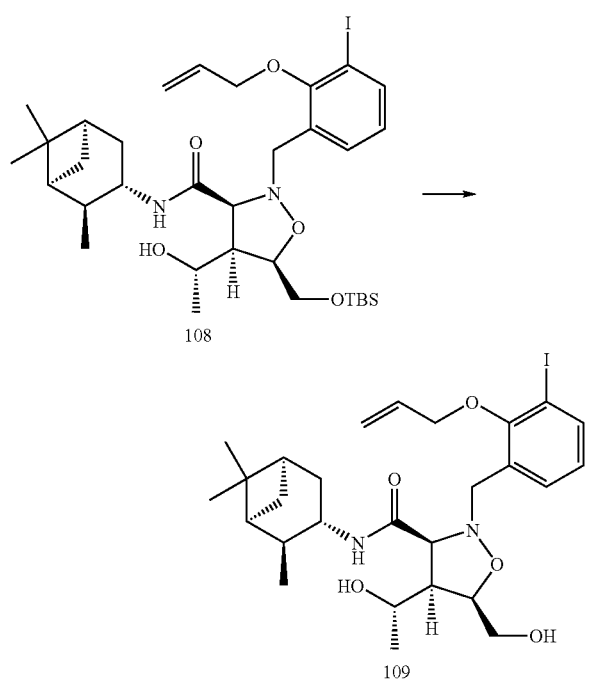

To a solution of the TBS ether 108 (0.25 g, 0.35 mmol, 1 eq) in THF (5 mL) at 0° C. was added pyridine (6 mL) and a solution of HF/pyridine (1.2 mL). The reaction was allowed to warm to rt over 1 h while stirring. The reaction solution was quenched with an excess of TMSOMe (30 mL) and stirred for an additional 30 min. The reaction was then concentrated to an oil and purified by silica gel chromatography to yield 0.21 g of compound 109. Yield 67%.

Part H

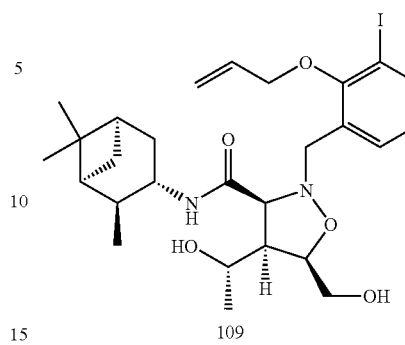
109

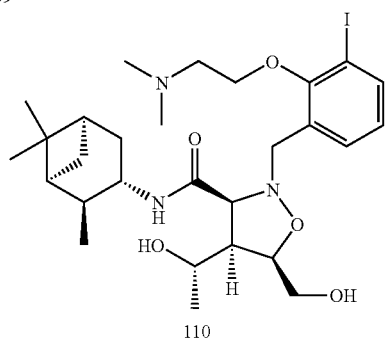
110

To a solution of the alkene 109 (0.14 g, 0.2 mmol, 1 eq) in t-BuOH (16 mL), THF (8 mL) and H$_2$O (2 mL) was added NMO (80 mg, 0.8 mmol, 4 eq) followed by the dropwise addition of OsO$_4$ (0.21 g, 2.9 mL, 2.5% solution in 2-methyl-2-propanol, 0.02 mmol, 0.1 eq). After 3 h, the reaction mixture was diluted with DCM (5 mL), brine and 10% Na$_2$S$_2$O$_3$ and the organic phase was separated. The aqueous phase was extracted with DCM (2×60 mL), and the combined organics were dried over Na$_2$SO$_4$, filtered and concentrated in vacuo to afford a solid. The solid was dissolved in THF/water (10:1, 1.2 mL) and treated with periodic acid (80 mg, 0.4 mmol, 2 eq) in single portion and stirred for 12 h. The solution was diluted with DCM (5 mL) and washed with brine, dried over Na$_2$SO$_4$, filtered and in vacuo to afford an oil. The resulting oil was suspended in MeOH (5 mL) and treated with acetic acid (100 uL), dimethylamine (20 mg, 2 M in THF, 0.5 mmol, 2.5 eq) and NaBH$_3$CN (30 mg, 0.5 mmol, 2.5 eq) and stirred for 12 h. The solution was diluted with 0.1 M NaOH (1 mL), saturated NaCl (1 mL) and extracted with EtOAc (3×3 mL). The combined organic was concentrated in vacuo to afford an oil. The oil was purified by silica gel chromatography (DCM/MeOH/AcOH, 99.5:0:0.5 to 97.5:2:0.5) to afford 75 mg of compound 110. Yield 60%.

Part I

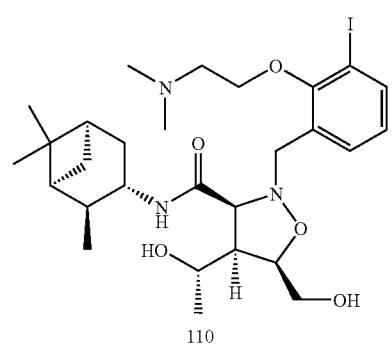
110

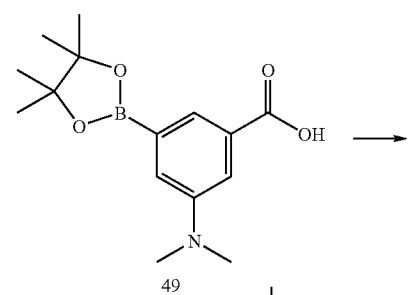

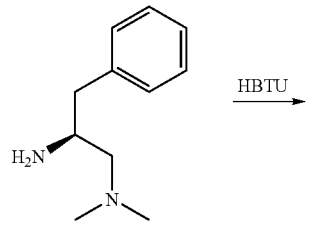

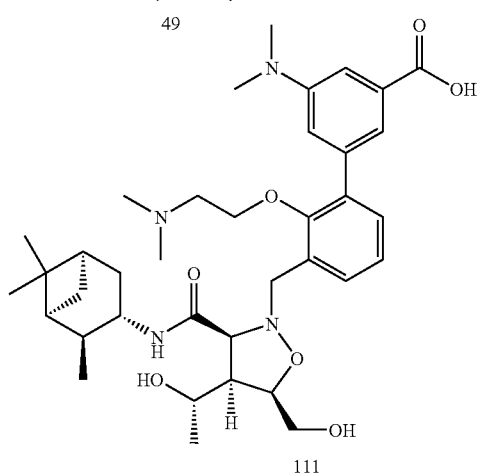

111

A flask containing aryl iodide 110 (25 mg, 0.04 mmol, 1 eq), pinacolboronate 49 (17 mg, 0.06 mmol, 1.5 eq), potassium acetate (5 mg, 0.048 mmol, 1.2 eq), cesium carbonate (39 mg, 0.12 mmol, 3 eq) and Pd(dppf)Cl$_2$ (6.5 mg, 8 μmol, 0.2 eq) was purged with argon and DMSO (2 mL) was added. The mixture was heated to 70° C. for 3 h and then cooled to rt. The solution was diluted with DCM (10 mL), water (5 mL) and the pH was adjusted to 6.8 with 0.1 N HCl. The aqueous phase was extracted with DCM (2×10 mL) and the combined organics were washed with brine (20 mL), dried over MgSO$_4$, filtered and concentrated in vacuo to afford a dark brown oil. The resulting oil was purified by flash chromatography (2.5-5% CH$_2$Cl$_2$/MeOH) to afford 15 mg of compound III as a yellow solid. Yield 57%.

To a solution of 111 (8 mg, 0.02 mmol, 1 eq) in DMF (1.5 mL) was added HBTU (9 mg, 0.02 mmol, 1 eq), amine 112 (4 mg, 0.02 mmol, 1 eq) and Et$_3$N (4 mg, 5 uL, 0.04 mmol, 2 eq). The solution was stirred for 2 h, diluted with water (0.5 mL) and purified by reverse-phase HPLC (MeCN/water with 40 mM NH$_4$HCO$_2$) to yield 7 mg of compound 100. Yield 67%. MS (ESI(+)) m/z 828 (M+H)$^+$.

Part J

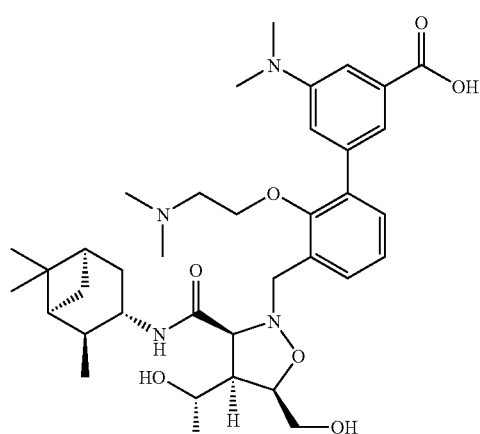

111

Example 57

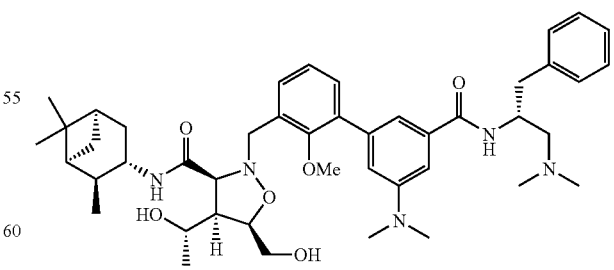

Prepared in an analogous fashion as described in Example 1 using (R)—N$^1$,N$^1$-dimethyl-3-phenylpropane-1,2-diamine in place of (S)—N$^1$,N$^1$,4,4-tetramethylpentane-1,2-diamine. Yield 65%. MS (ESI(+)) m/z 770.7. (M+H)$^+$.

Example 58

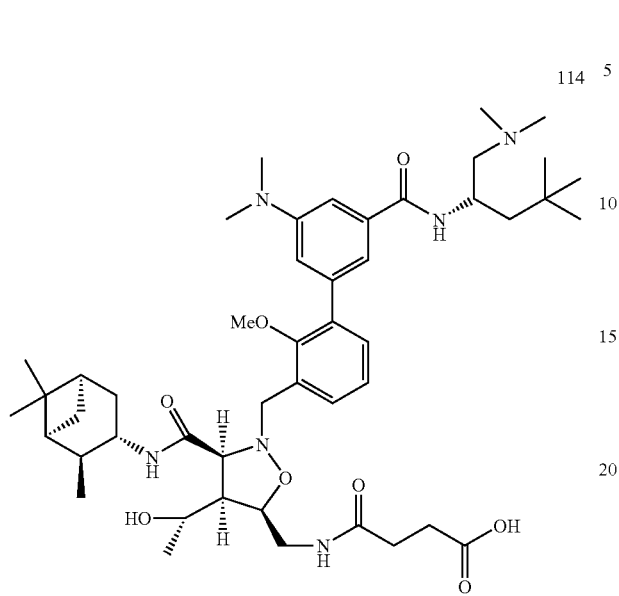

Prepared in an analogous fashion as described in Example 31 using compound 60 in place of compound 72 and succinic anhydride in place of acetic anhydride. 65% Yield. MS (ESI(+)) m/z 770.7 (M+H)$^+$.

Example 59

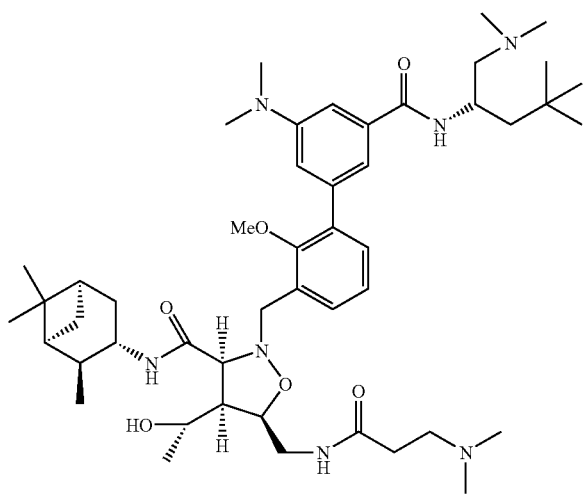

Prepared in an analogous fashion as described in Example 37 using compound 61 in place of compound 70 and 3-(dimethylamino)propanoic acid in place of mono-methylsuccinate. 28% Yield. MS (ESI(+)) m/z 849.6 (M+H)$^+$.

Example 60

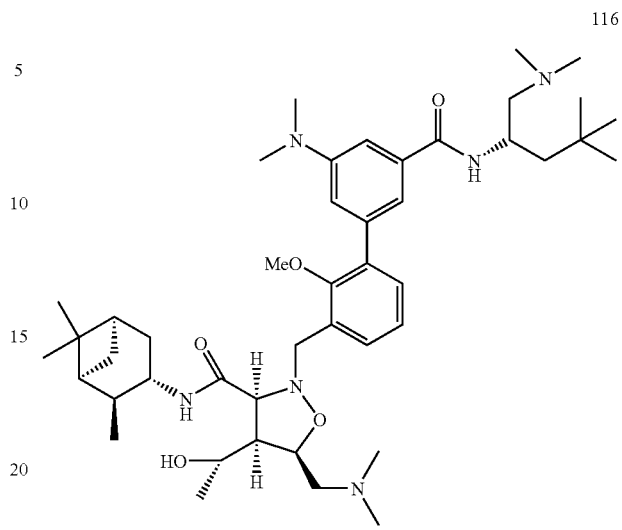

Prepared in an analogous fashion as described in Example 54 using compound 61 in place of compound 70 and formaldehyde in place of isobuteraldehyde. 36% Yield. MS (ESI(+)) m/z 777.6 (M+H)$^+$.

Example 61

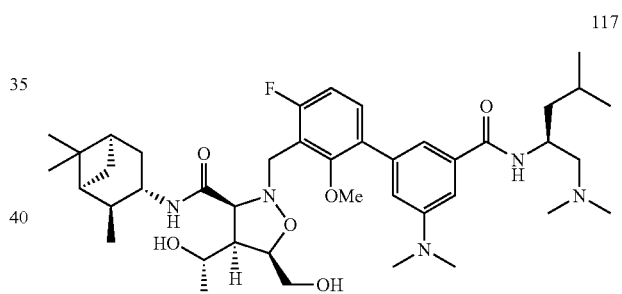

Part A

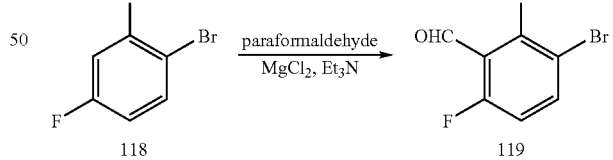

To a mixture of MgCl$_2$ (2.0 g, 20.9 mmol, 2 eq) and paraformaldehyde (0.943 g, 31.4 mmol, 3 eq) in THF (50 mL) under argon, was added triethylamine (2.92 mL, 20.9 mmol, 2 eq). The mixture was stirred at room temperature, under argon, for 10 min and phenol 118 (2.00 g, 10.5 mmol, 1 eq) was added. The reaction was heated to reflux for 2 h then allowed to cool to rt. Diethyl ether (100 mL) was added and the solution was washed with HCl 1 N (3×100 mL), dried over Na$_2$SO$_4$, filtered and concentrated to dryness to afford crude 119 (2.07 g) which was taken on without further purification. Yield 90%.

Part B

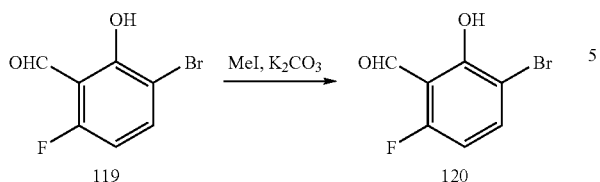

To a solution of crude phenol 119 (2.1 g, 9.5 mmol, 1 eq) in DMF (50 mL) at rt was added K$_2$CO$_3$ (1.88 g, 13.6 mmol, 1.4 eq) followed by MeI (0.848 mL, 13.6 mmol, 1.4 eq). The reaction mixture was stirred at 40° C. under argon for 5 h and then quenched with 6 N HCl (10 ml). The mixture was diluted with 1 N HCl (250 mL) and extracted with DCM (3×100 mL). Pooled organics were washed with water (3×100 mL) then brine (100 mL). The solution was dried over Na$_2$SO$_4$, filtered and concentrated to dryness. The residue was purified by flash chromatography (EtOAc in Hexane, gradient 0% to 20%) to afford 1.02 g of product 120. Yield 42%.

Part C

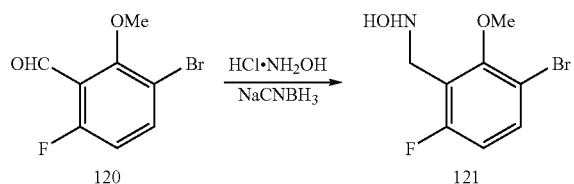

Aldehyde 120 (1.0 g, 4.37 mmol, 1 eq) and hydroxylamine hydrochloride (364 mg, 5.24 mmol, 1.2 eq) were dissolved in THF/MeOH/water (4:2:1, 13 mL). The solution was stirred at rt for 5 min then a crystal of methyl orange and sodium cyanoborohydride (550 mg, 8.74 mmol, 2 eq) were added. The pH was adjusted to 2 and the resulting ruby red color was maintained for the duration of the reaction by the regular addition of 6 N HCl. After stirring for 2 h another portion of sodium cyanoborohydride (380 mg, 6.07 mmol, 2 eq) was added. After stirring for 1 h, the mixture was filtered on paper, rinsing with THF. The filtrate was diluted with 1 N NaOH (100 mL) and extracted with DCM (3×50 mL). Pooled organics were washed with water (3×), brine and then dried over Na$_2$SO$_4$. The crude product was purified by flash chromatography (EtOAc in Hexane, gradient 0% to 70%) to afford 703 mg of hydroxylamine 121. Yield 64%.

Part D

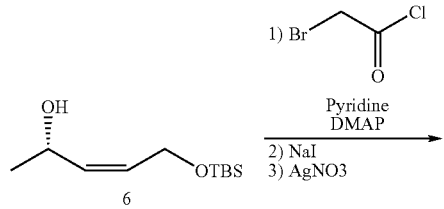

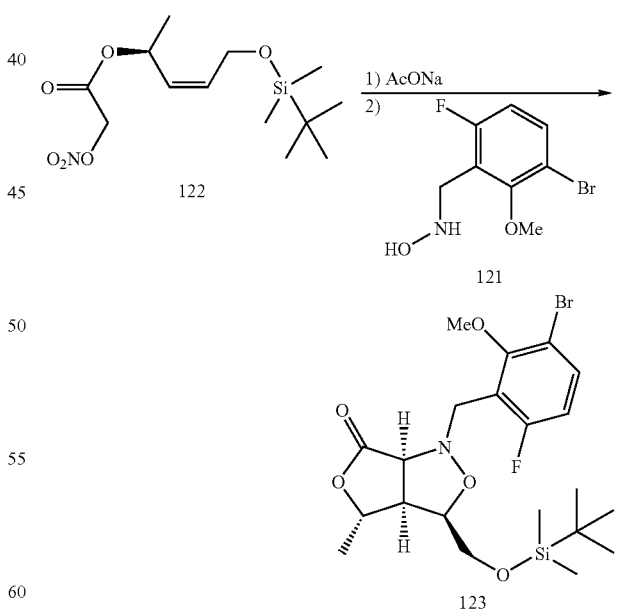

A solution of allylic alcohol 6 (5.0 g, 23 mmol, 1 eq), pyridine (3.75 mL, 46 mmol, 2 eq) and DMAP (281 mg, 2.3 μmol, 0.1 eq) in DCM (120 mL) was cooled in an ice/water bath and bromoacetyl chloride (2.47 mL, 29.9 mmol, 1.3 eq) was added. The solution was stirred at 0° C. for 30 min then allowed to reach rt. After 30 min, the reaction was successively washed with 1 N HCl (200 mL), water (100 mL), 5% NaHCO$_3$ (100 mL), brine (100 mL) with 10% Na$_2$SO$_3$ (100 mL) then brine (100 mL), dried over Na$_2$SO$_4$, filtered then concentrated in vacuo to an amber liquid.

This liquid was diluted with acetone (40 mL) and NaI (3.44 g, 23 mmol, 1 eq) was added. The mixture was stirred at rt for 6 h then diluted with EtOAc (100 mL), washed with water (1×) then 10% Na$_2$SO$_3$ (2×), dried over Na$_2$SO$_4$, filtered and concentrated in vacuo to an amber oil.

This oil was restored in acetonitrile (50 mL) and AgNO$_3$ (5.0 g, 29 mmol, 1.25 eq) was added. The reaction was stirred overnight at rt then partitioned between water (200 mL) and diethyl ether (150 mL). The aqueous layer was separated and washed once more with ether (100 mL). The combined organic layers were washed with brine (2×), dried over Na$_2$SO$_4$, filtered and concentrated in vacuo. The residue was purified by flash chromatography (EtOAc in Hexane, gradient from 0% to 10%) affording 122 (4.27 g) as a clear liquid. Yield 58%.

Part E

Nitrite 122 (800 mg, 2.50 mmol, 1.05 eq) was dissolved in DMSO (5 mL) and sodium acetate (308 mg, 3.75 mmol, 1.50 eq) was added. The solution was stirred at rt for 30 min then poured into brine (30 mL) and extracted with diethyl ether (3×30 mL). The combined organic layers were washed with saturated NaHCO₃ (1×), water (2×) and brine (1×), dried over Na₂SO₄, filtered and concentrated to dryness.

The product was then reacted overnight with hydroxylamine 121 (588 mg, 2.35 mmol, 1 eq) in refluxing toluene (20 mL). The solution was concentrated and the residue purified by flash chromatography (EtOAc in hexane, gradient 0% to 30%) to afford lactone 123 (923 mg). Yield 78%.

Part F

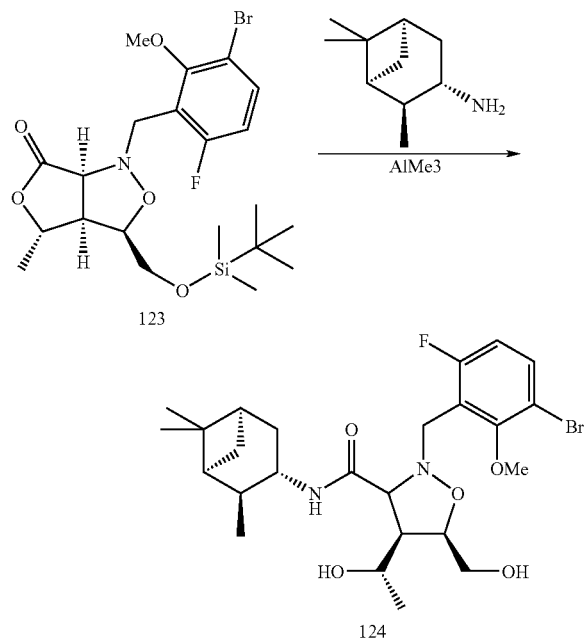

Lactone 123 (923 mg, 1.83 mmol, 1 eq) is dissolved in THF (8 mL) and HCl 6N (0.6 mL) is added. The solution is stirred at room temperature for 2 h then diluted with DCM (100 mL) and washed with 5% NaHCO₃ (3×) and brine (1×), dried over Na₂SO₄, filtered and concentrated to dryness.

To a solution of the residue in dry DCM (6 mL) was added a solution of (+)-isopinocampheylamine (614 μL, 3.66 mmol, 2 eq) previously treated in dry DCM (6 mL) with trimethylaluminum in hexanes (2.0 M, 1.83 mL, 3.66 mmol, 2 eq) for 15 min. The solution was stirred at rt overnight then diluted with dry DCM and quenched with Na₂SO₄·10H₂O (5.9 g 18.3 mmol, 10 eq). The mixture was stirred vigorously at rt for 5 h then filtered on Celite. The filtrate was concentrated to dryness and the residue purified by flash chromatography (EtOAc in Hexane, gradient 0% to 80%) to afford 994 mg of 124. Yield 71%.

Part G

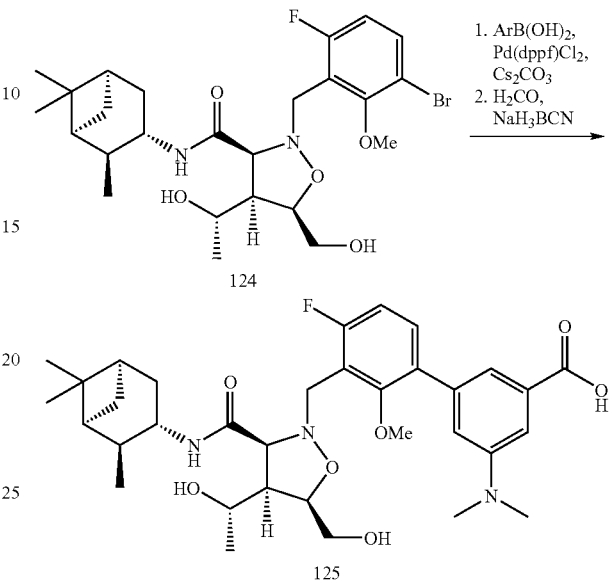

A flask containing bromide 122 (360 mg, 662 μmol, 1 eq), 3-amino-5-carboxyphenylboronic acid (240 mg, 1.32 mmol, 2 eq), cesium carbonate (383 mg, 1.99 mmol, 3 eq), potassium acetate (65 mg, 662 μmol, 1 eq) and Pd(dppf)Cl₂ (48 mg, 66 μmol, 0.1 eq) was purged with argon and DMSO (5 mL) was added. The reaction mixture was added to water (300 mL), acidified with 6M HCl until the aqueous layer attained a pH of 4, and extracted with DCM (3×100 mL). The combined organic layers were washed with water (1×100 mL) dried over Na₂SO₄ and concentrated to a brown oil.

This crude oil was dissolved in MeOH (10 mL) and treated with HOAc (38 μL, 662 μmol, 1 eq), 37% formalin (493 μL, 6.62 mol, 10 eq) and sodium cyanoborohydride (333 mg, 5.29 mmol, 8 eq). After stirring at rt for 40 min, the reaction mixture was partitioned between water (50 mL) and DCM (20 mL) and acidified with 6M HCl until the aqueous layer attained a pH of 4. The layers were separated and the aqueous extracted with DCM (3×20 mL). The combined organic layers were washed with water (1×), dried over Na₂SO₄, and concentrated to a brown oil. This oil was purified by silica gel flash chromatography (DCM/MeOH/AcOH 90:10:1 in DCM 0% to 100%) to give 119 mg 123 as a brown solid. Yield 29%.

Part H

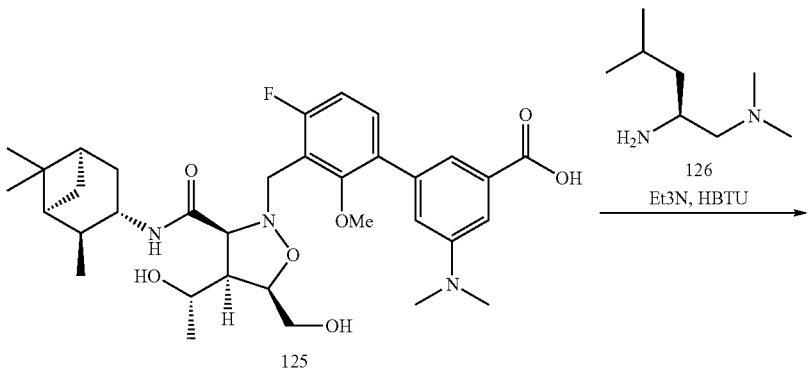

-continued

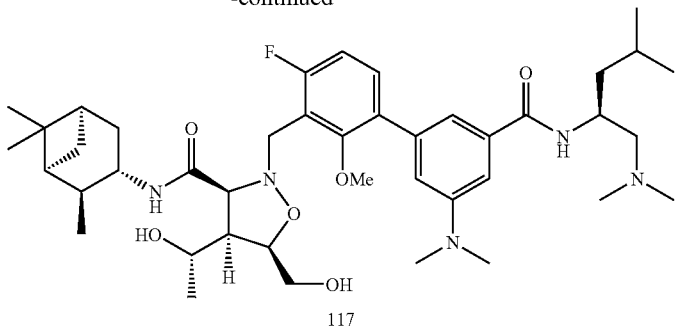
117

A solution of 123 (33 mg, 53 µmol, 1 eq) in DCM (1 mL) was treated with Et₃N (22 µL, 158 µmol, 3 eq), diamine 124 (11 mg, 79 µmol, 1.5 eq), and HBTU (30 mg, 79 µmol, 1.5 eq). After 3 h, the mixture was concentrated to dryness. The residue was purified by HPLC to afford 1 (6 mg) after lyophilization. Yield 15%. MS (ESI(+)) m/z 755.22 (M+H)⁺.

Example 62

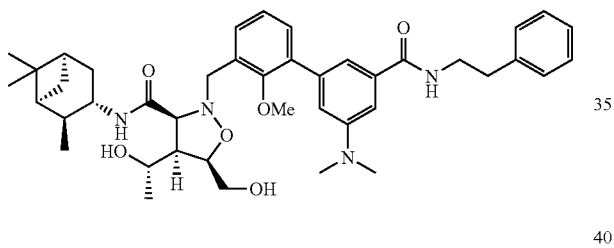
126

Prepared in an analogous fashion as described in Example 1 using 2-phenylethaneamine in place of (S)—N¹,N¹,4,4-tetramethylpentane-1,2-diamine. Yield 50%.

Example 63

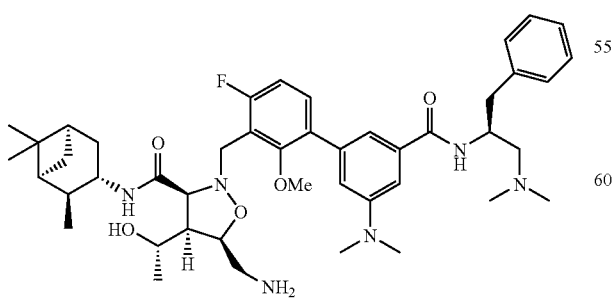
127

Part A

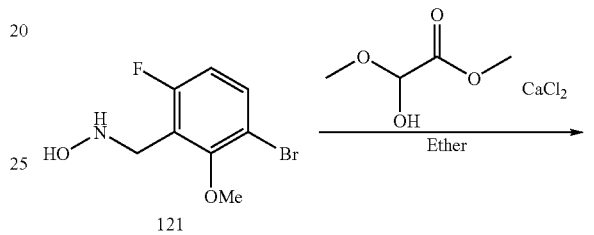
121

To a solution of hydroxylamine 121 (12.3 g, 49.2 mmol, 1 eq) in anhydrous diethyl ether (270 mL) was added the methyl ester (7.68 g, 63.9 mmol, 1.3 eq) and anhydrous calcium chloride (7.10 g, 63.9 mmol, 1.3 eq). The reaction mixture was stirred at room temperature for 3 hours and then filtered through a Celite plug. The filtrate was washed with DCM and diethyl ether. Pool organics was then concentrated to dryness to obtain crude 128 (15.75 g) which was taken on without further purification.

Part B.

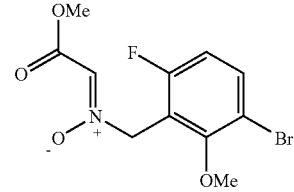
128

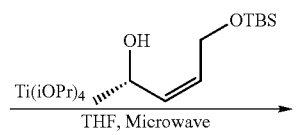
128

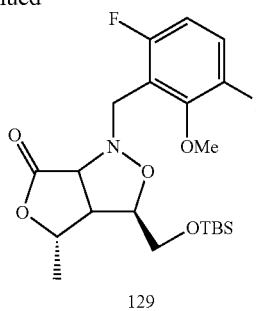

129

Nitrone 128 (15.75 g, 49.2 mmol, 1 eq), allylic alcohol (12.78 g, 59.0 mmol, 1.2 eq) and Ti(iOPr)$_4$ (21.62 mL, 73.8 mmol, 1.5 eq) were dissolved in anhydrous THF (100 mL) and heated in the microwave at 140° C. for 10 min The reaction mixture was diluted with EtOAc (30 mL) and 3-(dimethylamino)-1,2-propanediol (30 mL) was added. After stirring overnight, the mixture was washed with Rochelle's salt, water and brine. The mixture was then filtered over Celite and washed with EtOAc, water and then brine. The organic was dried over Na$_2$SO$_4$, and concentrated to dryness to obtain crude 129 (24.82 g) which was taken on without further purification.

Part C.

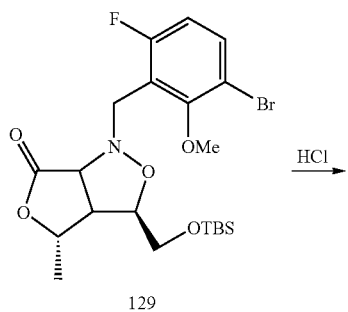

129

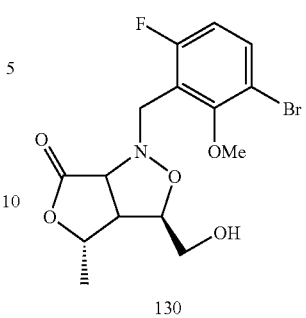

130

To a solution of lactone 129 (4.82 g, 49.2 mmol, 1 eq) in THF (270 mL) was added concentrated HCl (24.6 mL, 148 mmol, 3 eq) and stirred at room temperature for 1.5 hours. The reaction was then basified to pH 7 with saturated NaHCO$_3$ and extracted with EtOAc. Pool organics were washed with brine, dried over Na$_2$SO$_4$, filtered and concentrated to dryness. The crude product was purified by flash chromatography (EtOAc in Hexane, gradient 20% to 40%) to afford 130 (15.6 g). Yield 81%.

Part D.

130

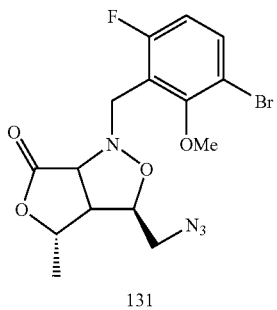

131

To a solution of lactone 130 (6.6 g, 16.91 mmol, 1 eq) in DCM (71 mL) was added Hunig's base (8.86 mL, 50.7 mmol, 3 eq) and trifluoromethanesulfonic anhydride (3.43 mL, 20.3 mmol, 1.2 eq) at 0° C. and stirred for 15 minutes. The reaction mixture was then warmed to room temperature and DMF (84 mL) and NaN$_3$ (3.3 g, 50.7 mmol, 3 eq) was added and stirred overnight at room temperature. The reaction mixture was washed with NaHCO$_3$ and brine, dried over Na$_2$SO$_4$, filtered and concentrated to dryness. The crude product was purified by flash chromatography (EtOAc in Hexane, gradient 30% to 50%) to obtain 131 (6.85 g). Yield 98%.

Part E.

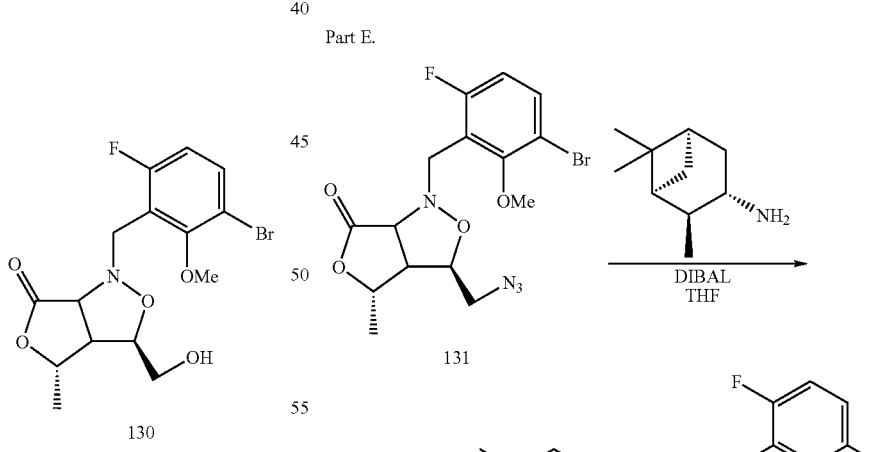

131

132

To a solution of (+)-isopinocampheylamine (1.22 mL, 7.23 mmol, 6 eq) in THF (10 mL) was added DIBAL (6.03 mL, 1 M in DCM, 6.02 mmol, 5 eq) and stirred for 30 minutes at 0° C. The mixture was then warmed to room temperature and allowed to stir for another 2 hours. A solution of lactone 131 (0.5 g, 1.2 mmol, 1 eq) in THF (5 mL) was added and the mixture was stirred for 30 minutes at room temperature. The reaction was diluted with EtOAc (35 mL) and quenched by the addition of saturated aqueous Rochelle salt (35 mL) and the mixture was rapidly stirred overnight. The mixture was extracted with diethyl ether and the pooled organics were washed with water and then brine, dried over $Na_2SO_4$, filtered and concentrated to dryness. The crude material was purified by flash chromatography (EtOAc in Hexane, gradient 10% to 30%) to afford 132 (0.42 g). Yield 61%.

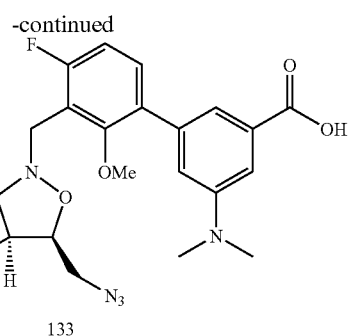

133

Part F.

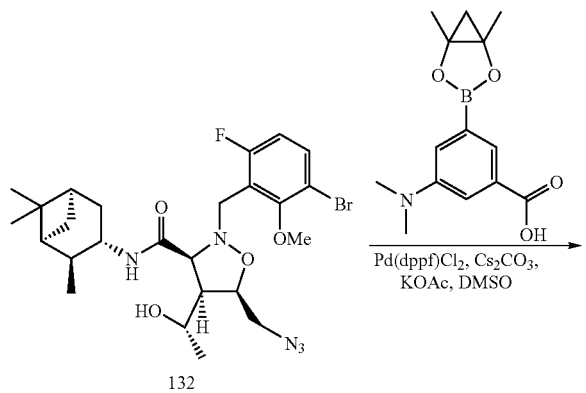

A flask containing aryl bromide 132 (470 mg, 0.83 mmol, 1 eq), 3-amino-5-carboxyphenylboronic acid (36.1 mg, 1.24 mmol, 1.5 eq), cesium carbonate (80.8 mg, 2.48 mmol, 3 eq), potassium acetate (122 mg, 1.24 mmol, 1.5 eq) and Pd(dppf)$Cl_2$ (121 mg, 0.17 mmol, 0.2 eq) was purged with argon and DMSO (10 mL) added. The mixture was heated at 70° C. for 3 hours. The reaction mixture was added to water (10 mL), acidified with 6 N HCl until the aqueous layer attained a pH of 4, and extracted with EtOAc (3×10 mL). The combined organic layers were washed with water, separated, dried over $Na_2SO_4$, filtered and concentrated to dryness. The crude material was purified by flash chromatography (EtOAc in Hexane, gradient 30% to 50%) to afford 133 (46 mg). Yield 8.5%.

Part J.

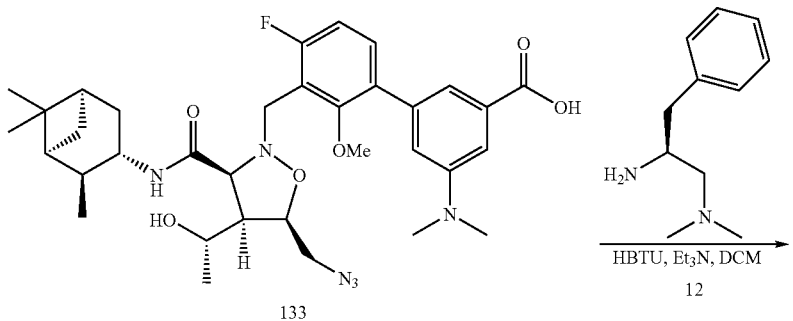

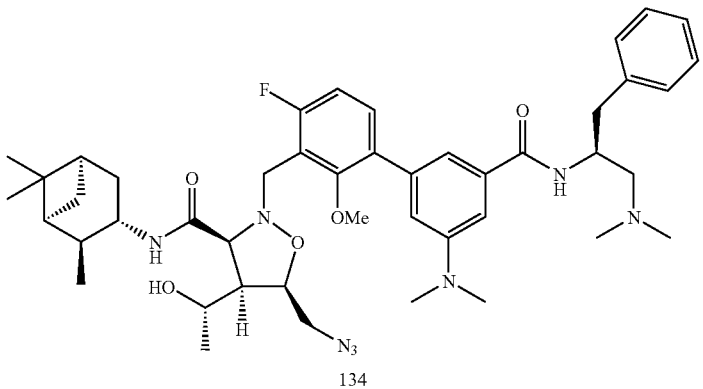

134

A solution of 133 (64.7 mg, 0.099 mmol, 1 eq) in DCM (5 mL) was treated with Et₃N (41.4 µL, 0.23 mmol, 3 eq), (S)—N1,N1-dimethyl-3-phenylpropane-1,2-diamine (26.5 mg, 0.149 mmol, 1.5 eq) and HBTU (75 mg, 0.198 mmol, 2 eq). After 2 hours, the mixture was diluted with DCM (15 mL), washed with saturated K₂CO₃ solution (15 mL) and extracted with DCM (2×15 mL). The combined organic layers were dried over Na₂SO₄, filtered and concentrated to dryness. The crude material was purified by flash chromatography (MeOH in DCM, gradient 1% to 5%) to afford 134 (43 mg). Yield 53%.

Part K.

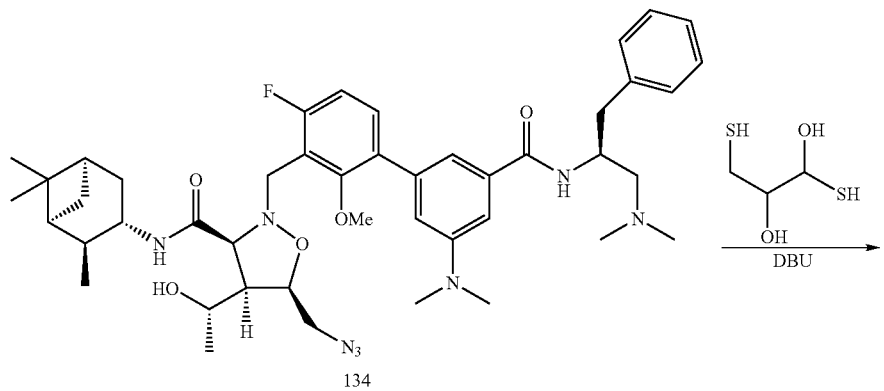

134

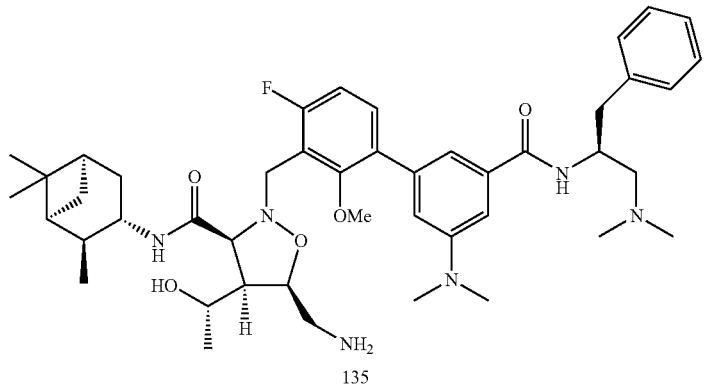

135

A solution of 134 (43 mg, 0.053 mmol, 1 eq) in DMF (4 mL) was treated with dithiothreitol (24.5 mg, 0.159 mmol, 3 eq) and DBU (23.9 µL, 0.159 mmol, 3 eq) and stirred at 0° C. After 15 minutes, the mixture was purified by HPLC to afford 135 (4.1 mg) after lyophilization. Yield 12.7%. MS (ESI(+)) m/e 788.13 (M+H)⁺.

Example 64

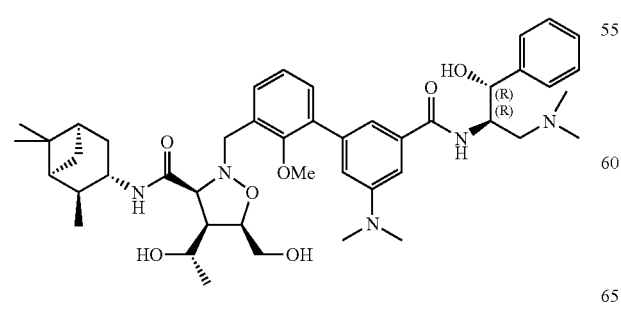

136

Part A.

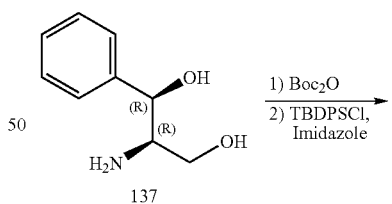

137

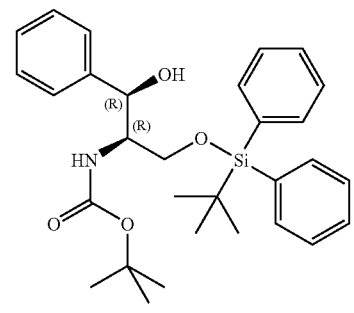

138

Aminodiol 137 (5.0 g, 29.9 mmol, 1 eq) was dissolved in MeOH (30 mL) at 0° C. and diterbutyl dicarbonate (7.18 g, 32.9 mmol, 1.1 eq) was added. The solution was stirred at 0° C. for 2 h then concentrated to dryness.

The residue was taken in DMF (120 mL) and imidazole (4.48 g, 65.8 mmol, 2.2 eq) was added. The solution was cooled in an ice/water bath and ter-butyldiphenylsilyl chloride (9.86 g, 32.9 mmol, 1.2 eq) was added as a solution in DMF (20 mL). The solution was stirred at rt for 18 h then at 60° C. for 2 h. The reaction was poured on saturated NaHCO$_3$ (300 mL) and the solution extracted with EtOAc (3×100 mL). The combined organics were dried over Na$_2$SO$_4$, filtered, concentrated. The residue was purified by flash chromatography (Hex/EtOAc 0% to 20%) to afford 138 as a colorless oil (6.15 g, 12.1 mmol). Yield 41%.

Part B.

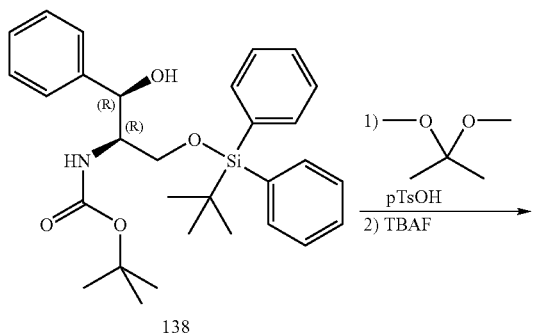

138

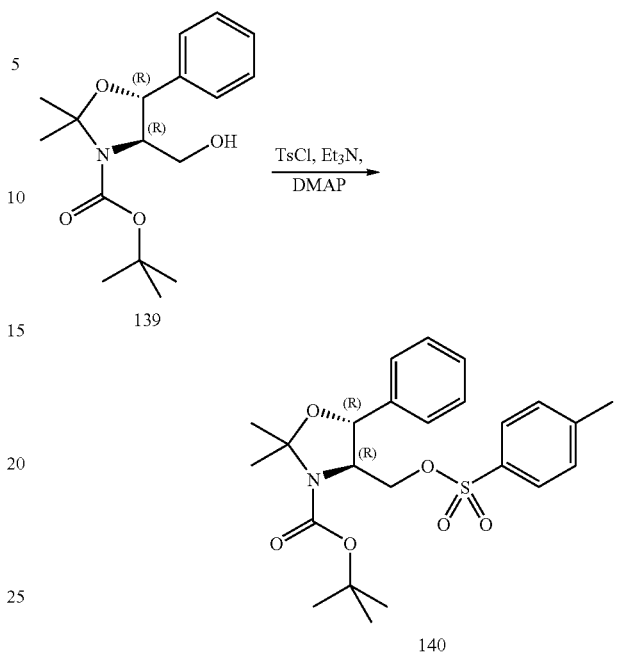

139

Compound 138 (6.1 g, 12 mmol, 1 eq) was refluxed with 2,2-dimethoxypropane (2.96 mL, 24.1 mmol, 2 eq) in toluene (60 mL) using paratoluenesulfonic acid monohydrate (23 mg, 0.12 mmol, 0.1 eq) as a catalyst. After 30 min, the reaction was allowed to cool to rt then washed with 5% NaHCO$_3$ (3×20 mL) and brine (1×20 L), dried over Na$_2$SO$_4$, filtered and concentrated to dryness.

The crude was dissolved in THF (60 mL) and a 1.0M solution of ter-butylammonium fluoride was added (60 mL, 60 mmol, 5 eq). The solution was stirred at 60° C. for 2 h then its volume was reduced on a rotary evaporator. The residue was partitioned between water (100 mL) and CHCl$_3$ (60 mL). The layers were separated and the aqueous extracted with CHCl$_3$ (2×60 mL). The combined organics were washed with brine (1×60 mL), dried over Na$_2$SO$_4$, filtered and concentrated. The residue was purified by flash chromatography (Hex/EtOAc 0% to 40%) to afford 139 (3.13 g, 10.2 mmol) as a colorless oil. Yield 84%.

Part C.

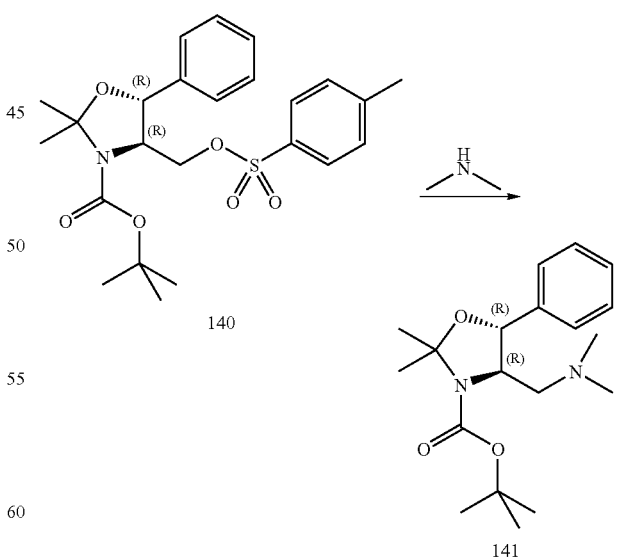

Alcohol 139 (3.13 g, 10.2 mmol, 1 eq) and tosyl chloride (2.13 g, 11.2 mmol, 1.1 eq) are dissolved in DCM (20 mL) then triethylamine (2.84 mL, 20.3 mmol, 2 eq) and catalytic DMAP (124 mg, 1 mmol, 01 eq) were added. The orange solution was stirred at rt for 3 h then diluted with DCM (60 mL), washed with HCl 1 N (3×30 mL) and brine (1×30 mL), dried over Na$_2$SO$_4$, filtered, concentrated. The residue was purified by flash chromatography (Hex/EtOAc 0% to 30%) to afford 140 (4.08 g, 8.8 mmol) as a white solid. Yield 87%.

Part D.

In a sealed reactor, tosylate 140 (4.08 g, 8.8 mmol, 1 eq) was heated at 60° C. in a 1.0M solution of dimethylamine in THF (88 mL, 177 mmol, 20 eq). After 44 h, the solution was concentrated and the residue purified by flash chromatography (DCM and DCM/MeOH/NH₄OH 80:20:0.5 0% to 50%) to afford 141 (2.46 g, 7.36 mmol) as a clear oil. Yield 83%.

Part E.

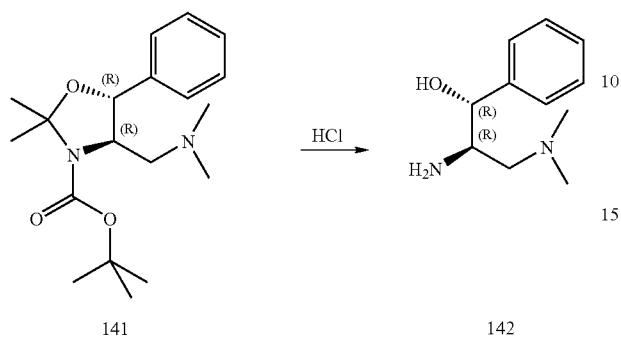

Compound 141 (487 mg, 1.45 mmol, 1 eq) was treated with a 4.0M solution of HCl in dioxane (5 mL) and water (100 μL) at rt for 1 h30. The solution was then concentrated and dried under high vacuum to obtain the hydrochloric salt of 142 (339 mg, 1.45 mmol) as an off-white foam in a quantitative yield.

Acid 10 (30 mg, 49 μmol, 1 eq), amine 142 (14 mg, 59 μmol, 1.2 eq) and HBTU (22 mg, 59 μmol, 1.2 eq) were dispersed in DCM (1 mL) and triethylamine (41 μL, 295 μmol, 6 eq) was added. The reaction was stirred at rt for 30 min then concentrated to dryness. The residue was purified by HPLC to afford 136 (13 mg, 16 μmol) as a lyophilized powder. Yield 33%. MS (ESI(+)) m/e 786.27 (M+H)⁺.

Example 65

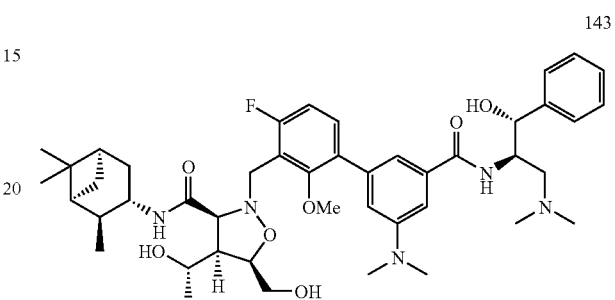

Part F.

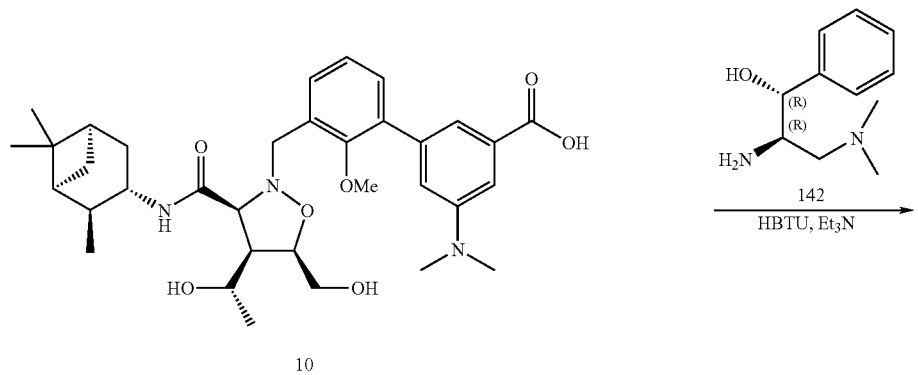

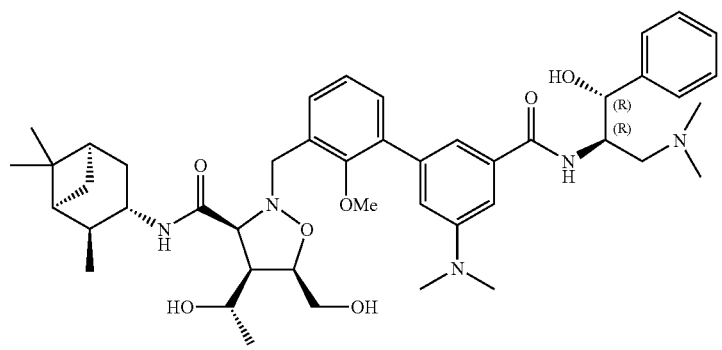

Part A.

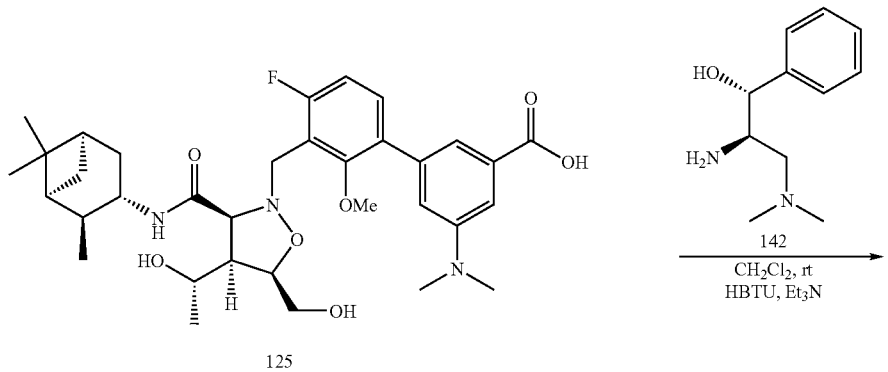

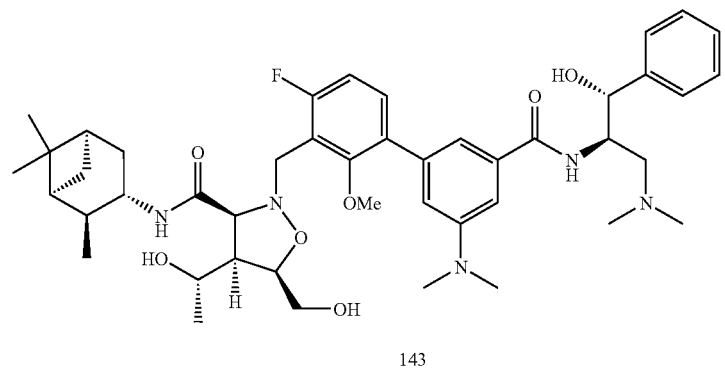

To a stirred solution of acid 125 (150 mg, 0.24 mmol, 1.0 equiv) in CH$_2$Cl$_2$ (3 mL, 0.08M) was added triethylamine (100 μL, 0.717 mmol, 3.0 equiv) followed by benzyl alcohol 142 (45 mg, 0.24 mmol, 1.0 equiv) and HBTU (100 mg, 0.26 mmol, 1.1 equiv.). After 14 hours, the reaction mixture was diluted with CH$_2$Cl$_2$, washed with water, dried with sodium sulfate, and concentrated in vacuo. The resulting oil was purified by HPLC (acidic method) to afford 143 as a brown oil (9.2 mg, 5% yield). LCMS (ESI(+)) m/e 804 (M+H)$^+$.

Example 66

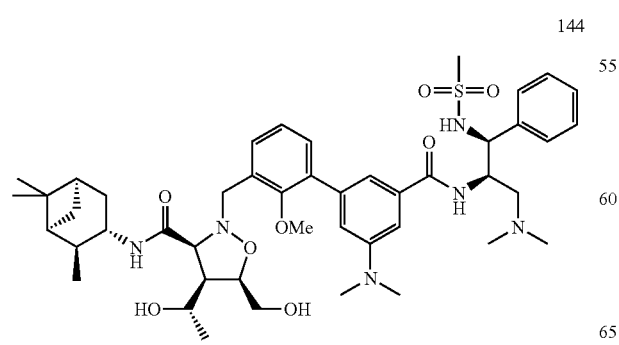

144

Part A.

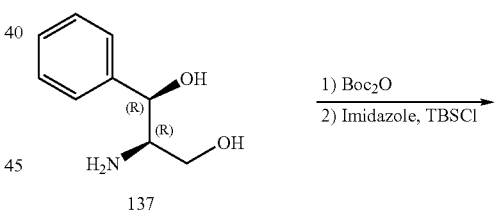

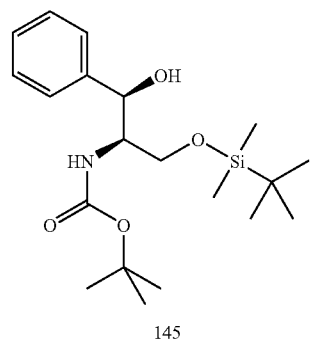

145

Aminodiol 137 (4.0 g, 23.9 mmol, 1 eq) was dissolved in MeOH (50 mL) at 0° C. and diterbutyl dicarbonate (6.27 g, 28.7 mmol, 1.2 eq) was added. The solution was stirred at 0° C. for 2 h then concentrated to dryness.

The residue was taken in DMF/DMSO 2:1 (60 mL) and imidazole (3.26 g, 47.8 mmol, 2 eq) then ter-butyldimethylsilyl chloride (4.33 g, 28.7 mmol, 1.2 eq) were added. The solution was stirred at rt overnight. After 16 h, some more imidazole (3.26 g, 47.8 mmol, 2 eq) then ter-butyldimethylsilyl chloride (4.33 g, 28.7 mmol, 1.2 eq) were added. After 3 h, the reaction was poured on saturated $NaHCO_3$ (200 mL) and the solution extracted with EtOAc (3×100 mL). The combined organics were dried over $Na_2SO_4$, filtered, concentrated. The residue was purified by flash chromatography (Hex/EtOAc 0% to 20%) to afford 145 as a clear oil (7.91 g, 20.7 mmol). Yield 87%.

Part B.

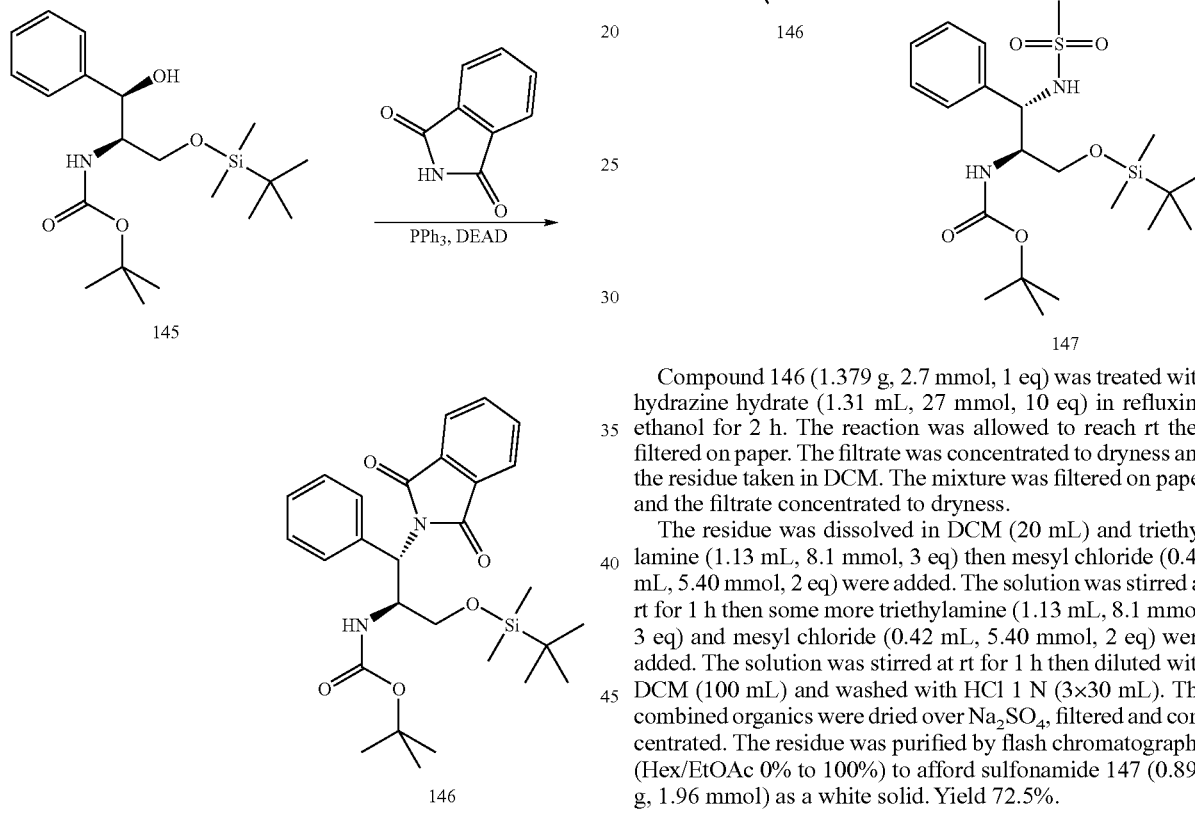

145

Alcohol 145 (2.08 g, 5.45 mmol, 1 eq), phthalimide (0.96 g, 6.54 mmol, 1.2 eq) and triphenylphosphine (1.71 g, 6.54 mmol, 1.2 eq) were dissolved in dry THF (20 mL) under Ar and diethylazodicarboxylate (1.04 mL, 6.54 mmol, 1.2 eq) was added dropwise. The reaction was stirred for 2 h then a solution of triphenylphosphine (340 mg, 1.3 mmol, 0.2 eq) in THF (3 mL) then diethylazodicarboxylate (0.20 mL, 1.3 mmol, 0.2 eq) were added. The solution was stirred at rt for 1 h then concentrated to dryness. The residue was purified by flash chromatography (Hex/EtOAc 0% to 25%) to afford 146 (1.38 g, 5.45 mmol). Yield 49%.

Part C.

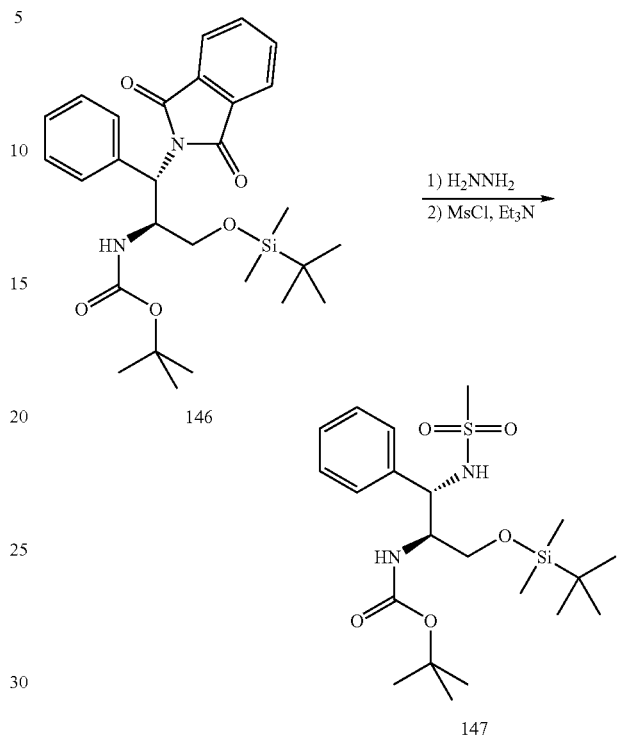

146

147

Compound 146 (1.379 g, 2.7 mmol, 1 eq) was treated with hydrazine hydrate (1.31 mL, 27 mmol, 10 eq) in refluxing ethanol for 2 h. The reaction was allowed to reach rt then filtered on paper. The filtrate was concentrated to dryness and the residue taken in DCM. The mixture was filtered on paper and the filtrate concentrated to dryness.

The residue was dissolved in DCM (20 mL) and triethylamine (1.13 mL, 8.1 mmol, 3 eq) then mesyl chloride (0.42 mL, 5.40 mmol, 2 eq) were added. The solution was stirred at rt for 1 h then some more triethylamine (1.13 mL, 8.1 mmol, 3 eq) and mesyl chloride (0.42 mL, 5.40 mmol, 2 eq) were added. The solution was stirred at rt for 1 h then diluted with DCM (100 mL) and washed with HCl 1 N (3×30 mL). The combined organics were dried over $Na_2SO_4$, filtered and concentrated. The residue was purified by flash chromatography (Hex/EtOAc 0% to 100%) to afford sulfonamide 147 (0.898 g, 1.96 mmol) as a white solid. Yield 72.5%.

Part D.

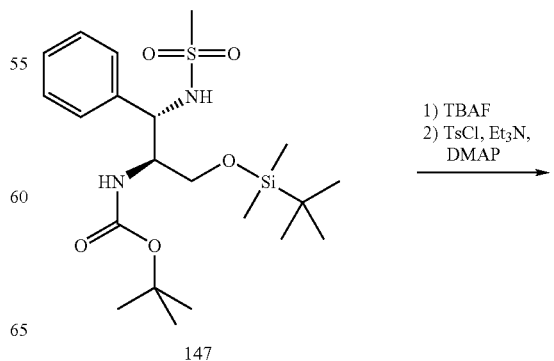

147

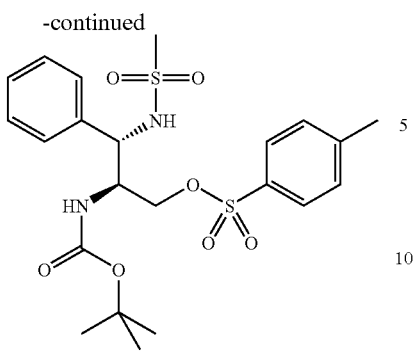

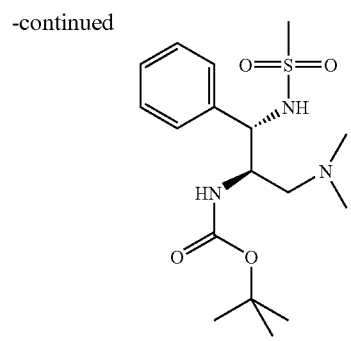

Compound 147 (0.898 g, 1.96 mmol, 1 eq) was dissolved in dry THF (20 mL) and a 11.0M solution of terbutylammonium fluoride was added (3.9 mL, 3.9 mmol, 2 eq). The solution was stirred at rt for 2 h then its volume was reduced on a rotary evaporator. The residue was partitioned between water (60 mL) and CHCl$_3$ (30 mL). The layers were separated and the aqueous extracted with CHCl$_3$ (2×30 mL). The combined organics were washed with brine (1×30 mL), dried over Na$_2$SO$_4$, filtered and concentrated.

The residue was taken in DCM (10 mL) then tosyl chloride (448 mg, 2.35 mmol, 1.2 eq), triethylamine (545 μL, 3.9 mmol, 2 eq) and catalytic DMAP (24 mg, 196 μmol, 0.1 eq) were added. The solution was stirred at rt for 4 h then diluted with DCM (60 mL), washed with HCl 1 N (3×20 mL) and brine (1×20 mL), dried over Na$_2$SO$_4$, filtered, concentrated. The residue was purified by flash chromatography (Hex/EtOAc 0% to 30%) to afford 148 (713 mg, 1.43 mmol) as a white solid. Yield 73%.

Part E.

In a sealed reactor, tosylate 148 (713 mg, 1.43 mmol, 1 eq) was heated at 60° C. in a 1.0M solution of dimethylamine in THF (28 mL, 57.2 mmol, 40 eq). After 16 h, the solution was concentrated and the residue purified by flash chromatography (DCM and DCM/MeOH/NH$_4$OH 80:20:0.5 0% to 80%) to afford 149 (416 mg, 1.12 mmol) as a clear oil. Yield 78%.

Part F.

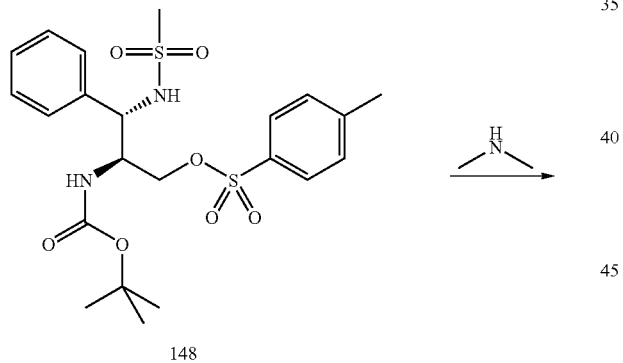

Part G.

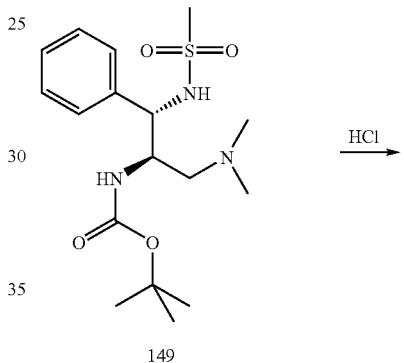

Compound 149 (385 mg, 1.04 mmol, 1 eq) was treated with a 4.0M solution of HCl in dioxane (10 mL) at rt for 1. The turbid solution was then concentrated and dried under high vacuum to obtain the hydrochloric salt of 150 (319 mg, 1.04 mmol) as white solid in a quantitative yield.

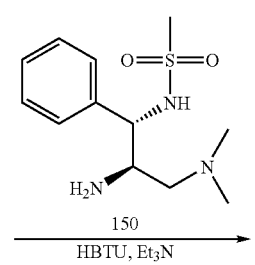

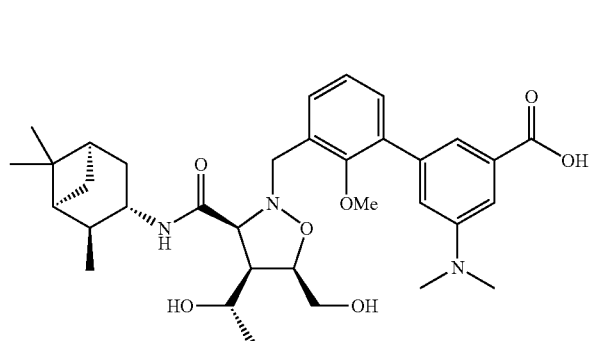

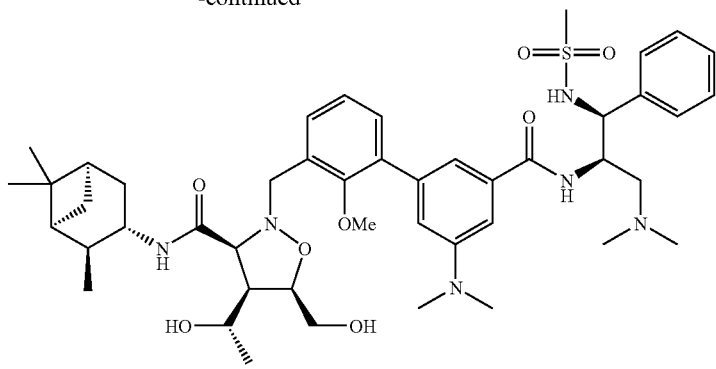
144
Acid 10 (30 mg, 49 μmol, 1 eq), amine 150 (17 mg, 54 μmol, 1.1 eq) and HBTU (21 mg, 54 μmol, 1.1 eq) were dispersed in DCM (1 mL) and triethylamine (41 μL, 295 μmol, 6 eq) was added. The reaction was stirred at rt for 30 min then concentrated to dryness. The residue was purified by HPLC to afford 144 (11.8 mg, 13.6 μmol) as a lyophilized powder. Yield 27.8%. MS (ESI(+)) m/e 863.25 (M+H)$^+$.
Example 67
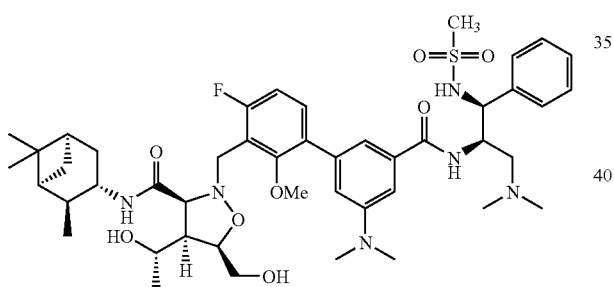
151
Part A.
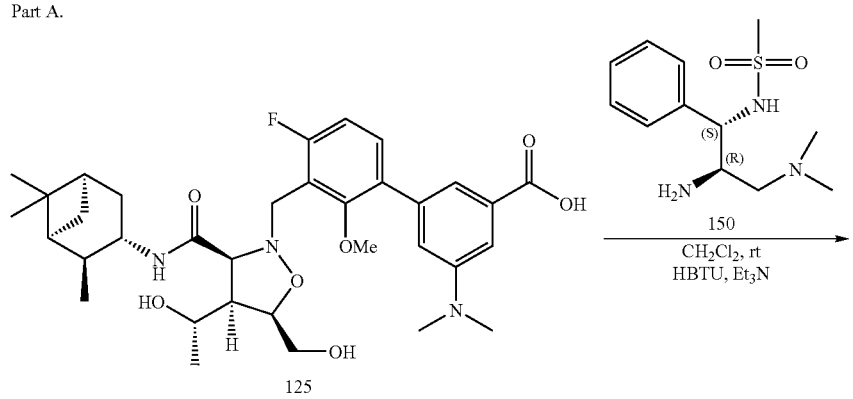

-continued

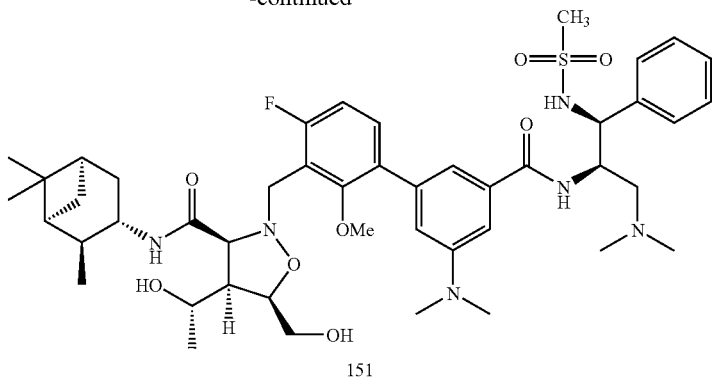

151

To a stirred solution of acid 125 (59 mg, 0.094 mmol, 1.0 equiv.) in CH$_2$Cl$_2$ (3 mL, 0.03M) was added triethylamine (40 µL, 0.282 mmol, 3.0 equiv.) followed by benzyl sulfonamide 150 (28 mg, 0.103 mmol, 1.1 equiv.) and HBTU (43 mg, 0.113 mmol, 1.2 equiv.). After five minutes, the reaction mixture was diluted with CH$_2$Cl$_2$, washed with water, dried with sodium sulfate, and concentrated in vacuo. The resulting oil was purified by HPLC (basic method) to afford 151 as a brown oil (15.7 mg, 19% yield). LCMS (ESI(+)) m/e 881 (M+H)$^+$.

xample 68

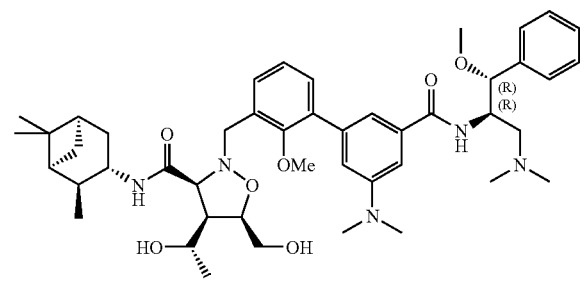

152

Part A.

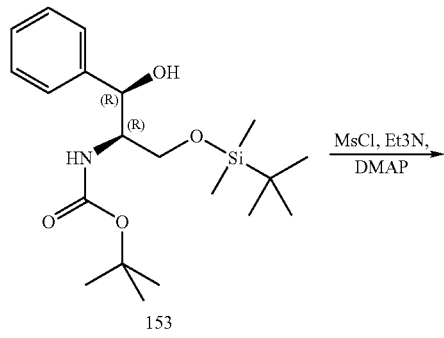

153

-continued

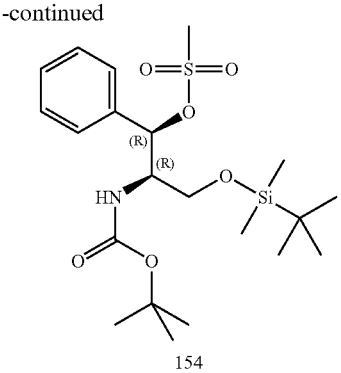

154

Compound 153 (2.95 g, 7.72 mmol, 1 eq) was dissolved in DCM (30 mL) and triethylamine (1.18 mL, 8.49 mmol, 1.1 eq) and DMAP (47 mg, 0.38 mmol, 0.05 eq) were added. The solution was cooled in an ice/water bath and mesyl chloride (0.60 mL, 7.72 mmol, 1 eq) was added. The solution was stirred at rt for 3 h then triethylamine (1.18 mL, 8.49 mmol, 1.1 eq) and mesyl chloride (0.60 mL, 7.72 mmol, 1 eq) were added. The solution was stirred for 30 min, then partitioned between water (30 mL) and DCM (90 mL). The layers were separated then the organics were washed with HCl 1 N (3×20 mL), dried over Na$_2$SO$_4$, filtered, concentrated. The residue was purified by flash chromatography (Hex/EtOAc 0% to 25%) to afford 154 (3.16 g, 6.87 mmol) as an oil. Yield 89%.

Part B.

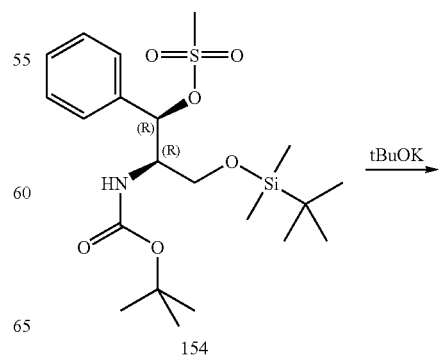

154

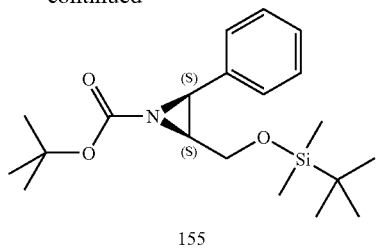

155

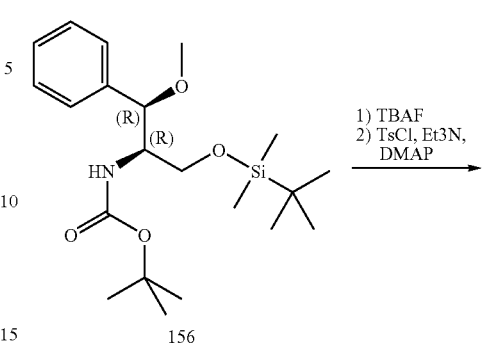

156

Mesylate 154 (2.619 g, 5.70 mmol, 1 eq) was dissolved in dry THF (40 mL) under Ar and potassium tertbutoxide (0.655 g, 5.84 mmol, 1.025 eq) was added dropwise as a solution in dry THF (20 mL). The reaction was stirred at rt for 3 h then quenched with water (60 mL) and extracted with EtOAc (3×40 mL). The pooled organics were washed with brine (1×30 mL), dried over Na$_2$SO$_4$, filtered and concentrated. The residue was purified by flash chromatography to obtain aziridine 155 (1.96 g, 5.41 mmol) as a white wax. Yield 95%.

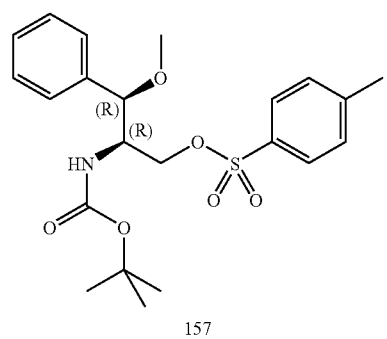

157

Part C.

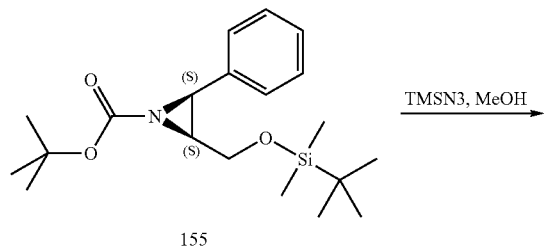

155

Compound 156 (1.646 g, 4.16 mmol, eq) was dissolved in dry THF (20 mL) and a 1.0M solution of terbutylammonium fluoride was added (8.3 mL, 8.32 mmol, 2 eq). The solution was stirred at rt for 2 h then its volume was reduced on a rotary evaporator. The residue was partitioned between water (60 mL) and CHCl$_3$ (30 mL). The layers were separated and the aqueous extracted with CHCl$_3$ (2×30 mL). The combined organics were washed with brine (1×30 mL), dried over Na$_2$SO$_4$, filtered and concentrated.

The residue was taken in DCM (10 mL) then tosyl chloride (952 mg, 4.99 mmol, 1.2 eq), triethylamine (1.16 mL, 8.32 mmol, 2 eq) and catalytic DMAP (51 mg, 416 μmol, 01 eq) were added. The solution was stirred at rt for 4 h then diluted with DCM (60 mL), washed with HCl 1 N (3×20 mL) and brine (1×20 mL), dried over Na$_2$SO$_4$, filtered, concentrated. The residue was purified by flash chromatography (Hex/EtOAc 0% to 30%) to afford 157 (886 mg, 2.0 mmol) as a white solid. Yield 49%.

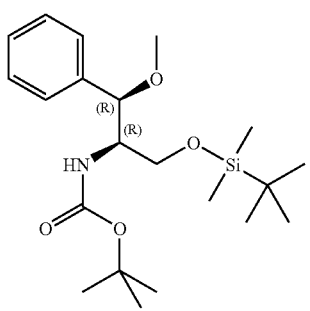

156

Part E.

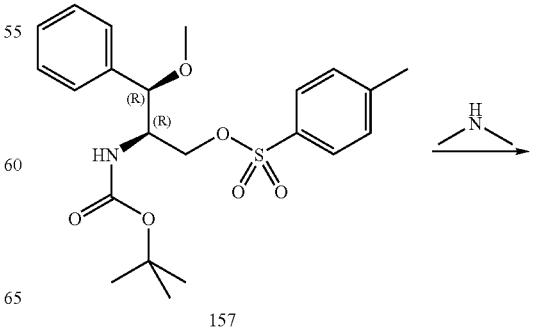

157

In a sealed reactor behind a glass shield, a solution of aziridine 155 (1.87 g, 5.14 mmol, 1 eq) and trimethylsilylazide (2 mL, 20.5 mmol, 4 eq) in methanol (40 mL) was heated at 70° C. for 5 h. The solution was allowed to cool to rt then concentrated. The residue was purified by flash chromatography (Hex/EtOAc 0% to 15%) to afford adduct 156 (1.72 g, 4.36 mmol). Yield 85%

-continued

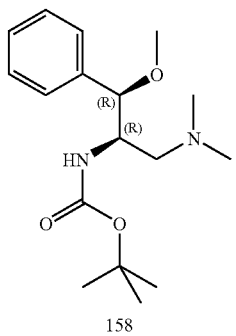

158

Part F.

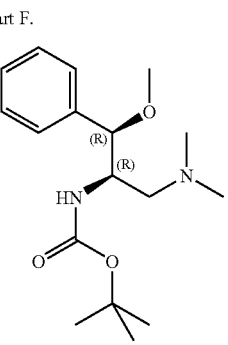

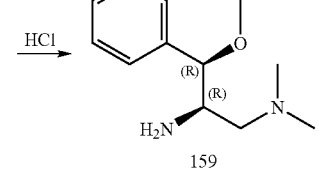

In a sealed reactor, tosylate 157 (800 mg, 1.84 mmol, 1 eq) was heated at 60° C. in a 1.0M solution of dimethylamine in THF (37 mL, 37 mmol, 20 eq). After 16 h, the solution was concentrated and the residue purified by flash chromatography (DCM and DCM/MeOH/NH$_4$OH 80:20:0.5 0% to 80%) to afford 158 (352 mg, 1.14 mmol) as a clear oil. Yield 62%.

Compound 158 (300 mg, 0.97 mmol, 1 eq) was treated with a 4.0M solution of HCl in dioxane (10 mL) at rt for 1. The turbid solution was then concentrated and dried under high vacuum to obtain the hydrochloric salt of 159 (238 mg, 0.97 mmol) as white solid in a quantitative yield.

Part G.

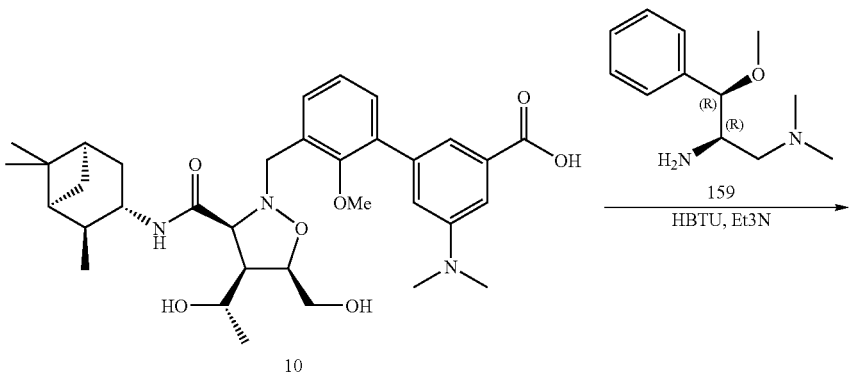

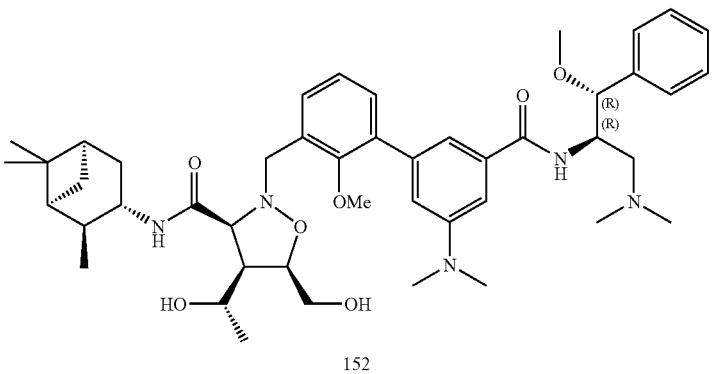

152

Acid 10 (40 mg, 66 μmol, 1 eq), amine 159 (18 mg, 720 μmol, 1.1 eq) and HBTU (27 mg, 72 μmol, 1.1 eq) were dispersed DCM (1 mL) and triethylamine (27 μL, 197 μmol, 3 eq) was added. The reaction was stirred at rt for 30 min then concentrated to dryness. The residue was purified by HPLC to afford 152 (18 mg, 23 μmol) as a lyophilized powder. Yield 34%. MS (ESI(+)) m/e 800.34 (M+H)+.

Example 69

160

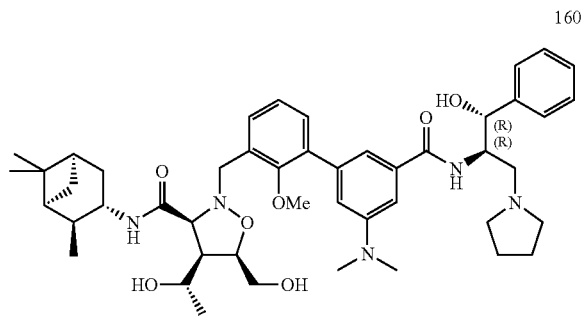

Part A.

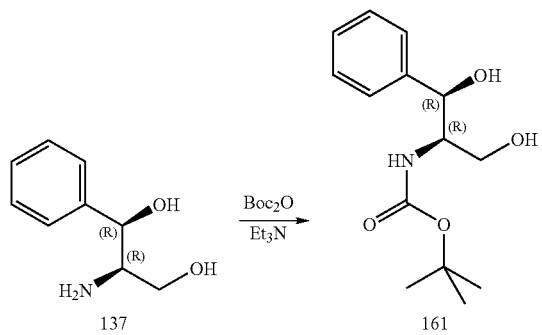

Aminodiol 137 (1-0 g, 5.98 mmol, 1 eq) was dissolved in DCM (50 mL) and diterbutyl dicarbonate (1.28 g, 5.86 mmol, 0.98 eq) then triethylamine (1.17 mL, 12 mmol, 2 eq) were added. The reaction was stirred at rt. After 1 h, the solution was diluted with DCM (50 mL), washed with HCl 1 N (3×20 mL) and brine (1×20 mL), dried over Na2SO4, filtered and concentrated to dryness to afford 161 (1.35 g, 5.05 mmol) which was used without further purification. Yield 84%.

Part B.

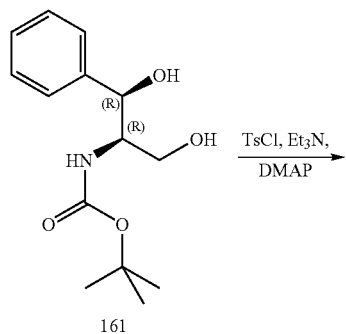

-continued

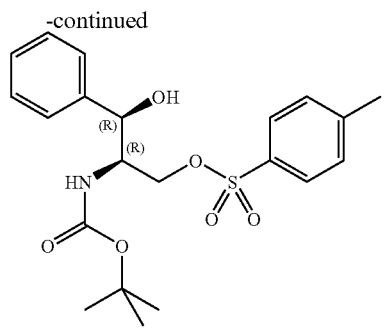

Compound 162 (1.13 g, 4.2 mmol, 1 eq) was dissolved in DCM (20 mL) then tosyl chloride (0.97 g, 5.1 mmol, 1.2 eq), triethylamine (1.2 mL, 8.5 mmol, 2 eq) and catalytic DMAP (100 mg, 0.85 mol, 0.2 eq) were added. The solution was stirred at rt for 4 h then diluted with DCM (60 mL), washed with HCl 1 N (3×20 mL) and brine (1×20 mL), dried over Na2SO4, filtered, concentrated. The residue was purified by flash chromatography (Hex/EtOAc 0% to 60%) to afford 162 (0.84 g, 2.0 mmol) as a white solid. Yield 47%.

Part C.

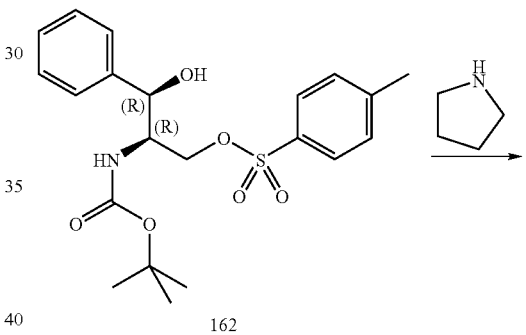

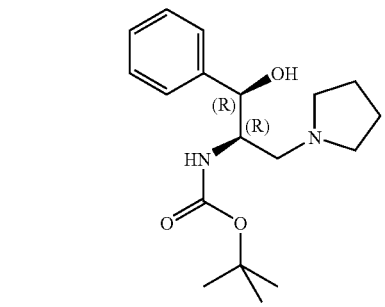

Tosylate 162 (0.88 g, 2.09 mmol, 1 eq) was dissolved in DMF (30 mL) and pyrrolidine (350 μL, 4.17 mmol, 2 eq) was added. The solution was stirred at 60° C. overnight. After 16 h, the reaction was allowed to cool to rt, diluted with water (90 mL) and extracted with EtOAc (3×30 mL). The combined organics were washed with brine, dried over Na2SO4, filtered, concentrated. The residue was purified by flash chromatography (DCM and DCM/MeOH/NH4OH 80:20:0.5 0% to 80%) to afford 163 (224 mg, 699 μmol) as an oil. Yield 33%.

Part D.

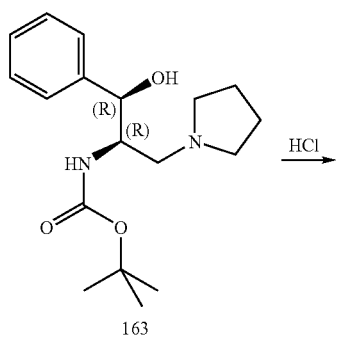

→ HCl

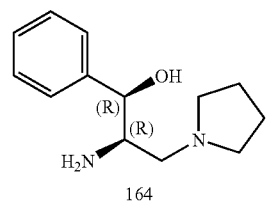

Compound 163 (224 mg, 699 μmol, 1 eq) was treated with a 4.0M solution of HCl in dioxane (10 mL) at rt for 1. The turbid solution was then concentrated and dried under high vacuum to obtain the hydrochloric salt of 164 (154 mg, 699 μmol) as white solid in a quantitative yield.

Part E.

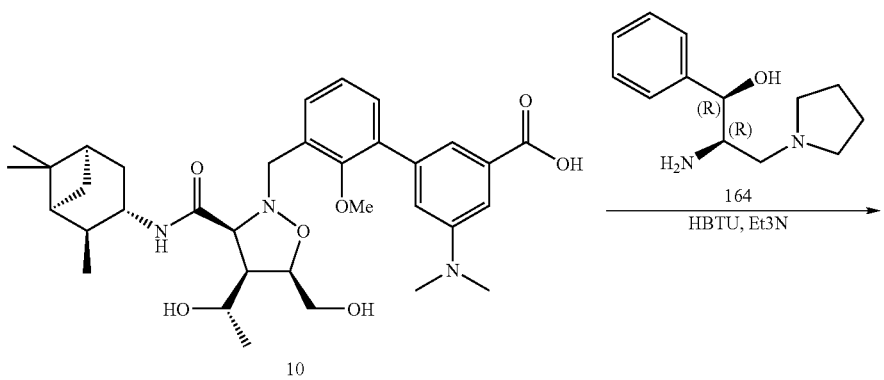

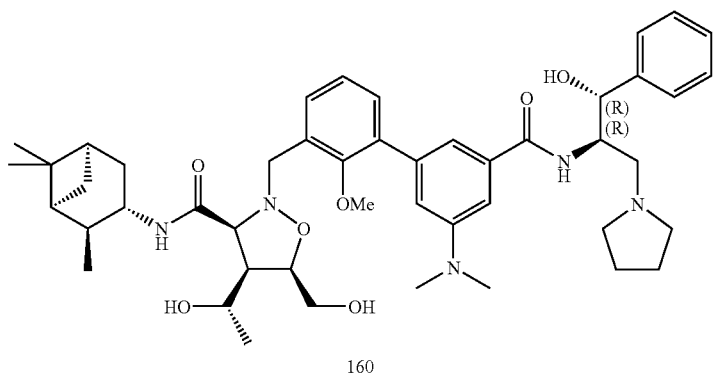

Acid 10 (100 mg, 164 μmol, 1 eq), amine 164 (44 mg, 197 μmol, 1.2 eq) and HBTU (75 mg, 197 μmol, 1.2 eq) were dispersed in DCM (1 mL) and triethylamine (69 μL, 492 μmol, 3 eq) was added. The reaction was stirred at rt for 30 min then concentrated to dryness. The residue was purified by HPLC to afford 160 (9.1 mg, 11 μmol) as a lyophilized powder. Yield 6.8%. MS (ESI(+)) m/e 812.56 (M+H)$^+$.

Example 70

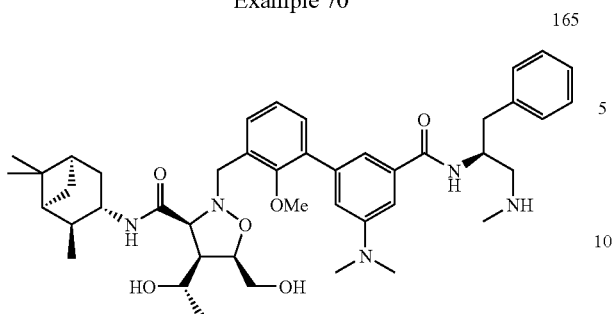

165

Part A.

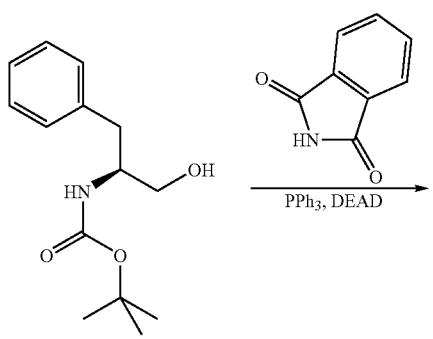

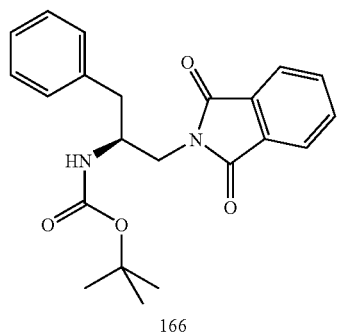

166

Boc-(S)-phenylaminol (2.01 g, 8.24 mmol, 1 eq), phthalimide (1.45 g, 9.88 mmol, 1.2 eq) and triphenylphosphine (3.24 g, 12.4 mmol, 1.5 eq) were dissolved in dry THF (20 mL) under Ar. Diisopropylazodicarboxylate (2.43 mL, 12.4 mmol, 1.5 eq) was added dropwise and the reaction stirred at rt. After 2 h, the solution was concentrate to dryness and the residue purified by flash chromatography (Hex/EtOAc 15% to 25%) to afford 166 (1.63 g, 4.28 mmol). Yield 52%.

Part B.

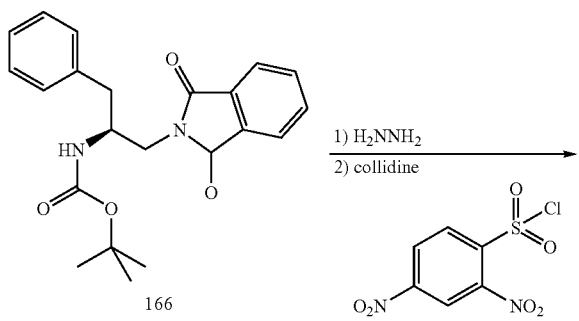

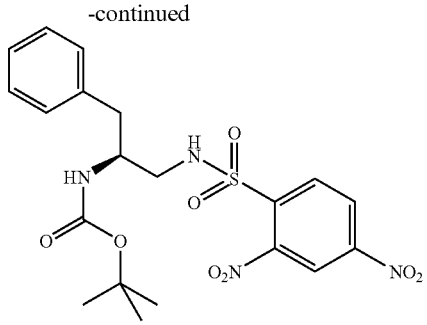

167

Compound 166 (3.46 g, 9.09 mmol, 1 eq) was treated with hydrazine hydrate (2.25 mL, 45.5 mmol, 5 eq) in refluxing ethanol for 2 h. The reaction was allowed to reach rt then filtered on paper. The filtrate was concentrated to dryness and the residue taken in DCM. The mixture was filtered on paper and the filtrate concentrated to dryness.

The residue was taken in DCM (20 mL) and 2,4,6-collidine (0.658 mL, 4.99 mmol, 1 eq) then 2,4-dinitrophenylsulfonyl chloride (1.40 g, 5.24 mmol, 1.05 eq) were added. After 5 h, the reaction was diluted with DCM (100 mL), washed with HCl 1 N (3×20 mL), water (1×20 mL) and brine (1×20 mL), dried over $Na_2SO_4$, filtered and concentrated. The residue was purified by flash chromatography (Hex/EtOAc 10% to 25%) to afford 167 (1.63 g, 3.99 mmol) as a yellow powder. Yield 68%.

Part C.

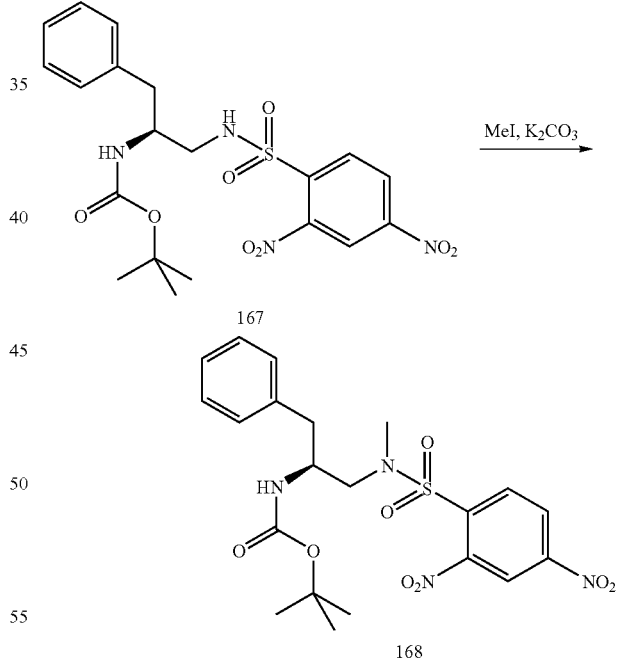

Compound 167 (777 mg, 1.62 mmol, 1 eq) and potassium carbonate (447 mg, 3.24 mmol, 2 eq) were dissolved in acetone (20 mL) and iodomethane (204 μL, 3.24 mmol, 2 eq) was added. The reaction was stirred at rt for 20 h then diluted with HCl 1 N (100 mL) and extracted with EtOAc (3×25 mL). The combined organics were washed with water (1×20 mL) and brine (1×20 mL), dried over $Na_2SO_4$, filtered and concentrated. The residue was purified by flash chromatography (Hex/EtOAc 10% to 25%) to afford 168 (685 mg, 1.39 mmol) as a yellow is powder. Yield 85%.

Part D.

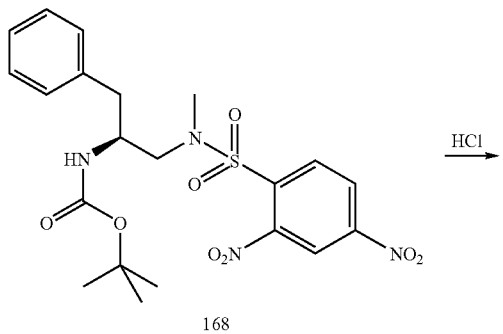

168

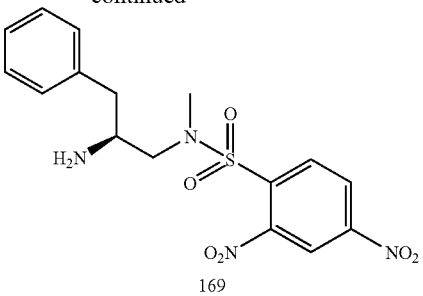

169

Compound 168 (685 mg, 1.4 mmol, 1 eq) was treated with a 4.0M solution of HCl in dioxane (10 mL) at rt for 1. The turbid solution was then concentrated and dried under high vacuum to obtain the hydrochloric salt of 169 (604 mg, 1.4 mmol) as yellow foam in a quantitative yield.

Part E.

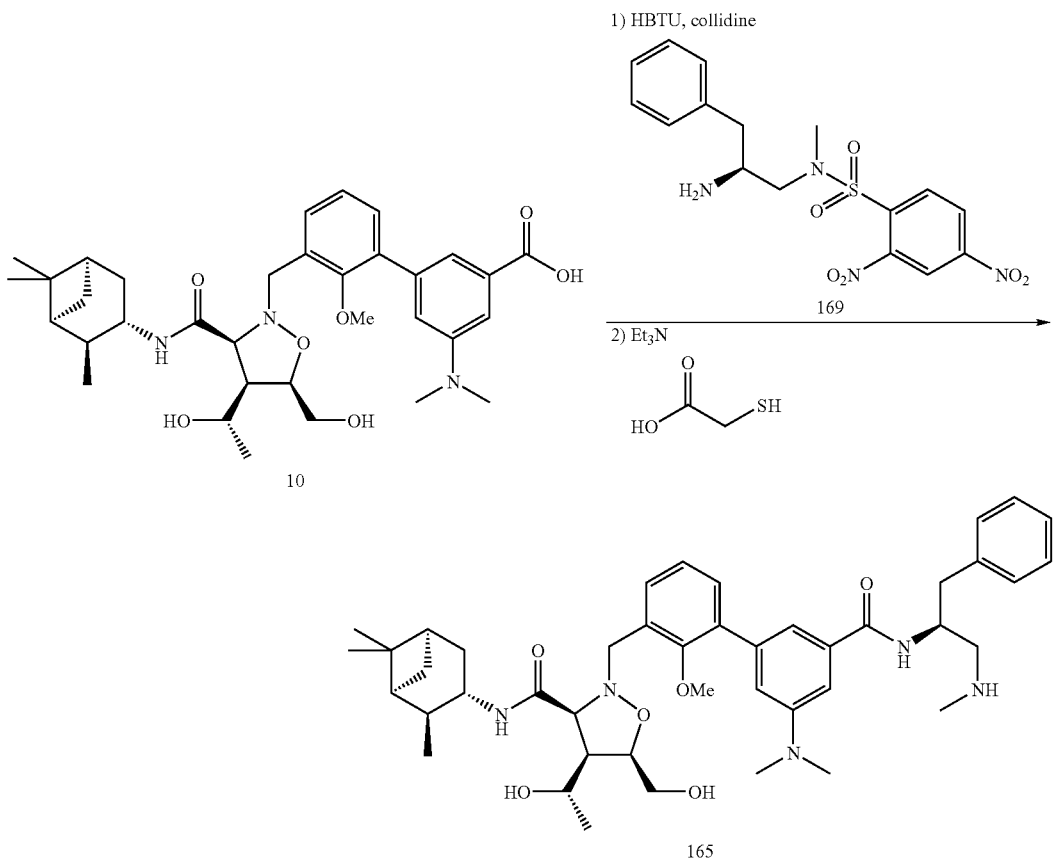

Acid 10 (40 mg, 66 μmol, 1 eq), amine 169 (31 mg, 79 μmol, 1.2 eq) and HBTU (30 mg, 79 μmol, 1.2 eq) were dispersed in DCM (1 mL) and 2,4,6-collidine (26 μL, 197 μmol, 3 eq) was added. The reaction was stirred at rt for 1 h then mercaptoacetic acid (108 mL, 1.32 mmol, 20 eq) was added. The reddish solution was stirred at rt for 1 h then concentrated to dryness. The residue was purified by HPLC to afford 165 (7.3 mg, 9.6 μmol) as a lyophilized powder. MS (ESI(+)) m/e 756.33 (M+H)$^+$. Yield 14.6%.

Example 71

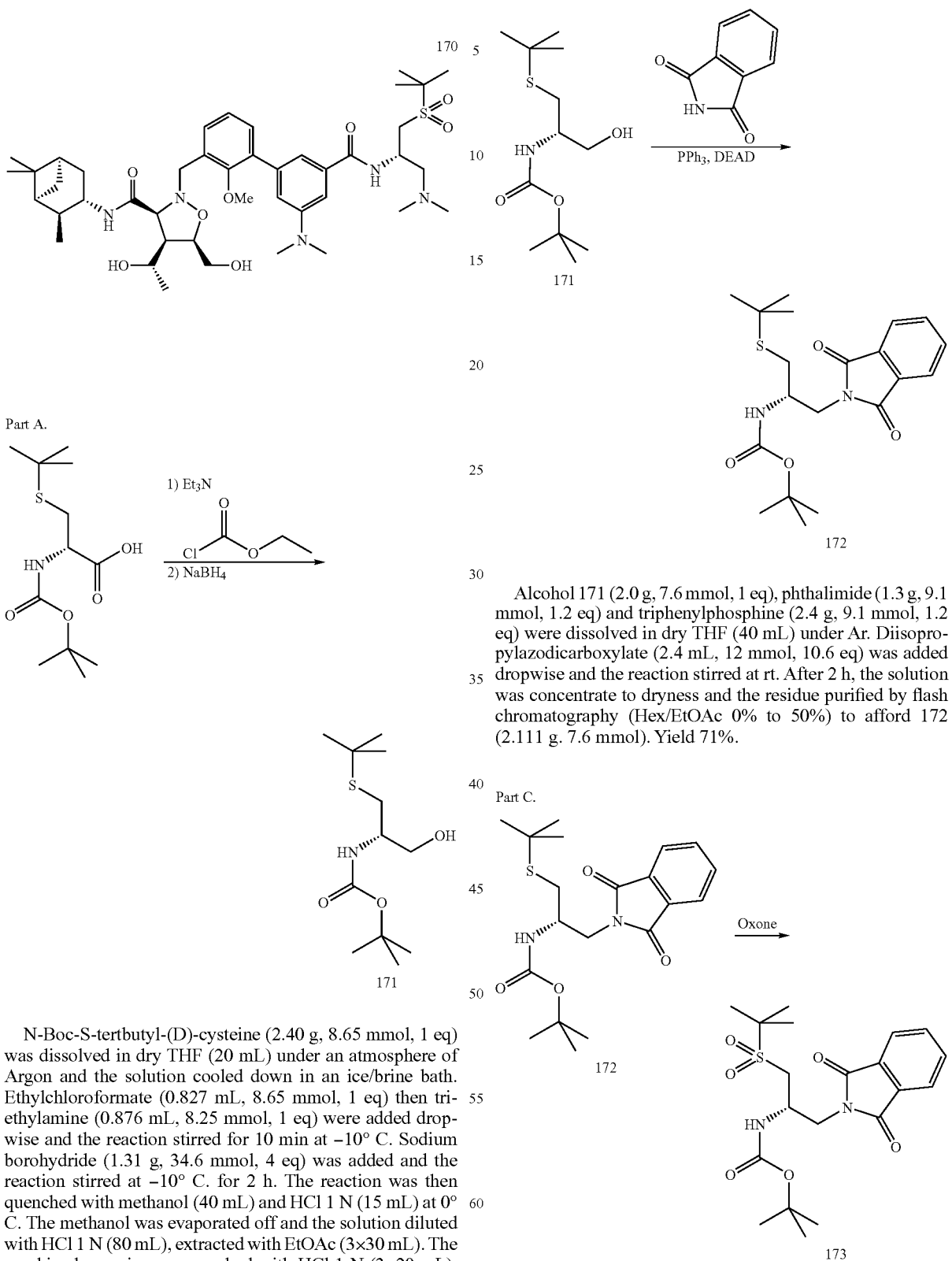

Part A.

N-Boc-S-tertbutyl-(D)-cysteine (2.40 g, 8.65 mmol, 1 eq) was dissolved in dry THF (20 mL) under an atmosphere of Argon and the solution cooled down in an ice/brine bath. Ethylchloroformate (0.827 mL, 8.65 mmol, 1 eq) then triethylamine (0.876 mL, 8.25 mmol, 1 eq) were added dropwise and the reaction stirred for 10 min at −10° C. Sodium borohydride (1.31 g, 34.6 mmol, 4 eq) was added and the reaction stirred at −10° C. for 2 h. The reaction was then quenched with methanol (40 mL) and HCl 1 N (15 mL) at 0° C. The methanol was evaporated off and the solution diluted with HCl 1 N (80 mL), extracted with EtOAc (3×30 mL). The combined organics were washed with HCl 1 N (3×20 mL), NaOH 1 N (3×20 mL) and brine (1×20 mL), dried over Na$_2$SO$_4$, filtered and concentrated to afford 171 (2.08 g, 7.90 mmol) which was used without further purification. Yield 91%.

Part B.

Alcohol 171 (2.0 g, 7.6 mmol, 1 eq), phthalimide (1.3 g, 9.1 mmol, 1.2 eq) and triphenylphosphine (2.4 g, 9.1 mmol, 1.2 eq) were dissolved in dry THF (40 mL) under Ar. Diisopropylazodicarboxylate (2.4 mL, 12 mmol, 10.6 eq) was added dropwise and the reaction stirred at rt. After 2 h, the solution was concentrate to dryness and the residue purified by flash chromatography (Hex/EtOAc 0% to 50%) to afford 172 (2.111 g. 7.6 mmol). Yield 71%.

Part C.

Thioether 172 (2.1 g, 5.4 mmol, 1 eq) was dissolved in methanol (100 mL) and Oxone (9.9 g, 16 mmol, 3 eq) was added as a solution in water (20 mL). The reaction was stirred at rt for 1 h then quenched with 20% sodium bisulfite (20 mL). The solution was diluted with water (200 mL) and extracted with chloroform (3×40 mL). The combined organics were washed with brine (1×30 mL), dried over Na$_2$SO$_4$, filtered and concentrated to afford 173 (2.2 g, 5.2 mmol) which was used without further purification. Yield 97%.

Part D.

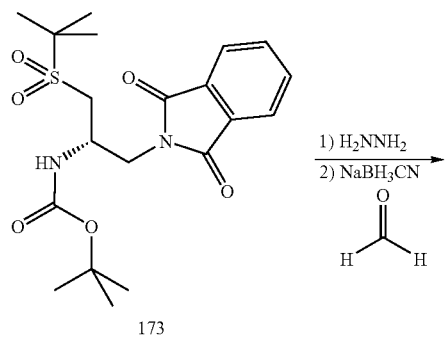

173

Sulfone 173 (2.20 g, 5.2 mmol, 1 eq) was treated with hydrazine hydrate (2.5 mL, 52 mmol, 10 eq) in refluxing ethanol for 2 h. The reaction was allowed to reach rt then filtered on paper. The filtrate was concentrated to dryness and the residue taken in DCM. The mixture was filtered on paper and the filtrate concentrated to dryness.

The residue was taken in methanol (40 mL) and formaldehyde 37% (1.1 mL, 15 mmol, 3 eq) was added. The solution was stirred at rt for 10 min then sodium cyanoborohydride (0.96 g, 15 mmol, 3 eq) was added. The reaction was stirred at rt for 1 h then quenched with 5% NaHCO$_3$ (40 mL). The volume of the reaction was reduced on a rotary evaporator and the residual aqueous solution extracted with DCM (3×20 mL). The combined organics were washed with brine (1×20 mL) then dried over Na$_2$SO$_4$, filtered and concentrated to afford 174 (1.416 g, 4.4 mmol) which was used without further purification. Yield 86%.

Part E.

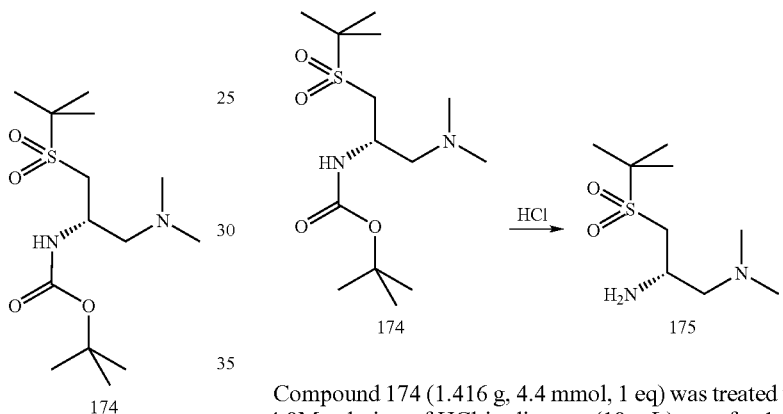

Compound 174 (1.416 g, 4.4 mmol, 1 eq) was treated with a 4.0M solution of HCl in dioxane (10 mL) at rt for 1. The turbid solution was then concentrated and dried under high vacuum to obtain the hydrochloric salt of 175 (1.13 g, 4.4 mmol) as yellow foam in a quantitative yield.

Part F.

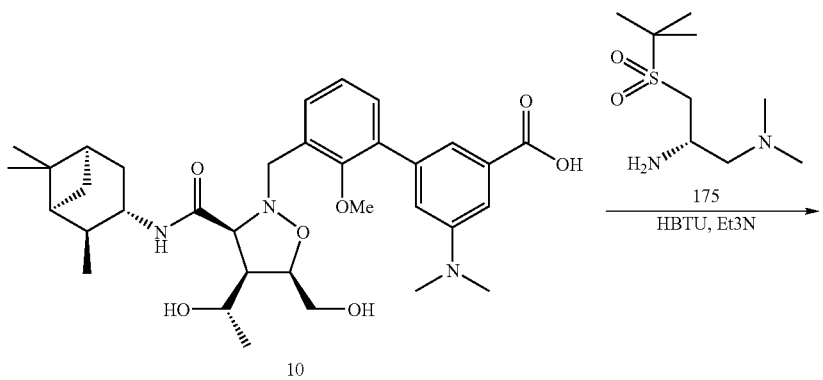

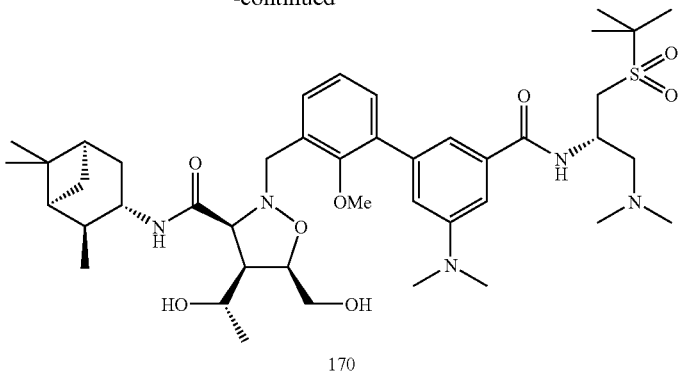

170

Acid 10 (40 mg, 66 µmol, 1 eq), amine 175 (31 mg, 79 µmol, 1.2 eq) and HBTU (30 mg, 79 µmol, 1.2 eq) were dispersed in DCM (1 mL) and triethylamine (27 µL, 197 µmol, 3 eq) was added. The reaction was stirred at rt for 1 h then concentrated to dryness. The residue was purified by HPLC to afford 170 (9.6 mg, 12 µmol) as a lyophilized powder. Yield 18%. MS (ESI(+)) m/e 814.47 (M+H)+.

Example 72

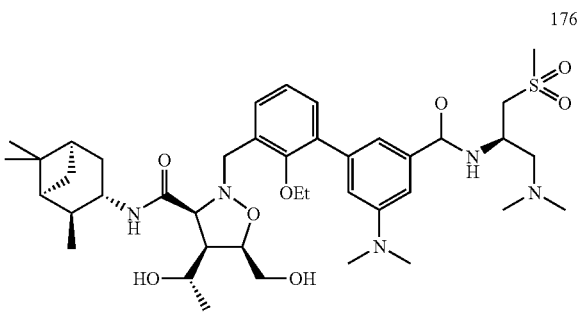

176

Part A.

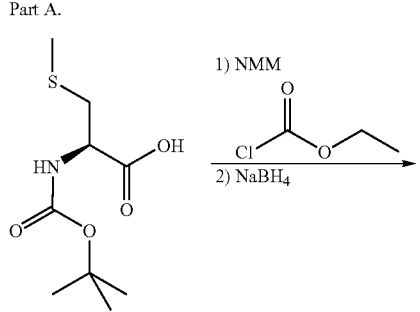

-continued

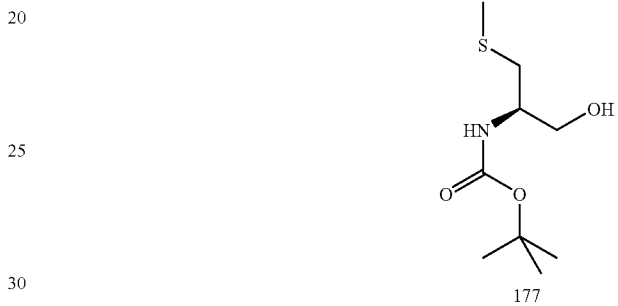

177

N-Boc-S-methyl-(L)-cysteine (1.50 g, 6.37 mmol, 1 eq) was dissolved in dry THF (20 mL) under an atmosphere of Argon and the solution cooled down in an ice/brine bath. Ethylchloroformate (0.610 mL, 6.37 mmol, 1 eq) then N-methylmorpholine (0.701 mL, 6.37 mmol, 1 eq) were added dropwise and the reaction stirred for 10 min at −10° C. Sodium borohydride (0.965 g, 25.5 mmol, 4 eq) was added and the reaction stirred at −10° C. for 2 h. The reaction was then quenched with methanol (40 mL) and HCl 1 N (15 mL) at 0° C. The methanol was evaporated off and the solution diluted with HCl 1 N (80 mL), extracted with EtOAc (3×30 mL). The combined organics were washed with HCl 1 N (3×20 mL), NaOH 1 N (3×20 mL) and brine (1×20 mL), dried over Na₂SO₄, filtered and concentrated to afford 177 (1.1 g, 5.04 mmol) which was used without further purification. Yield 79%.

Part B.

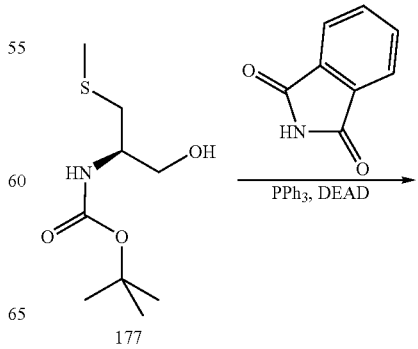

177

-continued

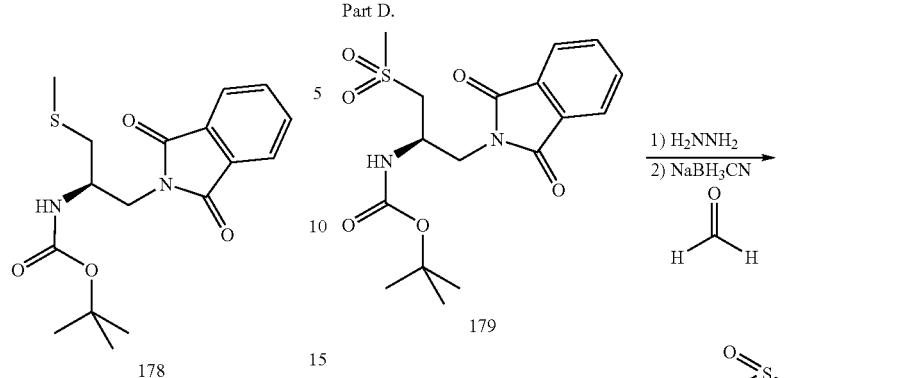

Alcohol 177 (1.11 g, 5.04 mmol, 1 eq), phthalimide (0.889 g, 6.05 mmol, 1.2 eq) and triphenylphosphine (1.98 g, 7.56 mmol, 1.5 eq) were dissolved in dry THF (30 mL) under Ar. Diisopropylazodicarboxylate (1.46 mL, 7.56 mmol, 1.5 eq) was added dropwise and the reaction stirred at rt. After 2 h, the solution was concentrate to dryness and the residue purified by flash chromatography (Hex/EtOAc 0% to 50%) to afford 178 (1.43 g, 4.12 mmol). Yield 82%.

Part C.

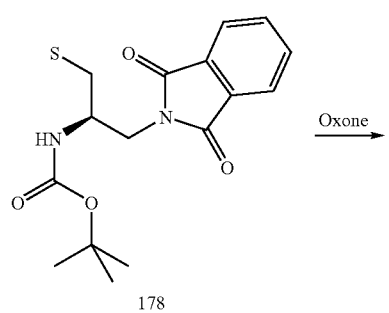

Thioether 178 (1.43 g, 4.1 mmol, 1 eq) was dissolved in methanol (100 mL) and Oxone (5.1 g, 8.2 mmol, 2 eq) was added as a solution in water (20 mL). The reaction was stirred at rt for 1 h then quenched with 20% sodium bisulfite (20 mL). The solution was diluted with water (200 mL) and extracted with chloroform (3×40 mL). The combined organics were washed with brine (1×30 mL), dried over Na$_2$SO$_4$, filtered and concentrated to afford 179 (1.3 g, 3.4 mmol) which was used without further purification. Yield 83%.

Sulfone 179 (1.3 g, 3.4 mmol, 1 eq) was treated with hydrazine hydrate (1.06 mL, 34 mmol, 10 eq) in refluxing ethanol for 2 h. The reaction was allowed to reach rt then filtered on paper. The filtrate was concentrated to dryness and the residue taken in DCM. The mixture was filtered on paper and the filtrate concentrated to dryness.

The residue was taken in methanol (40 mL) and formaldehyde 37% (0.75 mL, 10 mmol, 3 eq) was added. The solution was stirred at rt for 10 min then sodium cyanoborohydride (0.64 g, 10 mmol, 3 eq) was added. The reaction was stirred at rt for 1 h then quenched with 5% NaHCO$_3$ (40 mL). The volume of the reaction was reduced on a rotary evaporator and the residual aqueous solution extracted with DCM (3×20 mL). The combined organics were washed with brine (1×20 mL) then dried over Na$_2$SO$_4$, filtered and concentrated to afford 180 (0.85 g, 3 mmol) which was used without further purification. Yield 90%.

Part E.

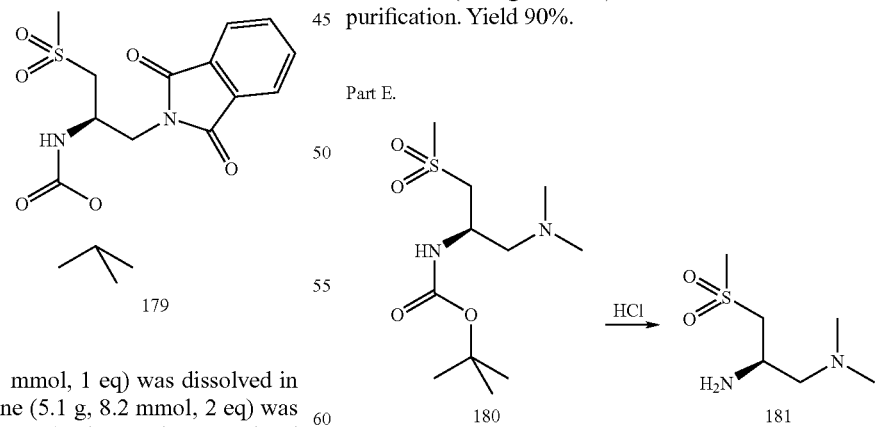

Compound 180 (0.85 g, 3 mmol, 1 eq) was treated with a 4.0M solution of HCl in dioxane (10 mL) at rt for 1. The turbid solution was then concentrated and dried under high vacuum to obtain the hydrochloric salt of 181 (0.21 g, 1.17 mmol) as a white foam. Yield 39%.

Part F.

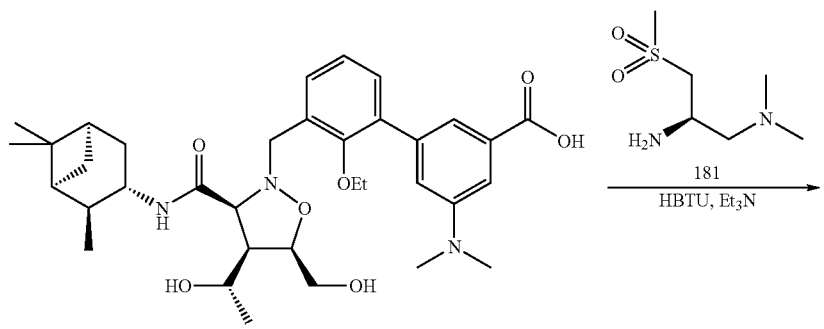

Acid described in Example 4 part G (50 mg, 80 μmol, 1 eq), amine 181 (17 mg, 96 μmol, 1.2 eq) and HBTU (36 mg, 96 μmol, 1.2 eq) were dispersed in DCM (1 mL) and triethylamine (34 μL, 240 μmol, 3 eq) was added. The reaction was stirred at rt for 1 h then concentrated to dryness. The residue was purified by HPLC to afford 176 (2.2 mg, 2.8 μmol) as a lyophilized powder. MS (ESI(+)) m/e 786.56 (M+H)$^+$. Yield 3.5%.

Example 73

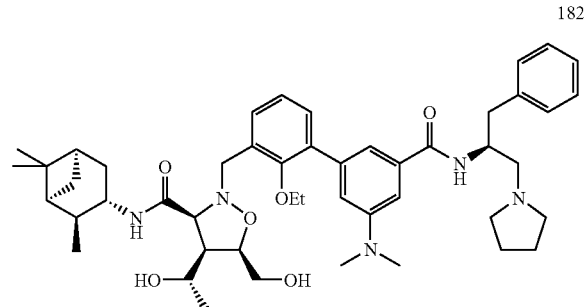

182

Part A.

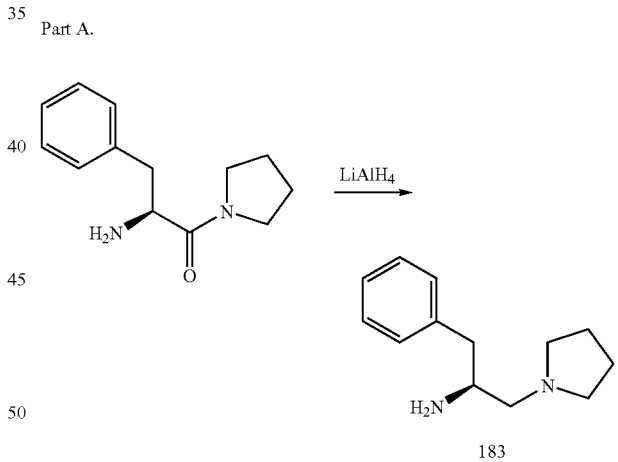

In a three-neck round-bottom flask topped with a condenser, (L)-Phenylalanine-pyrrolidide (1.00 g, 4.6 mmol, 1 eq) was dissolved in dry THF (20 mL) under an atmosphere of Argon. The solution was cooled in an ice/water bath and lithium aluminium hydride was added dropwise as a 2.0M solution in THF (9.2 mL, 18 mmol, 4 eq). The reaction was refluxed overnight under an atmosphere of Argon. After 18 h, the reaction was allowed to cool to rt, then cooled in an ice/water bath and quenched by the cautious, sequential, dropwise addition of water (0.7 mL), 15% NaOH (0.7 mL) and water (2.1 mL) to obtain a white precipitate. The reaction was filtered on paper and the cake rinsed with THF (60 mL). The filtrate was concentrated to obtained crude 183 as a yellow oil (0.917 g, 4.5 mmol) which was used without further purification. Yield 98%.

Part B.

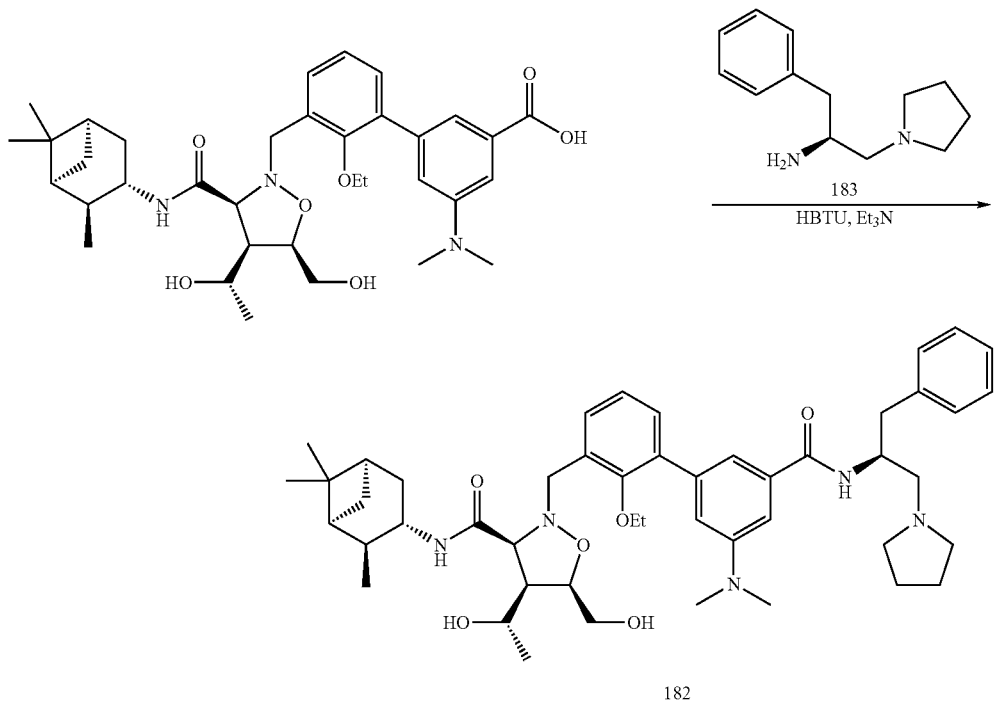

Acid prepared as described in Example 4 part G (80 mg, 128 μmol, 1 eq), amine 183 (31 mg, 154 μmol, 1.2 eq) and HBTU (58 mg, 154 μmol, 1.2 eq) were dispersed in DCM (1 mL) and triethylamine (54 μL, 385 μmol, 3 eq) was added. The reaction was stirred at rt for 1 h then concentrated to dryness. The residue was purified by HPLC to afford 182 (16.8 mg, 20 μmol) as a lyophilized powder. Yield 16.1%. MS (ESI(+)) m/e 810.65 (M+H)$^+$.

Example 74

Part A.

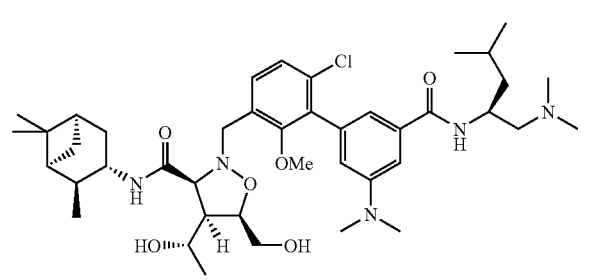

Sodium hydride 60% (3.1 g, 78 mmol, 2 eq) was dispersed in dry THF (40 mL) under an atmosphere of Argon. 3-chlorophenol (4.1 mL, 39 mmol, 1 eq) was added dropwise over 10 min as a solution in dry THF (10 mL). The solution was stirred for 1 h then diethylchloroformate (9.9 mL, 78 mmol, 2 eq) was added dropwise as a solution in dry THF (10 mL). The solution was stirred overnight at rt. After 14 h, the reaction was quenched by the addition of water (5 mL) dropwise, diluted with diethylether (120 mL). The organics were washed with water (2×30 mL) then NaOH (2×30 mL), dried over Na$_2$SO$_4$, filtered and concentrated. The residue was purified by flash chromatography (Hexane/EtOAc 0% then 10%) to obtain 184 as an oil (8.2 g, 36 mmol). Yield 93%.

Part B.

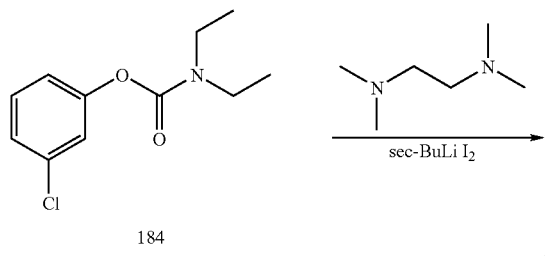

Dry THF (120 mL) was charged in a flame-dried round-bottom flask under an atmosphere of Argon and cooled in an dry ice/acetone bath. A 1.4M solution of sec-butyl lithium in cyclohexane (31 mL, 43 mmol, 1.2 eq), tetramethylethylenediamine (6.5 mL, 43 mmol, 1.2 eq) and a solution of 184 (8.2 g, 36 mmol, 1 eq) in dry THF (10 mL) were added sequentially. The solution was stirred at −78° C. for 2 h then iodine (11 g, 43 mmol, 1.2 eq) was added as a solution in dry THF (20 mL). The solution was stirred at −78° C. for 30 min then allowed to reach rt. After 2 h, the reaction was quenched with 5% $Na_2S_2O_3$ (100 mL) then extracted with EtOAc (3×100 mL). The combined organics were dried over $Na_2SO_4$, filtered and concentrated. The residue was purified by flash chromatography (Hexane/EtOAc 0% to 30%) to obtain 185 an oil (8.92 g, 25 mmol). Yield 70%.

Part C.

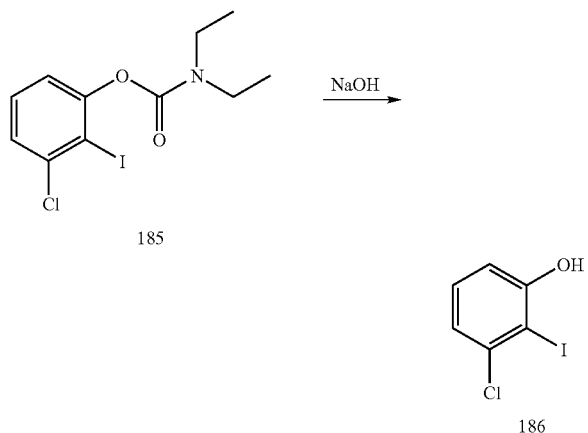

Carbamate 185 (10 g, 28 mmol, 1 eq) was treated with sodium hydroxide (11 g, 283 mmol, 10 eq) in refluxing ethanol (140 mL). After 14 h, the solution was allowed to cool to rt, acidified with HCl 6N then extracted with DCM (3×60 mL). The combined organics were dried over $Na_2SO_4$, filtered and concentrated. The residue was purified by flash chromatography (Hexane/DCM 0% to 100%) to obtain 186 an oil (3.75 g, 15 mmol). Yield 52%.

Part D.

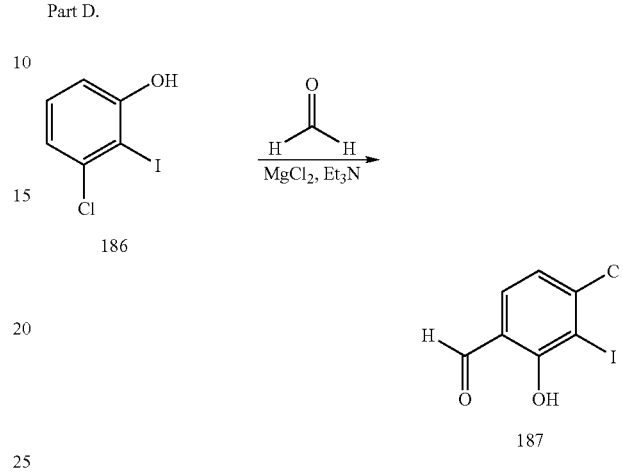

To a mixture of $MgCl_2$ (2.25 g, 23.6 mmol, 2 eq) and paraformaldehyde (1.06 g, 35.4 mmol, 3 eq) in THF (60 mL) under argon, was added triethylamine (3.29 mL, 23.6 mmol, 2 eq). The mixture was stirred at room temperature, under argon, for 10 min and phenol 186 (3.00 g, 11.8 mmol, 1 eq) was added. The reaction was heated to reflux for 3 h then allowed to cool to room temperature. Diethyl ether (100 mL) was added and the solution was washed with HCl 1 N (3×100 mL), dried over $Na_2SO_4$, filtered and concentrated to dryness to obtain crude 187 (3.33 g, 11.8 mmol) which was taken on without further purification. Yield 99%.

Part E.

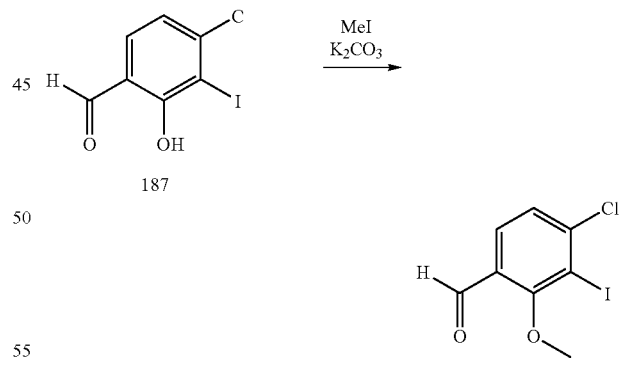

To a solution of crude phenol 187 (3.33 g, 11.8 mmol, 1 eq) in DMF (50 mL) at room temperature was added $K_2CO_3$ (2.18 g, 15.3 mmol, 1.30 eq) followed by MeI (0.956 mL, 15.3 mmol, 1.3 eq). The reaction mixture was stirred at 40° C. under argon for 5 h and then quenched with HCl 6N (10 ml). The mixture was diluted with HCl 1 N (250 mL) and extracted with DCM (3×100 mL). Pooled organics were washed with water (3×100 mL) then brine (1×100 mL). The solution was dried over $Na_2SO_4$, filtered and concentrated to dryness. The residue was purified by flash chromatography (EtOAc/Hexane, 0% to 20%) to afford 188 (2.42 g, 8.16 mmol). Yield 69%.

Part F.

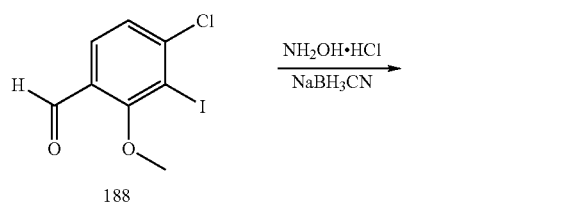

188

Aldehyde 188 (2.41 g, 8.13 mmol, 1 eq) and hydroxylamine hydrochloride (678 mg, 9.75 mmol, 1.2 eq) were dissolved in THF/MeOH/water (7:4:1, 12 mL). The solution was stirred at room temperature for 5 min then a crystal of methyl orange and sodium cyanoborohydride (1.02 g, 16.26 mmol, 2 eq) were added. The pH was adjusted to 2 and the resulting ruby red color was maintained for the duration of the reaction by the regular addition of 6N HCl. After stirring for 1 h, the mixture was filtered on paper, rinsing with THF. The filtrate was diluted with NaOH 1 N (100 mL) and extracted with DCM (3×50 mL). Pooled organics were washed with water (3×20 mL), brine (1×20 mL) and then dried over $Na_2SO_4$. The crude product was purified by flash chromatography (Hexane/EtOAc, 0% to 80%) to afford 189 (1.498 g, 4.78 mmol). Yield 58%.

Part G.

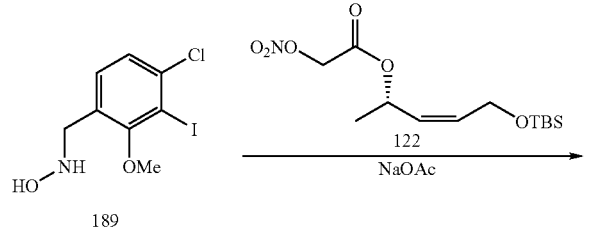

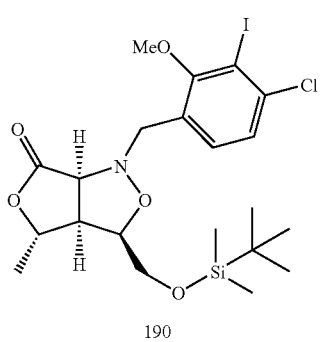

190

Nitrite 122 (850 mg, 2.66 mmol, 1.05 eq) was dissolved in DMSO (5 mL) and sodium acetate (327 mg, 3.99 mmol, 1.50 eq) was added. The solution was stirred at room temperature for 30 min then poured on brine (30 mL) and extracted with diethyl ether (3×30 mL). The combined organic layers were washed with saturated $NaHCO_3$ (1×20 mL), water (2×20 mL) and brine (1×20 mL), dried over $Na_2SO_4$, filtered and concentrated to dryness. The residue was then reacted overnight with hydroxylamine 189 (588 mg, 2.35 mmol, 1 eq) in refluxing toluene (20 mL). After 14 h, the solution was concentrated and the residue purified by flash chromatography (Hexane/EtOAc, 0% to 30%) to afford 190 (964 mg, 1.69 mmol). Yield 66%.

Part H.

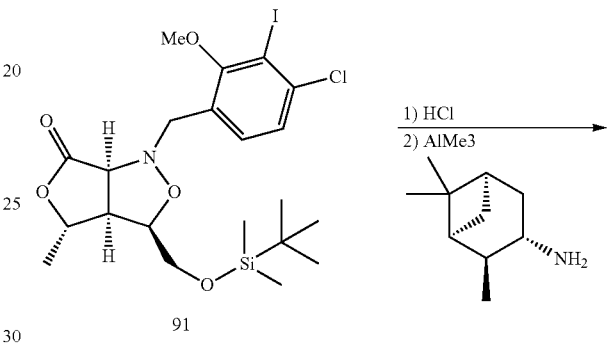

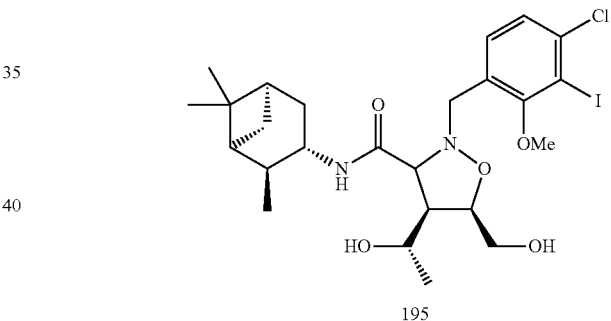

195

Lactone 190 (964 mg, 1.69 mmol, 1 eq) is dissolved in THF (8 mL) and HCl 6N (0.6 mL) is added. The solution is stirred at room temperature for 2 h then diluted with DCM (100 mL) and washed with 5% $NaHCO_3$ (3×) and brine (1×), dried over $Na_2SO_4$, filtered and concentrated to dryness.

To a solution of the residue in dry DCM (6 mL) was added a solution of (+)isopinocampheylamine (569 µL, 3.39 mmol, 2 eq) previously treated in dry DCM (6 mL) with 2.0M trimethylaluminum in hexanes (1.83 mL, 3.39 mmol, 2 eq) for 15 min. The solution was stirred at room temperature overnight. After 14 h, was added a solution of (+)isopinocampheylamine (285 µL, 1.69 mmol, 1 eq) previously treated in dry DCM (3 mL) with 2.0M trimethylaluminum in hexanes (850 µL, 1.69 mmol, 1 eq) for 15 min. After 5 h, the solution was diluted with dry DCM (150 mL) and quenched with $Na_2SO_4 \cdot 10H_2O$ (8.2 g, 25.4 mmol, 15 eq). The mixture was stirred vigorously at room temperature for 15 h then filtered on Celite. The filtrate was concentrated to dryness and the residue purified by flash chromatography (Hexane/EtOAc, 0% to 100%) to afford 191 (659 mg, 1.09 mmol). Yield 64%.

Part I.

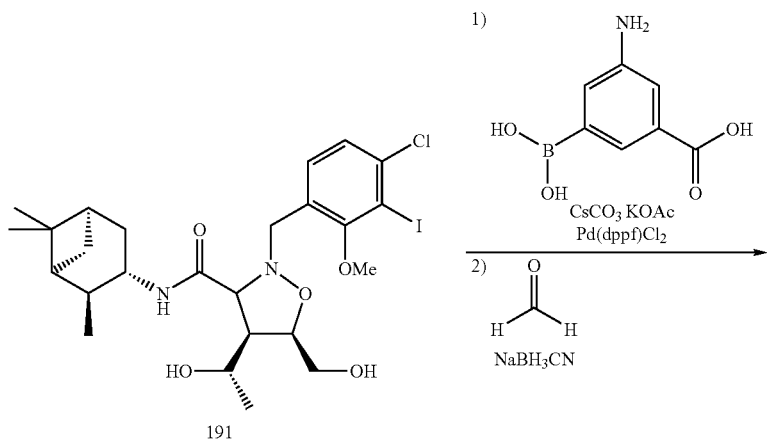

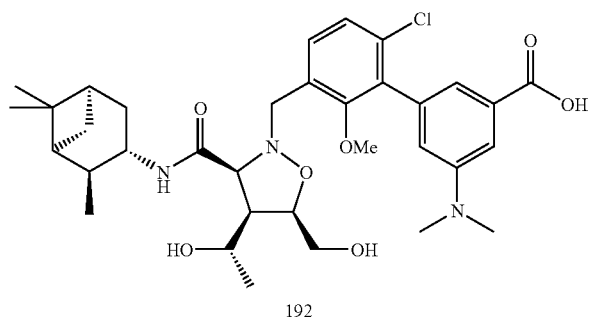

A flask containing iodide 191 (659 mg, 1.09 mmol, 1 eq), 3-amino-5-carboxyphenylboronic acid (240 mg, 2.17 mmol, 2 eq), cesium carbonate (628 mg, 3.25 mmol, 3 eq), potassium acetate (107 mg, 1.09 μmol, 1 eq) and Pd(dppf)Cl$_2$ (79 mg, 109 μmol, 0.1 eq) was purged with argon and DMSO (5 mL) was added. The reaction was heated at 60° C. for 24 h. The reaction mixture was added to water (100 mL), acidified with 6M HCl until the aqueous layer attained a pH of 4, and extracted with DCM (3×50 mL). The combined organic layers were washed with water (1×50 mL) dried over Na$_2$SO$_4$ and concentrated to a brown oil.

This crude oil was dissolved in MeOH (10 mL) and treated with 37% formalin (162 μL, 2.17 mol, 2 eq) and sodium cyanoborohydride (205 mg, 3.25 mmol, 3 eq). After stirring at room temperature for 30 min, the reaction mixture was quenched with sat NaHCO$_3$ (4 mL) and partitioned between water (50 mL) and DCM (20 mL). The aqueous layer was acidified to pH 4 with 6M HCl. The layers were separated and the aqueous extracted with DCM (3×20 mL). The combined organic layers were washed with water (1×20), dried over Na$_2$SO$_4$, and concentrated to a brown oil which was used without purification in the next reaction.

Part J.

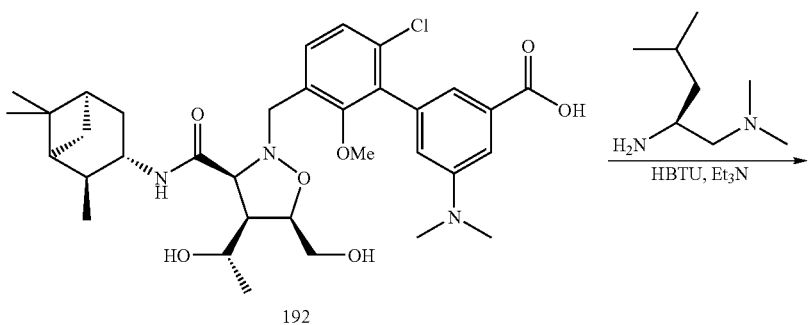

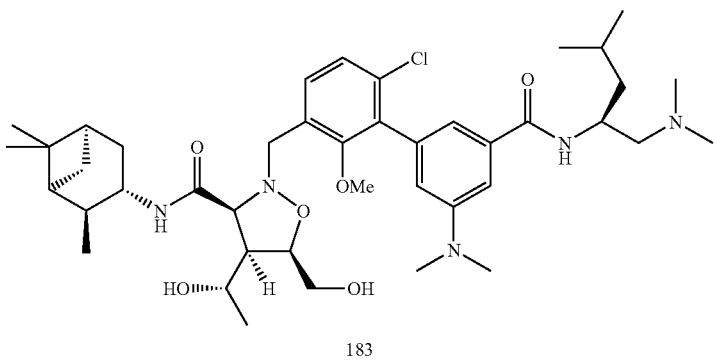

183

Compound 192 was taken in DCM (2 mL) then amine derived from leucine (78 mg, 543 µmol, 0.5 eq), HBTU (206 mg, 543 µmol, 0.5 eq) and triethylamine (151 µL, 1086 µmol, 1 eq) were added. The reaction was stirred at rt for 1 h then concentrated to dryness. The residue was purified by flash chromatography (DCM and DCM/MeOH/NH₄OH 4:1:0.1 0% to 100%) then by HPLC to afford 183 (5.0 mg, 6.5 µmol) as a lyophilized powder. Yield 0.6% (from 191). MS (ESI(+)) m/e 770.49 (M+H)⁺.

Example 75

Part A.

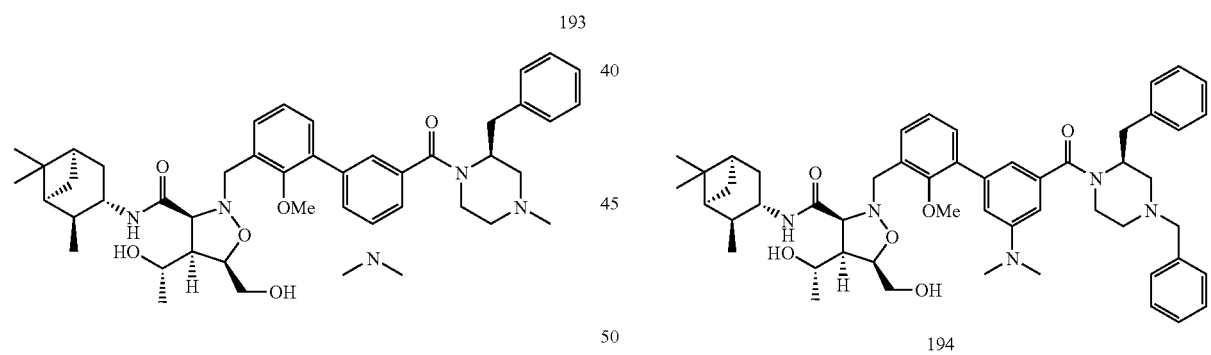

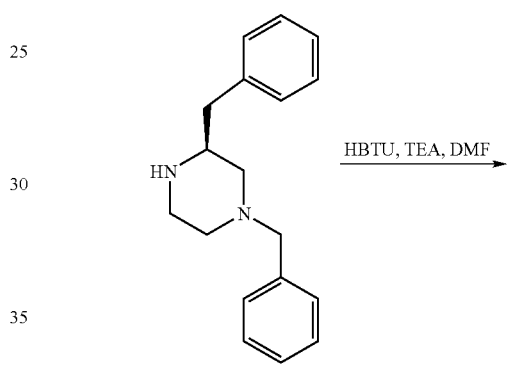

194

To a solution of benzoic acid derivate 10 (50 mg, 0.08 mmol, 1.0 eq.) in DMF (3 mL) was added 2M solution of (S)—N⁴-Benzyl-2-Benzylpiperazine (0.04 mg, 0.2 mmol, 2 eq.) in THF followed by triethylamine (10 mg, 0.1 mmol, 1.5 eq.) and HBTU (30 mg, 0.07 mmol, 0.9 eq.). After stirring for 40 h a 23° C., the reaction mixture was diluted with EtOAc (100 mL) and a saturated NaCl solution (200 mL). The pH of the mixture was adjusted to 12 with 6 N NaOH and extracted with Ethyl acetate (2×100 mL). The combined organic extracts were dried (Na₂SO₄), filtered and concentrated in vacuo to give of 100 mg of a brown oil. This material was purified using silica gel chromatography (2.5-10% MeOH/DCM) to give 33 mg of 194 as brown solid. Yield 47%. MS (ESI(+)) m/z 858.62 (M+H)⁺.

Part B.

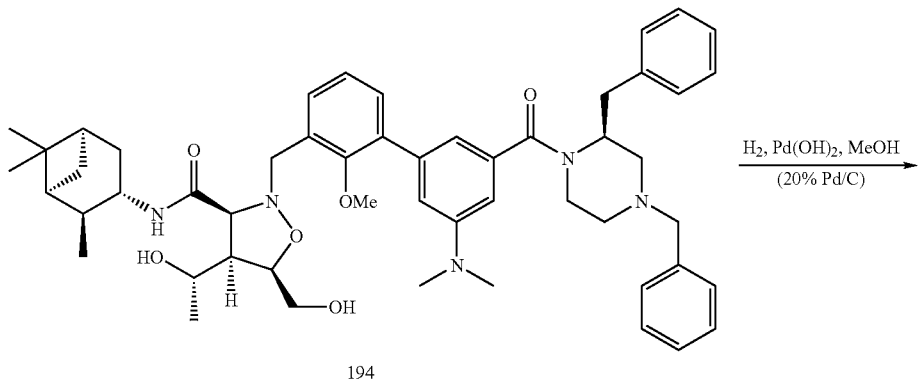

To a solution of (S)—N⁴-Benzyl-2-Benzylpiperazine amide 194 (27 mg, 0.031 mmol, 1 eq.) in MeOH (3 mL) under $H_2$ (balloon) was added 44 mg Pd(OH)₂ (44 mg, 0.031 mmol, 1 eq.). After stirring at 23° C. for 18 h, the reaction mixture was filtered through Celite 545 and washed with MeOH (2×50 mL). The filtrate was concentrated in vacuo to provide crude 195 (14.5 mg) as a light brown solid, which was used directly on the next reaction. Yield: 60%. MS (ESI(+)) m/z 768.37 (M+H)⁺.

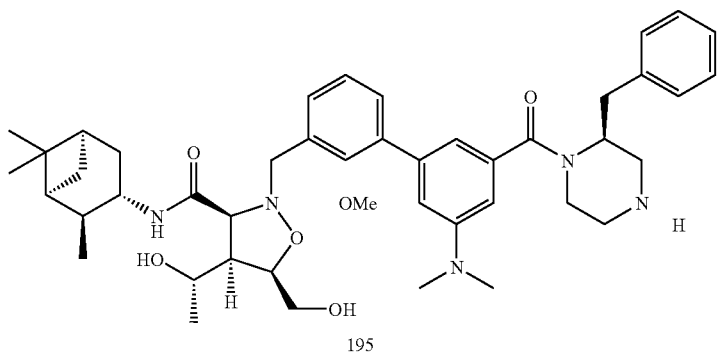

Part C.

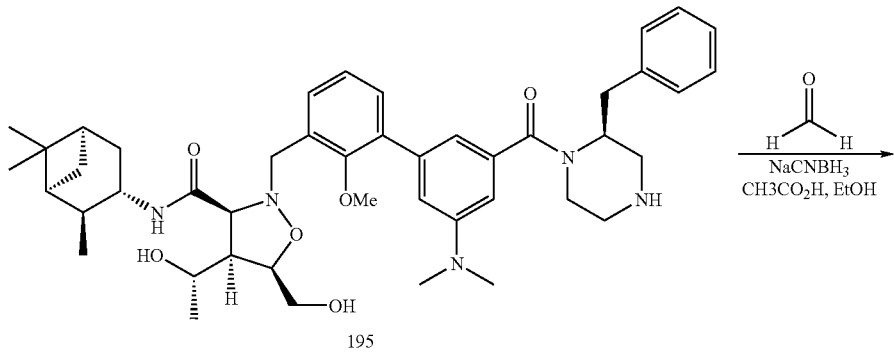

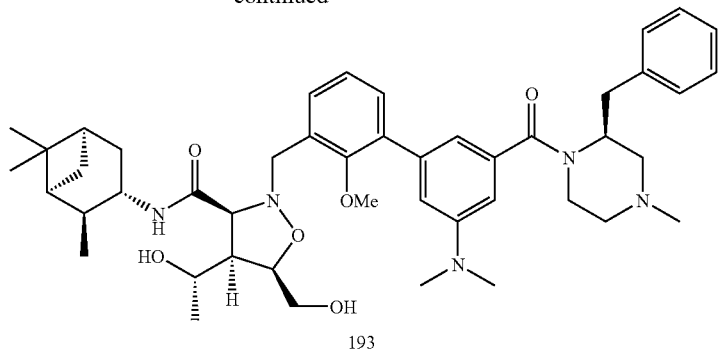

193

To a solution of 12 mg starting material 195 (0.02 mmol, 1 eq.) in EtOH (1 mL) was added formaldehyde of a 37% aqueous solution (4 mg, 0.05 mmol. 3 eq.), acetic acid (0.9 mg, 0.02 mmol, 1 eq.), and sodium cyanoborohydride (3 mg, 0.05 mmol, 3 eq.). After stirring at 23° C. for 16 h, the reaction mixture was filtered through Celite 545 and concentrated to dryness to afford an orange solid. The material was diluted with a saturated solution of NaCl, water and EtOAc. The pH of the mixture was adjusted to 10 with 6 N NaOH and extracted with Ethyl acetate (2×50 mL). The combined organics were dried over MgSO$_4$, filtered and concentrated in vacuo. The crude product was purified by HPLC to afford 4 mg of (S)—N$^4$-methyl-2-benzylpiperazine amide product 193. Yield 33%. MS (ESI(+)) m/z 782.58 (M+H)$^+$.

Example 76

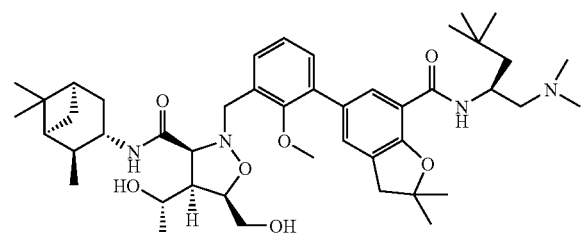

196

Part A.

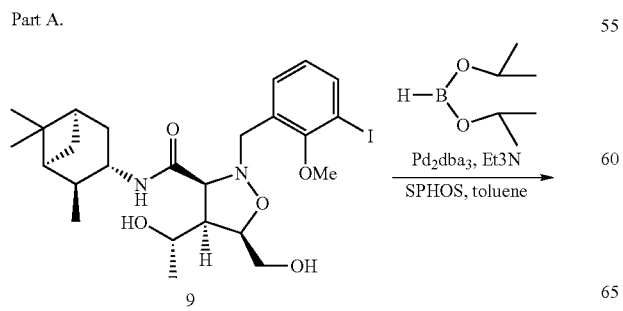

9

-continued

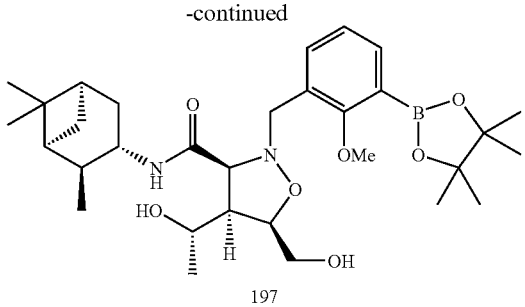

197

To a solution of 9 (1 g) in toluene (10 mL) under Argon was added dioxaborolane (1 mL), SPHOS (0.04 g), triethylamine (0.7 mL) and Pd catalyst (0.02 g). The solution was purged with Argon then heated at 80 C for 2 h. LCMS showed mainly starting material. Another 60 mg SPHOS, 30 mg Pd catalyst and 0.3 mL of dioxaborolane were added. The solution was heated at 80° C. for another 5 h, and then cooled to 23° C. and methanol (10 mL) was added. The mixture was push through a short plug of silica gel and concentrated. Flash chromatography on silica gel (Hexane to 30%, 50% ethyl acetate in hexanes) gave 1 g of desired product 197.

Part B.

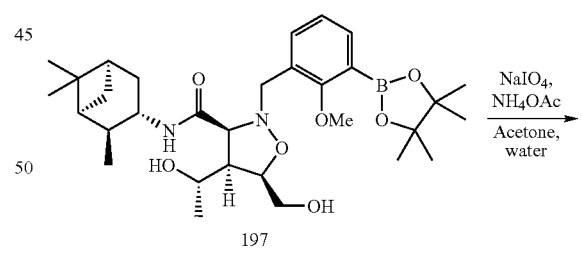

197

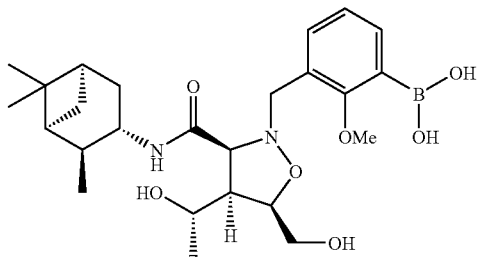

198

To a solution of pinacolboron 197 (1 g) in mixed solvents of acetone and water (1:1, 20 mL) at rt was added sodium periodate (2 g) and ammonium acetate (0.8 g). The mixture was allowed to stir at 23° C. for 12 hr. The reaction was evaporated to dryness and the residue taken up in ethyl acetate (100 mL), 0.1 N HCl (10 mL) was used to wash the organic layer. The organic layer washed with brine, dried over $MgSO_4$ and evaporated to provide 198 as a yellow solid 750 mg and used directly in the next reaction (Part D of this example).

Part C.

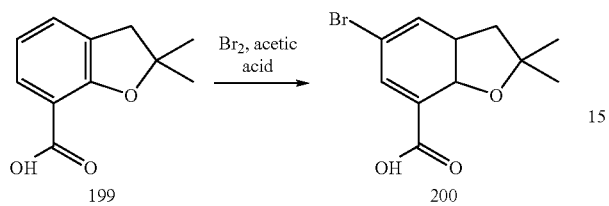

To a solution of dihydro benzofuran carboxylic acid 199 (150 mg) in acetic acid (3 mL) at 0 C was added an acetic acid solution of bromine (120 μl in 1 mL of acetic acid) drop wise. The mixture was allowed to stir at 23° C. for 12 hr. The reaction was quenched with sodium sulfite solution (2 M) until the red color disappeared. The mixture was concentrated under reduced pressure and residue was taken up in 150 mL DCM, which was washed with 2 M sodium sulfite, brine, dried and concentrated to give 200 mg of crude product 200 which was used directly in the next reaction (Part D of this example).

Part D.

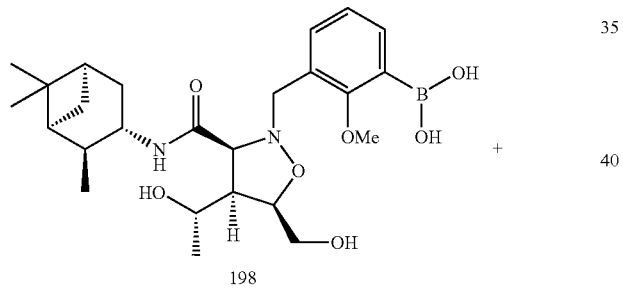

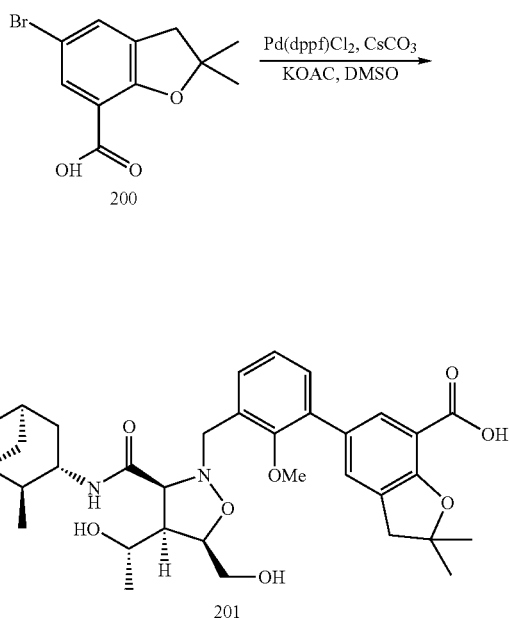

To a solution of boronic acid 198 (100 mg) in DMSO (5 mL) at 23° C. was added aryl bromide 200 (85 mg), cesium carbonate (200 mg), potassium acetate (20 mg) and Pd catalyst (17 mg). The mixture was purged with Argon and heated at 75° C. for 5 h. LCMS showed desired product and reaction was concentrated. HPLC purification gave 20 mg of desired product 201.

Part E.

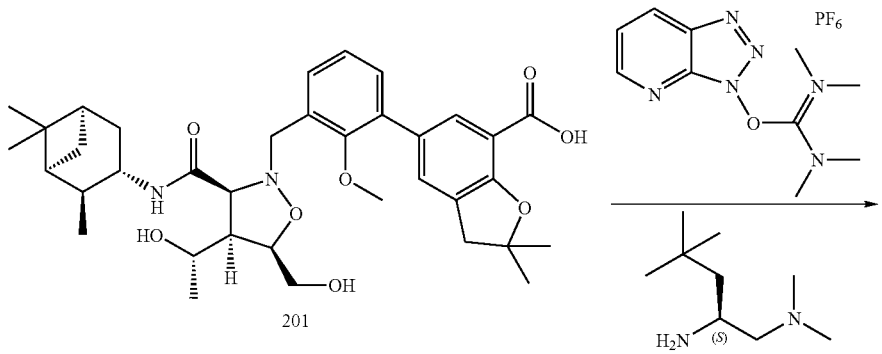

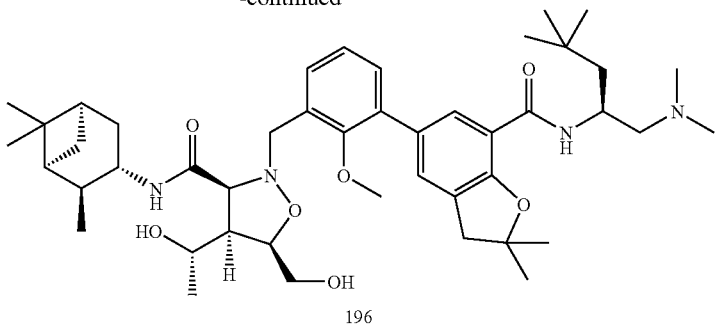
196
To a solution of 201 (5 mg) in DCM (1 mL) was added crude amine (10 uL), HATU (4 mg). The mixture was allowed to stir at 23° C. for 2 hrs. The crude mixture was then diluted with methanol (800 uL) and purified by HPLC (basic 10-100) to give desired product 196 3.5 mg. MS (ESI(+)) m/e 777.58 (M+H)+.
Example 77
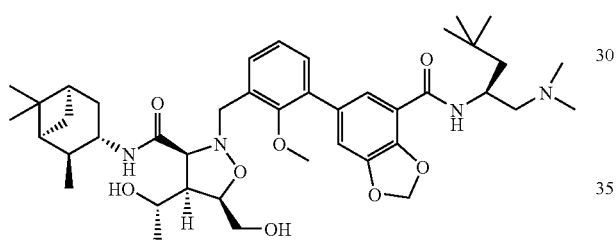
202
Part A.
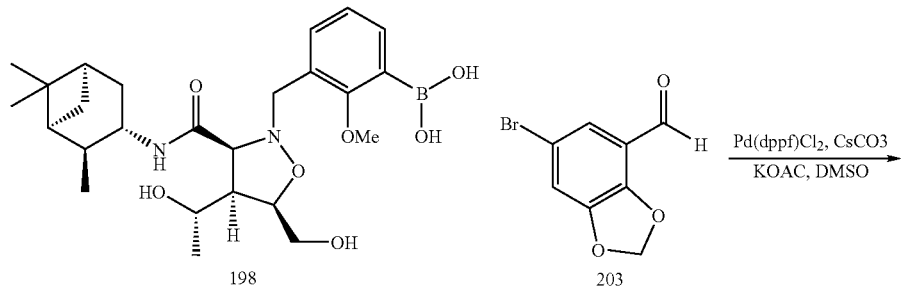
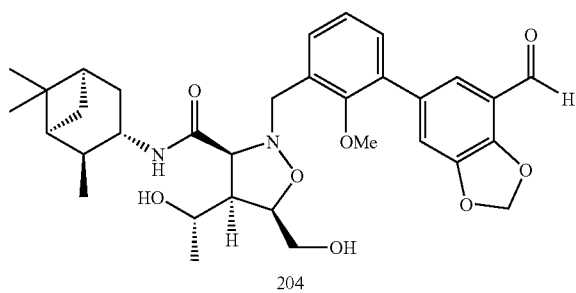
204

To a solution of boronic acid 198 (50 mg) in DMSO (1.5 mL) at 23° C. was added aryl bromide 203 (35 mg), cesium carbonate (100 mg), potassium acetate (10 mg) and Pd catalyst (9 mg). The mixture was purged with Argon and heated at 75° C. for 5 h. LCMS showed desired product and then reaction concentrated. Purification by HPLC (acidic 10-100) resulted in 30 mg of desired product 204.

Part B.

and extraction with DCM (3×15 mL). The organic layers were dried on $Na_2SO_4$ and concentrated to give 205 as a white foam and used without further purification in part C of this example.

Part C.

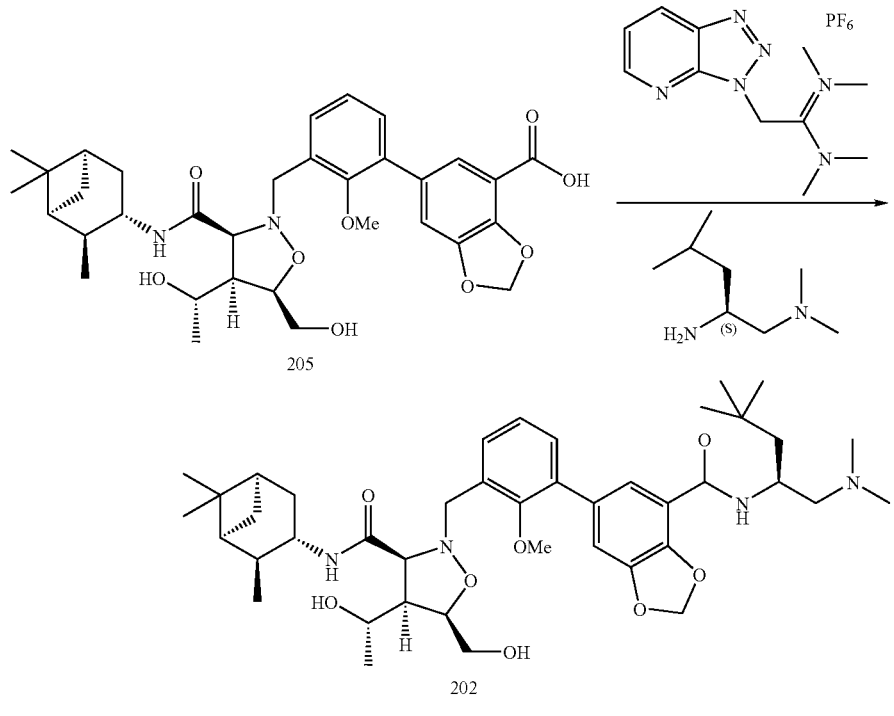

To a solution of 205 (7 mg) in DCM (0.6 mL) was added crude amine (10 uL), HATU (4 mg). The mixture was allowed to stir at 23° C. for 2 hr. The crude mixture was diluted with methanol (800 uL) and purified by JPLC (basic 10-100) gave desired product 202 3 mg. MS (ESI(+)) m/e 751.72 $(M+H)^+$.

Example 78

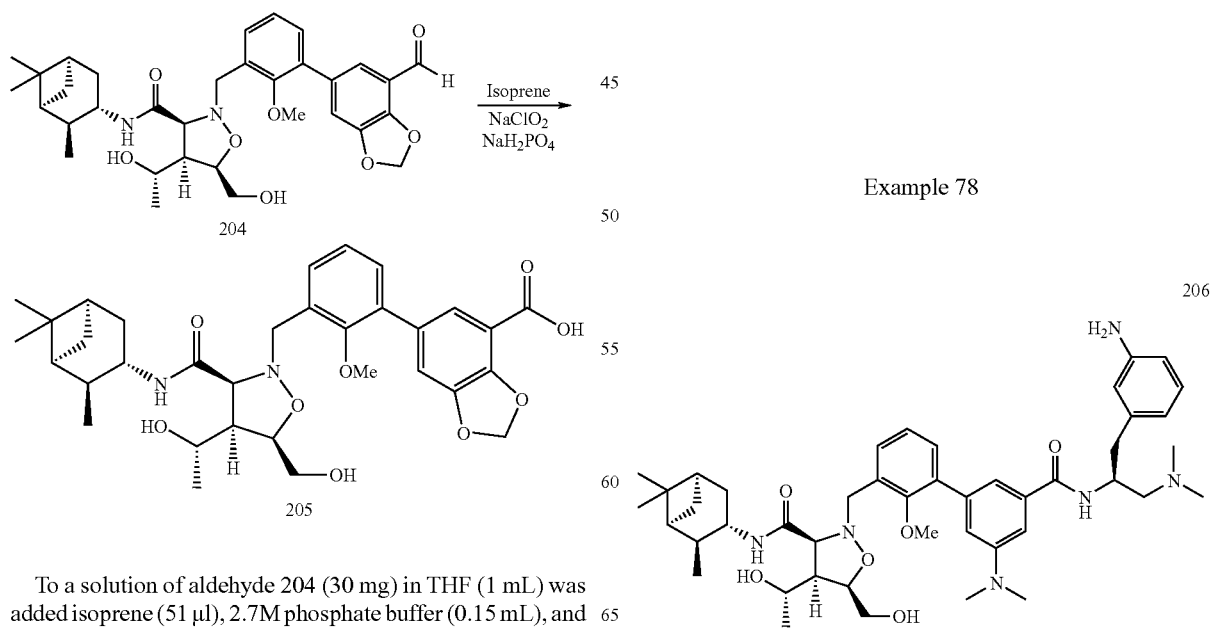

To a solution of aldehyde 204 (30 mg) in THF (1 mL) was added isoprene (51 μl), 2.7M phosphate buffer (0.15 mL), and $NaClO_2$ (18 mg) at 23° C. The reaction was stopped after 2 h by adding water (30 mL), acidifying to pH 1 with 6M HCl, Part A.

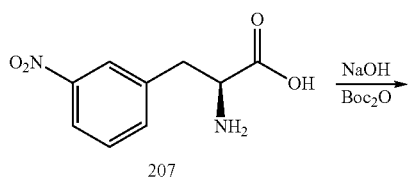

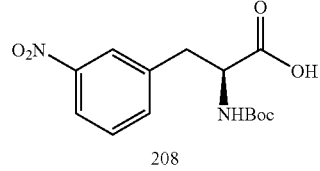

To a solution of phenylalanine 207 (0.5 g) in mixed solvents of dioxane (5 mL) and 1 N sodium hydroxide (5 mL) was added di-tert-butyl dicarbonate (0.7 g). The reaction mixture was stirred at 23° C. for 1.5 h. KHSO$_4$ (1 M) was added until the pH of the solution was 5. Ethyl acetate (3×100 mL) was used to extract the mixture. The combined organic layers were washed with brine, dried with Na$_2$SO$_4$ and concentrated to give 583 mg crude product 208 which was used without further purification in part B of this example.

Part B.

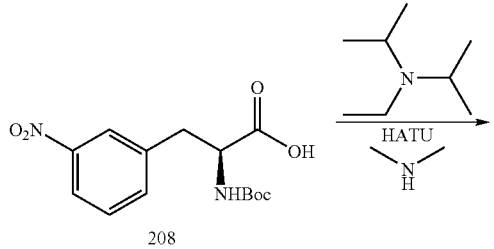

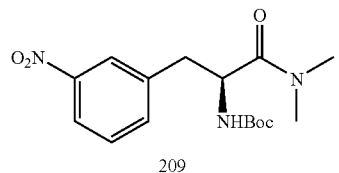

To a solution of Boc protected phenylalanine 208 (583 mg) in DCM (10 mL) at 23° C. was added HATU (544 mg), dimethyl amine (203 mg) and DIPEA (0.8 mL). The reaction mixture was stirred at 23° C. for 2 hr. The reaction mixture was then diluted with DCM (50 mL), washed with sat. sodium bicarbonate, sat. NH$_4$Cl, brine, dried over MgSO$_4$ and then concentrated to dryness. Flash chromatography on silica gel (10% ethyl acetate in Hexane, 40%, 60%) gave 500 mg desired product 209 (66% for two steps).

Part C.

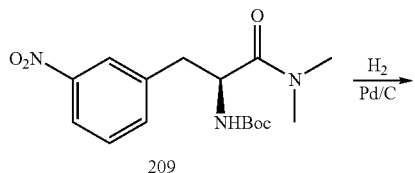

-continued

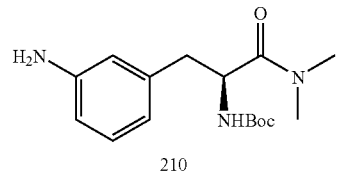

209 (500 mg) was dissolved in methanol (10 mL). The reaction solution was purged with N$_2$, palladium on carbon (10%, 0.6 g) was added, and a balloon full of H$_2$ was attached to the reaction flask. The reaction was stirred at 23° C. for 45 min and then the mixture was filtered through a short plug of celite. The Celite plug was washed with 2 portions of ethyl acetate. The organic solutions were combined and concentrated to give 450 mg of 210.

Part D.

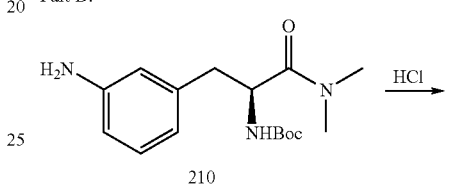

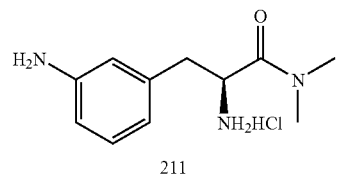

210 (100 mg) was dissolved in dry THF (1 mL) at 23° C. followed by the addition of HCl (4 M, 1 mL). The mixture was stirred at 23° C. for 4 hr then concentrated to dryness. Ethyl acetate (2×5 mL) was used to drive off the excess HCl to give 105 mg crude 211 which was used without further purification in part E of this example.

Part E.

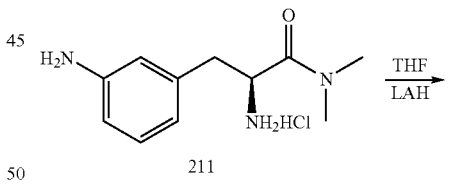

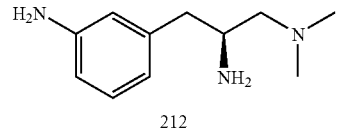

To a solution of 211 (100 mg) in THF (1.5 mL) under argon at 0° C. was added a solution of LAH (1 M, 1.7 mL) drop wise. The resulting mixture was warmed to 23° C. and stirred 12 h. The reaction mixture was quenched by the slow addition of water (0.2 mL), 15% NaOH (0.2 mL), and water (0.6 mL). Subsequent addition of 10 ml sodium/potassium tartrate solution and DCM (3×100 mL) was used to extract the aqueous solution. The combined organic solution was dried with MgSO$_4$ and concentrated to give crude oily product 212 (70 mg), which was used without further purification in part F of this example.

Part F.

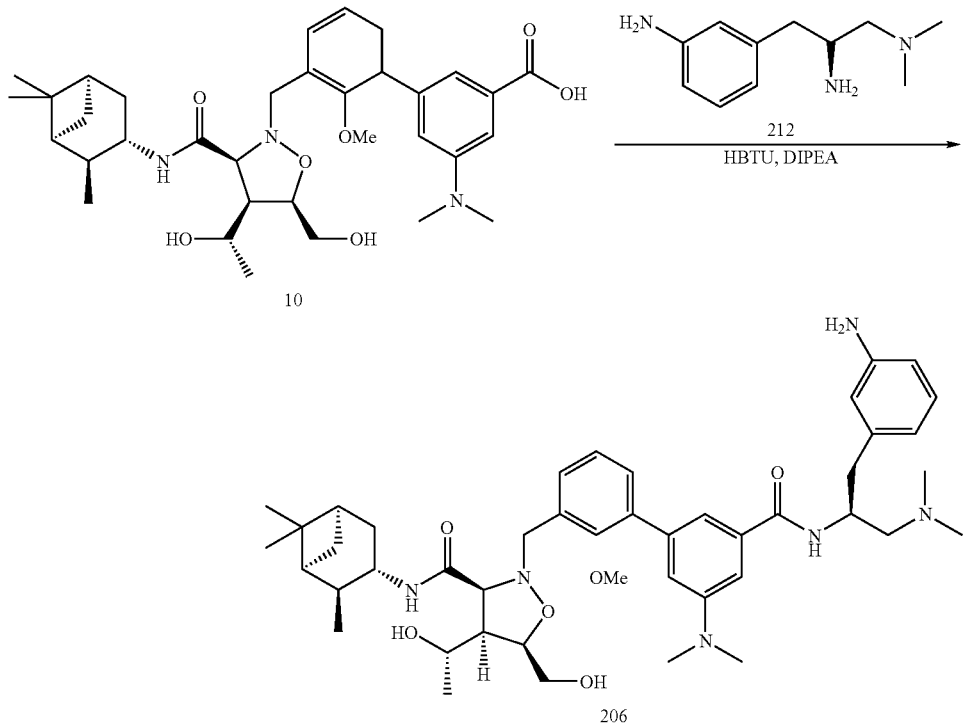

To a solution of 10 (14 mg) in DCM (3 mL) was added crude amine 212 (13 mg), HBTU (14 mg) and DIPEA (14 μl). The mixture was allowed to stir at 23° C. for 2 hr at which point the reaction mixture was diluted with DCM (50 mL) washed with sat. Sodium bicarbonate, sat. NH$_4$Cl, brine, dried over MgSO$_4$ and concentrated. HPLC purification (acidic method, 10-100) gave 2.8 mg of desired product 206. MS (ESI(+)) m/e 785.61 (M+H)$^+$.

Example 79

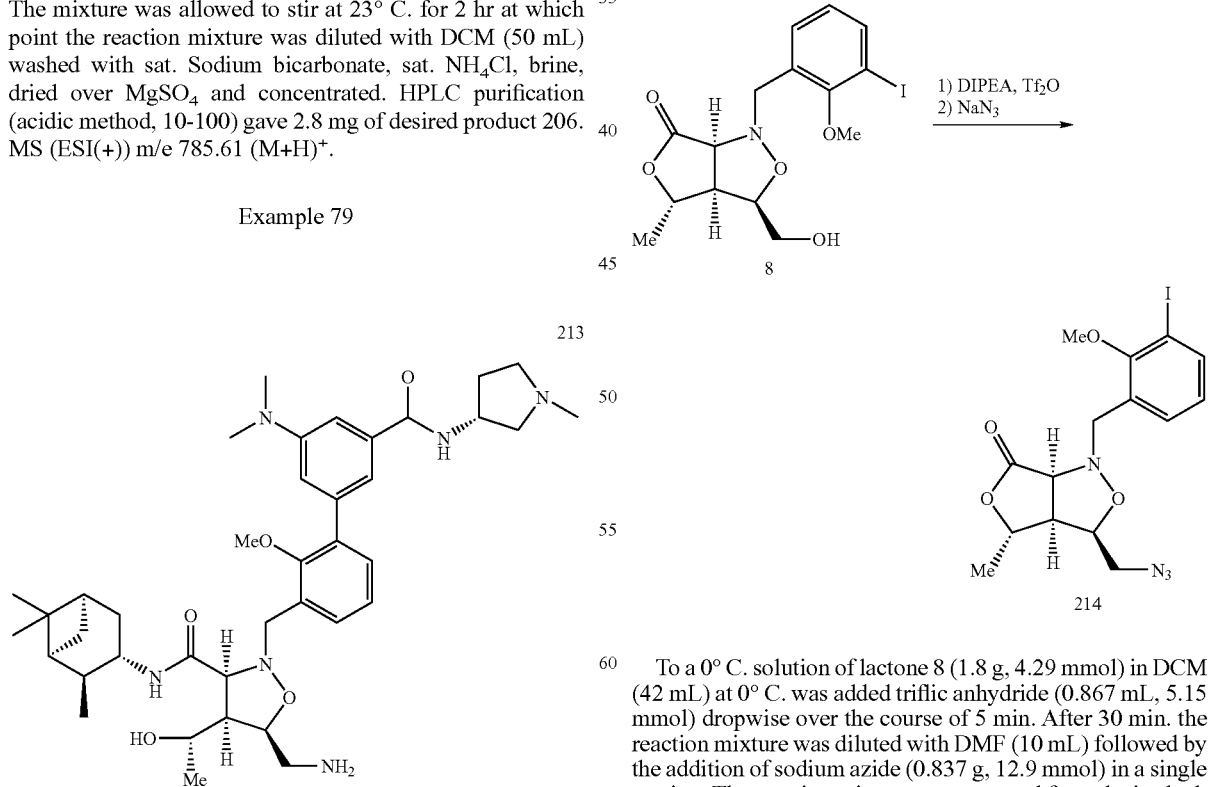

Part A.

To a 0° C. solution of lactone 8 (1.8 g, 4.29 mmol) in DCM (42 mL) at 0° C. was added triflic anhydride (0.867 mL, 5.15 mmol) dropwise over the course of 5 min. After 30 min. the reaction mixture was diluted with DMF (10 mL) followed by the addition of sodium azide (0.837 g, 12.9 mmol) in a single portion. The reaction mixture was removed from the ice bath and was allowed to warm slowly to 23° C. After stirring for 12 h, the reaction was quenched by the addition of water, extracted with EtOAc (2×100 mL), dried over MgSO₄, filtered and concentrated to an oil. The crude oil was purified by gradient flash chromatography (30-80% EtOAc/hexanes) to afford 1.7 g (89%) of azide 214.

Part B.

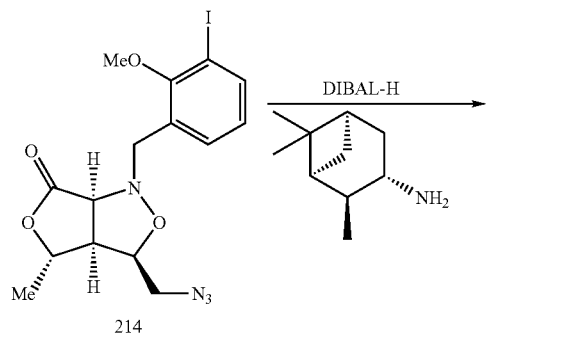
214

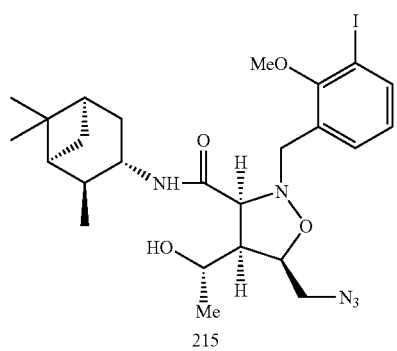
215

To a 0° C. solution of (+)-isopinocampheylamine (5.75 mL, 34.3 mmol) in THF (60 mL) was added 2M DIBAL in toluene (14.3 mL, 28.6 mmol). After stirring for 2 h, the reaction mixture was added to a solution of lactone 214 (2.54 g, 5.72 mmol) dissolved in THF (10 mL). The combined reaction mixture was stirred for 2 h, then poured into an Erlenmeyer flask containing a saturated solution of Rochelle salts and EtOAc. After stirring for 5 h. the reaction mixture was extracted with Ethyl Acetate (3×100 mL), dried (MgSO₄), filtered and concentrated to an oil. The crude oil was purified by gradient flash chromatography (30-70% EtOAc/hexanes) to afford 2.79 g (82%) of azide 215.

Part C.

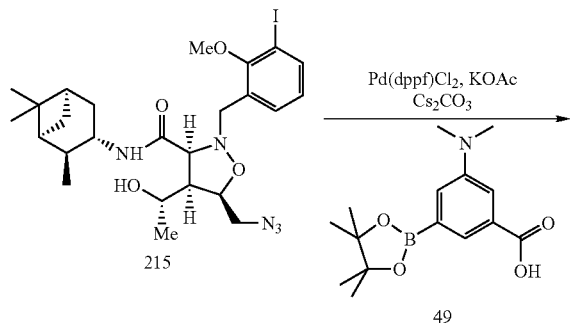
215
49

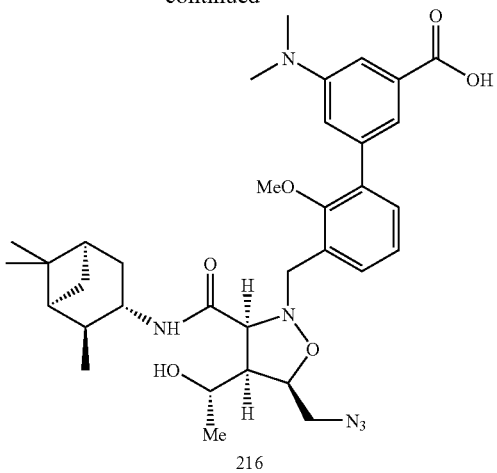
216

Isoxazolidine 215 (302 mg, 0.505 mmol), pinacol boronate 49 (368 mg, 1.26 mmol), Pd(dppf)Cl₂ (82 mg, 0.101 mmol), potassium acetate (65 mg, 0.657 mmol), and cesium carbonate (494 mg, 1.52 mmol) were dissolved in anhydrous DMSO (5 mL) and flushed under positive argon pressure. The reaction mixture was stirred at 60° C. for 2 h, then allowed to cool to ambient temperature. The reaction mixture was diluted with EtOAc (20 mL) and water (10 mL) and the aqueous phase was adjusted to pH 4 with 6M HCl. The reaction mixture was extracted with EtOAc (3×100 mL) and the combined organics were dried (MgSO₄), filtered and concentrated to an oil. The crude oil was purified by gradient flash chromatography (10-35% Acetone/hexanes) to afford 170 mg (53%) of biphenyl acid 216.

Part D.

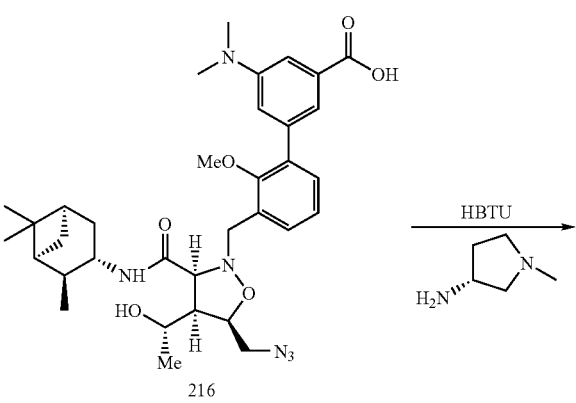
216
217

Biphenyl acid 216 (320 mg, 0.504 mmol) and HBTU (287 mg, 0.756 mmol) were dissolved in DMF (5 mL) followed by addition of (R)-1-methylpyrrolidin-3-amine (101 mg, 1.01 mmol). After stirring for 2 h, the reaction mixture was diluted with EtOAc (100 mL) and a saturated sodium bicarbonate solution. The mixture was extracted with EtOAc (3×100 mL), dried (MgSO$_4$), filtered and concentrated to an oil. The crude oil was purified by gradient flash chromatography (2-5% MeOH/DCM) to afford 176 mg (49%) of azide 217.

Part E.

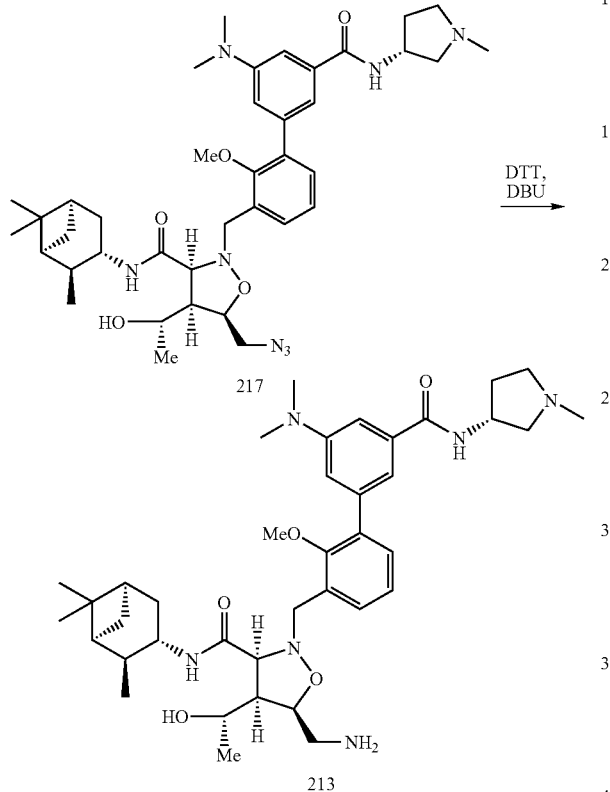

Azide 217 (13 mg, 0.018 mmol) and dithiothreitol (8.7 mg, 0.054 mmol) were dissolved in DMF (1 mL), followed by addition of DBU (8.5 uL, 0.054 mmol). After stirring for 1 h, the reaction mixture was purified directly on HPLC (Acetonitrile/40 mmol ammonium bicarbonate aqueous), to yield 6 mg (47%) of amine 213. MS ((ESI(+)) m/e 691.5 (M+H)$^+$.

Example 80

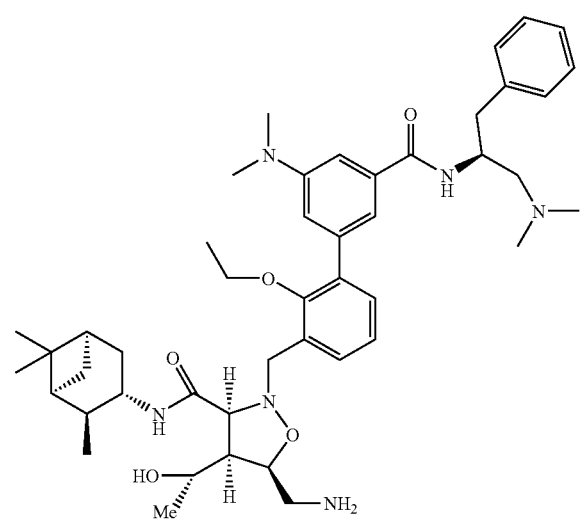

Part A.

Compound 218 was attained using compound 21 and following the protocol outlined in Example 79. MS ((ESI(+)) m/e 783.1 (M+H)$^+$.

Example 81

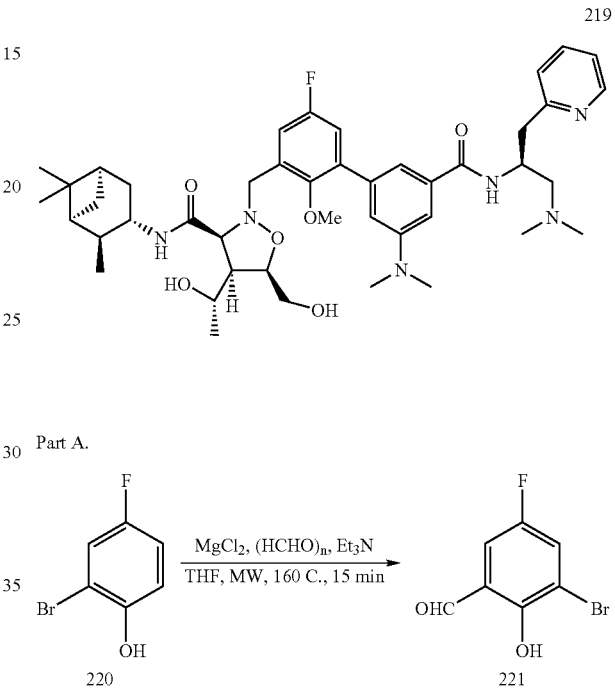

Part A.

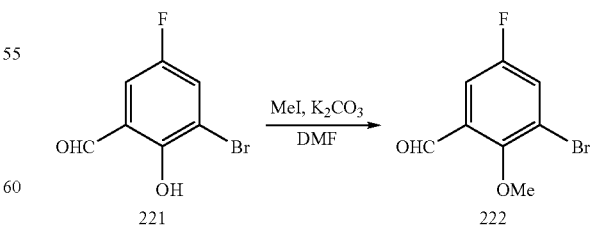

To a solution of MgCl$_2$ (powder 325 mesh, 5.0 g, 52 mmol, 2 eq), paraformaldehyde (3.0 g, 79 mmol, 3 eq) and Et$_3$N (7.0 mL, 52 mmol, 2 eq) in THF (60 mL) was added 220 (5.0 g, 26 mmol, 1 eq), heated in the microwave at 160 C for 15 min. TLC (3:2 Hexane:DCM) showed complete consumption of 220. THF was evaporated and the reaction mixture was taken up in EtOAc, washed with brine, dried, filtered and concentrated in vacuo to afford 5.2 g of 221 which was used without purification. Yield 93%.

Part B.

To a solution of 221 (6.0 g, 31 mmol, 1 eq) in DMF (38 mL) was added K$_2$CO$_3$ (3.0 g, 41 mmol, 1.3 eq), stirred at rt for 10 min, resulting in a suspension. Iodomethane (3.0 mL, 41 mmol, 1.3 eq) was added dropwise and allowed to stir at rt overnight. TLC (9:1 Hexane:EtOAc) showed no remaining 221. The mixture was diluted into water and extracted with EtOAc. The organic was separated, washed with brine, dried, filtered and concentrated in vacuo to afford 222 as an oil. The crude material was purified by column chromatography (silica gel, 50% DCM in hexane) to afford 2.4 g of 222 as a white solid.

Part C.

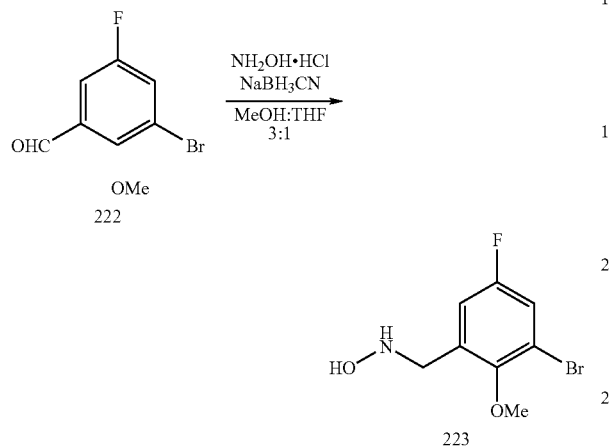

To a solution of 222 (2.5 g, 11 mmol, 1 eq) in MeOH-THF (3:1, 20 mL) was added an aqueous solution of hydroxylamine hydrochloride salt (0.75 g, 11 mmol, 1.2 eq in 4 mL of water) in one portion. The pH was adjusted to 9 with NaOH (6N), and stirred at rt for 1 hr where TLC (2:1 Hexane:EtOAc) showed complete consumption of 222. NaBH$_3$CN (1.3 g, 21 mmol, 2 eq) was added with a crystal of methyl red and the solution acidified to pH 2-3 using HCl in MeOH (20 V/V). The pH of the reaction solution was maintained at pH 3 over the course of 12 h by addition of small amounts of the methanolic HCl solution, where it was basified to pH 9 with NaOH (2 N). The solution was extracted with EtOAc, washed with brine, dried, filtered and concentrated in vacuo to afford an orange oil. The crude material was purified by column chromatography (silica gel, 55% EtOAc in Hexane) to afford 2.7 g of 223 as a cream solid.

Part D.

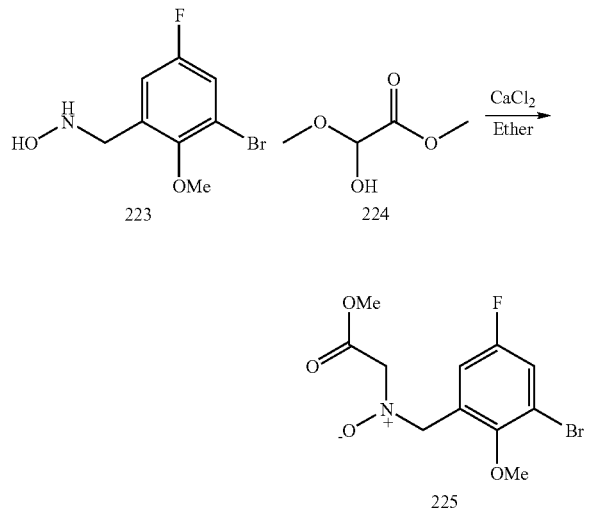

To a solution of 223 (1.8 g, 7.0 mmol, 1 eq) and glyoxylate ester 224 (1.0 g, 9.0 mmol 1.3 eq) in diethyl ether (20 mL) was added anhydrous CaCl$_2$ (1.0 g, 9.0 mmol, 1.3 eq), left stirring at rt for 3 h, resulting in a suspension. The suspension was filtered through a Celite plug washing with DCM and ether. The resultant yellow solution was concentrated in vacuo to afford 2.0 g of 225 as yellow oil and used directly without purification.

Part E.

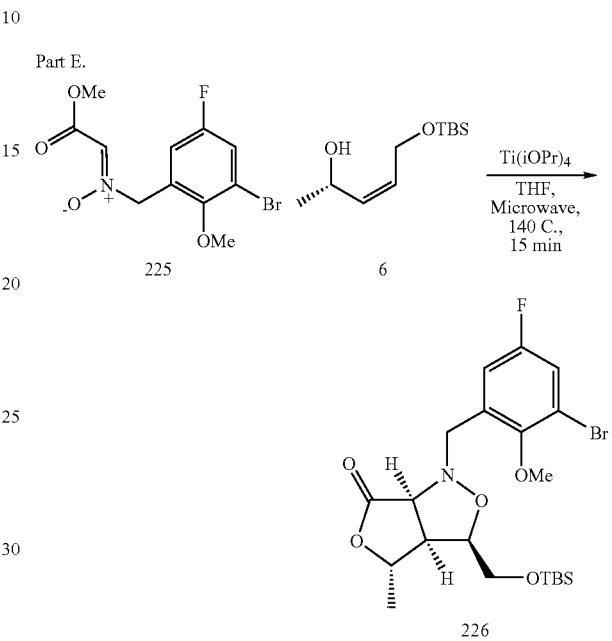

To a solution of 225 (0.497 g, 1.48 mmol, 1 eq) in anhydrous THF (10 mL) was added (S,Z)-5-tert-butyldimethylsiloxy)pent-3-en-2-ol 6 (0.5 mL, 1.77 mmol, 1.2 eq) and Ti(iOPr)$_4$ (0.65 mL, 2.22 mmol, 1.5 eq) heated in the microwave at 140 C for 15 min. TLC (30:1 DCM:Et$_2$O) showed consumption of nitrone 225 and the allylic alcohol 6. 3-(dimethylamino)-1,2-propanediol (1 mL) in EtOAc (1 mL) was added and the dark brown solution left stirring at rt overnight. The dark brown solution was diluted with EtOAc and quenched with Rochelle's salt solution, washed with water, brine, dried, and concentrated in vacuo to afford a brown oil. The crude material was purified by column chromatography (silica gel, 10% EtOAc in Hexane) to afford 0.490 g of 226 as a brown oil.

Part F.

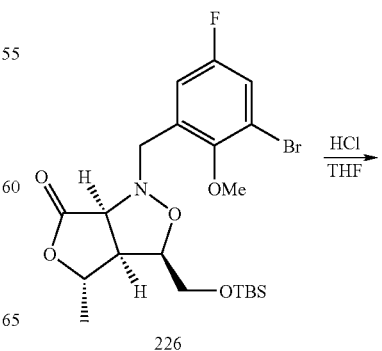

371

-continued

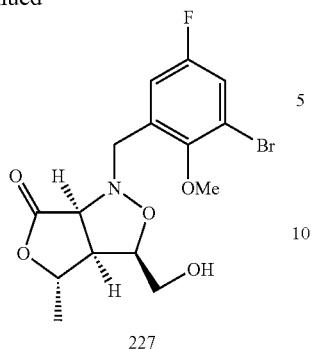

227

To a solution of 226 (0.40 g, 0.903 mmol, 1 eq) in THF (5 mL) was added concentrated 6 N HCl (0.45 mL, 2.71 mmol, 3 eq) and stirred at rt for 2 h. TLC (1:2 hexane:EtOAc) of neutralized aliquot showed complete consumption of 226. The reaction was neutralized with NaHCO₃, extracted with EtOAc, washed with brine, dried, filtered and concentrated in vacuo to afford a brown oil. The crude material was purified by column chromatography (silica gel, 50% EtOAc in Hexane) to afford 0.251 g of 227 as a brown solid. 81% yield Part G.

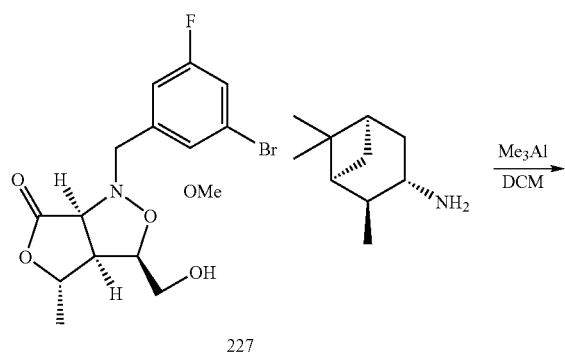

227

372

-continued

228

To a solution of (+−)isocamphenylamine (0.314 g, 2.0 mmol, 2 eq) flushed with Ar in anhydrous DCM (5 mL), was added Me₃Al (2 M solution in Hexane, 0.513 mL, 1.02 mmol, 2 eq) dropwise over 20 min and the resultant clear solution stirred for 40 m at rt. A solution of the lactone 227 (0.4 g, 0.1.0 mmol, 1 eq) in DCM (15 mL) was added by dropwise and the reaction mixture was stirred at rt for 12 h until all the 227 was consumed as indicated by TLC (2:1 EtOAc:Hexane) The reaction was diluted with DCM and quenched on dropwise addition to a rapidly stirring solution Rochelle's salt, and stirred at rt for 2 h. The organic layer was separated and washed with water, brine, dried, and concentrated in vacuo to afford a yellow oil. The crude material was purified by column chromatography (silica gel, 50% EtOAc in Hexane) to afford 0.33 g of 228 as a yellow oil. Yield 53%

Part H.

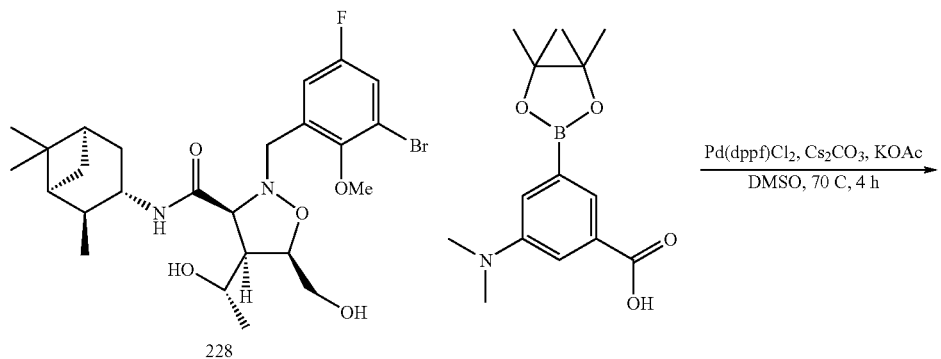

228

-continued

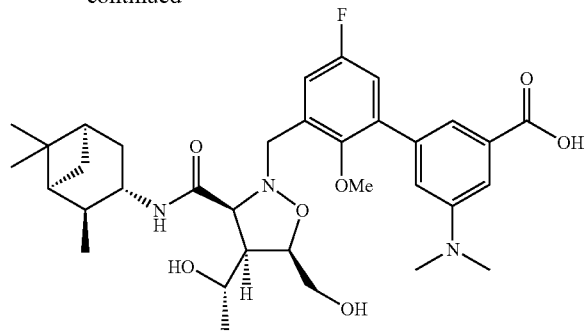

229

To a solution of isoxazolidine 228 (100 mg, 0.179 mmol, 1 eq) in DMSO (5 mL), flushed with argon, was added the pinacolboronate (68 mg, 0.232 mmol, 1.3 eq), potassium acetate (26 mg, 0.268 mmol, 1.5 eq) and cesium carbonate (175 mg, 0.526 mmol, 3 eq). Upon stirring for 10 min, Pd(dppf)Cl$_2$ (29 mg, 0.036 mmol, 0.2 eq) was added as a single portion. The mixture was heated to 70 C for 4 h, then allowed to cool to rt. EtOAc and brine were added and the pH adjusted 3-4 with HCl (2N). The organic layer was separated, washed with water, brine, dried, and concentrated in vacuo to afford a brown black oil. The crude material was purified by column chromatography (silica gel, 4% MeOH in DCM) to afford 35 mg of 229 as a brown solid. 30% yield.

Part I.

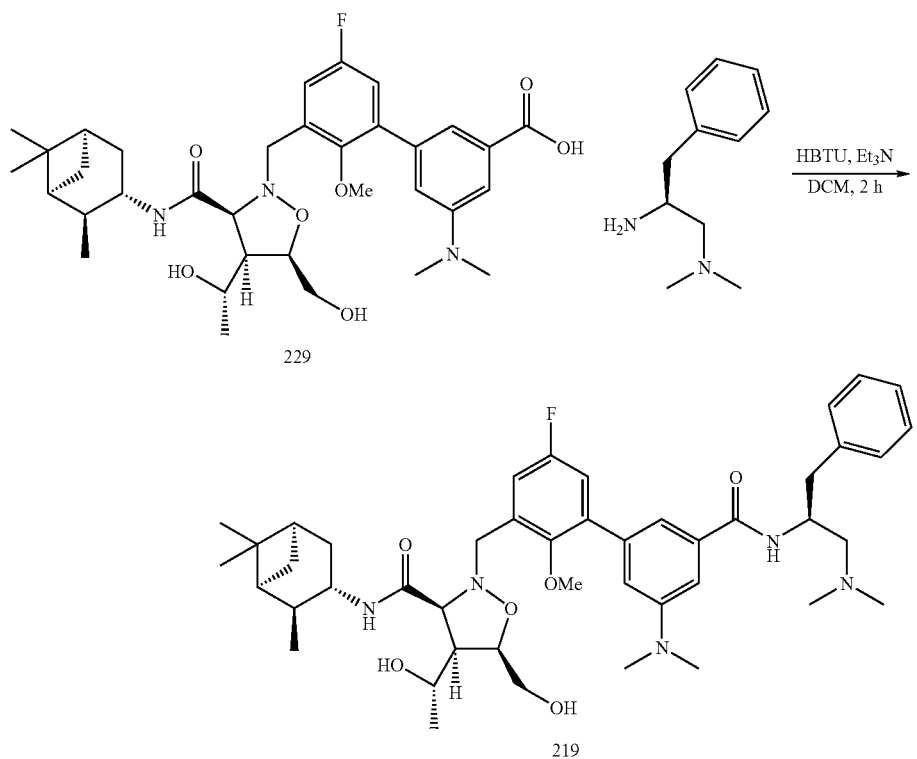

A solution of 229 (35 mg, 0.055 mmol, 1 eq) in DCM (3 mL) was added Et$_3$N (23 uL, 0.165 mmol, 3 eq) and HBTU (42 mg, 0.110 mmol, 2 eq) and allowed to stir at rt for 10 min. To this solution was added the amine (9.8 mg, 0.055 mmol, 1 eq) and allowed to stir at rt for 2 h. The reaction was taken up in DCM, washed with K$_2$CO$_3$, water, brine, dried, and concentrated in vacuo to afford a brown solid. The crude material was diluted with MeOH (2 mL) and purified by reverse-phase HPLC (MeCN/water with 40 mM NH₄HCO₃) to afford 13 mg of 219 as a white solid. 20% yield

Example 82

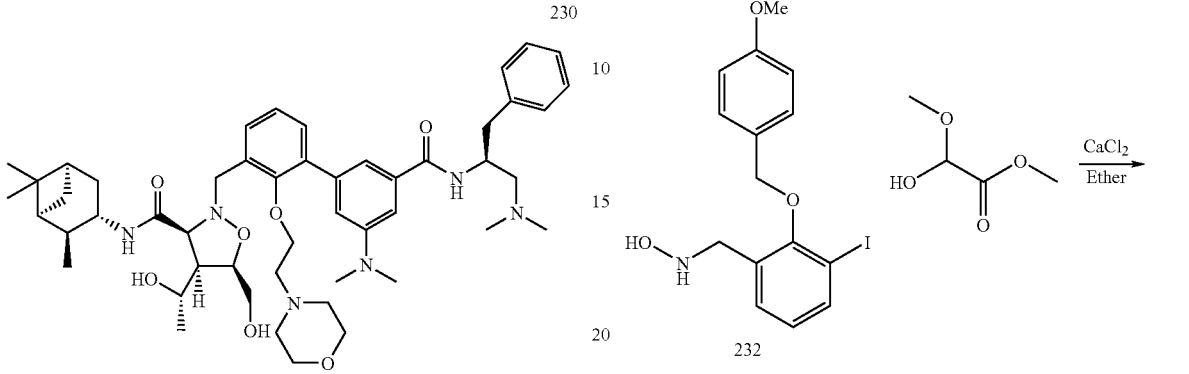

230

Part A

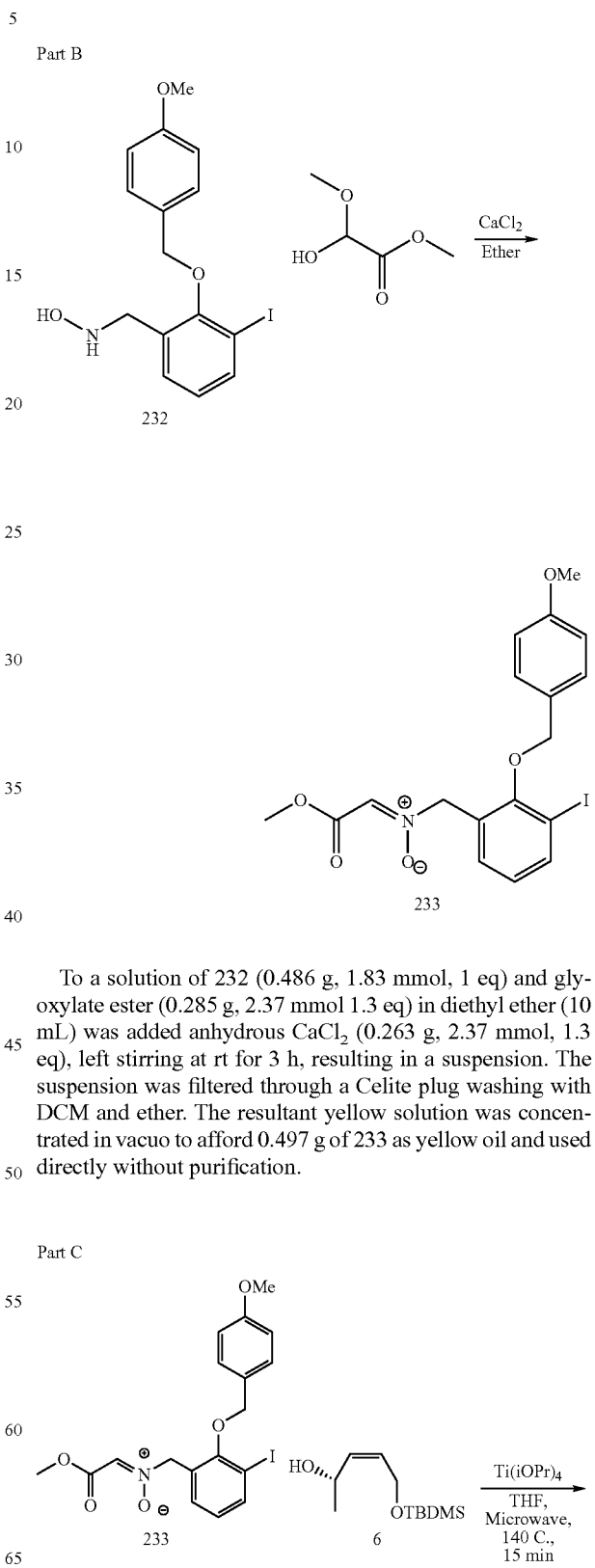

over MgSO₄, filtered and concentrated in vacuo. The crude product was purified by silica gel chromatography (50-100% EtOAc/hexane) to afford 8 g of compound 232. Yield 64%.

Part B

Aldehyde 231 (12 g, 33 mmol, 1 eq) and hydroxylamine hydrochloride (2.7 g, 39 mmol, 1.18 eq) were dissolved in THF/MeOH (3:1, 60 mL). Water (2 mL) was added and the pH was adjusted to 9 with 6 N KOH. The reaction mixture was stirred at rt overnight and then NaBH₃CN (3.1 g, 49 mmol) was added followed by a crystal of methyl orange. The pH was adjusted to 3 and the resulting ruby red color was maintained for the duration of the reaction by the frequent addition of 1 N HCl. After stirring for 2 h another portion of NaBH₃CN (1 g, 13 mmol, 0.4 eq) was added. The solution was stirred for 16 h and then neutralized to pH 7 and diluted with DCM. The mixture was washed with water (3×10 mL), brine and dried To a solution of 232 (0.486 g, 1.83 mmol, 1 eq) and glyoxylate ester (0.285 g, 2.37 mmol 1.3 eq) in diethyl ether (10 mL) was added anhydrous CaCl₂ (0.263 g, 2.37 mmol, 1.3 eq), left stirring at rt for 3 h, resulting in a suspension. The suspension was filtered through a Celite plug washing with DCM and ether. The resultant yellow solution was concentrated in vacuo to afford 0.497 g of 233 as yellow oil and used directly without purification.

Part C

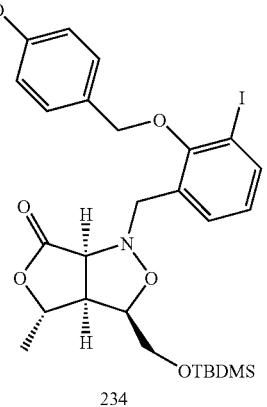

Nitrone 233 (5 g, 11 mmol, 1 eq), allylic alcohol 6 (2 g, 11 mmol, 1 eq) and Ti(iOPr)₄ (4 g, 4 mL, 13 mmol, 1.18 eq) were dissolved in toluene (40 mL) and heated in a microwave at 120° C. for 10 min. The reaction mixture was diluted with EtOAc (10 mL) and 3-(dimethylamino)-1,2-propanediol (4 mL) was added. After stirring for 2 h, EtOAc (10 mL) was added and the mixture was washed with water (3×10 mL), brine (10 mL), dried over MgSO₄, filtered and concentrated in vacuo. The crude residue was purified by silica gel chromatography (10-30% Hexane-EtOAc) to afford 2.5 g of compound 234. Yield 35%.

Part D

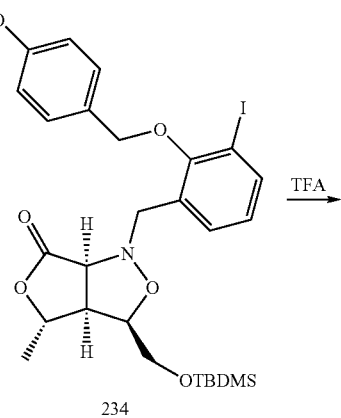

To a solution of PMB ether 234 (2 g, 3 mmol, 1 eq) in DCM (150 mL) was added TFA (3 g, 31 mmol, 10.33 eq) dropwise at 0° C. The solution was stirred for 1.5 h and quenched with saturated NaHCO₃ (60 mL). The organic phase was separated, washed with brine, dried over Na₂SO₄, filtered and concentrated in vacuo to afford an oil. The resulting oil was purified by silica chromatography (10-30% hexane-EtOAc) to afford 1.2 g of compound 235. Yield 74%.

Part E

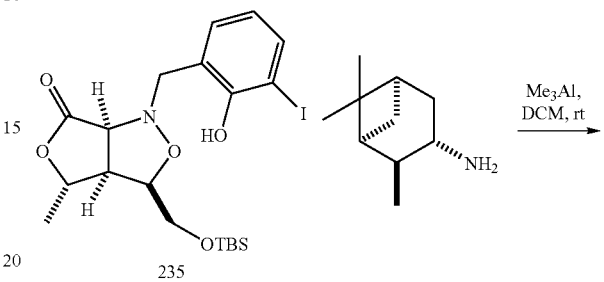

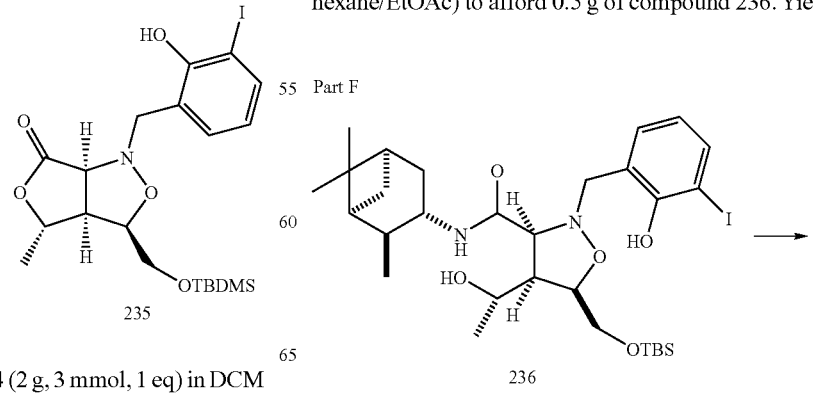

To a solution of (+)-isopinocampheylamine (0.6 g, 0.7 mL, 4 mmol, 2 eq) in DCM (10 mL) at rt was added Me₃Al (0.4 g, 3 mL, 2 M solution in toluene, 6 mmol, 3 eq) dropwise over 2.5 min. The solution was stirred at rt for 10 min prior to the dropwise addition of a solution of lactone 235 (1 g, 2 mmol, 1 eq) in DCM (15 mL). The reaction was stirred for 24 h, diluted with DCM (125 mL) and a saturated solution of Rochelle's salt (125 mL). The mixture was vigorously stirred for 2 h until two phases formed. The layers were separated and the organic phase was washed with water, brine, dried over MgSO₄, filtered and concentrated in vacuo to afford a solid. The solid was purified by silica gel chromatography (25% hexane/EtOAc) to afford 0.5 g of compound 236. Yield 39%.

Part F

379
-continued

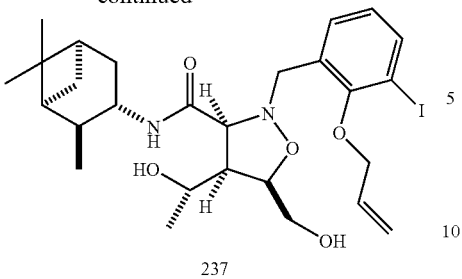

237

Phenol 236 (187 mg, 0.27 mmol, 1 eq) was dissolved in DMF (3.5 mL) and treated with K₂CO₃ (111 mg, 0.8 mmol, 3 eq), allylbromide (49 mg, 0.4 mmol, 1.48 eq). The solution was stirred for 2.5 h, diluted with water and extracted with diethyl ether (3×4 mL). The organic phase was separated, dried over Na₂SO₄, filtered and concentrated in vacuo to afford a solid. The resulting solid was dissolved in THF/Et₃N (1:1, 6 mL) and treated with a solution of HF/pyridine (1 mL) at 0° C. The solution was stirred for 1 h at rt and quenched with TMSOMe (25 mL) and concentrated in vacuo to afford a solid which was purified by silica gel chromatography (20% DCM/hexane) to afford 0.21 g of compound 237 as a white solid. Yield 67%.

Part G

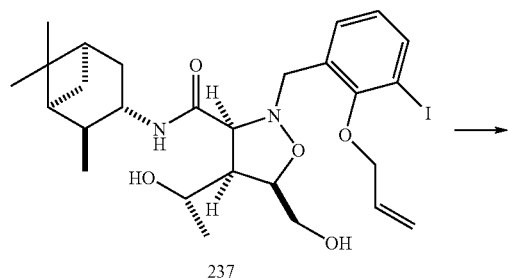

237

380
-continued

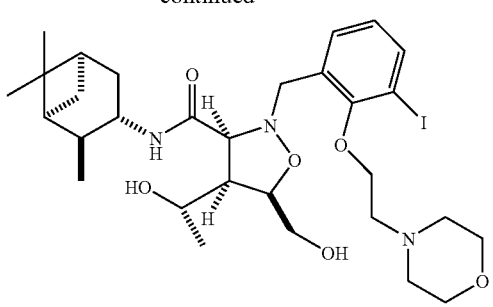

238

To a solution of the alkene 237 (0.14 g, 0.2 mmol, 1 eq) in t-BuOH (16 mL), THF (8 mL) and H₂O (2 mL) was added NMO (80 mg, 0.8 mmol, 4 eq) followed by the dropwise addition of OsO₄ (0.21 g, 2.9 mL, 2.5% solution in 2-methyl-2-propanol, 0.02 mmol, 0.1 eq). After 3 h, the reaction mixture was diluted with DCM (5 mL), brine and 10% Na₂S₂O₃ and the organic phase was separated. The aqueous phase was extracted with DCM (2×60 mL), and the combined organics were dried over Na₂SO₄, filtered and concentrated in vacuo to afford a solid. The solid was dissolved in THF/water (10:1, 1.2 mL) and treated with periodic acid (80 mg, 0.4 mmol, 2 eq) in single portion and stirred for 12 h. The solution was diluted with DCM (5 mL) and washed with brine, dried over Na₂SO₄, filtered and in vacuo to afford an oil. The resulting oil was suspended in DCM (5 mL) and treated with AcOH (10 uL), morpholine (40 mg, 0.4 mmol, 2 eq) and sodium triacetoxyborohydride (140 mg, 0.4 mmol, 2 eq) and stirred for 12 h. The solution was diluted with 0.1 M NaOH (1 mL), saturated NaCl (1 mL) and extracted with EtOAc (3×3 mL). The combined organic was concentrated in vacuo to afford an oil. The oil was purified by silica gel chromatography (DCM/MeOH/AcOH, 99.5:0:0.5 to 97.5:2:0.5) to afford 75 mg of compound 238.

Part H

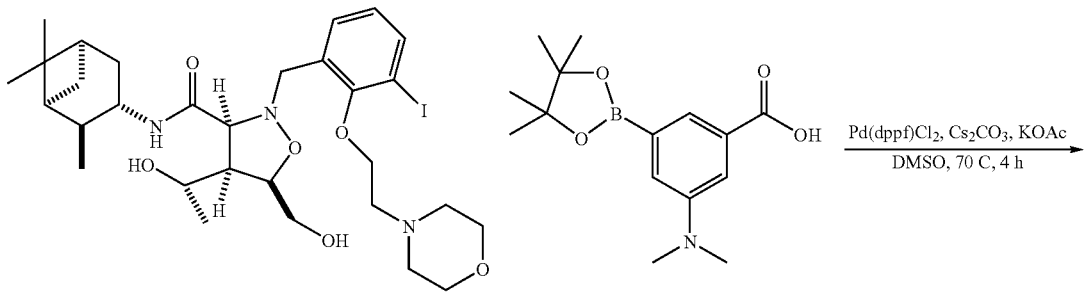

238

-continued

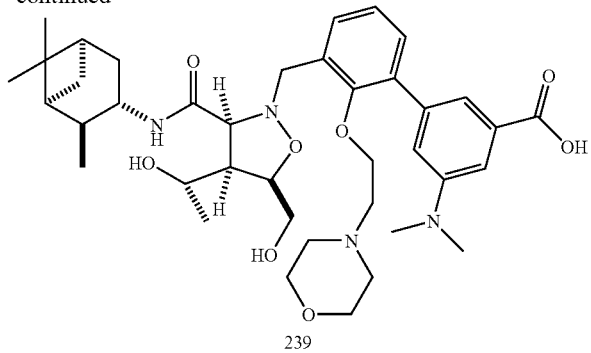

239

A flask containing aryl iodide 238 (25 mg, 0.04 mmol, 1 eq), pinacolboronate (17 mg, 0.06 mmol, 1.5 eq), KOAc (5 mg, 0.048 mmol, 1.2 eq), cesium carbonate (39 mg, 0.12 mmol, 3 eq) and Pd(dppf)Cl$_2$ (6.5 mg, 8 μmol, 0.2 eq) was purged with argon and DMSO (2 mL) was added. The mixture was heated to 70° C. for 3 h and then cooled to rt. The solution was diluted with DCM (10 mL), water (5 mL) and the pH was adjusted to 6.8 with 0.1 N HCl. The aqueous phase was extracted with DCM (2×10 mL) and the combined organics were washed with brine (20 mL), dried over MgSO$_4$, filtered and concentrated in vacuo to afford a dark brown oil. The resulting oil was purified by flash chromatography (2.5-5% CH$_2$Cl$_2$/MeOH) to afford 16 mg of compound 239 as a yellow solid. Yield 54%.

Part I

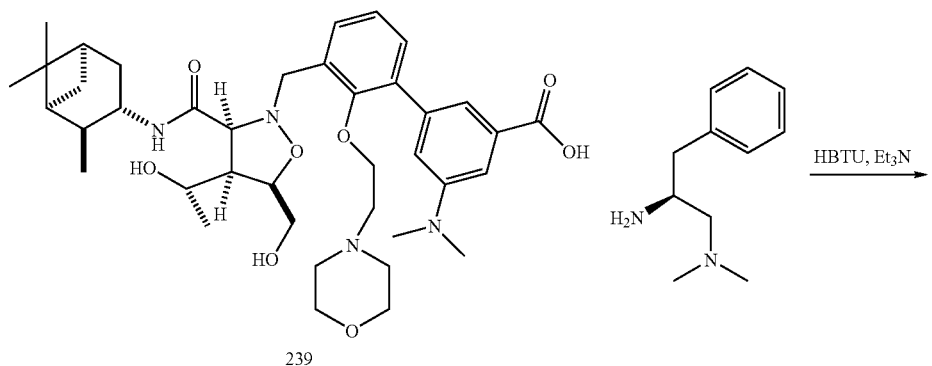

239

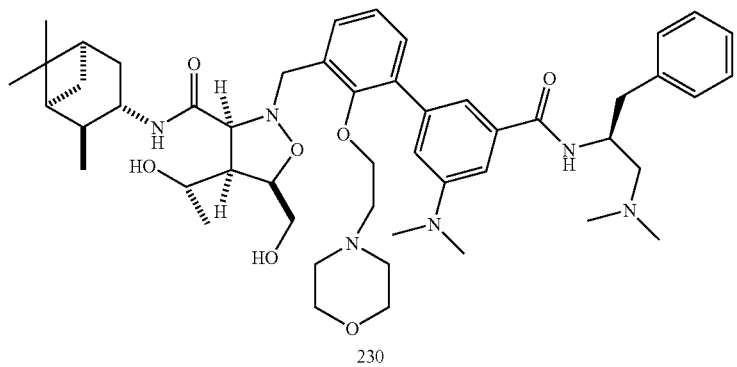

230

To a solution of 239 (8 mg, 0.02 mmol, 1 eq) in DMF (1.5 mL) was added HBTU (9 mg, 0.02 mmol, 1 eq), amine (4 mg, 0.02 mmol, 1 eq) and Et$_3$N (4 mg, 5 uL, 0.04 mmol, 2 eq). The solution was stirred for 2 h, diluted with water (0.5 mL) and purified by reverse-phase HPLC (MeCN/water with 40 mM NH$_4$HCO$_2$) to yield 7 mg of compound 230. Yield 67%. MS (ESI(+)) m/z 870.1 (M+H)$^+$.

Example 83

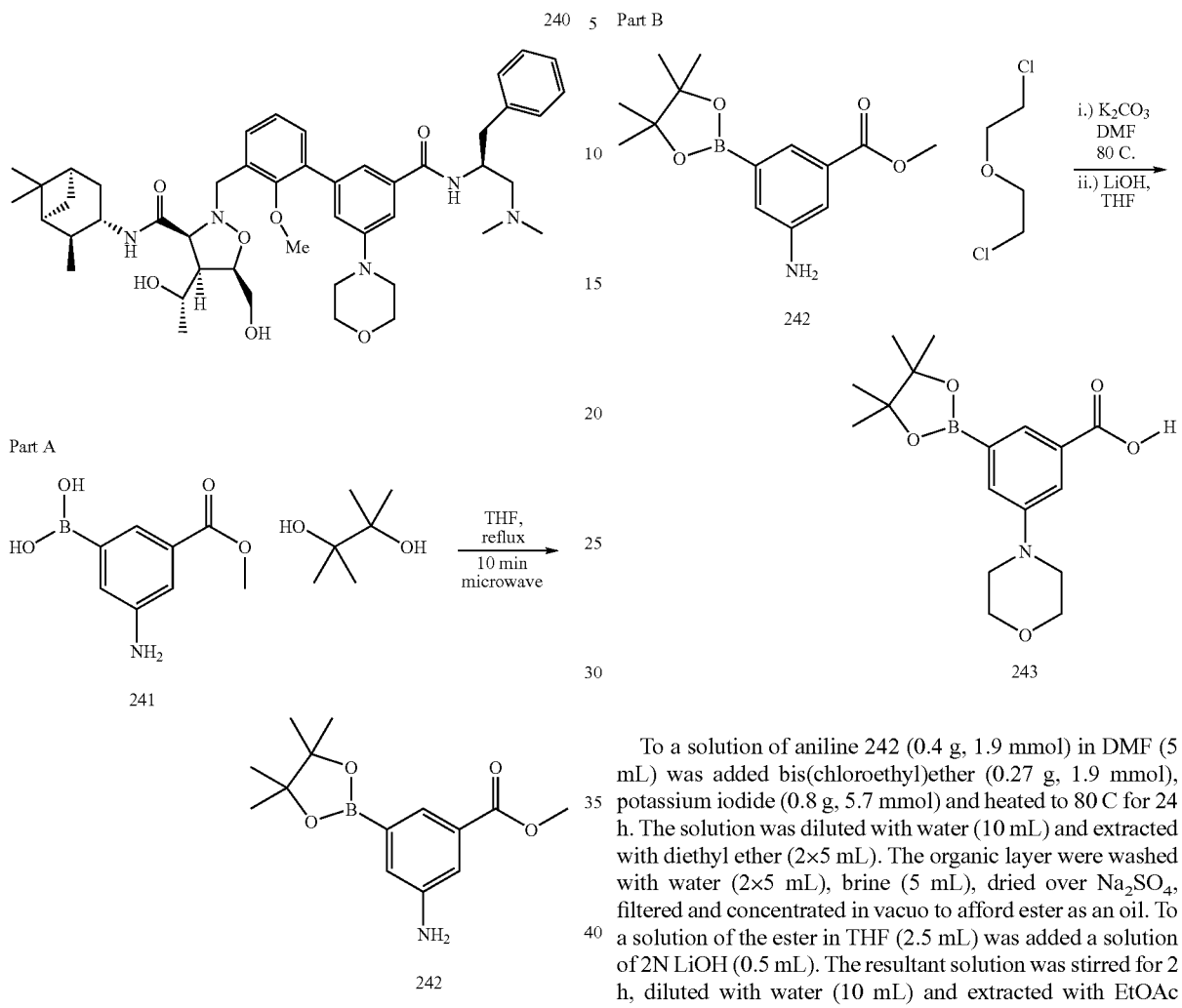

Part A

Methyl(3-Amino-5-carboxylphenyl)boronate 241 (1.5 g, 8.3 mmol, 1 eq) and pinacol (2.9 g, 25 mmol, 3 eq) were combined with THF (7 mL) and heated in a microwave to 140 C for 10 min, the reaction mixture was cooled to rt and then concentrated to an orange oil. The crude material 242 was used without further purification Part B To a solution of aniline 242 (0.4 g, 1.9 mmol) in DMF (5 mL) was added bis(chloroethyl)ether (0.27 g, 1.9 mmol), potassium iodide (0.8 g, 5.7 mmol) and heated to 80 C for 24 h. The solution was diluted with water (10 mL) and extracted with diethyl ether (2×5 mL). The organic layer were washed with water (2×5 mL), brine (5 mL), dried over $Na_2SO_4$, filtered and concentrated in vacuo to afford ester as an oil. To a solution of the ester in THF (2.5 mL) was added a solution of 2N LiOH (0.5 mL). The resultant solution was stirred for 2 h, diluted with water (10 mL) and extracted with EtOAc (2×10 mL). The organic layers were washed with brine (10 mL), water (10 mL) and dried ($Na_2SO_4$), filtered and concentrated in vacuo to afford an oil. The oil was subjected to column chromatography (30% EtOAc in hexane to afford 243 as a white solid. 42% yield Part C

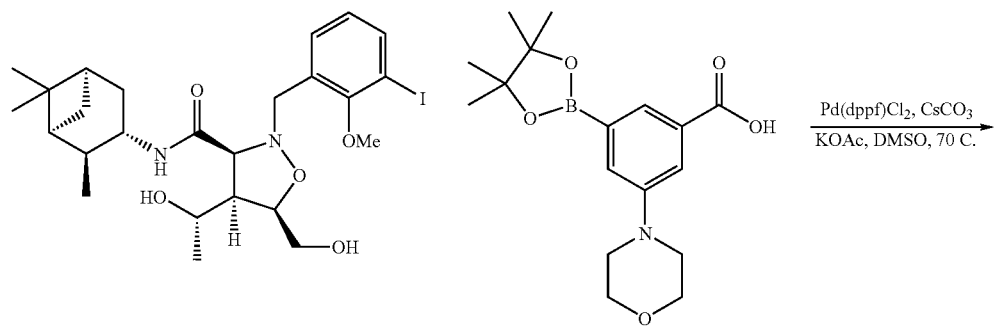

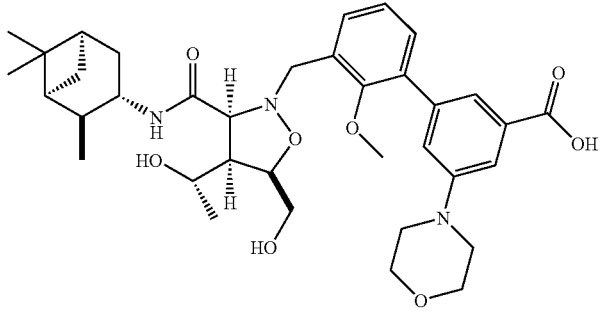

245

A flask containing aryl iodide 9 (40 mg, 0.07 mmol, 1 eq), pinacolboronate 243 (30 mg, 0.09 mmol, 1.5 eq), KOAc (6.8 mg, 0.069 mmol, 1.2 eq), cesium carbonate (68 mg, 0.2 mmol, 3 eq) and Pd(dppf)Cl₂ (10 mg, 14 μmol, 0.2 eq) was purged with argon and DMSO (2 mL) was added. The mixture was heated to 70° C. for 3 h and then cooled to rt. The solution was diluted with DCM (10 mL), water (5 mL) and the pH was adjusted to 6.8 with 0.1 N HCl. The aqueous phase was extracted with DCM (2×10 mL) and the combined organics were washed with brine (20 mL), dried over MgSO₄, filtered and concentrated in vacuo to afford a dark brown oil. The resulting oil was purified by flash chromatography (2.5-5% CH₂Cl₂/MeOH) to afford 15 mg of compound 245 as a yellow solid. Yield 22%.

Part D

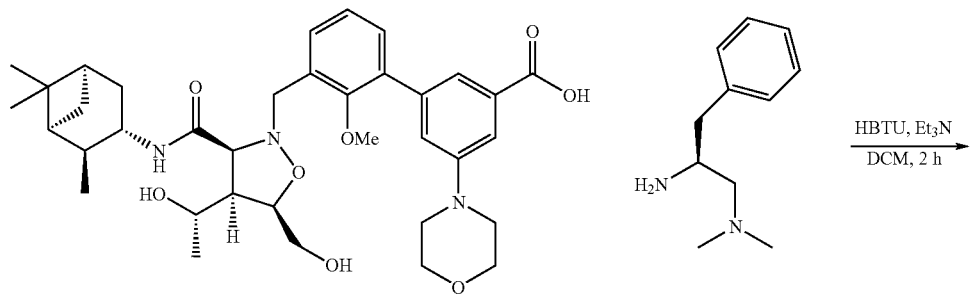

245

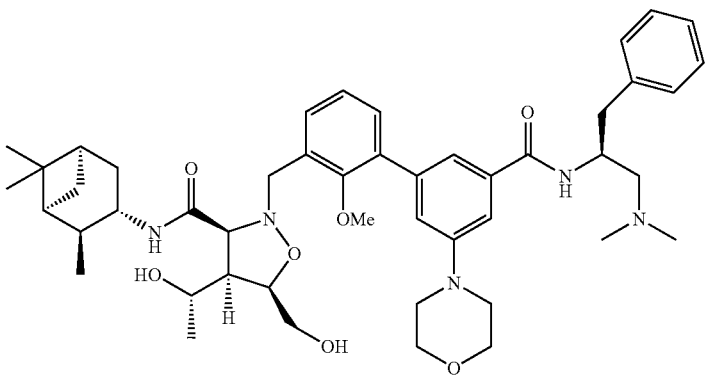

246

A solution of 245 (10 mg, 0.015 mmol, 1 eq) in DCM (1 mL) was added Et₃N (4 uL, 0.031 mmol, 2 eq) and HBTU (8.7 mg, 0.023 mmol, 1.5 eq) and allowed to stir at rt for 10 min. To this solution was added the amine (3.3 mg, 0.023 mmol, 1.5 eq) and allowed to stir at rt for 2 h. The reaction was taken up in DCM, washed with K₂CO₃, water, brine, dried, and concentrated in vacuo to afford a brown solid. The crude material was diluted with MeOH (2 mL) and purified by reverse-phase HPLC (MeCN/water with 40 mM NH$_4$HCO$_3$) to afford 4 mg of 246 as a white solid. 32% yield MS (ESI(+)) m/z 813.0 (M+H)$^+$.

Example 84

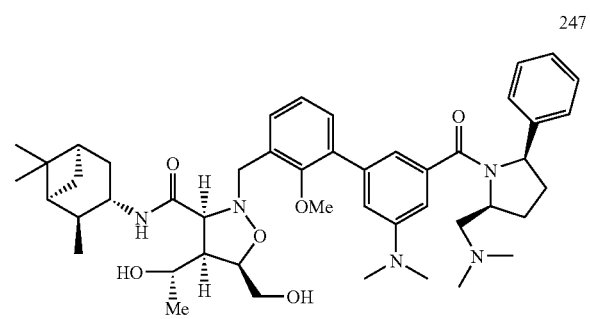

247

Part A

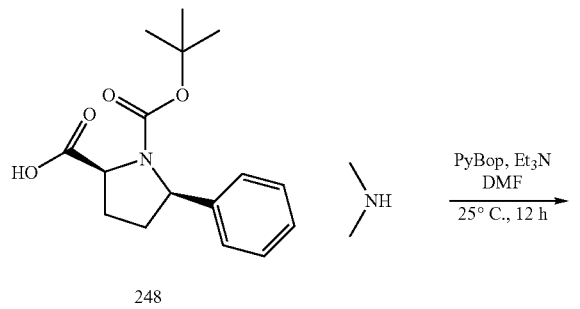

248

To a solution of 248 (5 g, 17 mmol, 1 eq) and PyBop (11.6 g, 22 mmol, 1.3) in DCM (60 mL) was added dimethylamine (1.5 g, 17 mL, 34 mmol, 2 eq) at 0° C. The solution was stirred for 10 min followed by dropwise addition of DIPEA (4.4 g, 5.9 mL, 34 mmol, 2 eq). After stirring for 6 h, the solution was diluted with sat NaHCO$_3$ (40 mL) and the aqueous phase was extracted with DCM (2×50 mL). The combined organic phases were washed with brine, separated, dried over MgSO$_4$, filtered and concentrated in vacuo to afford an oil. The resulting oil was purified by silica gel chromatography (50-100% hexane/EtOAc) to afford 249 as a clear oil.

Part B

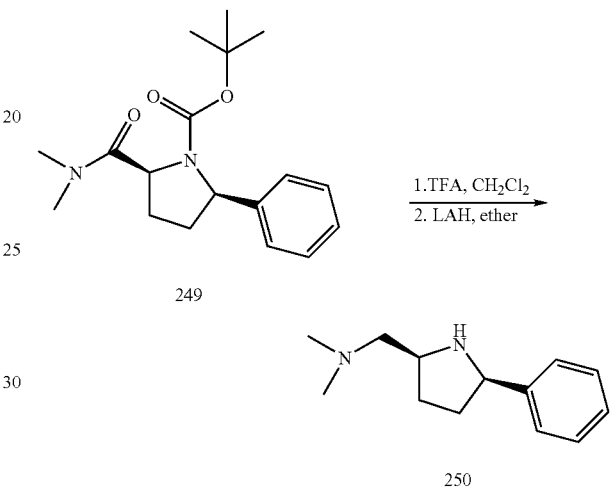

To a solution of amide 249 (4.5 g, 14 mmol, 1 eq) in DCM (100 mL) was added TFA (10 mL) at 0° C. After stirring for 2 h at rt, the solvent was removed in vacuo to afford an oil. The resulting oil was suspended in THF and cooled to 0° C., to which was added LiAlH$_4$ (4 g, 108 mmol, 6.8 eq) in portions, and heated at reflux for 12 h under argon. The solution was cooled to rt and quenched with water (4 mL), allowed to stir for 5 min, followed by 15% NaOH (4 mL) and stirred for additional 5 min, and finally water (12 mL) was added and the suspension was stirred until the white precipitate formed. The solid was filtered and washed with EtOAc and the filtrate was concentrated in vacuo to afford 250 as an oil which was used without further purification.

Part C

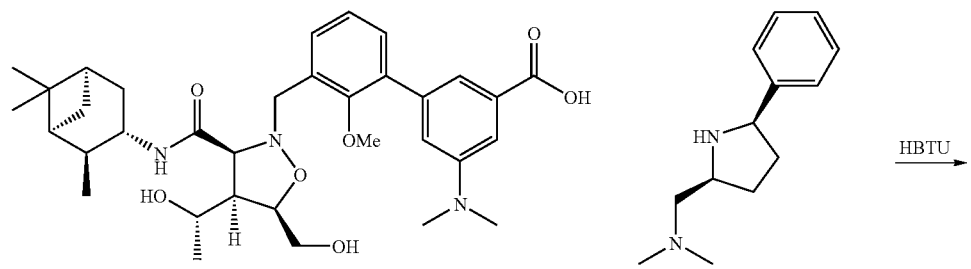

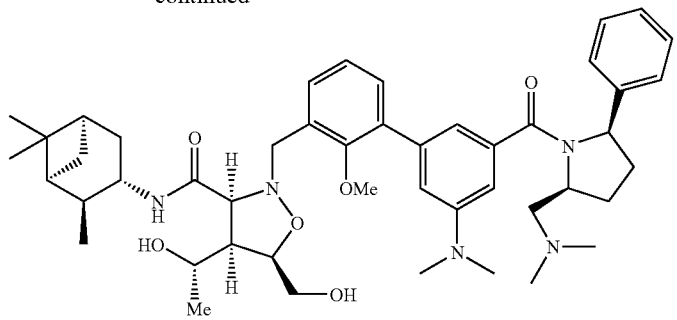

247

Biphenyl acid 10 (40 mg, 0.064 mmol, 1 eq) and HBTU (49 mg, 0.13 mmol, 2 eq) were dissolved in DMF (1 mL) followed by the addition of N,N-dimethyl-1-((2S,5R)-5-phenylpyrrolidin-2-yl)methanamine 250 (23 mg, 0.13 mmol, 2 eq). The reaction mixture was stirred for 2 h, diluted with EtOAc and quenched with a saturated aqueous NaHCO₃ solution. The reaction mixture was extracted with EtOAc (3×100 mL) and the combined organics were dried over MgSO₄, filtered and concentrated in vacuo to afford an oil. The crude oil was purified by silica gel chromatography (2-5% MeOH/DCM, 0.1% Et₃N) to afford 23 mg of biphenyl amide 247. Yield 45%.

Example 85

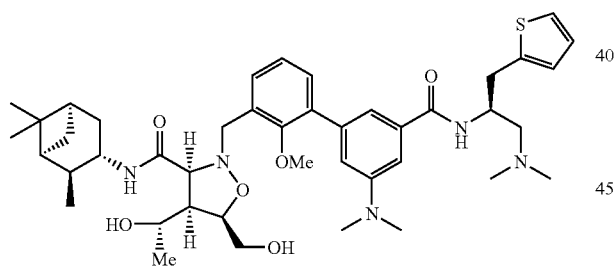

251

Part A

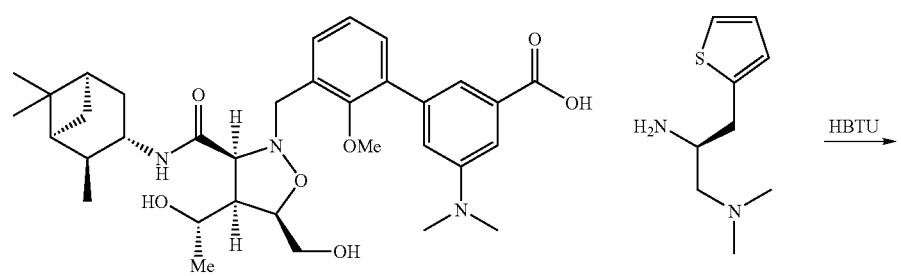

10

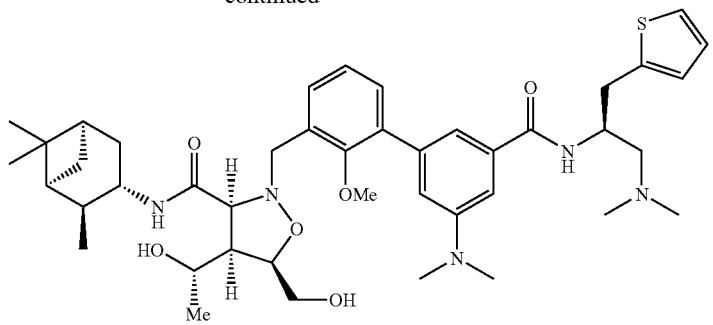

251

Biphenyl acid 10 (40 mg, 0.064 mmol, 1 eq) and HBTU (49 mg, 0.13 mmol, 2 eq) were dissolved in DMF (1 mL) followed by the addition of (S)—$N^1,N^1$-dimethyl-3-(thiophen-2-yl)propane-1,2-diamine (23 mg, 0.13 mmol, 2 eq). The reaction mixture was stirred for 2 h, diluted with EtOAc and quenched with a saturated aqueous $NaHCO_3$ solution. The reaction mixture was extracted with EtOAc (3×100 mL) and the combined organics were dried over $MgSO_4$, filtered and concentrated in vacuo to afford an oil. The crude oil was purified by silica gel chromatography (2-5% MeOH/DCM, 0.1% $Et_3N$) to afford 23 mg of biphenyl amide 251. Yield 45%.

Example 86

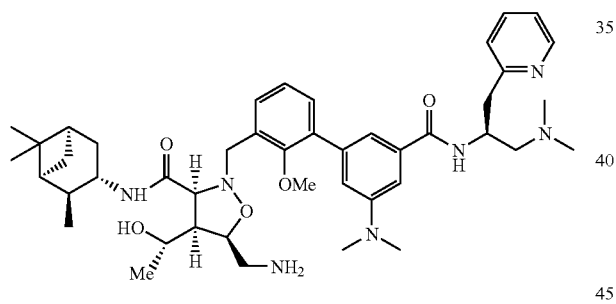

252

Part A.

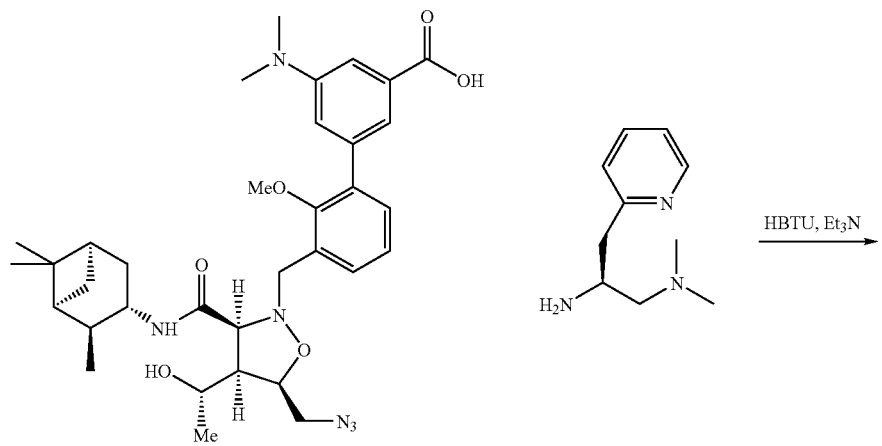

216

-continued

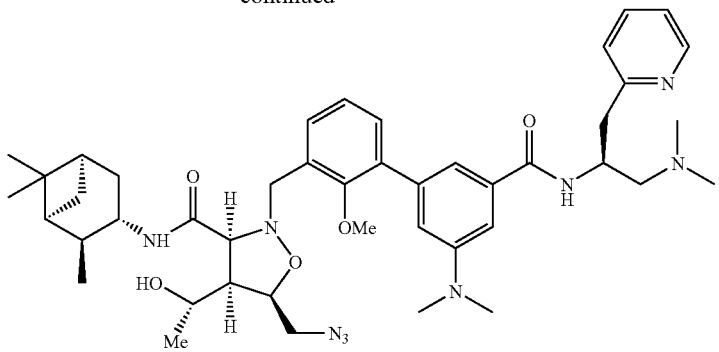

253

Biphenyl acid 216 (130 mg, 0.205 mmol, 1 eq), Et₃N (62 uL, 0.615 mmol, 3 eq) and HBTU (155 mg, 0.410 mmol, 2 eq) were dissolved in DCM (5 mL) followed by addition of amine (74 mg, 0.410 mmol, 2 eq). After stirring for 2 h, the reaction mixture was diluted with EtOAc (100 mL) and a saturated sodium bicarbonate solution. The mixture was extracted with EtOAc (3×100 mL), dried over MgSO₄, filtered and concentrated to an oil. The crude oil was purified by silica gel chromatography (2-5% MeOH/DCM) to afford 49 mg of azide 253. Yield 30%.

Part B.

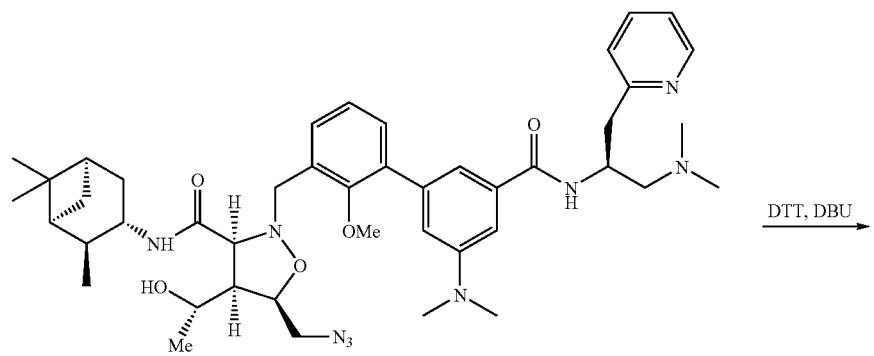

253

DTT, DBU

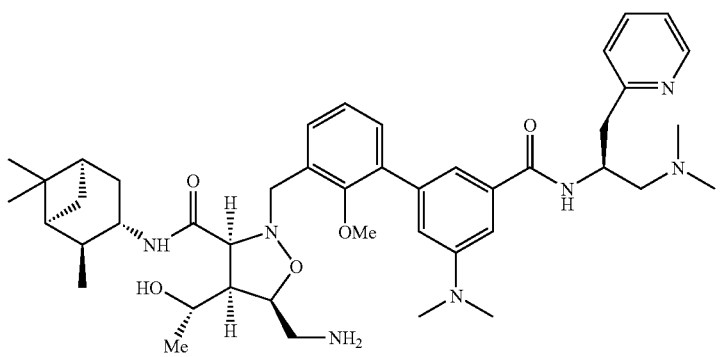

252

Azide 217 (30 mg, 0.038 mmol, 1 eq) and dithiothreitol (17 mg, 0.113 mmol, 3 eq) were dissolved in DMF (1 mL) followed by addition of DBU (17 uL, 0.113 mmol, 3 eq). After stirring for 1 h, the reaction mixture was purified directly by reverse-phase HPLC (CH₃CN/water with 40 mM NH₄HCO₃), to yield 17 mg of amine 253. Yield 62 %

Example 87

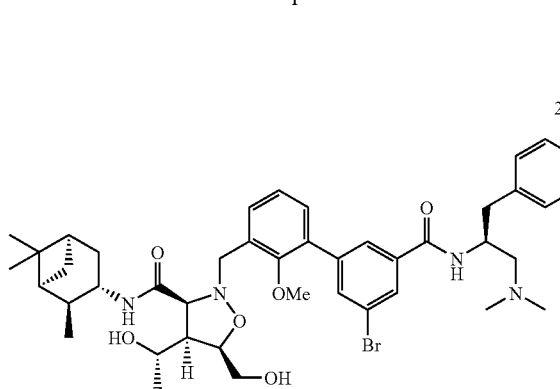

253

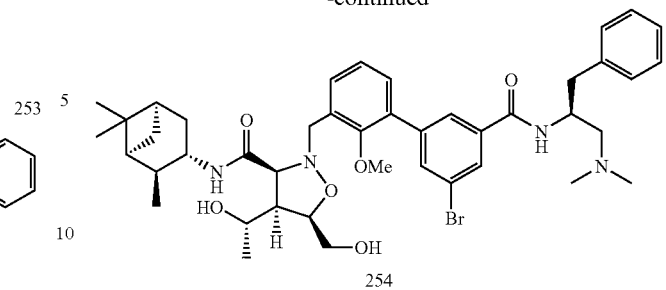

254

A flask containing boronate (20 mg, 0.035 mmol, 1 eq.), 3,4-dibromobenzoic acid (30 mg, 0.11 mmol, 3 eq.), cesium carbonate (50 mg, 1 mmol, 3 eq.), potassium acetate (5 mg, 0.03 mmol, 1 eq.) and Pd(dppf)Cl$_2$ (5 mg, 0.003 mmol, 0.1 eq.) was purged with argon and DMSO (1 mL) added. The mixture was heated at 60° during 3 h, then 45° overnight. The reaction mixture was partitioned between water (30 mL) and DCM (20 mL) and acidified with 6M HCl until the aqueous layer attained a pH of 1. The layers were separated and the aqueous extracted (2×20 mL DCM). The combined organic layers were dried on Na2SO4 and concentrated to a brown oil.

To an aliquot containing ca 50% of this crude oil (0.019 mmol, 1 eq.) in DMF (1 mL) was added the amine (8 uL, 0.04 mmol, 2 eq.), DIEA (10 uL) and HBTU (15 mg, 0.04 mmol, 2 eq.). When the reaction appeared complete by HPLC, the mixture was diluted with MeOH (1 mL) and purified by reverse-phase HPLC (MeCN/40 mM ammonium formate 25%→80%) to give 254 as a white solid (4 mg, 27%). MS (ESI(+)) m/e 807.6 (M+H)$^+$.

Example 88

Part A.

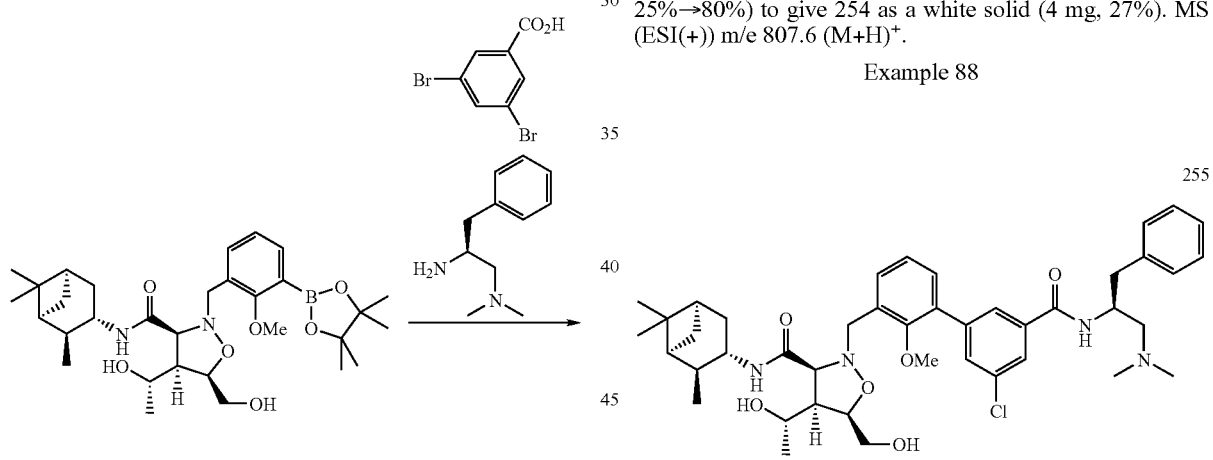

255

Part A.

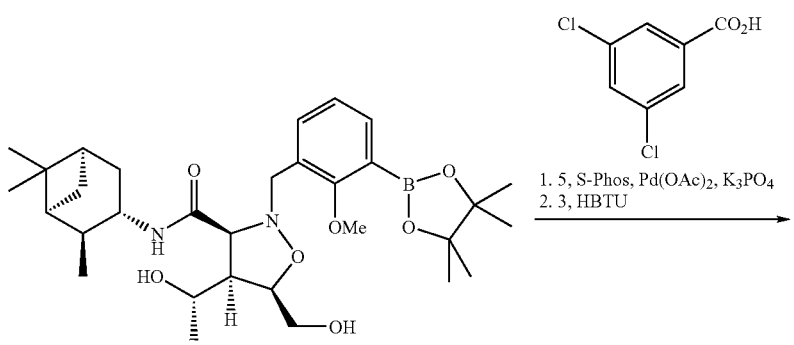

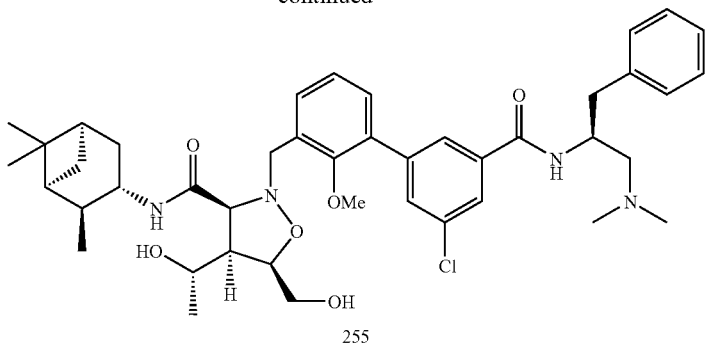

255

A flask containing boronate (30 mg, 0.05 mmol, 1 eq.), 3,4-dichlorobenzoic acid (20 mg, 0.1 mmol, 2 eq.), S-Phos (2 mg, 0.005 mmol, 0.1 eq.), potassium phosphate (50 mg, 0.2 mmol, 4 eq.) and a dash of palladium acetate was purged with argon and THF (2 mL) added. The mixture was heated at 40° overnight. The reaction mixture acidified with 6M HCl and extracted with DCM. The combined organic layers were dried on Na2SO4 and concentrated to a brown oil.

To an aliquot containing this crude oil (0.05 mmol, 1 eq.) in DMF (1 mL) was added (S)—N1,N1-dimethyl-3-phenylpropane-1,2-diamine (30 uL, 0.15 mmol, 3 eq.) and HBTU (30 mg, 0.08 mmol, 1.5 eq.). When the reaction appeared complete by HPLC, the mixture was diluted with MeOH (1 mL) and purified by reverse-phase HPLC (MeCN/40 mM ammonium formate 25%→80%) to give 255 as a white solid (3 mg, 8%). MS (ESI(+)) m/e 761.7 (M+H)+.

Example 89

256

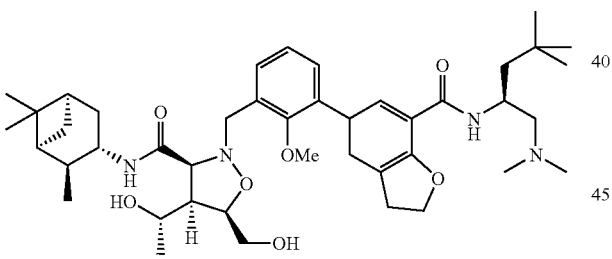

Part A.

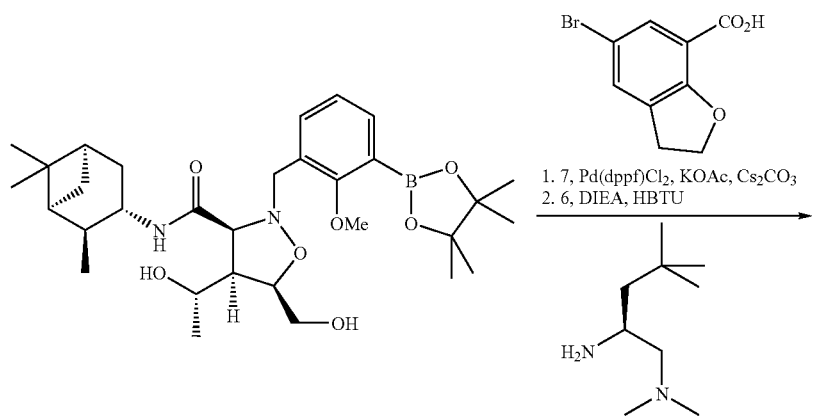

1. 7, Pd(dppf)Cl2, KOAc, Cs2CO3
2. 6, DIEA, HBTU

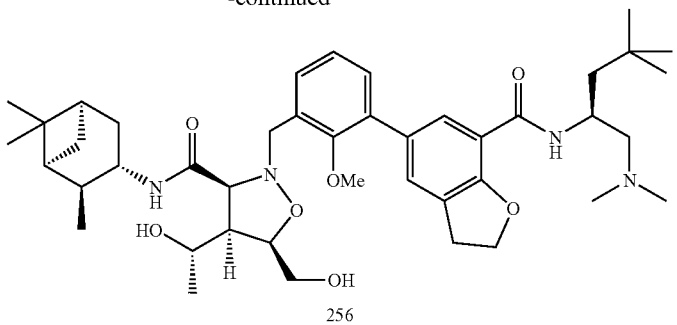
256

Compound 256 was synthesized according to the procedure described in Example 88. MS (ESI(+)) m/e 749.6 (M+H)$^+$.

Example 90

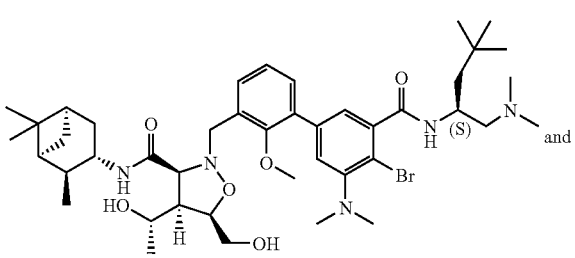
257 and

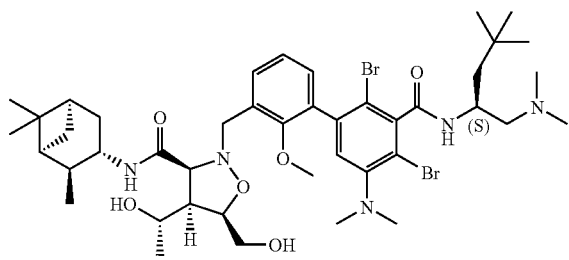
258

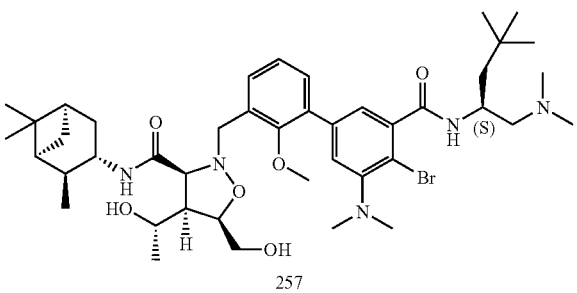
257

258

A solution of crude compound 1 (8 mg, 0.01 mmol, 1 eq.) in MeCN (500 uL) was treated portionwise with a 1:1100 solution of bromine in MeCN until LC showed consumption of 1. The reaction mixture purified by reverse-phase HPLC (MeCN/40 mM ammonium formate 25%→80%) to give an inseparable mixture that appears by NMR to contain approximately equal amounts of 257 and 258, as a white solid (3 mg, 30%). MS (ESI(+)) m/e 830.6 (M+H)$^+$.

Example 91

Part A.

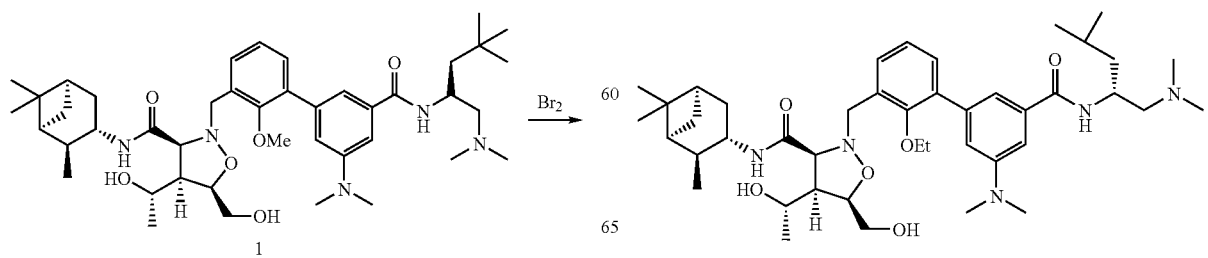
1        259

Part A.
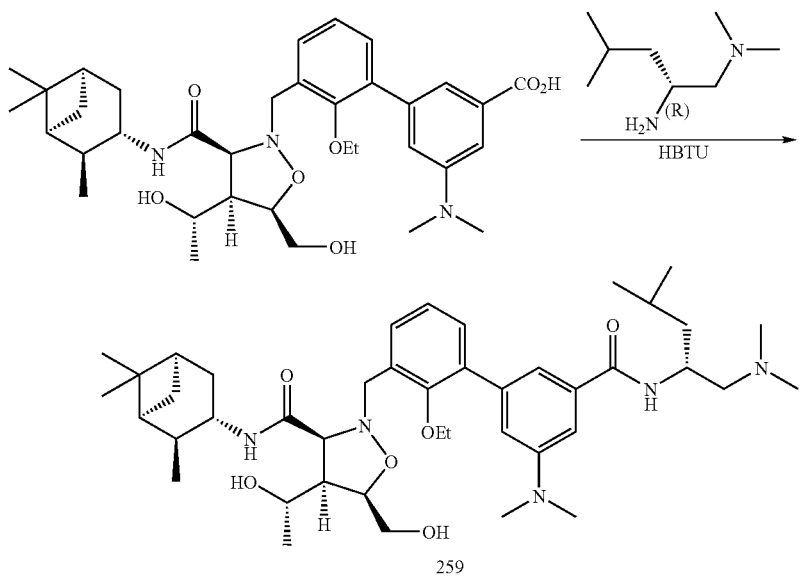
To an aliquot of crude acid (example 3 part G) (0.024 mmol, 1 eq.) in DMF (1 mL) was added amine (11 uL, 0.05 mmol, 2 eq.) and HBTU (30 mg, 0.08 mmol, 3 eq.). When the reaction appeared complete by HPLC, the mixture was diluted with MeOH (1 mL) and purified by reverse-phase HPLC (MeCN/40 mM ammonium formate 25%→80%) to give 259 as a white solid (3 mg, 17%). MS (ESI(+)) m/e 750.6 (M+H)$^+$.
Example 92
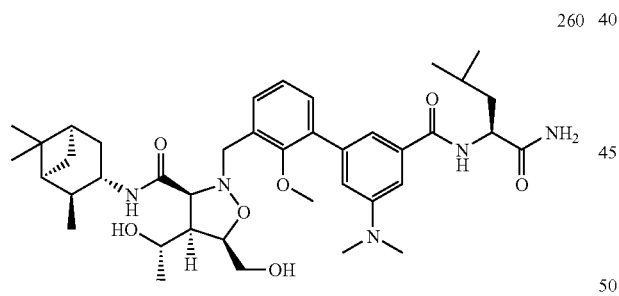
Part A.
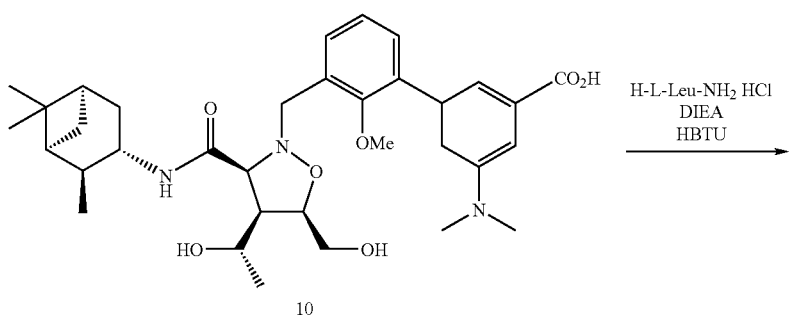

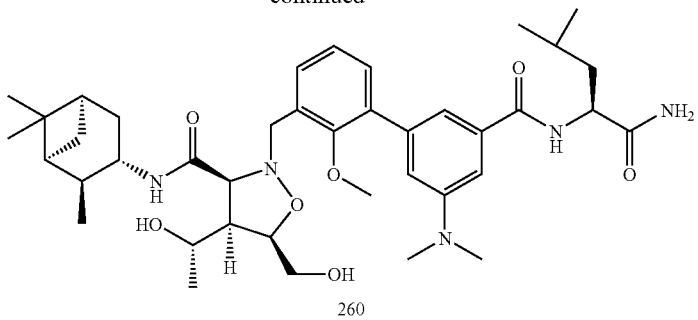

260

To acid 10 (10 mg, 0.016 mmol, 1 eq.) in DMF (1 mL) was added DIEA (10 uL), H-L-Leu-NH2 HCl (8 mg, 0.05 mmol, 3 eq.) and HBTU (20 mg, 0.05 mmol, 3 eq.). When the reaction appeared complete by HPLC, the mixture was diluted with MeOH (1 mL) and purified by reverse-phase HPLC (MeCN/40 mM ammonium formate 25%→80%) to give 260 as a white solid (3 mg, 25%). MS (ESI(+)) m/e 722.6 (M+H)$^+$.

Example 93

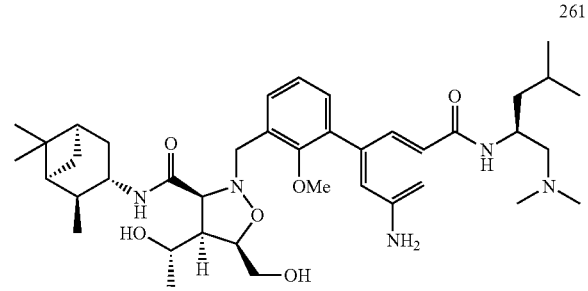

261

Part A.

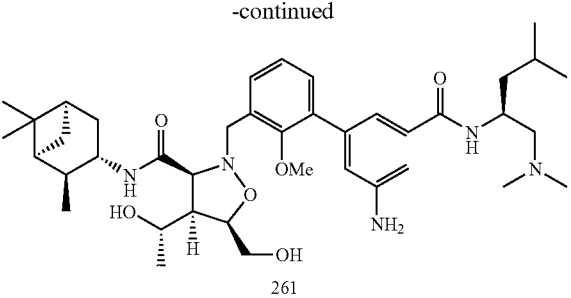

261

A flask containing iodide 9 (200 mg, 0.35 mmol, 1 eq.), boronate (126 mg, 0.7 mmol, 2 eq.), cesium carbonate (340 mg, 1 mmol, 3 eq.), potassium acetate (35 mg, 0.35 mmol, 1 eq.) and Pd(dppf)Cl$_2$ (20 mg, 0.035 mmol, 0.1 eq.) was purged with argon and DMSO (11 mL) added. The mixture was heated at 60° during 3 h, then additional Pd(dppf)Cl$_2$ (20 mg, 0.035 mmol, 0.1 eq.) added and stirring continued at ambient temperature overnight. The reaction mixture was treated with tetrabutylammonium bromide (230 mg) and extracted from water (30 mL) 3×30 mL DCM. The combined organic layers were washed with brine (20 mL), dried on Na$_2$SO$_4$, and concentrated to a brown oil.

To an aliquot containing ca. 50% of this crude oil (0.017 mmol, 1 eq.) in DMF (5 mL) was added amine (25 mg, 0.017 mmol, 1 eq.) and HBTU (200 mg, 0.5 mmol, 3 eq.). When the reaction appeared complete by HPLC, the mixture was diluted with MeOH (1 mL) and purified by reverse-phase HPLC (MeCN/40 mM ammonium formate 25%→80%) to give 261 as a white solid. MS (ESI(+)) m/e 708.5 (M+H)$^+$.

Example 94

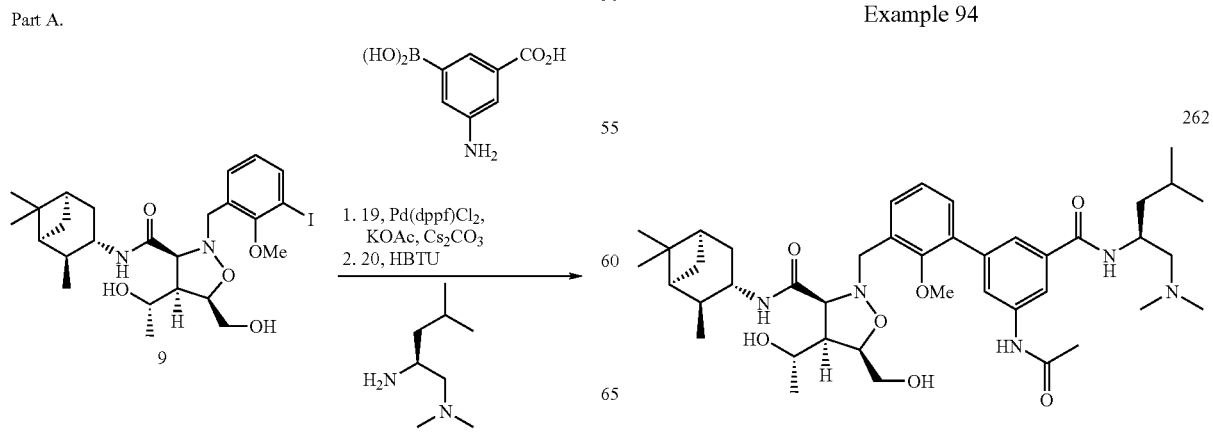

262

Part A.

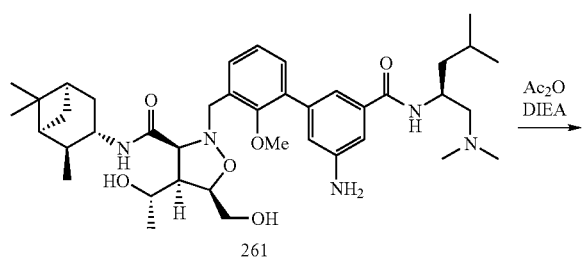
261

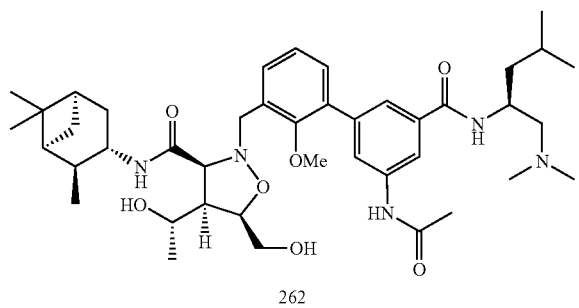
262

A flask containing amine 261 (12 mg, 0.017 mmol, 1 eq.) in DCM (1 mL) and MeOH (100 uL) was added DIEA (10 uL, 0.05 mmol, 3 eq.) and acetic anhydride (5 uL, 0.05 mmol, 3 eq.). After shaking overnight, the reaction mixture was diluted with aqueous NaHCO3 and extracted (3×5 mL DCM). The combined organic layers were dried on Na2SO4 and concentrated to give 262 as brownish solid (3 mg 22%). MS (ESI(+)) m/e 750.8 (M+H)$^+$.

Example 95

263

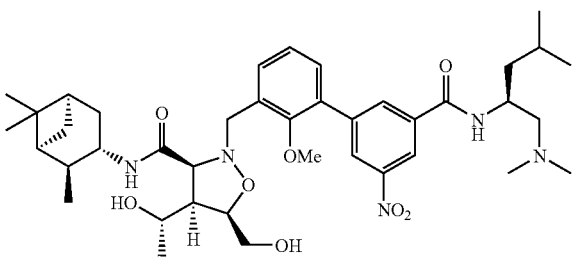

Part A.

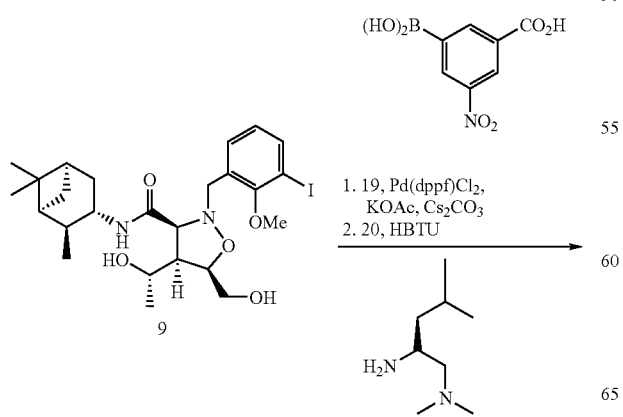

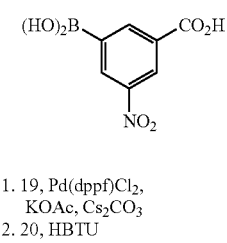

-continued

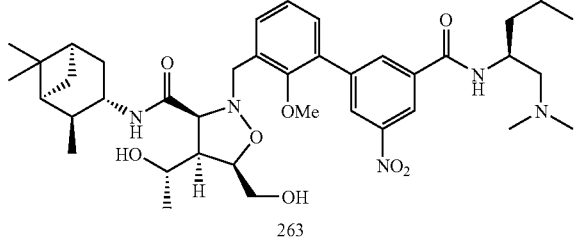
263

Compound 263 was synthesized according to the procedure described in Example 88 using (R)—N1,N1,4-trimethylpentane-1,2-diamine in place of (S)—N1,N1-dimethyl-3-phenylpropane-1,2-diamine. Yield 9 mg (53%). MS (ESI(+)) m/e 738.5 (M+H)$^+$.

Example 96

264

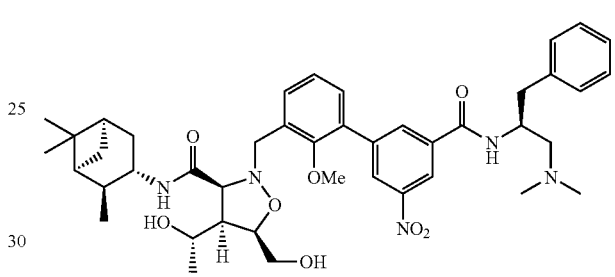

Part A.

Compound 264 was synthesized according to the procedure described in Example 88, using (S)—N1,N1-dimethyl-3-phenylpropane-1,2-diamine. Yield 3 mg (16%). MS (ESI(+)) m/e 772.5 (M+H)$^+$.

Example 97

265

Part A.

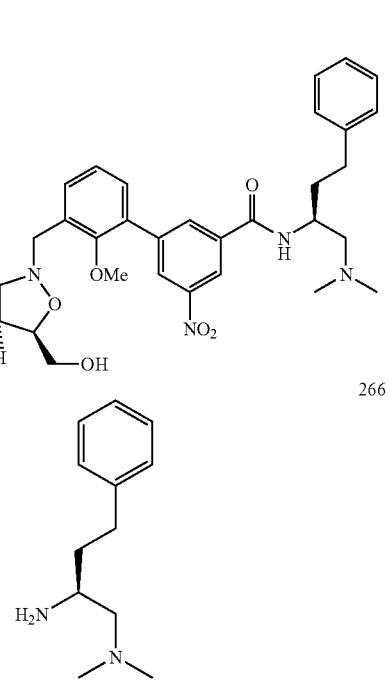
266

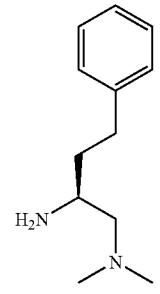

Compound 265 was synthesized according to the procedure described in Example 88, using amine 266 in place of (S)—N1,N1-dimethyl-3-phenylpropane-1,2-diamine and intermediate acid described in Example 95 part A. Yield 3 mg (16%). MS (ESI(+)) m/e 786.5 (M+H)$^+$.

Example 98

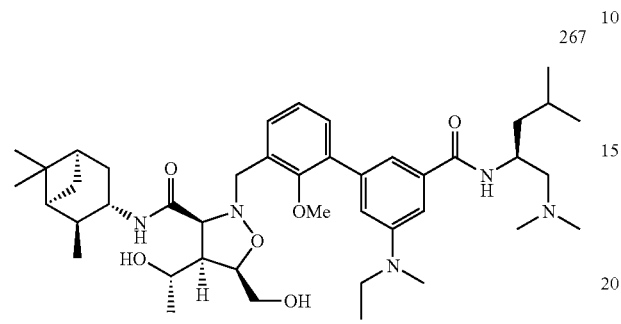
267

Part A.

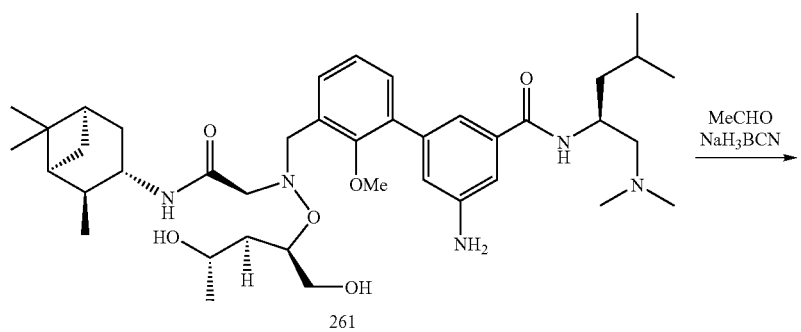
261

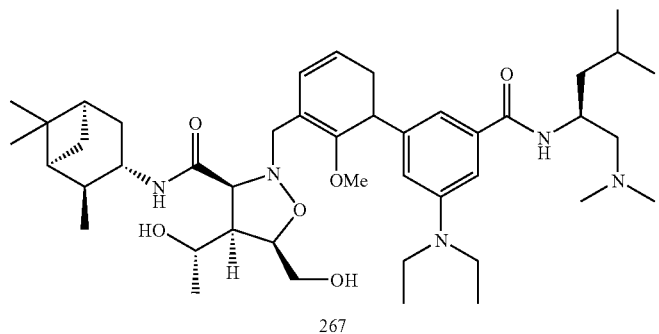
267

An aliquot of crude 261 (0.03 mmol, 1 eq.) in MeOH (1 mL) was treated with acetaldehyde (20 uL, 0.3 mmol, 10 eq.) and sodium cyanoborohydride (8 mg, 0.12 mmol, 4 eq.). Acetic acid (5 uL) was added and the solution shaken overnight at 50°. When the reaction appeared complete by HPLC, the mixture was diluted with MeOH (1 mL) and purified by reverse-phase HPLC (MeCN/40 mM ammonium formate 25%→80%) to give 267 as a white solid (3 mg, 15%). MS (ESI(+)) m/e 764.7 (M+H)$^+$.

Example 99

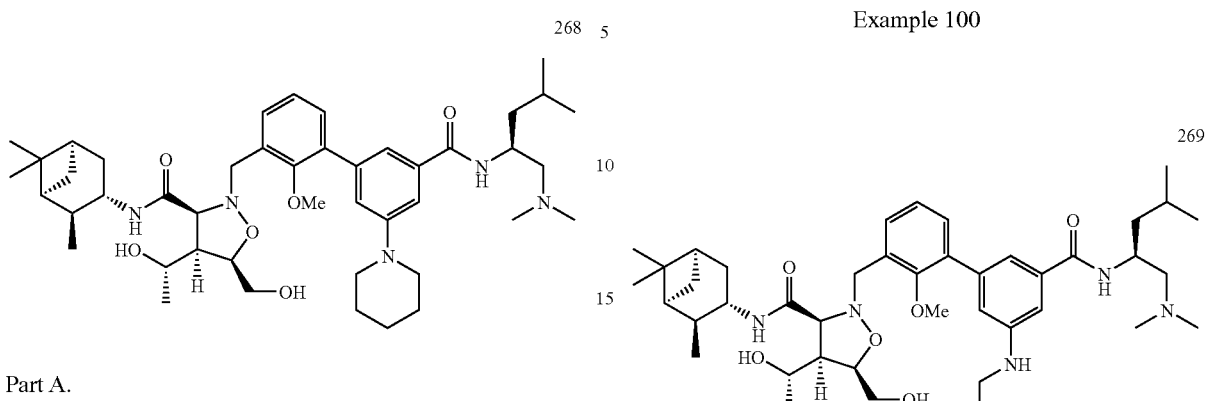

Part A.

Compound 268 was synthesized according to the procedure described in Example 98, using glutaraldehyde in place of acetaldehyde. Yield 3 mg (14%). MS (ESI(+)) m/e 776.6 (M+H)+.

Example 100

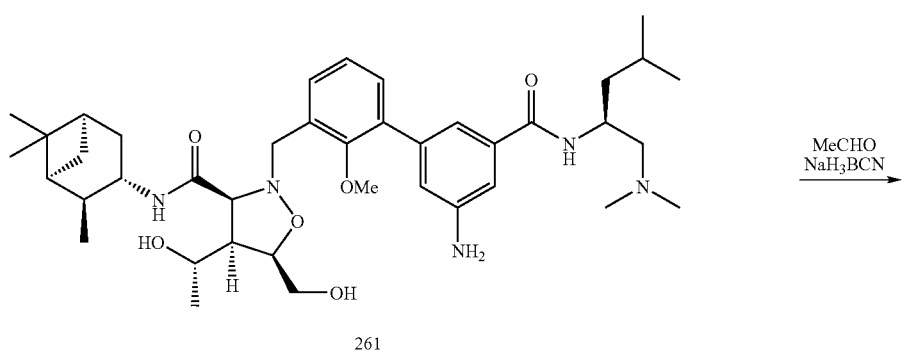

Part A.

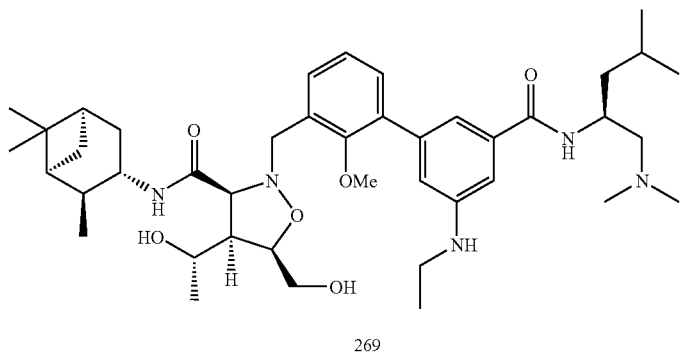

An aliquot of crude 261 (0.03 mmol, 1 eq.) in MeOH (1 mL) was treated with acetaldehyde (10 uL, 0.15 mmol, 5 eq.) and sodium cyanoborohydride (6 mg, 0.09 mmol, 3 eq.). The solution was shaken overnight at ambient temperature. The mixture was diluted with MeOH (1 mL) and purified by reverse-phase HPLC (MeCN/40 mM ammonium formate 25%→80%) to give 269 as a white solid (3 mg, 14%). MS (ESI(+)) m/e 736.6 (M+H)+.

Example 101

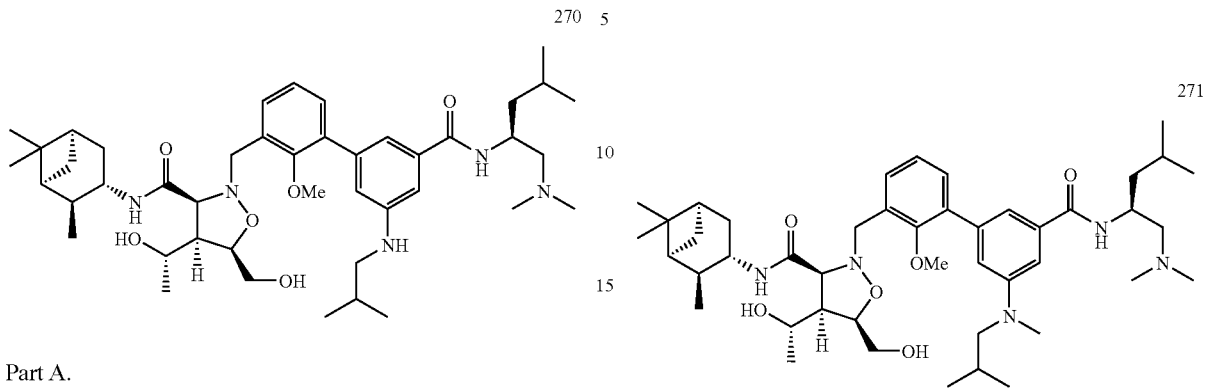

Part A.

Compound 270 was synthesized according to the procedure described in Example 94, using isobutaraldehyde in place of acetaldehyde. Yield 3 mg (14%). MS (ESI(+)) m/e 764.7 (M+H)$^+$.

Example 102

Part A.

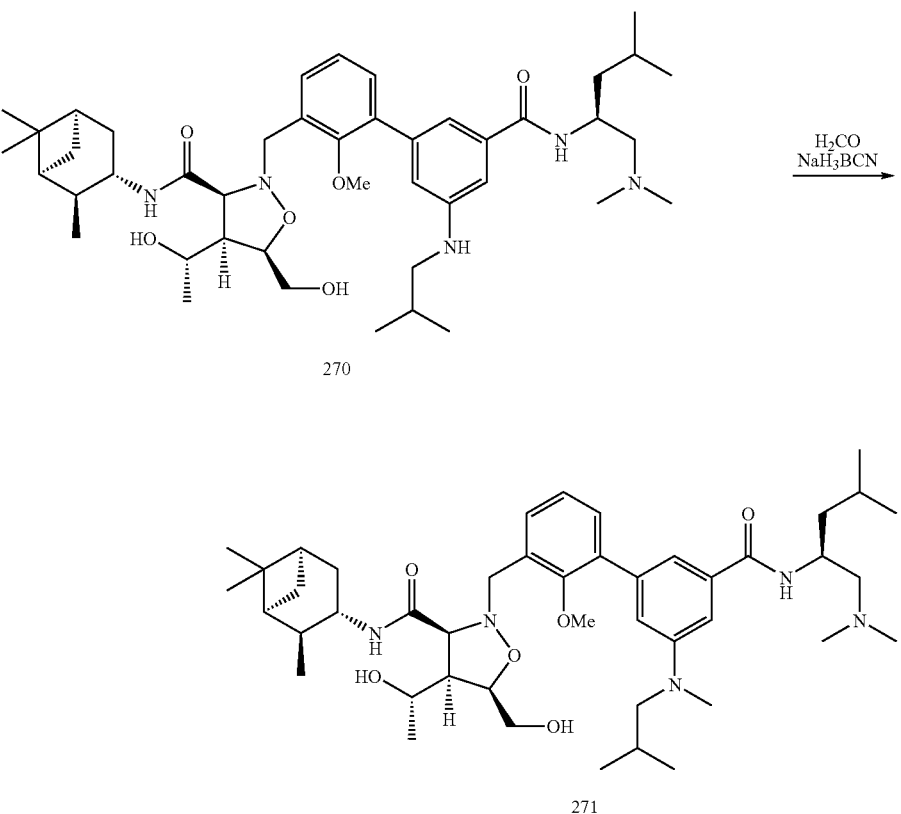

Crude reaction mixture from the production of 270 (0.03 mmol, 1 eq.) was stripped of all volatiles in vacuo and taken up in MeOH (1 mL). Acetic acid (5 uL), 37% formalin (10 uL), and sodium cyanoborohydride (4 mg, 0.8 mmol, 3 eq.) were added. After 4 h, the mixture was diluted with MeOH (1 mL) and purified by reverse-phase HPLC (MeCN/40 mM ammonium formate 25%→80%) to give 271 as a white solid (3 mg, 14%). MS (ESI(+)) m/e 778.7 (M+H)$^+$.

Example 103

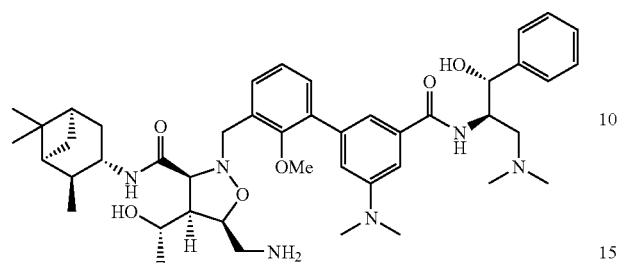

272

Part A.

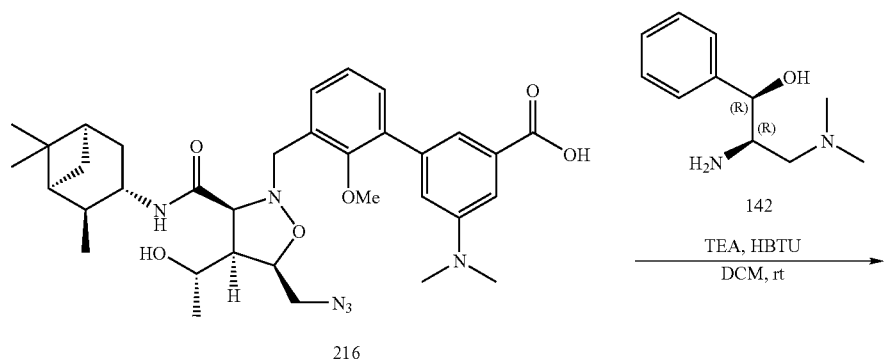

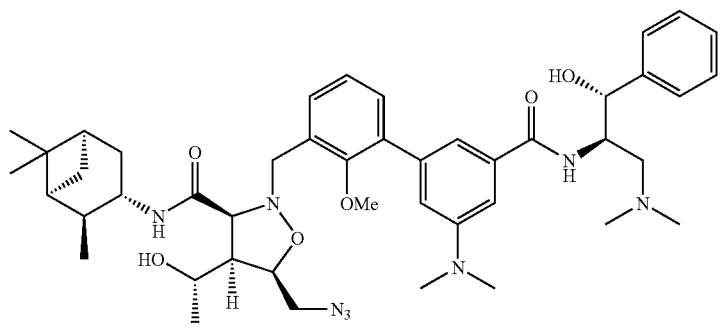

273

To a solution of 216 (45.4 mg, 0.07 mmol, 1 eq) in DCM (5 mL) was added TEA (30 µL, 0.22 mmol, 3 eq) and HBTU (54.2 mg, 0.14 mmol, 2 eq). The solution was stirred at rt for 10 min. Diamine 142 (28.7 mg, 0.11 mmol, 1.5 eq) was then added. After stirring at rt for 2 h, the mixture was diluted with DCM (15 mL) and washed with saturated potassium carbonate solution (10 mL). The aqueous layer was extracted with DCM (2×10 mL). The combined organic layers were dried over $Na_2SO_4$, filtered and concentrated in vacuo. The material was purified by silica gel chromatography (80% EtOAc/DCM with 1% triethylamine-5% MeOH/DCM with 1% triethylamine) to give 40 mg of 273. Yield 69%. MS (ESI(+)) m/z 811.28 $M^+$.

Part B.

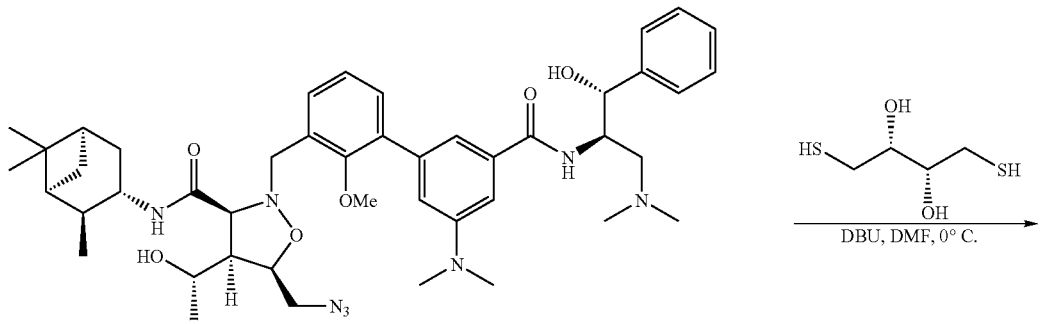

273

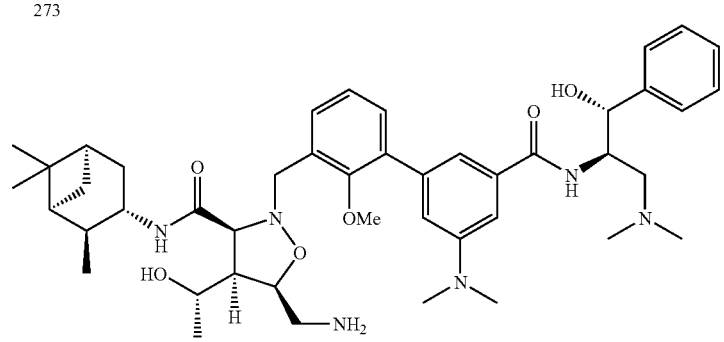

272

To a solution of 273 (40 mg, 0.05 mmol, 1 eq) in DMF (2 mL) at 0° C. was added dithiothreitol (22.8 mg, 0.15 mmol, 3 eq) and DBU (22.3 µL, 0.15 mmol, 3 eq). The solution was stirred at 0° C. for 30 min. The crude reaction was kept at 0° C. and purified by HPLC to give 16 mg of 272. Yield 41%. MS (ESI(+)) m/z 785.33 M+.

Example 104

274

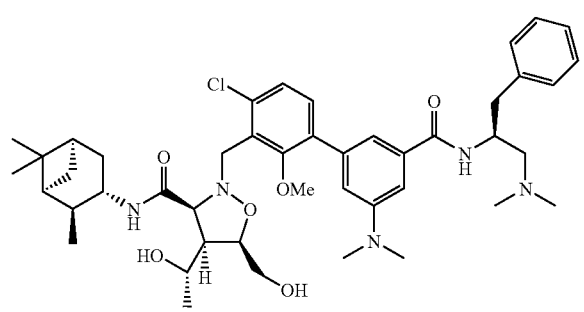

Part A.

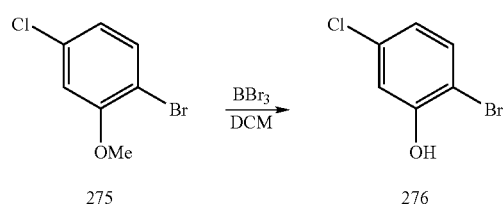

To a solution of 1-bromo-5-chloro-2 methoxyphenyl 275 (2.5 g, 11 mmol, 1 eq) in DCM (100 mL) was added dropwise BBr$_3$ (1 M solution in DCM, 38.5 mmol, 3.5 eq) over 20 min at −40 C. The solution was warmed to rt and stirred for 12 h. TLC (3:2 Hexane:DCM) showed complete consumption of 275. The solution was quenched with NaHCO$_3$ and stirred until two phases appeared. The organic was separated, washed with brine, dried, filtered and concentrated in vacuo to afford 0.80 g of 276 as a white solid which was used without purification. Yield 32%

Part B.

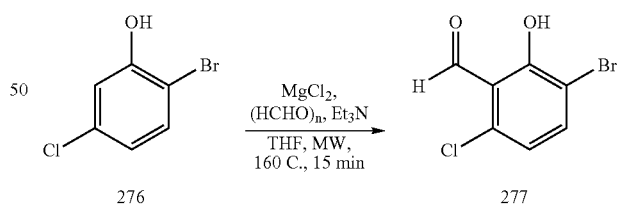

To a solution of MgCl$_2$ (powder 325 mesh, 0.734 g, 7.71 mmol, 2 eq), paraformaldehyde (0.347 g, 11.57 mmol, 3 eq) and Et$_3$N (1.08 mL, 7.71 mmol, 2 eq) in THF (20 mL) was added 276 (0.800 g, 3.68 mmol, 1 eq), heated in the microwave at 160 C for 15 min. TLC (3:2 Hexane:DCM) showed complete consumption of 3. THF was evaporated and the reaction mixture was taken up in EtOAc, washed with brine, dried, filtered and concentrated in vacuo to afford 0.52 g of 277 which was used without purification. Yield 47%

Part C.

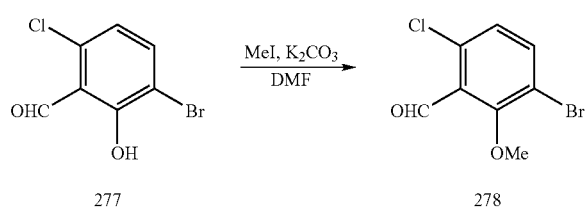

To a solution of 277 (0.518 g, 2.2 mmol, 1 eq) in DMF (5 mL) was added K₂CO₃ (0.456 g, 3.3 mmol, 1.5 eq), stirred at rt for 10 min, resulting in a suspension. Iodomethane (0.206 mL, 3.3 mmol, 1.5 eq) was added dropwise and allowed to stir at rt overnight. TLC (9:1 Hexane:EtOAc) showed no remaining 277. The mixture was diluted into water and extracted with EtOAc. The organic was separated, washed with brine, dried, filtered and concentrated in vacuo to afford 0.505 g of 278 as an orange oil which was used without purification. Yield 92%

Part D.

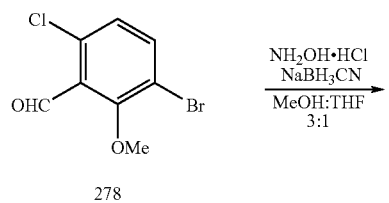

To a solution of 278 (0.505 g, 2.02 mmol, 1 eq) in MeOH-THF (3:1, 5 mL) was added an aqueous solution of hydroxylamine (0.169 g, 2.43 mmol, 1.2 eq in 2.5 mL of water) in one portion. The pH was adjusted to 9 with NaOH (6N), and stirred at rt for 1 hr where TLC (2:1 Hexane:EtOAc) showed complete consumption of 278. NaBH₃CN (0.254 g, 2.43 mmol, 2 eq) was added with a fleck of methyl red and the solution acidified to pH 2-3 using HCl in MeOH (20 V/V). The pH of the reaction solution was maintained at pH 3 over the course of 12 h by addition of small amounts of the methanolic HCl solution, where it was basified to pH 9 with NaOH (2 N). The solution was extracted with EtOAc, washed with brine, dried, filtered and concentrated in vacuo to afford an orange oil. The crude material was purified by column chromatography (silica gel, 55% EtOAc in Hexane) to afford 0.486 g of 279 as a cream solid. Yield 90%.

Part E.

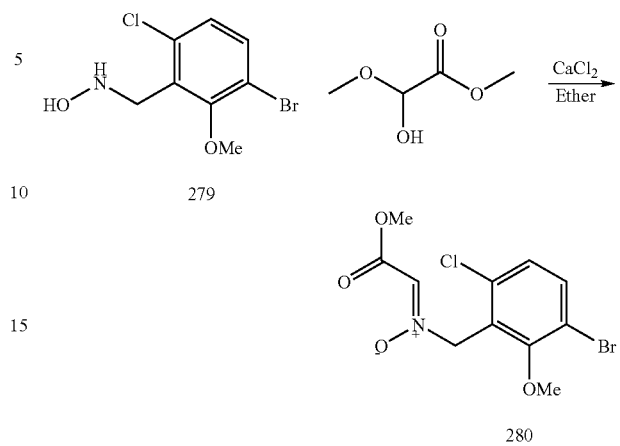

To a solution of 279 (0.486 g, 1.83 mmol, 1 eq) and glyoxylate ester (0.285 g, 2.37 mmol 1.3 eq) in diethyl ether (10 mL) was added anhydrous CaCl₂ (0.263 g, 2.37 mmol, 1.3 eq), left stirring at rt for 3 h, resulting in a suspension. The suspension was filtered through a Celite plug washing with DCM and ether. The resultant yellow solution was concentrated in vacuo to afford 0.497 g of 280 as yellow oil and used directly without purification. MS (ESI(+)) m/z 337.8 (M+H)⁺ Yield 81%.

Part F.

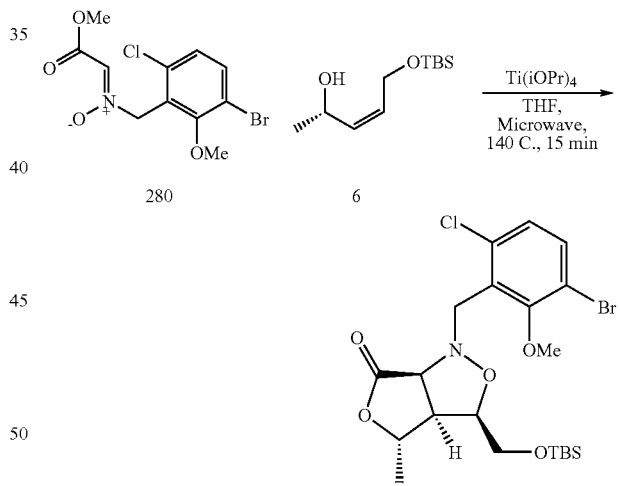

To a solution of 280 (0.497 g, 1.48 mmol, 1 eq) in anhydrous THF (10 mL) was added (S,Z)-5-tert-butyldimethylsiloxy)pent-3-en-2-ol 6 (0.5 mL, 1.77 mmol, 1.2 eq) and Ti(O-iPr)₄ (0.65 mL, 2.22 mmol, 1.5 eq) heated in the microwave at 140 C for 15 min. TLC (30:1 DCM:Et₂O) showed consumption of nitrone 280 and the allylic alcohol 6. 3-(dimethylamino)-1,2-propanediol (1 mL) in EtOAc (1 mL) was added and the dark brown solution left stirring at rt overnight. The dark brown solution was diluted with EtOAc and quenched with Rochelle's salt solution, washed with water, brine, dried and concentrated in vacuo to afford a brown oil. The crude material was purified by column chromatography (silica gel, 10% EtOAc in Hexane) to afford 0.490 g of 281 as a brown oil. MS (ESI(+)) m/z 521.9 (M+H)+ Yield 64%

Part G.

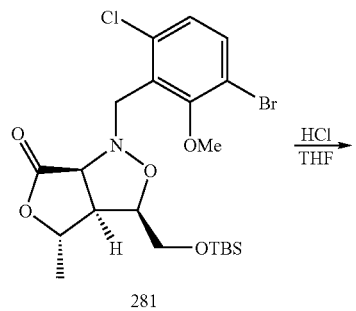

281

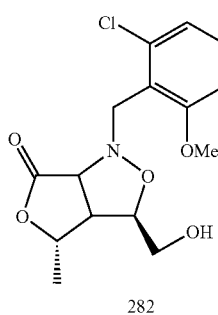

282

To a solution of 281 (0.470 g, 0.903 mmol, 1 eq) in THF (5 mL) was added concentrated 6 N HCl (0.45 mL, 2.71 mmol, 3 eq) and stirred at rt for 2 h. TLC (1:2 hexane:EtOAc) of neutralized aliquot showed complete consumption of 281. The reaction was neutralized with NaHCO₃, extracted with EtOAc, washed with brine, dried, filtered and concentrated in vacuo to afford a brown oil. The crude material was purified by column chromatography (silica gel, 50% EtOAc in Hexane) to afford 0.251 g of 282 as a brown solid. MS (ESI(+)) m/z 407.7 (M+H)+ Yield 70%

Part H.

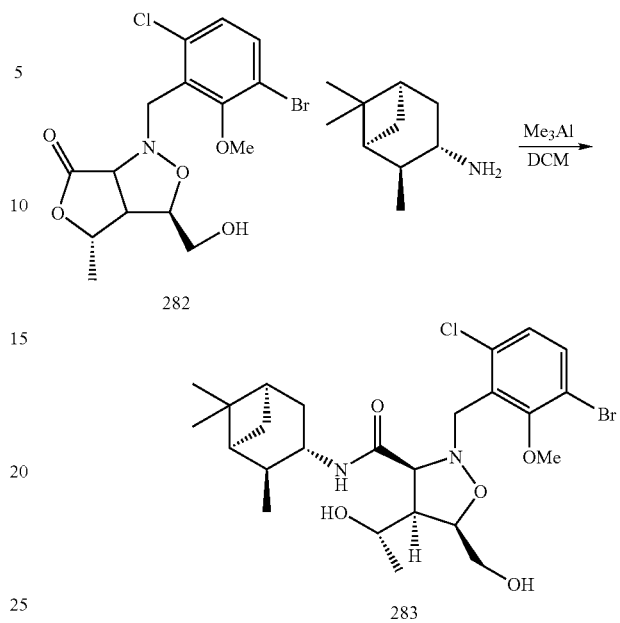

282

283

To a solution of (+−)isocamphenylamine (0.291 g, 1.897 mmol, 3 eq) flushed with Ar in anhydrous DCM (3 mL), was added Me₃Al (2 M solution in Hexane, 0.632 mL, 1.26 mmol, 2 eq) dropwise over 20 min and the resultant clear solution stirred for 40 min at rt. A solution of the lactone 282 (0.264 g, 0.632 mmol, 1 eq) in DCM (3 mL) was added by cannula flask slowly, turning the reaction yellow with gas evolution. The reaction mixture was stirred at rt for 12 h TLC (2:1 EtOAc: Hexane) showed a clean reaction with one marginally faster running spot The reaction was diluted with DCM and quenched on dropwise addition to a rapidly stirring solution Rochelle's salt, and stirred at rt for 2 h. The organic layer was separated and washed with water, brine, dried, and concentrated in vacuo to afford a yellow gum. The crude material was purified by column chromatography (silica gel, 50% EtOAc in Hexane) to afford 0.237 g of 283 as a yellow oil. MS (ESI(+)) m/z 560.8 (M+H)+ Yield 67%

Part I.

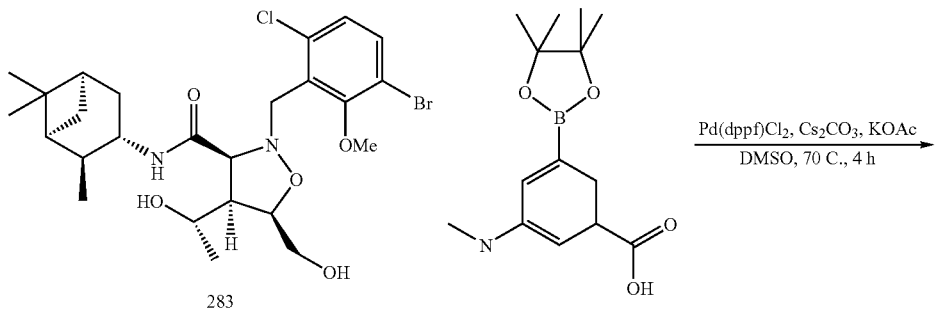

283

-continued

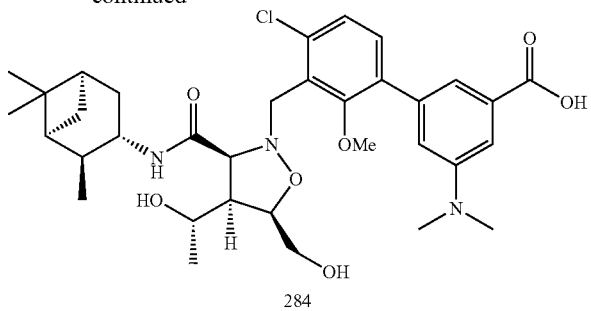
284

To a solution of isoxazolidine 283 (100 mg, 0.179 mmol, 1 eq) in DMSO (5 mL), flushed with argon, was added the pinacolboronate (68 mg, 0.232 mmol, 1.3 eq), potassium acetate (26 mg, 0.268 mmol, 1.5 eq) and cesium carbonate (175 mg, 0.526 mmol, 3 eq). Upon stirring for 10 min, Pd(dppf)Cl$_2$ (29 mg, 0.036 mmol, 0.2 eq) was added as a single portion. The mixture was heated to 70 C for 4 h, then allowed to cool to rt. EtOAc and brine were added and the pH adjusted to 3-4 with HCl (2N). The organics was separated, washed with water, brine, dried, and concentrated in vacuo to afford a brown black oil. The crude material was purified by column chromatography (silica gel, 4% MeOH in DCM) to afford 35 mg of 284 as a brown solid. MS (ESI(+)) m/z 644.0 (M+H)$^+$ Yield 30%

Part I.

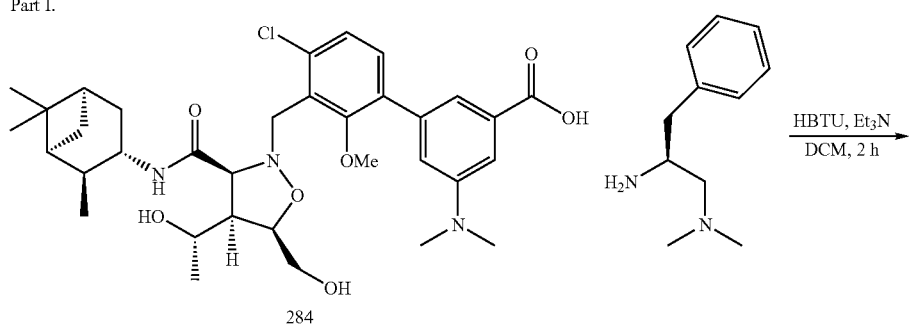
284

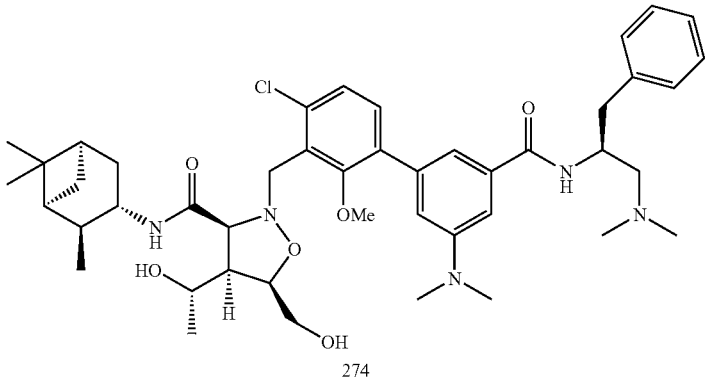
274

A solution of 284 (35 mg, 0.055 mmol, 1 eq) in DCM (3 mL) was added Et$_3$N (23 uL, 0.165 mmol, 3 eq) and HBTU (42 mg, 0.110 mmol, 2 eq) and allowed to stir at rt for 10 min. To this solution was added (S)—N1,N1-dimethyl-3-phenylpropane-1,2-diamine (9.8 mg, 0.055 mmol, 1 eq) and allowed to stir at rt for 2 h. The reaction was taken up in DCM, washed with K$_2$CO$_3$, water, brine, dried and concentrated in vacuo to afford a brown solid. The crude material was diluted with MeOH (2 mL) and purified by reverse-phase HPLC (MeCN/ water with 40 mM NH$_4$HCO$_3$) to afford 13 mg of 274 as a white solid. MS (ESI(+)) m/z 804.2 (M+H)$^+$ Yield 30%

Example 105

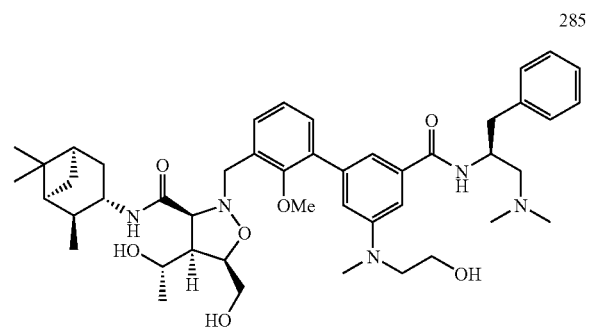
285

Part A.

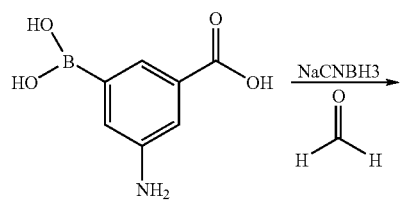

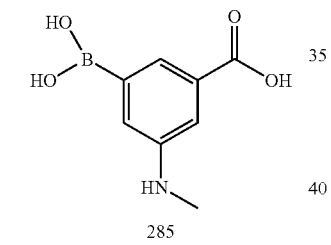
285

3-amino-5-boronobenzoic acid (1 g, 5.5 mmol) was dissolved in 25 ml MeOH and 412 uL of a 37% solution of formaldehyde was added (0.166 mg, 5.5 mmol, 1 eq). Sodium cyanoborohydride (347 mg, 5.5 mmol, 1 eq) was added and the reaction stirred for 30 minutes at room temperature. The solution was dried via rotary evaporation and the resulting material was purified over silica gel (5-10% MeOH in DCM containing 0.2% acetic acid) to obtain 285 (333 mg, 31% yield). The monoalkylated product was carried on to a second reductive alkylation.

Part B.

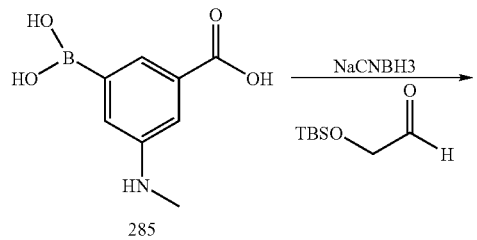
285

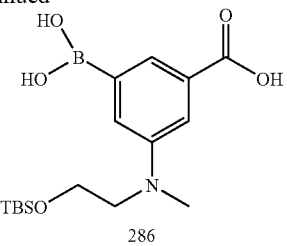
286

Boronic acid 285 (102 mg, 0.5 mmol) 2 mL MeOH and 100 uL of 3 (92 mg, 0.5 mmol, 1 eq) was added. Sodium cyanoborohydride (49 mg, 0.75 mmol, 1.5 eq) was added and the reaction stirred for 90 minutes at room temperature. The solution was dried via rotary evaporation and the resulting material was purified over silica gel (5-10% MeOH in DCM containing 0.2% acetic acid) to obtain 286 (333 mg) 31% Yield.

Part C.

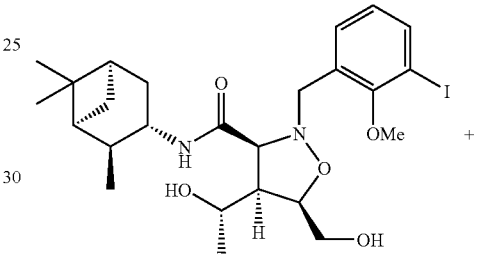
9

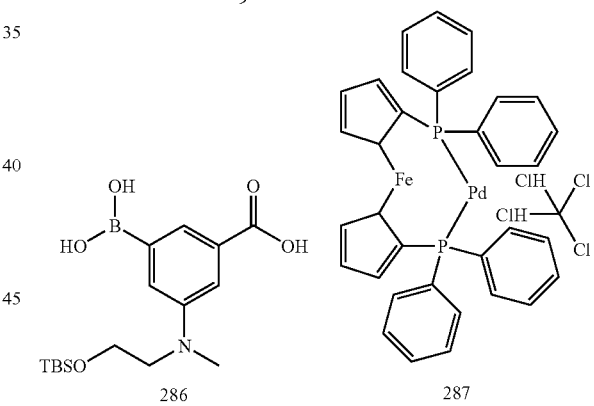
286 287

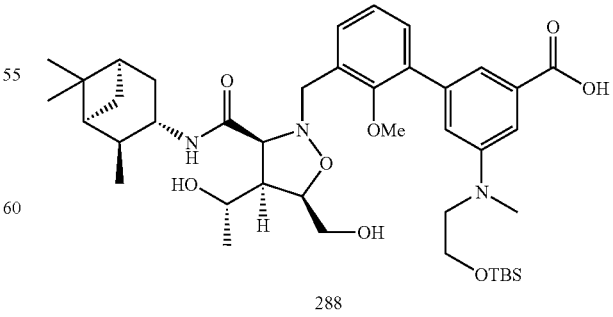
288

Boronic acid 286 (162 mg, 0.280 mmol) was dissolved in DMSO (7 mL) and potassium acetate (28 mg, 0.280 mmol, 1 eq) and cesium carbonate (277 mg, 0.850 mmol, 3 eq) was added. Iodide 9 (100 mg, 0.280 mmol, 1 eq) was added and the stirred solution was degassed by subjecting the flask to three 60 second pulses of alternating vacuum and argon purge cycles. Palladium catalyst 287 (46 mg, 0.057 mmol, 0.2 eq) was added and the solution heated to 60 degrees for 2 hours. The reaction was acidified to pH and extracted with DCM. Organic extracts were combined and dried over sodium sulfate and concentrated to dryness. The crude product was purified by flash (5% MeOH in DCM) to afford 288 (94 mg) 44% Yield.

Part D.

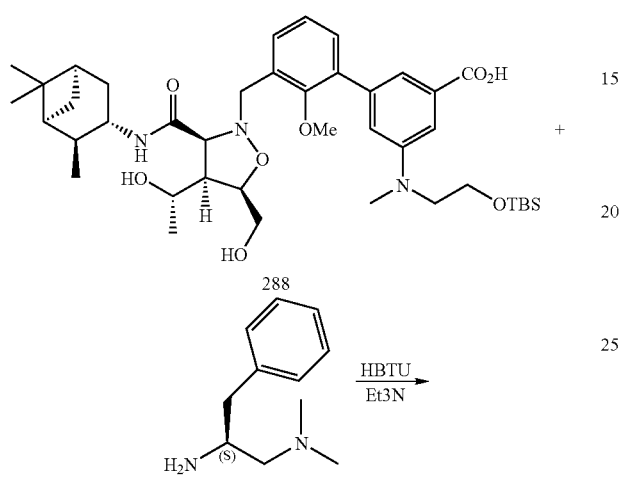

288

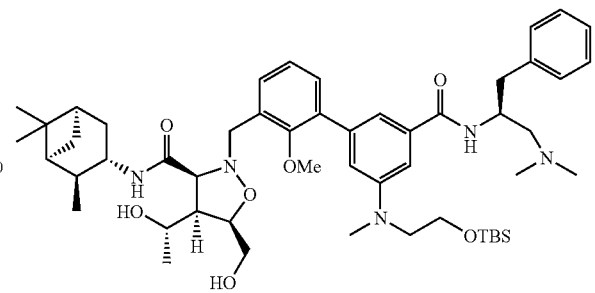

289

Biphenyl acid 288 (50 mg, 0.066 mmol) was dissolved in DMF (0.5 mL) and combined with (S)—N1,N1-dimethyl-3-phenylpropane-1,2-diamine (13 mg, 0.073 mmol, 1.1 eq). Triethylamine (27 uL, 0.2 mmol, 3 eq) was added followed by HBTU (25 mg, 0.066 mmol, 1 eq). After 4 hours the crude reaction was purified by flash (5% MeOH in DCM, containing 0.2% NH$_4$OH) to yield 289 (42 mg). 69% Yield.

Part E.

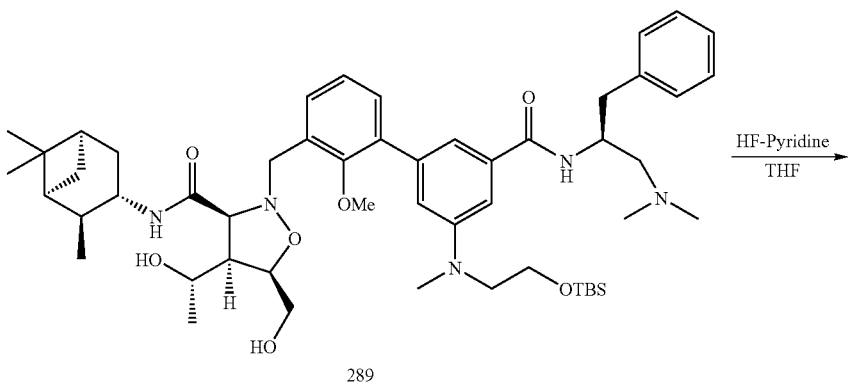

289

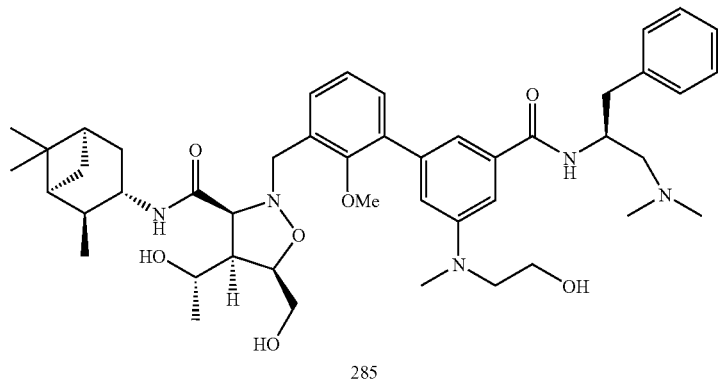

285

TBS ether 289 (42 mg, 0.046 mmol) was dissolved in THF (1 mL) and HF-Pyridine added (30 uL, 0.092 mmol, 2 eq). After 6 hours of stirring, the crude material was purified by flash (5% MeOH in DCM, containing 0.2% NH$_4$OH) to yield 285 (4.5 mg). 12% Yield. MS (ESI(+)) m/e 800.5 (M+H)$^+$.

Example 106

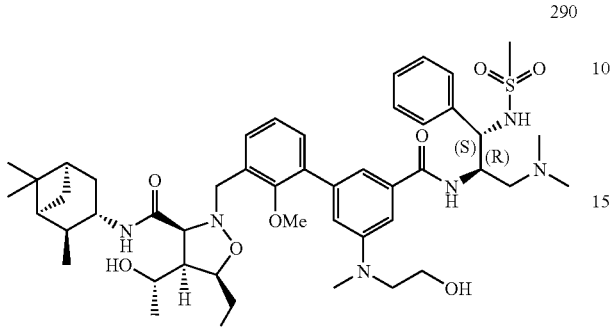

290

Part A.

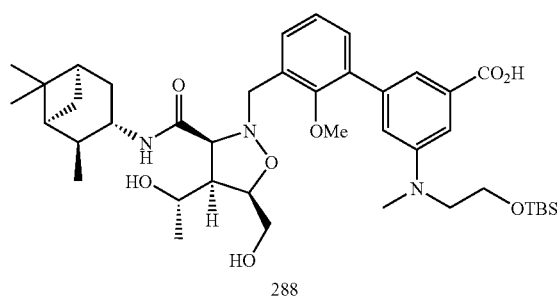

288

Part B.

-continued

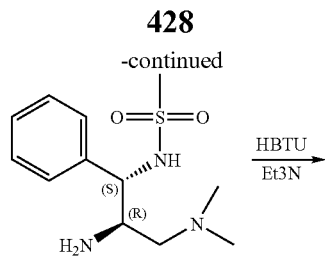

150

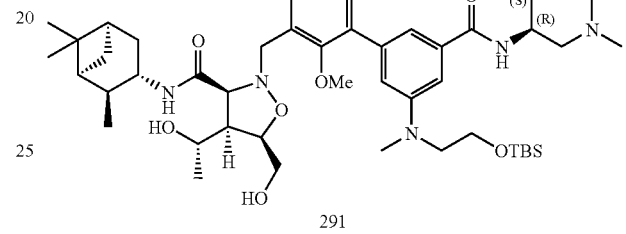

291

Biphenyl acid 288 (25 mg, 0.033 mmol) was dissolved in DMF (0.5 mL) and combined with amine 150 (10 mg, 0.033 mmol, 1 eq). Triethylamine (14 uL, 0.099 mmol, 3 eq) was added followed by HBTU (13 mg, 0.033 mmol, 1 eq). After 4 hours the crude reaction was purified by flash (5%-10% MeOH in DCM) to yield 291 (9 mg). 27% Yield.

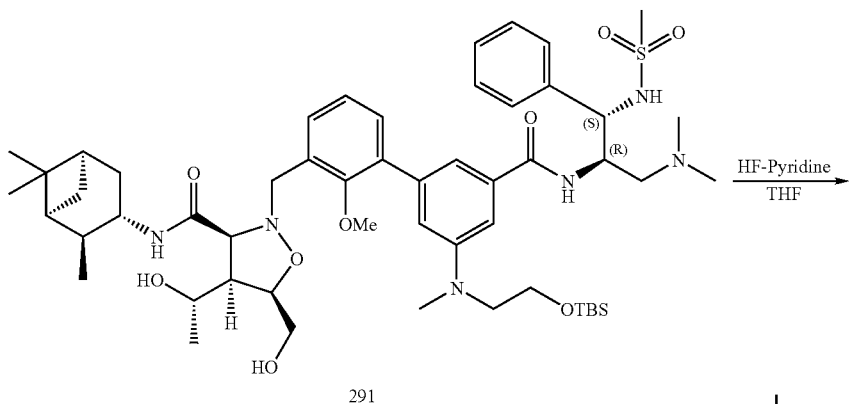

291

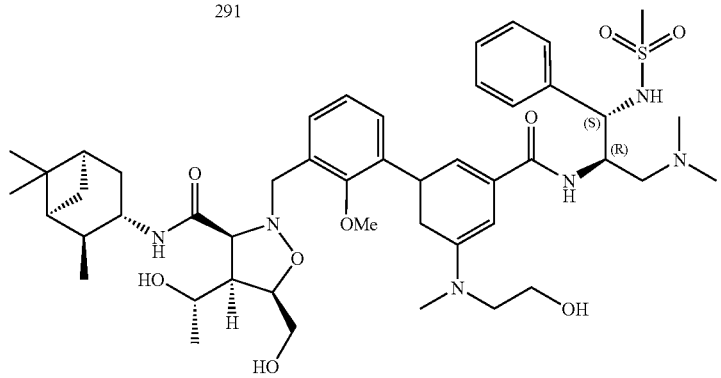

289

TBS ether 291 (9 mg, 0.009 mmol) was dissolved in THF (0.4 mL) and HF-Pyridine added (2.7 uL, 0.022 mmol, 2.5 eq). After 12 hours of stirring, the crude material was purified by flash (5% MeOH in DCM, containing 0.2% NH$_4$OH) to yield 289 (2 mg). 25% Yield. MS (ESI(+)) m/e 893.5 (M+H)$^+$.

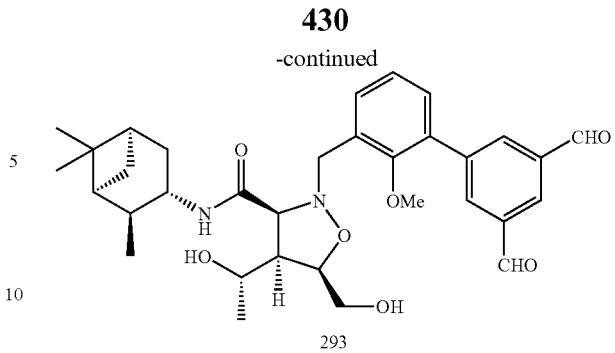
293

To a solution of iodo-core 9 (1.00 g, 1.74 mmol, 1.0 eq) in DMSO (20 mL) under Ar was added cesium carbonate (1.71 g, 5.24 mmol, 3.0 eq), potassium acetate (171 mg, 1.74 mmol, 1.0 eq) and 3,5-diformylphenylboronic acid (622 mg, 3.49 mmol, 2.0 eq). The solution was degassed by bubbling Ar through it for 5 min. PdCl$_2$(dppf).CH$_2$Cl$_2$ adduct (285 mg, 0.35 mmol, 0.2 eq) was then added and the resulting mixture stirred at 70° C. for 1 h. The reaction was allowed to cool to rt, quenched with brine (20 mL) and diluted with AcOEt (20 mL). The layers were separated and the organic one was washed with brine (5×10 mL), dried (MgSO4), filtered and concentrated in vacuo. The residue was purified by flash chromatography (Hex/AcOEt 3:7, 1:4 and 0:1). The product 293 (669 mg, 1.16 mmol, 66% yield) was obtained as a foam.

Part B.

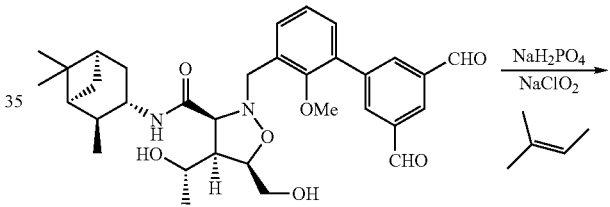
293

Example 107

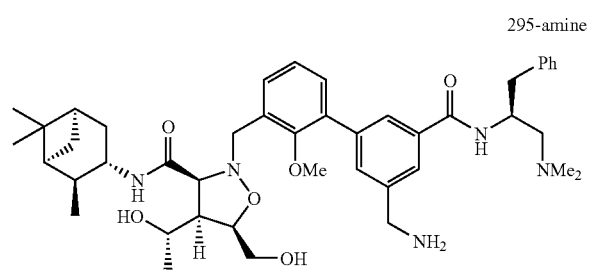
295-amine

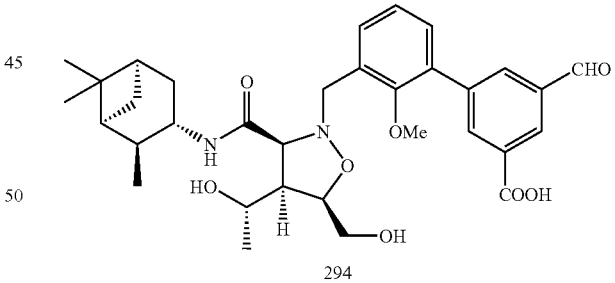
294

To a solution of 293 (650 mg, 1.12 mmol, 1.0 eq) in THF (12 mL) was added 2 M sodium hydrogenphosphate solution (842 ul, 1.69 mmol, 1.5 eq), isobutylene (788 ul, 11.2 mmol, 10.0 eq) and 1 M sodium chlorite solution (1.35 mL, 1.35 mmol, 1.2 eq). The reaction mixture was stirred at rt for 50 min, quenched with 10% Na$_2$S$_2$O$_3$ (10 mL) and stirred for 15 additional min, diluted with AcOEt (10 mL), the layers separated and the aqueous one extracted with AcOEt (2×10 mL). The comb org extracts were washed with brine, dried (MgSO4), filtered and concentrated in vacuo. The residue was purified by flash chromatography (DCM/MeOH 98:2 and 9:1). 294 was obtained as an off-white foam (204 mg, 0.34 mmol, 31% yield).

Part A.

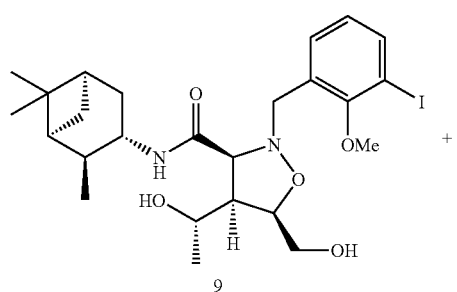
9

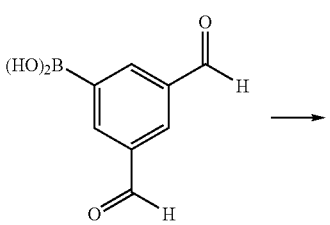

Part C.

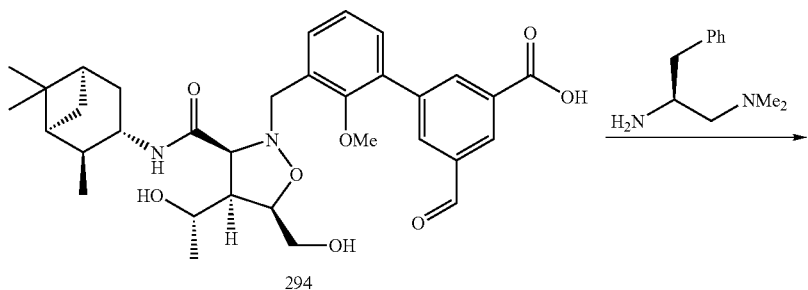

To a stirred solution of acid 294 (200 mg, 0.34 mmol, 1.0 eq) in dry DCM (1 mL) under Ar was added (S)—N1,N1-dimethyl-3-phenylpropane-1,2-diamine (120 mg, 0.67 mmol, 2.0 eq), Hunig's base (117 ul, 0.67 mmol, 2.0 eq) and HBTU (191 mg, 0.50 mmol, 1.5 eq). After 1 h, the reaction was quenched with water (5 mL), the layers separated and the aqueous one extracted with DCM (2×5 mL). The combined organic extracts were washed with brine (10 mL), dried (MgSO4), filtered and concentrated in vacuo. The residue was purified by flash chromatography (DCM/MeOH 9:1). Amide 295 (100 mg, 0.13 mmol, 39% yield) was obtained as a foam.

Part D.

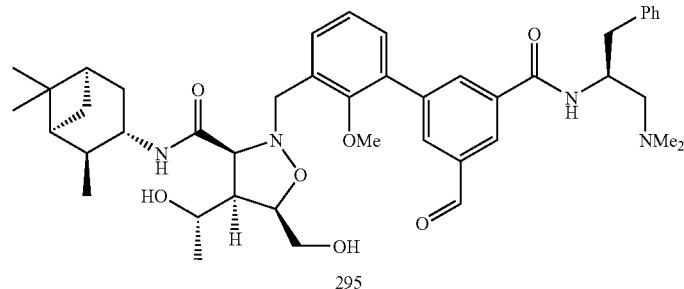

To a solution of aldehyde 295 (42 mg, 0.06 mmol, 1.0 eq) in THF (1.5 mL) and MeOH (0.45 mL) was added 0.5 M Ammonia in dioxane (2.23 mL, 1.11 mmol, 20.0 eq) followed by AcOH (32 ul, 0.56 mmol, 10.0 eq) and sodium cyanoborohydride (17 mg, 0.28 mmol, 5.0 eq). The resulting mixture was stirred at rt for 1 h, quenched with saturated sodium bicarbonate solution (10 mL) and extracted with AcOEt (3×10 mL). The combined organic extracts were washed with brine (20 mL), dried (MgSO4), filtered and concentrated in vacuo. A white foam was obtained, which was purified by preparative HPLC to render 295-amine (10 mg, 0.013 mmol, 24% yield) as a lyophilized powder. MS (ESI(+)) m/e 756.46 (M+H)+.

Example 108

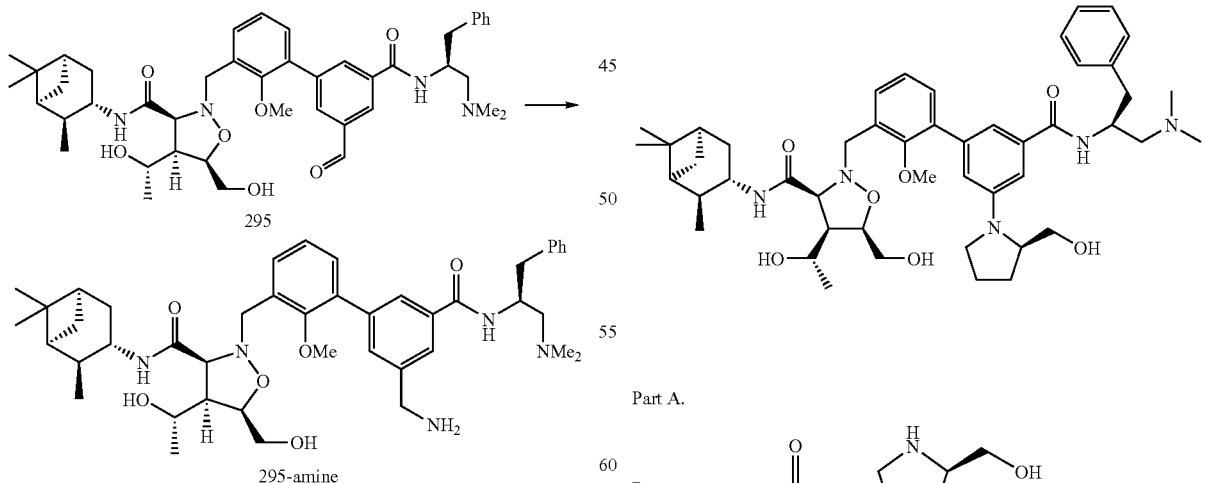

Part A.

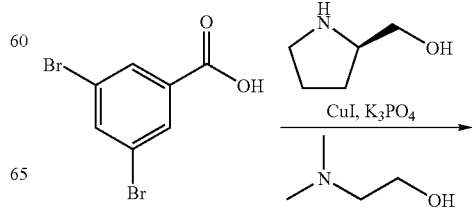

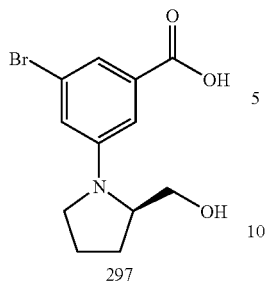

297

In a sealed reactor, 3,5-dibromobenzoic acid (1.0 g, 3.57 mmol, 1 eq), N,N-dimethylethanolamine (735 □ml, 7.15 mmol, 2 eq), potassium triphosphate 1.517 g, 7.15 mmol, 2 eq) and copper(I) iodide (68 mg, 0.357 mmol, 0.1 eq) were dissolved in water (10 mL). The solution was heated at 90° C. for 16 h then allowed to cool to rt and poured on HCl 1 N (100 mL). The mixture was brought to pH~4 using NaOH 1 N and HCl 1 N then extracted with EtOAc (3×30 mL). The combined organics were washed with brine, dried over Na$_2$SO$_4$, filtered, concentrated. The residue was purified by flash chromatography (DCM and DCM/MeOH/AcOH 90:10:1 0 to 50%) to obtain 297 (318 mg, 1.06 mmol) as an oil. Yield 30%.

Part B.

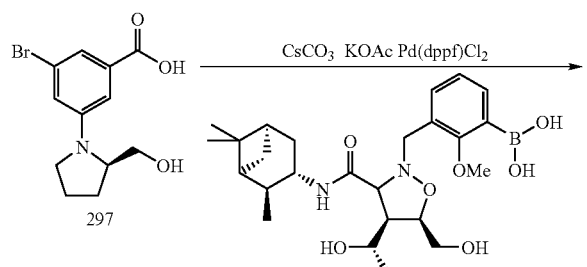

Part C.

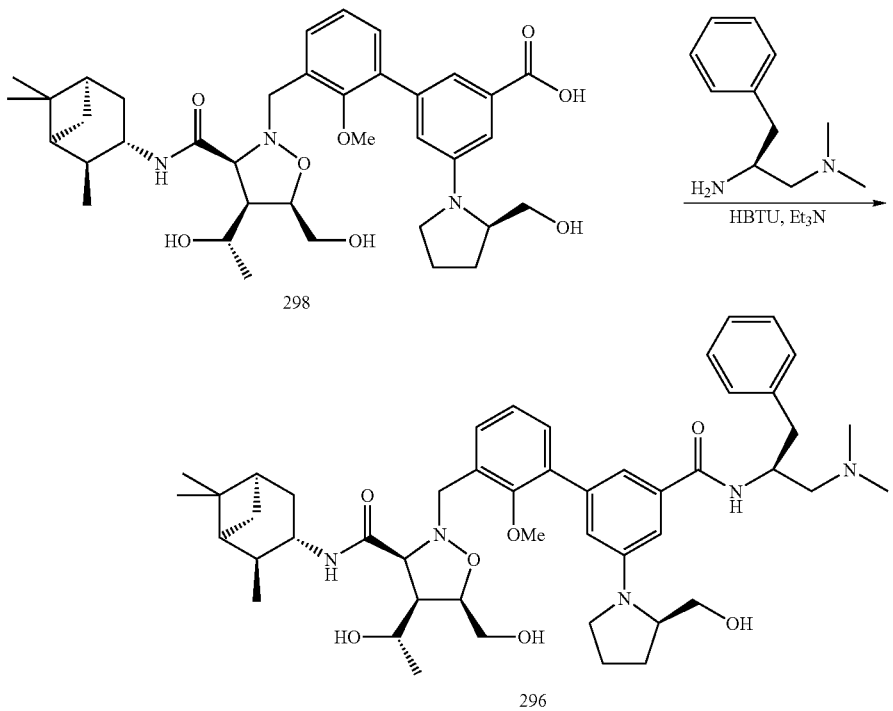

298

A flask containing boronate (described in Example 1, part G) (194 mg, 396 µmol, 1 eq), bromide 297 (142 mg, 475 µmol, 1.2 eq), cesium carbonate (387 mg, 1.18 mmol, 3 eq), potassium acetate (39 mg, 396 µmol, 1 eq) and Pd(dppf)Cl$_2$ (58 mg, 79 µmol, 0.2 eq) was purged with argon and DMSO (2 mL) was added. The reaction was heated at 60° C. for 5 h then allowed to cool to rt, diluted with water (100 mL) and acidified to pH~4 with HCl 0.02M. The mixture was extracted with DCM (3×30 mL). The combined organic layers were washed with water (1×30 mL) and brine (1×30 mL), dried over Na$_2$SO$_4$, filtered and concentrated to a brown oil which was purified by flash chromatography (DCM and DCM/MeOH/AcOH 90:10:1 0 to 70%) to obtain 298 (155 mg, 233 µmol) as an oil. Yield 59%.

296

Acid 298 (43 mg, 65 μmol, 1 eq), (S)—$N^1,N^1$-dimethyl-3-phenylpropane-1,2-diamine (14 mg, 77 μmol, 1.2 eq) and HBTU (29 mg, 77 μmol, 1.2 eq) were dispersed in DCM (1 mL) and triethylamine (27 μL, 194 μmol, 3 eq) was added. The reaction was stirred at rt for 1 h then concentrated to dryness. The residue was purified by HPLC to afford 296 (3.9 mg, 4.7 μmol) as a lyophilized powder. MS (ESI(+)) m/e 826.47 (M+H)⁺. Yield 7.3%.

Example 109

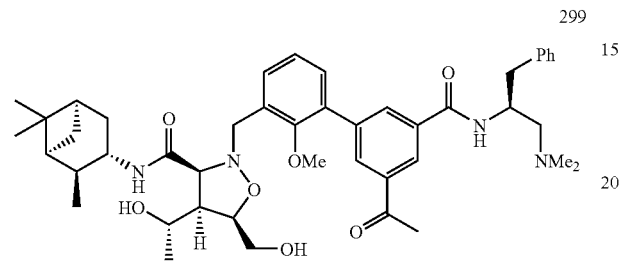

Part A.

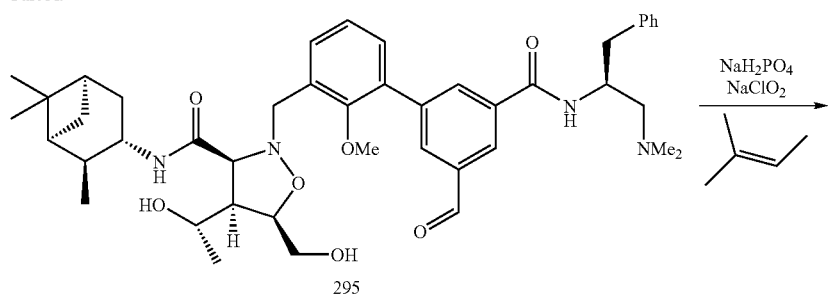

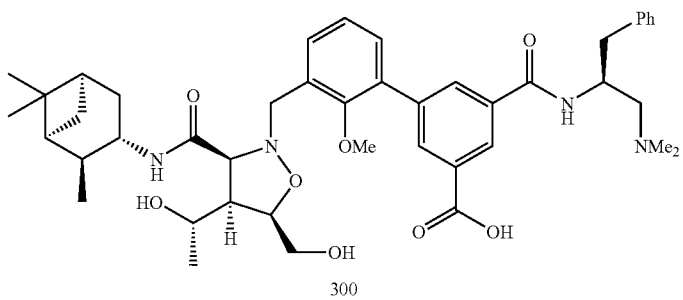

To a solution of 295 (100 mg, 0.13 mmol, 1.0 eq) in THF (2 mL) was added 2M sodium hydrogenphosphate solution (99 ul, 0.20 mmol, 1.5 eq), isobutylene (93 ul, 1.33 mmol, 10.0 eq) and 1M sodium chlorite solution (159 ul, 0.16 mmol, 1.2 eq). The reaction mixture was stirred at rt for 1 h, an equal amount of reagents were added and stirring continued for 30 additional min. The reaction was quenched with 10% $Na_2S_2O_3$ (5 mL) and stirred for 15 min, diluted with AcOEt (5 mL), the layers separated and the aqueous one extracted with AcOEt (2×5 mL). The combined organic extracts were washed with brine, dried (MgSO4), filtered and concentrated in vacuo. The residue 300 was used without further purification.

Part B.

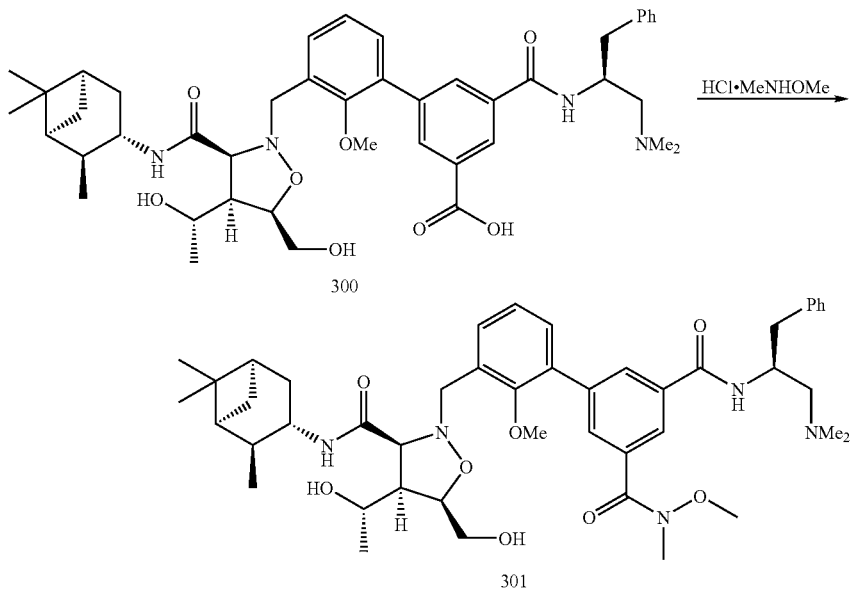

To a stirred solution of crude acid 300 (67 mg, 0.09 mmol, 1.0 eq) in dry DCM (1 mL) under Ar was added N,O-dimethyl hydroxylamine hydrochloride 5 (21 mg, 0.22 mmol, 2.5 eq), Hunig's base (56 ul, 0.44 mmol, 5.0 eq) and HBTU (49 mg, 0.13 mmol, 1.5 eq). After 1 h, the reaction was quenched with water (5 mL), the layers separated and the aqueous one extracted with DCM (2×5 mL). The combined organic extracts were washed with brine (10 mL), dried (MgSO$_4$), filtered and concentrated in vacuo. The residue 301 was used directly in the next reaction.

Part C.

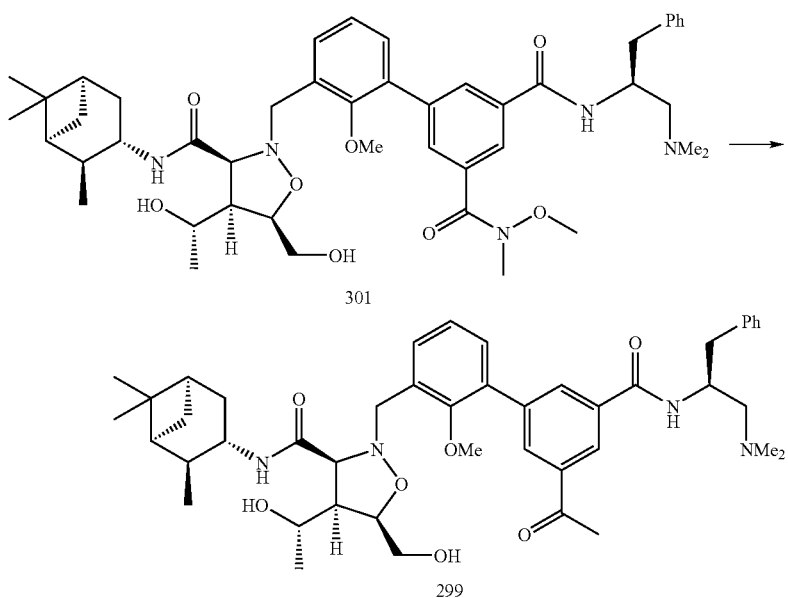

Crude Weinreb amide 301 (35 mg, 0.04 mmol, 1.0 eq) was dissolved in anhydrous THF (1 mL) under Ar and was cooled to −78° C. 1.6 M Methyllthium in Et$_2$O (54 ul, 0.09 mmol, 2.0 eq) was added and the reaction mixture was stirred for 30 min at −78° C. and allowed to warm to rt. The reaction was quenched with saturated NH$_4$Cl solution (5 mL) and diluted with Et₂O (5 mL), the layers separated, the aqueous one extracted with Et₂O (2×5 mL) and the combined organic extracts washed with brine (10 mL), dried (MgSO4), filtered and concentrated in vacuo. A foam was obtained, which was purified by preparative HPLC to render 299 (6 mg, 0.01 mmol, 18% yield) as a lyophilized powder. MS (ESI(+)) m/e 769.45 (M+H)⁺.

Example 110

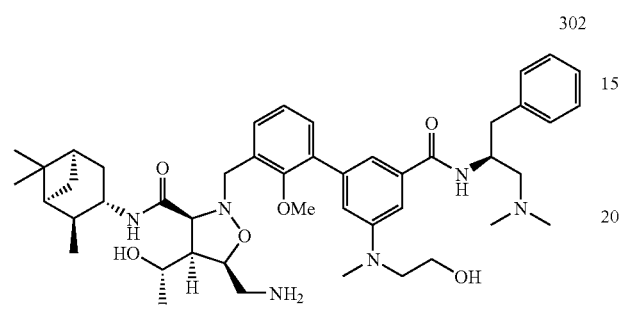

Part A.

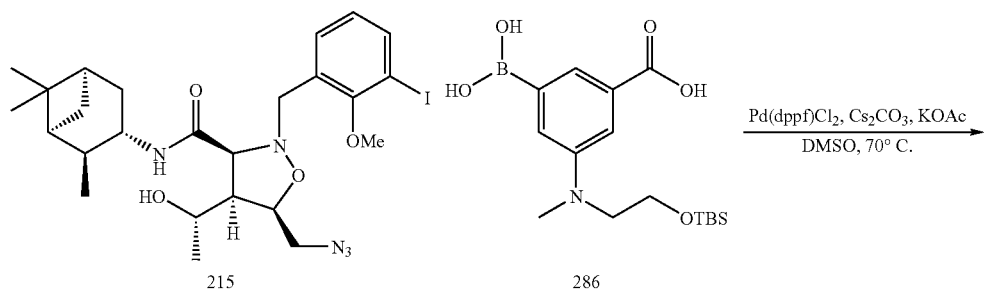

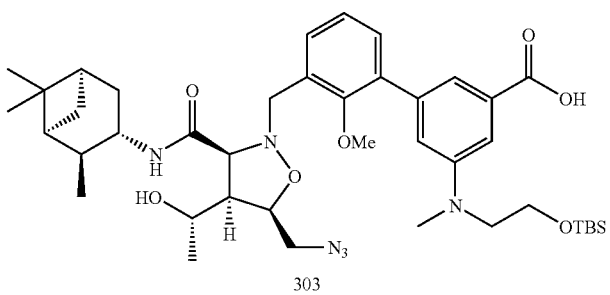

A solution of aryl iodide 215 (113 mg, 0.19 mmol, 1 eq), boronic acid 286 (80 mg, 0.23 mmol, 1.2 eq), cesium carbonate (185 g, 0.57 mmol, 3 eq) and potassium acetate (18.6 mg, 0.19 mmol, 1 eq) in DMSO (4.8 mL) was degassed by bubbling argon through the solution for 10 min. Pd(dppf)Cl₂ (27.7 mg, 0.04 mmol, 0.2 eq) was then added and the flask purged with argon. The mixture was heated at 70° C. for 1 h. The reaction mixture was added to brine (10 mL), acidified with 1 N HCl until the aqueous layer attained a pH of 3, and extracted with EtOAc (2×10 mL). The combined organic layers were dried over Na₂SO₄, filtered and concentrated in vacuo to afford a brown oil. The oil was purified by silica gel chromatography (40-60% EtOAc/hexane with 0.25% acetic acid) to give 17.3 mg of 303 as a brown oil. Yield 12%. MS (ESI(+)) m/z 779.53 M⁺.

Part B.

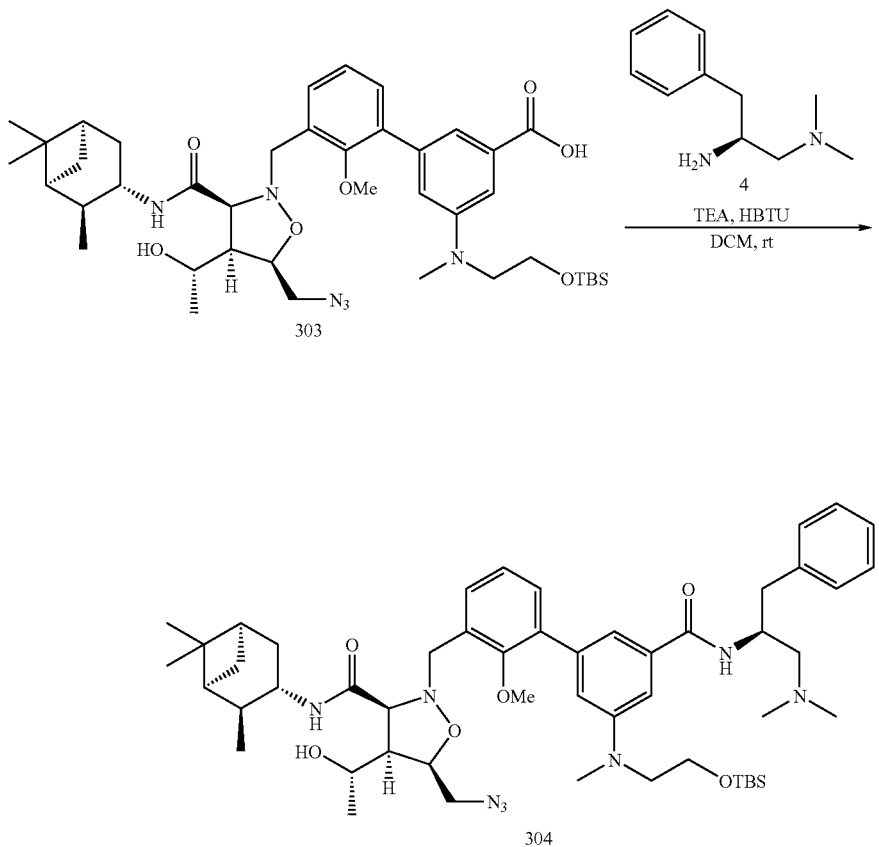

To a solution of 303 (17.3 mg, 0.022 mmol, 1 eq) in DCM (2 mL) was added TEA (10 μL, 0.067 mmol, 3 eq) and HBTU (16.8 mg, 0.044 mmol, 2 eq). The solution was stirred at rt for 10 min. (S)—N1,N1-dimethyl-3-phenylpropane-1,2-diamine (6 mg, 0.033 mmol, 1.5 eq) was then added. After stirring at rt for 2 h, the mixture was diluted with DCM (10 mL) and washed with saturated potassium carbonate solution (10 mL). The aqueous layer was extracted with DCM (2×10 mL). The combined organic layers were dried over $Na_2SO_4$, filtered and concentrated in vacuo. The material was purified by silica gel chromatography (60-75% EtOAc/hexane with 0.25% TEA) to give 15.1 mg of 304. Yield 72%. MS (ESI(+)) m/z 939.68 $M^+$.

Part C.

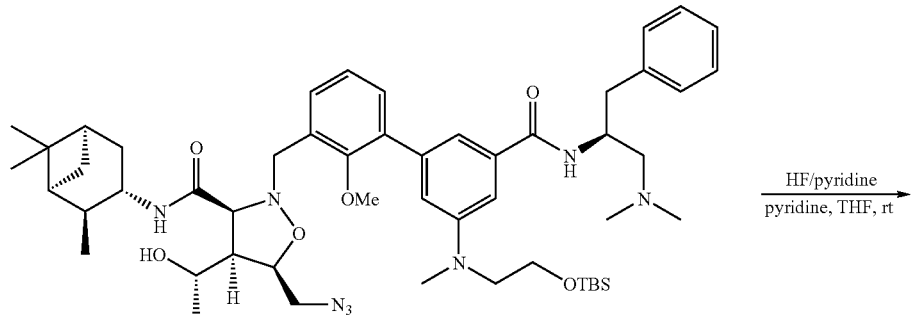

-continued

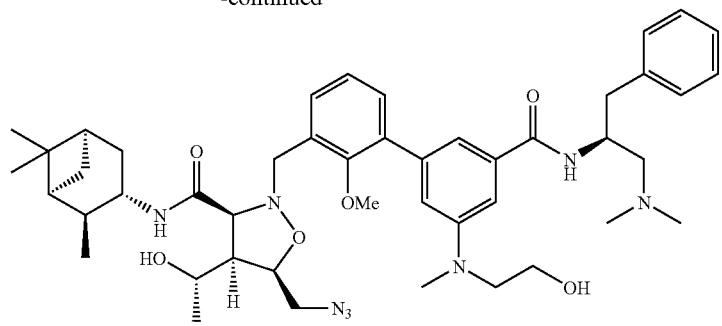
305

To a solution of 304 (15.1 mg, 0.016 mmol, 1 eq) in THF (1.5 mL) in a polyproplylene tube at rt was added a 1:1:1 THF:HF/pyridine:pyridine solution (70 μL). The solution was stirred at rt for 1 h, quenched with methoxytrimethylsilane (700 μL) and concentrated in vacuo. The crude 305 was used in the next step without further purification. MS (ESI(+)) m/z 825.44 M+.

Part D.

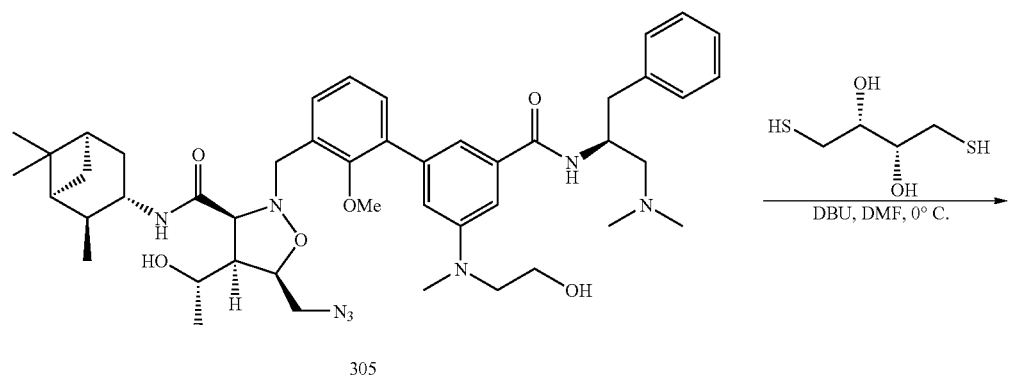
305

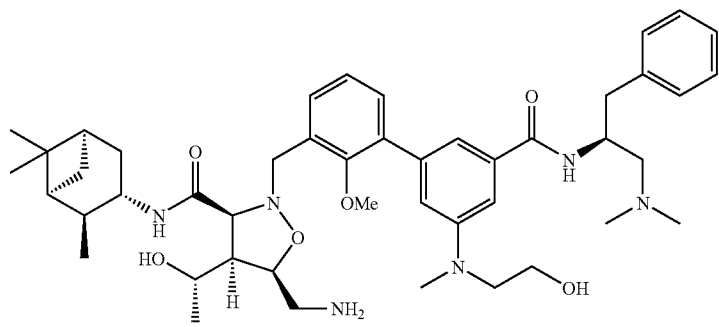
302

To a solution of 305 (14.3 mg, 0.017 mmol, 1 eq) in DMF (0.6 mL) at 0° C. was added dithiothreitol (8 mg, 0.052 mmol, 3 eq) and DBU (7.8 μL, 0.052 mmol, 3 eq). The solution was stirred at 0° C. for 20 min. The crude reaction was kept at 0° C. and purified by HPLC to give 0.8 mg of 302. Yield 6%. MS (ESI(+)) m/z 799.55 M+.

Example 111

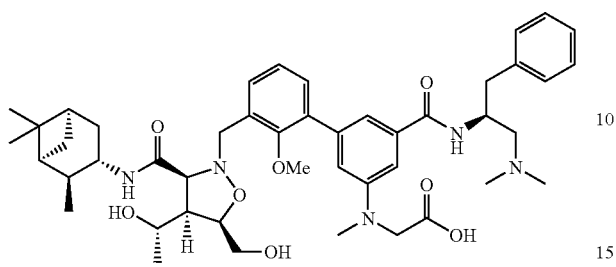

306

Part A.

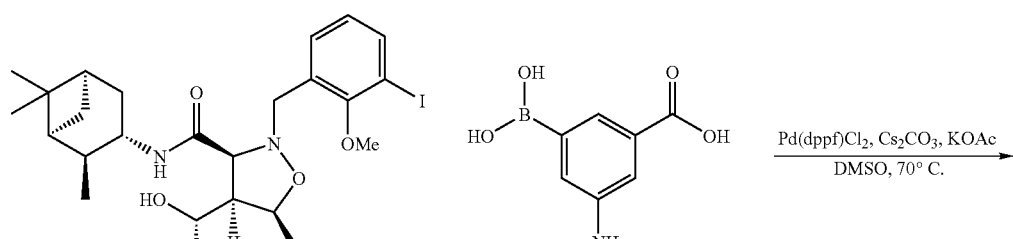

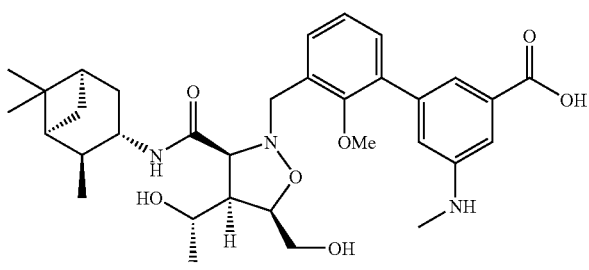

306

A solution of aryl iodide 9 (403.8 mg, 0.71 mmol, 1 eq), boronic acid 285 (151 mg, 0.78 mmol, 1.1 eq), cesium carbonate (689 g, 2.2 mmol, 3 eq) and potassium acetate (69.2 mg, 0.71 mmol, 1 eq) in DMSO (7.4 mL) was degassed by bubbling argon through the solution for 10 min. Pd(dppf)Cl$_2$ (103 mg, 0.14 mmol, 0.2 eq) was then added and the flask purged with argon. The mixture was heated at 70° C. for 10.5 h. The reaction mixture was added to brine (40 mL), acidified with 1 N HCl until the aqueous layer attained a pH of 3, and extracted with EtOAc (2×40 mL). The combined organic layers were dried over Na$_2$SO$_4$, filtered and concentrated in vacuo to afford a brown oil. The oil was purified by silica gel chromatography (75-95% EtOAc/hexane with 0.25% acetic acid) to give 124.3 mg of 306. Yield 29.6%. MS (ESI(+)) m/z 596.34 (M+H)$^+$.

Part B.

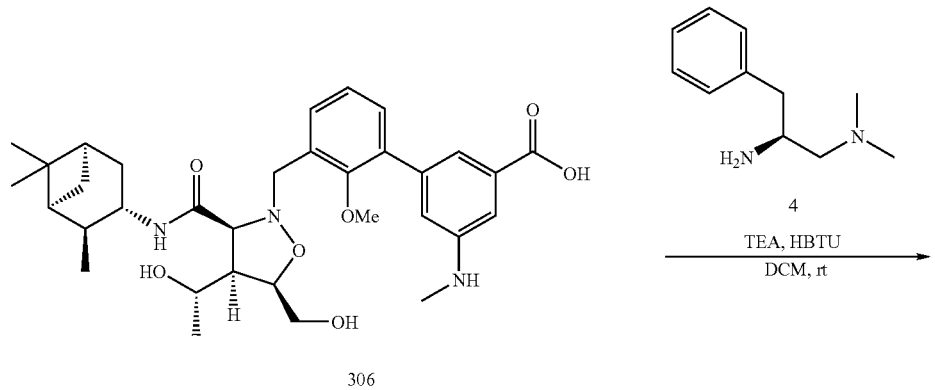

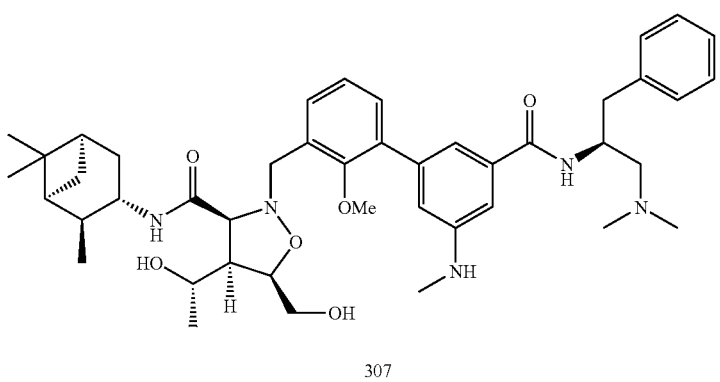

To a solution of 306 (25 mg, 0.04 mmol, 1 eq) in DCM (4 mL) was added TEA (17 µL, 0.12 mmol, 3 eq), HBTU (31.8 mg, 0.08 mmol, 2 eq) and (S)—N$^1$,N$^1$-dimethyl-3-phenyl-propane-1,2-diamine (15 mg, 0.08 mmol, 2 eq). After stirring at rt for 2 h, the mixture was diluted with DCM (15 mL) and washed with saturated potassium carbonate solution (10 mL). The aqueous layer was extracted with DCM (2×10 mL). The combined organic layers were dried over Na$_2$SO$_4$, filtered and concentrated in vacuo. The material was purified by silica gel chromatography (60-75% EtOAc/DCM with 0.25% TEA) to give 22.8 mg of 307. Yield 72%. MS (ESI(+)) m/z 756.45 M$^+$.

Part C.

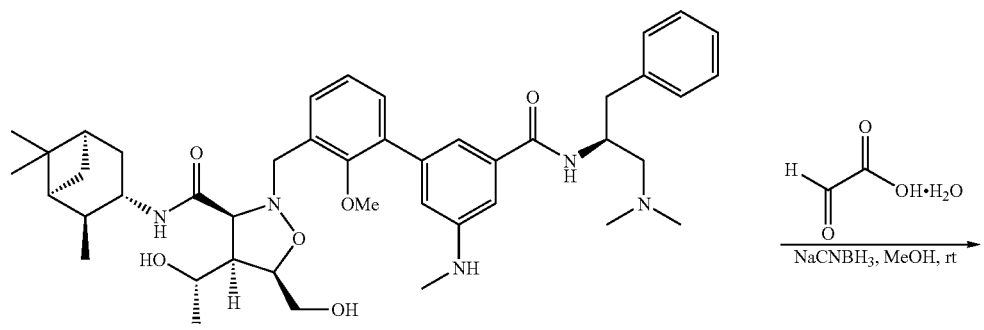

-continued
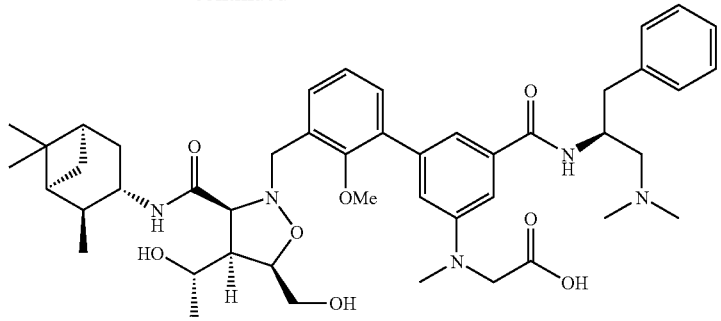
306
To a solution of 307 (6.7 mg, 0.009 mmol, 1 eq) in MeOH (0.5 mL) at rt was added glyoxylic acid monohydrate (1 mg, 0.011 mmol, 1.2 eq). The solution was stirred at rt for 10 min. Sodium cyanoborohydride (0.7 mg, 0.011 mmol, 1.2 eq) was then added. The solution was stirred at rt for 1 h and concentrated in vacuo. The crude reaction was purified by HPLC to give 5 mg of 306. Yield 69%. MS (ESI(+)) m/z 814.53 M+.
Example 112
308
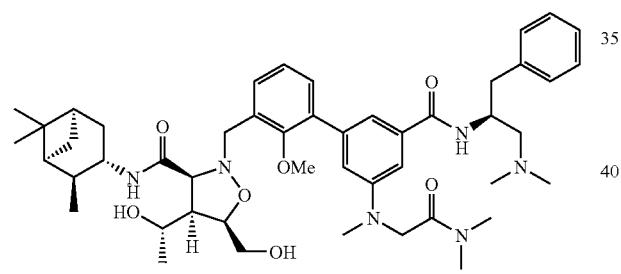
Part A.
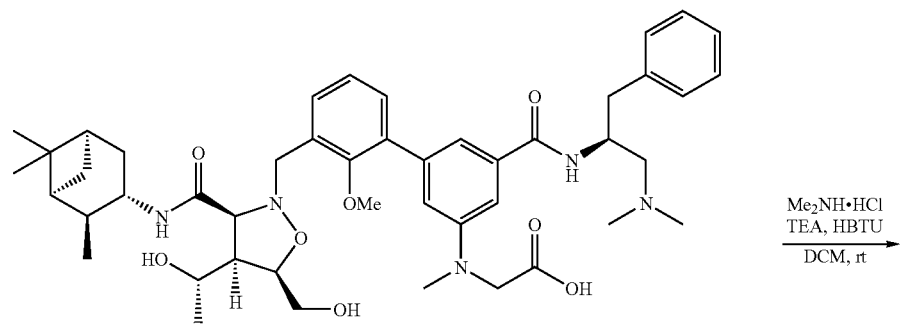
306

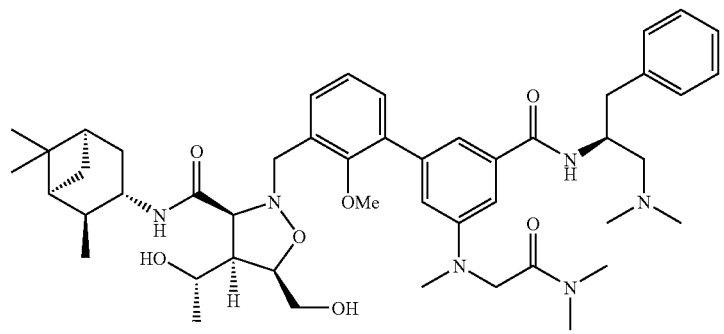
308
A solution of 306 (5.5 mg, 0.007 mmol, 1 eq), dimethylamine hydrochloride (1.7 mg, 0.02 mmol, 3 eq), HBTU (5.2 mg, 0.014 mmol, 2 eq) and TEA (4 μL, 0.028 mmol, 4 eq) in DCM (0.5 mL) was stirred at rt for 2 h. The crude reaction was concentrated in vacuo and purified by HPLC to give 4.4 mg of 308. Yield 77%. MS (ESI(+)) m/z 841.63 M⁺.
Example 113
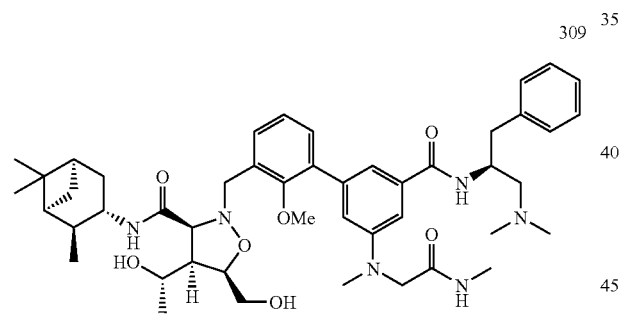
309
Part A.
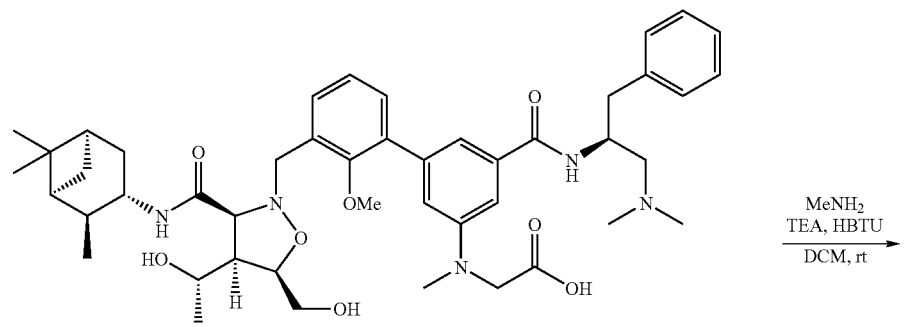
306

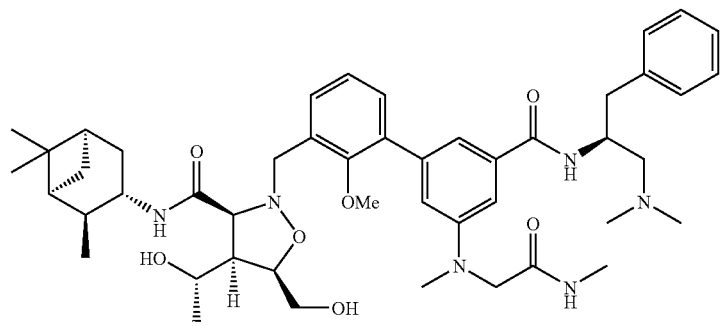
309
A solution of 306 (14 mg, 0.017 mmol, 1 eq), methylamine (26 µL, 2M in THF, 0.052 mmol, 3 eq), HBTU (13 mg, 0.034 mmol, 2 eq) and TEA (10 µL, 0.069 mmol, 4 eq) in DCM (1 mL) was stirred at rt for 2 h. The crude reaction was concentrated in vacuo and purified by HPLC to give 3.3 mg of 309. Yield 23%. MS (ESI(+)) m/z 827.60 M+.
Example 114
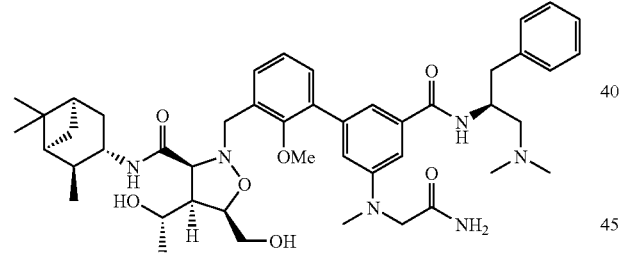
310
Part A.
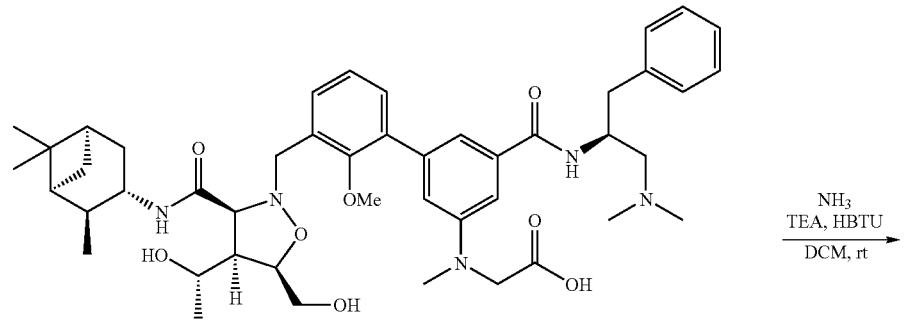
306

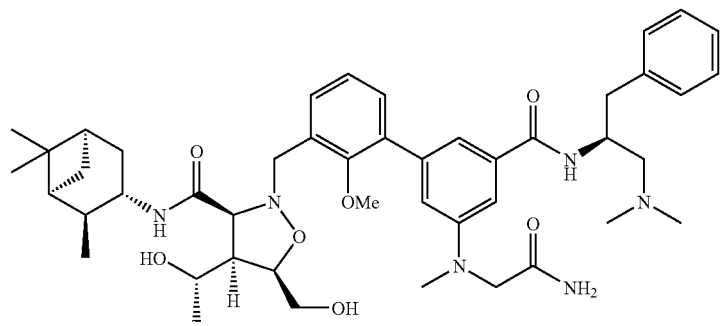
309
A solution of 306 (13.3 mg, 0.016 mmol, 1 eq), ammonia (7 µL, 7N in MeOH, 0.049 mmol, 3 eq), HBTU (12.4 mg, 0.033 mmol, 2 eq) and TEA (9 µL, 0.065 mmol, 4 eq) in DCM (1 mL) was stirred at rt for 2 h. The crude reaction was concentrated in vacuo and purified by HPLC to give 6 mg of 310. Yield 45%. MS (ESI(+)) m/z 813.58 M$^+$.
Example 115
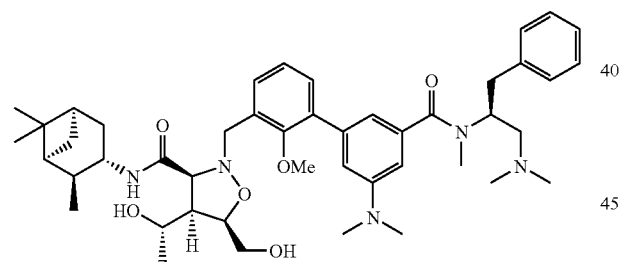
311
Part A.
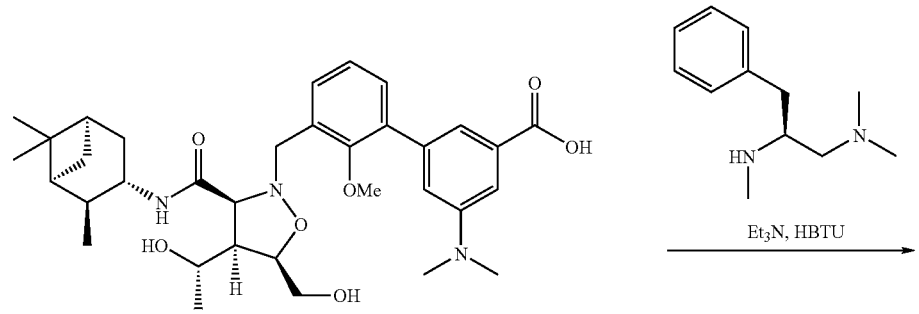

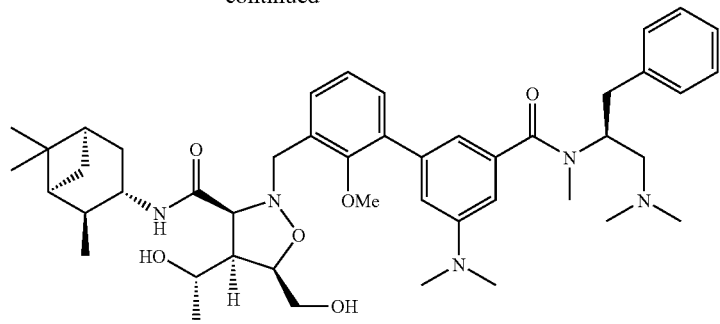

311

A solution of 10 (10 mg, 0.02 mmol, 1 eq) in DMF (1 mL) was treated with TEA (9 uL, 0.07 mmol, 3.0 eq), (S)—N1,N1,N2-trimethyl-3-phenylpropane-1,2-diamine (9 mg, 0.06 mmol, 3.0 eq) (derived from the requisite amino acid analogous to the procedure described in Example 73, part A), and HBTU (10 mg, 0.04 mmol, 2.0 eq). After stirring for 2 h at rt, the reaction mixture was diluted with MeOH (500 uL) and directly purified by reverse-phase HPLC (MeCN/water with 40 mM $NH_5CO_2$) to give 5 mg of compound 311 as a white solid. Yield 50%. MS (ESI(+)) m/z 784.4 (M+H)$^+$.

Example 116

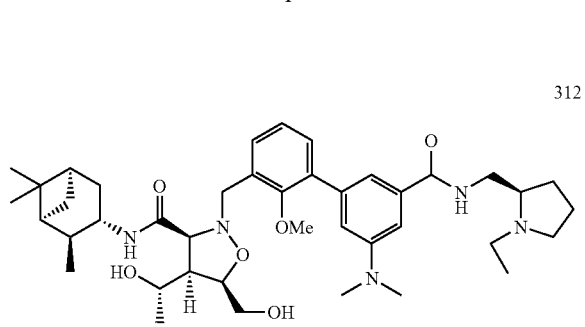

312

Part A.

Compound 312 was synthesized according to the procedure described in Example 1, part H. using commercially available (R)-2-aminomethyl-1-ethylpyrrolidine in place of (S)—$N^1$,$N^1$,4,4-tetramethylpentane-1,2-diamine. Yield 20%. MS (ESI(+)) m/z 720.4 (M+H)$^+$.

Example 117

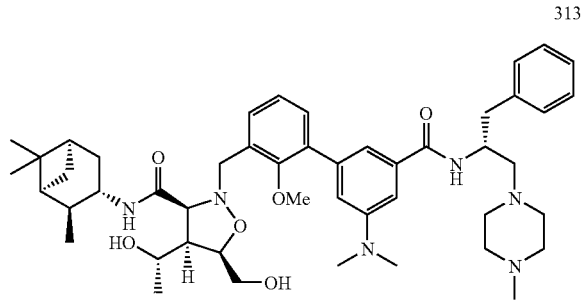

313

Part A.

Compound 313 was synthesized according to the procedure described in Example 1, part H using (R)-1-Benzyl-2-(4-methyl-piperazin-1-yl)-ethylamine (derived from the requisite amino acid analogous to the procedure described in Example 73, part A) in place of (S)—$N^1$,$N^1$,4,4-tetramethylpentane-1,2-diamine. Yield 41%. MS (ESI(+)) m/z 825.5 (M+H)$^+$.

Example 118

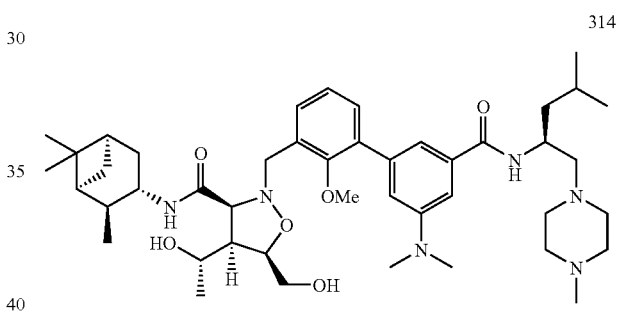

314

Part A.

Compound 314 was synthesized according to the procedure described in Example 1, part H using (S)-3-Methyl-1-(4-methyl-piperazin-1-ylmethyl)-butylamine (derived from the requisite amino acid analogous to the procedure described in Example 73, part A) in place of amine (S)—$N^1$,$N^1$,4,4-tetramethylpentane-1,2-diamine. Yield 28%. MS (ESI(+)) m/z 791.5 (M+H)$^+$.

Example 119

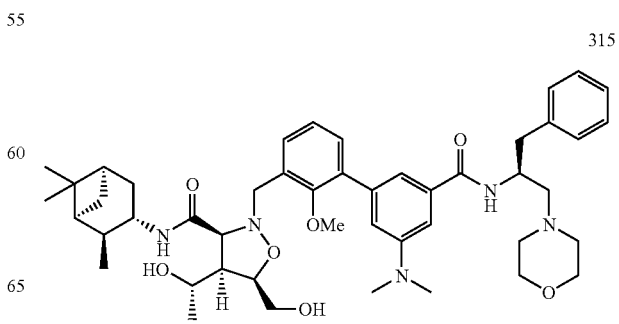

315

Part A.

Compound 315 was synthesized according to the procedure described in Example 1, part H using (S)-3-Methyl-1-morpholin-4-ylmethylamine (derived from the requisite amino acid analogous to the procedure described in Example 73, part A) in place of (S)—$N^1,N^1$,4,4-tetramethylpentane-1,2-diamine. Yield 25%. MS (ESI(+)) m/z 778.6 (M+H)$^+$.

Example 120

316

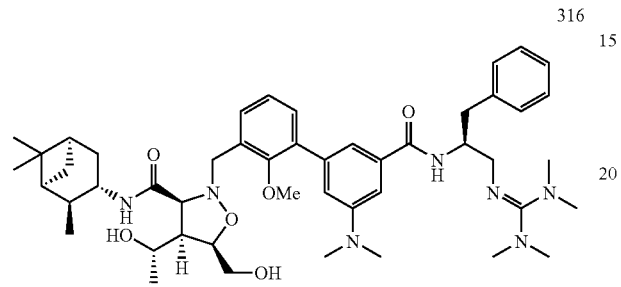

Part A.

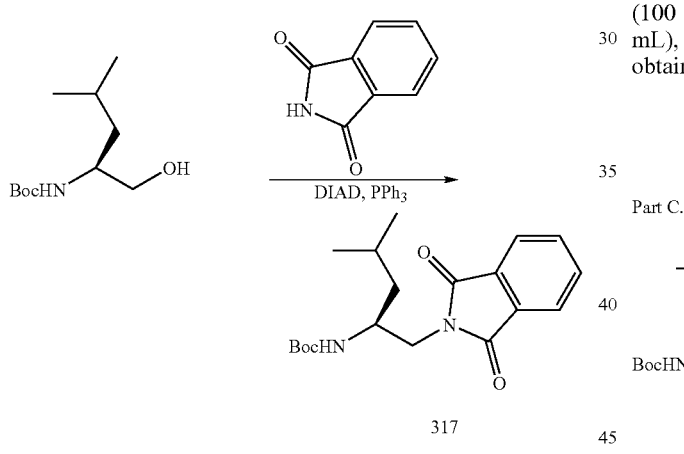

Boc-Leucinol (2.20 g, 10.1 mmol, 1 eq), phthalimide (1.79 g, 12.2 mmol, 1.2 eq) and triphenylphosphine (3.98 g, 15.2 mmol, 1.5 eq) were dissolved in dry THF (40 mL) under Ar and diisopropyldiazocarboxylate (3.17 mL, 15.2 mmol, 1.5 eq) was added dropwise. The solution was stirred at rt for 1 h30 then concentrated to dryness. The residue was purified by flash chromatography (Hexane then Hex/EtOAc 9:1) to afford 317 (2.99 g, 8.6 mmol) as a white solid. Yield 85%.

Part B.

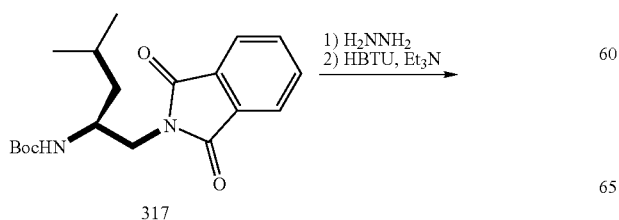

-continued

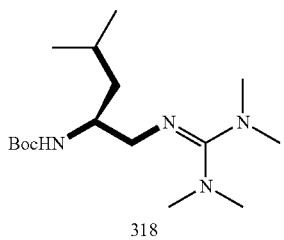

Compound 317 (1.0 g, 2.89 mmol, 1 eq) was treated with hydrazine hydrate (0.896 mL, 28.9 mmol, 10 eq) in refluxing ethanol for 2 h. The reaction was allowed to reach rt then filtered on paper. The filtrate was concentrated to dryness and the residue taken in DCM. The mixture was filtered on paper and the filtrate concentrated to dryness.

The residue was taken in DCM/THF 1:1 (40 mL) and HBTU (1.2 g, 3.1 mmol, 1.1 eq) then triethylamine (0.43 mL, 3.1 mmol, 1.1 eq) were added. The solution was stirred at rt for 3 h30, then concentrated. The residue was taken in EtOAc (100 mL) and the solution washed with NaOH 1 N (3×20 mL), dried over Na2SO4, filtered, concentrated to dryness to obtain 318 (1.051 g, 85% pure) as an oil. Yield 99%.

Part C.

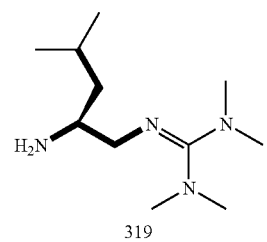

Compound 318 (1.051 g, 3.34 mmol, 1 eq) was treated with HCl 4M in dioxane for 1 h then concentrated to dryness. The residue was precipitated from methanol/diethyl ether and dried under vacuum to obtain in a quantitative yield the bis-hydrochloric salt of 319 as an off-white foam (800 mg, 2.89 mmol).

Part D.

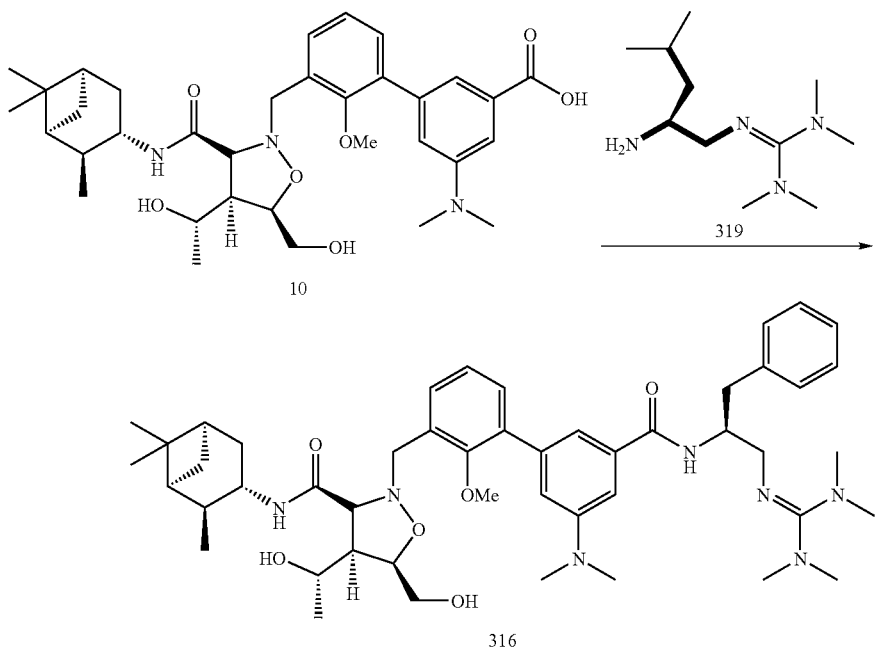

Compound 316 was synthesized according to the procedure described in Example 1, part H using amine 319 in place of (S)—N$^1$,N$^1$,4,4-tetramethylpentane-1,2-diamine Yield 32%. MS (ESI(+)) m/z 806.6 (M+H)$^+$.

Example 121

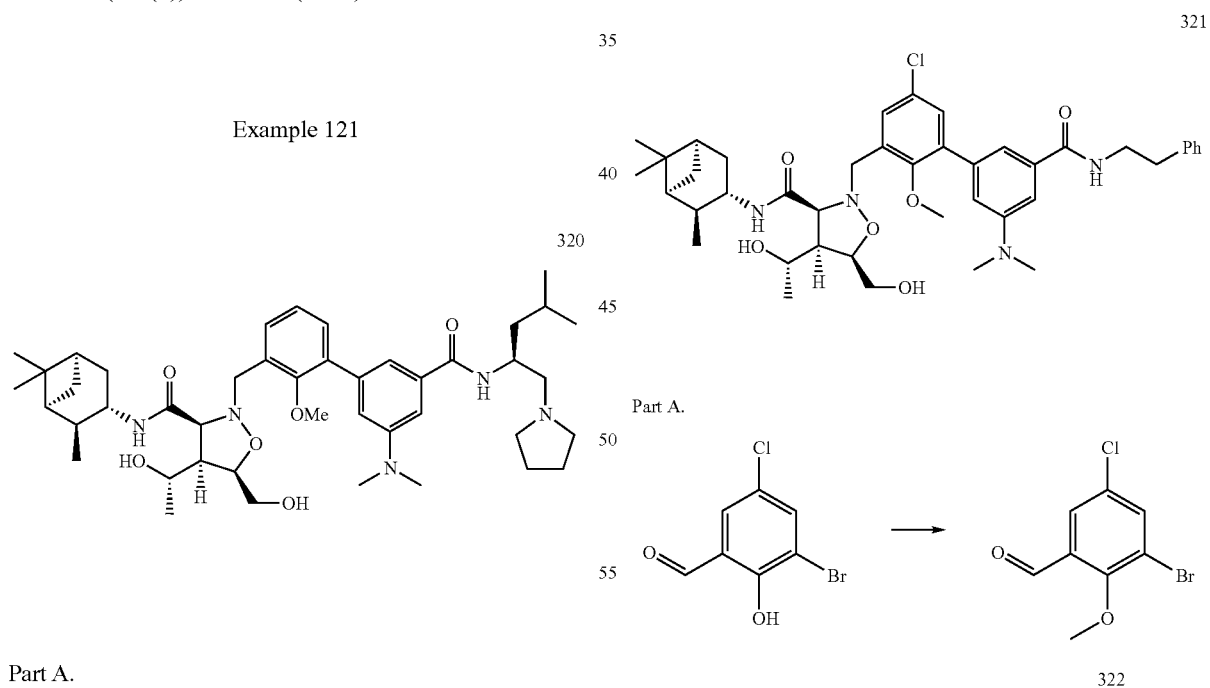

Part A.

Compound 320 was synthesized according to the procedure described in Example 1, part H using (S)-3-Methyl-1-pyrrolidin-1-ylmethyl-butylamine (derived from the requisite amino acid analogous to the procedure described in Example 73, part A) in place of (S)—N$^1$,N$^1$,4,4-tetramethyl-pentane-1,2-diamine. Yield 22%. MS (ESI(+)) m/z 762.6 (M+H)$^+$.

Example 122

Part A.

3-Bromo-5-chloro-2-hydroxybenzaldehyde (2 g, 8.5 mmol, 1 eq) was dissolved in DMF (10 mL) and treated with potassium carbonate (1.76 g, 12.7 mmol, 1.5 eq) and iodomethane (1.06 mL, 17 mmol, 2 eq) y The mixture was stirred at 50° C. for 14 h. The mixture was poured into water (100 mL) and extracted with ether (2×75 mL). The ether layers were washed successively with 15% aqueous NaOH, water, and then brine (50 mL each). Drying over magnesium sulfate and concentration in vacuo gave the ether 322 as a white solid (2.07 g, 98% yield).

Part B.

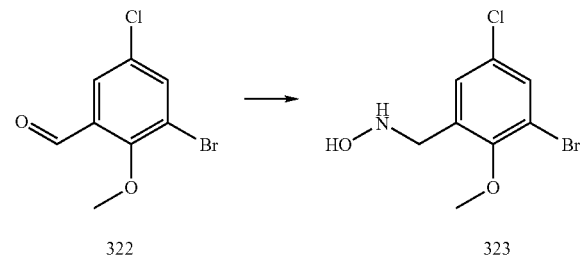

Aldehyde 322 (2.07 g, 8.38 mmol, 1 eq) and hydroxylamine hydrochloride (0.757 g, 10.9 mmol, 1.3 eq) were dissolved in THF/MeOH (1:3, 30 mL) at 23° C. The pH was adjusted to 9 with 6 N KOH. After stirring for 2 h, NaBH$_3$CN (0.526 g, 8.4 mmol, 1 eq) was added followed by a crystal of methyl orange. The pH was adjusted to 2 and the resulting ruby red color of the reaction mixture was maintained for the duration of the reaction by the frequent addition of 1 N HCl. After stirring for a total of 16 h, the reaction mixture was adjusted to pH 7 with 6 N KOH. The mixture was diluted with water (100 mL) and extracted with DCM (2×50 mL) and the combined organics were washed with water (50 mL), brine (20 mL), dried over MgSO$_4$, filtered and concentrated in vacuo to afford 2.0 g (90% yield) of hydroxylamine 323. The crude material was used without further purification.

Part C.

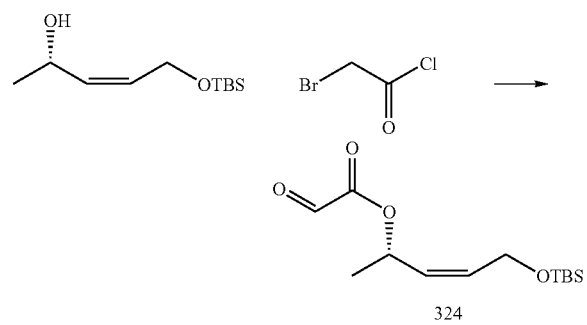

A 0° C. dichloromethane solution (120 mL) of (S)-allylic alcohol (5.0 g, 23 mmol, 1 eq) with pyridine (4 mL, 46 mmol, 2 eq) was treated with bromoacetyl chloride (2 mL, 30 mmol, 1.3 eq). After 20 min, the mixture was stirred for 1 h at 23° C. and then poured into 1 N HCl (200 mL). The layers were separated and the organic layer washed successively with water, 5% aqueous NaHCO$_3$, and brine (50 mL each) and dried over sodium sulfate. Concentration in vacuo gave a light amber oil (6.5 g, 83% yield). This oil was restored in acetone (40 mL) with sodium iodide (3.0 g, 19 mmol, 1.0 equiv) and stirred at 23° C. for 6 h. The mixture was then diluted with ethyl acetate (100 mL) and washed successively with water, 10% aqueous sodium sulfite, and brine (50 mL each), and the organic layer was dried over sodium sulfate and dried in vacuo to give a light amber oil. This oil was restore in dry acetonitrile (50 mL) and treated with silver nitrate (5.0 g, 29 mmol, 1.5 eq) and stirred 14 h at 23° C. The mixture was poured into water (200 mL) and extracted twice with ether (2×100 mL). The ether layers were washed with water (200 mL) and brine (100 mL), dried over MgSO$_4$ and concentrated in vacuo to a clear oil. A portion of this oil (500 mg, 1.56 mmol, 1 eq) was dissolved in dry DMSO (6 mL) and treated with sodium acetate (193 mg, 2.35 mmol, 1.5 eq) with stirring at 23° C. After 25 min, the mixture was poured into ice water (40 mL), extracted with ether (3×30 mL), and the ether layers were washed successively with saturated aqueous sodium bicarbonate, water, and brine and dried over sodium sulfate. Concentration in vacuo gave 324 as a clear oil (270 mg, 60% yield).

Part D.

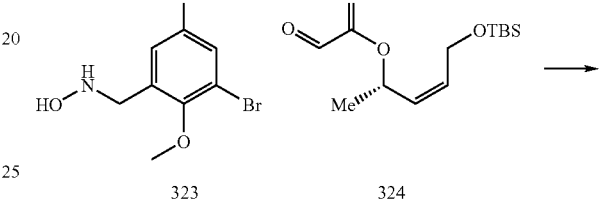

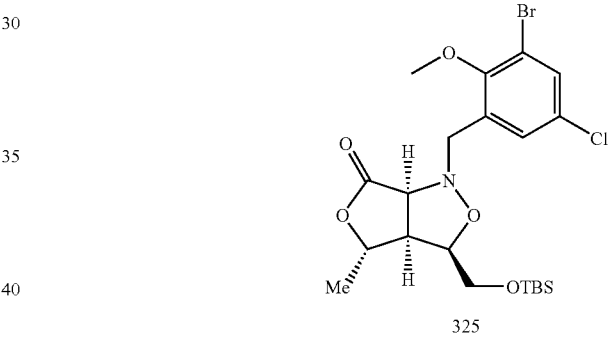

Hydroxylamine 323 (350.0 mg, 1.3 mmol, 1 eq) and allylic glyoxylate ester 324 (393 mg, 1.44 mmol, 1.1 eq) were dissolved in toluene (20 mL) and heated in at 80° C. for 2 h. The reaction mixture was concentrated in vacuo. The crude residue was purified by silica gel chromatography (10-50% EtOAc/hexane) to afford 420 mg of lactone 325 (61% yield).

Part E.

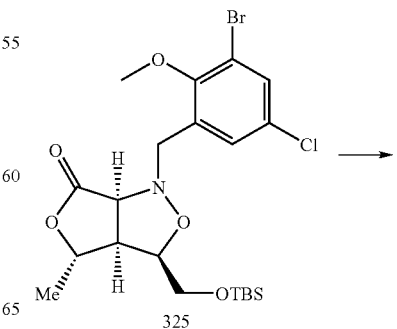

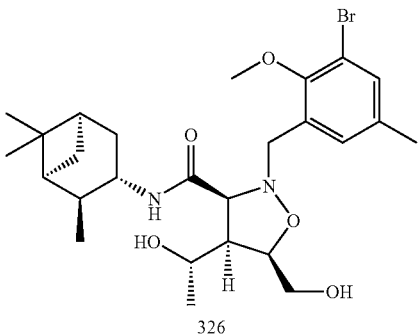

To a 0° C. solution of TBS-protected lactone 325 (410 mg, 0.8 mmol, 1 eq) in THF (4 mL) was added 6 N HCl (0.3 mL). The reaction mixture was stirred for 4 h and then quenched by the addition of a 5% aqueous sodium bicarbonate solution (30 mL). The reaction mixture was extracted with dichloromethane (2×40 mL) and the combined organics were washed with brine (30 mL), dried over MgSO$_4$, filtered and concentrated in vacuo. The crude residue of alcohol was restored in dry dichloromethane (5 mL). A 0° C. solution of (+)-isopinocampheylamine (0.4 mL, 2.36 mmol, 3 eq) in dichloromethane (5 mL) was treated with trimethylaluminum (1.2 mL, 2 M in toluene, 2.36 mmol, 3 eq) and the reaction mixture was stirred for 30 min. The solution of crude lactone alcohol (was then added dropwise. After stirring for 14 h at 23° C., dichloromethane (50 mL) and sodium sulfate-dodecahydrate (1.0 g) was added, and the mixture stirred for 3 h. Filtration and concentrated of the filtrate in vacuo afforded an oil that was purified by silica gel chromatography (30-70% EtOAc/Hexane) to afford 335 mg of amide 326 (76% yield).

Part F.

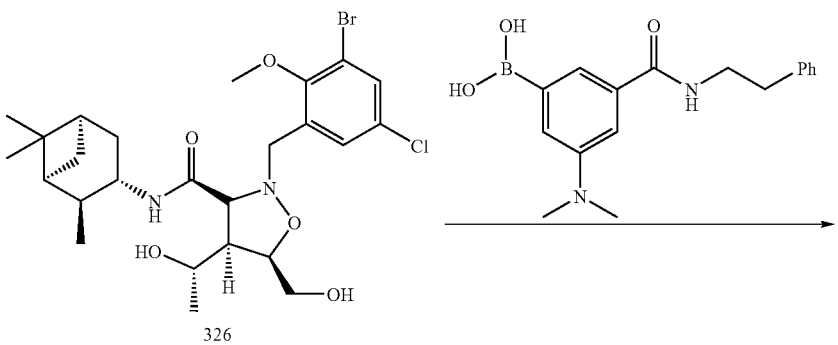

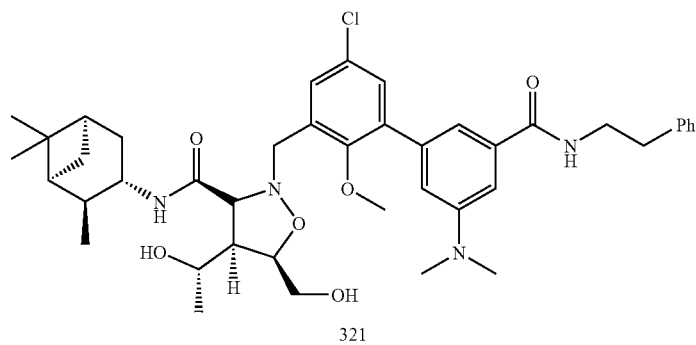

Amide 326 (25 mg, 0.045 mmol, 1 eq), 3-(dimethylamino)-5-(phenethylcarbamoyl)phenylboronic acid (17 mg, 0.054 mmol, 1.2 eq), Pd(OAc)$_2$ (1.0 mg, 0.0045 mmol, 0.1 eq), potassium carbonate (25 mg, 0.18 mmol, 4 eq), and S-Phos (Kevin W. Anderson and Stephen L. Buchwald, *Angew. Chem. Int. Ed.* 2005, 44, 2-6) (4.7 mg, 0.009 mmol, 0.2 eq) were dissolved in tetrahydrofuran (1 mL) and water (0.5 mL). The mixture was purged with argon and stirred at 50° C. for 5 h. The reaction mixture was diluted with EtOAc (20 mL) and water (10 mL) and layers separated. The organic layer was washed with brine (10 mL), dried over sodium sulfate, and concentrated in vacuo. Purification of the crude residue by HPLC (acetonitrile/30 mM aqueous ammonium bicarbonate) to afford 9 mg of biphenyl 321 (30% yield) as a white foam. MS (ESI(+)) m/e 747.5 (M+H$^+$).

Example 123

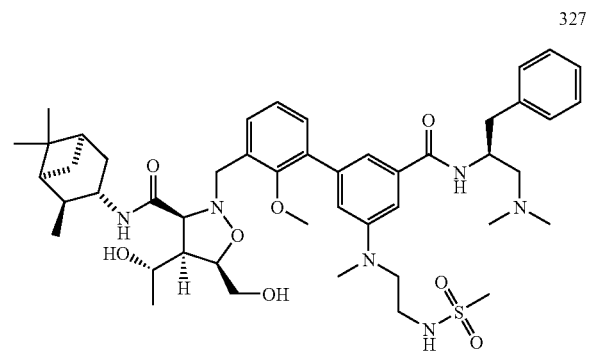

327

Part A.

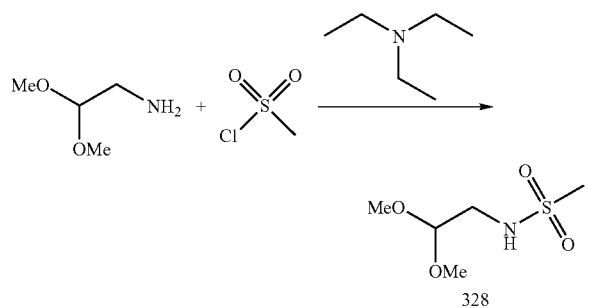

328

To a solution of aminoacetaldehyde dimethyl acetal (3.5 g, 33.3 mmol, 1 eq) in DCM (8 ml) under Ar at 0° C. was added triethylamine (9.28 mL, 66.6 mmol, 2 eq) followed by methanesulfonyl chloride (3.89 mL, 49.9 mmol, 1.5 eq). The resulting mixture was stirred at 0° C. for 15 min. The reaction was diluted with DCM (20 mL) and washed with saturated sodium bicarbonate solution (20 mL). The aqueous layer was extracted with DCM (2×20 mL). The combined organic layers were dried over MgSO$_4$, filtered and concentrated in vacuo. Compound 328 was obtained as a yellow oil, which was used without further purification.

Part B.

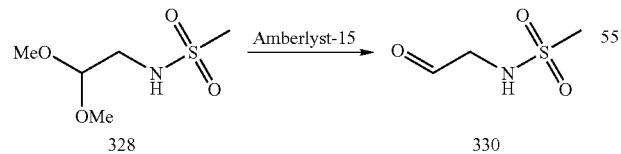

To a solution of 328 (3.0 g, 16.4 mmol, 1 eq) in acetone: water (1:1, 4 ml) was added Amberlyst-15 resins (3.0 g). The resulting mixture was stirred for 3 h. The suspension was filtered through celite and concentrated in vacuo. Compound 330 was obtained as a yellow oil and was used without further purification.

Part C.

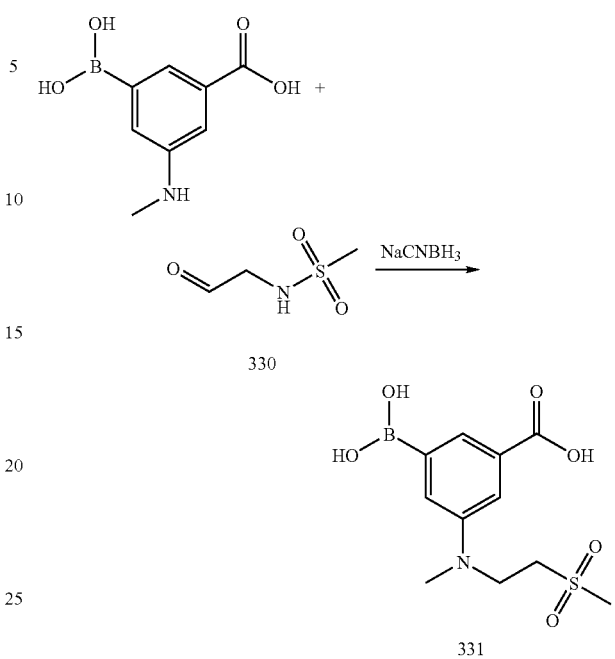

To a solution of the boronic acid (90 mg, 0.462 mmol, 1 eq) in THF (2 ml) was added 330 (158 mg, 1.154 mmol, 2.5 eq) in MeOH (1 mL), followed by acetic acid (52.8 µL, 0.923 mmol, 2.0 eq) and sodium cyanoborohydride (145 mg, 2.308 mmol, 5.0 eq). The resulting mixture was stirred for 30 min. The reaction mixture was diluted with EtOAc (10 mL) and quenched with brine. The aqueous layer was acidified with 1N HCl to pH 3, and extracted with EtOAc (3×20 mL). The combined organic layers were dried over MgSO$_4$, filtered and concentrated in vacuo to afford yellow oil. The oil was purified by silica gel chromatography (2-7% MeOH/DCM with 0.5% acetic acid) to give 94 mg of 331. Yield 64.4%. MS (ESI(+)) m/z 317.24 (M+H)$^+$.

Part D.

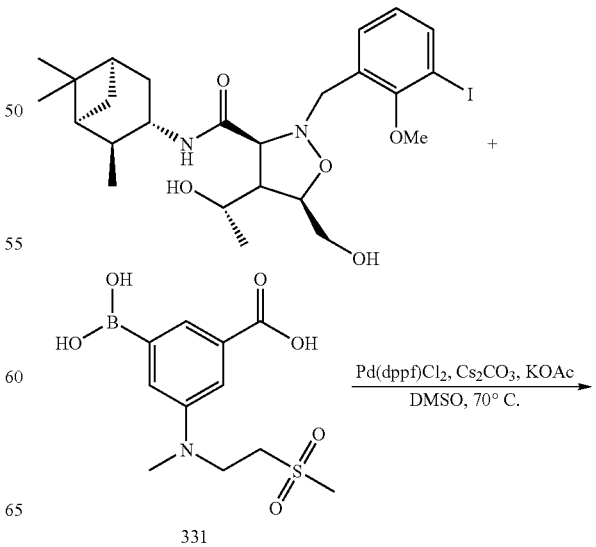

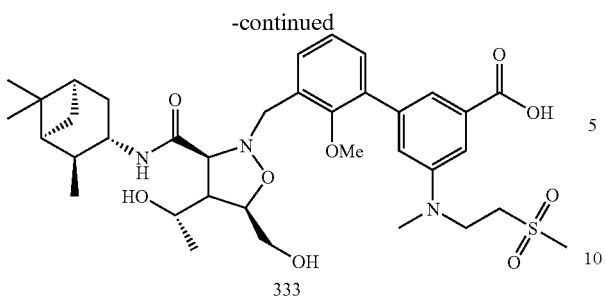

333

A solution of aryl iodide (140 mg, 0.245 mmol, 1 eq), 331 (85 mg, 0.269 mmol, 1.1 eq), cesium carbonate (159 mg, 0.489 mmol, 2 eq) and potassium acetate (24 mg, 0.245 mmol, 1 eq) in DMSO (3 mL) was degassed by bubbling argon through the solution for 10 min. Pd(dppf)Cl$_2$ (35.8 mg, 0.049 mmol, 0.2 eq) was then added and the flask purged with argon. The mixture was heated at 70° C. for 4 h. The reaction mixture was added to brine (10 mL), acidified with 1 N HCl until the aqueous layer attained a pH of 3, and extracted with EtOAc (3×20 mL). The combined organic layers were dried over MgSO$_4$, filtered and concentrated in vacuo to afford a brown oil. The oil was purified by silica gel chromatography (0-15% MeOH/EtOAc) to give 110 mg of 333. Yield 62.7%. MS (ESI(+)) m/z 717.44 (M+H)$^+$.

Part E.

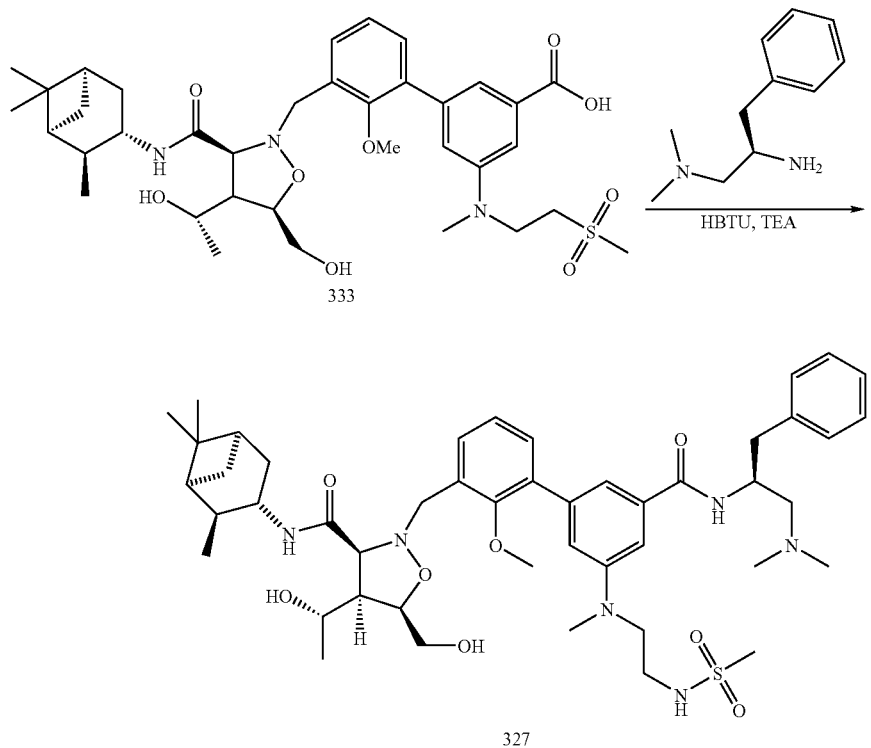

327

To a solution of 333 (30 mg, 0.04 mmol, 1 eq) in DMF (1 mL) was added HBTU (19 mg, 0.05 mmol, 1.2 eq) and (S)—N1,N1-dimethyl-3-phenylpropane-1,2-diamine (15 mg, 0.08 mmol, 2 eq), followed by TEA (17 µL, 0.12 mmol, 3 eq). After stirring at rt for 30 min, the mixture was diluted with EtOAc (10 mL) and washed with brine (3×10 mL). The organic layer was dried over MgSO$_4$, filtered and concentrated in vacuo. The material was purified by HPLC to give 11 mg of 327. Yield 30%. MS (ESI(+)) m/z 877.72 M+.

Example 124

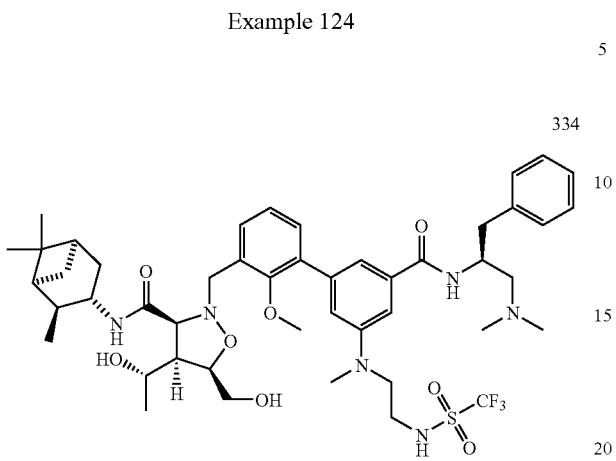

334

Part A.

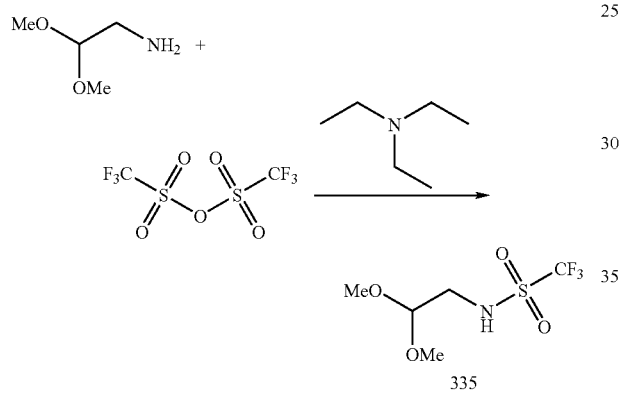

335

To a solution of aminoacetaldehyde dimethyl acetal (1.0 g, 9.51 mmol, 1 eq) in DCM (10 ml) under Ar at 0° C. was added triethylamine (2.64 mL, 19.02 mmol, 2 eq) followed by trifluoromethanesulfonic anhydride (2.40 mL, 14.27 mmol, 1.5 eq) dropwise. The resulting mixture was stirred at 0° C. for 1 h. The reaction was diluted with DCM (10 mL) and washed with saturated ammonium chloride solution (20 mL). The aqueous layer was extracted with DCM (2×20 mL). The combined organic layers were dried over MgSO4, filtered and concentrated in vacuo. Compound 335 was obtained as a pale yellow oil and used without further purification.

Part B.

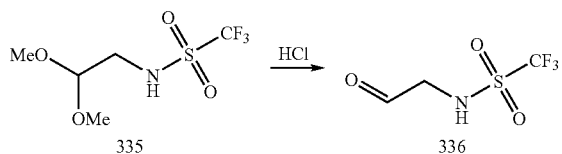

335  336

1N HCl (1 mL) was added to 2,2-(dimethoxyethyl)trifluoromethanesulfonamide (500 mg, 2.1 mmol, 1 eq) and the resulting mixture was heated at 100° C. for 2 h. The solution was evacuated to dryness to give 336 as a brown oil, which was used without further purification.

Part C.

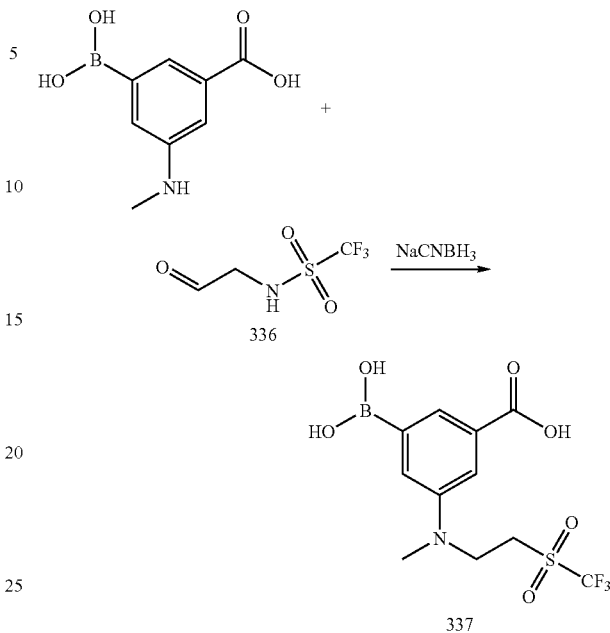

336

337

To a solution of the boronic acid (60 mg, 0.31 mmol, 1 eq) in THF (2 ml) was added the aldehyde 336 (147 mg, 0.77 mmol, 2.5 eq) in MeOH (1 mL), followed by acetic acid (35 μL, 0.62 mmol, 2.0 eq) and sodium cyanoborohydride (97 mg, 1.54 mmol, 5.0 eq). The resulting mixture was stirred for 30 min. The reaction mixture was diluted with EtOAc (10 mL) and quenched with brine. The aqueous layer was acidified with 1N HCl to pH 3, and extracted with EtOAc (3×20 mL). The combined organic layers were dried over MgSO4, filtered and concentrated in vacuo to afford yellow oil. The oil was purified by silica gel chromatography (2-10% MeOH/DCM with 0.5% acetic acid) to give 64 mg of the 337. Yield 56.2%. MS (ESI(+)) m/z 371.22 (M+H)+.

Part D.

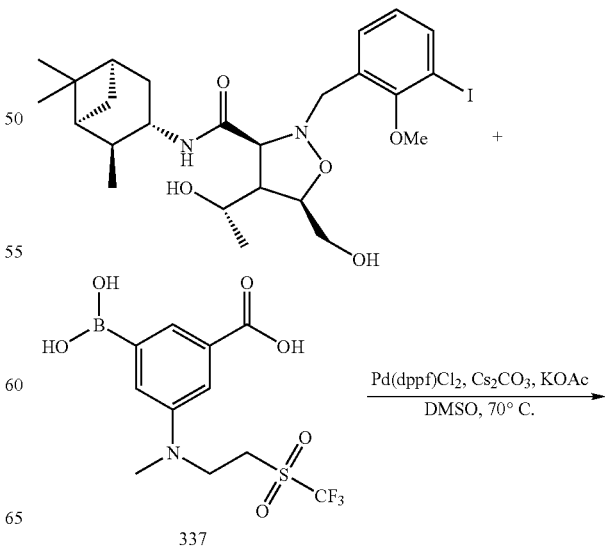

337

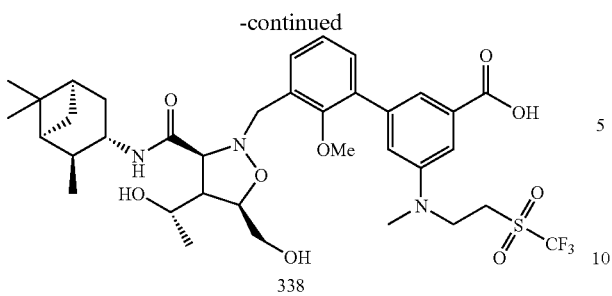

338

A solution of aryl iodide (90 mg, 0.157 mmol, 1 eq), boronic acid 337 (64 mg, 0.173 mmol, 1.1 eq), cesium carbonate (102 mg, 0.314 mmol, 2 eq) and potassium acetate (15 mg, 0.157 mmol, 1 eq) in DMSO (2 mL) was degassed by bubbling argon through the solution for 10 min. Pd(dppf)Cl$_2$ (23 mg, 0.031 mmol, 0.2 eq) was then added and the flask purged with argon. The mixture was heated at 70° C. for 4 h. The reaction mixture was added to brine (10 mL), acidified with 1 N HCl until the aqueous layer attained a pH of 3, and extracted with EtOAc (3×20 mL). The combined organic layers were dried over MgSO$_4$, filtered and concentrated in vacuo to afford a brown oil. The oil was purified by silica gel chromatography (0-15% MeOH/EtOAc) to give 55 mg of 338. Yield 44.6%. MS (ESI(+)) m/z 771.45 (M+H)$^+$.

Part E.

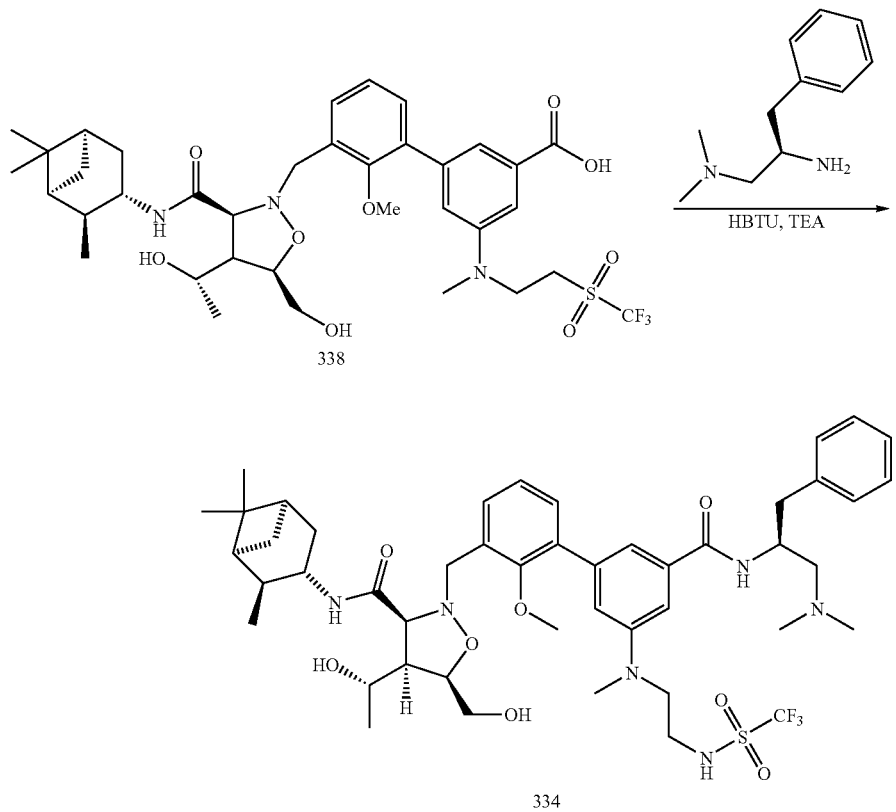

To a solution of 338 (55 mg, 0.071 mmol, 1 eq) in DMF (1 mL) was added HBTU (32.5 mg, 0.086 mmol, 1.2 eq) and (S)—N1,N1-dimethyl-3-phenylpropane-1,2-diamine (25 mg, 0.143 mmol, 2 eq), followed by TEA (30 µL, 0.213 mmol, 3 eq). After stirring at rt for 30 min, the mixture was diluted with EtOAc (10 mL) and washed with brine (3×10 mL). The organic layer was dried over MgSO$_4$, filtered and concentrated in vacuo. The material was purified by HPLC to give 16 mg of 334. Yield 24%. MS (ESI(+)) m/z 931.61 M$^+$.

Example 125

Bcl-2 and Bcl-xL binding affinity analysis data is presented below for various compounds of the invention. Note that "**" indicates that the $K_i$ is <1 nM, "*" indicates that the $K_i$ is 1-5 nM, "**" indicates that the $K_i$ is 5-9 nM, "*" indicates that the $K_i$ is >9 nM. Note that "††††" indicates that the $K_i$ is <1 μM, "†††" indicates that the $K_i$ is 1-5 μM, "††" that the $K_i$ is 5-10 μM, and "†" indicates that the $K_i$ is >10 μM.

| Compound | Bcl2 | Bcl-XI |
| --- | --- | --- |
| 1 | **** | †††† |
| 12 | ** | †† |
| 15 | **** | †††† |
| 23 | **** | †††† |
| 24 | **** | †††† |
| 25 | **** | †††† |
| 26 | **** | †††† |
| 33 | **** | †††† |
| 34 | **** | †††† |
| 35 | **** | †††† |
| 36 | **** | †††† |
| 37 | **** | †††† |
| 38 | **** | † |
| 53 | *** | † |
| 54 | *** | † |
| 55 | **** | ††† |
| 60 | **** | ††† |
| 61 | **** | †††† |
| 62 | **** | †† |
| 63 | **** | †† |
| 64 | **** | † |
| 65 | **** | † |
| 66 | **** | †† |
| 67 | **** | †† |
| 68 | **** | †††† |
| 69 | ** | † |
| 70 | *** | † |
| 71 | * | ††† |
| 72 | **** | †††† |
| 73 | **** | †††† |
| 74 | * | †† |
| 75 | ** | ††† |
| 76 | ** | † |
| 77 | ** | ††† |
| 78 | * | †† |
| 79 | * | †† |
| 80 | ** | †† |
| 81 | * | † |
| 82 | * | † |
| 83 | * | † |
| 84 | * | † |
| 85 | * | †† |
| 86 | * | † |
| 87 | * | † |
| 91 | * | † |
| 92 | * | † |
| 93 | * | † |
| 94 | *** | † |
| 95 | ** | †† |
| 96 | ** | †† |
| 97 | * | † |
| 98 | * | †† |
| 99 | * | † |
| 100 | **** | ††† |
| 111 | **** | †††† |
| 112 | **** | †††† |
| 113 | **** | †††† |
| 114 | **** | †††† |
| 115 | **** | †††† |
| 126 | **** | †††† |
| 127 | **** | †††† |
| 136 | **** | †††† |
| 143 | **** | †††† |
| 144 | **** | †††† |
| 151 | **** | †††† |
| 152 | **** | †††† |
| 160 | **** | †††† |
| 165 | **** | †††† |
| 170 | *** | ††† |
| 176 | *** | ††† |
| 182 | **** | †††† |
| 183 | *** | ††† |
| 193 | *** | ††† |
| 196 | **** | †††† |
| 202 | **** | †††† |
| 206 | **** | †††† |
| 213 | **** | † |
| 218 | **** | ††† |
| 219 | *** | ††† |
| 230 | **** | †††† |
| 240 | **** | ††† |
| 247 | **** | †††† |
| 251 | **** | †††† |
| 252 | **** | ††† |
| 253 | **** | †††† |
| 255 | **** | †††† |
| 256 | **** | †††† |
| 257 | **** | †††† |
| 258 | **** | †††† |
| 259 | **** | ††† |
| 260 | *** | †††† |
| 262 | ** | ††† |
| 263 | **** | †††† |
| 264 | **** | †††† |
| 265 | **** | †††† |
| 267 | **** | ††† |
| 268 | *** | ††† |
| 269 | **** | †††† |
| 270 | *** | ††† |
| 271 | **** | †††† |
| 272 | **** | ††† |
| 274 | **** | ††† |
| 285 | **** | †††† |
| 290 | **** | †††† |
| 296 | **** | †††† |
| 299 | **** | †††† |
| 302 | **** | ††† |
| 306 | **** | †††† |
| 308 | **** | †††† |
| 309 | **** | †††† |
| 310 | **** | †††† |
| 311 | **** | †††† |
| 312 | **** | †††† |
| 313 | **** | †††† |
| 314 | **** | †††† |
| 315 | **** | †††† |
| 316 | **** | †††† |
| 320 | **** | †††† |
| 321 | * | †† |
| 295-amine | **** | †††† |

Incorporation by Reference

Incorporated by reference are all of the U.S. patents, U.S. patent application publications, and PCT patent application publications designating the U.S. cited herein.

EQUIVALENTS

Those skilled in the art will recognize, or be able to ascertain using no more than routine experimentation, many equivalents to the specific embodiments of the invention described herein. Such equivalents are intended to be encompassed by the following claims.

607
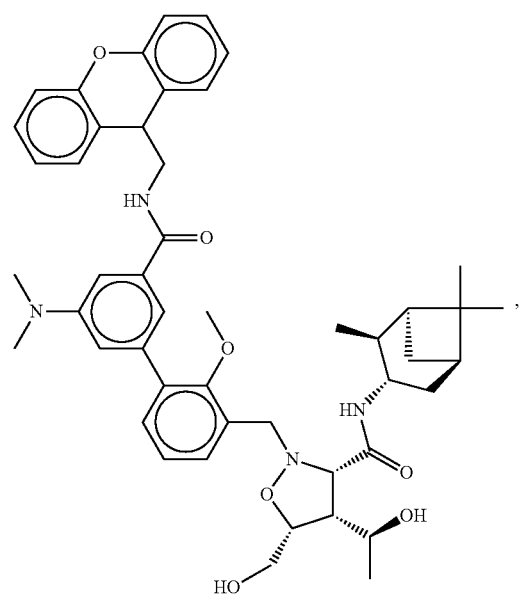
608
-continued
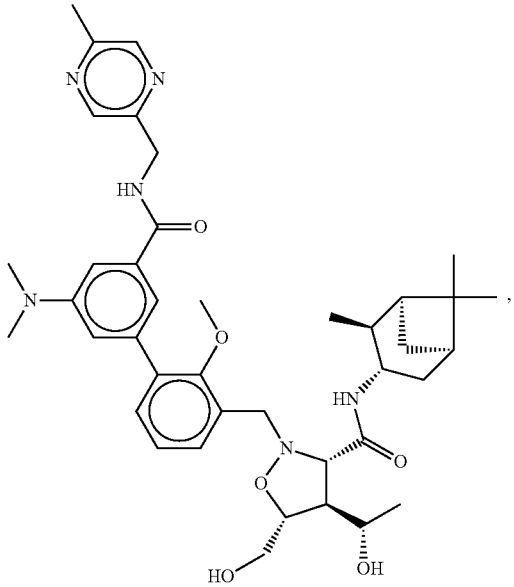
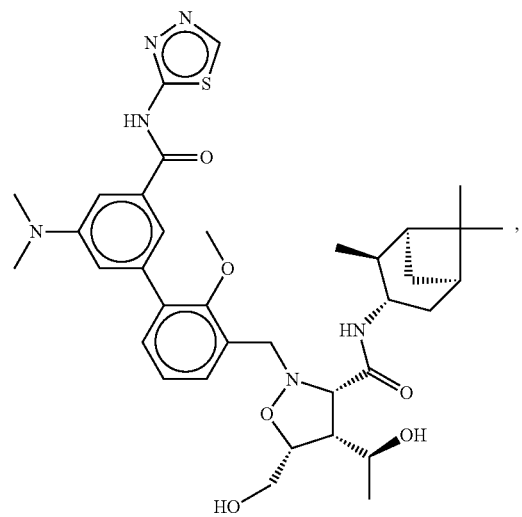
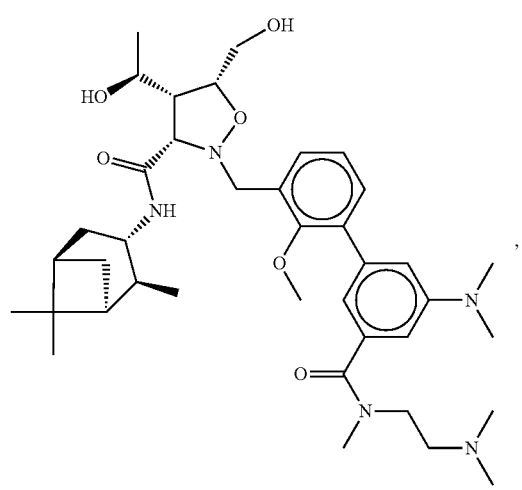
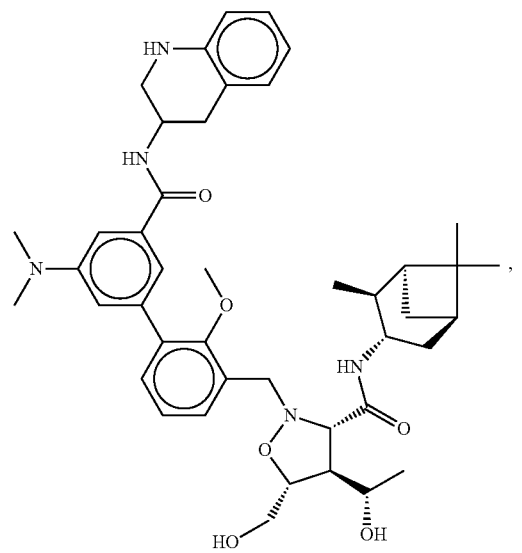

609 610
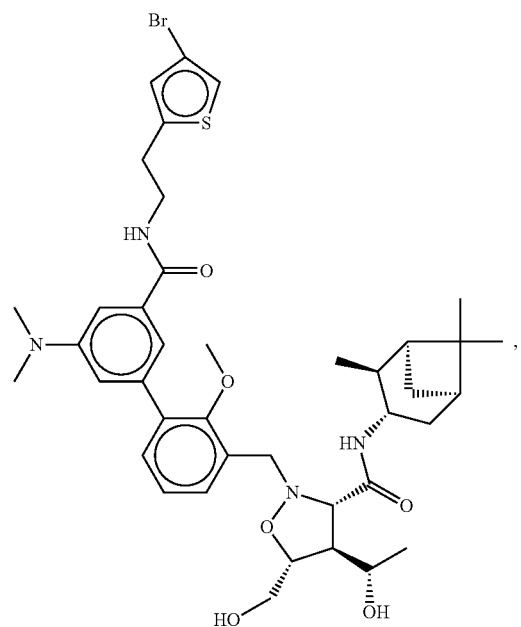 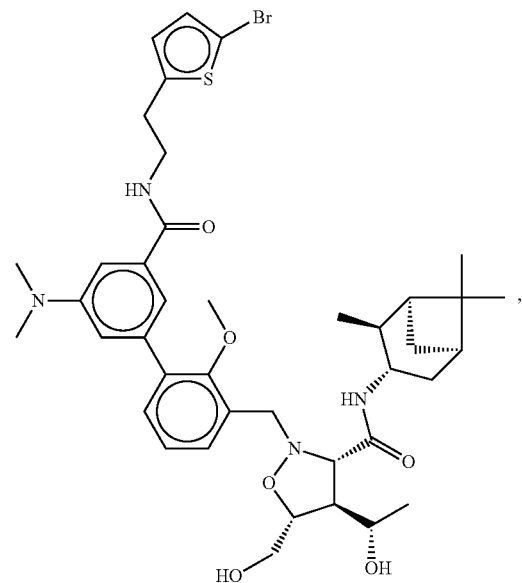
-continued
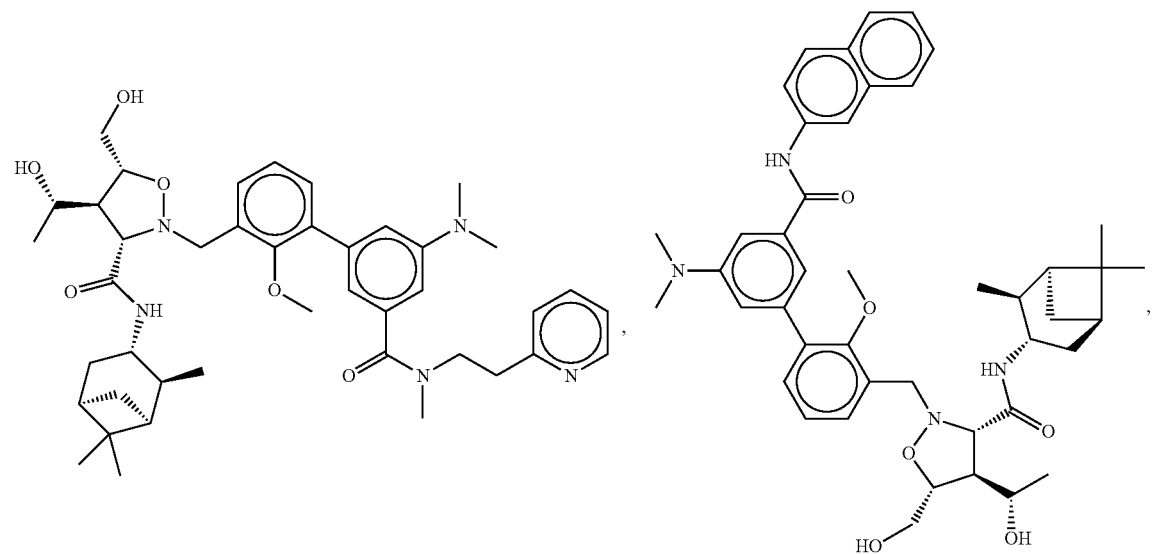

611
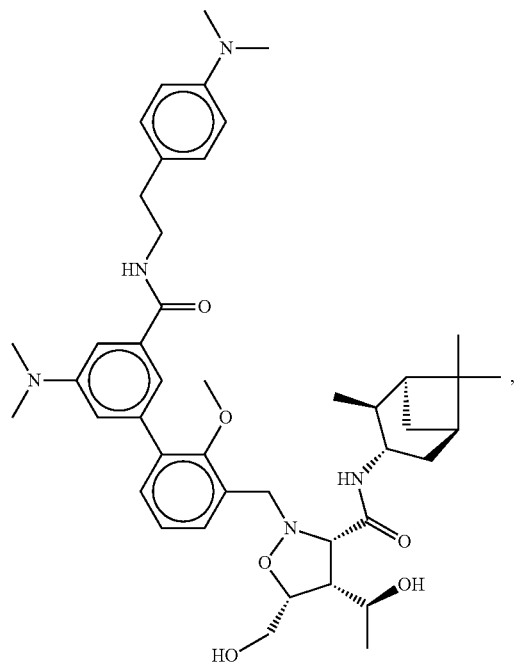
612
-continued
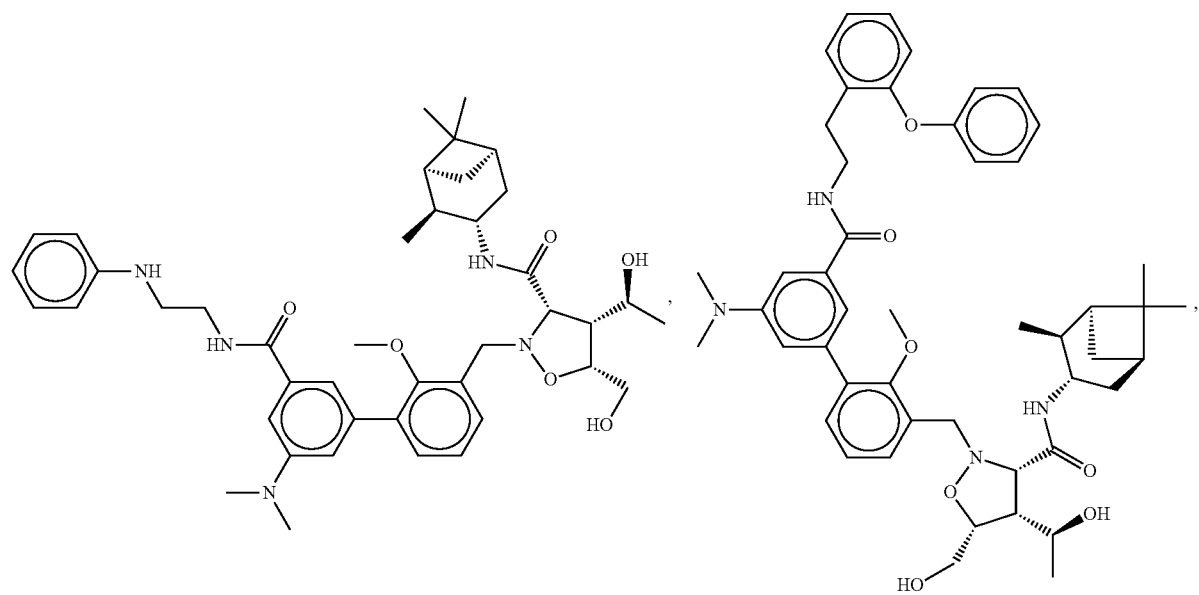

613 614
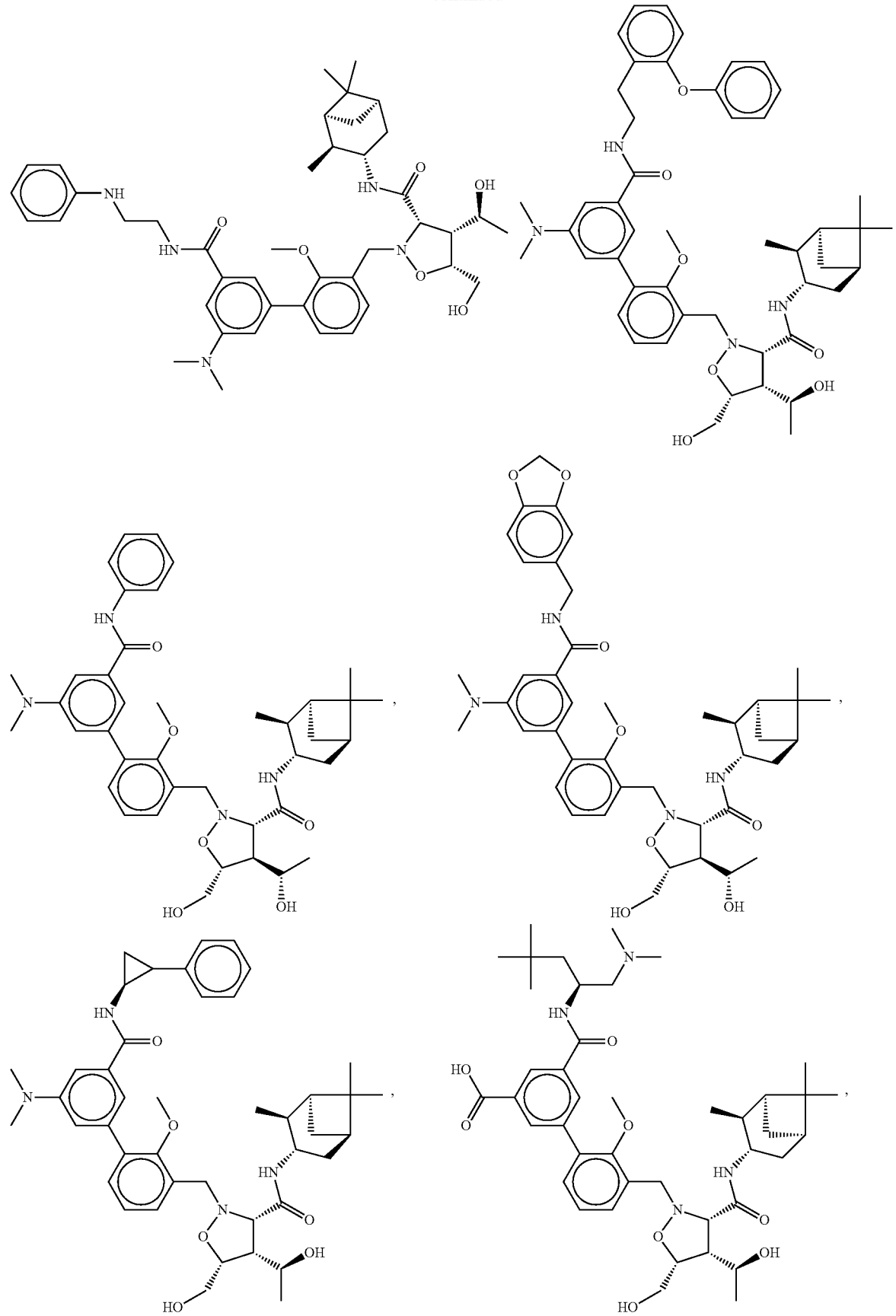
-continued 615 616
-continued
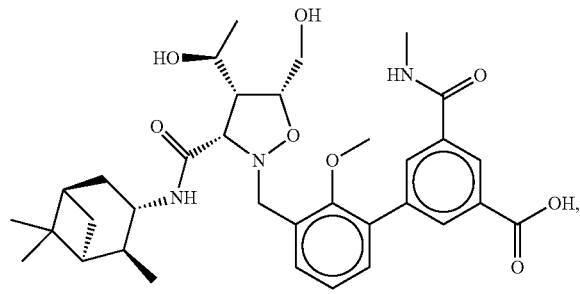
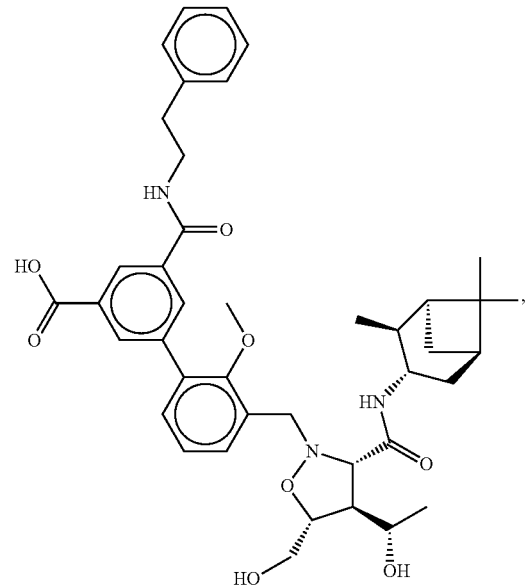
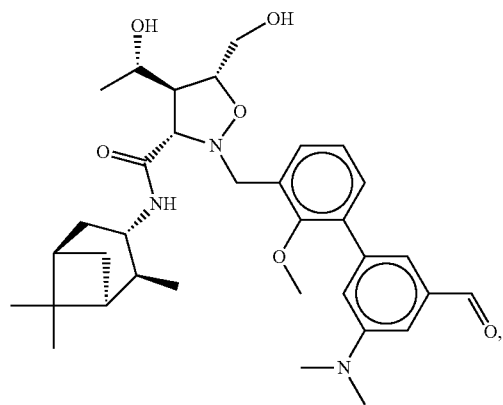
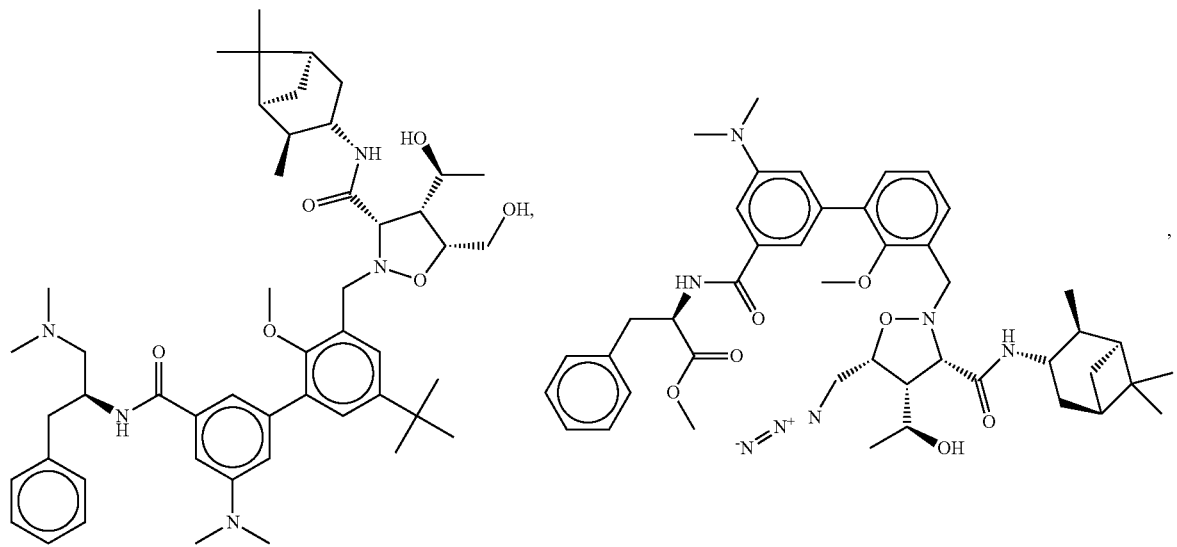

617 618
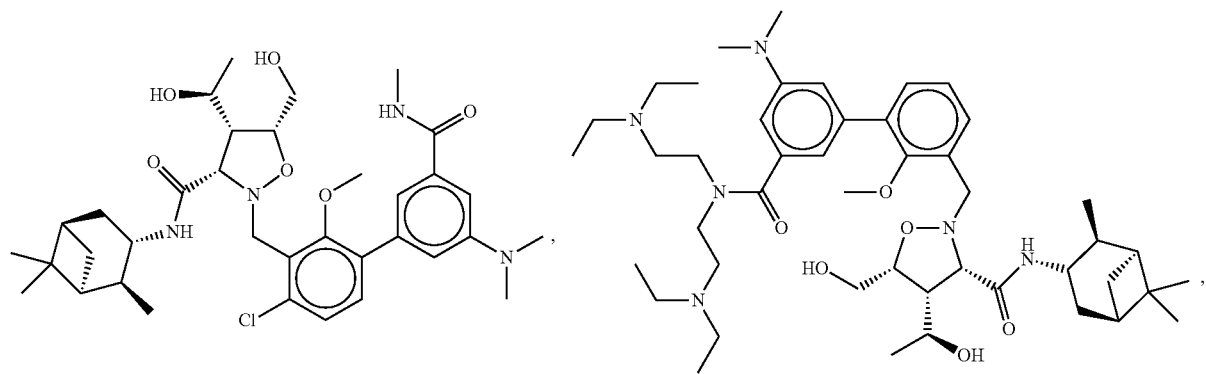
-continued
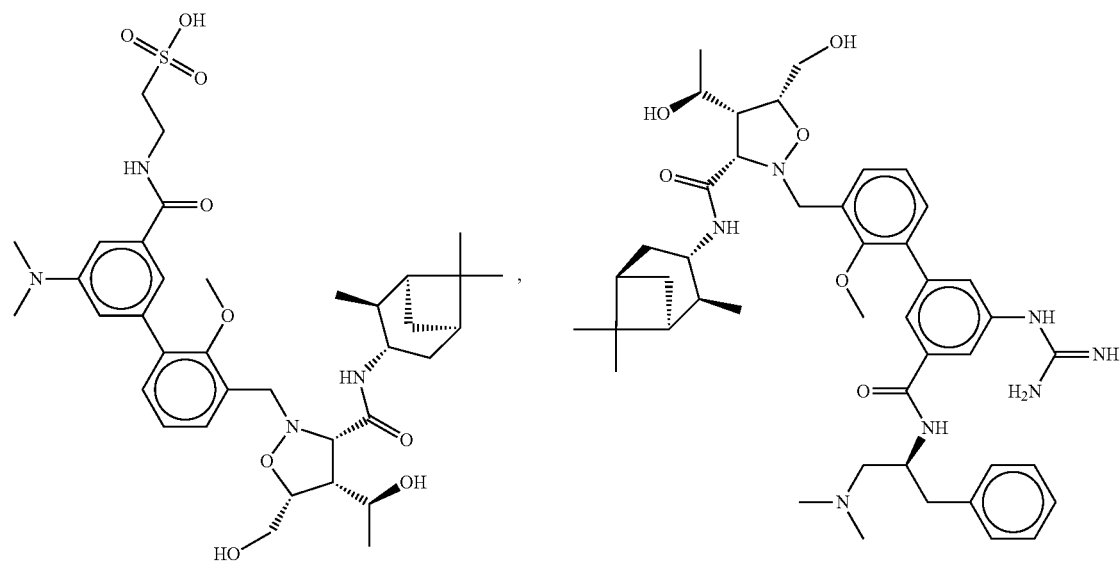
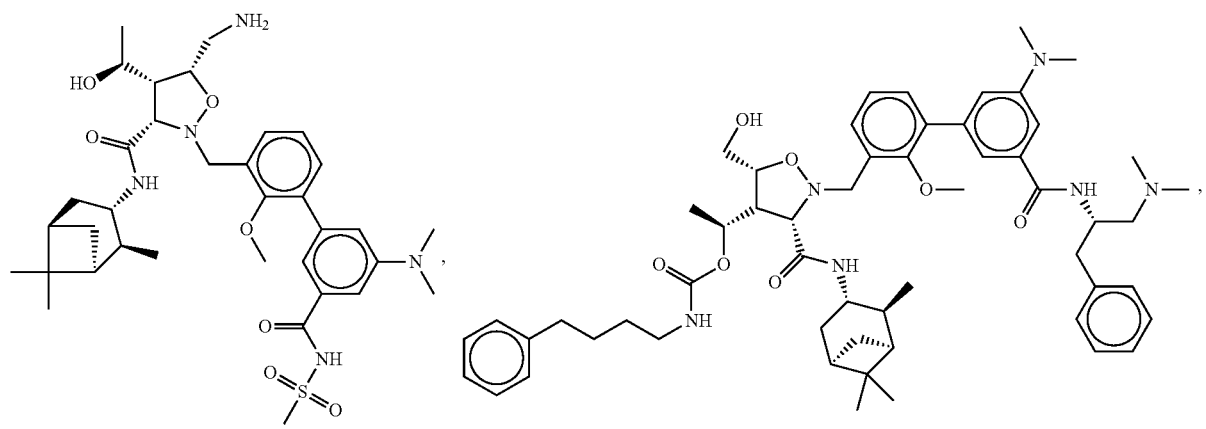

619 620
-continued
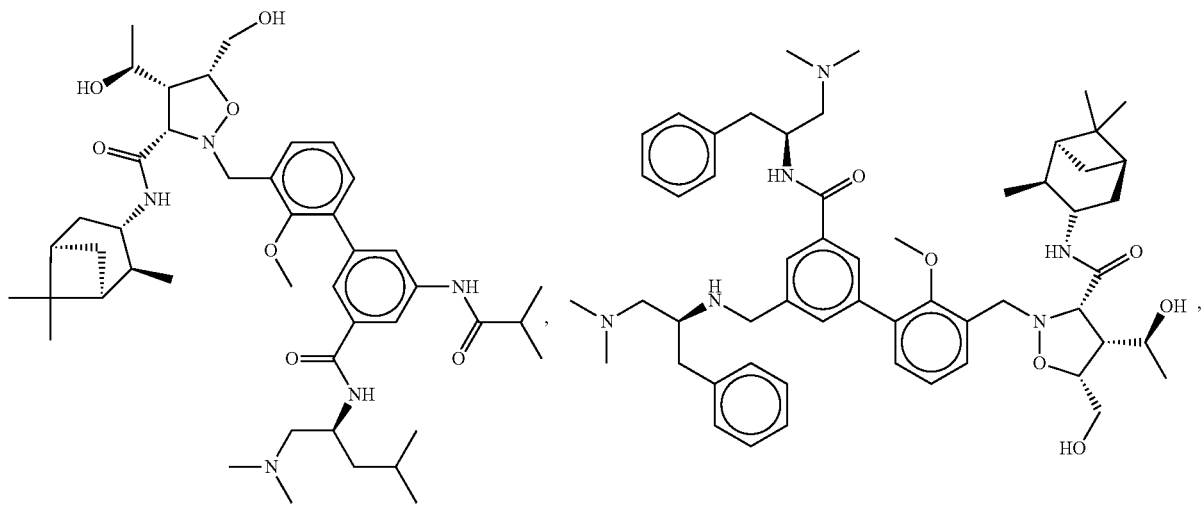
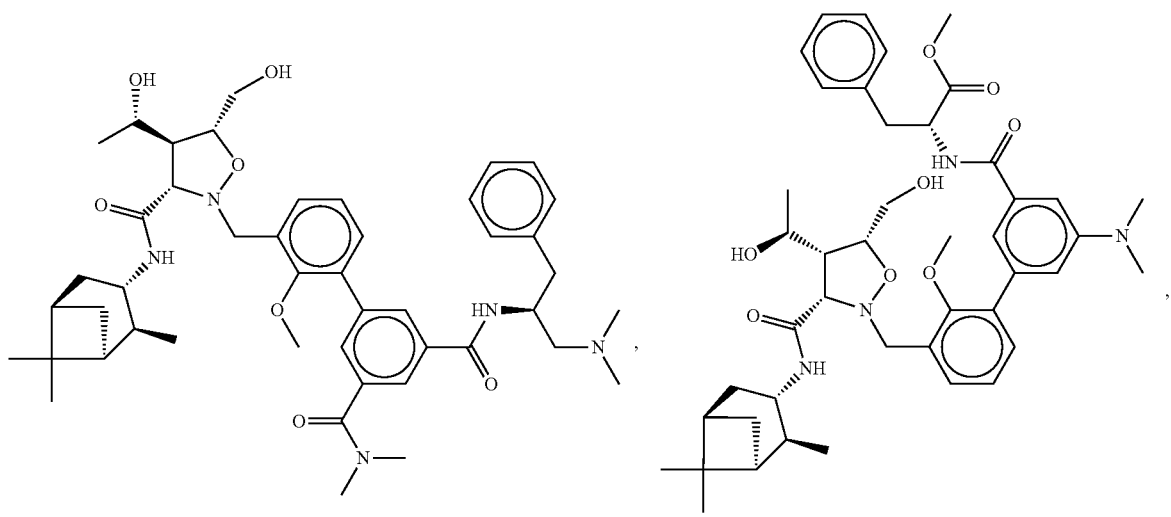
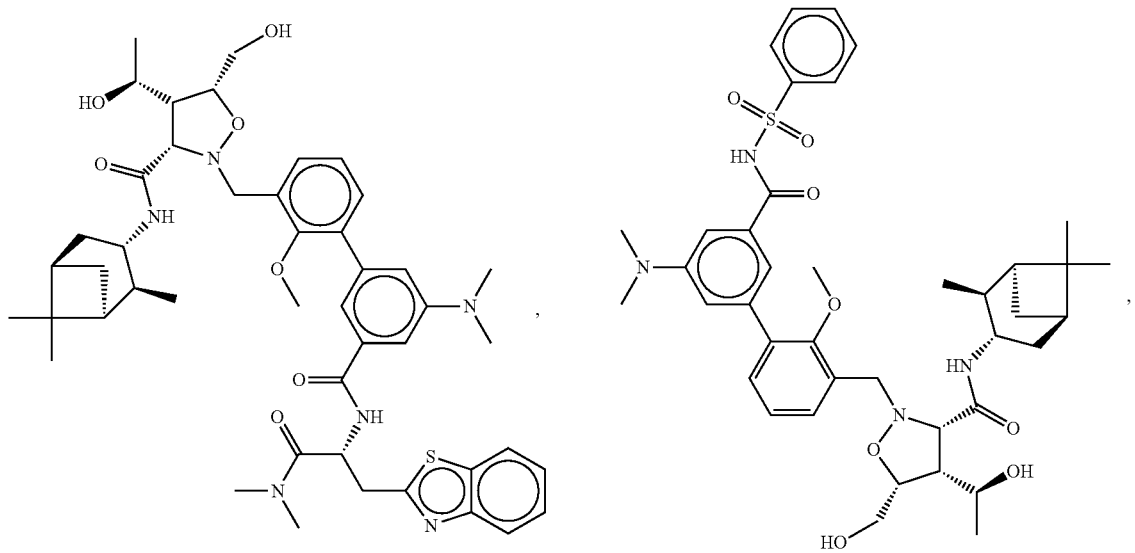

621
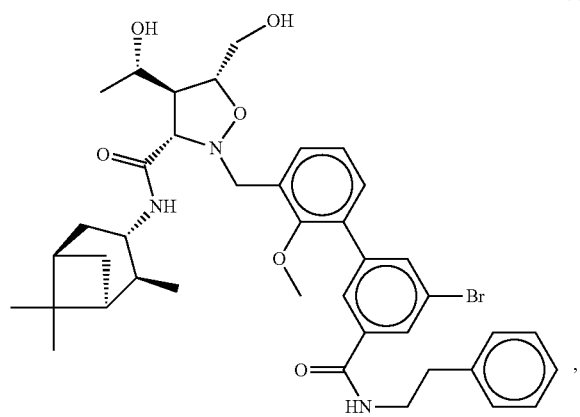
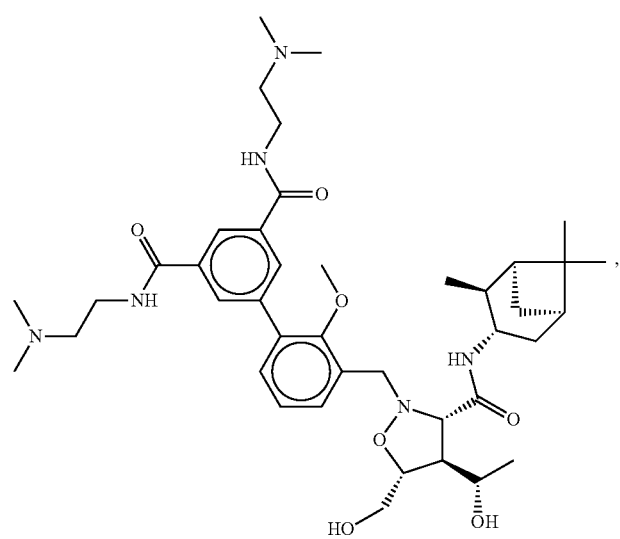
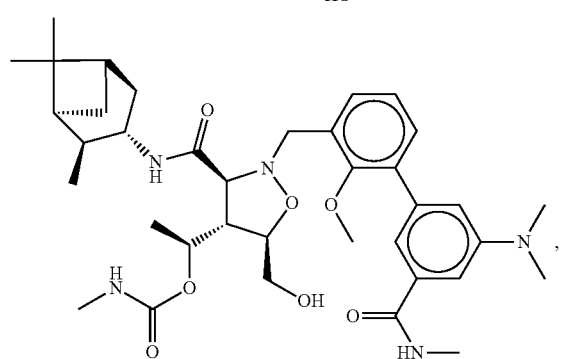
622
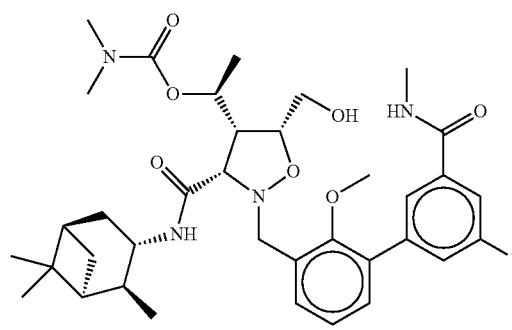
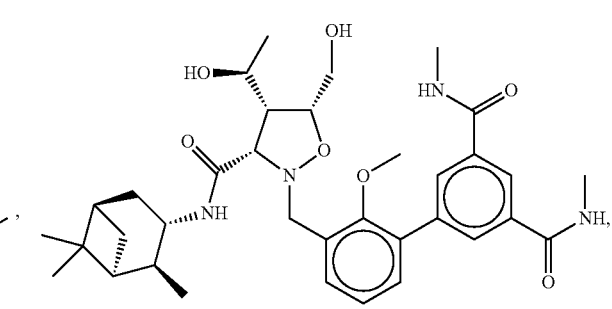

-continued
623
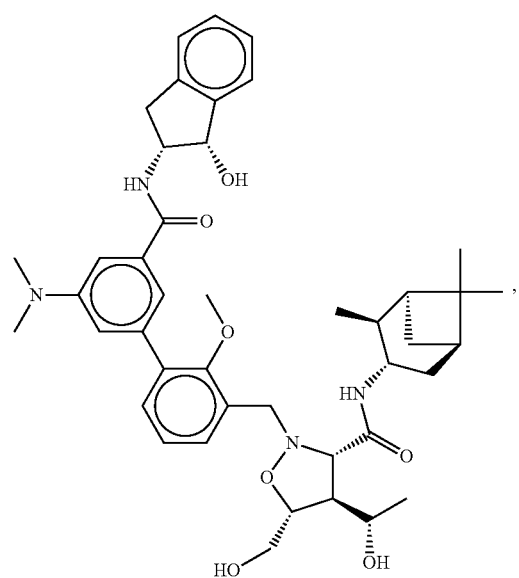
624
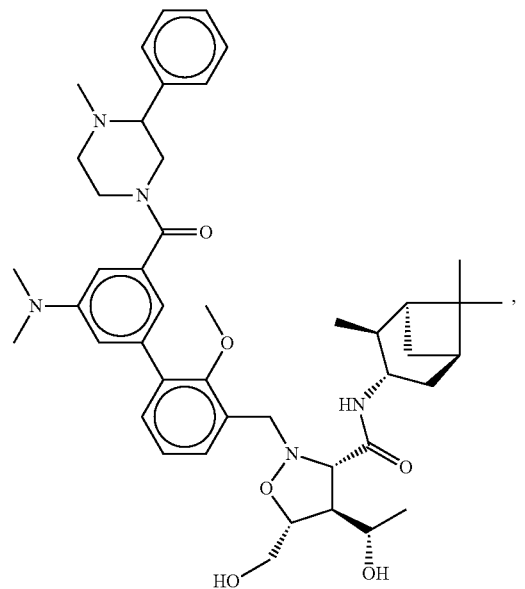
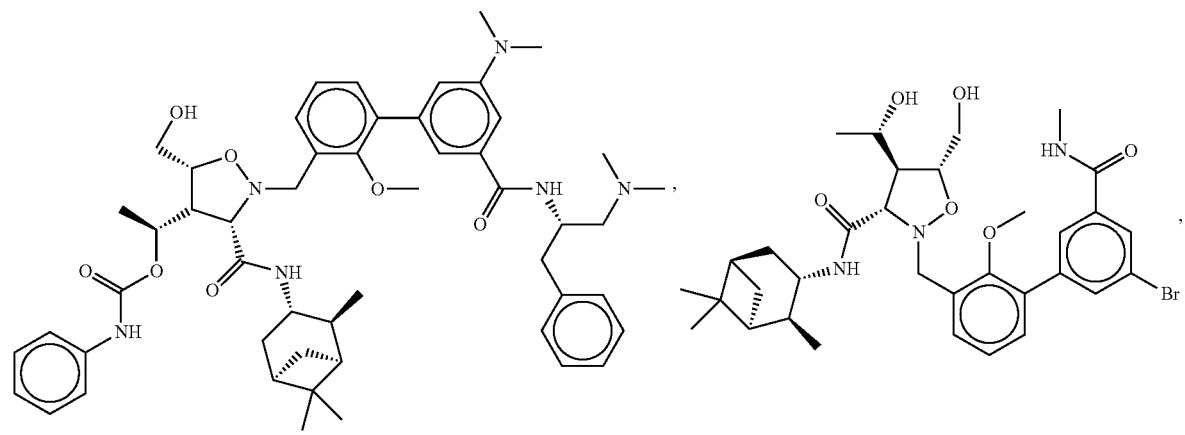
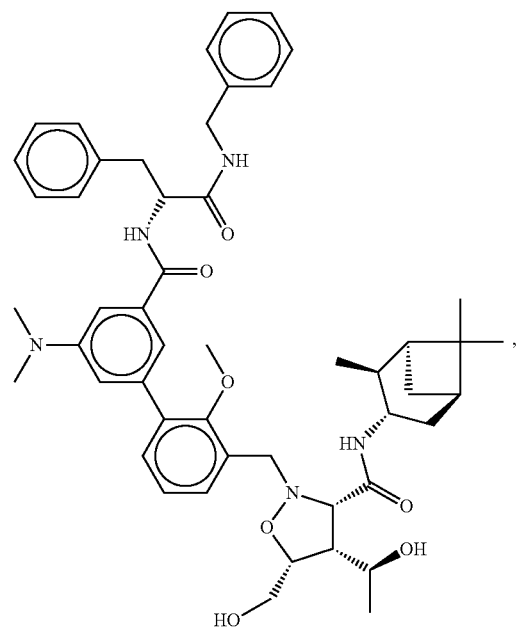

-continued
625
626
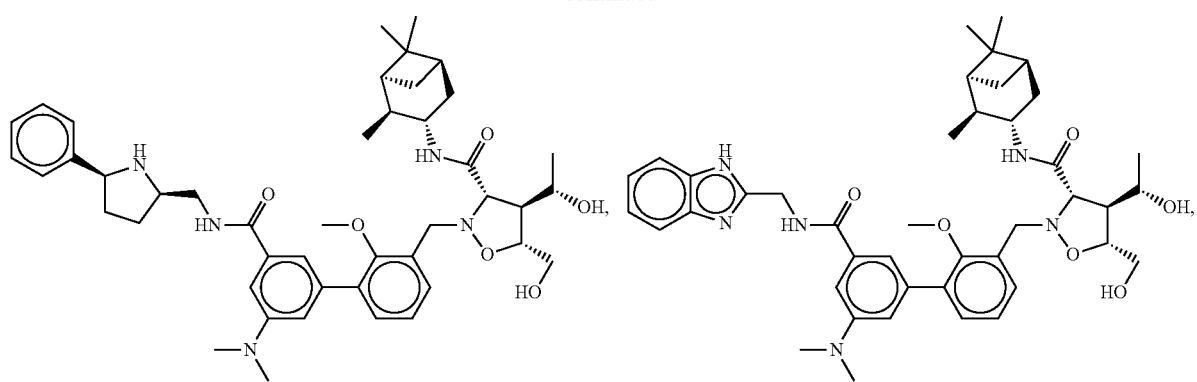
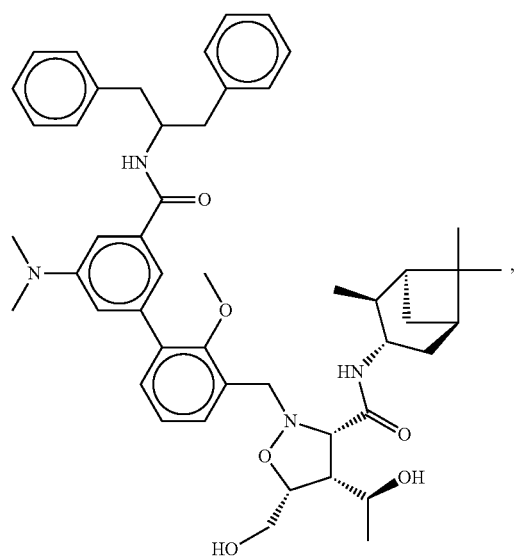
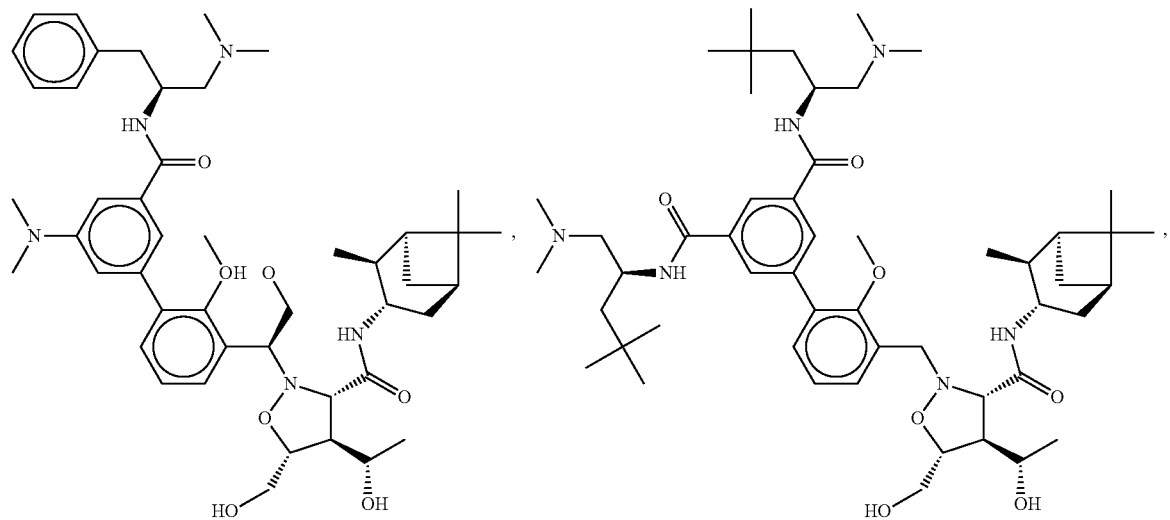

-continued
627 628
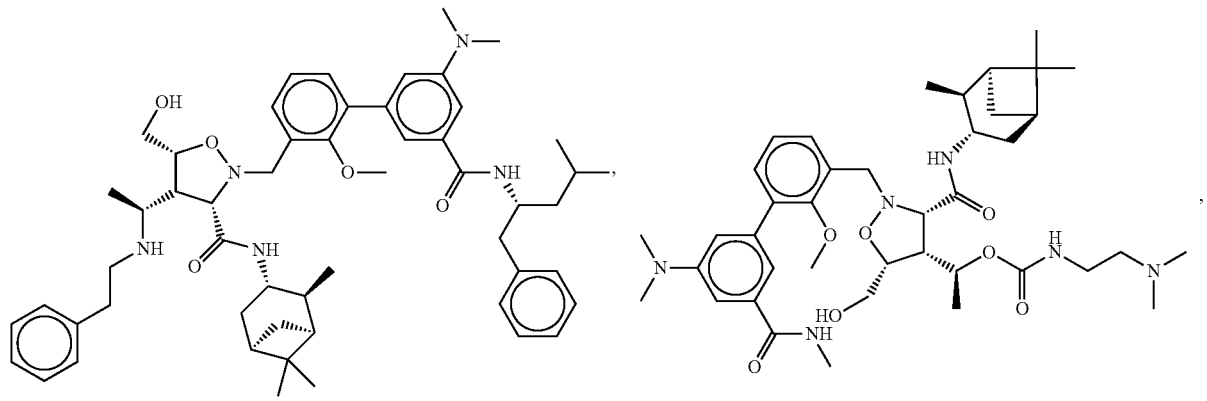
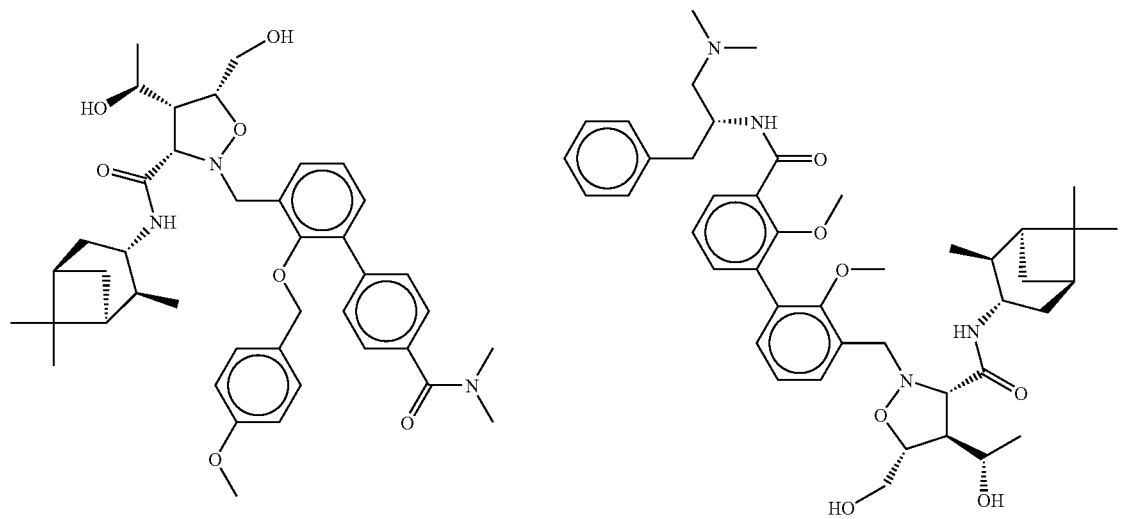
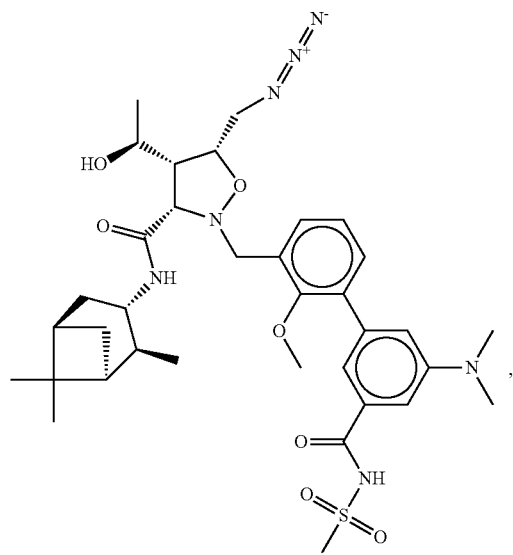

-continued
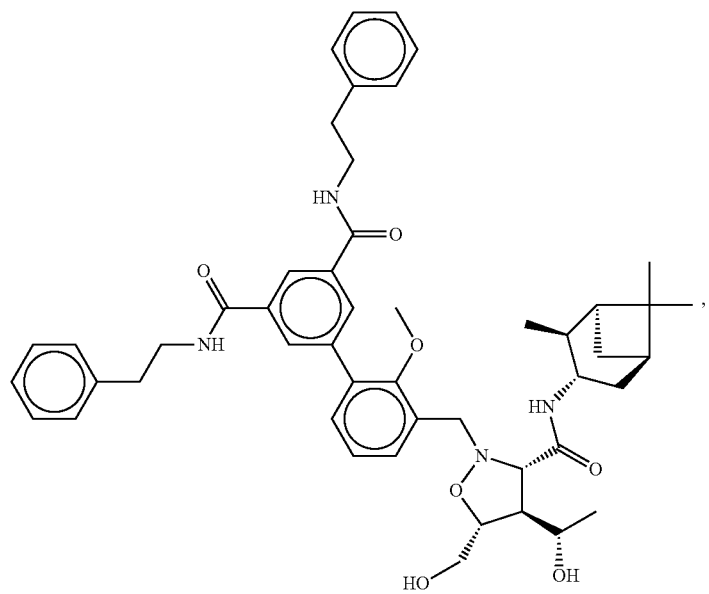
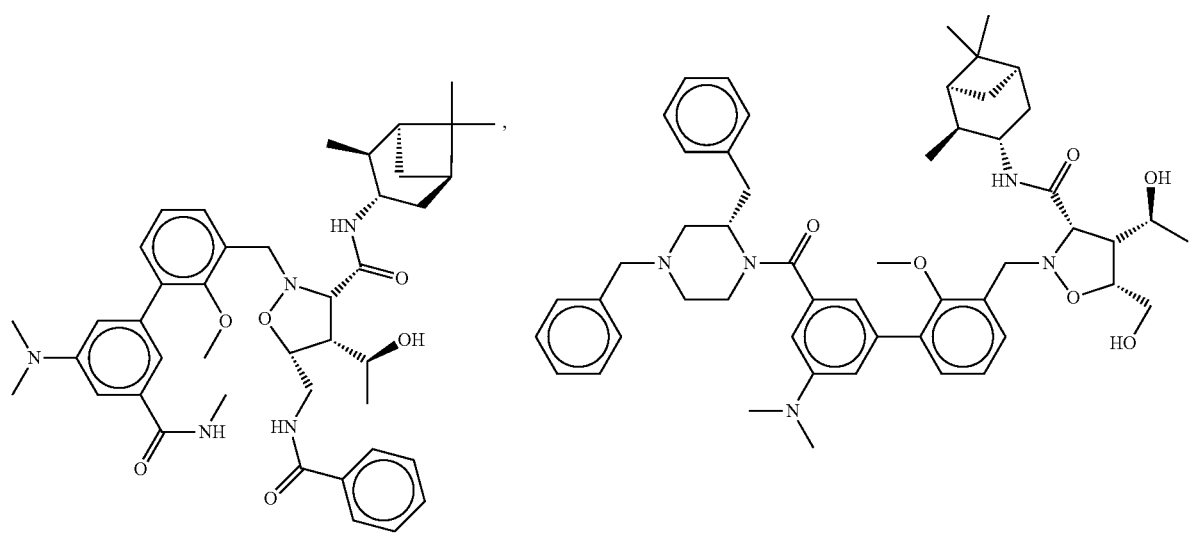
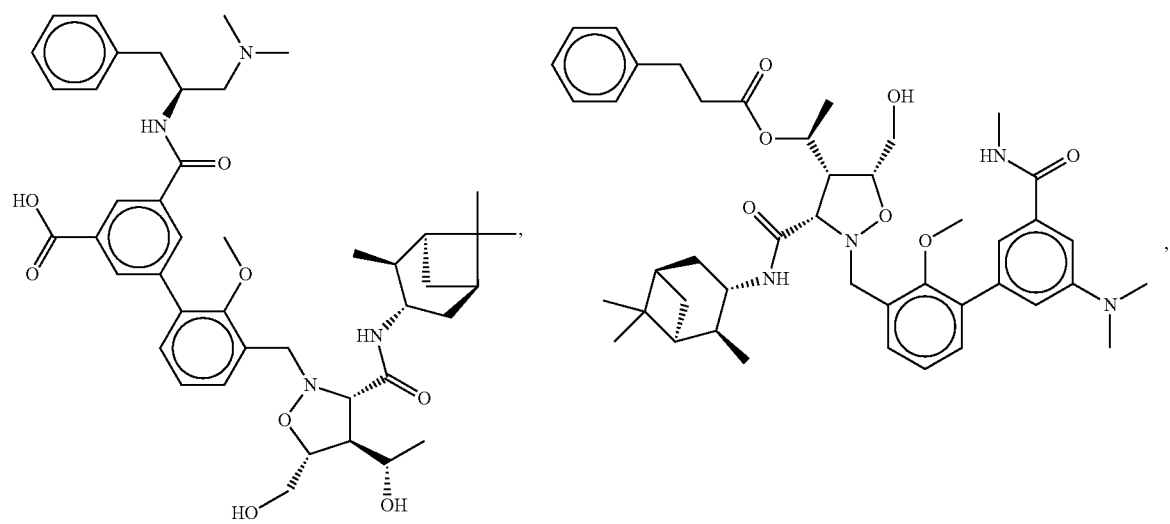

-continued
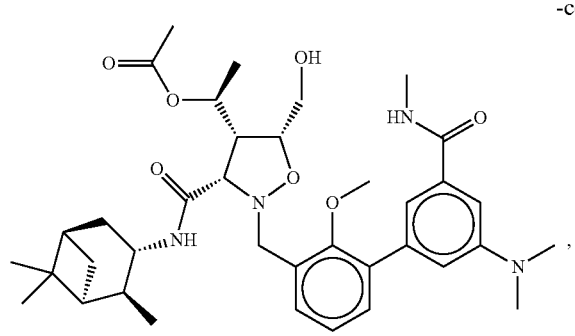
631
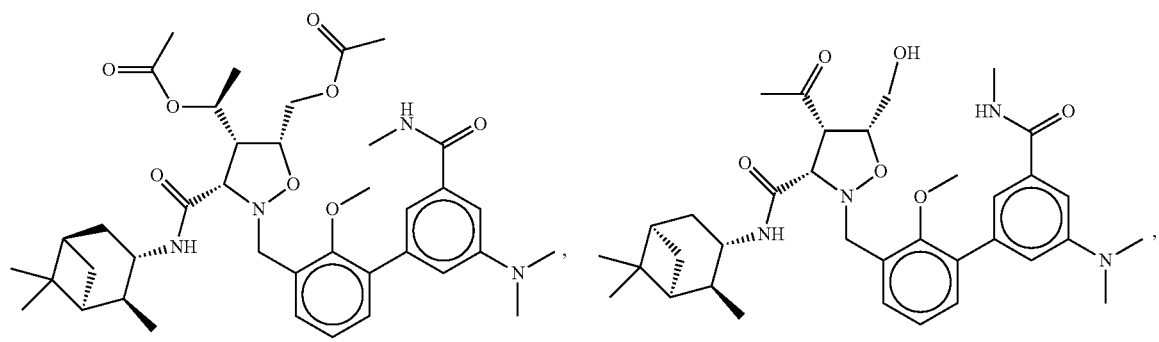
632
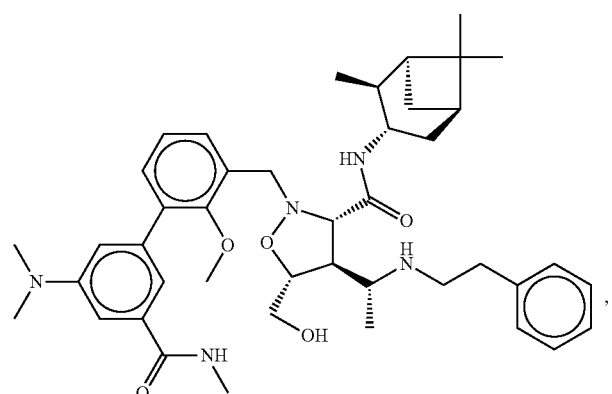
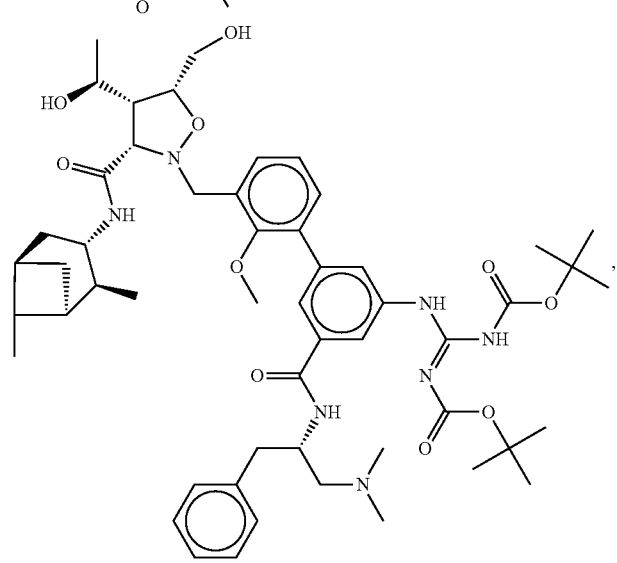

633                                        634
-continued
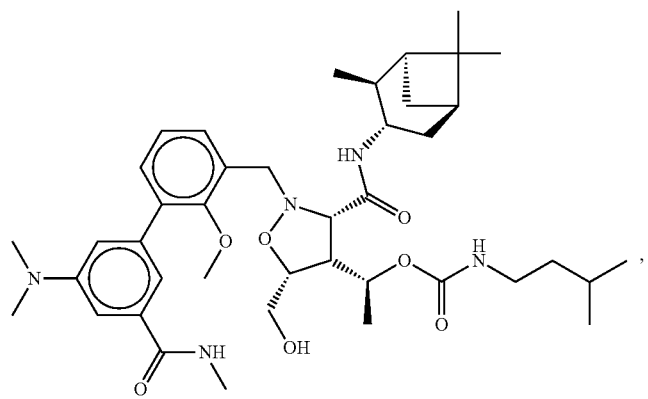
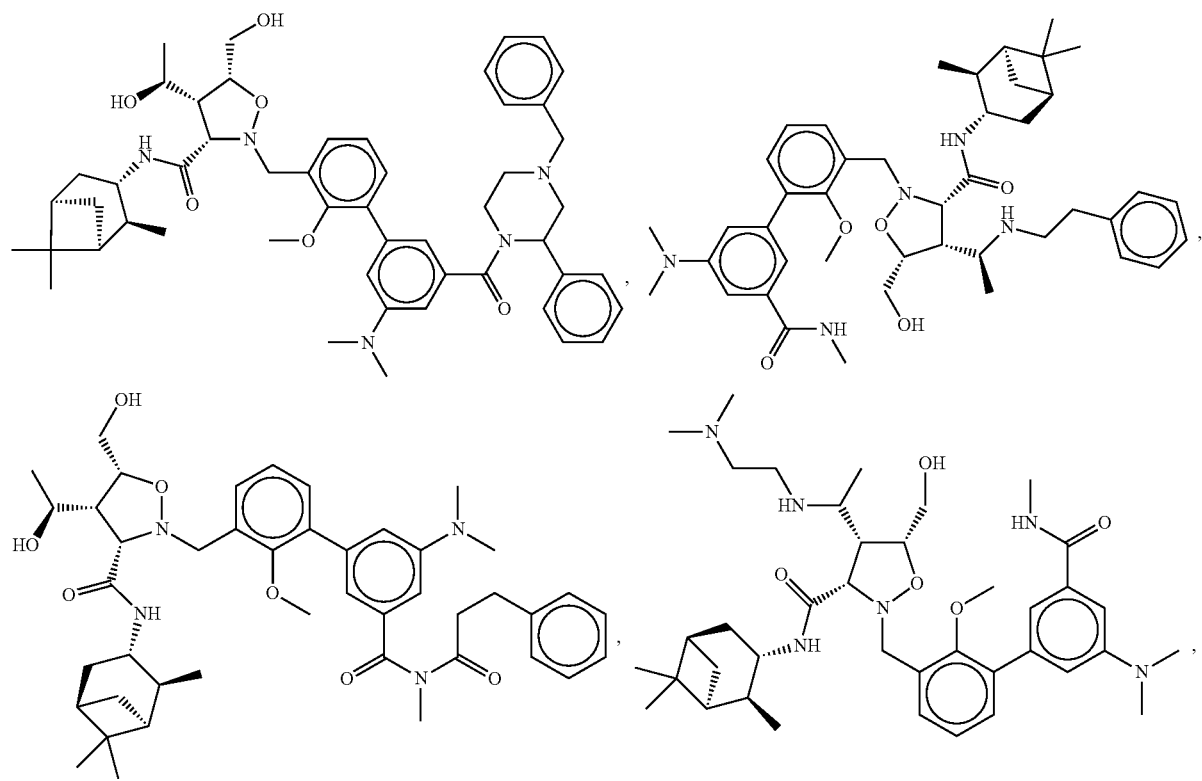
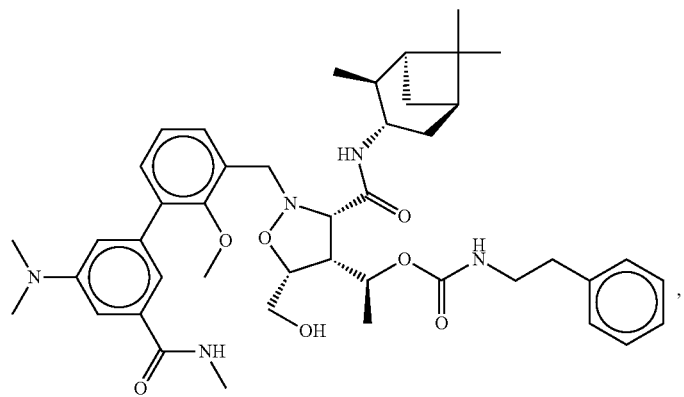

635 636
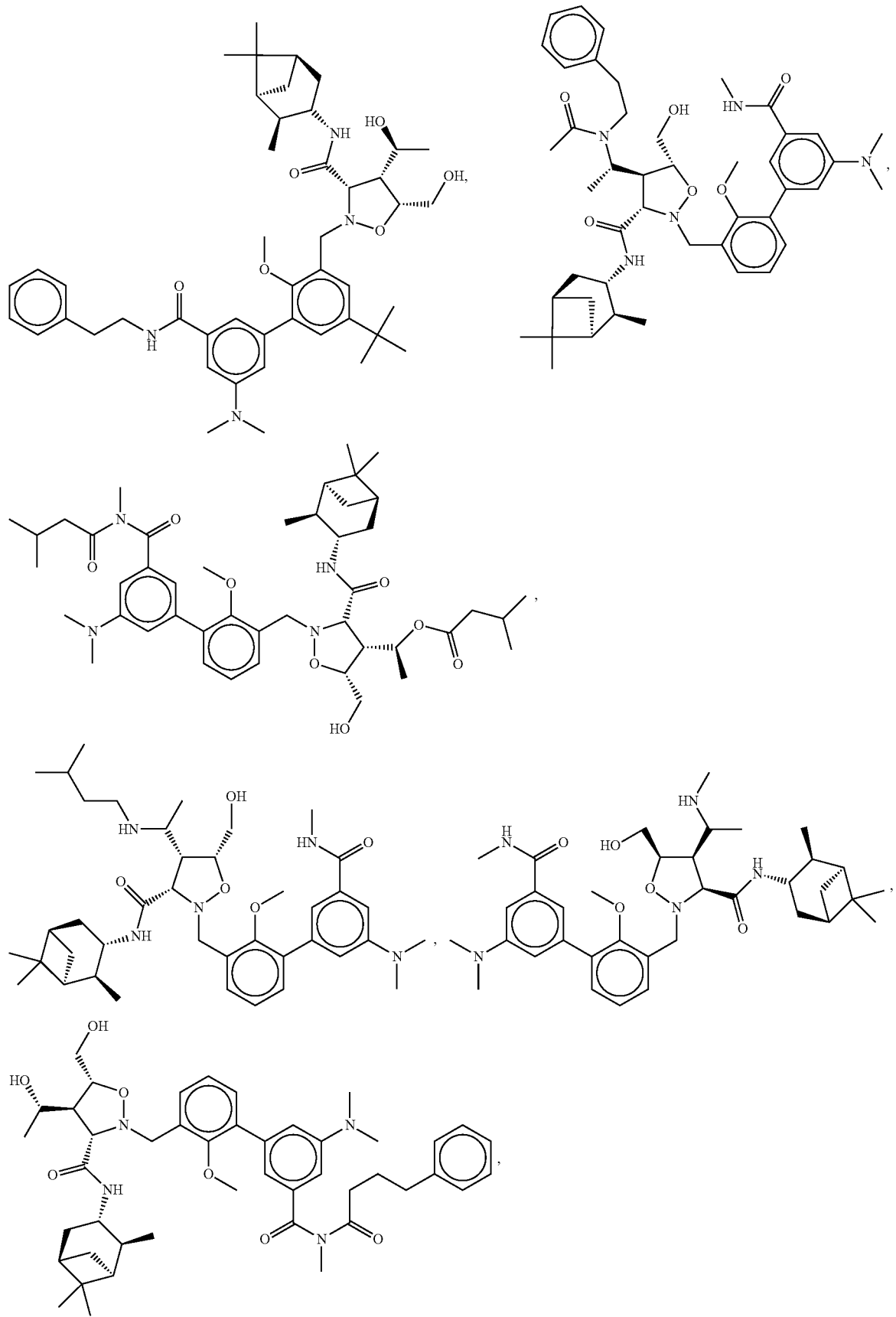

637
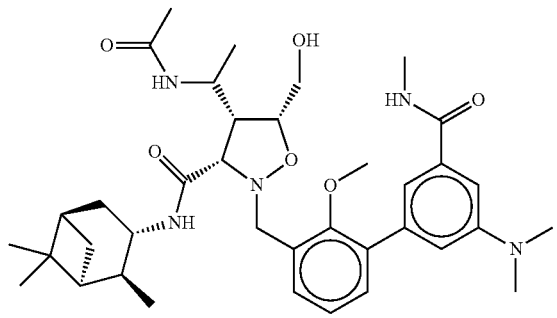
and
638
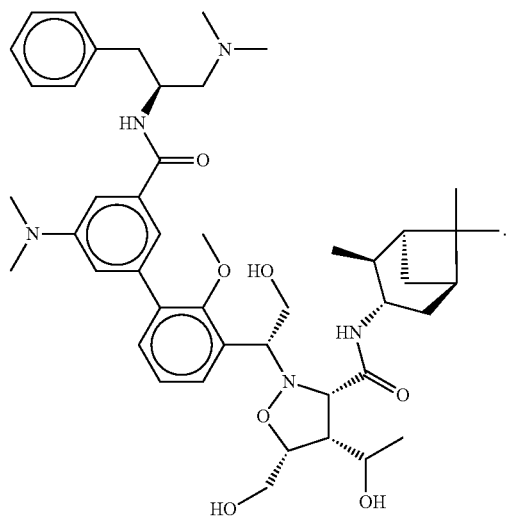
37. A compound selected from the group consisting of:
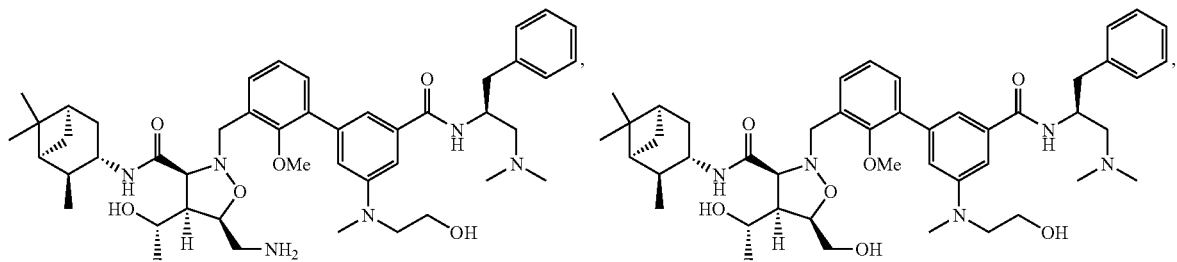
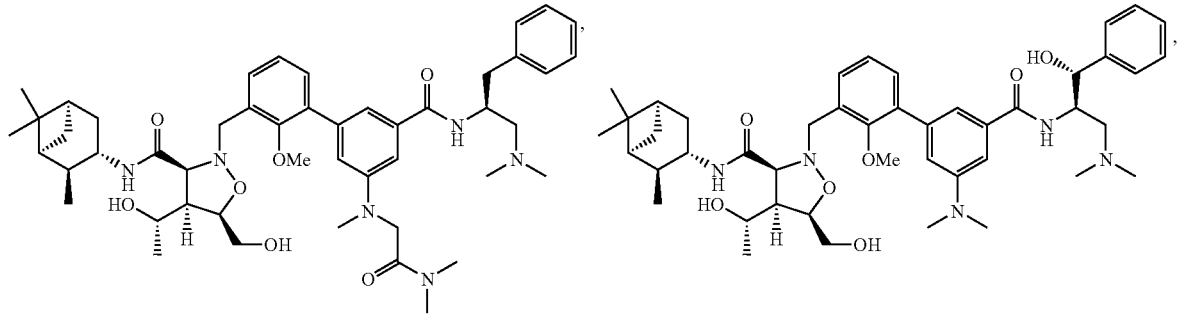
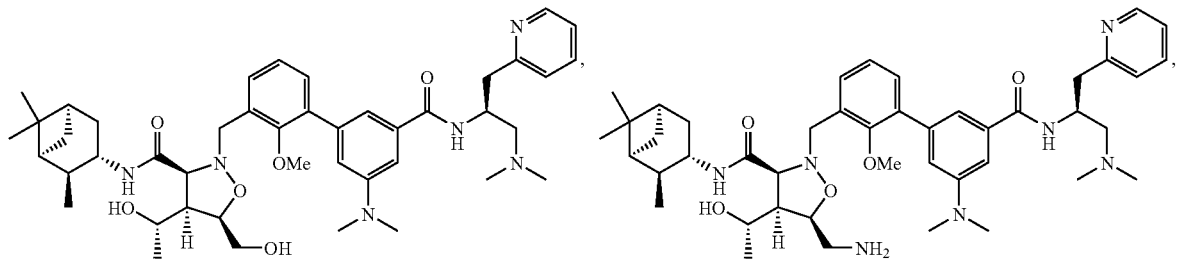

-continued
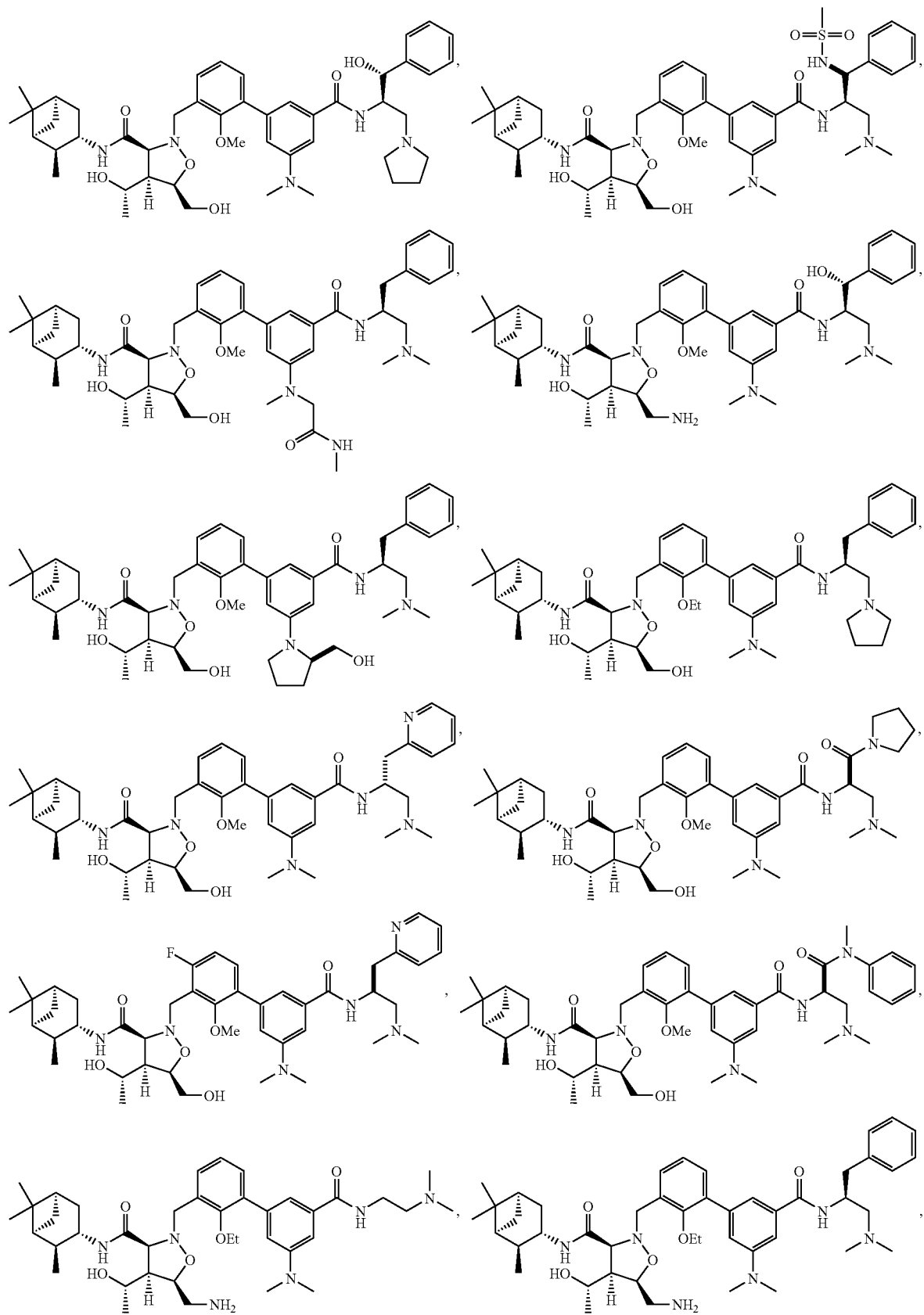

641
642
-continued
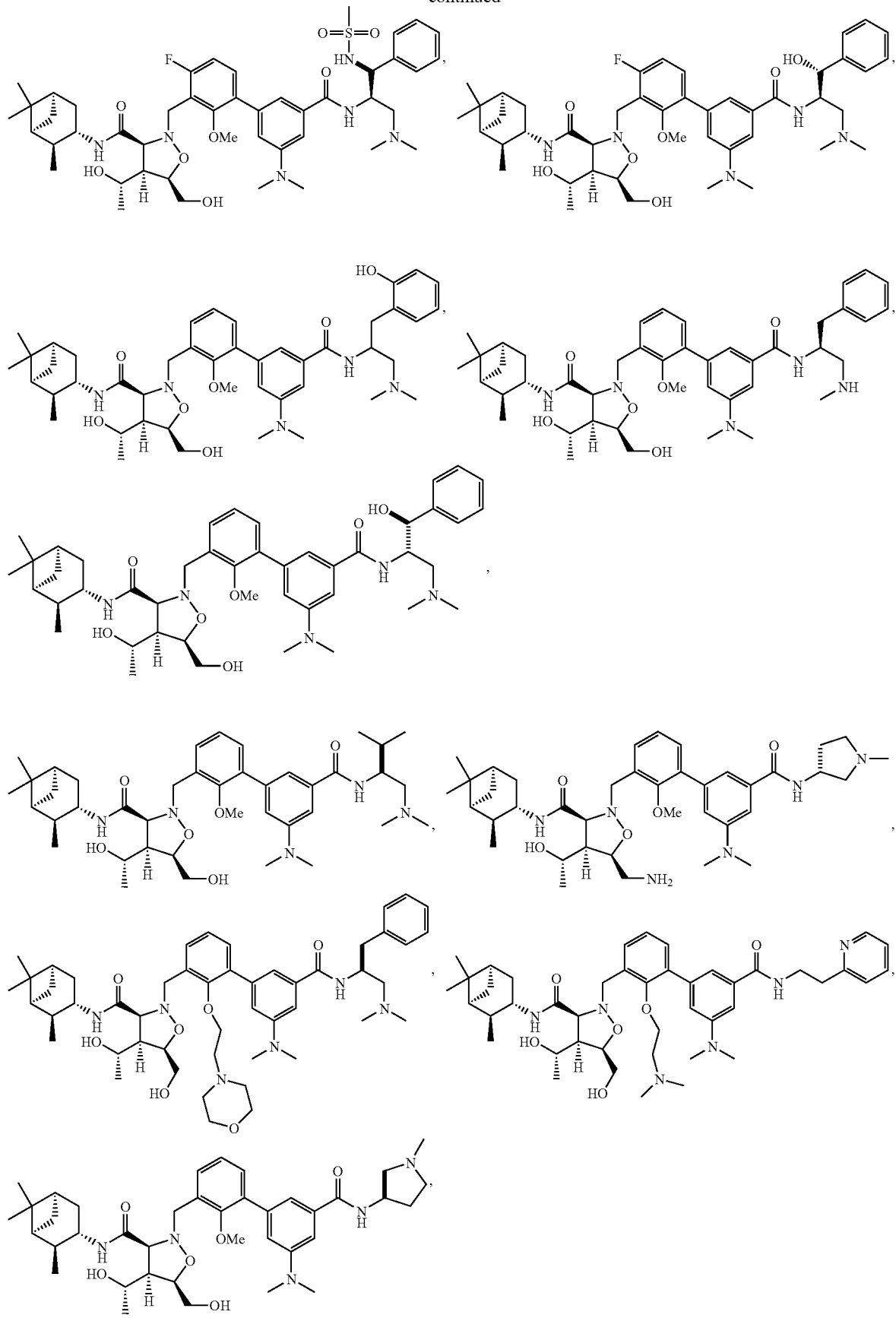

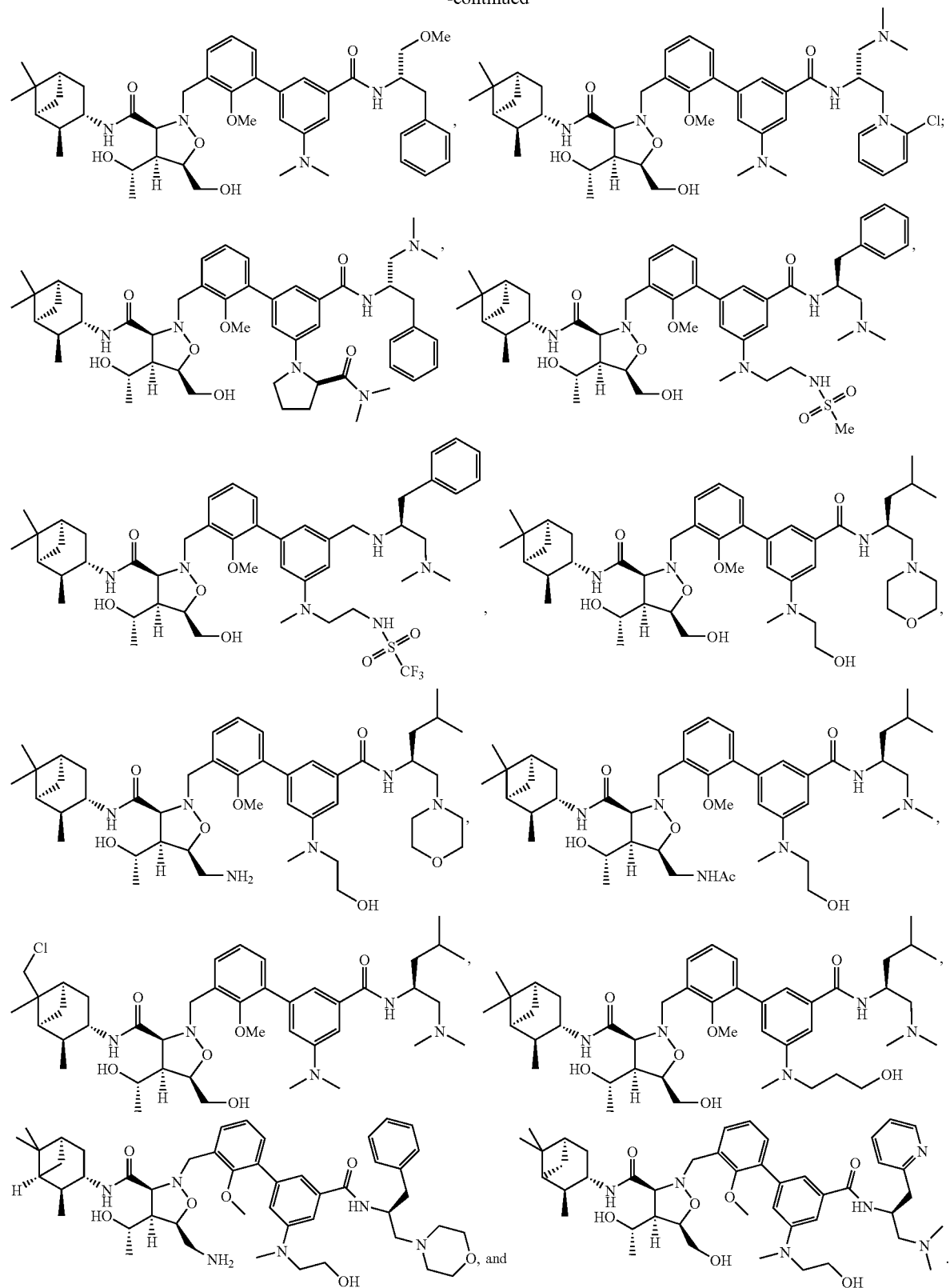

What is claimed is:

1. A compound of formula 1:

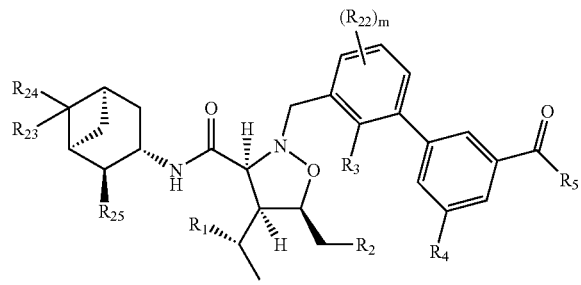

or a pharmaceutically acceptable salt thereof;
wherein independently for each occurrence
m is 0, 1, 2, or 3;
n, o, and p are independently for each occurrence 1, 2, 3, 4, or 5;
$R_1$ is —OH, —OC(O)$R_6$, —OC(O)N($R_6$)($R_7$), or —N($R_6$)($R_7$);
$R_2$ is —OH, —OC(O)Me, —OCH$_2$CO$_2$H, —OCH$_2$CO$_2$Et, —N$_3$, —N($R_8$)($R_9$), —N(R)C(O)N($R_8$)($R_9$), or —N(R)C(O)$R_{10}$; or has the formula 1b;

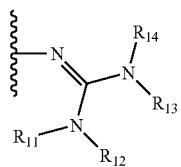

$R_3$ is alkyl, halide, alkoxy, (cycloalkyl)alkoxy, aralkyloxy, or —O(CH$_2$)$_2$—N($R_{15}$)($R_{16}$);
$R_4$ is alkyl, alkoxy, hydroxyalkyl, alkoxyalkyl, halide, nitro, amino, acyl, amido, acylamino, aminoalkyl, acylaminoalkyl, acylaminoalkylamino, sulfonylaminoalkylamino, carboxylate, or —N═C(N(R)$_2$)$_2$;
$R_5$ is —OH or —N($R_{17}$)($R_{18}$);
$R_6$ and $R_7$ are independently for each occurrence H, alkyl, aralkyl, heteroaralkyl, or —[C($R_{15}$)($R_{16}$)]$_n$—$R_{19}$;
$R_8$ and $R_9$ are independently for each occurrence H, alkyl, aralkyl, or heteroaralkyl;
$R_{10}$ is alkyl, haloalkyl, or —[C($R_{15}$)($R_{16}$)]$_o$—COOR;
R, $R_{11}$, $R_{12}$, $R_{13}$, $R_{14}$, $R_{15}$, and $R_{16}$ are independently for each occurrence H or alkyl;
$R_{17}$ and $R_{18}$ are independently for each occurrence H, alkyl, aralkyl, heteroaralkyl, alkoxy, or —[C($R_{19}$)($R_{20}$)]$_p$—$R_{21}$;
$R_{19}$ and $R_{20}$ are independently for each occurrence H, hydroxy, alkyl, alkoxy, amino, aminoalkyl, acylamino, sulfonylamino, aryl, aralkyl, cycloalkyl, heterocyclyl, heterocyclylalkyl, heteroaryl, or heteroaralkyl;
$R_{21}$ is independently for each occurrence H, alkyl, aryl, heteroaryl, heterocyclyl, heterocyclylalkyl, alkoxy, alkylsulfonyl, arylsulfonyl, alkylsulfonamido, arylsulfonamido, amino, amido, or carboxyl;
$R_{22}$ independently for each occurrence is halide or alkyl;
$R_{23}$ is selected from the group consisting of alkyl, hydroxyalkyl, alkoxyalkyl, acyloxyalkyl, and haloalkyl;
$R_{24}$ is selected from the group consisting of alkyl, hydroxyalkyl, alkoxyalkyl, acyloxyalkyl, and haloalkyl; and
$R_{25}$ is selected from the group consisting of alkyl, hydroxyalkyl, alkoxyalkyl, acyloxyalkyl, and haloalkyl.

2. The compound of claim 1, wherein $R_1$ is selected from the group consisting of —OH, —OC(O)Me, —OC(O)(CH$_2$)$_2$Ph, —OC(O)CH$_2$CHMe$_2$, —OC(O)NHMe, —OC(O)NMe$_2$, —OC(O)NHCH$_2$(4-(OH)-Ph), —OC(O)NHPh, —OC(O)NHCH$_2$Ph, —OC(O)NH(CH$_2$)$_4$Ph, —OC(O)NH(CH$_2$)$_2$Ph, —OC(O)NH(CH$_2$)$_2$Me, —OC(O)NH(CH$_2$)$_2$NMe$_2$, —OC(O)NH(CH$_2$)$_2$NHC(O)Me, —OC(O)NH(CH$_2$)$_2$CHMe$_2$, —NHMe, —NH(CH$_2$)$_2$Ph, —NHC(O)Me, and —NH(CH$_2$)$_2$NMe$_2$.

3. The compound of claim 1, wherein $R_1$ is —OH.

4. The compound of claim 1, wherein $R_2$ is —OH, —OC(O)Me, —OCH$_2$CO$_2$H, —OCH$_2$CO$_2$Et, —N$_3$, —N═C(NMe$_2$)$_2$, —NH$_2$, —NMe$_2$, —NHC(O)Me, —NHC(O)CF$_3$, —NHC(O)Ph, —NHC(O)NHPh, —NHC(O)CH$_2$CH$_2$CO$_2$H, —NHC(O)CH$_2$CH$_2$CO$_2$Me, —NHCH$_2$Ph, —NHCH$_2$(4-pyridyl), —NHCH$_2$(2-pyridyl), —NHCH$_2$(4-(CO$_2$H)Ph), —NHCH$_2$(3-(CO$_2$H)Ph), —NHEt, —NHCHMe$_2$, —NHCH$_2$CHMe$_2$, —N(CH$_2$CHMe$_2$)$_2$, —NHCH$_2$(cyclopropyl), or —NHC(O)CH$_2$CH$_2$NMe$_2$.

5. The compound of claim 1, wherein $R_2$ is —OH or —NH$_2$.

6. The compound of claim 1, wherein $R_2$ is —NH$_2$.

7. The compound of claim 1, wherein $R_2$ is —OH.

8. The compound of claim 1, wherein $R_3$ is —OMe, —OEt, —OCH$_2$(cyclopropyl), F, —O(CH$_2$)$_2$NMe$_2$, —O(CH$_2$)$_2$(4-morpholino), —OCH$_2$(4-(MeO)Ph), or —OCH$_2$(2-pyridyl).

9. The compound of claim 1, wherein $R_3$ is —OMe.

10. The compound of claim 1, wherein $R_4$ is —NMe$_2$, —NEt$_2$, —NHEt, —NHCH$_2$CHMe$_2$, —N(Me)CH$_2$CHMe$_2$, —N(Me)CH$_2$CH$_2$NHC(O)Me, —N(Me)CH$_2$CH$_2$NHS(O)$_2$Me, —N(Me)CH$_2$CH$_2$NHS(O)$_2$CF$_3$, —NHCH$_2$CH$_2$NMe$_2$, —NHCH$_2$CH$_2$NMeCH$_2$CH$_2$Cl, —NHCH$_2$CH$_2$OH, —N(Me)CH$_2$CH$_2$OH, —N(CH$_2$CH$_2$OH)$_2$, —N(Me)CH$_2$CO$_2$H, —N(Me)CH$_2$C(O)NH$_2$, —N(Me)CH$_2$C(O)NHMe, —N(Me)CH$_2$C(O)NMe$_2$, —NHC(O)Me, —NHC(O)CHMe$_2$, 1-pyrrolidinyl, 1-piperidinyl, 4-morpholino, (R)-2-(hydroxymethyl)-1-pyrrolidinyl, (S)-2-(hydroxymethyl)-1-pyrrolidinyl, (R)-2-(C(O)NMe$_2$)-1-pyrrolidinyl, (S)-2-(C(O)NMe$_2$)-1-pyrrolidinyl, —NH$_2$, —NO$_2$, Br, Cl, F, —C(O)Me, —C(O)NMe$_2$, —C(O)NH$_2$, —CO$_2$H, —CHO, —CH$_2$OH, —CH(Me)OH, —CH$_2$NH$_2$, —CH$_2$NHMe, —CH$_2$NMe$_2$, —CH$_2$NHC(O)Me, —CF$_3$, or tert-butyl.

11. The compound of claim 1, wherein $R_4$ is amino.

12. The compound of claim 1, wherein $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

13. The compound of claim 1, wherein $R_4$ is —NMe$_2$.

14. The compound of claim 1, wherein $R_{22}$ is selected from the group consisting of F, Cl, and tert-butyl; and m is 0 or 1.

15. The compound of claim 1, wherein $R_{22}$ is F; and m is 0 or 1.

16. The compound of claim 1, wherein $R_{22}$ is selected from the group consisting of F, Cl, and tert-butyl; and m is 1.

17. The compound of claim 1, wherein $R_{22}$ is F; and m is 1.

18. The compound of claim 1, wherein $R_{23}$ is selected from the group consisting of methyl, hydroxymethyl, alkoxymethyl, acyloxymethyl, and halomethyl.

19. The compound of claim 1, wherein $R_{24}$ is selected from the group consisting of methyl, hydroxymethyl, alkoxymethyl, acyloxymethyl, and halomethyl.

20. The compound of claim 1, wherein $R_{23}$ is methyl.

21. The compound of claim 1, wherein $R_{24}$ is methyl.

22. The compound of claim 1, wherein $R_{23}$ is methyl; and $R_{24}$ is methyl.

23. The compound of claim 1, wherein $R_{25}$ is selected from the group consisting of methyl, hydroxymethyl, alkoxymethyl, acyloxymethyl, and halomethyl.

24. The compound of claim 1, wherein $R_{25}$ is methyl.

25. The compound of claim 1, wherein $R_{23}$ is methyl; $R_{24}$ is methyl; and $R_{25}$ is methyl.

26. The compound of claim 1, wherein $R_1$ is —OH; and $R_2$ is —OH or —NH$_2$.

27. The compound of claim 1, wherein $R_1$ is —OH; $R_2$ is —OH or —NH$_2$; and $R_3$ is —OMe.

28. The compound of claim 1, wherein $R_1$ is —OH; $R_2$ is —OH or —NH$_2$; $R_3$ is —OMe; and $R_4$ is amino.

29. The compound of claim 1, wherein $R_1$ is —OH; $R_2$ is —OH or —NH$_2$; $R_3$ is —OMe; and $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl.

30. The compound of claim 1, wherein $R_1$ is —OH; $R_2$ is —OH or —NH$_2$; $R_3$ is —OMe; and $R_4$ is —NMe$_2$.

31. The compound of claim 1, wherein $R_1$ is —OH; $R_2$ is —OH or —NH$_2$; $R_{23}$ is methyl; $R_{24}$ is methyl; and $R_{25}$ is methyl.

32. The compound of claim 1, wherein $R_1$ is —OH; $R_2$ is —OH or —NH$_2$; $R_3$ is —OMe; $R_{23}$ is methyl; $R_{24}$ is methyl; and $R_{25}$ is methyl.

33. The compound of claim 1, wherein $R_1$ is —OH; $R_2$ is —OH or —NH$_2$; $R_3$ is —OMe; $R_4$ is amino; $R_{23}$ is methyl; $R_{24}$ is methyl; and $R_{25}$ is methyl.

34. The compound of claim 1, wherein $R_1$ is —OH; $R_2$ is —OH or —NH$_2$; $R_3$ is —OMe; $R_4$ is —NMe$_2$, —N(Me)CH$_2$CH$_2$OH, —N(Me)CH$_2$C(O)NMe$_2$, —N(Me)CH$_2$C(O)NHMe, (R)-2-(hydroxymethyl)-1-pyrrolidinyl, or (R)-2-(C(O)NMe$_2$)-1-pyrrolidinyl; $R_{23}$ is methyl; $R_{24}$ is methyl; and $R_{25}$ is methyl.

35. The compound of claim 1, wherein $R_1$ is —OH; $R_2$ is —OH or —NH$_2$; $R_3$ is —OMe; $R_4$ is —NMe$_2$; $R_{23}$ is methyl; $R_{24}$ is methyl; and $R_{25}$ is methyl.

36. A compound selected from the group consisting of:

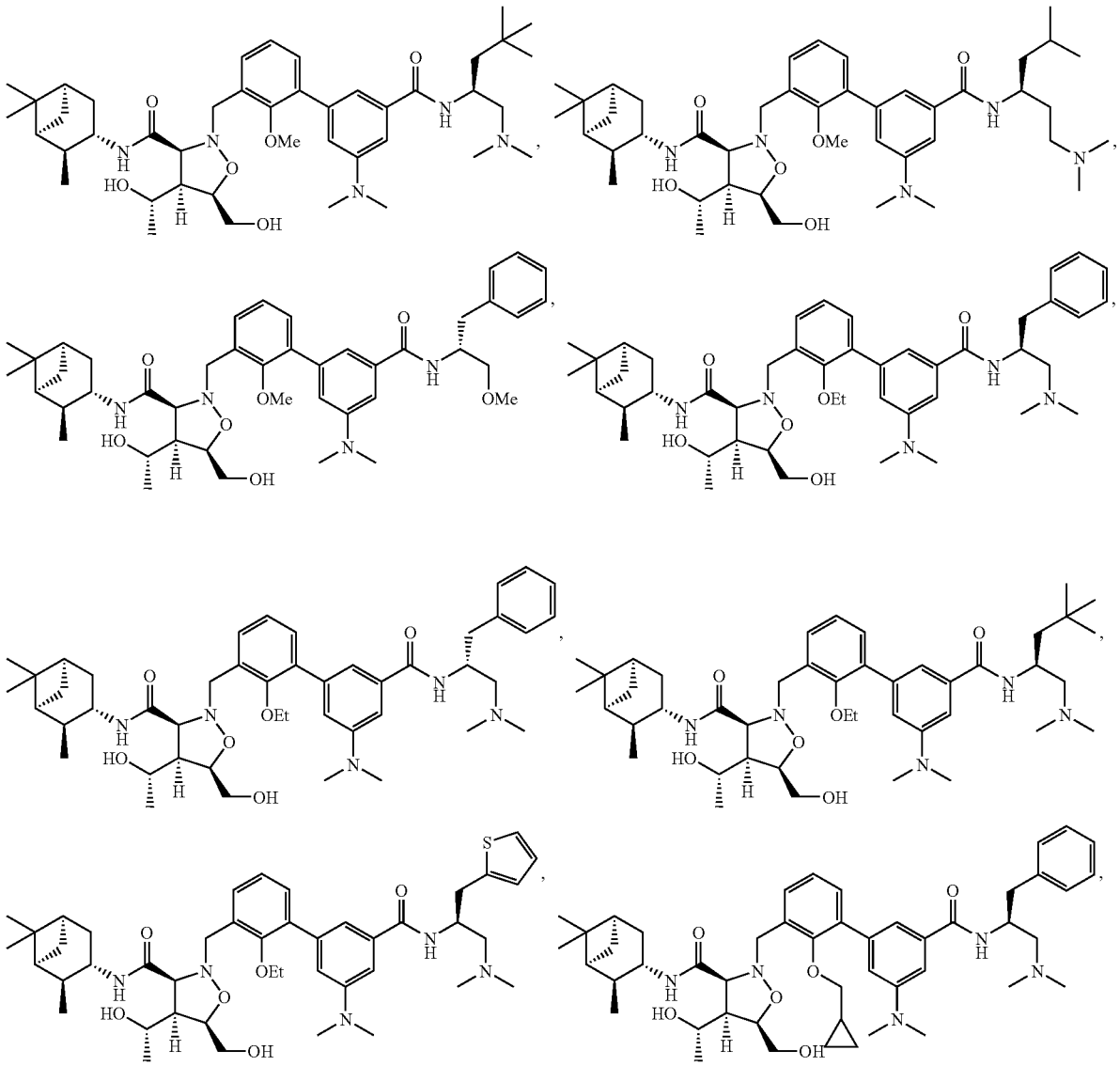

481
482
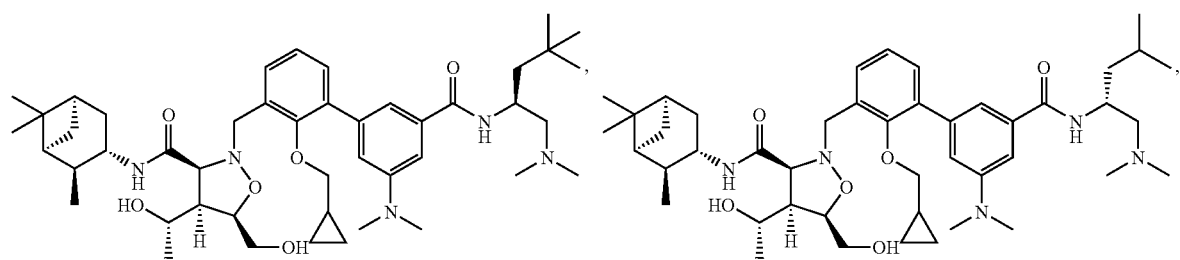
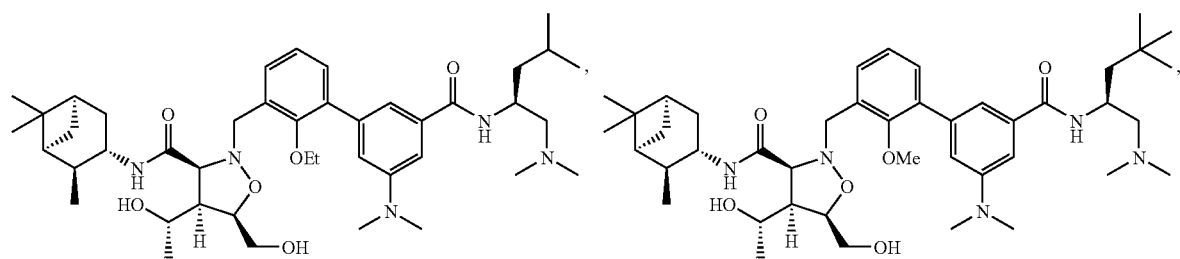
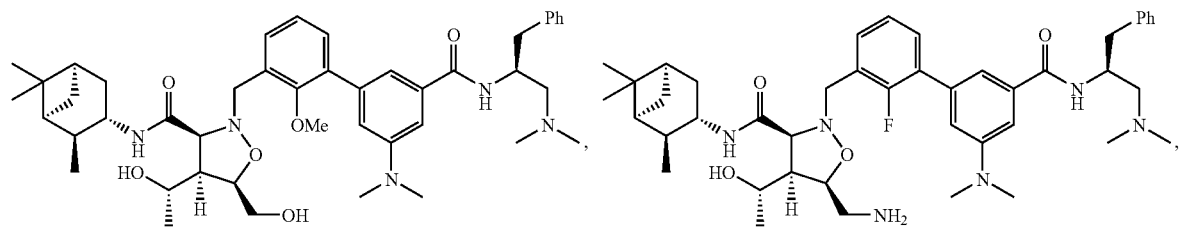
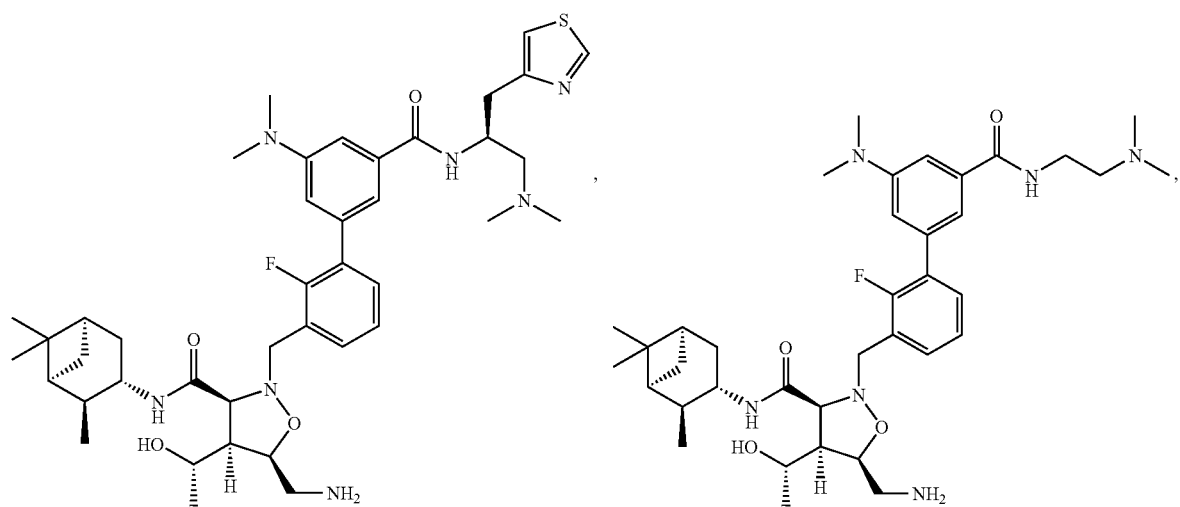

483
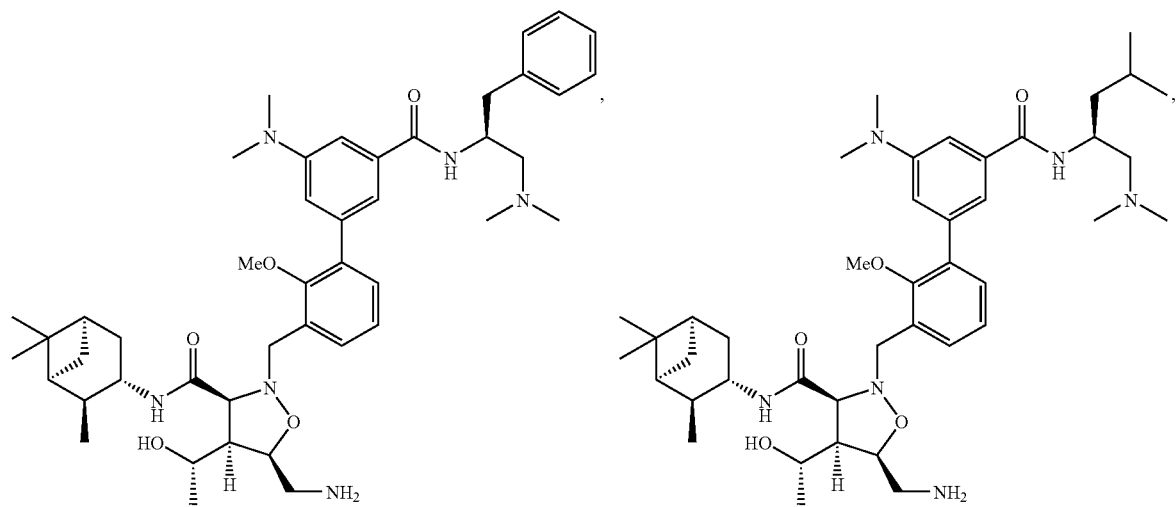
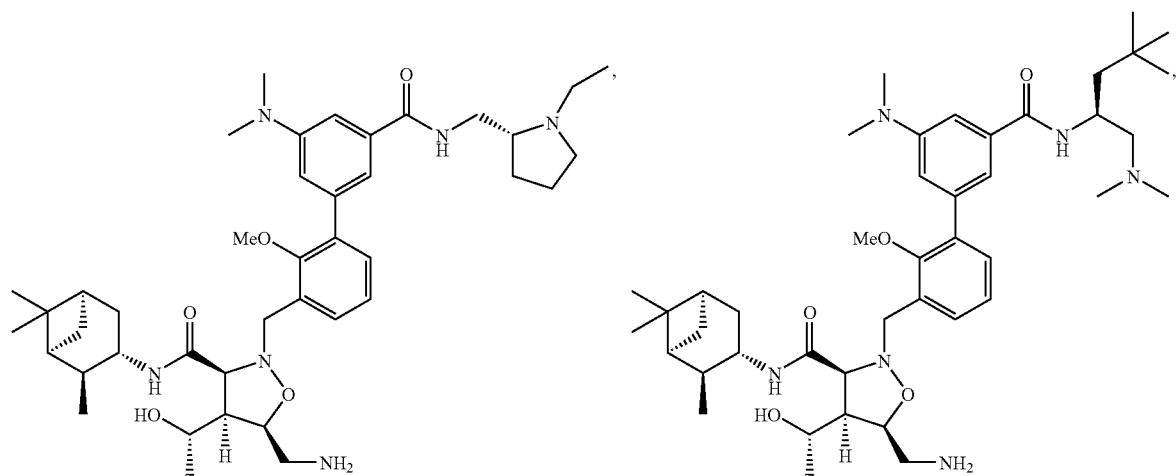
484
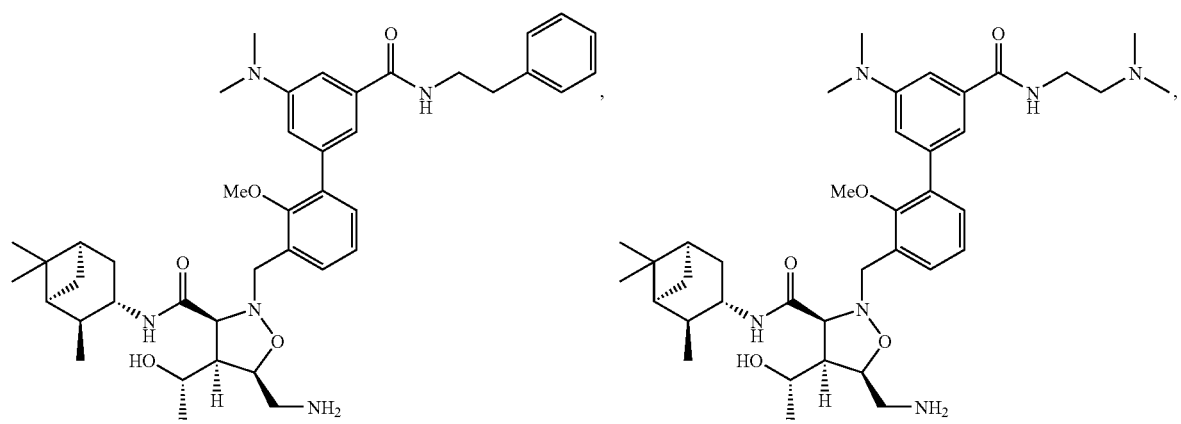

485 486
-continued
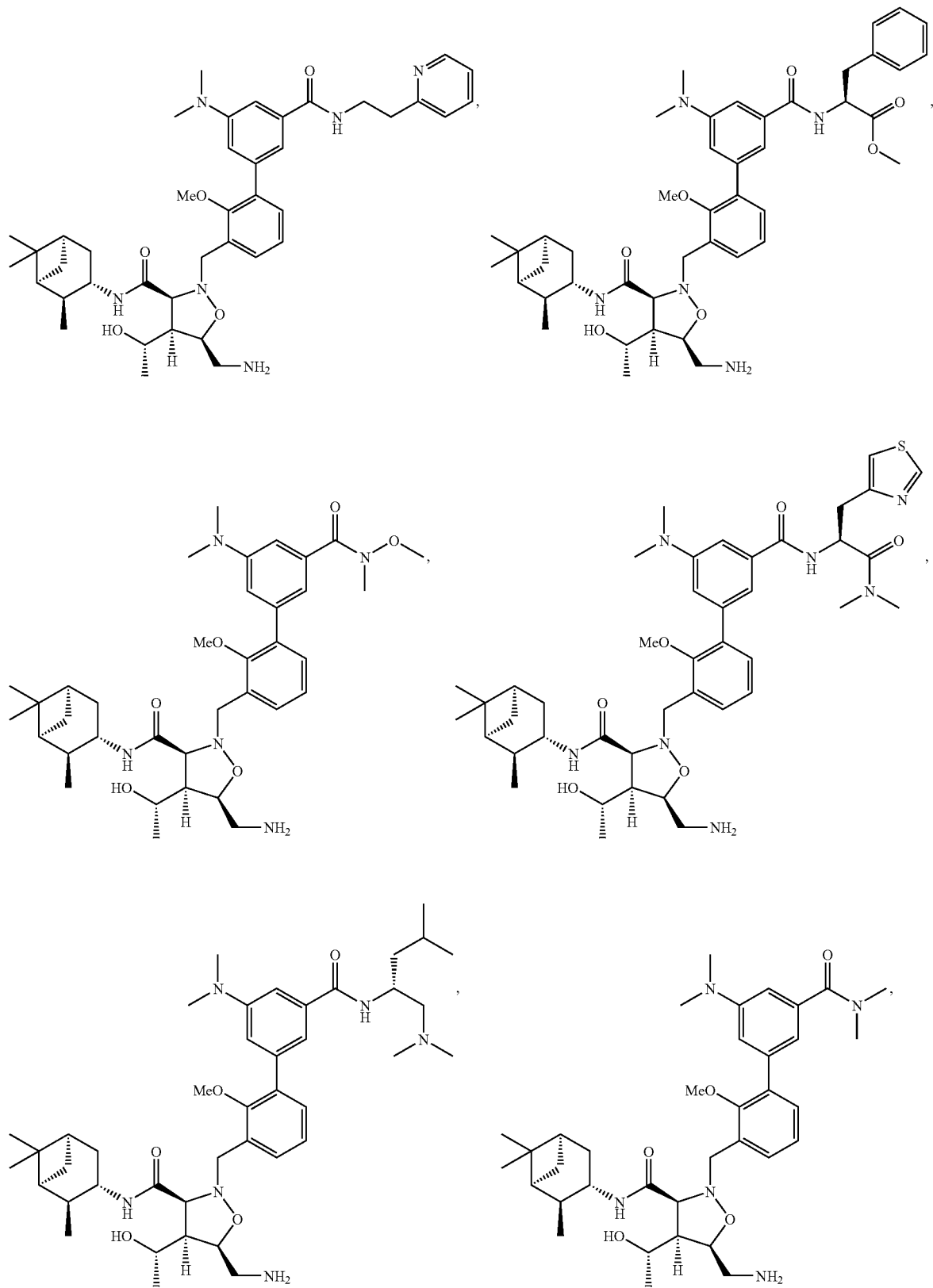

487                                    488
-continued
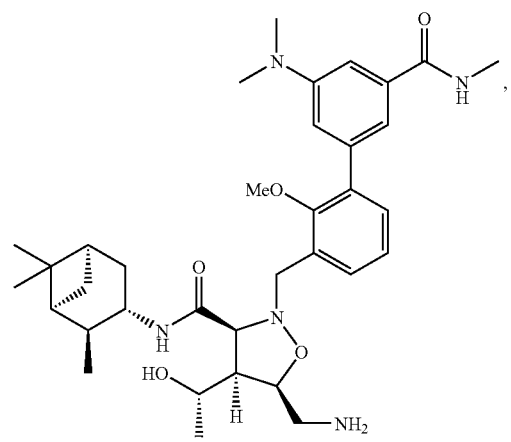 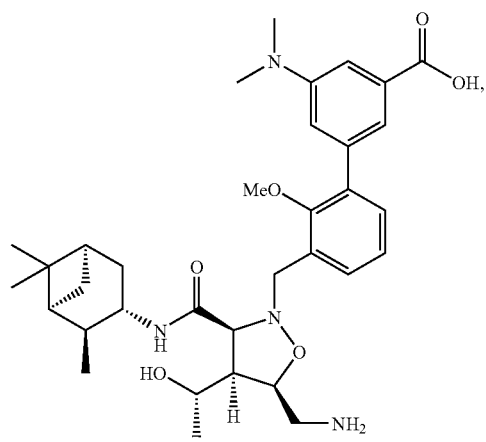
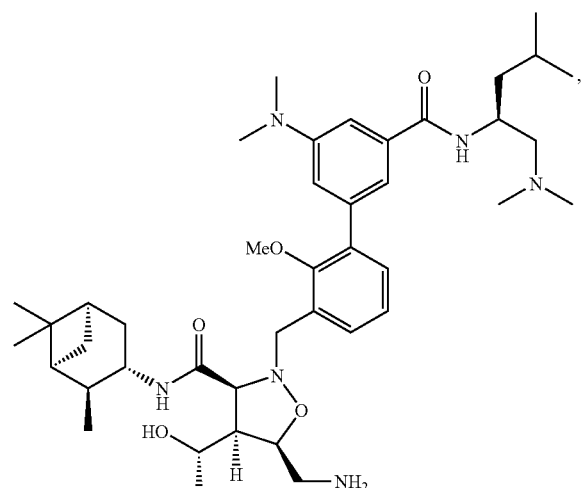 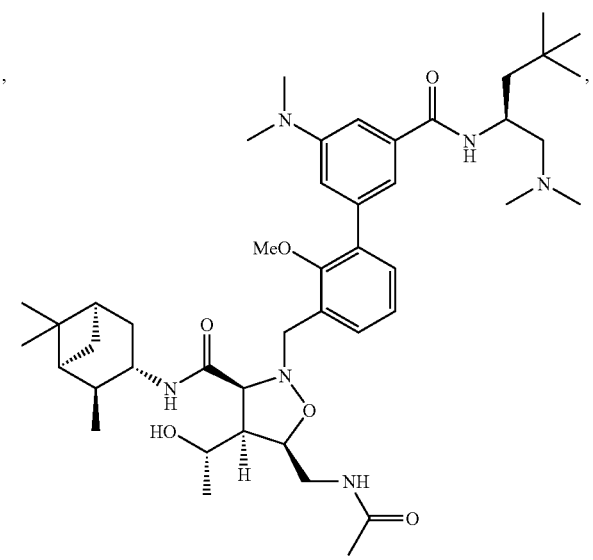
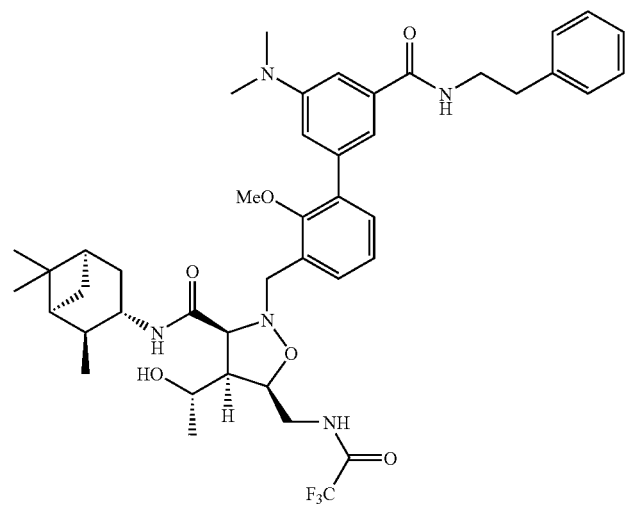 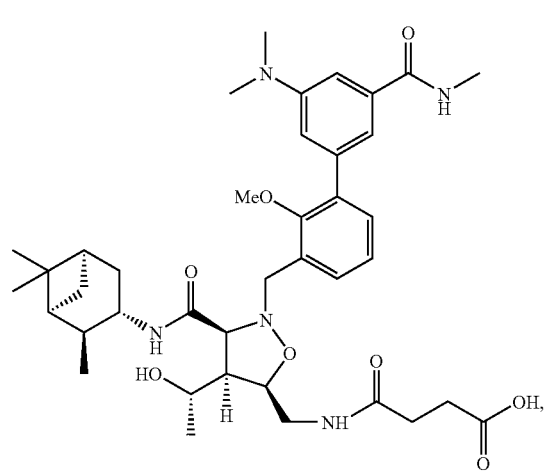

489    490
-continued
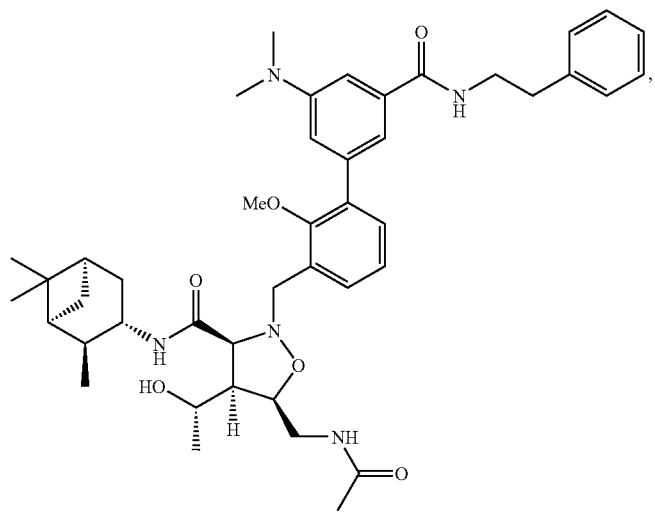
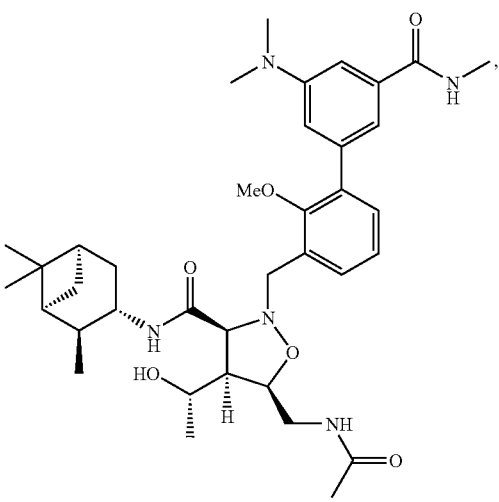
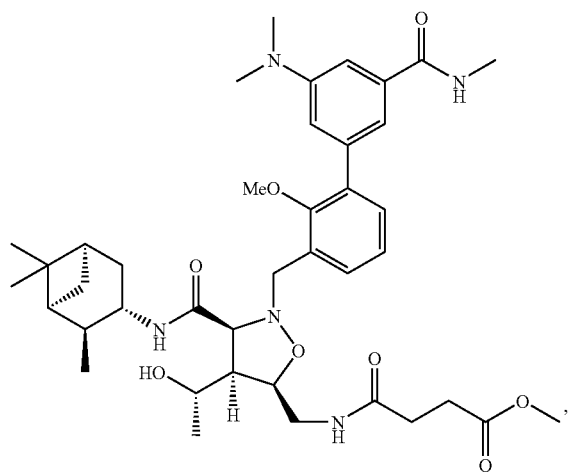
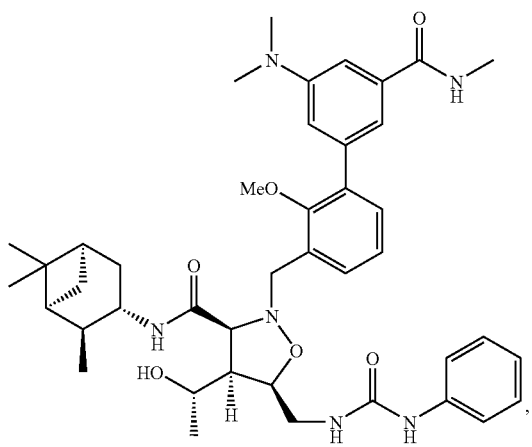
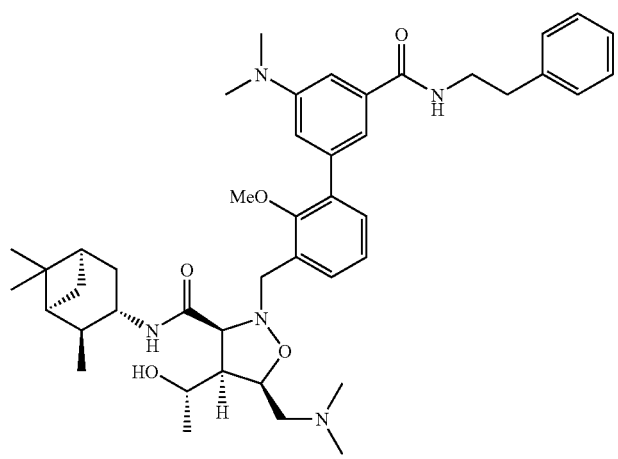
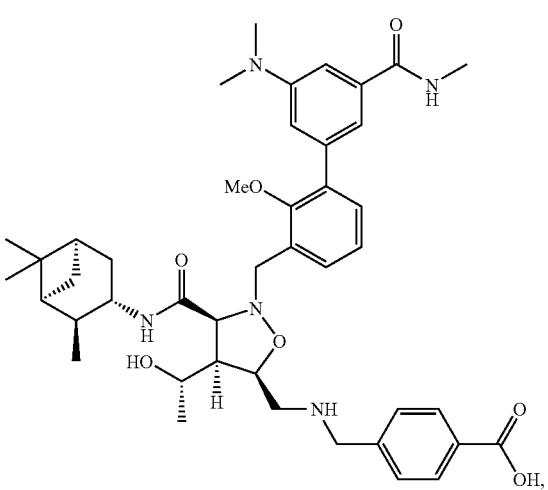

-continued
491
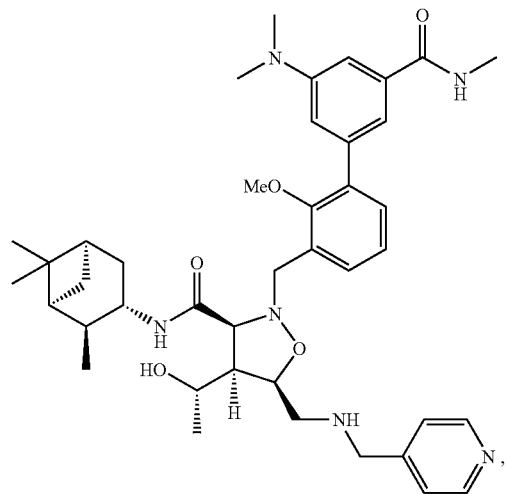
492
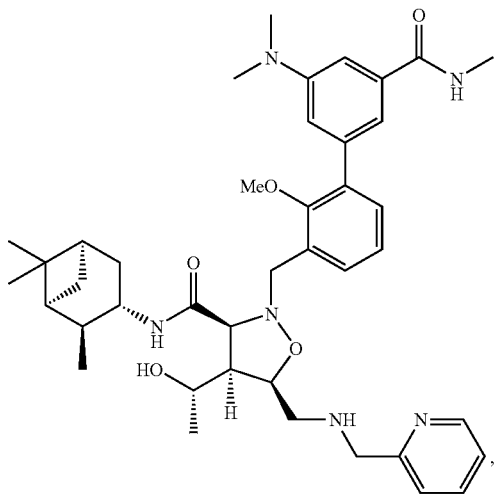
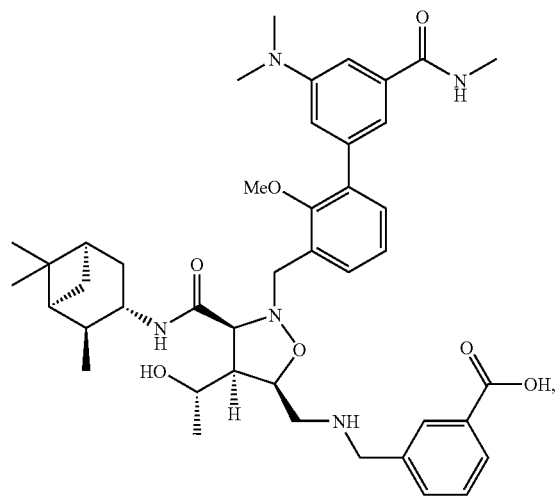
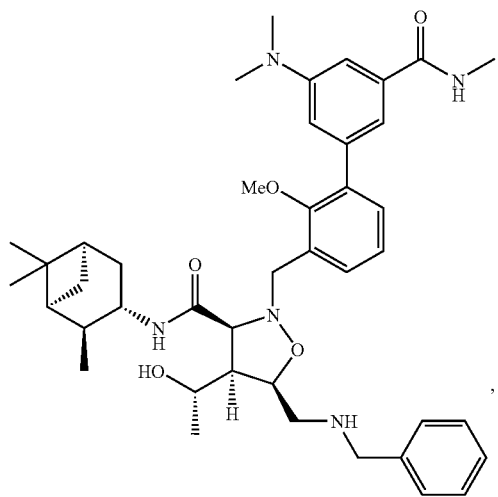
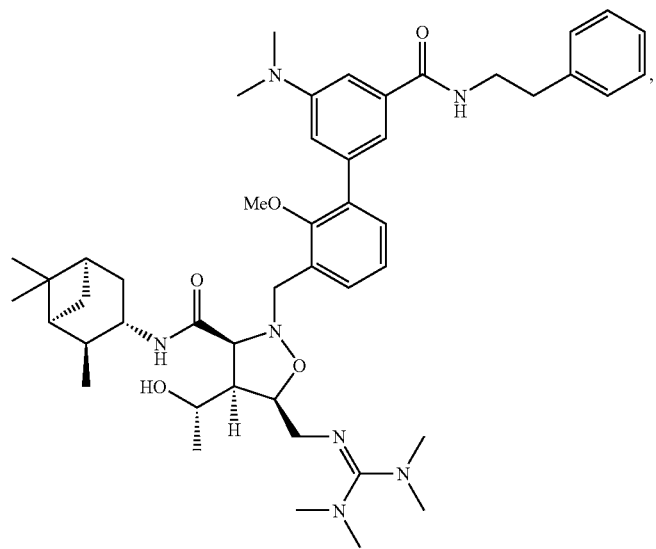
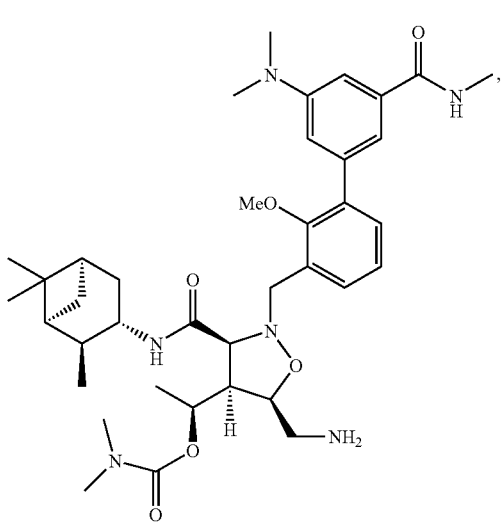

493
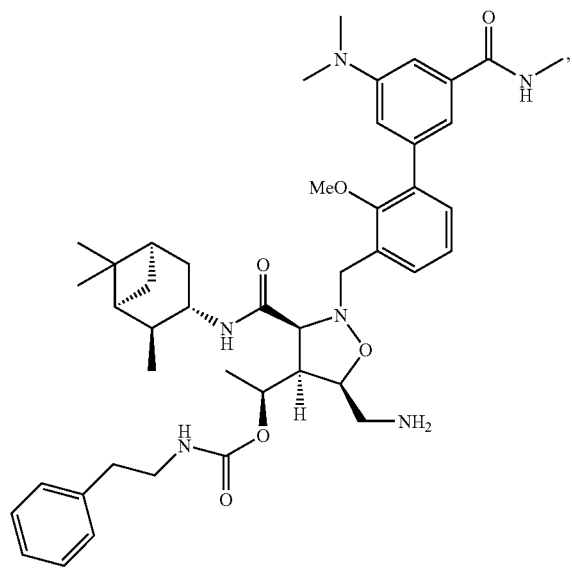
494
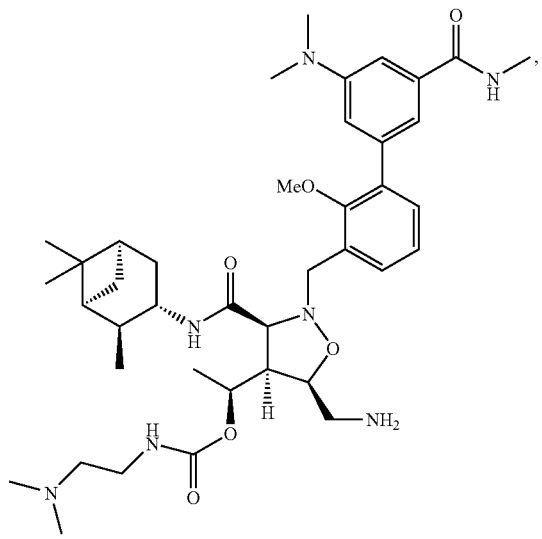
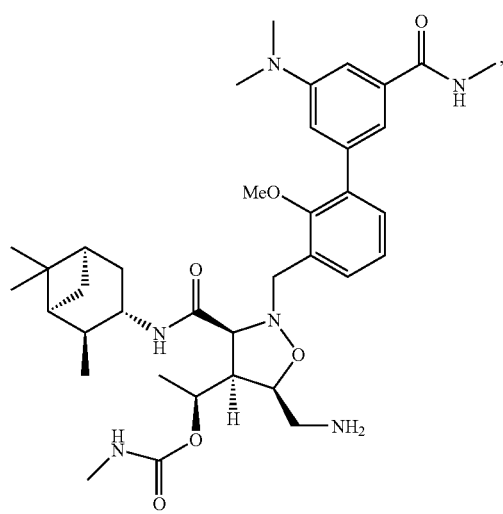
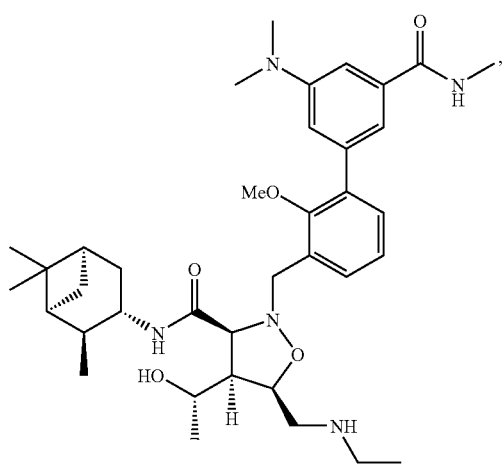
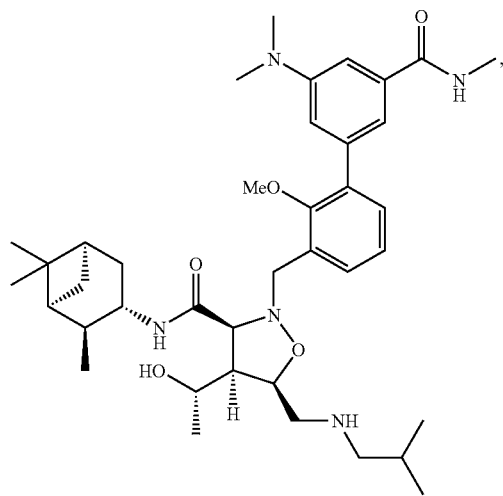
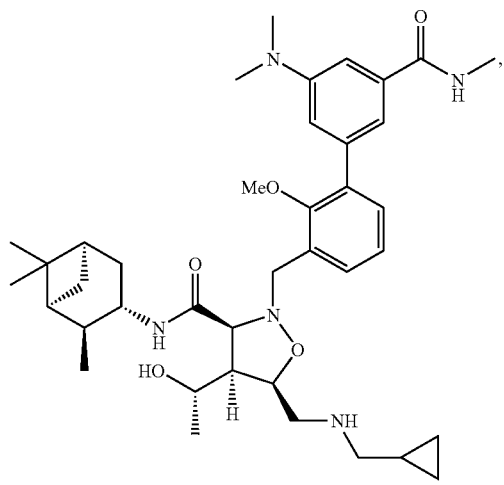

495
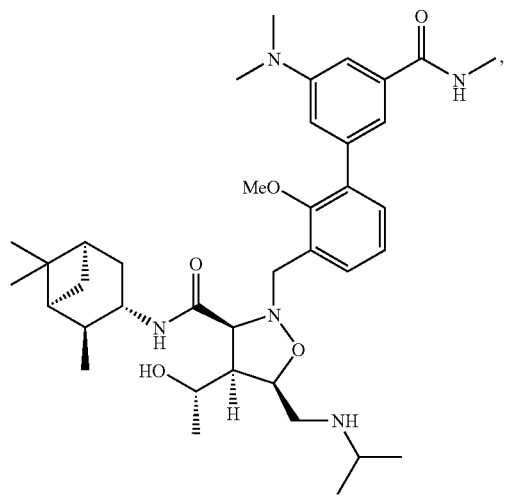
496
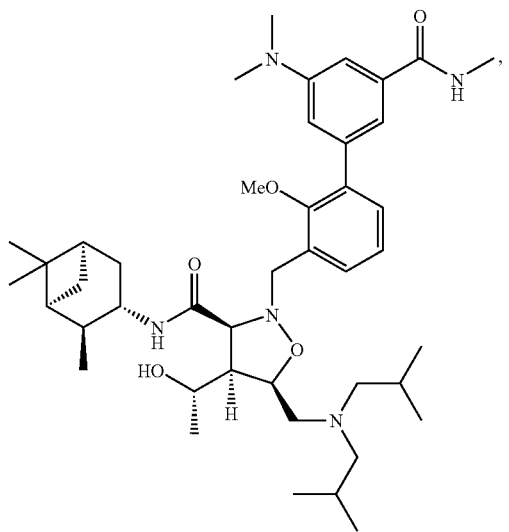
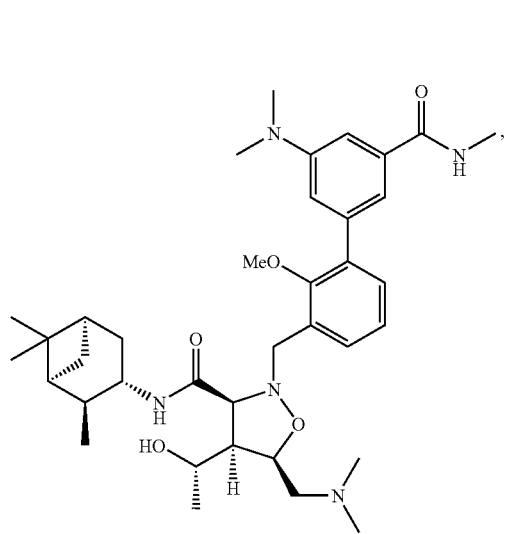
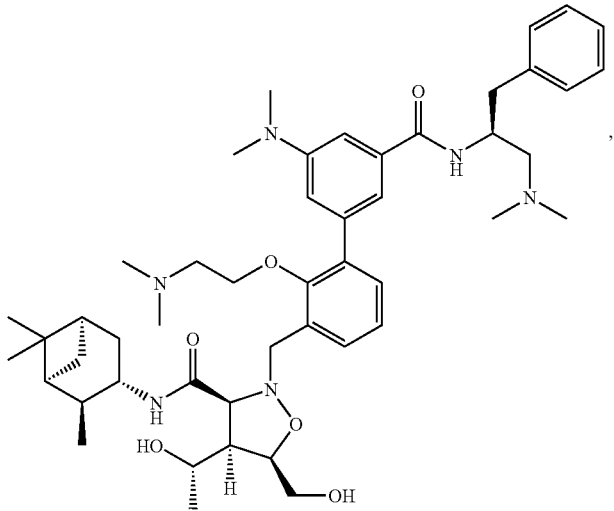
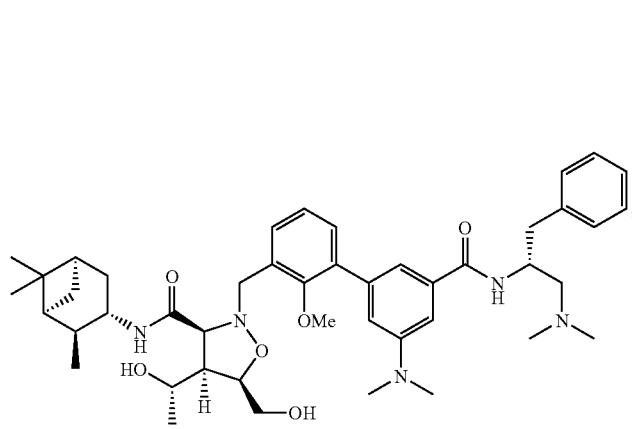
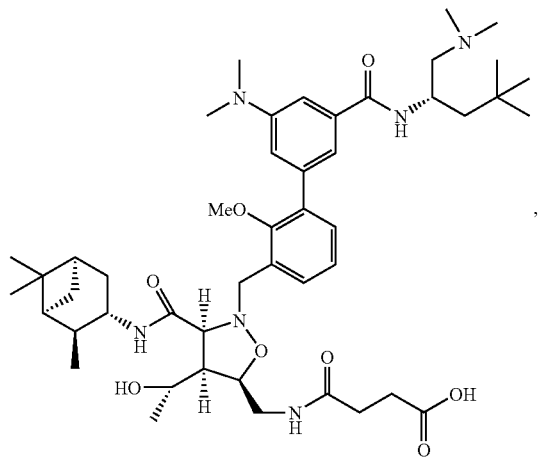

497 498
-continued
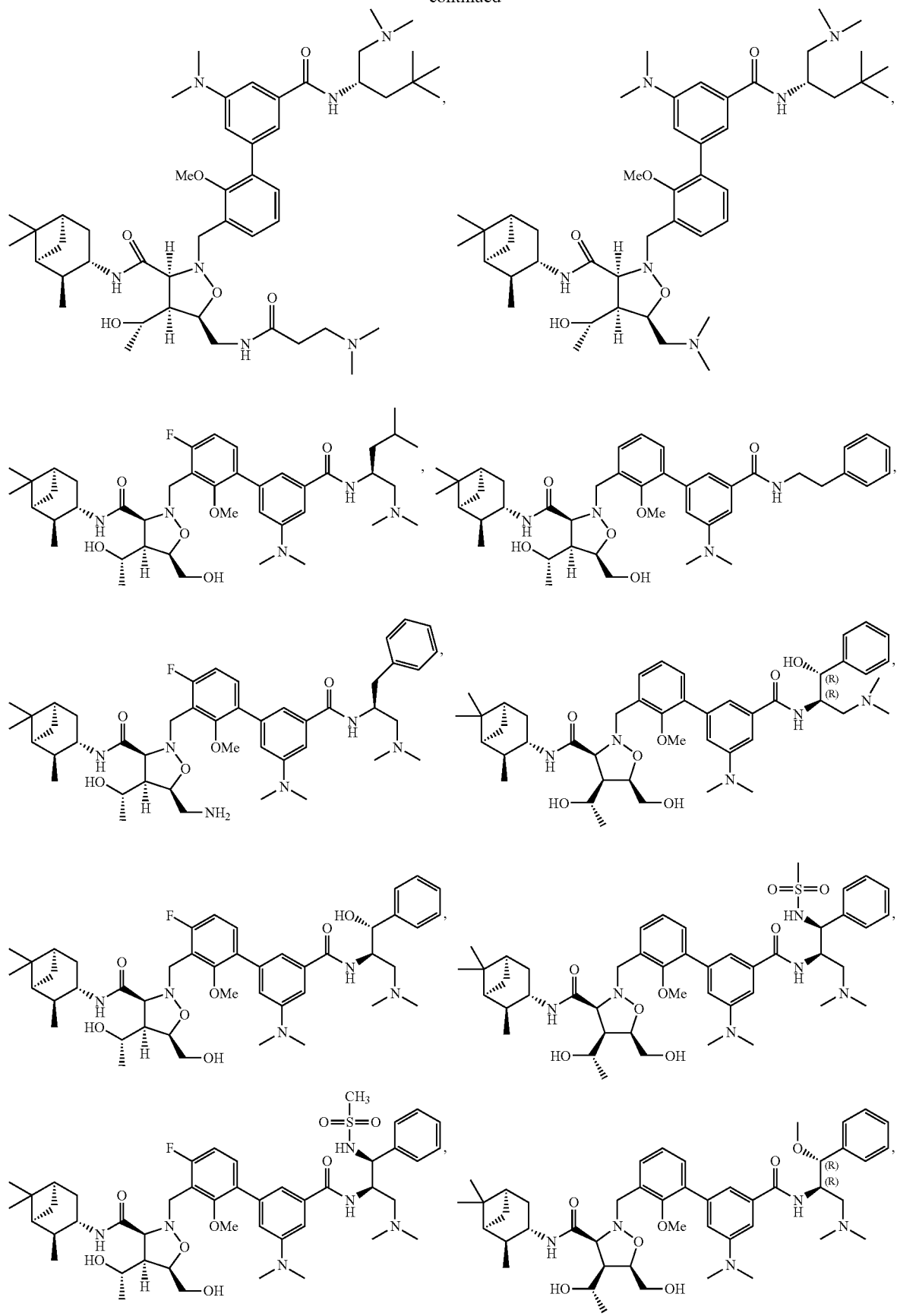

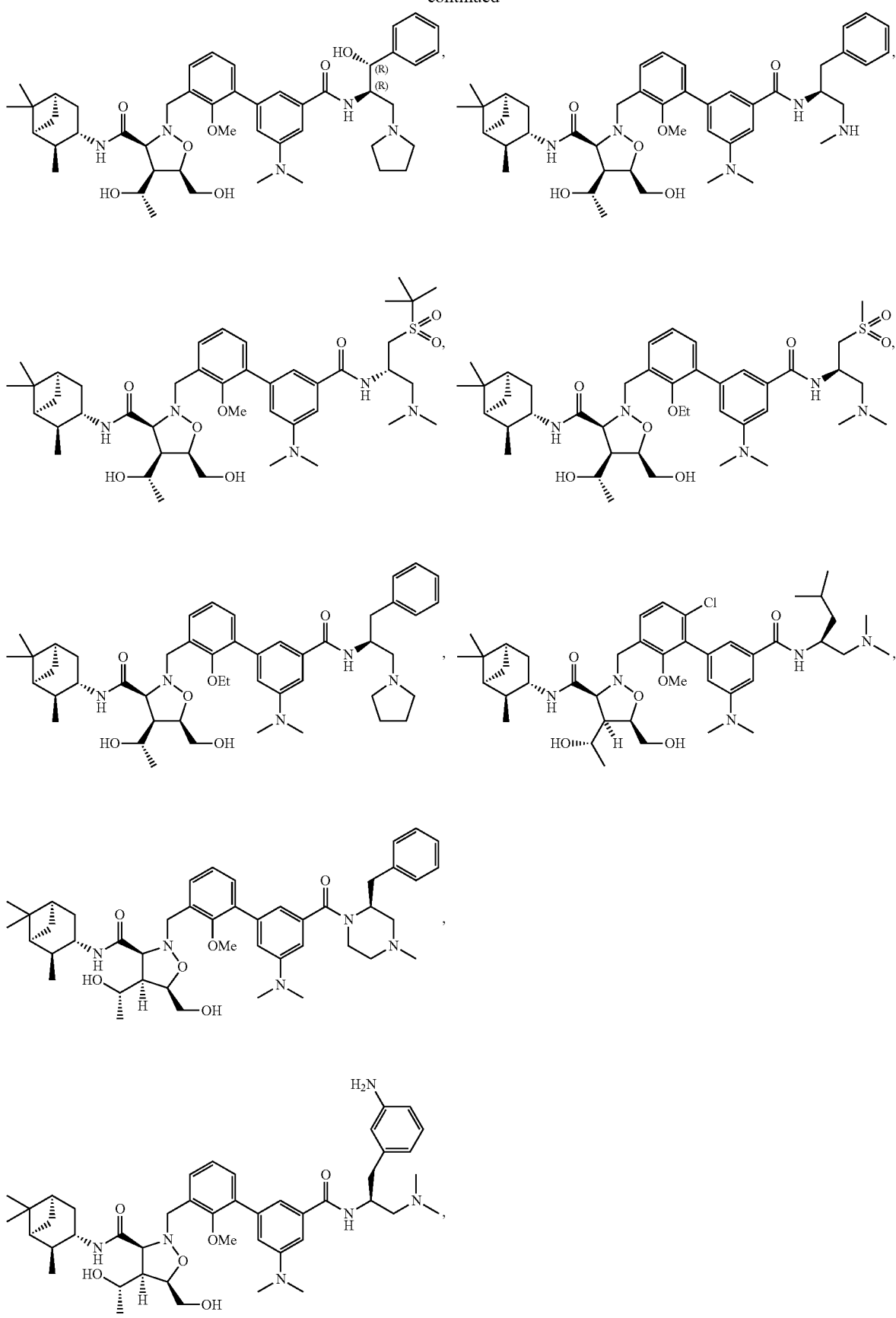

501 502
-continued
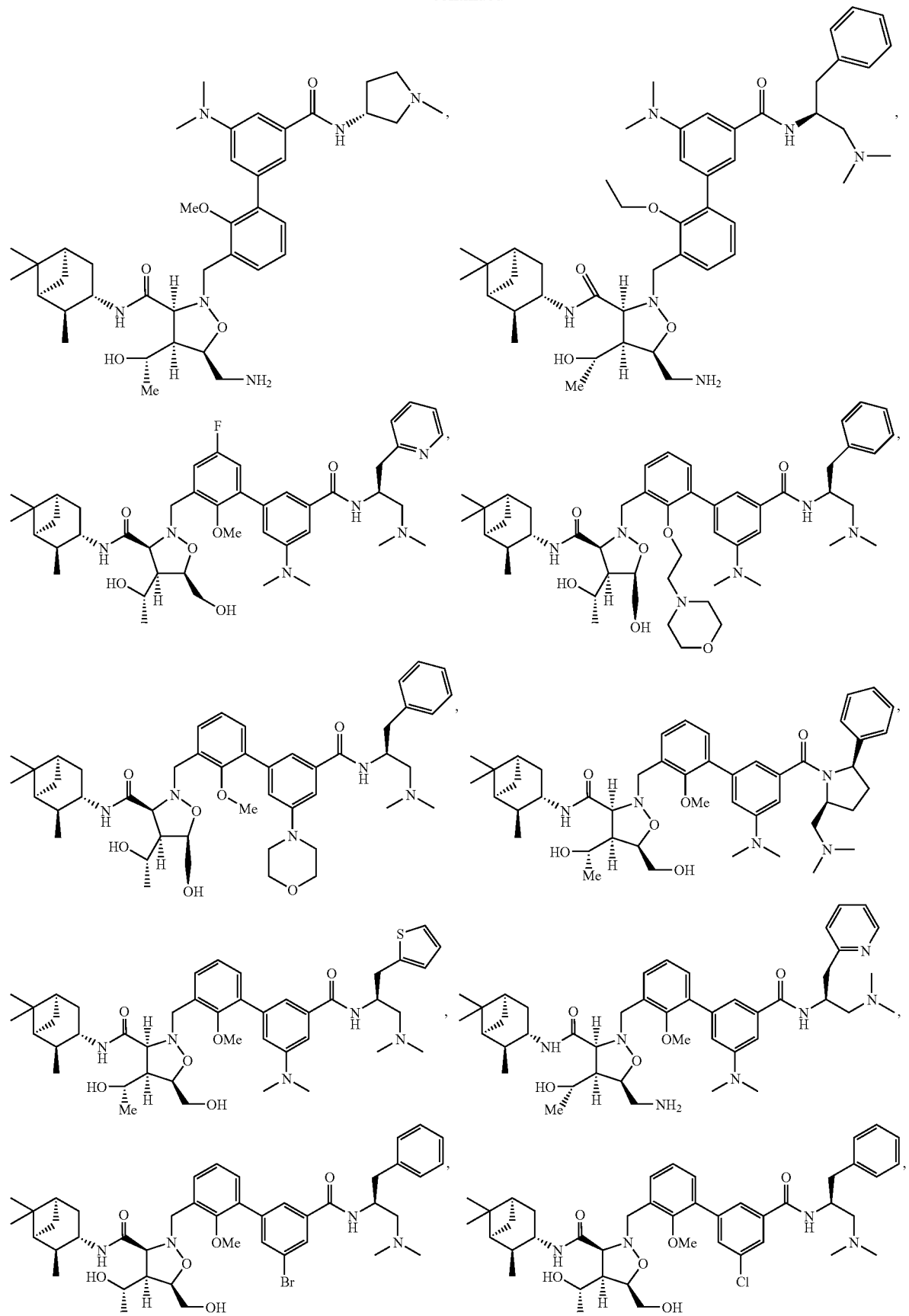

503
504
-continued
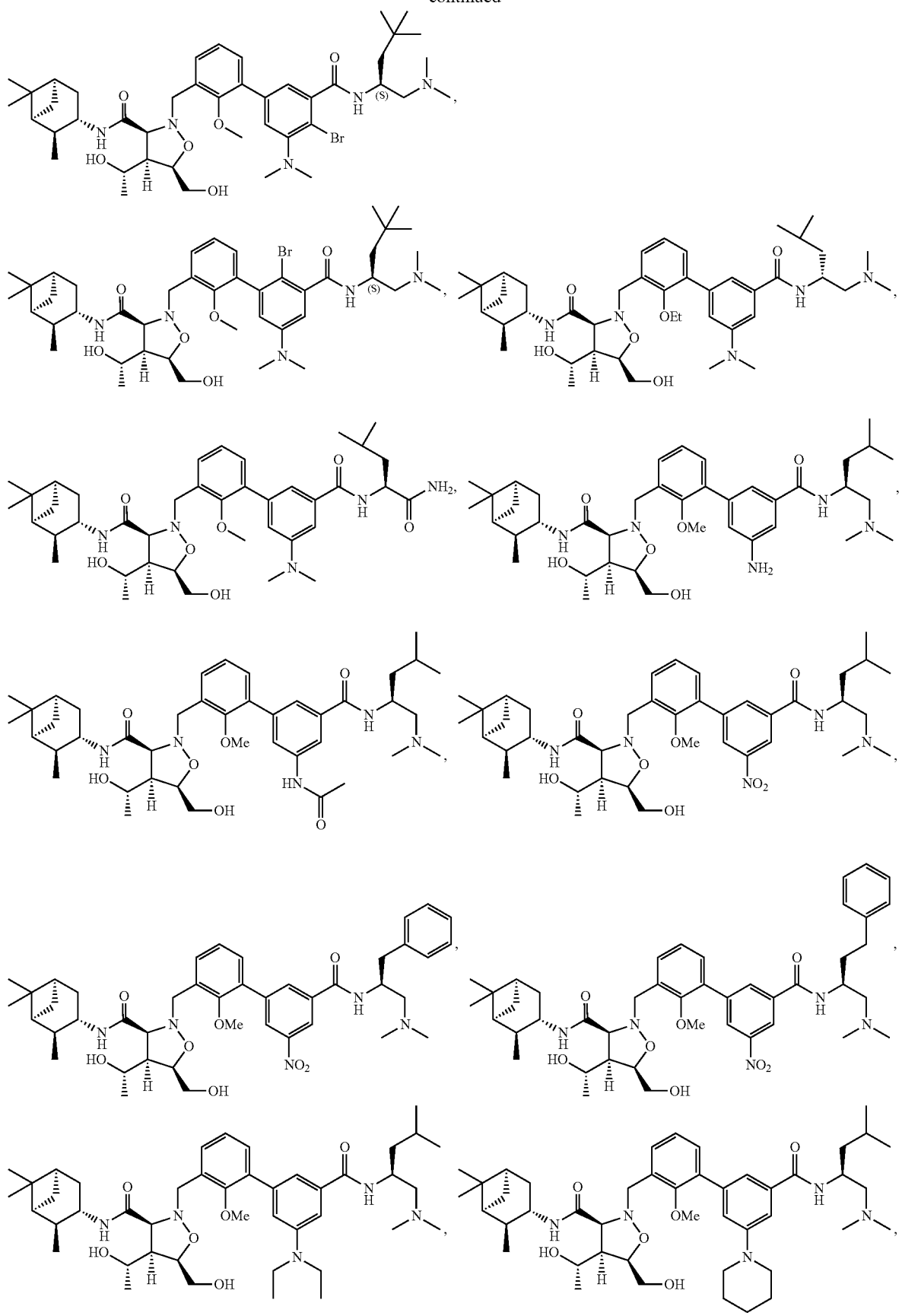

505 506
-continued
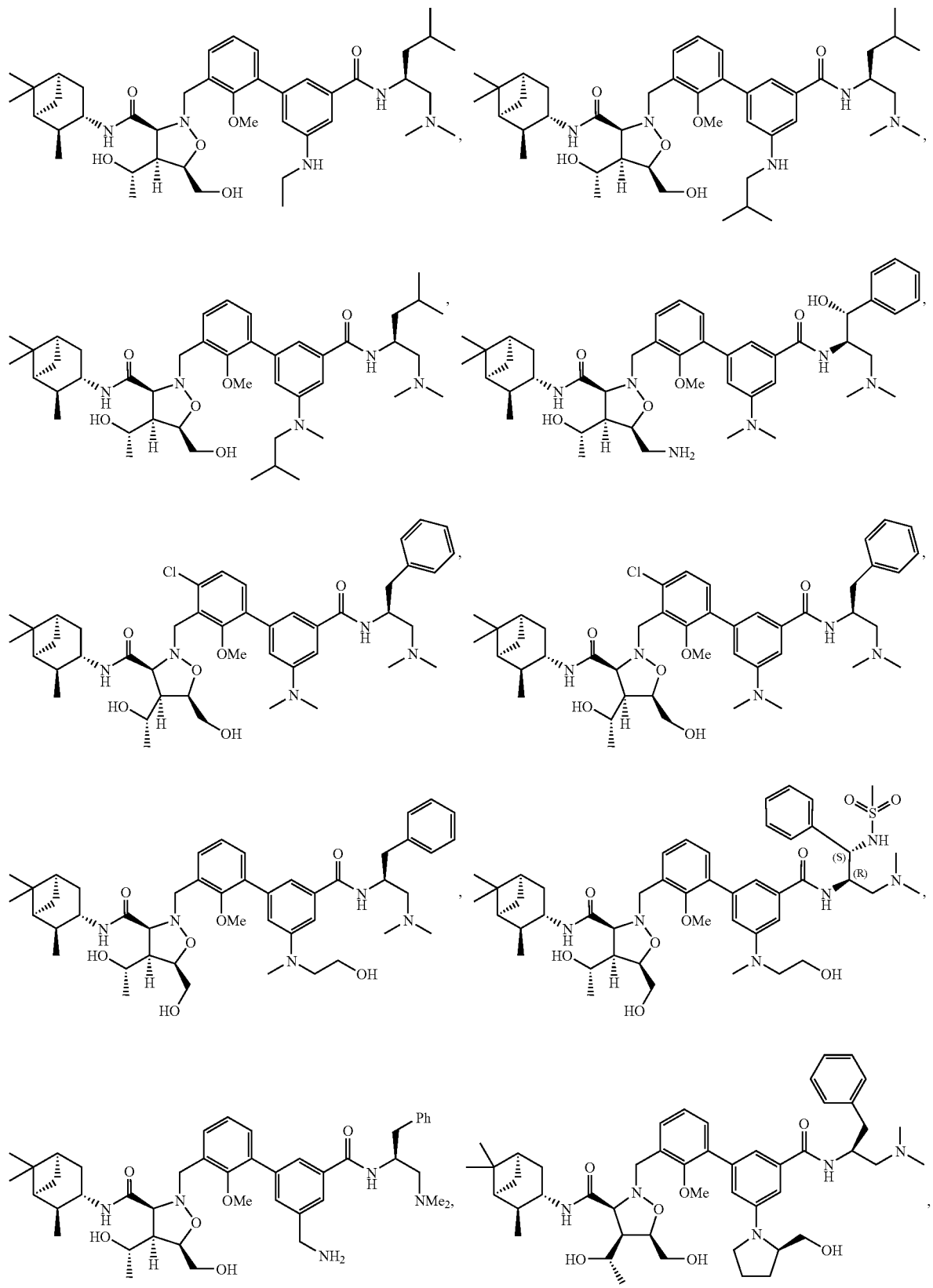

507 508
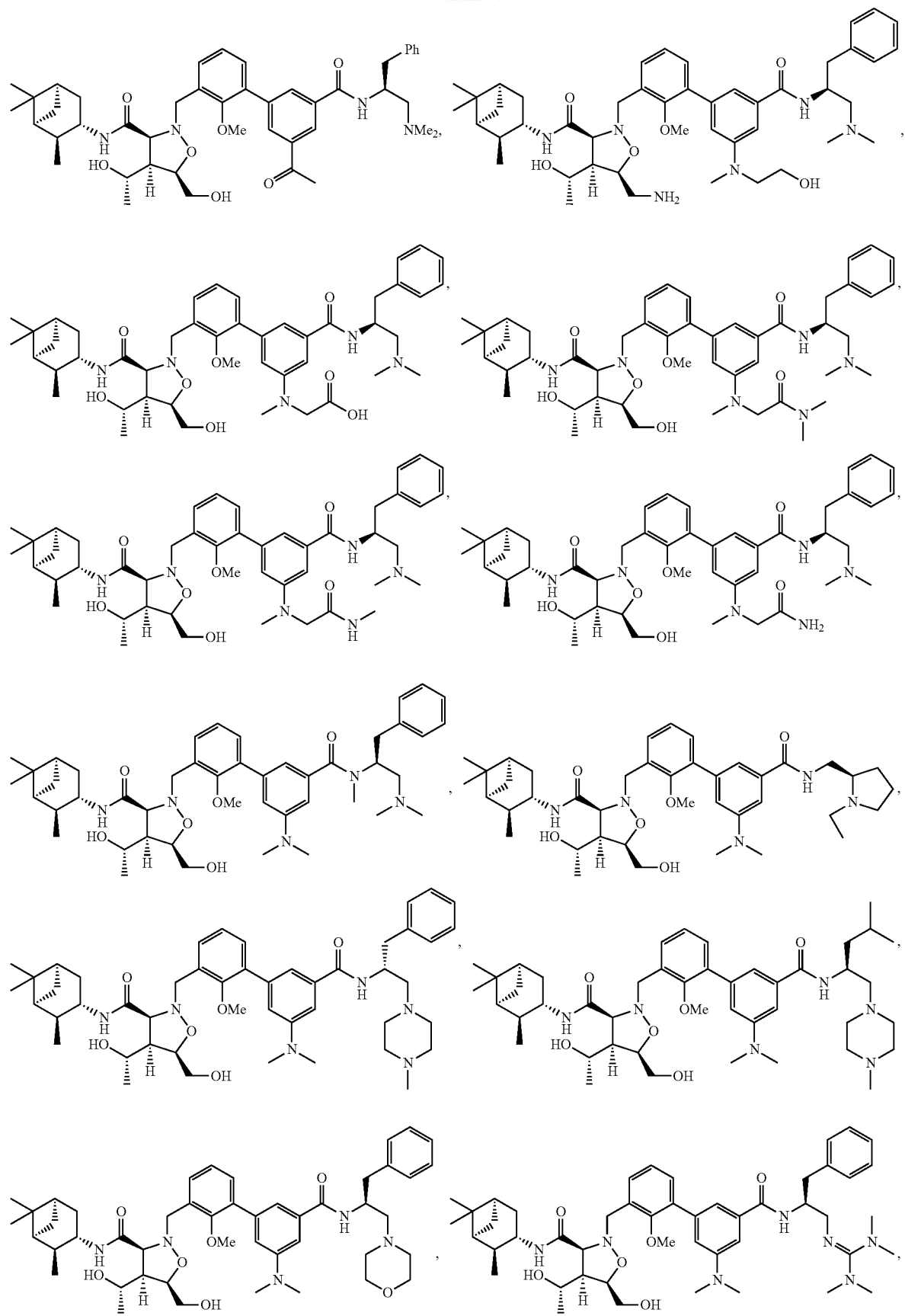
-continued

509 510
-continued
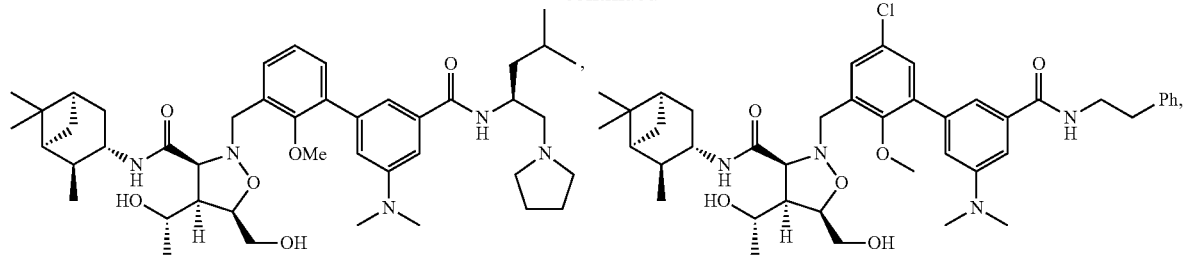
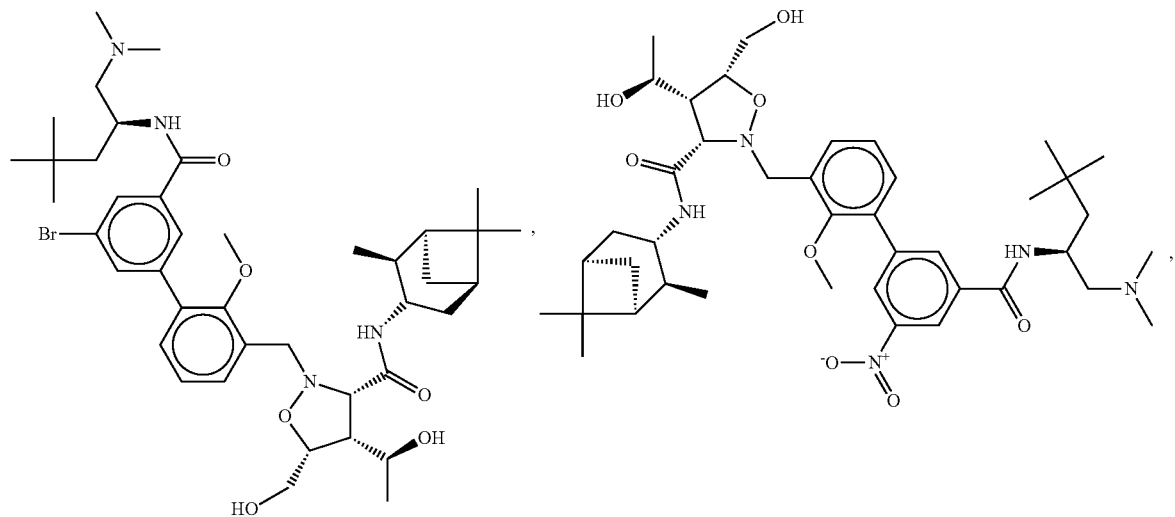
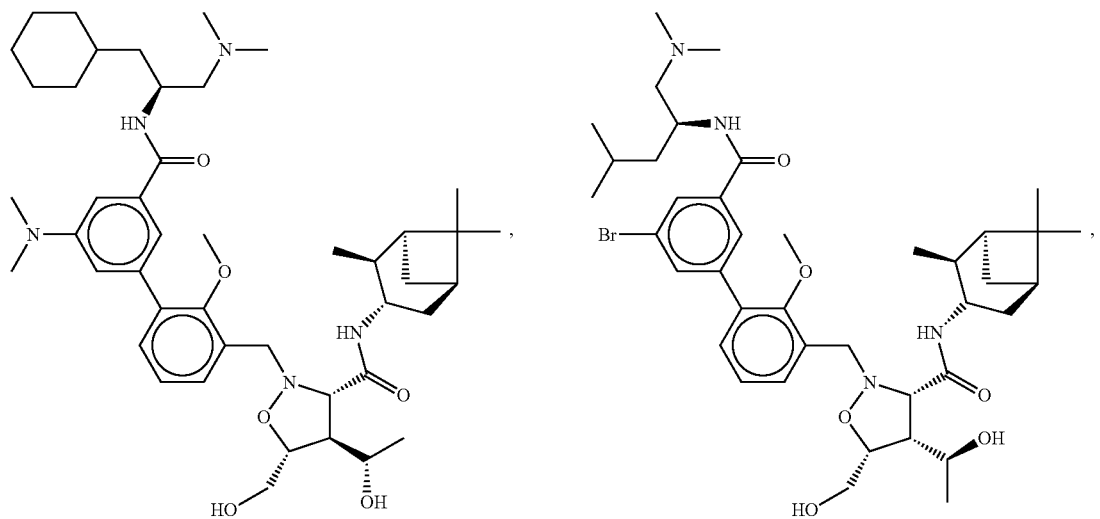

-continued
511
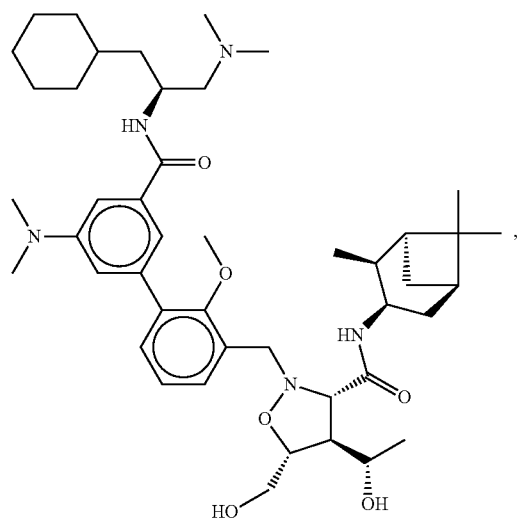
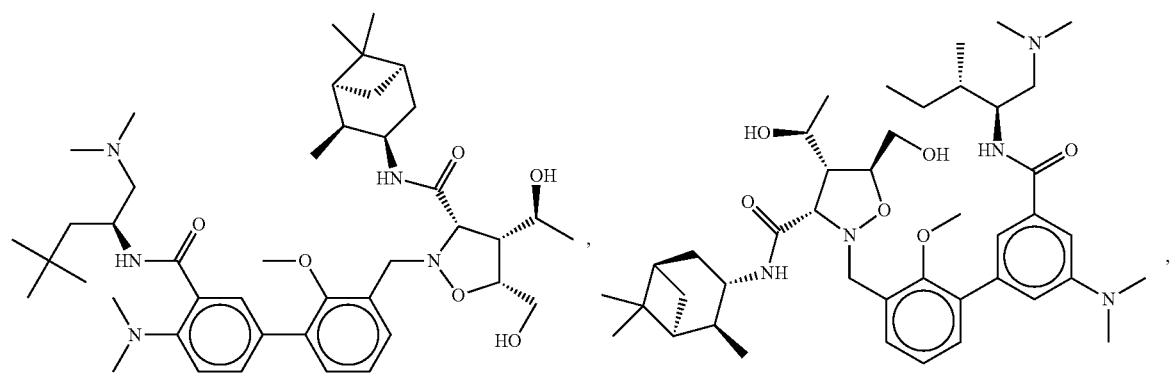
512
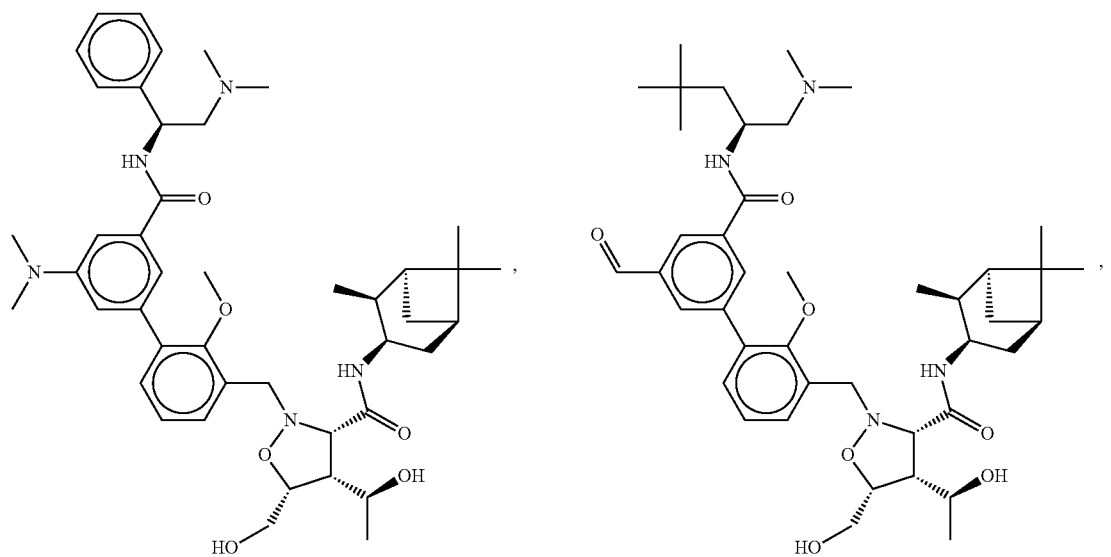

513                                                           514
-continued
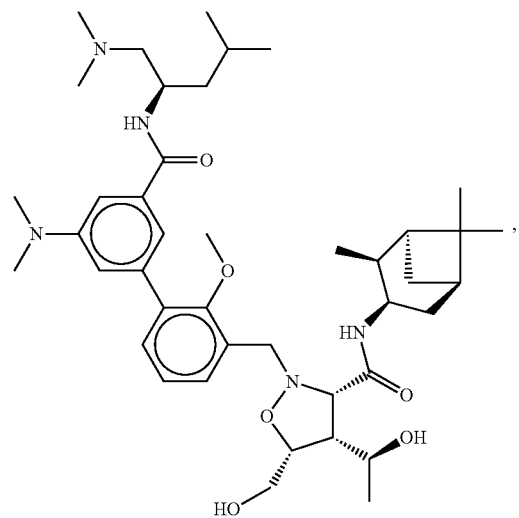
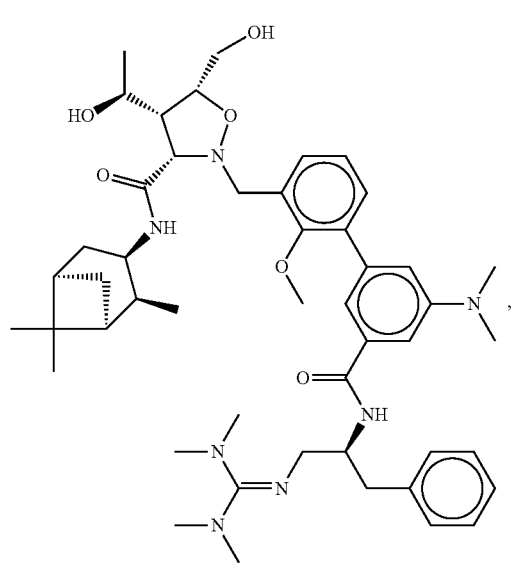
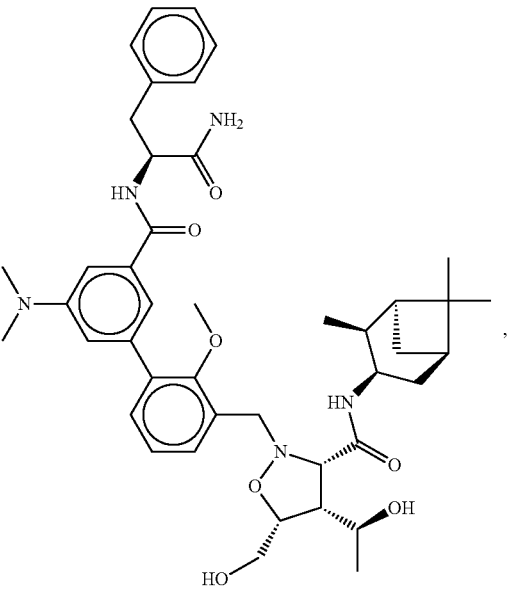
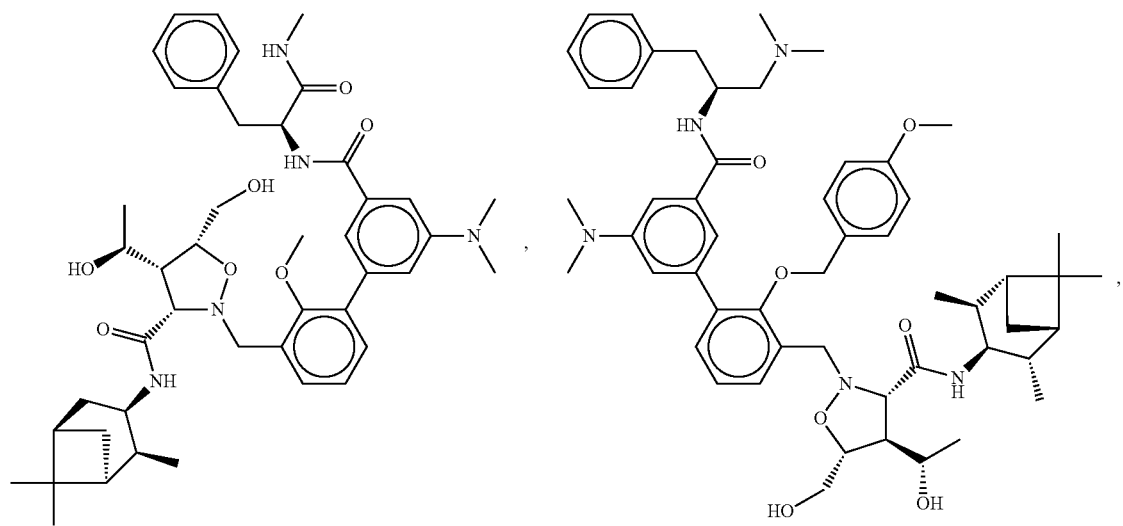

515
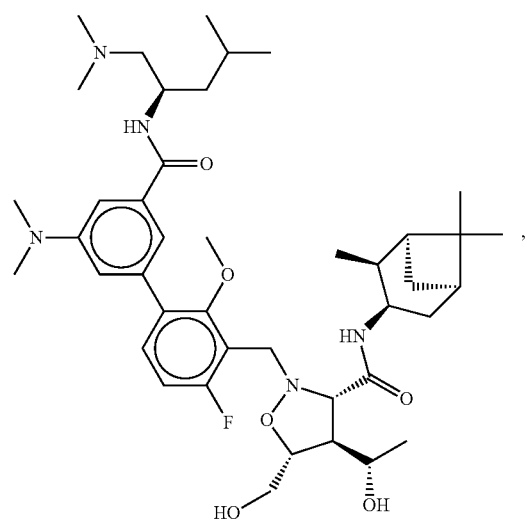
516
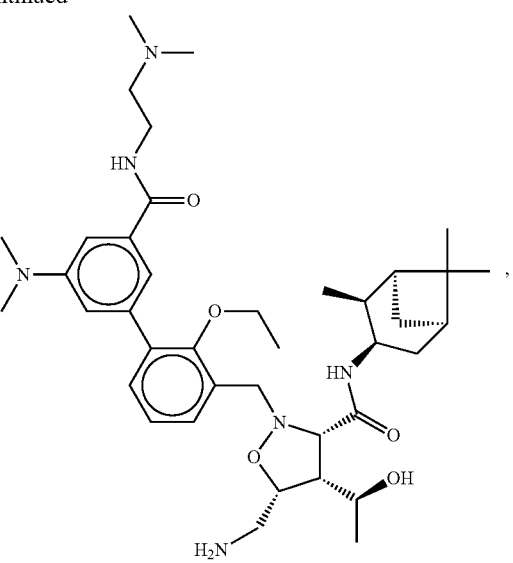
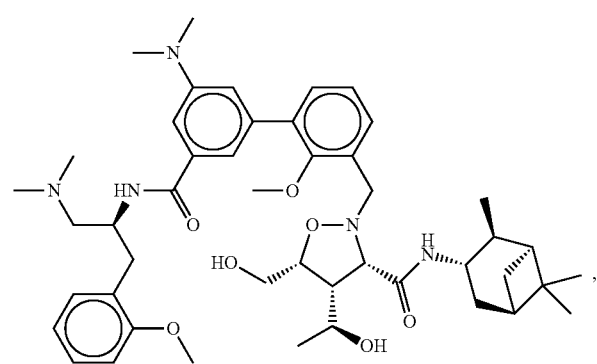
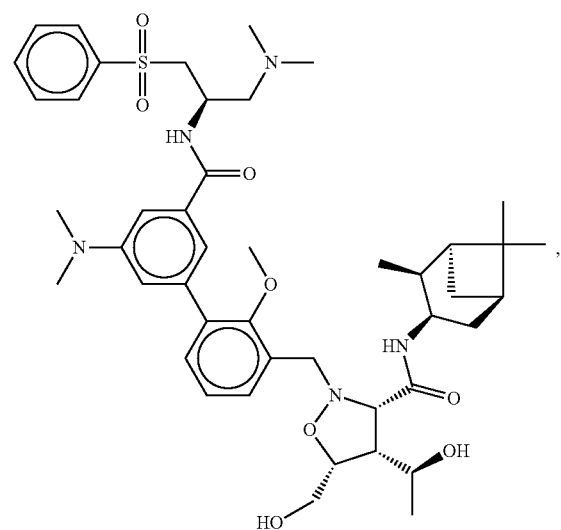
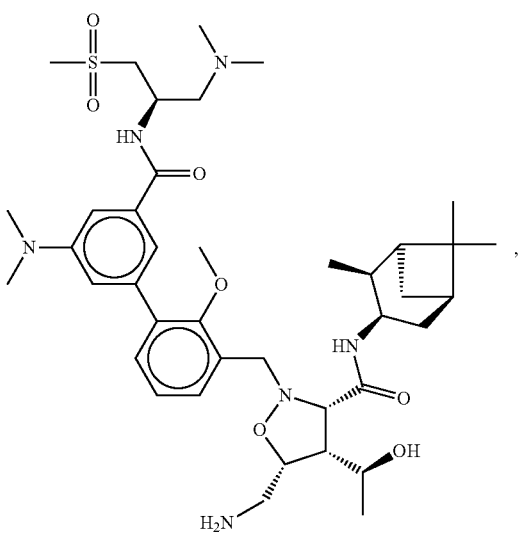

517
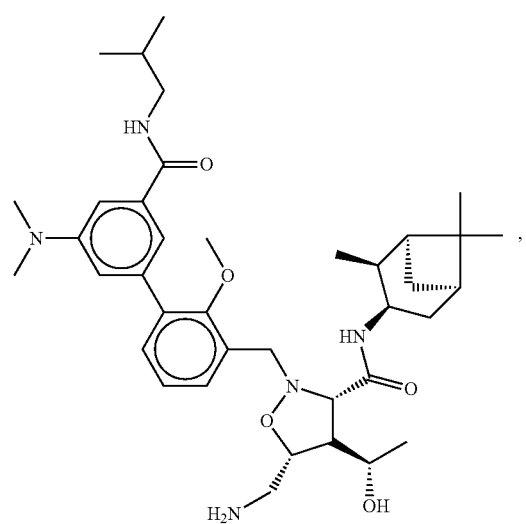
518
-continued
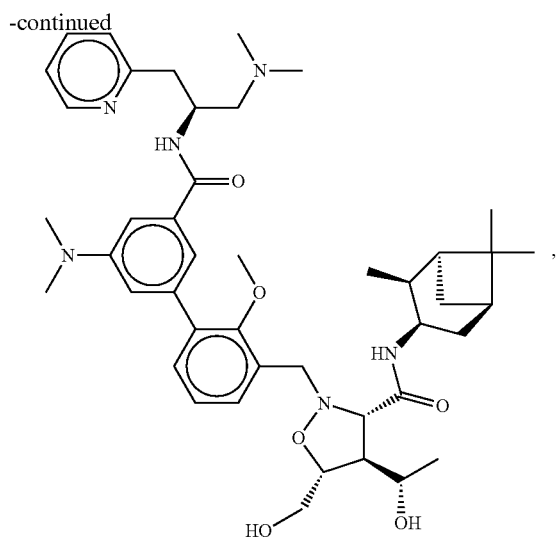
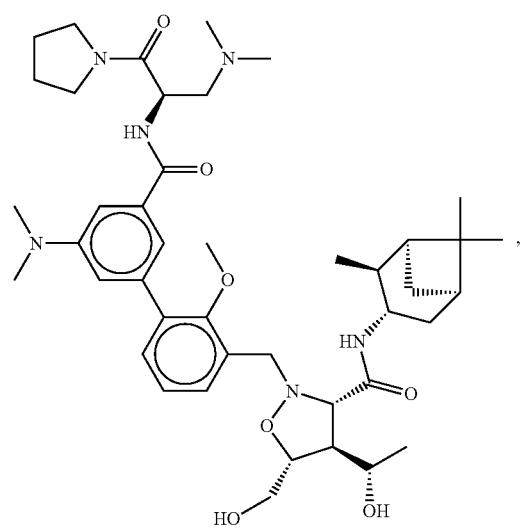
,
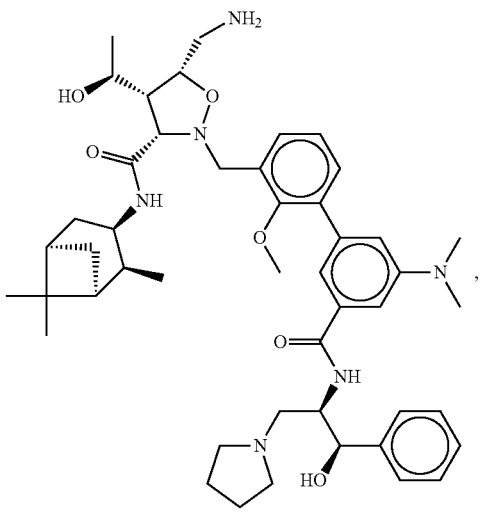
,
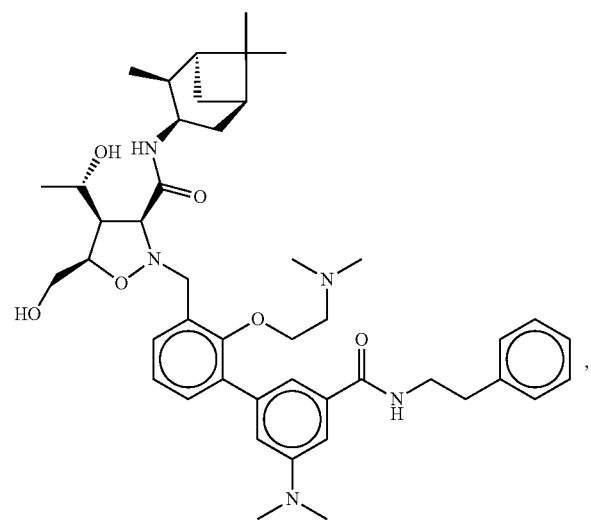
,
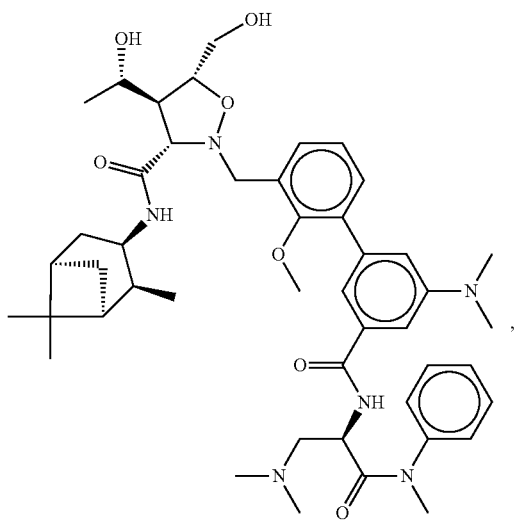
,

519
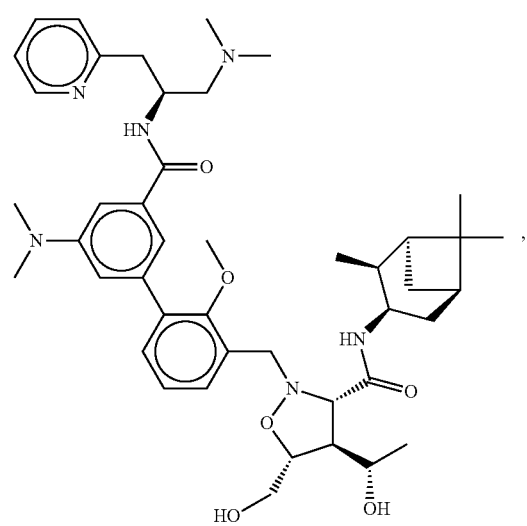
520
-continued
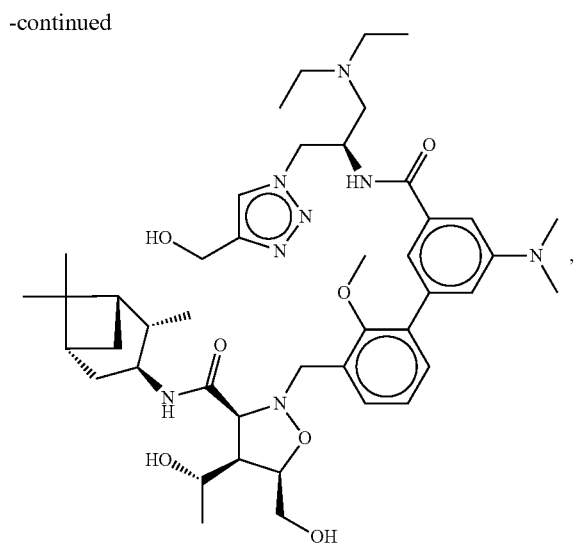
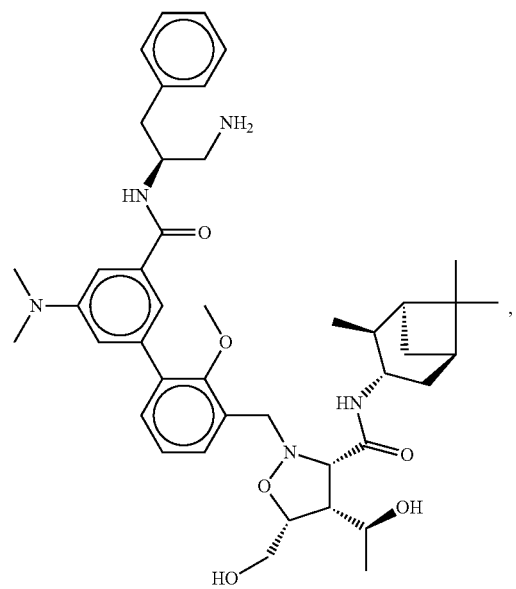
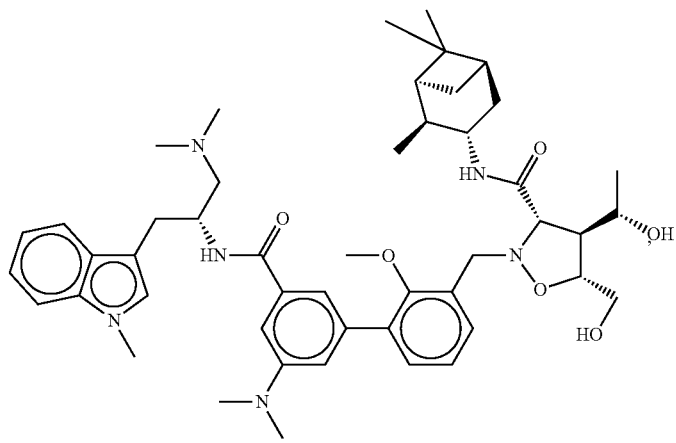
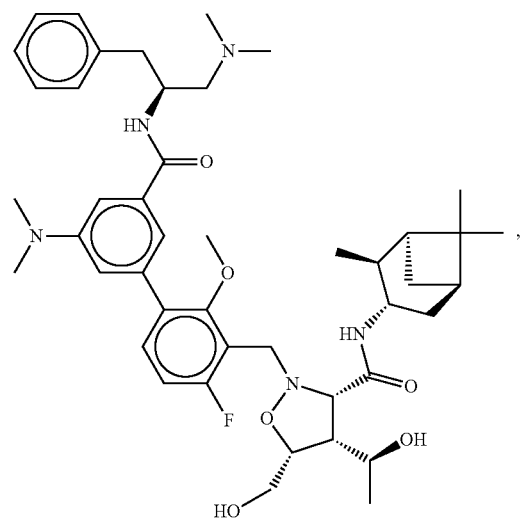
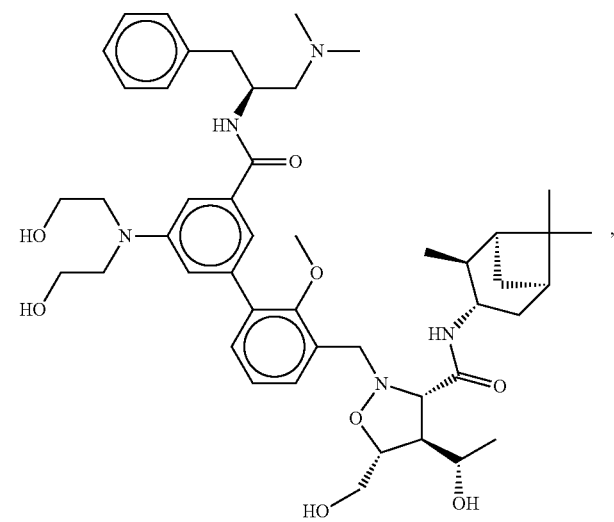

-continued
| 521 | 522 |
|---|---|
| 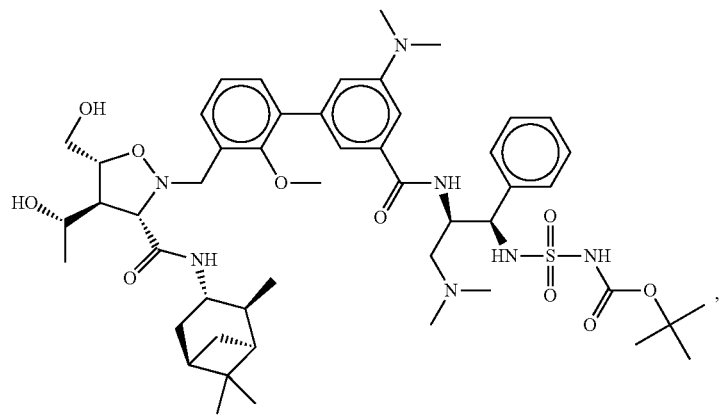 | 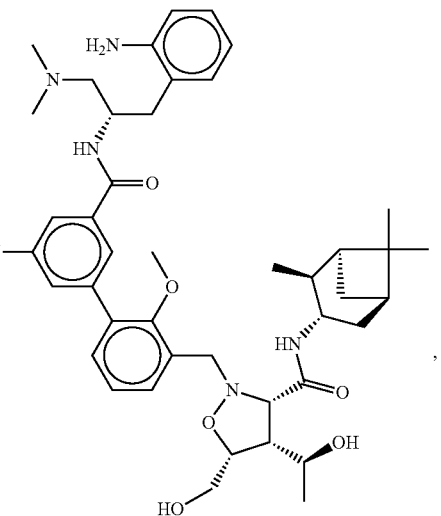 |
| 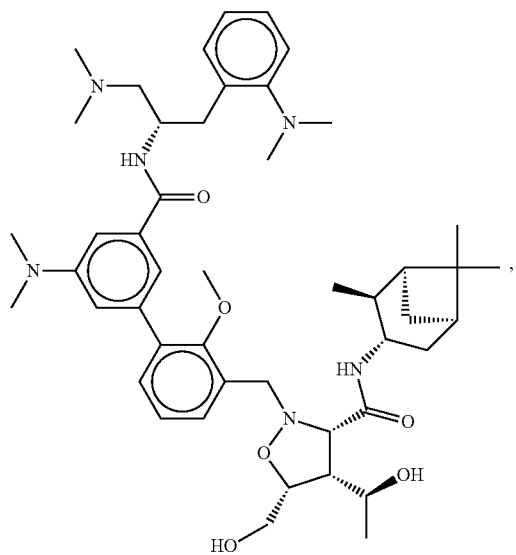 | 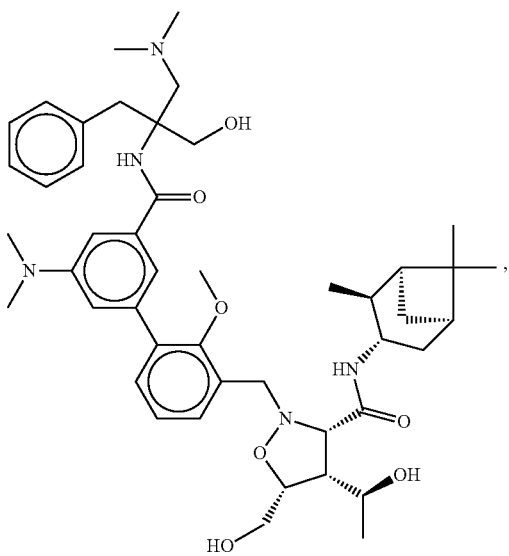 |
| 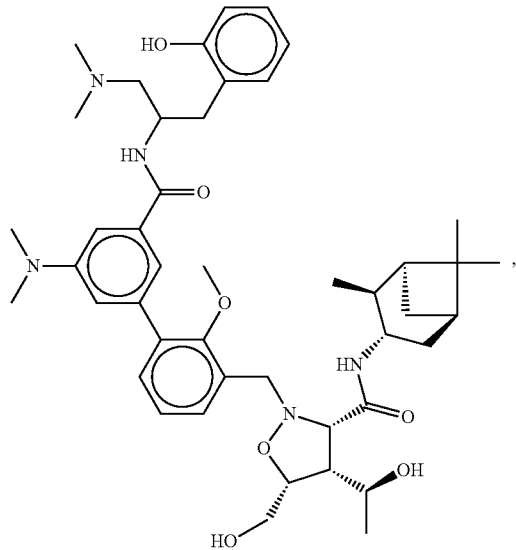 | 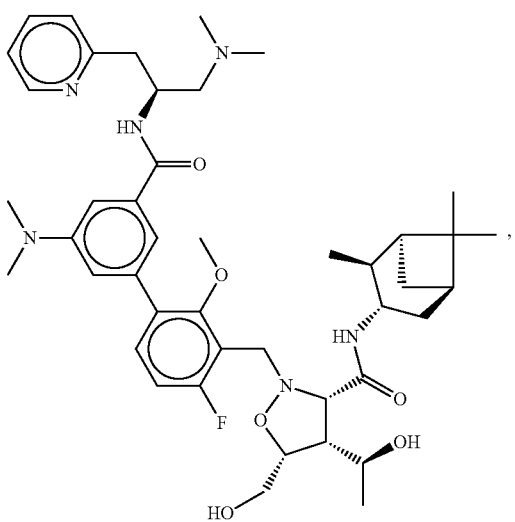 |

523
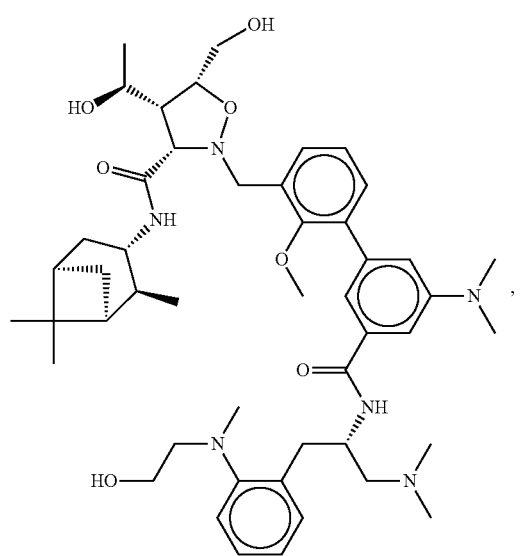
524
-continued
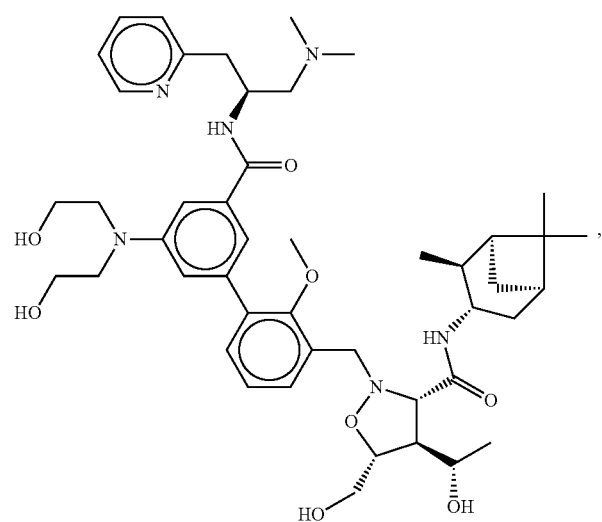
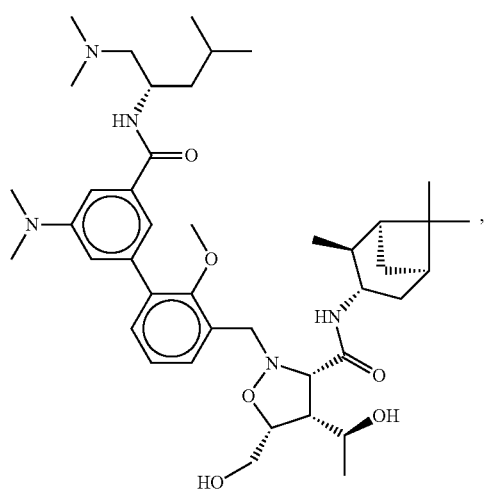
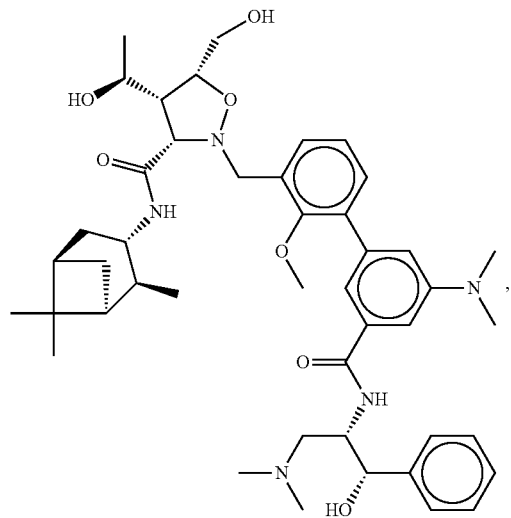
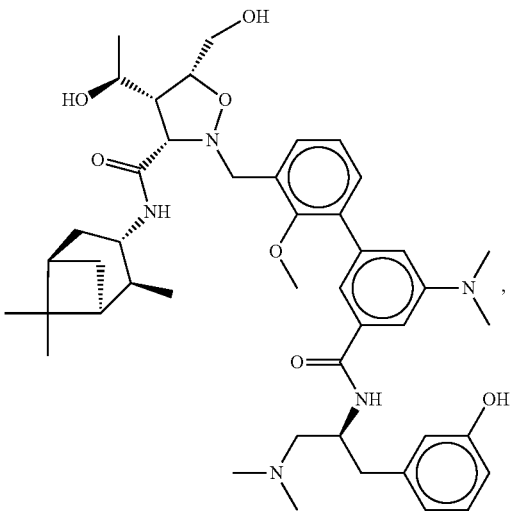

525
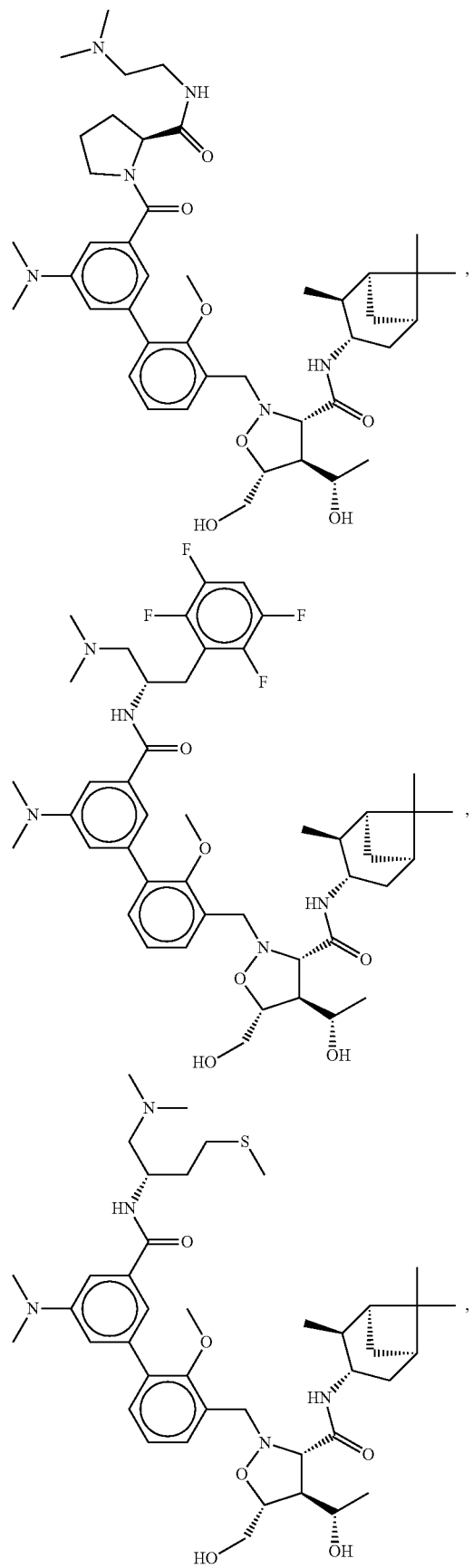
526
-continued

527
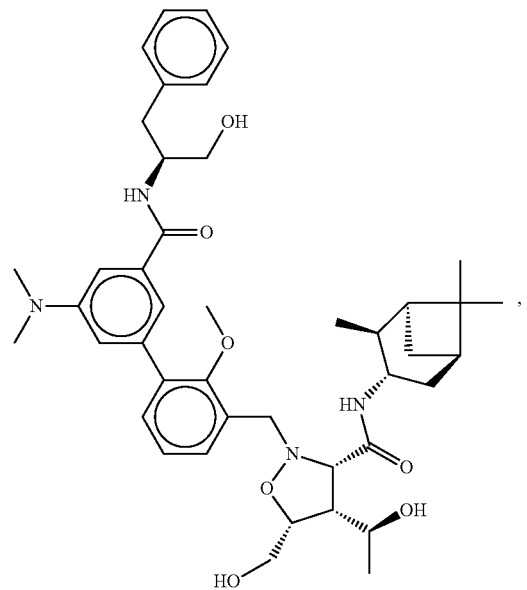
528
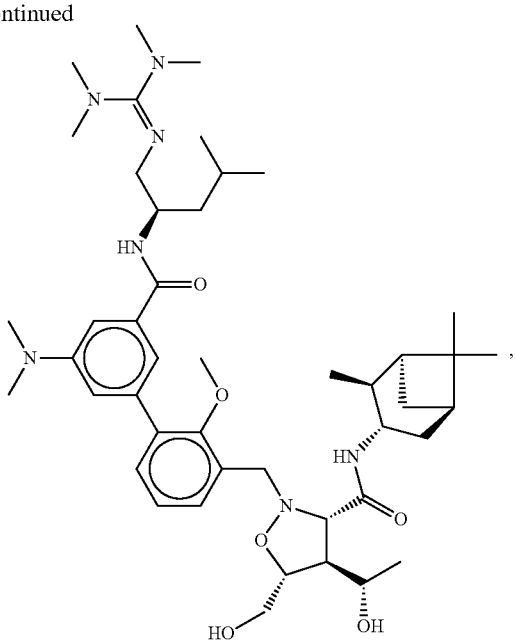
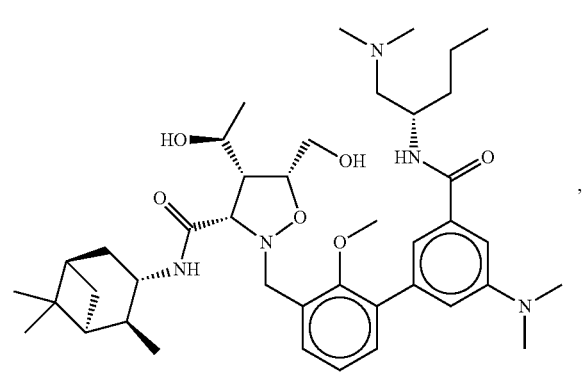
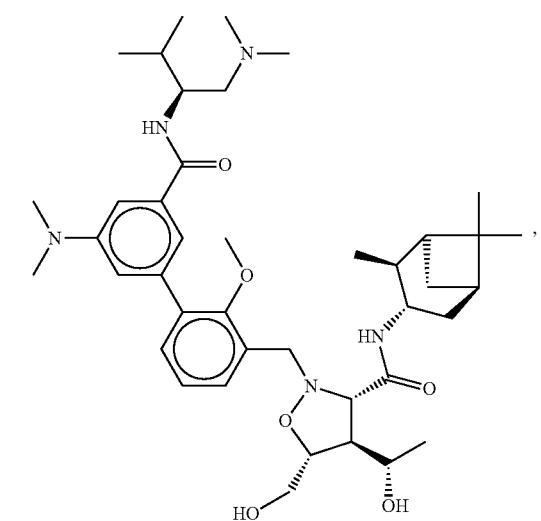
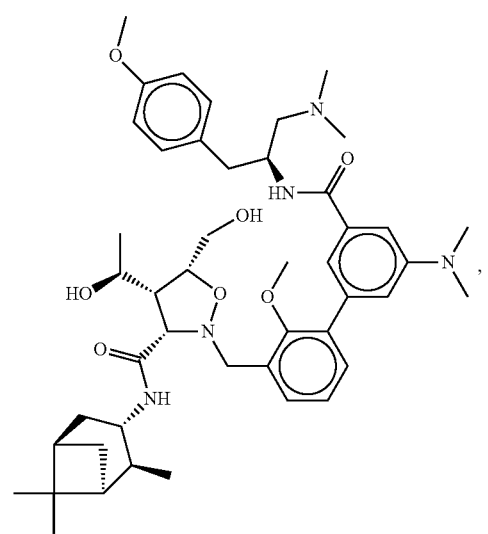

529 530
-continued
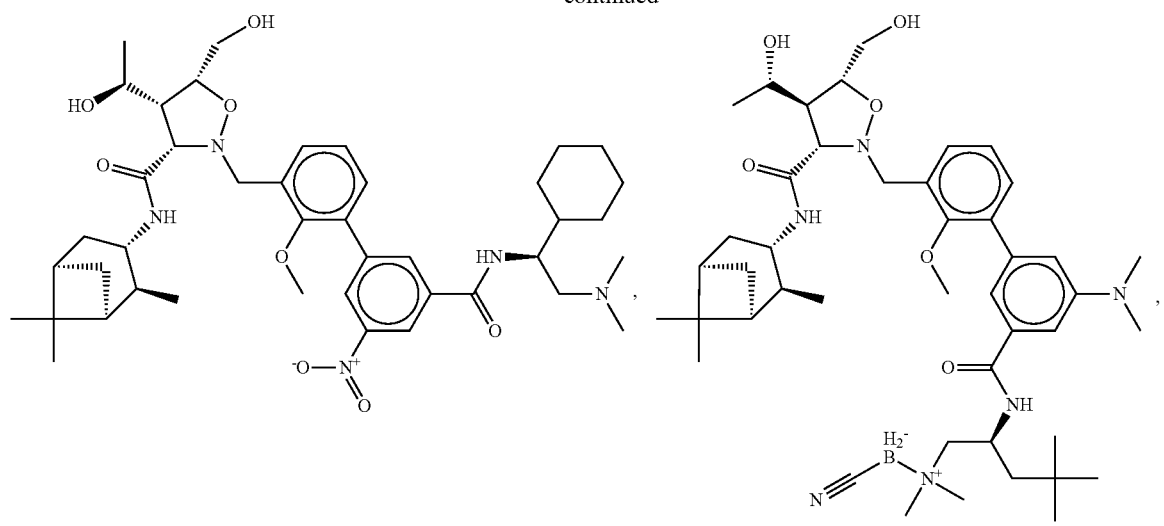
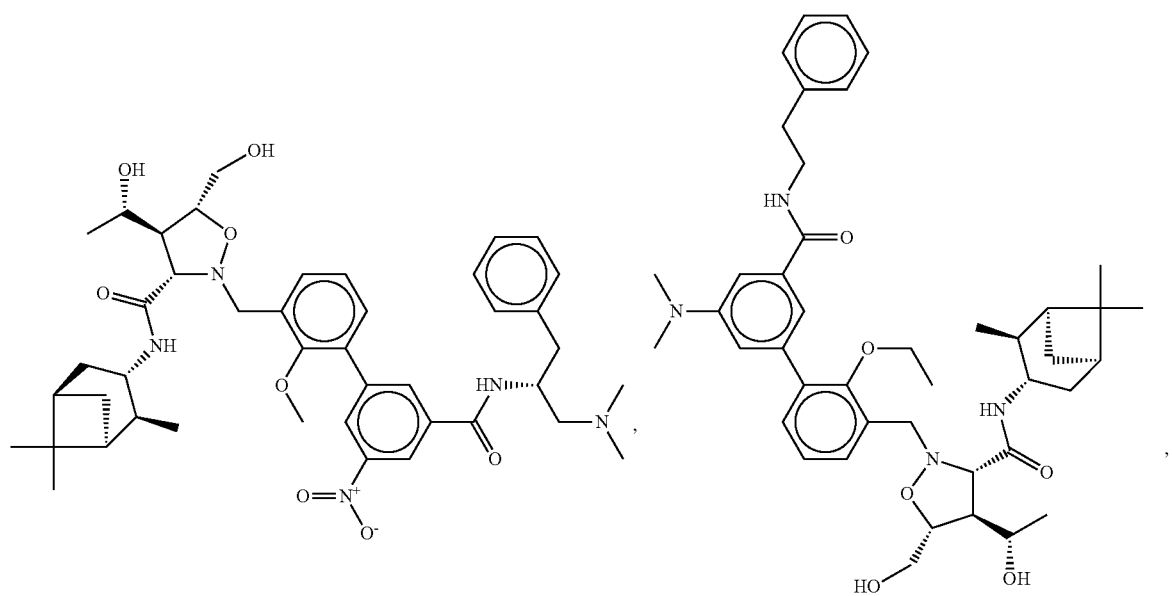
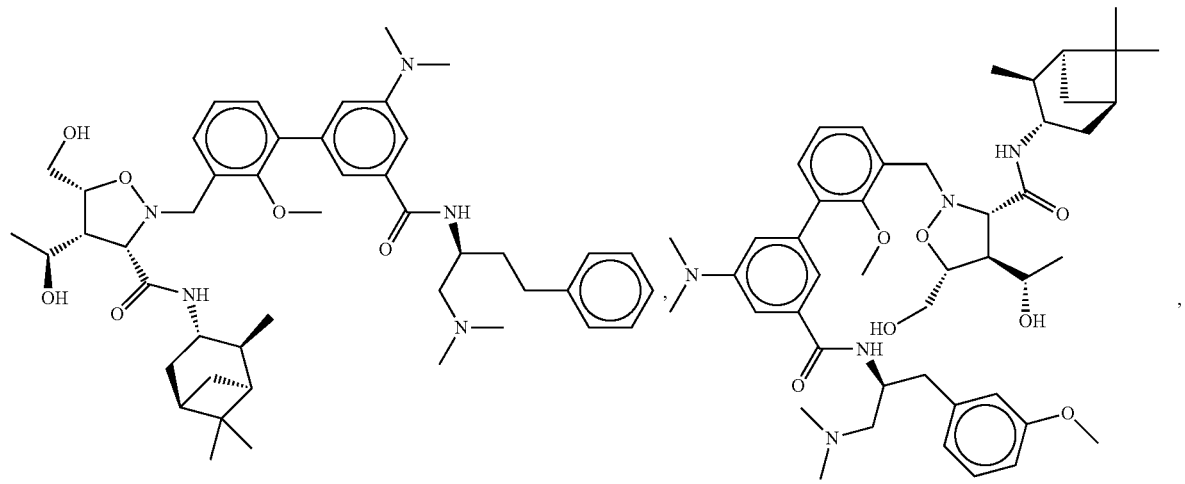

531 532
-continued
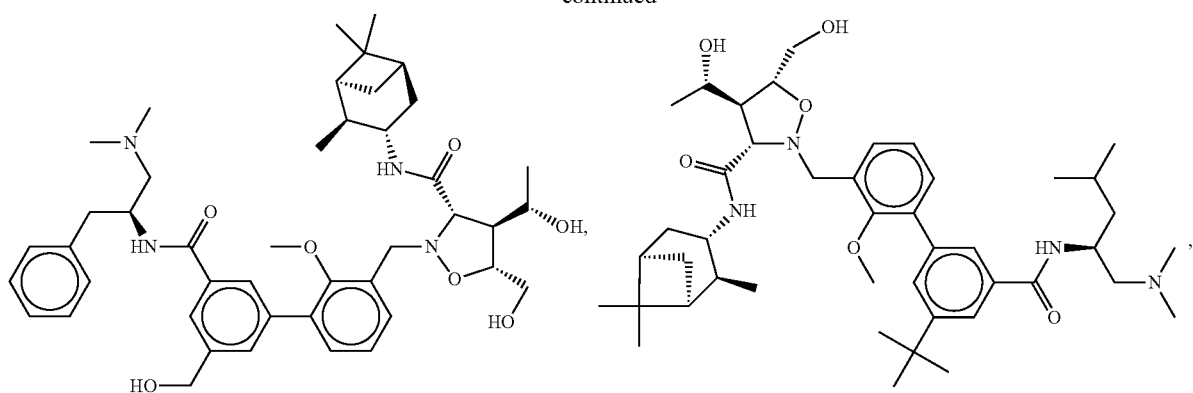
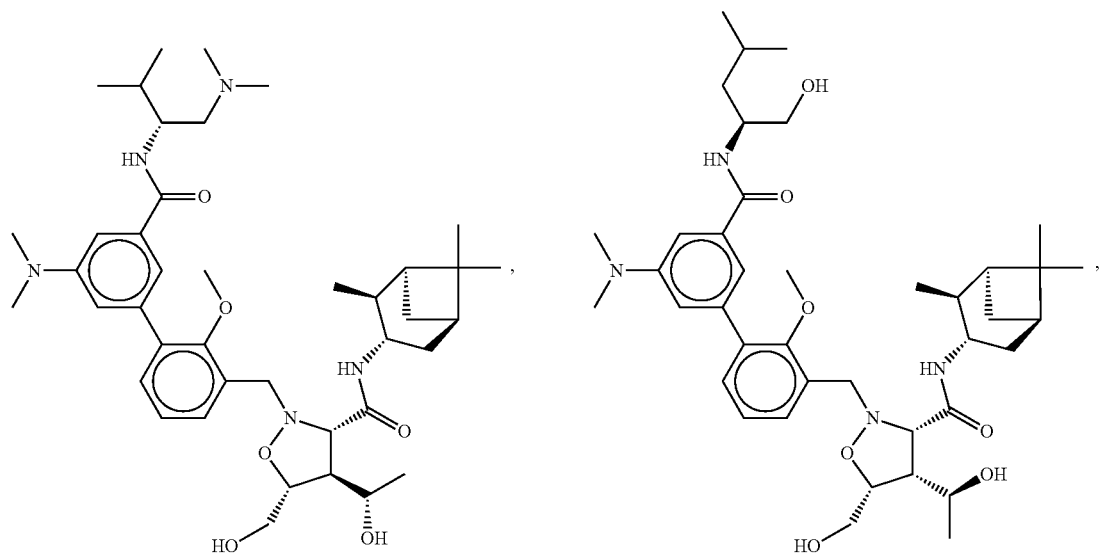
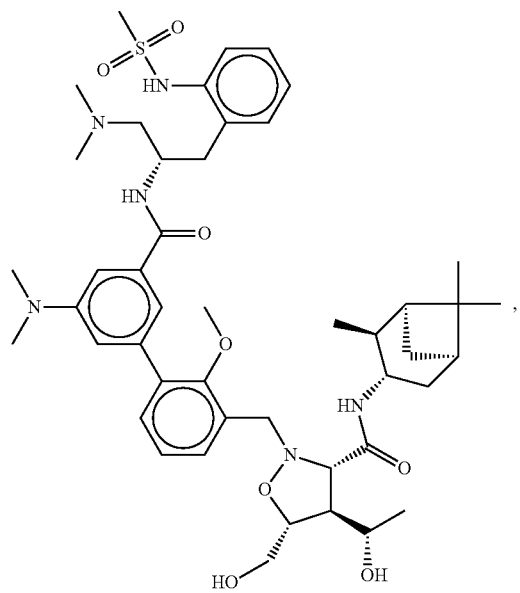

533
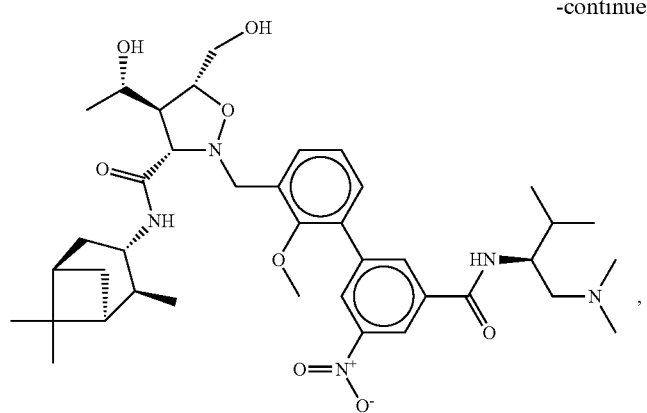
534
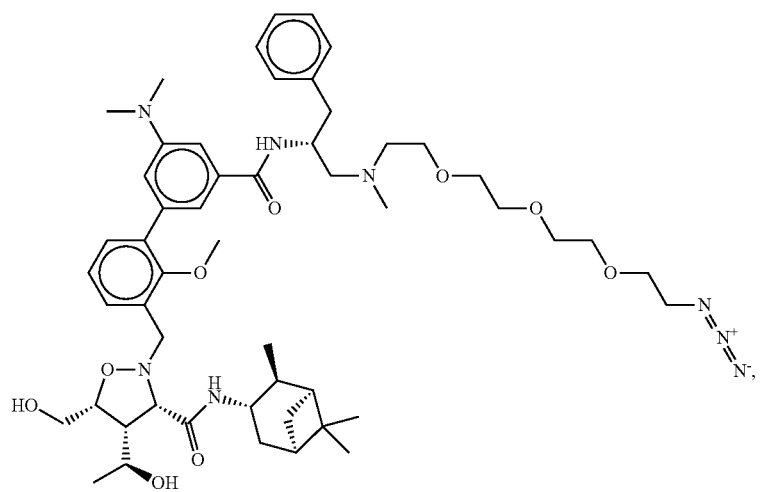
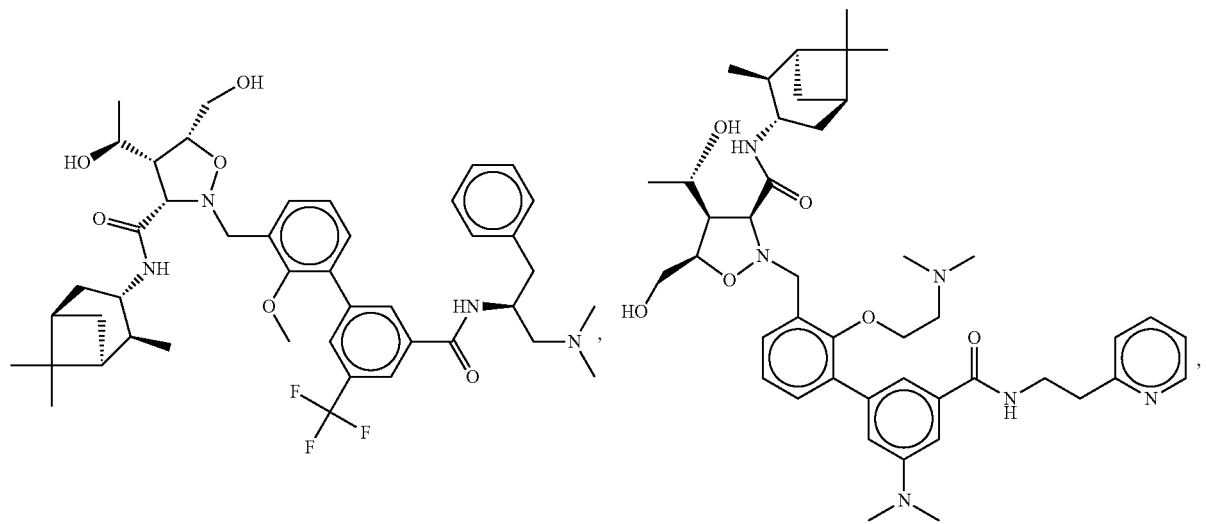

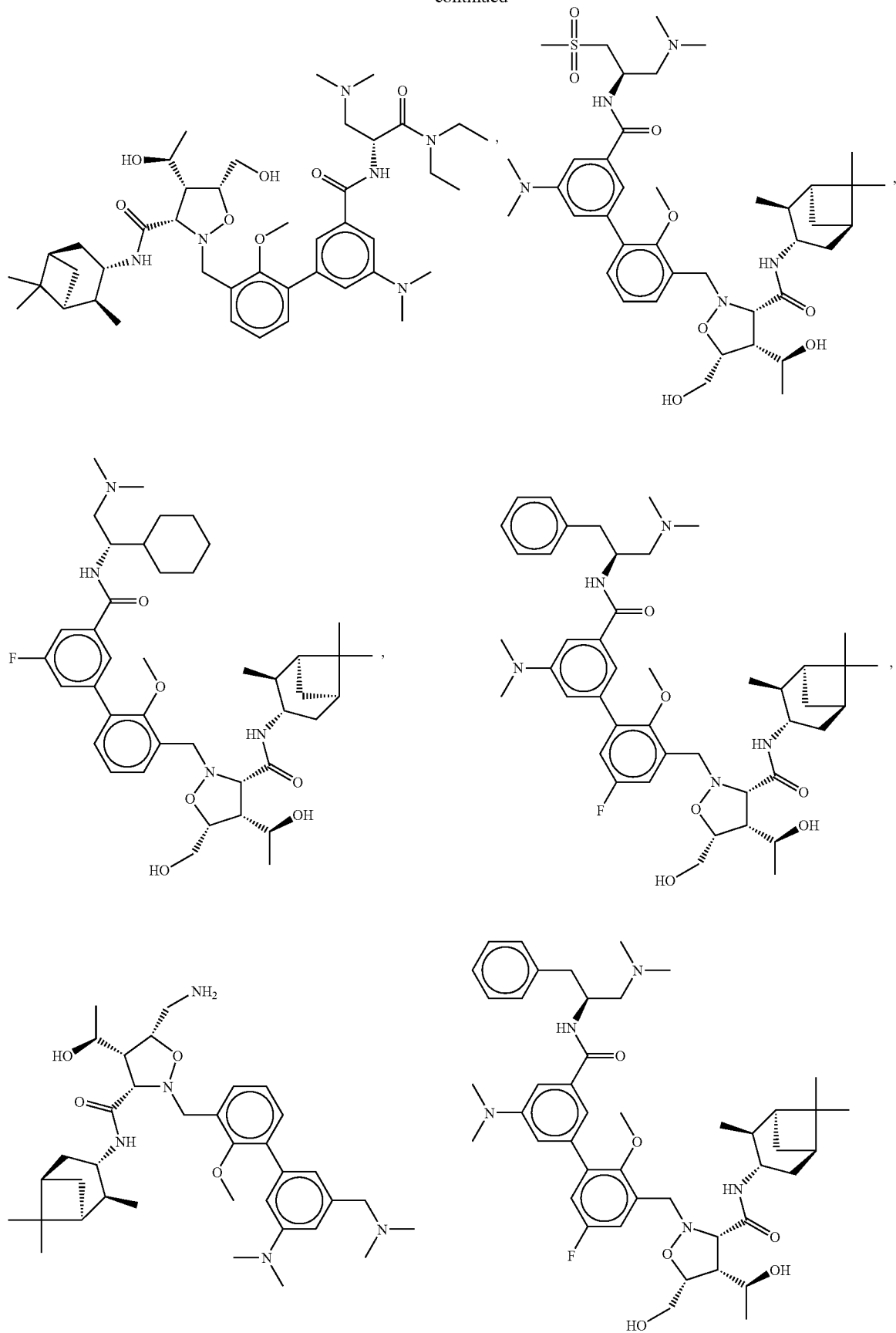

537 538
-continued
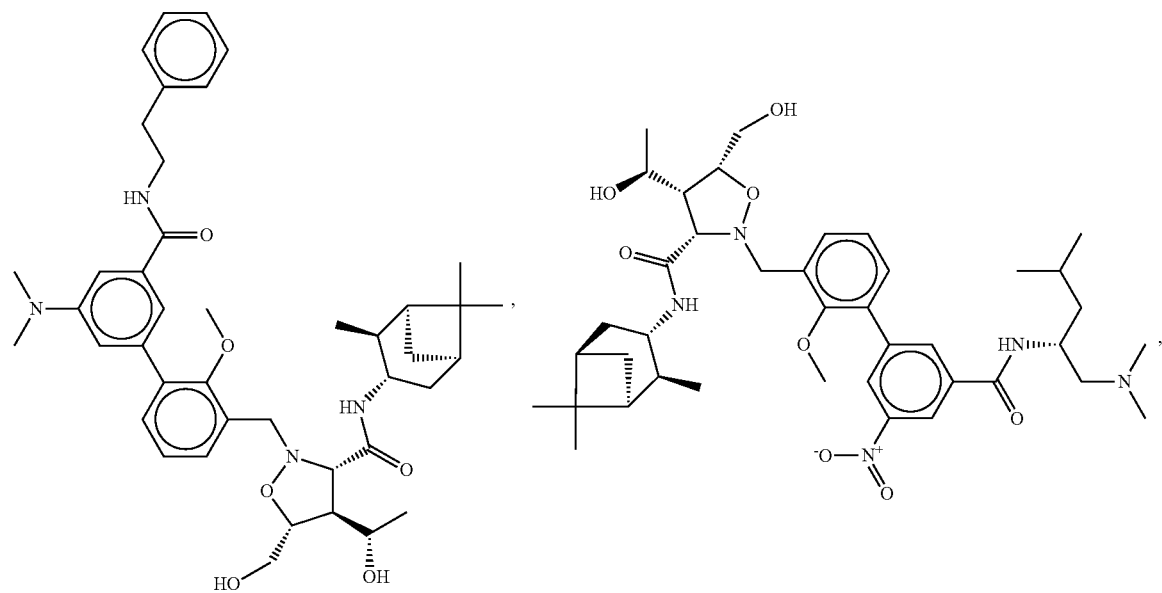
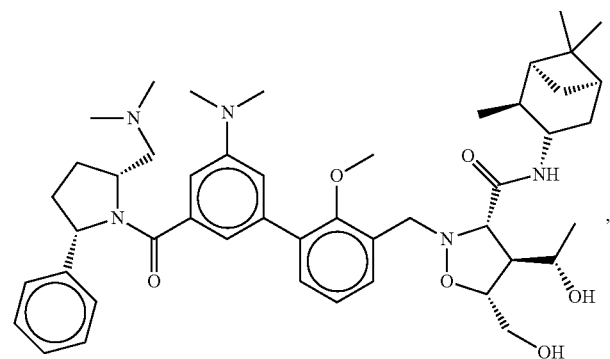
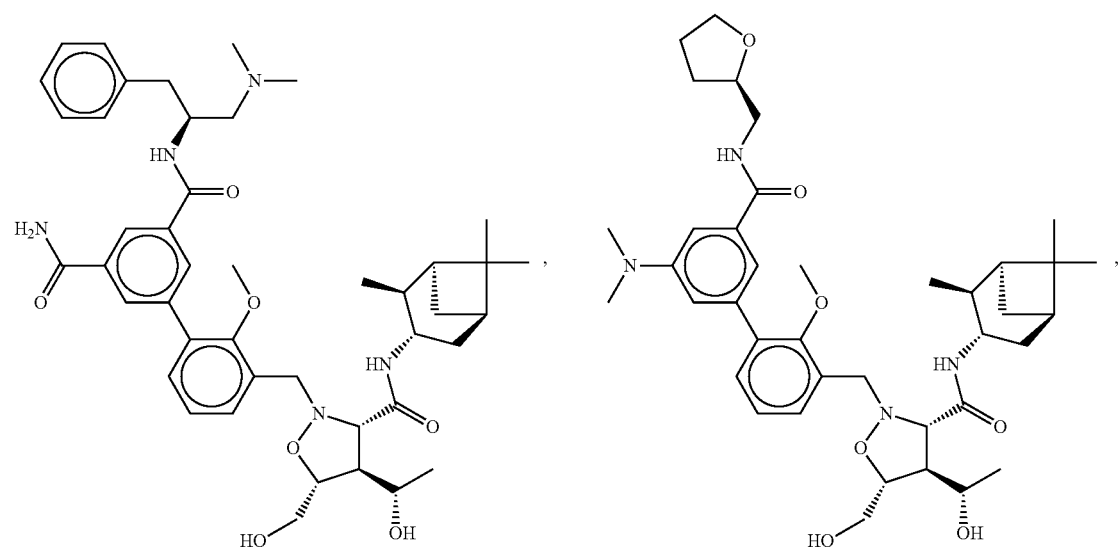

-continued
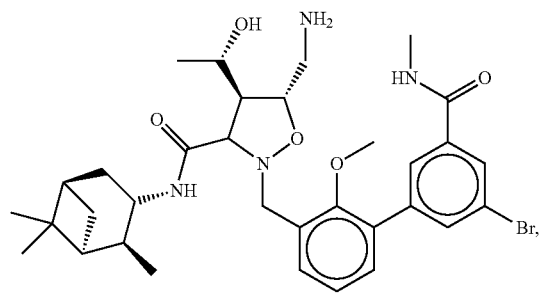
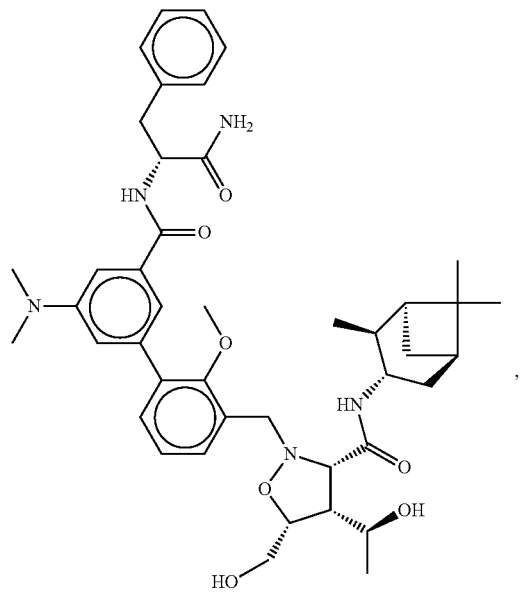
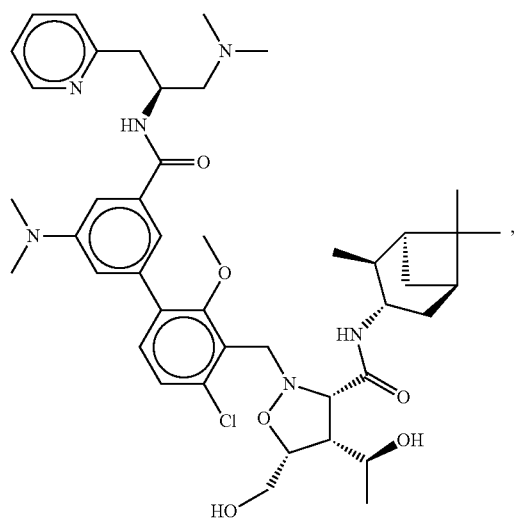
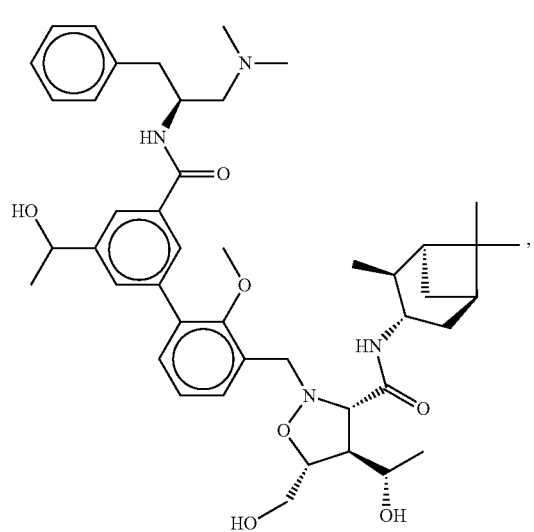
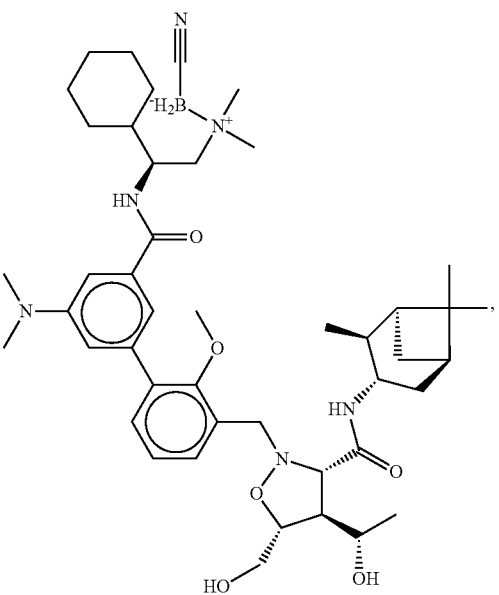

541
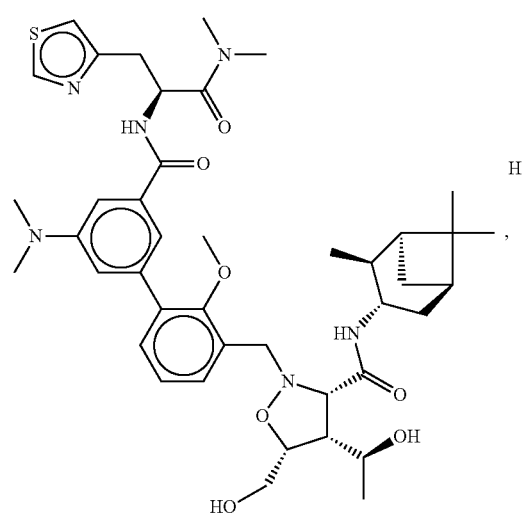
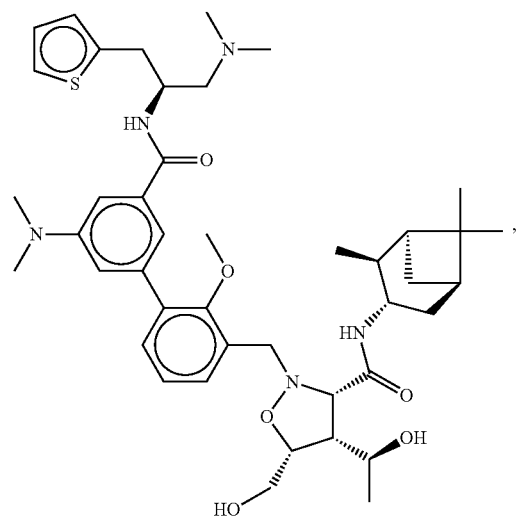
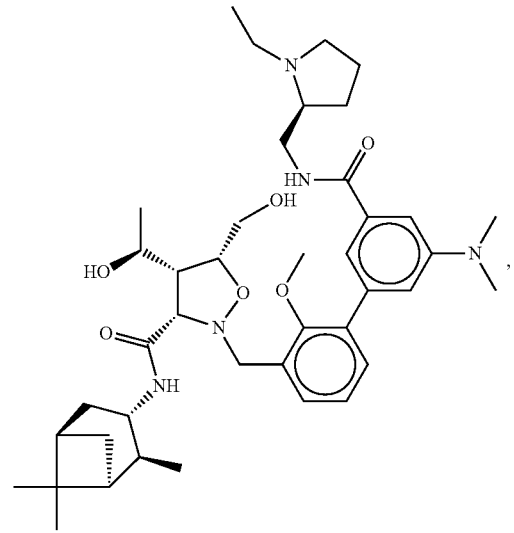
-continued
542
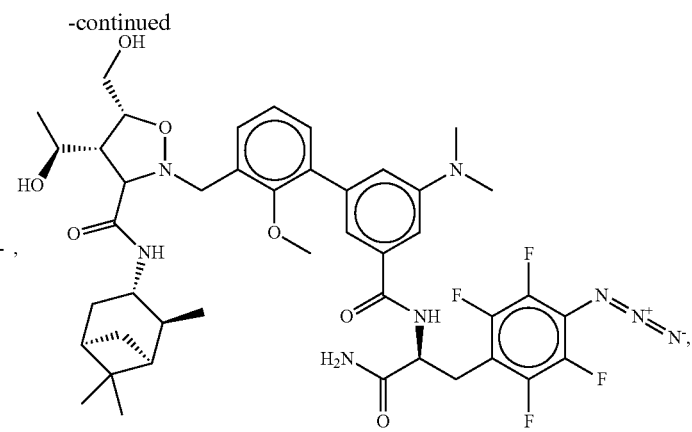
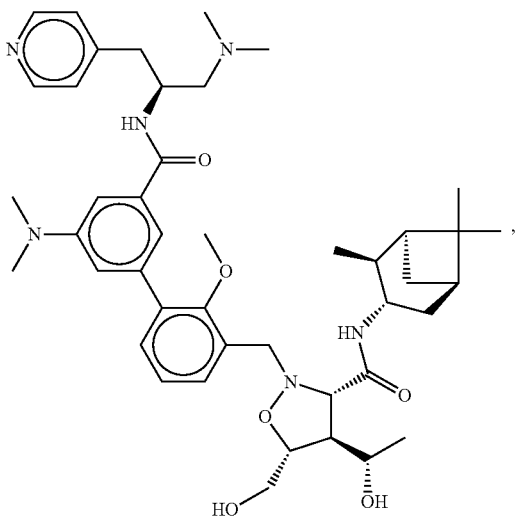
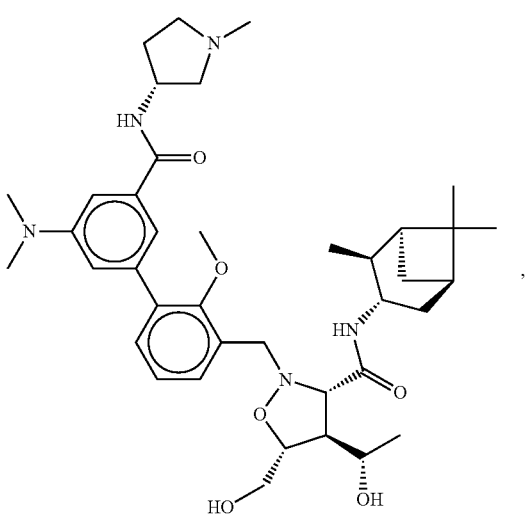

543 544
-continued
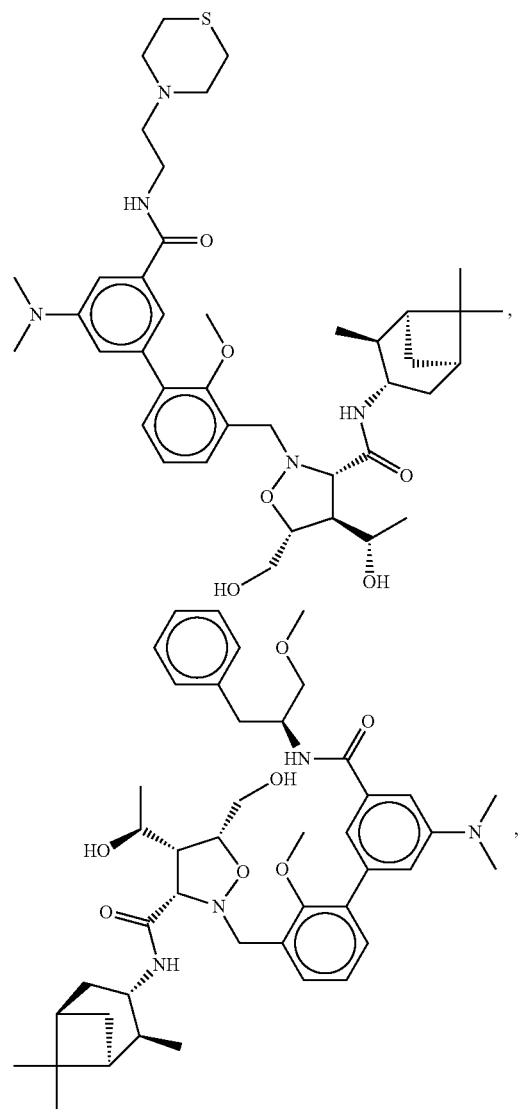
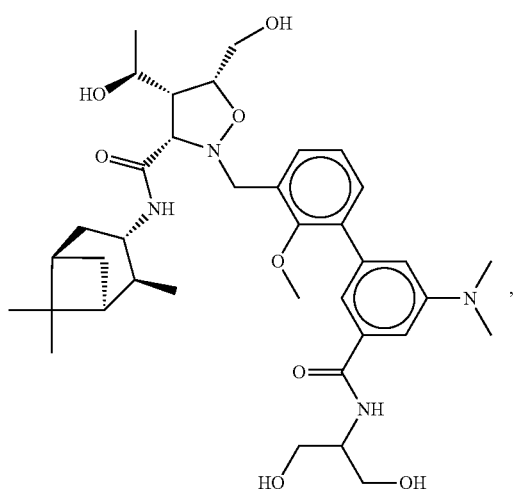
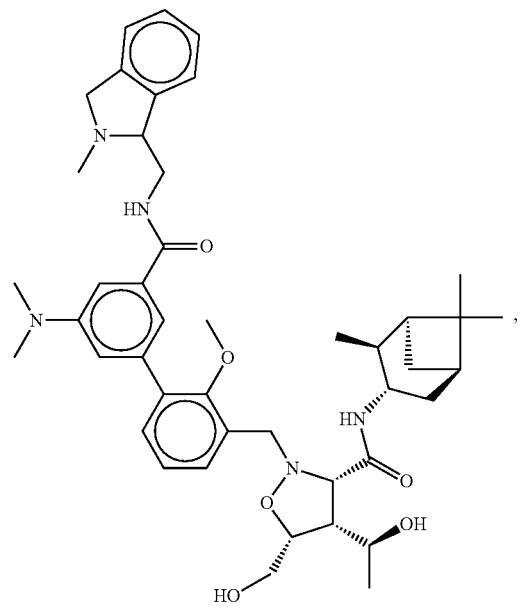
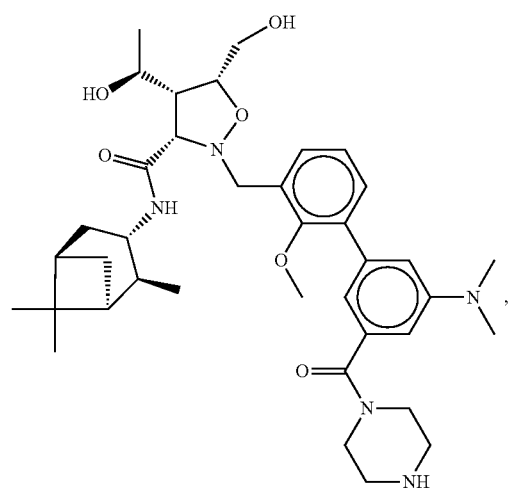

545
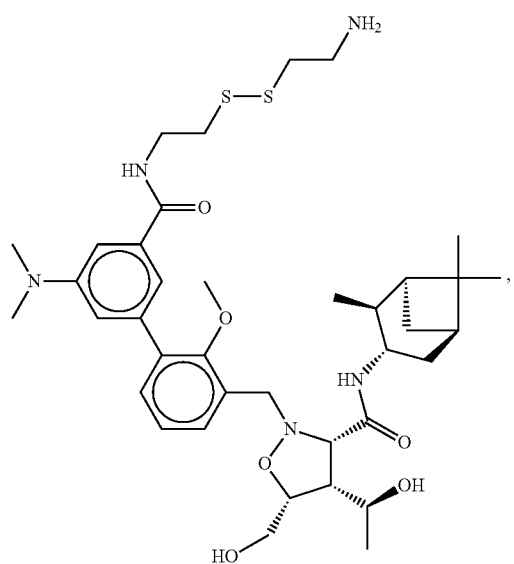
546
-continued
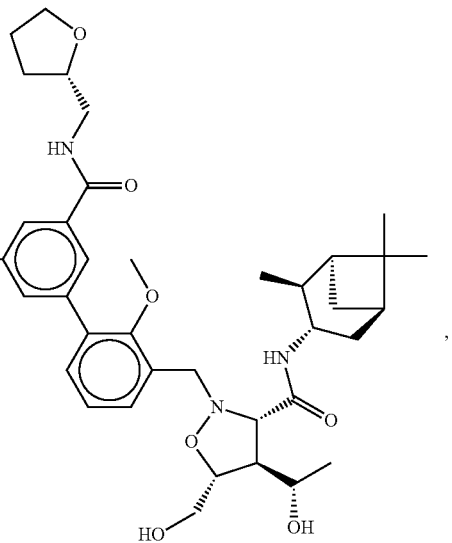
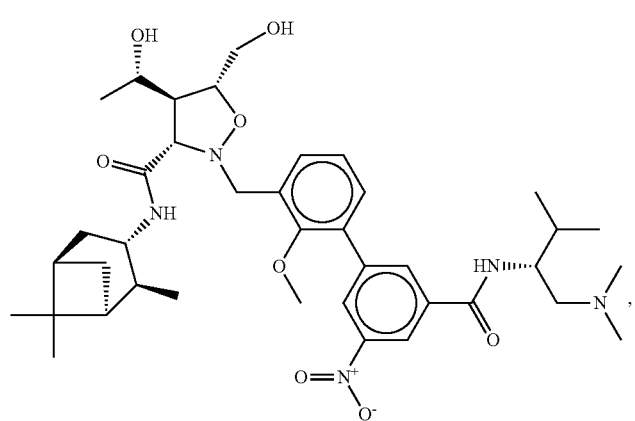
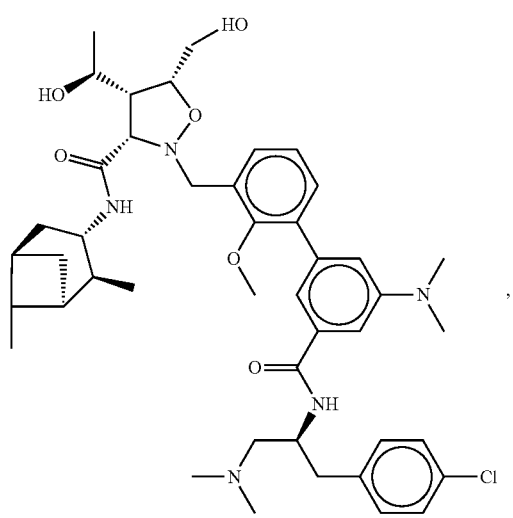
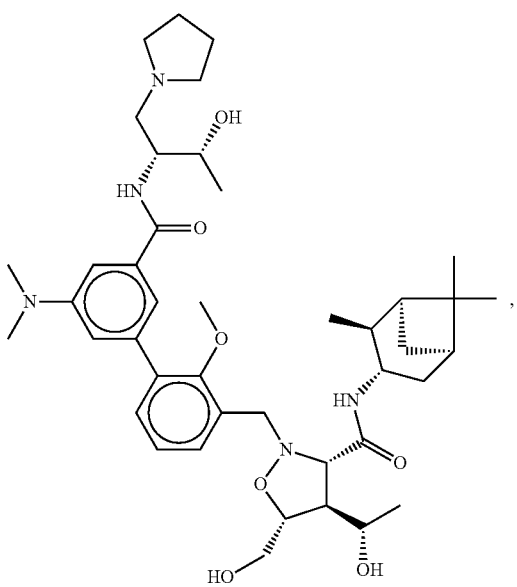

-continued
547
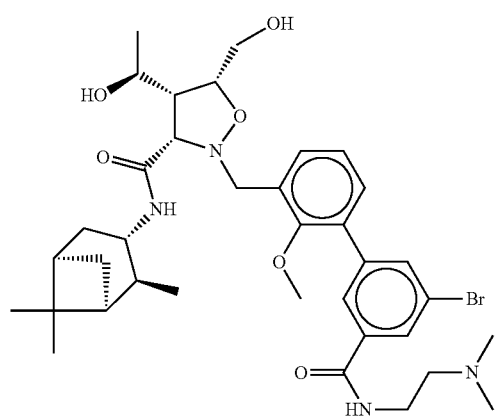
548
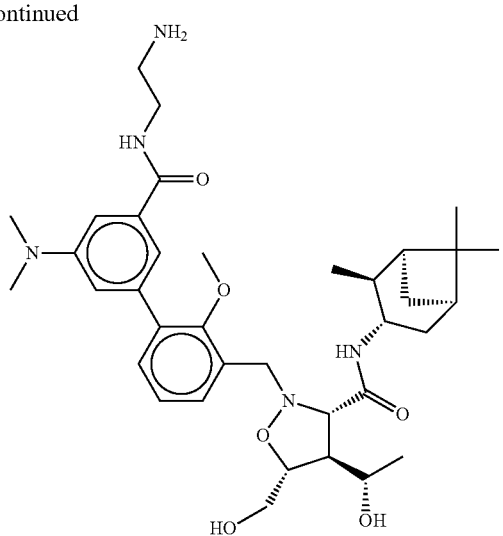
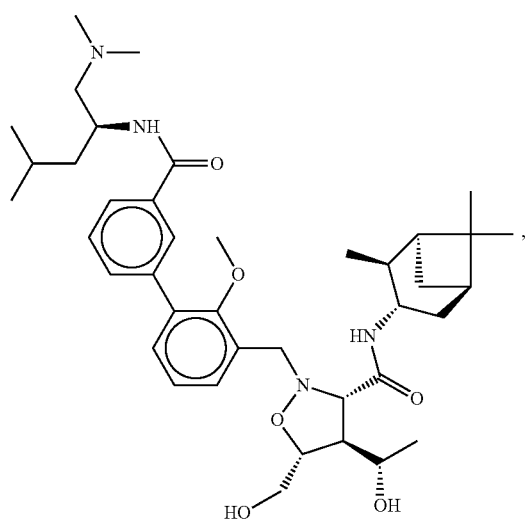
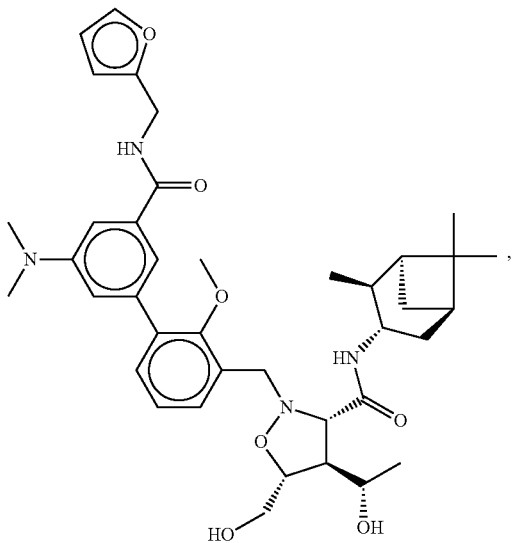
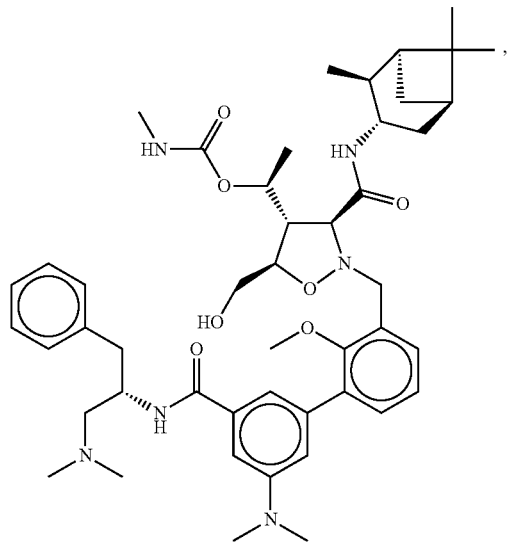
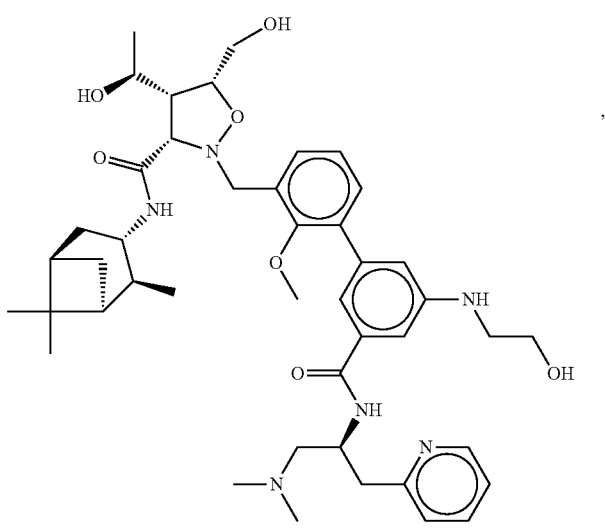

-continued
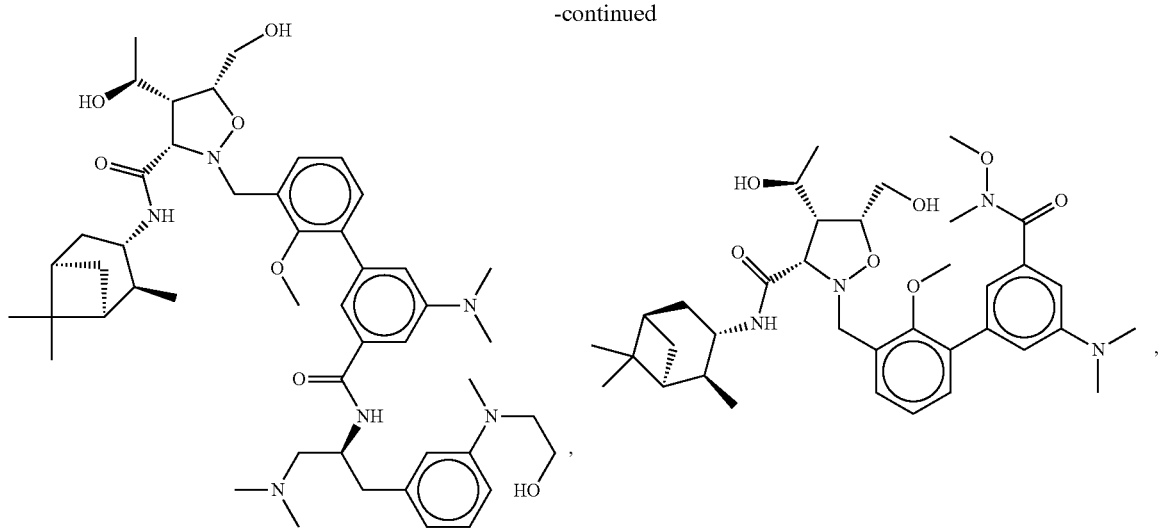
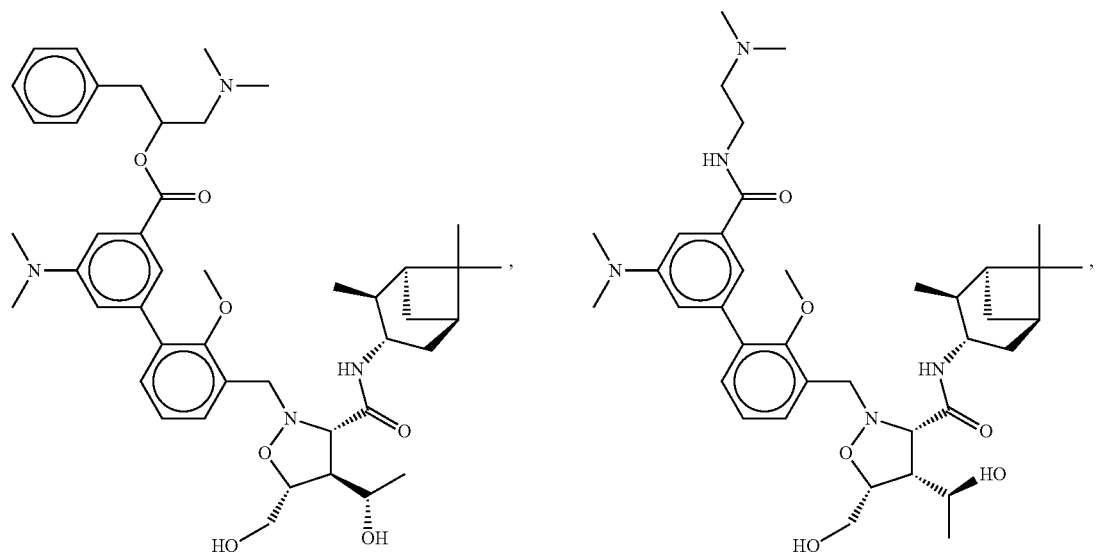
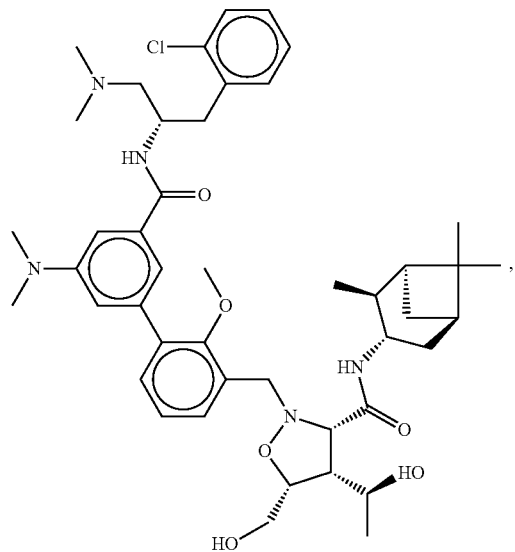

-continued
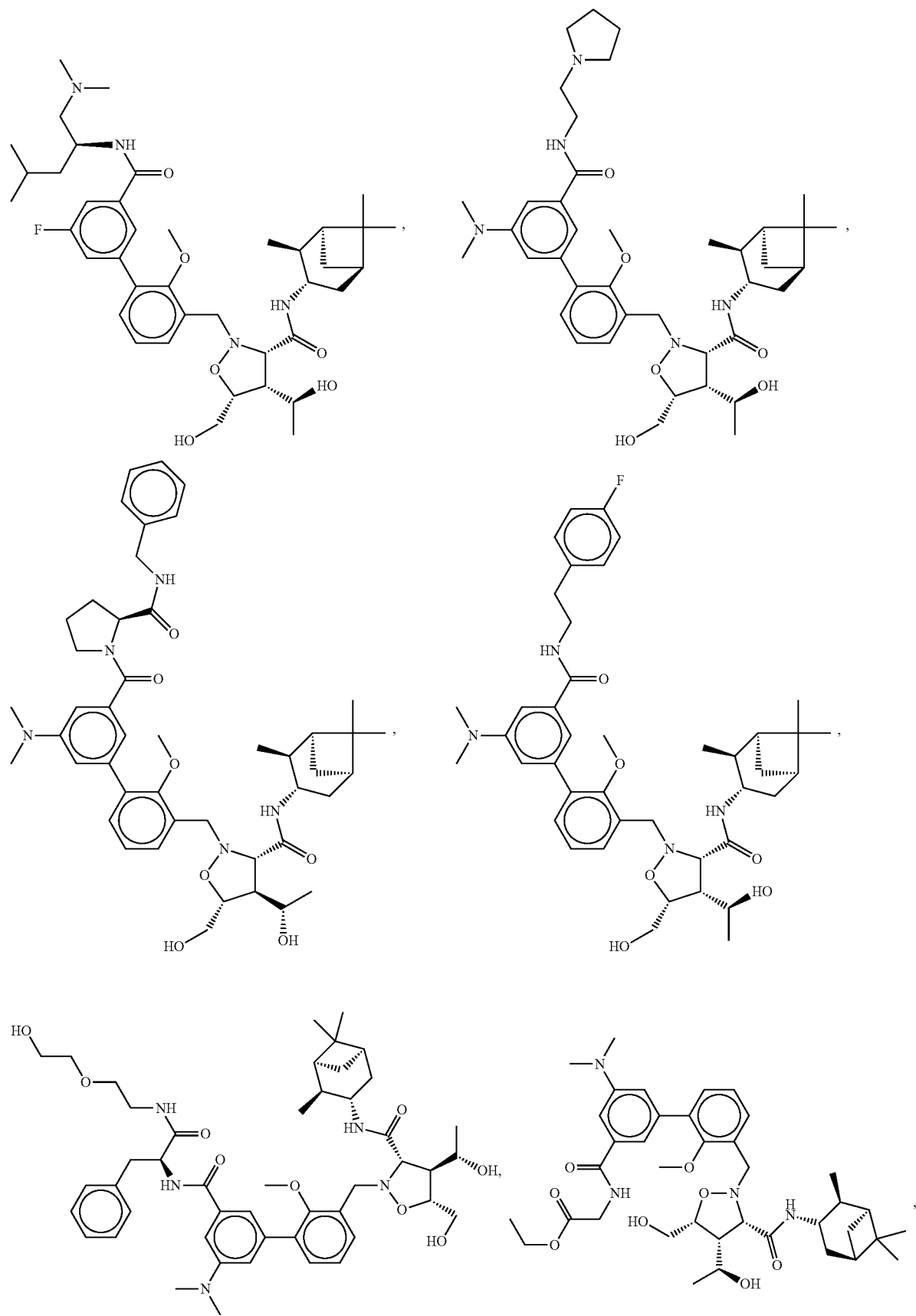

-continued
553
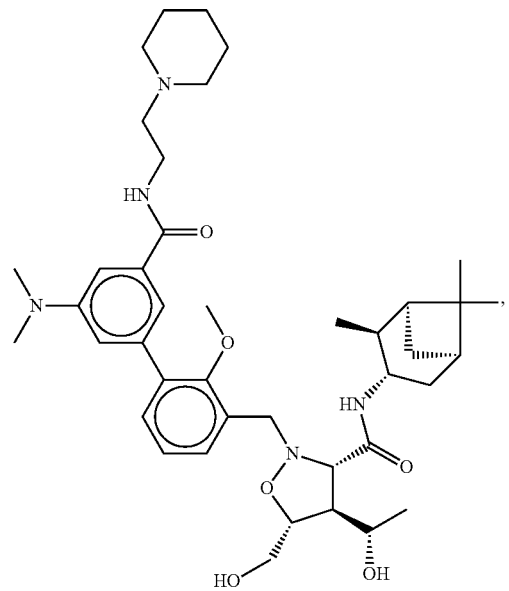
554
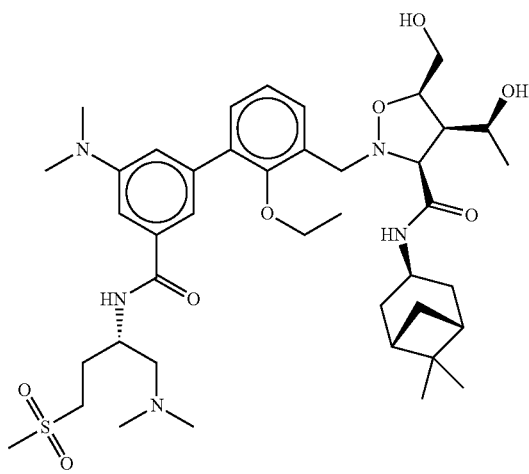
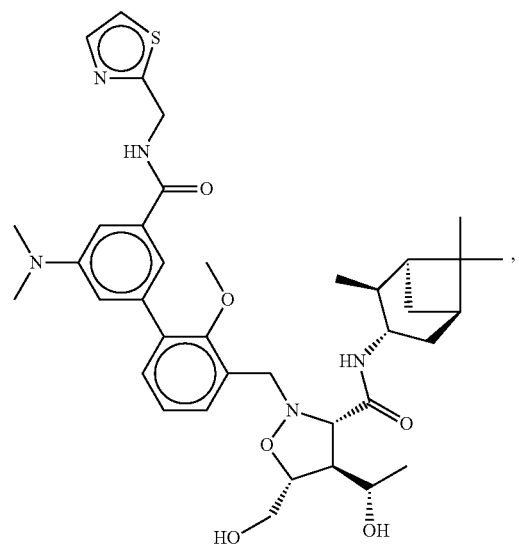
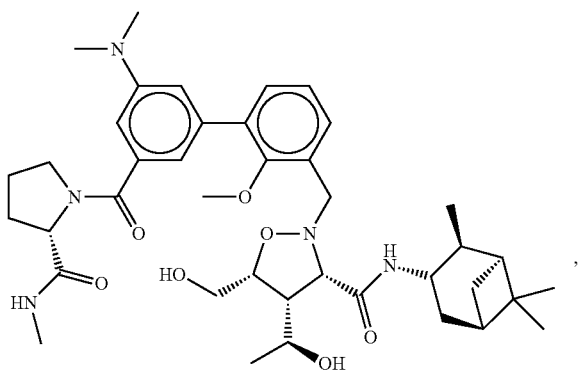
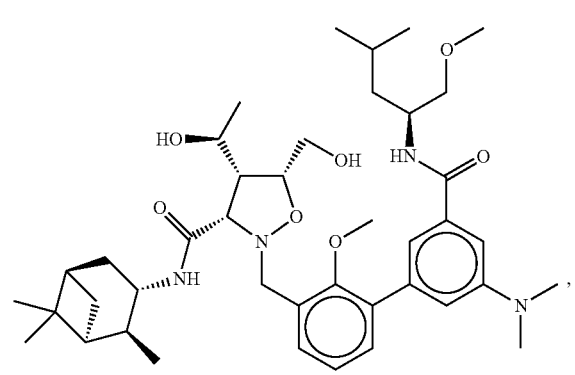
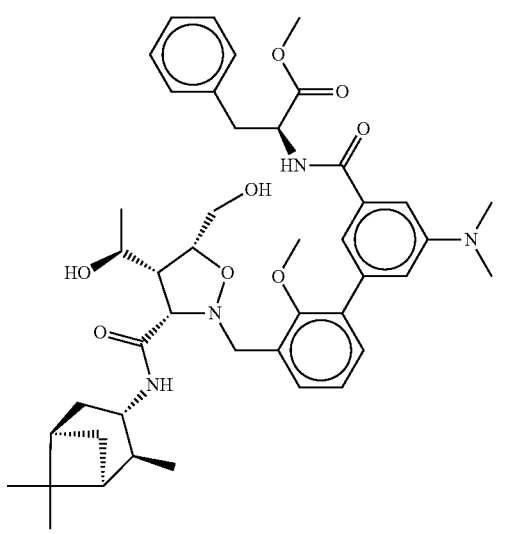

555
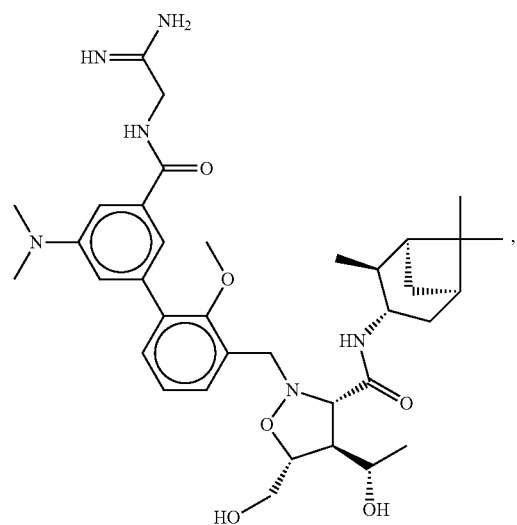
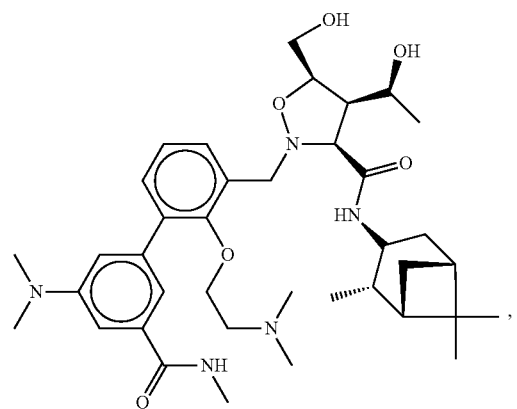
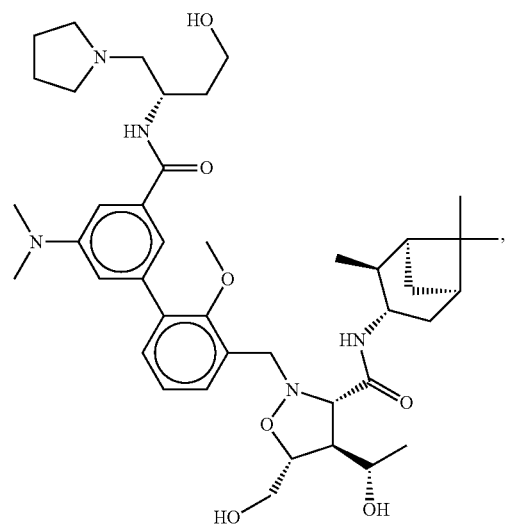
-continued
556
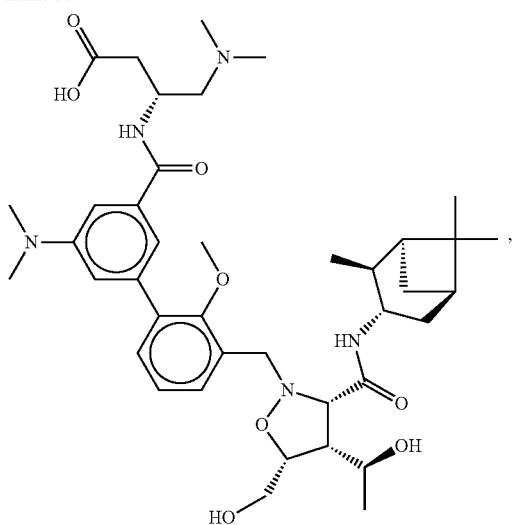
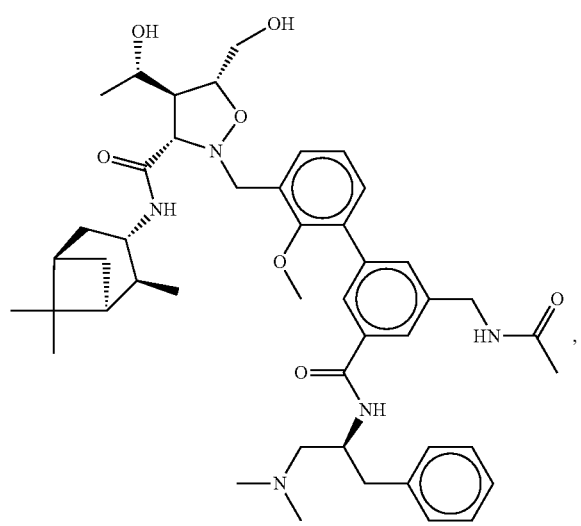

557
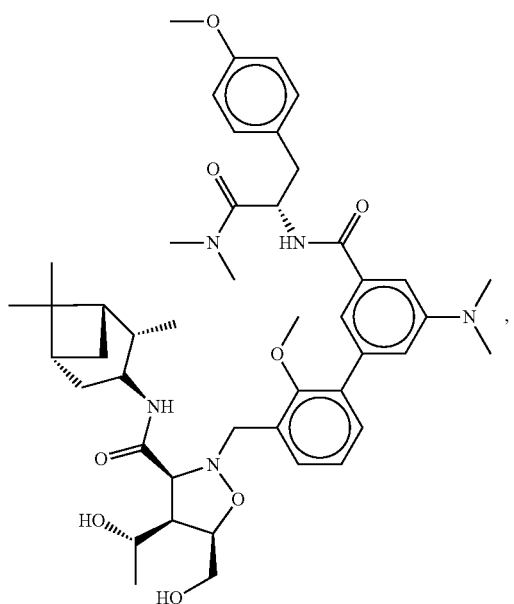
558
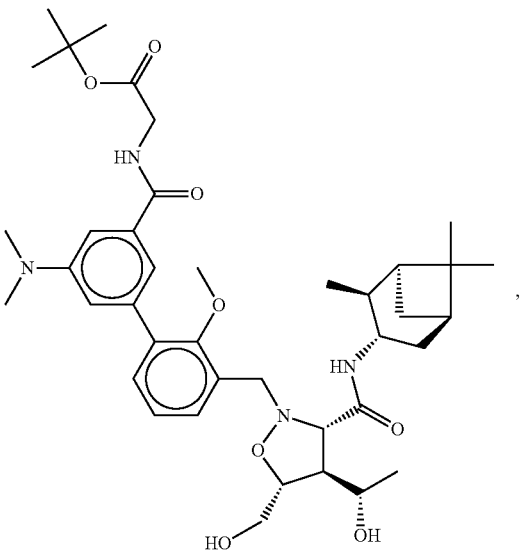
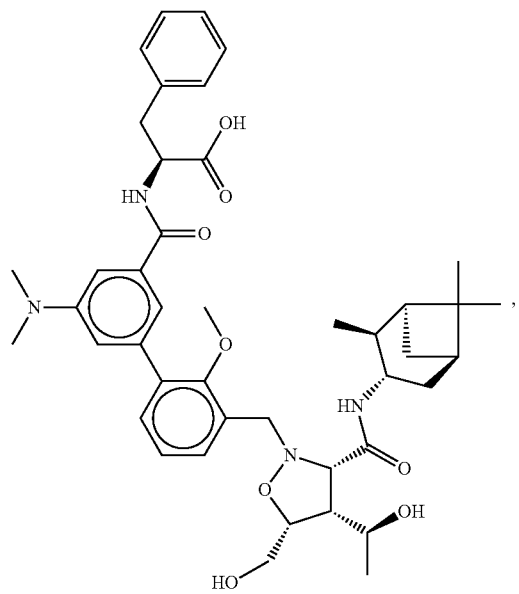
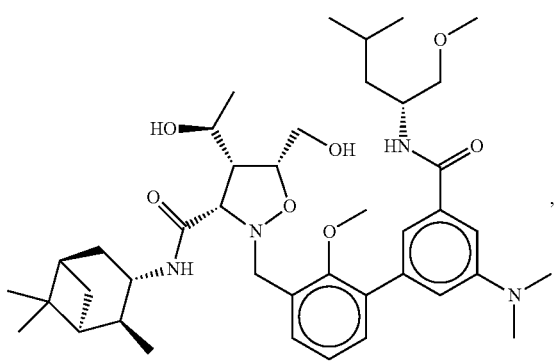
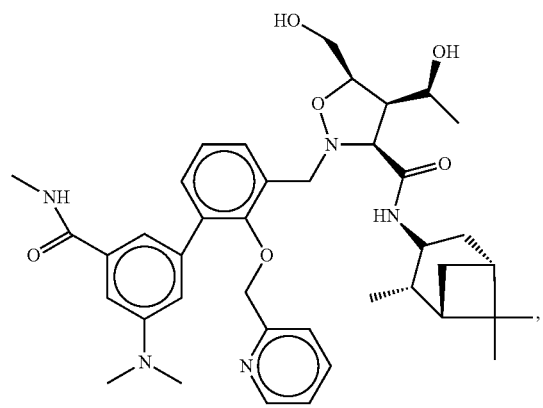

559 560
-continued
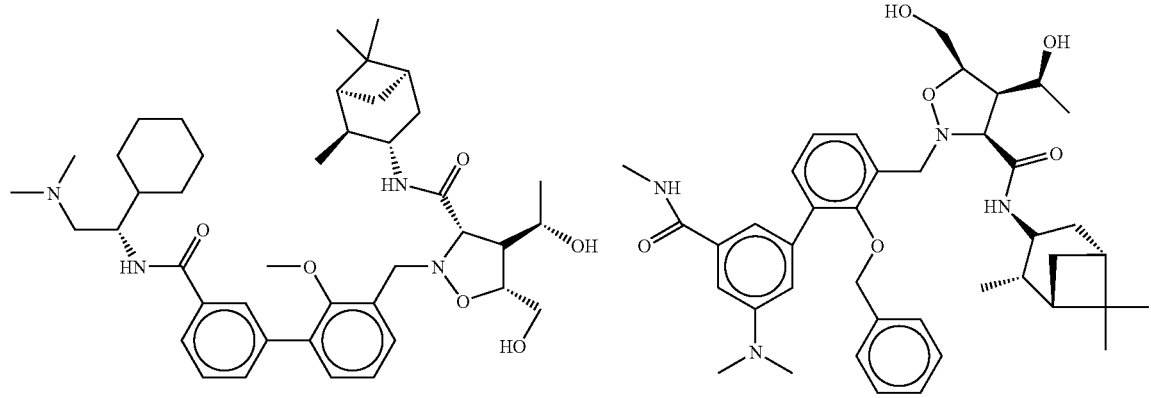
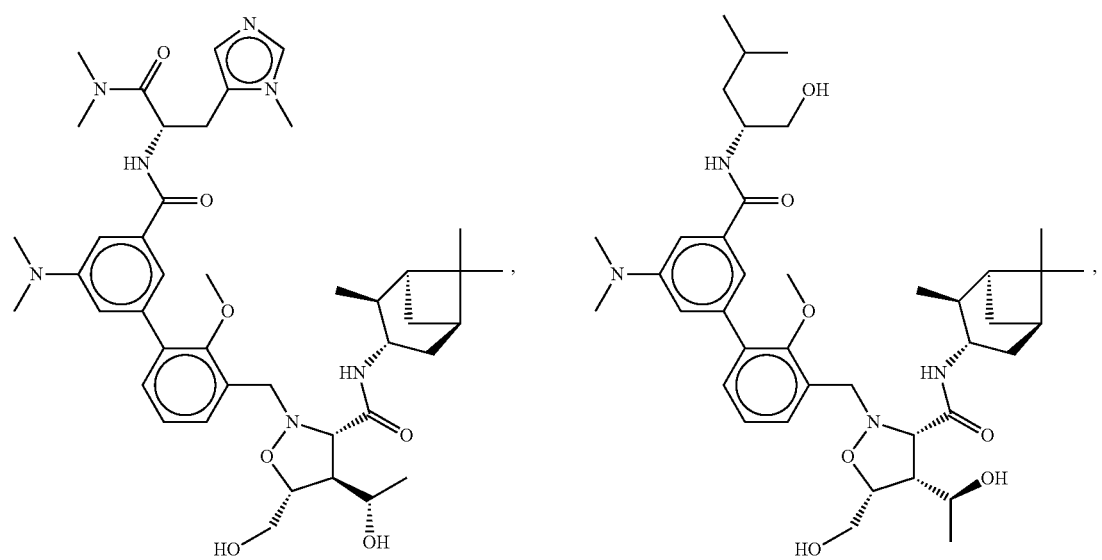
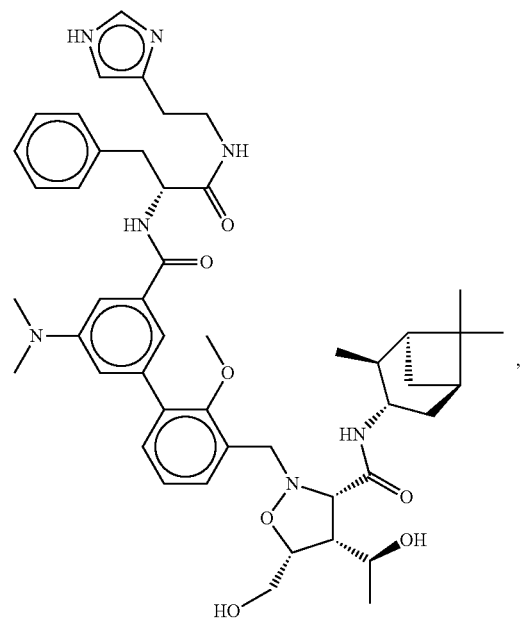

561
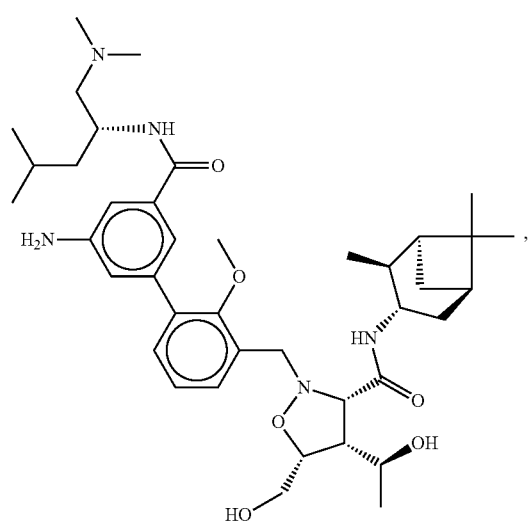
562
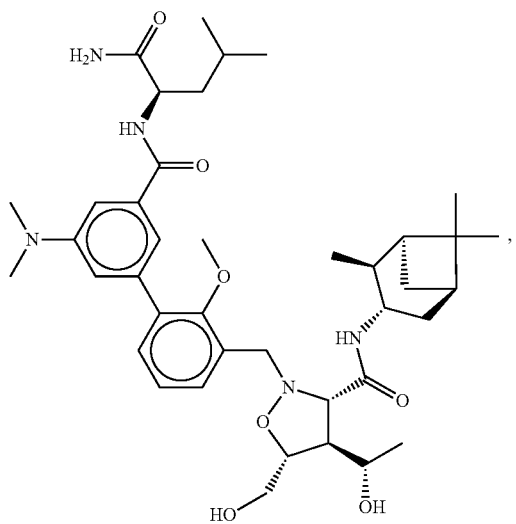
-continued
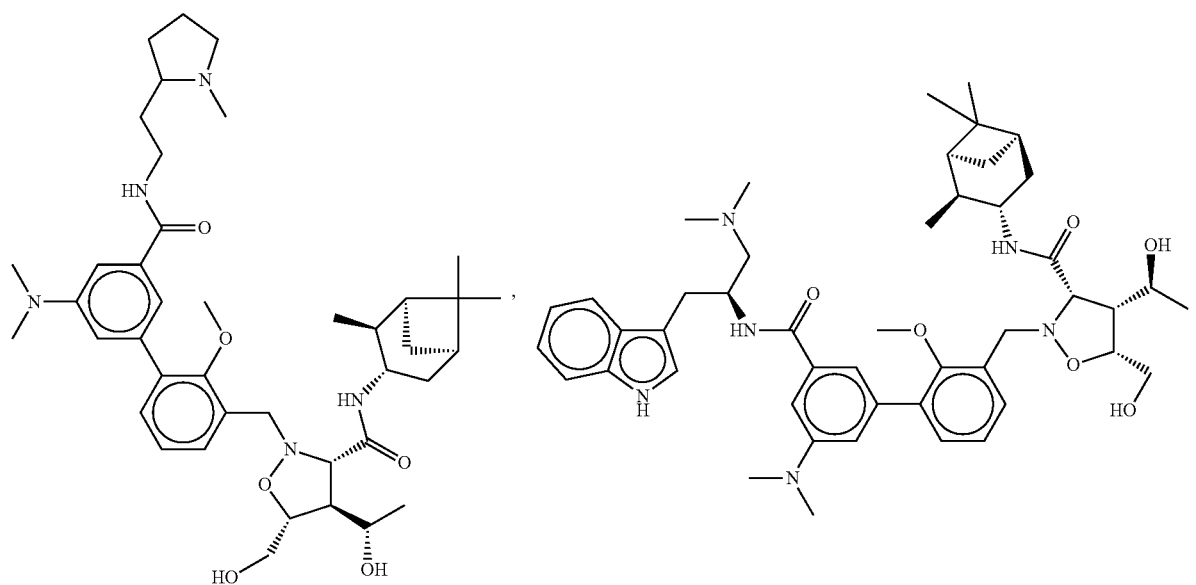
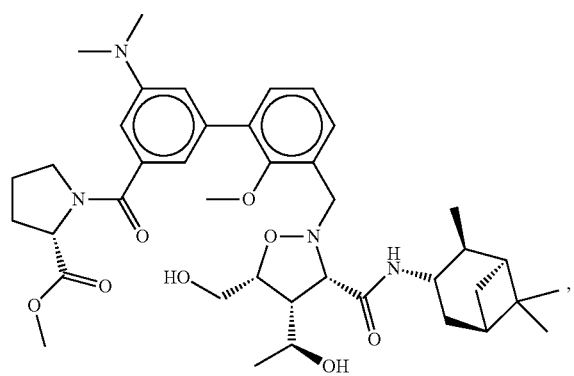

563
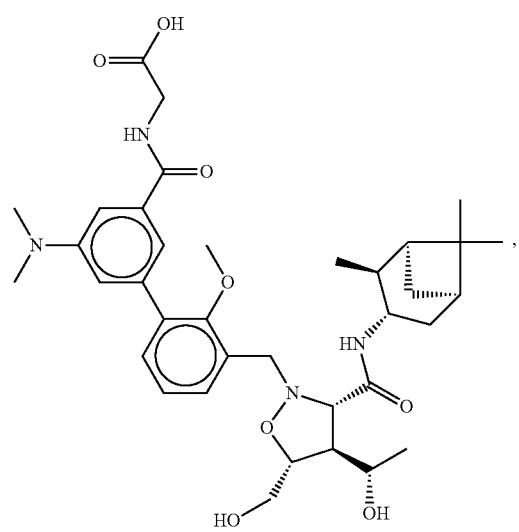
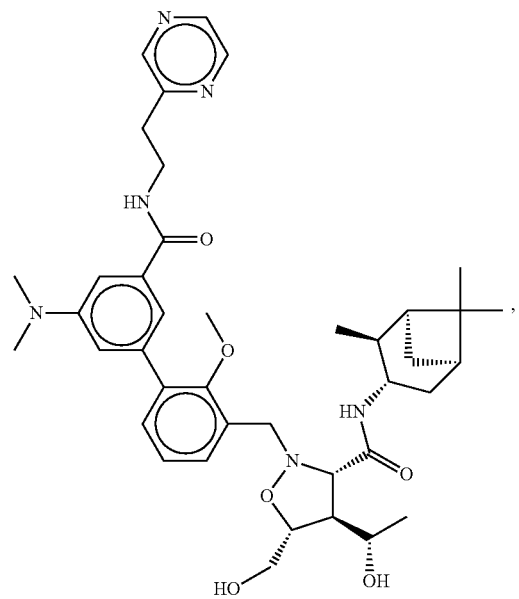
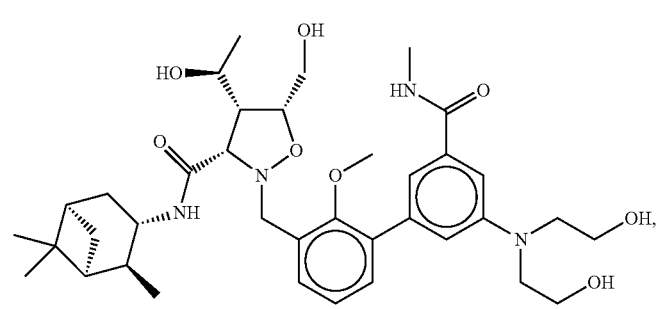
564
-continued
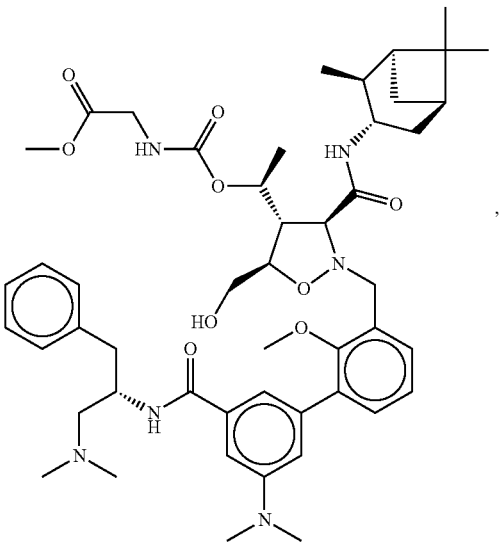
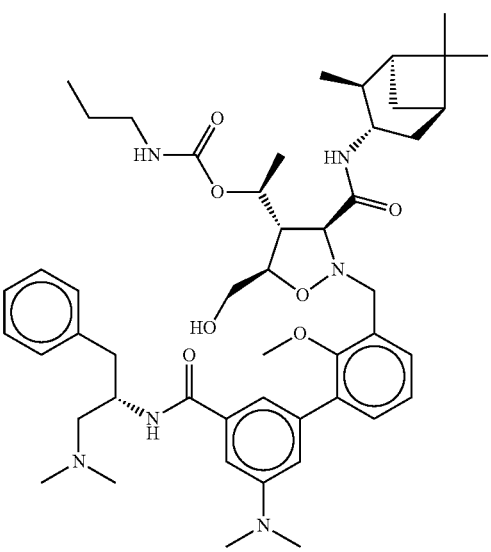
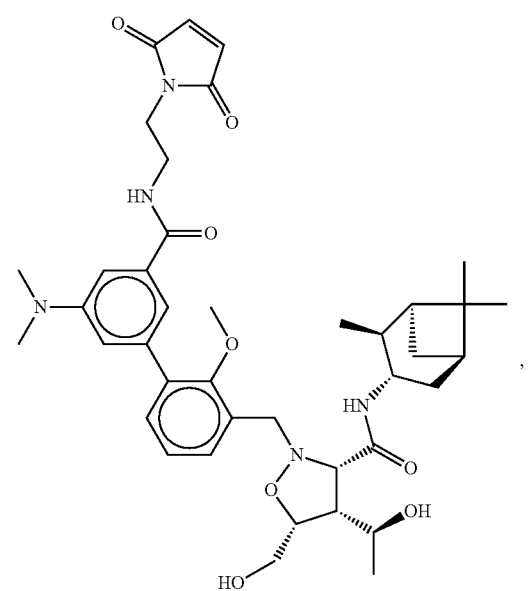

565
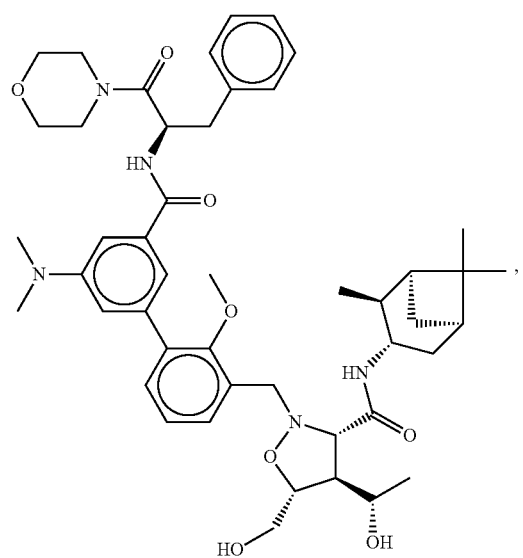
566 -continued
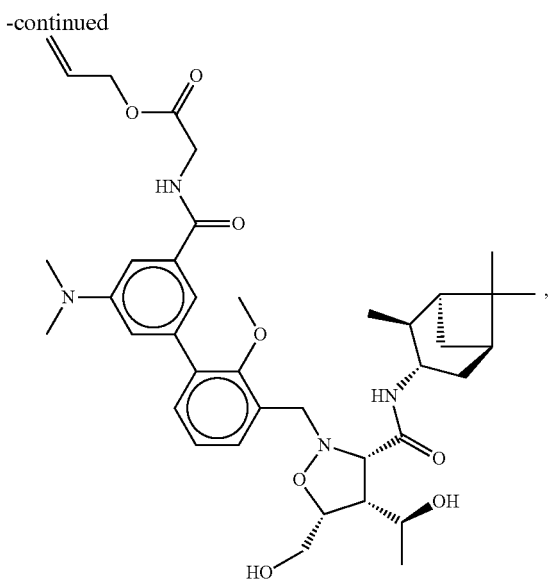
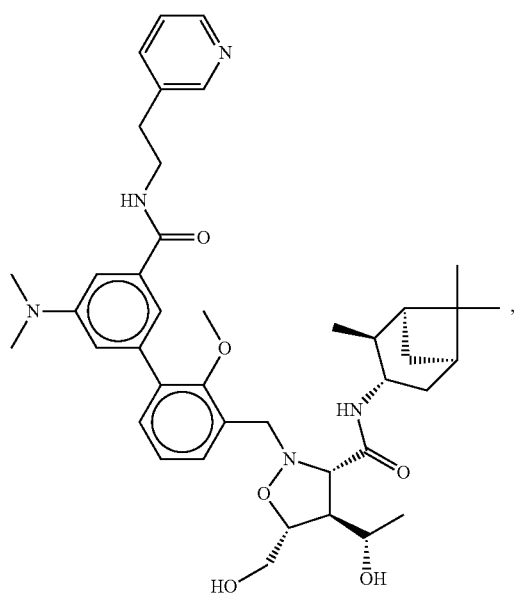
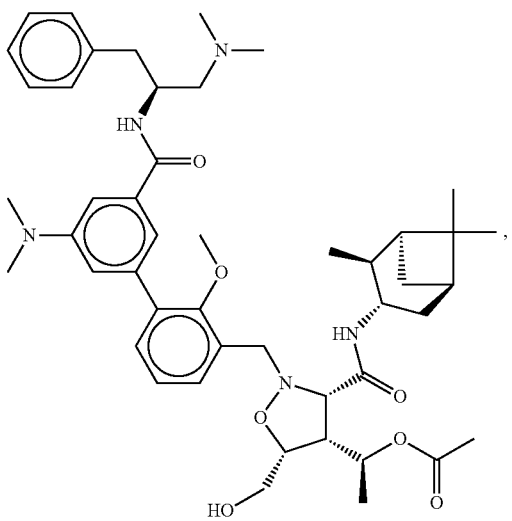
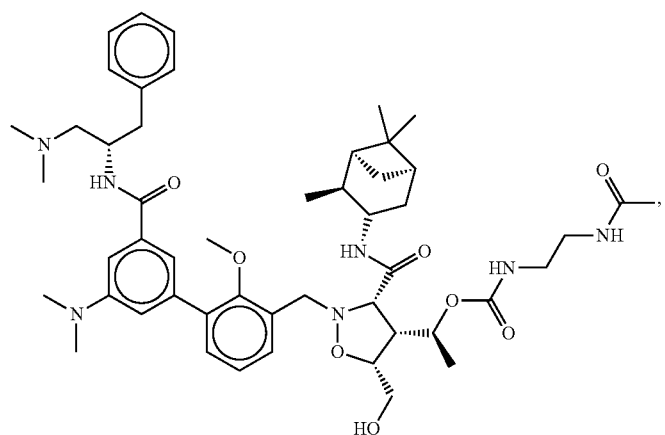

567
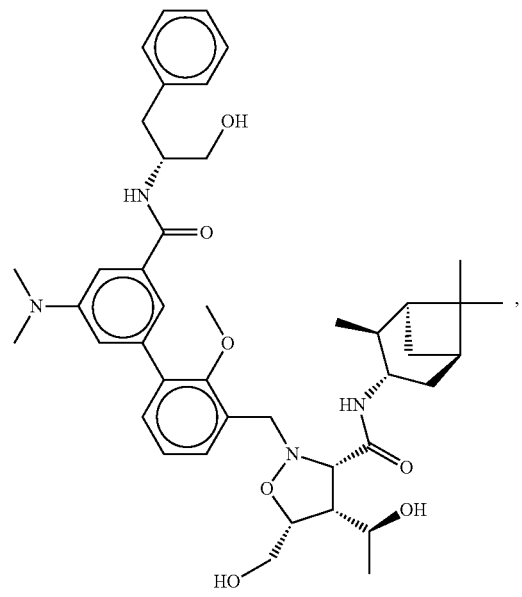
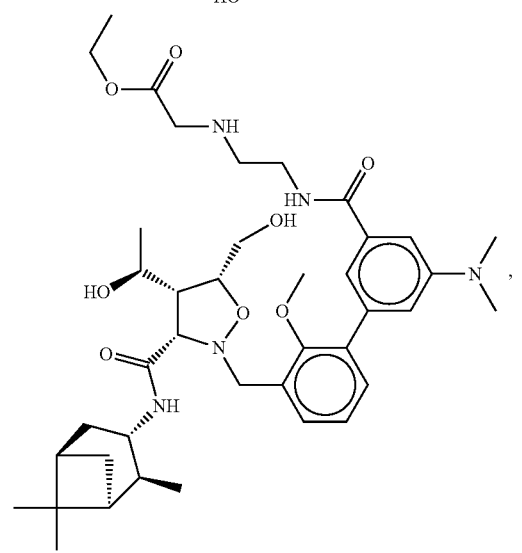
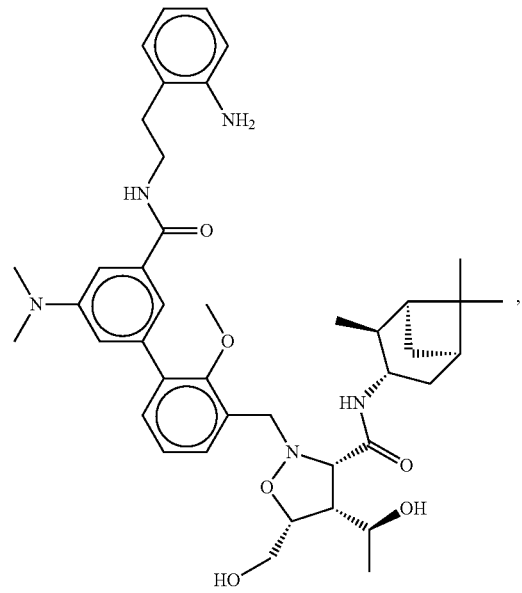
568
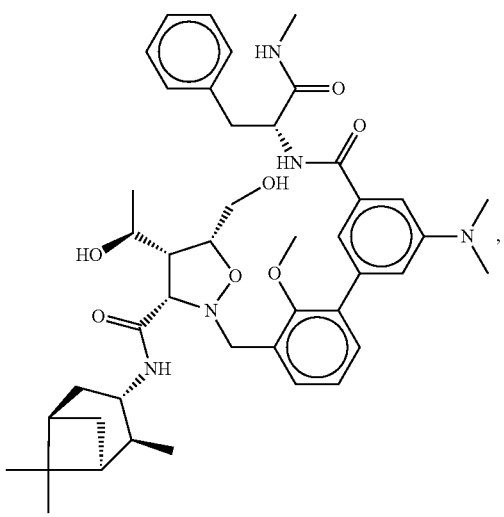
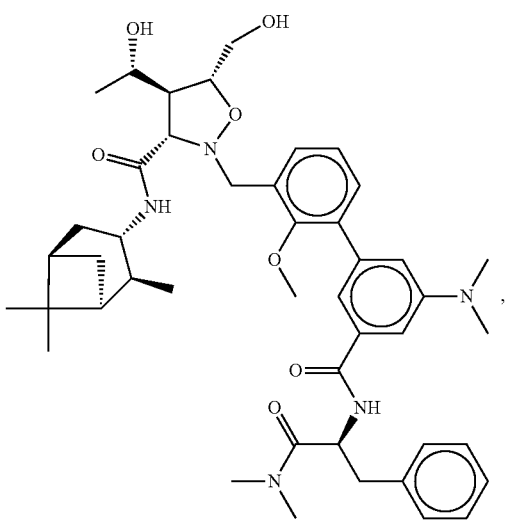

569 570
-continued
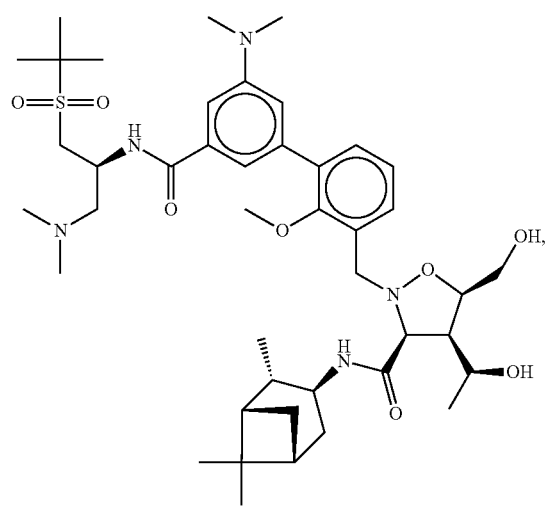
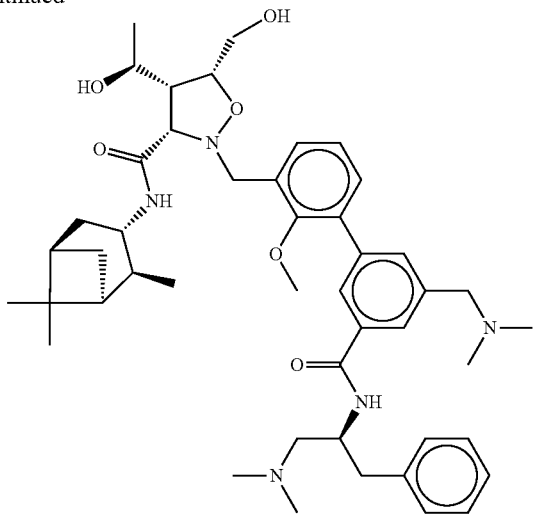
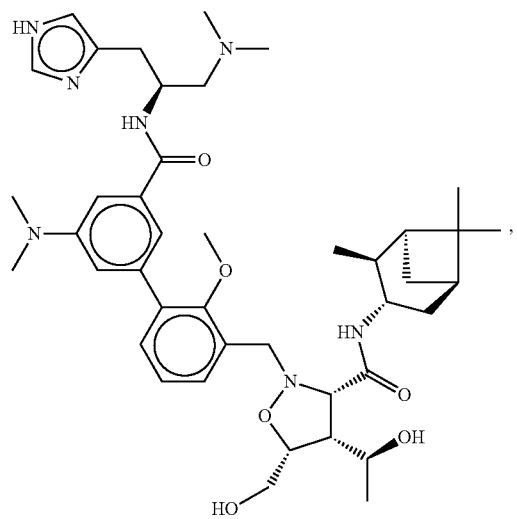
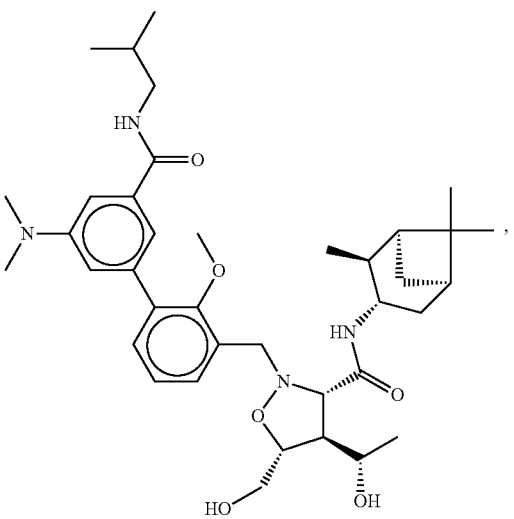
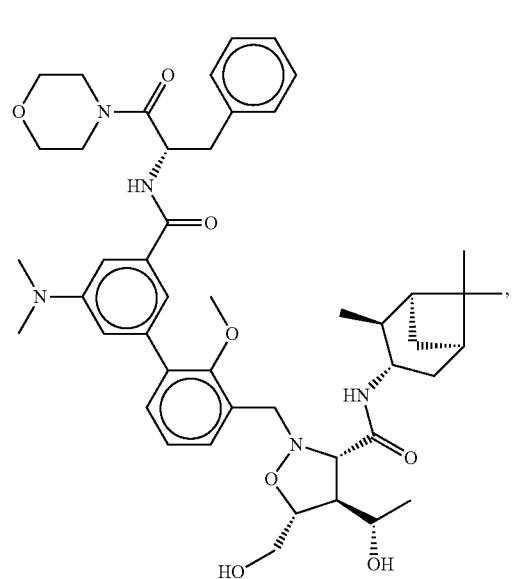
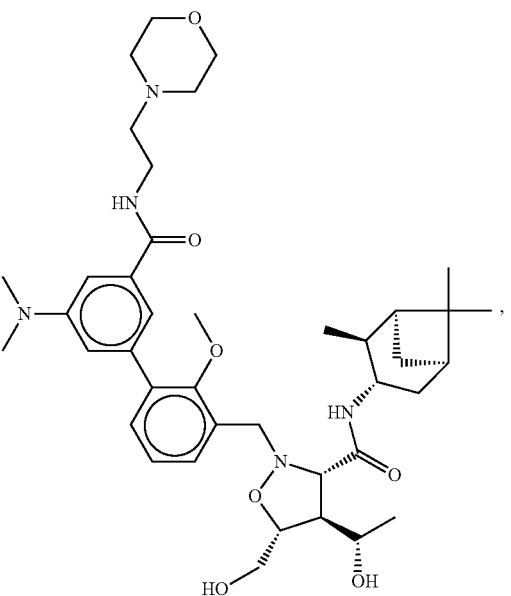

-continued
571 572
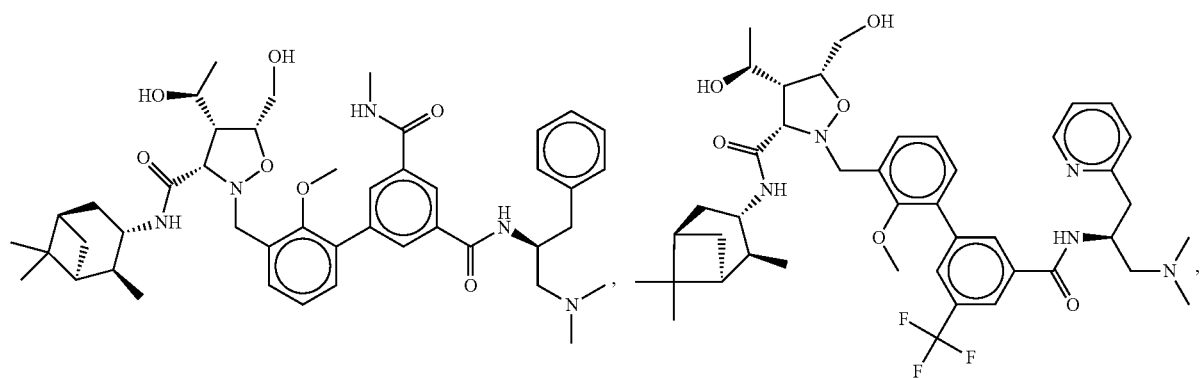
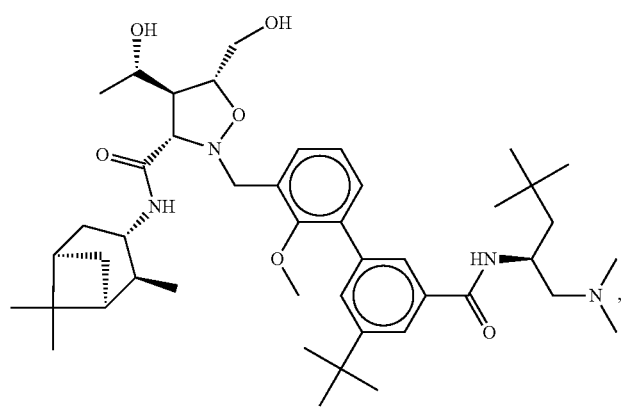
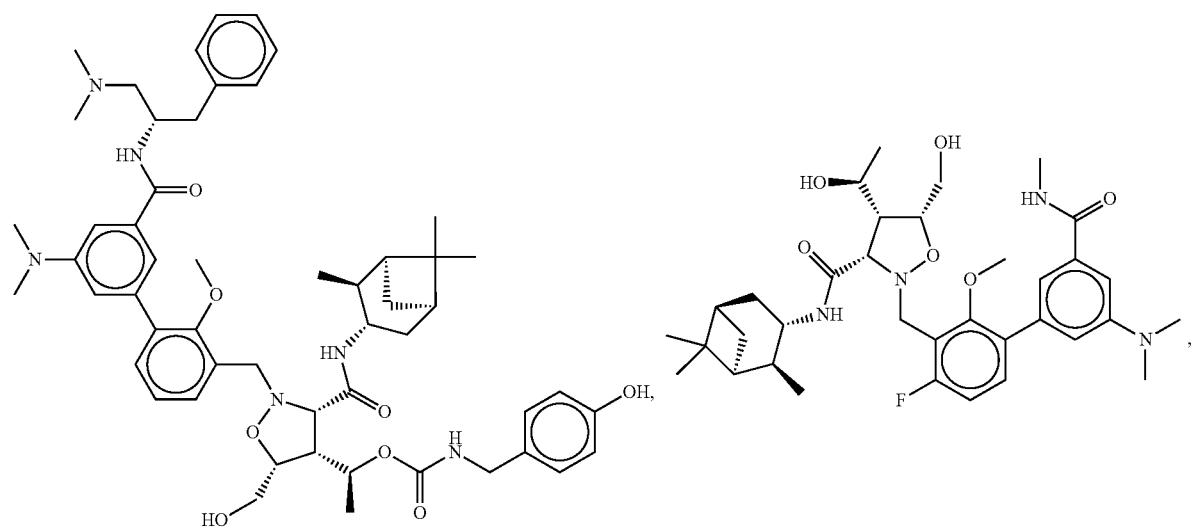

573 574
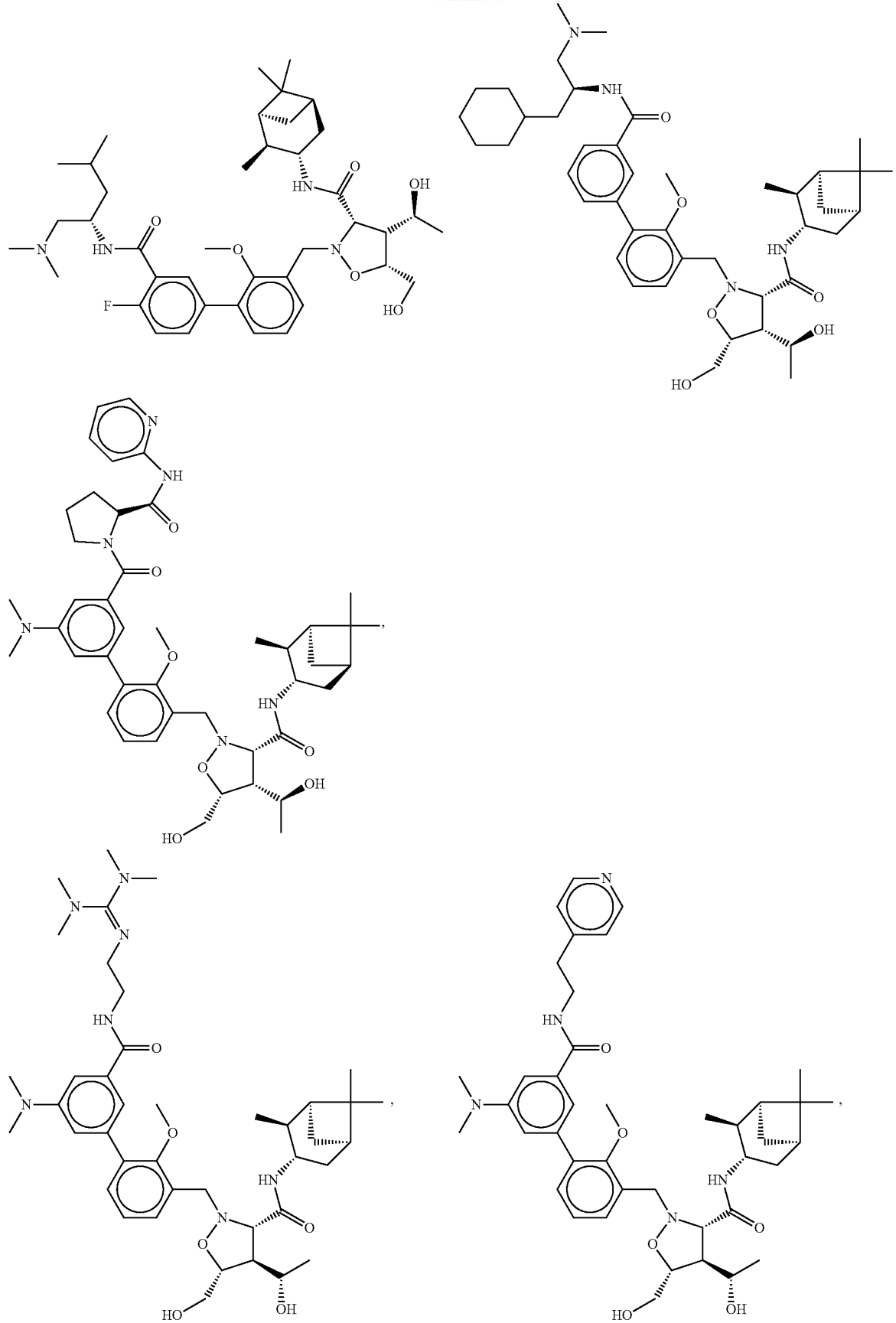
-continued

575
-continued
576
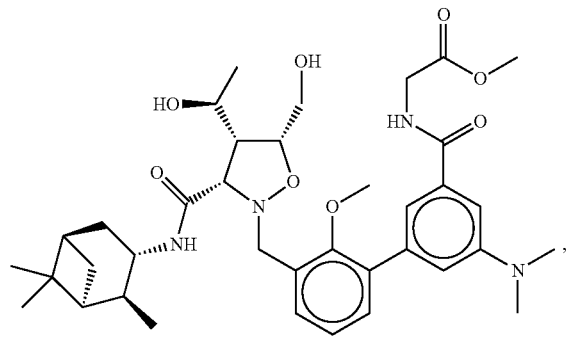
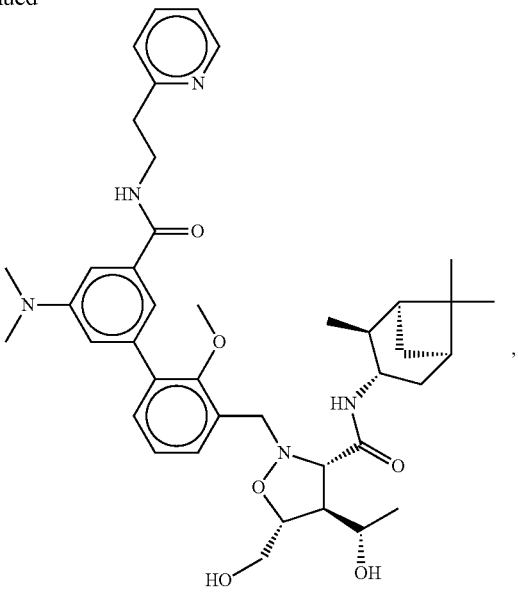
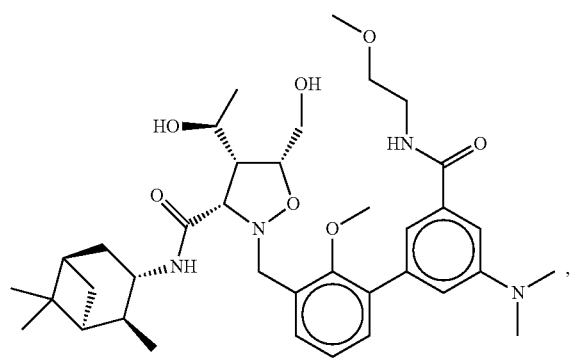
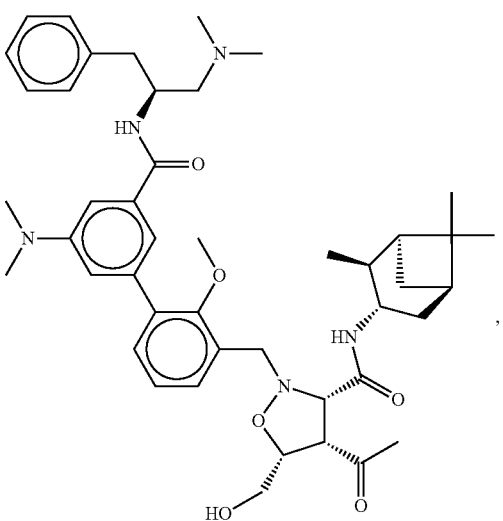
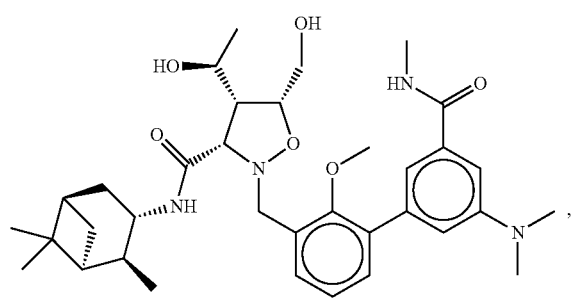
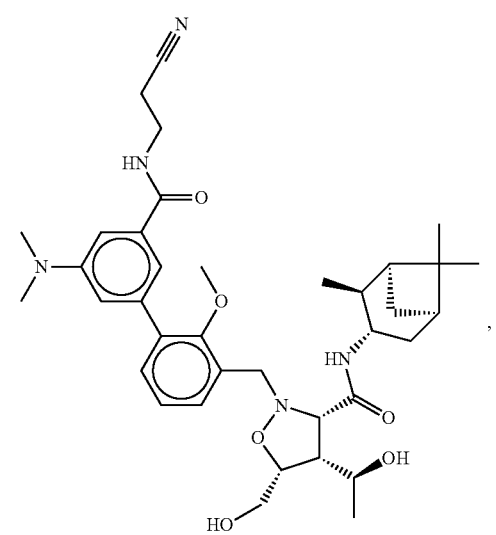

-continued
577    578
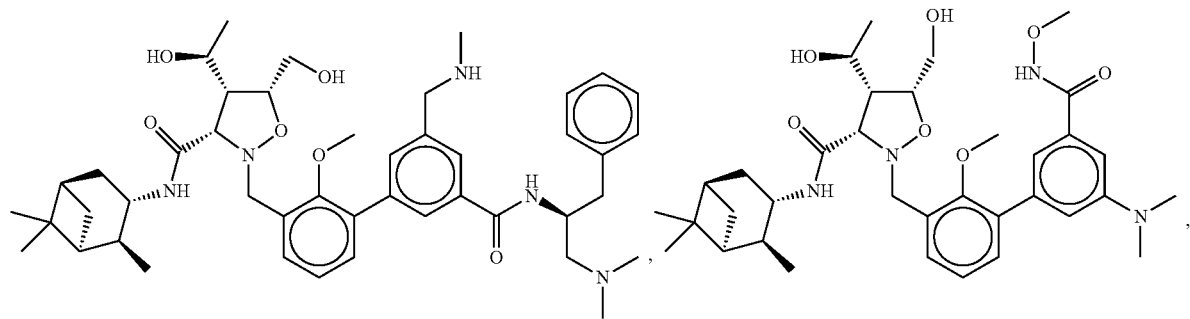
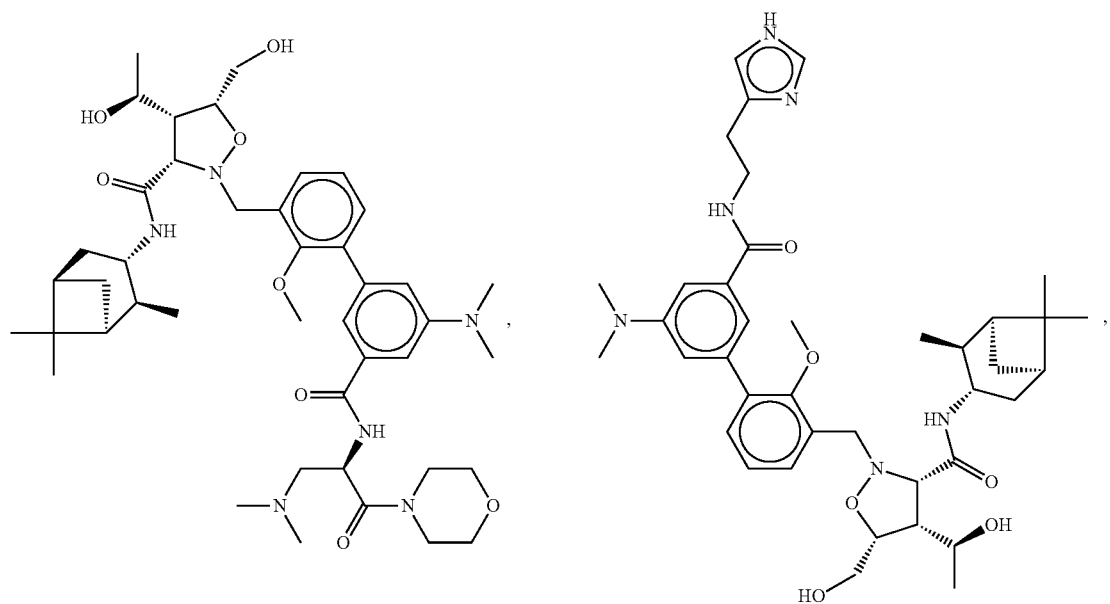
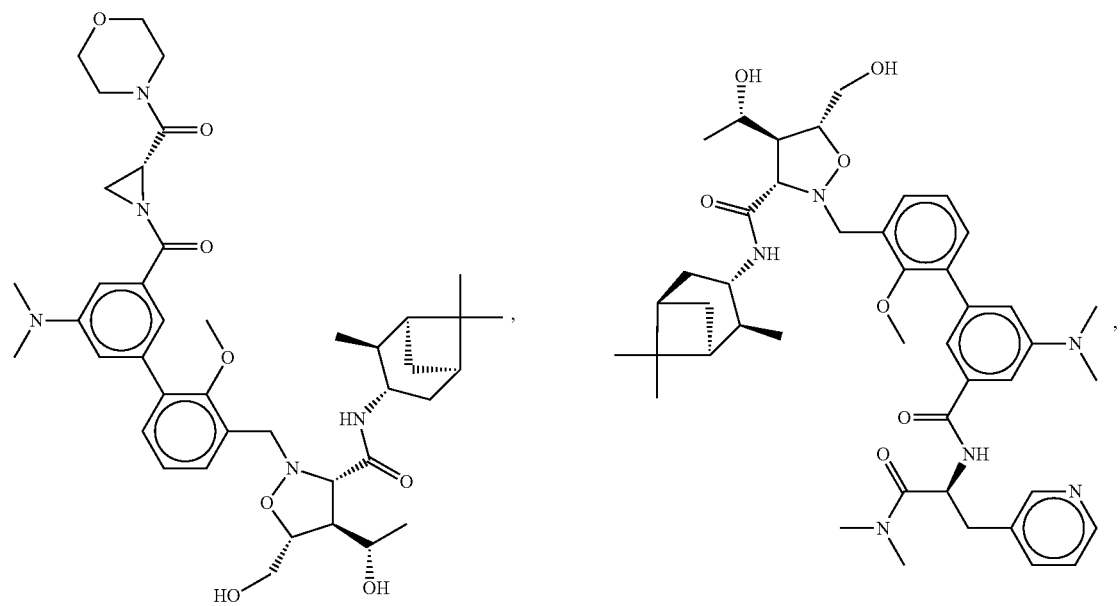

579 580
-continued
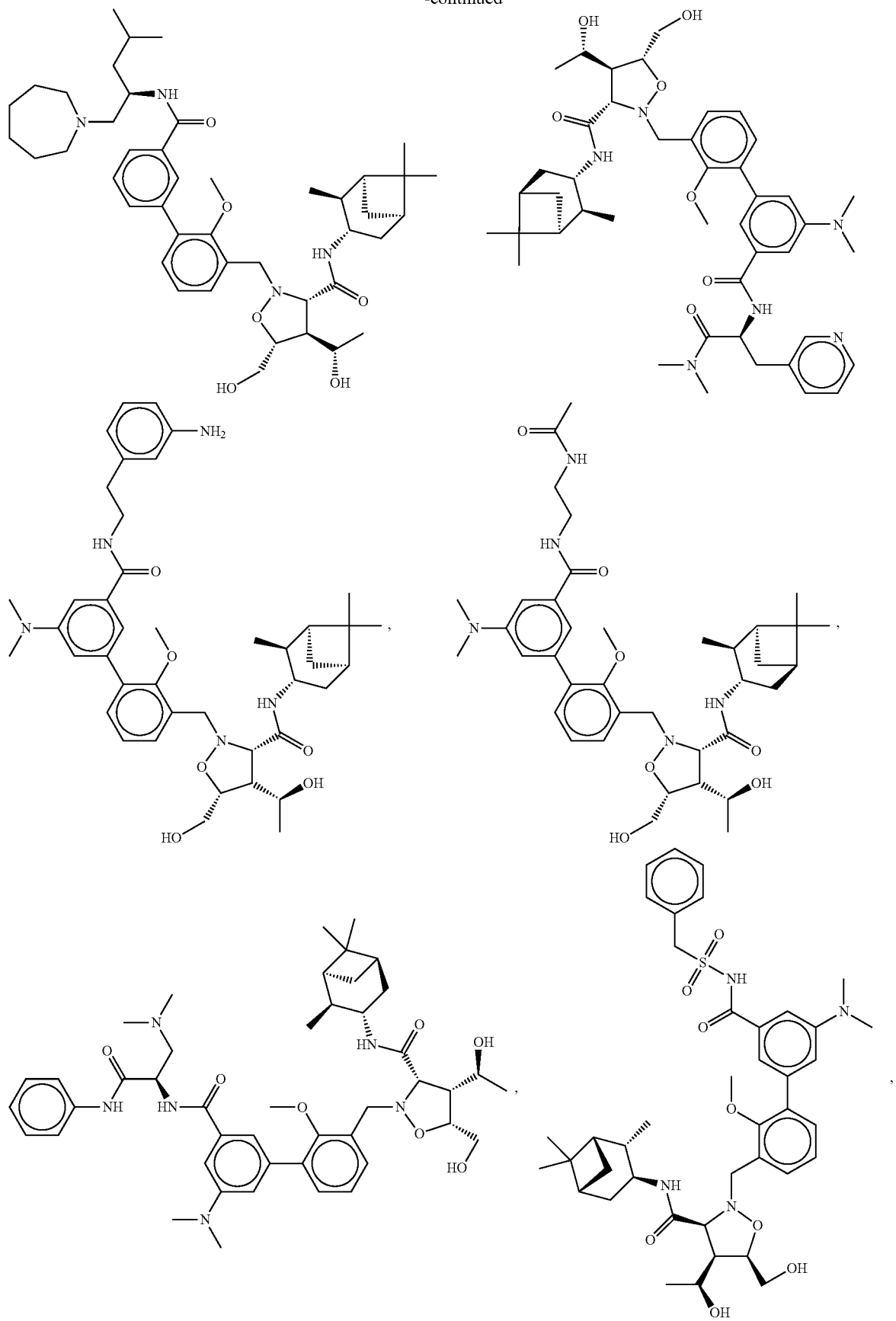

581
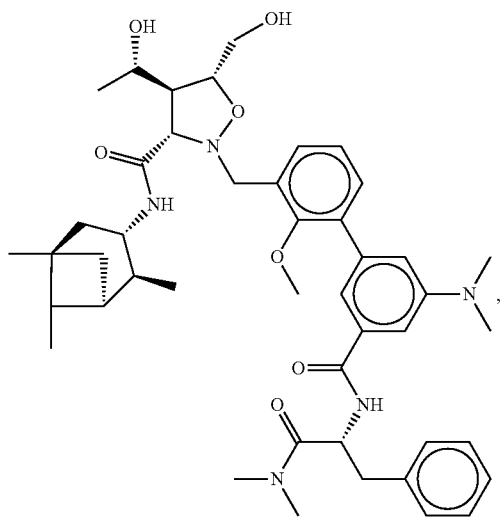
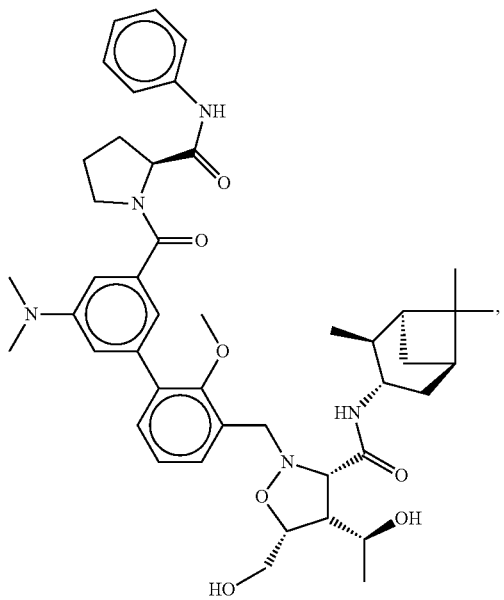
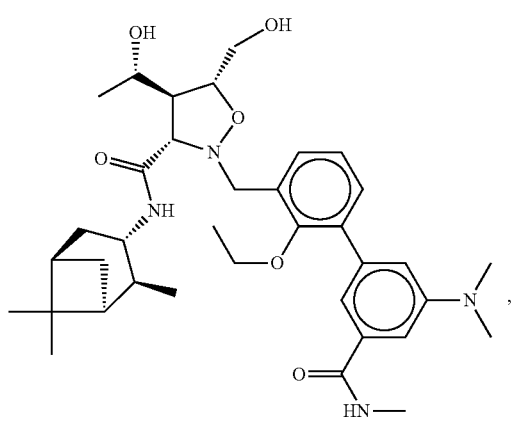
582
-continued
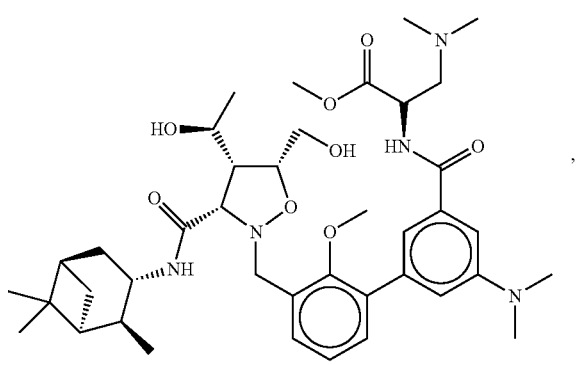
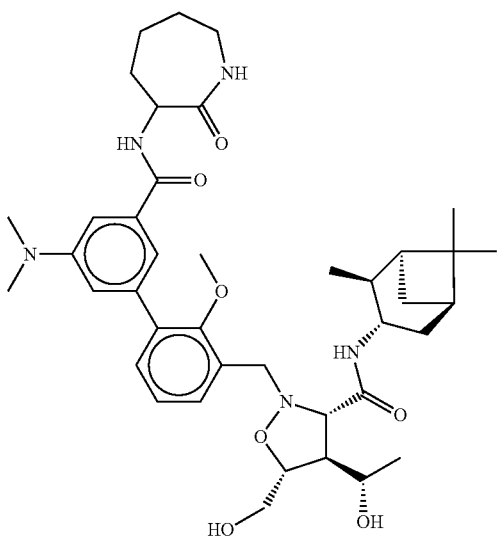

583
584
-continued
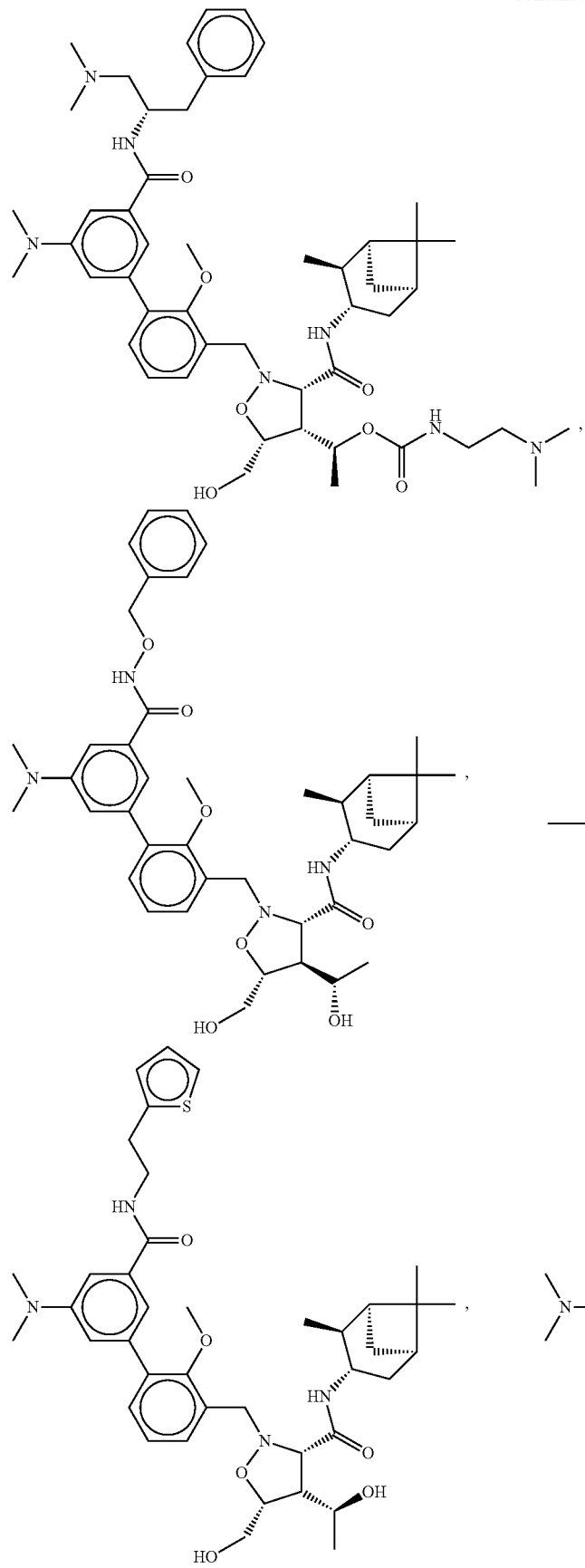
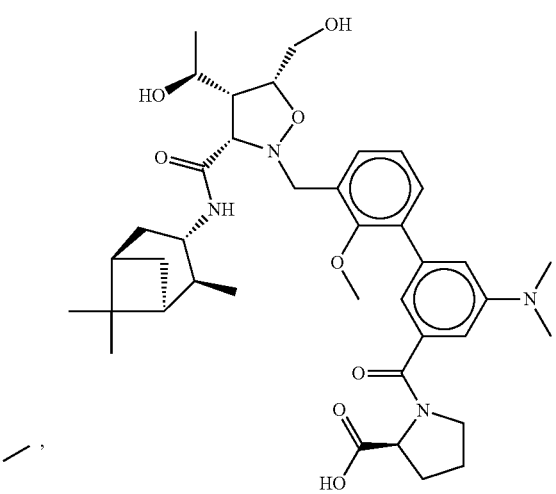
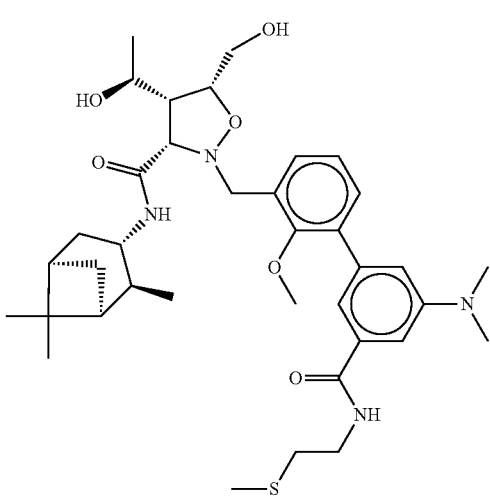
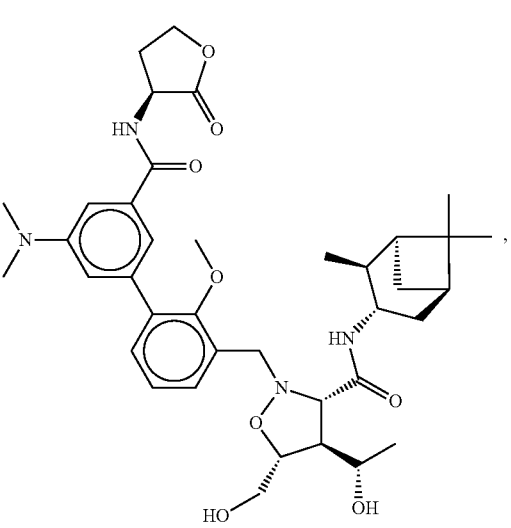

585
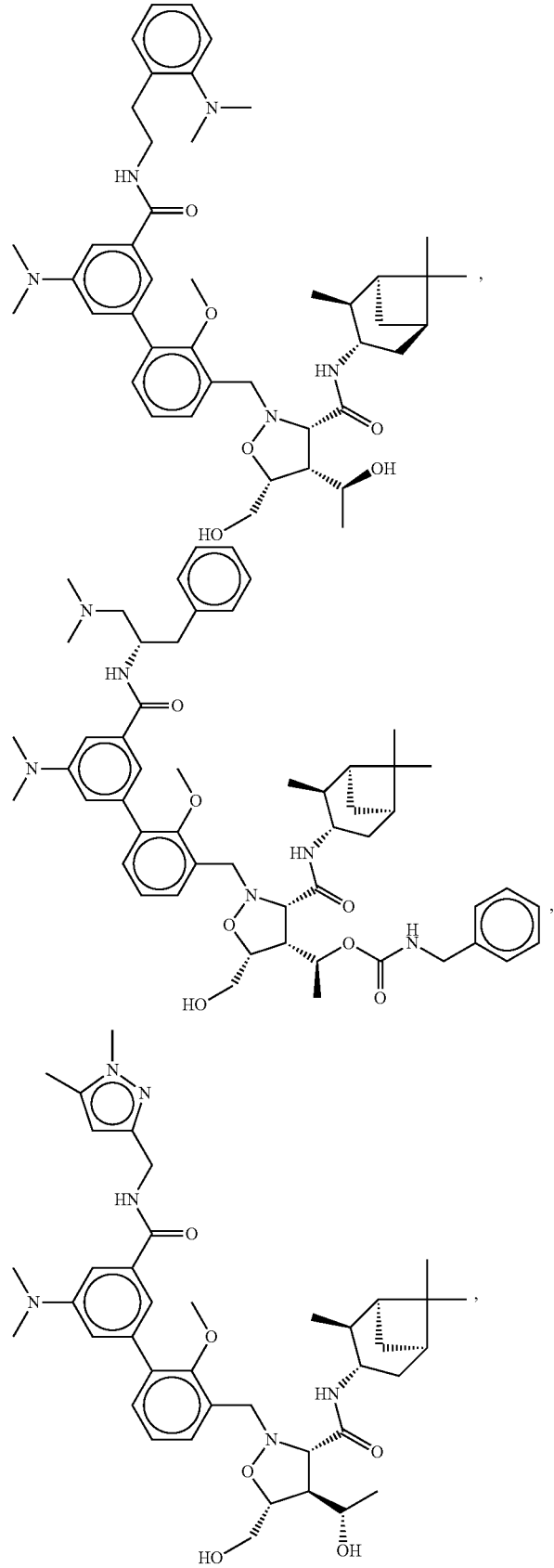
586
-continued
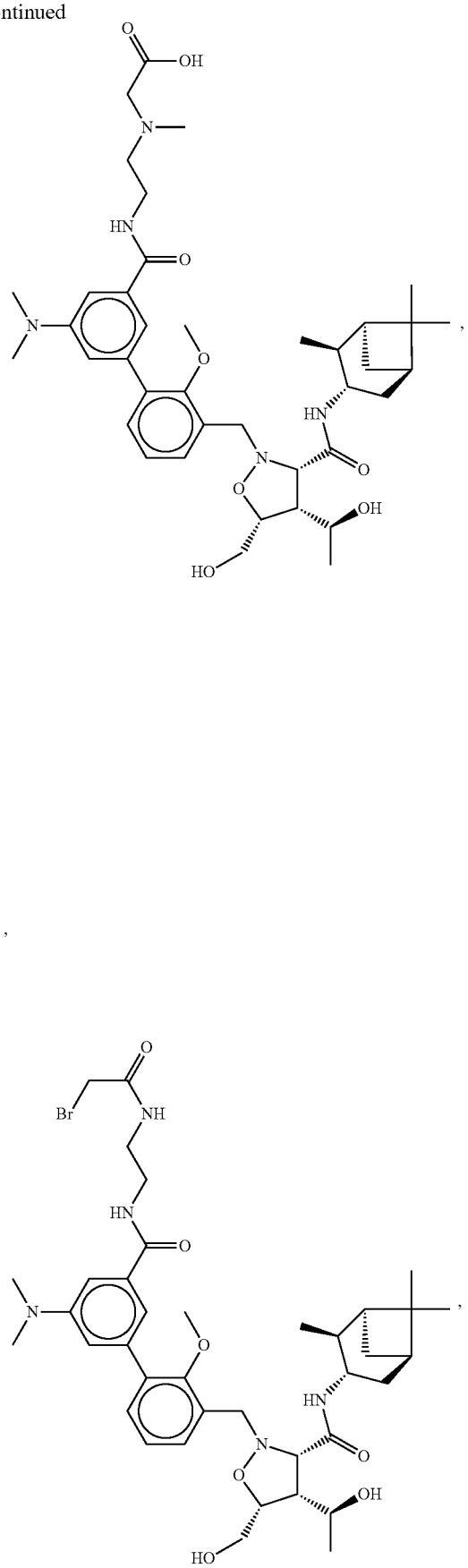

587
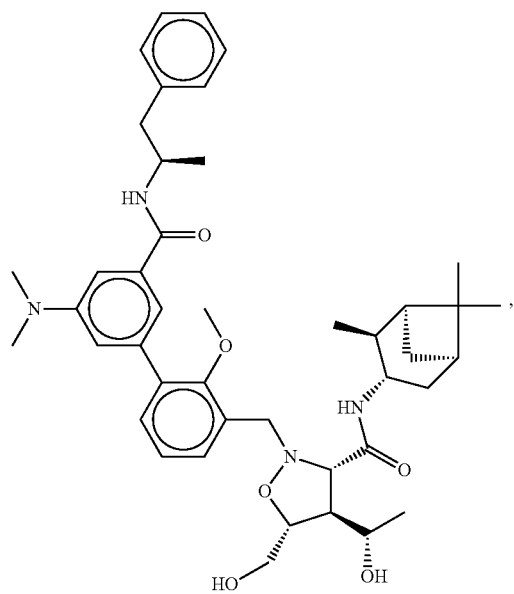
588
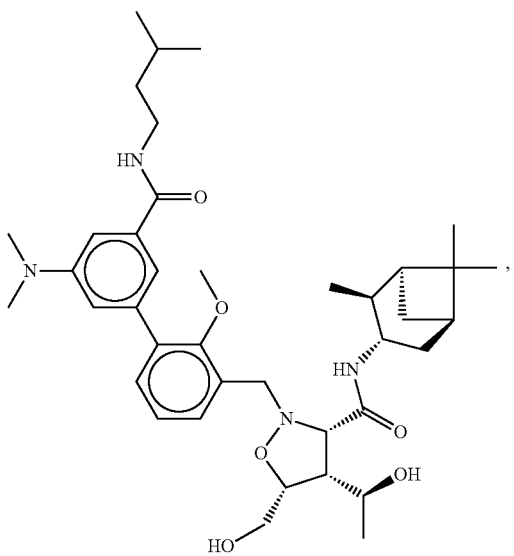
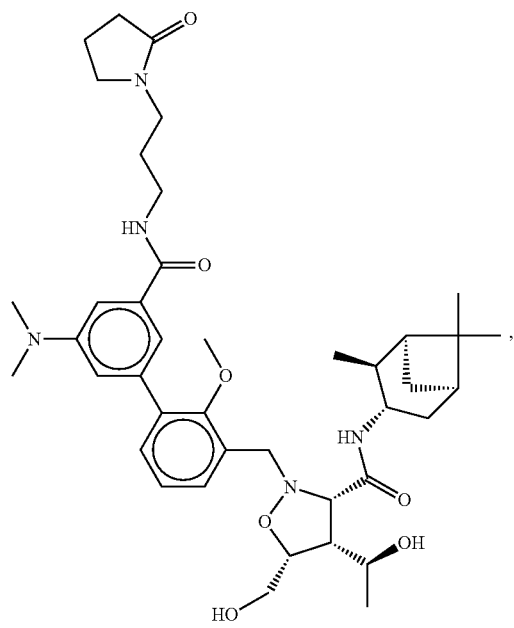
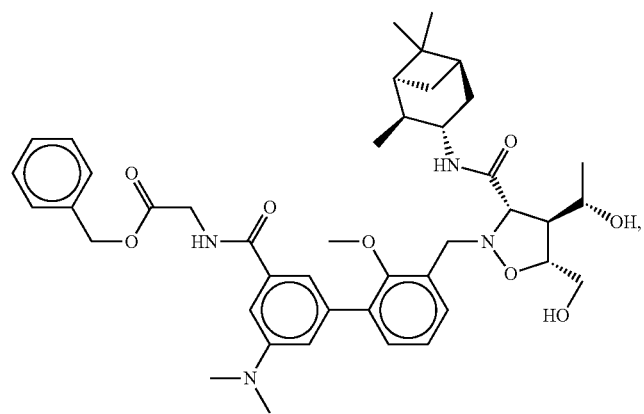

589
590
-continued
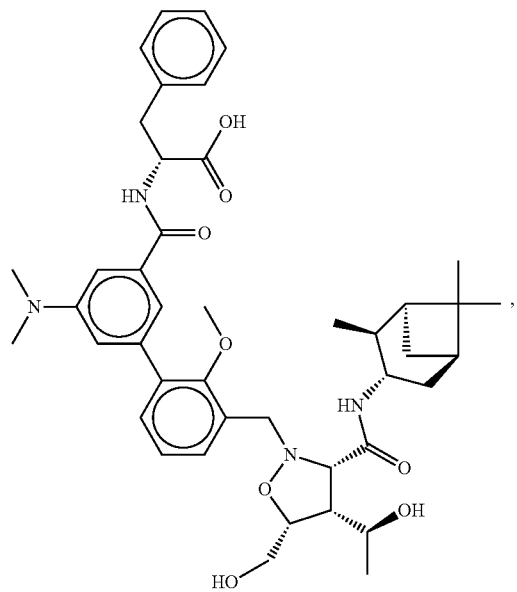
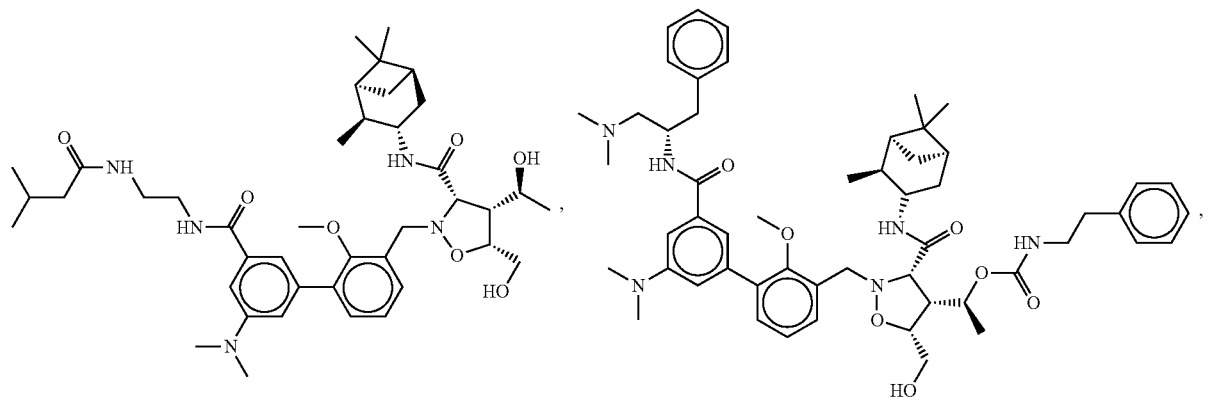
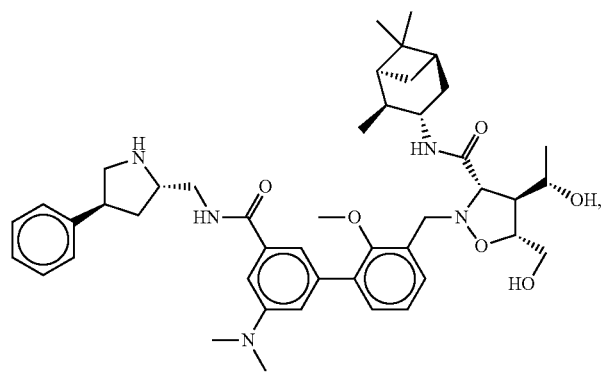

591
592
-continued
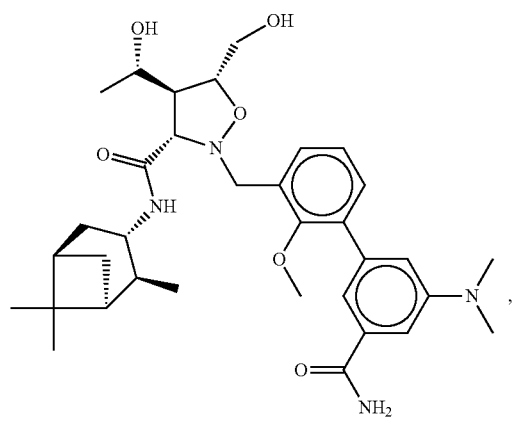
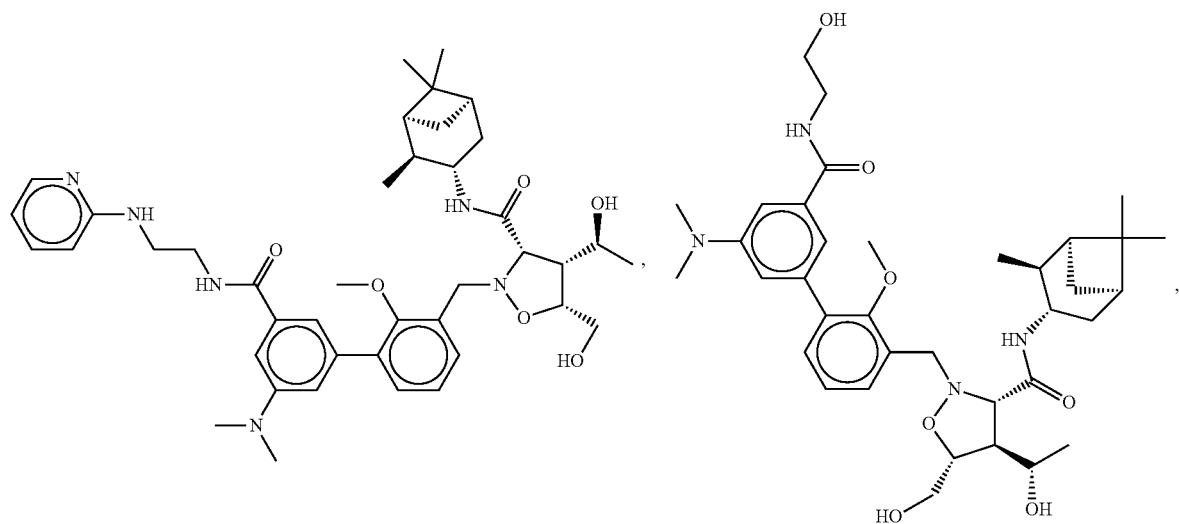
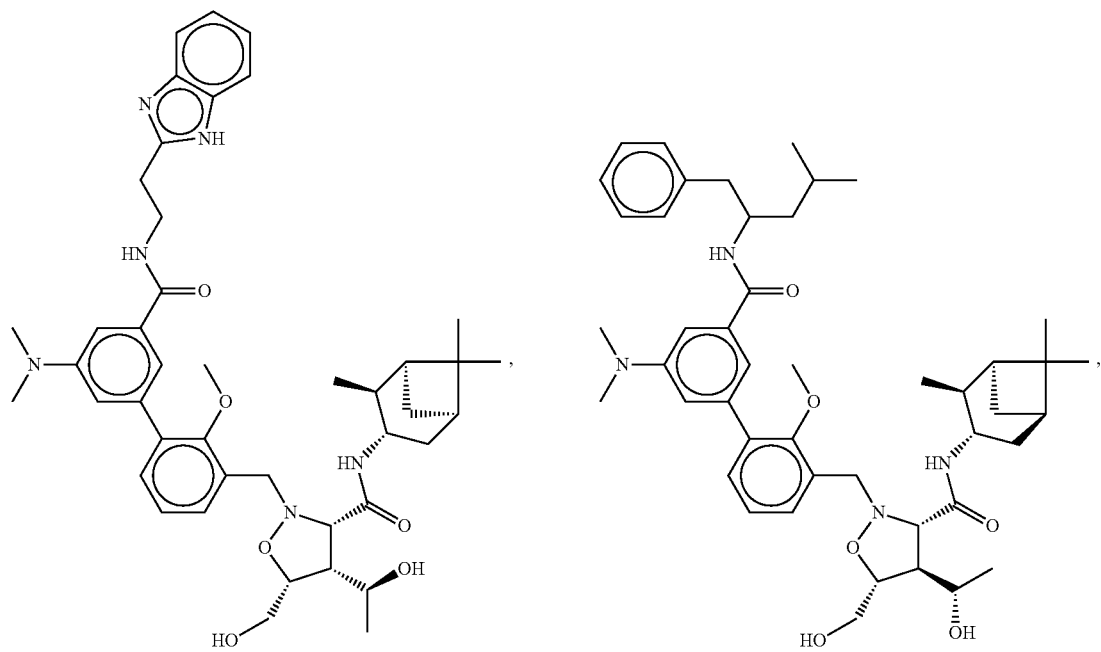

593
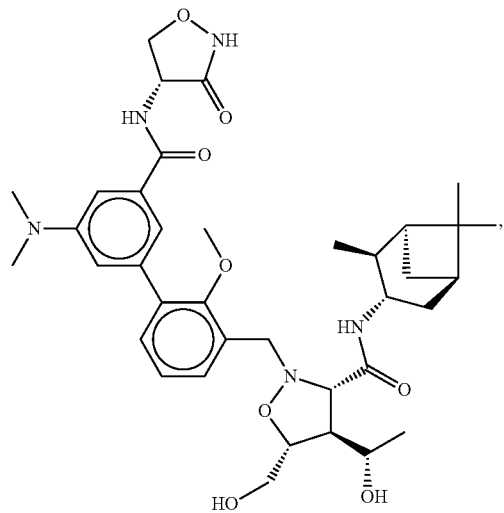
594
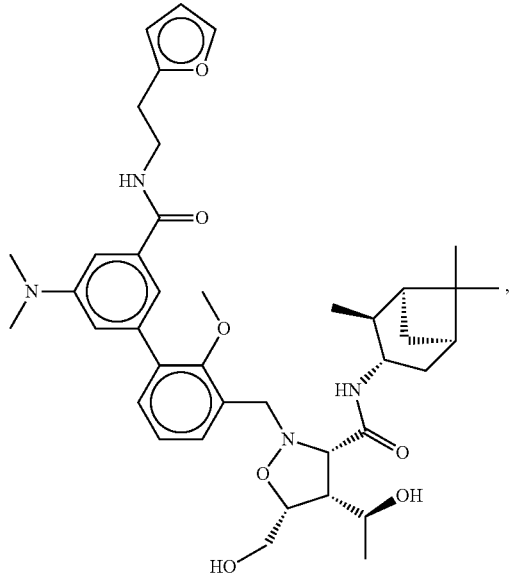
-continued
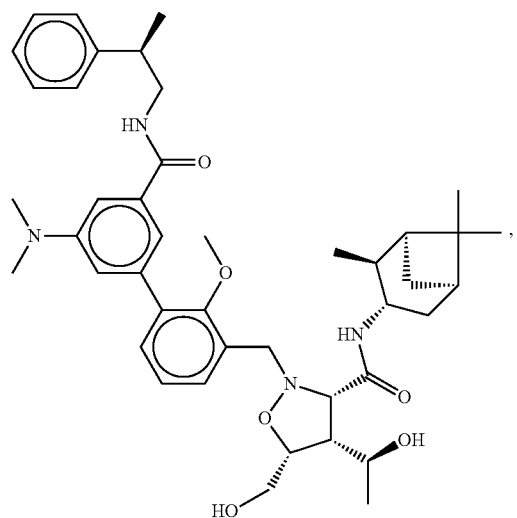
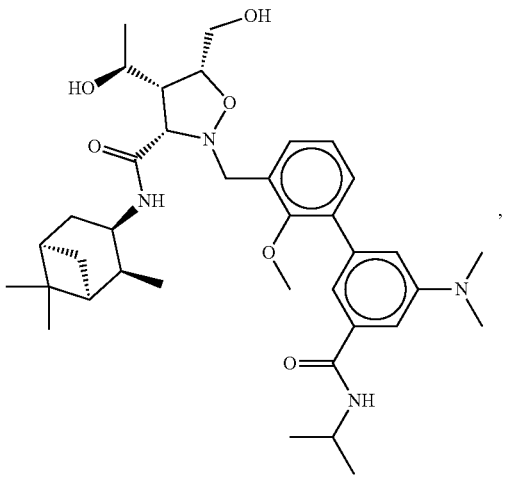
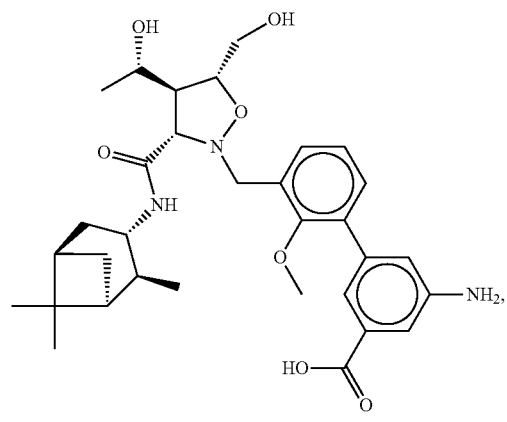
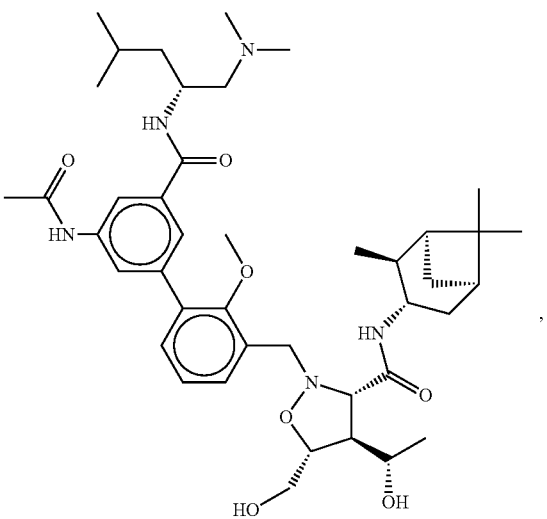

595
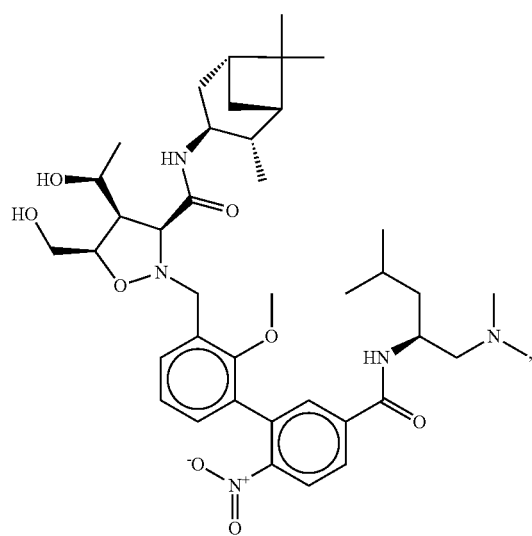
596
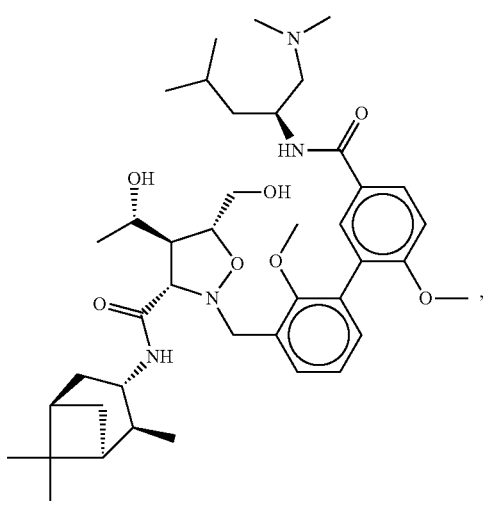
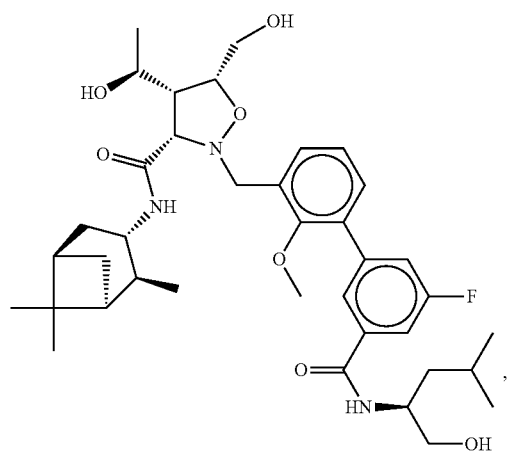
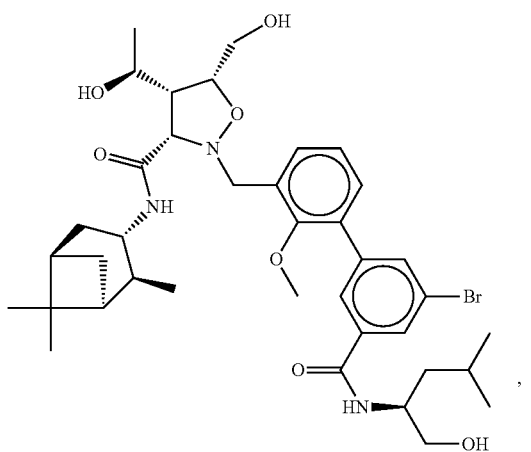
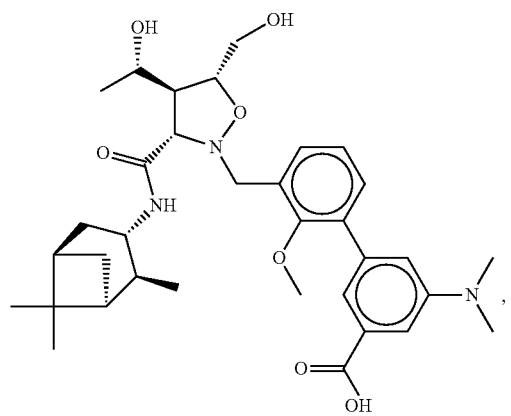

597
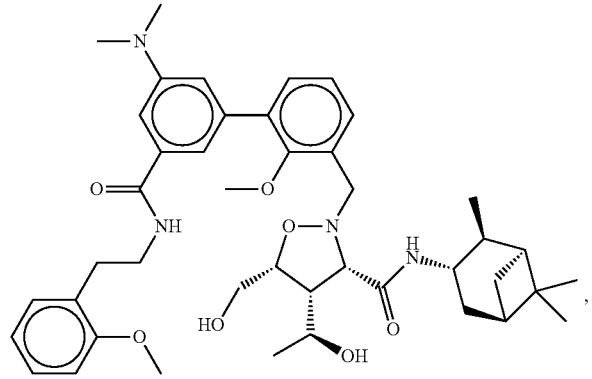
598
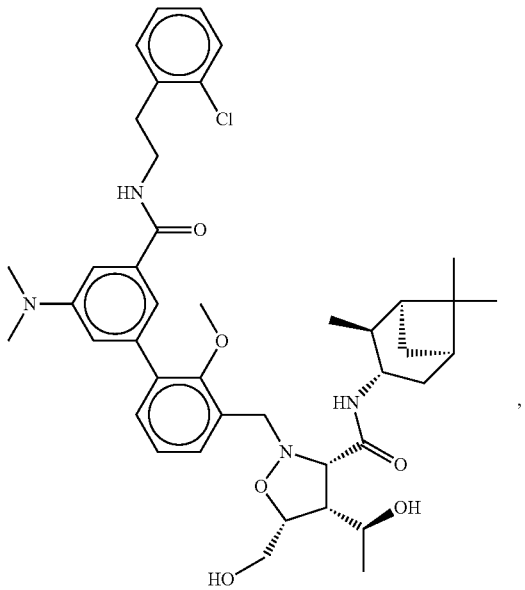
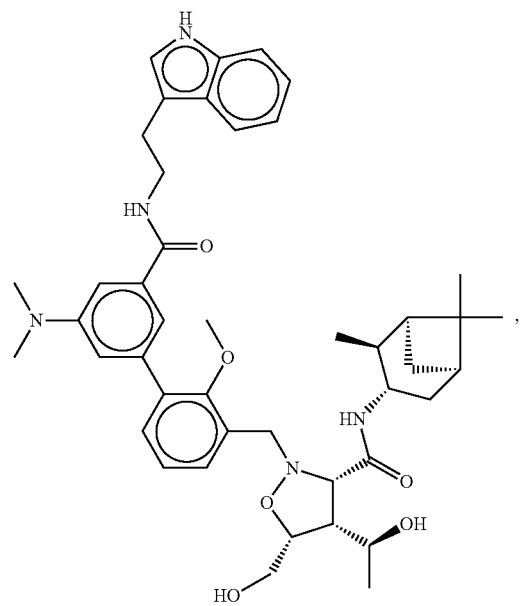
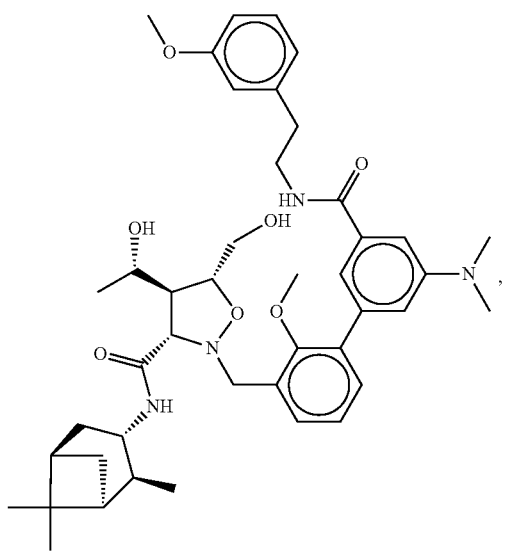

-continued
599
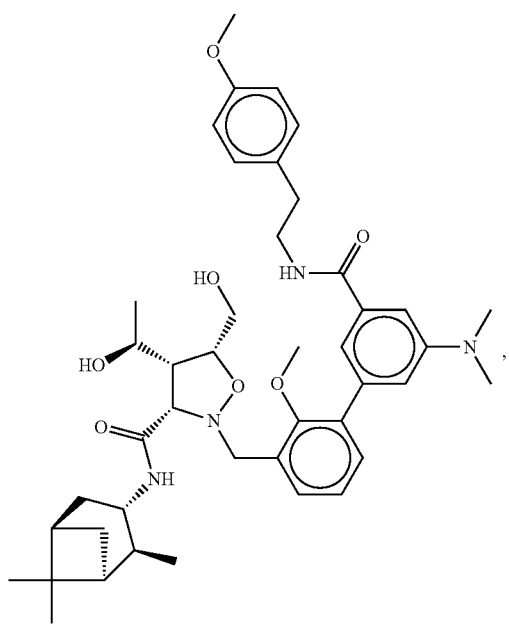
600
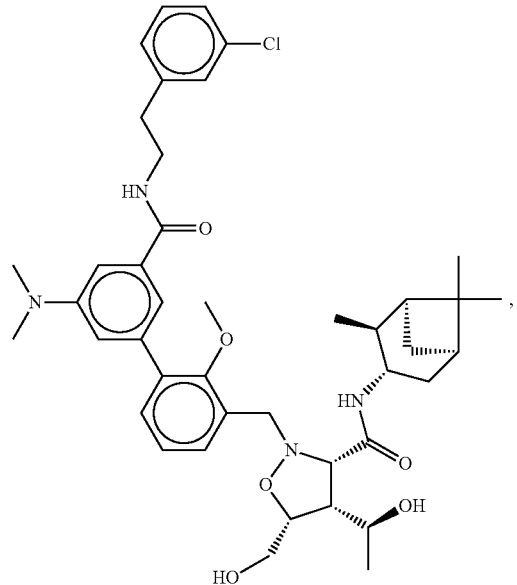
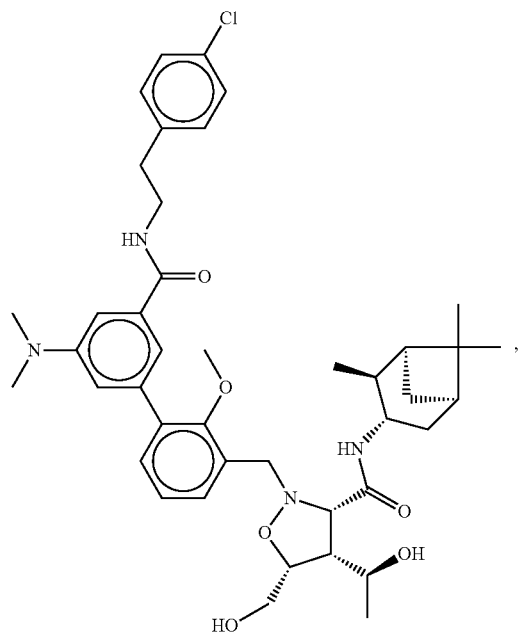
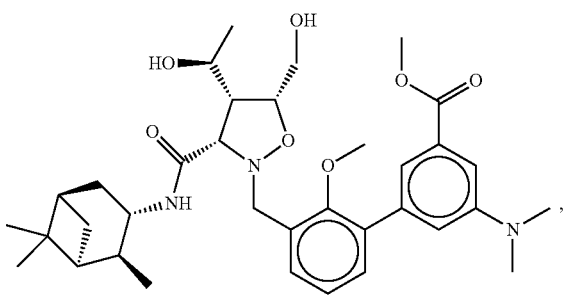

-continued
| 601 | 602 |
|---|---|
| 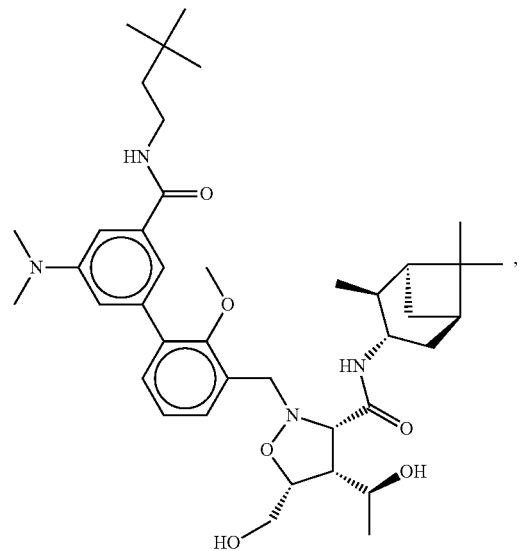 | 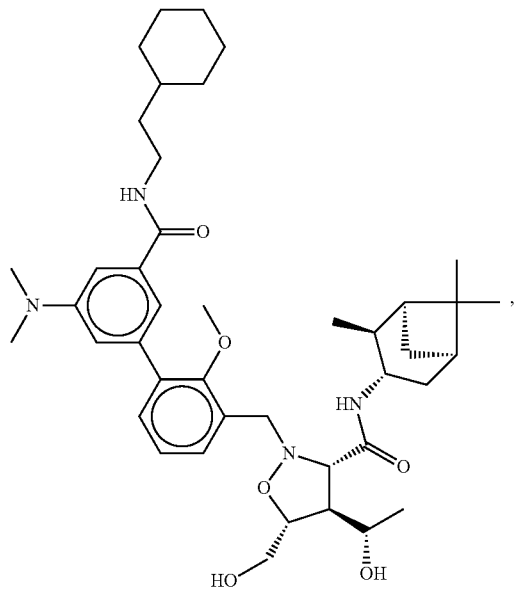 |
| 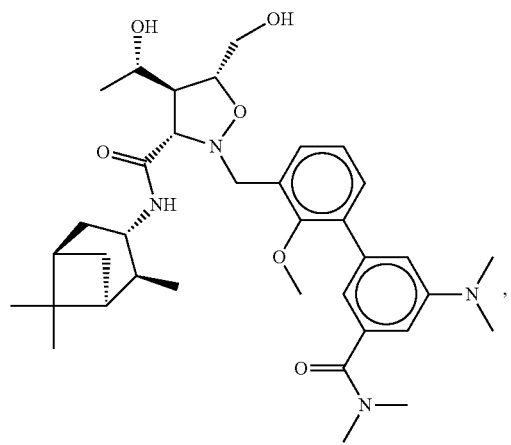 | 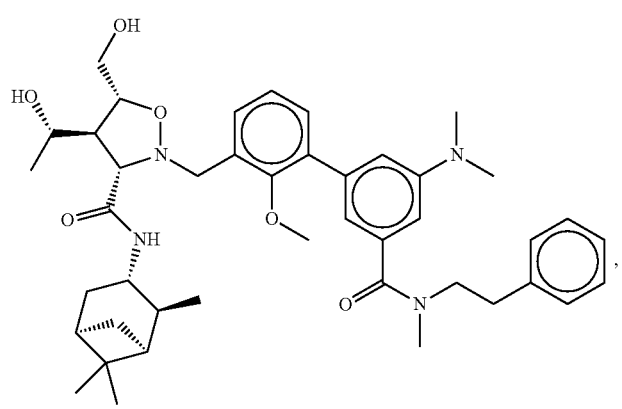 |
| 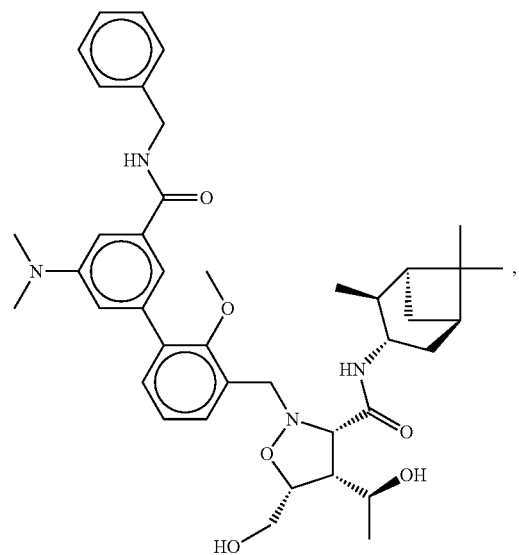 | 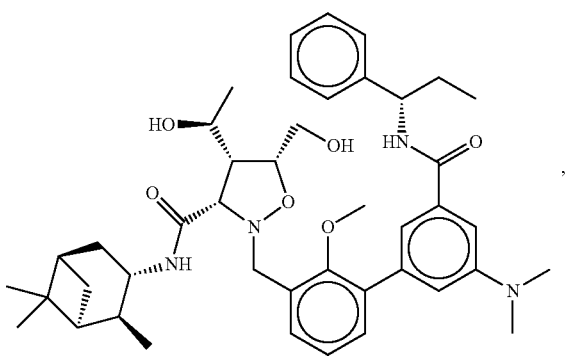 |

603 604
-continued
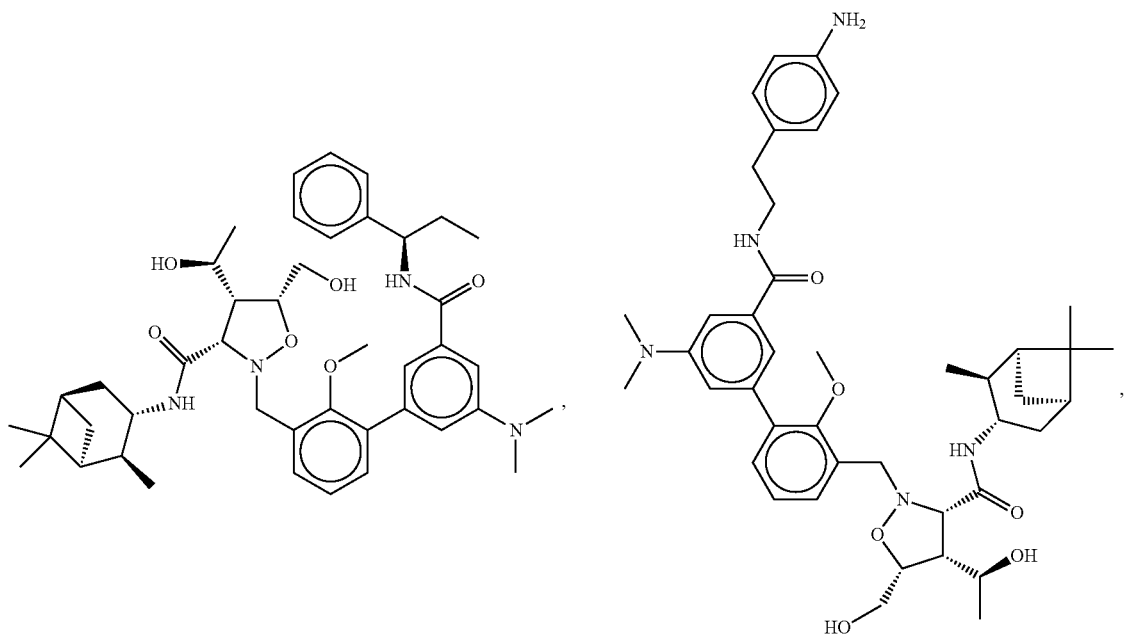
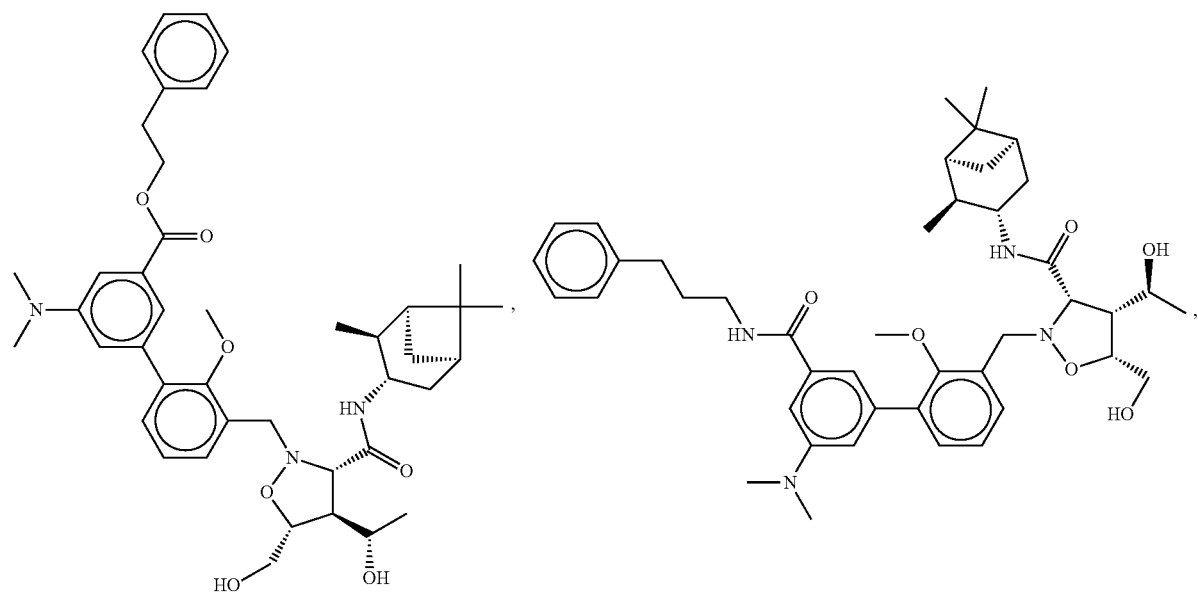

| 605 | 606 |
|---|---|
| 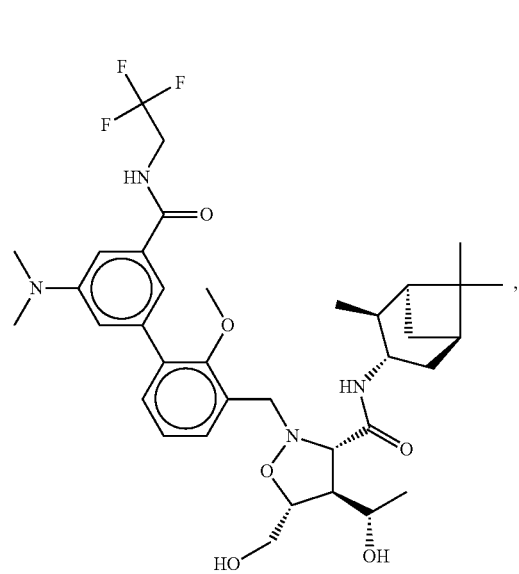 | 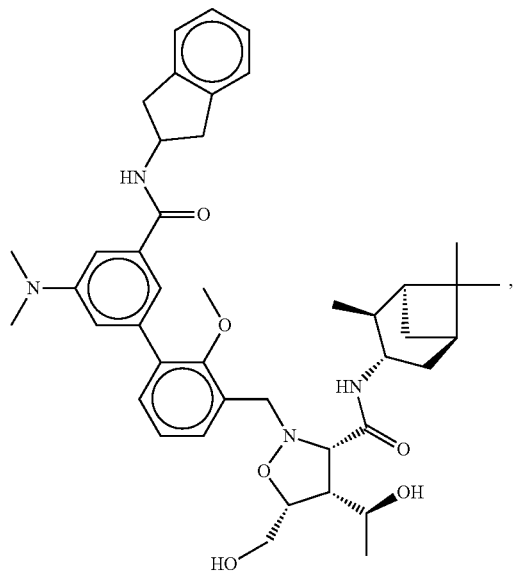 |
| 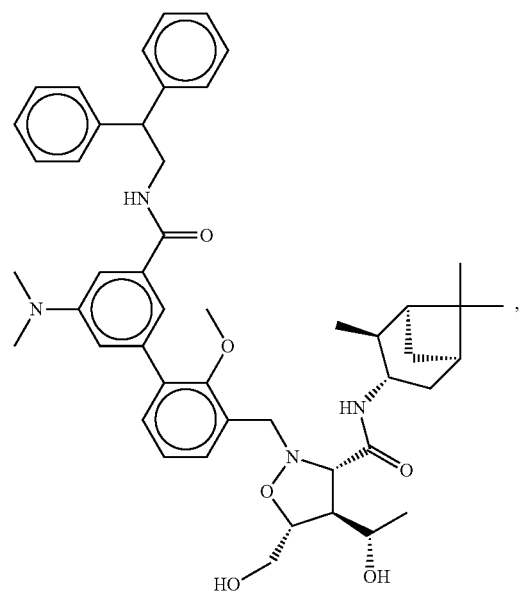 | 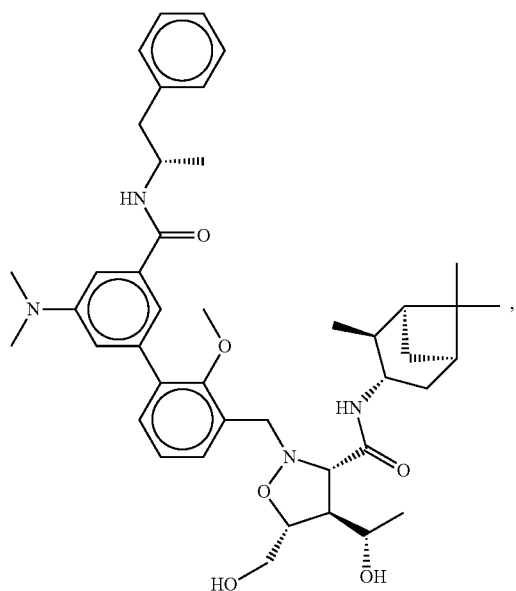 |